(12) United States Patent
Leonard et al.

(10) Patent No.: US 11,884,940 B2
(45) Date of Patent: Jan. 30, 2024

(54) MULTI-SUBSTRATE METABOLISM FOR IMPROVING BIOMASS AND LIPID PRODUCTION

(71) Applicant: Provivi, Inc., Santa Monica, CA (US)

(72) Inventors: Effendi Leonard, Anaheim Hills, CA (US); Micah Sheppard, Los Angeles, CA (US); Thomas Heel, Los Angeles, CA (US); Kathryn Christina Wu, Los Angeles, CA (US)

(73) Assignee: Provivi, Inc., Santa Monica, CA (US)

( * ) Notice: Subject to any disclaimer, the term of this patent is extended or adjusted under 35 U.S.C. 154(b) by 0 days.

(21) Appl. No.: 17/550,212

(22) Filed: Dec. 14, 2021

(65) Prior Publication Data

US 2022/0177857 A1 Jun. 9, 2022

Related U.S. Application Data

(62) Division of application No. 16/401,690, filed on May 2, 2019, now Pat. No. 11,220,675.

(60) Provisional application No. 62/665,809, filed on May 2, 2018.

(51) Int. Cl.
| | |
|---|---|
| *C12N 9/04* | (2006.01) |
| *C12P 7/64* | (2022.01) |
| *C12N 9/02* | (2006.01) |
| *C12N 9/18* | (2006.01) |
| *C12N 15/52* | (2006.01) |
| *C12N 15/81* | (2006.01) |
| *C12P 7/6409* | (2022.01) |

(52) U.S. Cl.
CPC .......... *C12N 9/0006* (2013.01); *C12N 9/0071* (2013.01); *C12N 9/18* (2013.01); *C12N 15/52* (2013.01); *C12N 15/815* (2013.01); *C12P 7/6409* (2013.01); *C12Y 101/0104* (2013.01); *C12Y 101/01042* (2013.01); *C12Y 101/01044* (2013.01); *C12Y 101/01049* (2013.01); *C12Y 114/19005* (2013.01); *C12Y 301/01031* (2013.01)

(58) Field of Classification Search
CPC .............................. C12N 9/0006; C12P 7/6409
See application file for complete search history.

(56) References Cited

U.S. PATENT DOCUMENTS

| | | | |
|---|---|---|---|
| 6,150,144 A | 11/2000 | Akimoto et al. | |
| 8,916,365 B2 * | 12/2014 | Macool | C12N 9/0006 435/189 |
| 11,220,675 B2 | 1/2022 | Leonard et al. | |
| 2019/0338295 A1 | 11/2019 | Leonard et al. | |

FOREIGN PATENT DOCUMENTS

| | | | |
|---|---|---|---|
| WO | WO-2016207339 A1 | 12/2016 | |
| WO | WO-2017087846 A1 * | 5/2017 | ............. A01N 31/02 |

OTHER PUBLICATIONS

Wang. Over-expression, purification, and characterization of recombinant NAD-malic enzyme from *Escherichia coli* K12. Protein Expr. Purif. 53:97-103(2007).*
U.S. Appl. No. 16/401,690, filed May 2, 2019, US 2019-0338295 A1, Nov. 7, 2019, U.S. Pat. No. 11,220,675, Jan. 11, 2022, Registered.
Aoshima and Igarashi, "Nondecarboxylating and Decarboxylating Isocitrate Dehydrogenases: Oxalosuccinate Reductase as an Ancestral Form of Isocitrate Dehydrogenase". Journal of Bacteriology (Mar. 2008); 190(6): 2050-2055. Epub Jan. 18, 2008.
Chuang, et al., "Co-expression of heterologous desaturase genes in *Yarrowia lipolytica*", New Biotechnology (Sep. 30, 2010); 27(4): 277-282.
Dujon. Q6C6Z1_YARLI. UniProtKB Database 2017, 2 pages.
Dulermo, et al., "Analysis of ATP-citrate lyase and malic enzyme mutants of *Yarrowia lipolytica* points out the importance of mannitol metabolism in fatty acid synthesis." Biochim Biophys Acta. (Sep. 2015); 1851(9): 1107-1117. Epub May 8, 2015.
Emanuelsson, et al., "Predicting Subcellular Localization of Proteins Based on their N-terminal Amino Acid Sequence." Journal of Molecular Biology (Jul. 21, 2000); 300(4): 1005-1016.
Extended European Search Report in European Application No. 19172410.3, dated Jul. 25, 2019, 10 pages.
Fernandez-Moya and Da Silva, "Engineering *Saccharomyces cerevisiae* for high-level synthesis of fatty acids and derived products", FEMS Yeast Research (Nov. 1, 2017); 17(7): 1-15.
Hagstrm, et al., "A moth pheromone brewery: production of (Z)-11-hexadecenol by heterologous co-expression of two biosynthetic genes from a noctuid moth in a yeast cell factory". Microbial Cell Factories (Dec. 13, 2013); 12(1): 125, 11 pages.
Halperin, et al., "Effects of Palmitoyl CoA on Citrate and Malate Transport by Rat Liver Mitochondria." Proc Natl Acad Sci U S A. (Apr. 1972); 69(4): 1003-1007.
Il'Ichev, et al., "Sprayable Microencapsulated Sex Pheromone Formulation for Mating Disruption of Oriental Fruit Moth (*Lepidoptera: Tortricidae*) in Australian Peach and Pear Orchards." Journal of Economic Entomology (Dec. 2006); 99(6): 2048-2054.

(Continued)

Primary Examiner — Yong D Pak
(74) Attorney, Agent, or Firm — Cooley LLP

(57) ABSTRACT

The present application relates to methods to improve biomass or lipid production in a microorganism from one or more fatty acid and one or more simple carbon co-substrates. Produced lipids may include unsaturated $C_6$-$C_{24}$ fatty acids, alcohols, aldehydes, and acetates which may be useful as final products or precursors to insect pheromones, fragrances, flavors, and polymer intermediates. The application further relates to recombinant microorganisms modified for improved production of biomass or lipid, or improved lipid selectivity. Also provided are methods of producing one or more lipid using the recombinant microorganisms, as well as compositions comprising the recombinant microorganisms and/or optionally one or more of the product lipid.

9 Claims, 39 Drawing Sheets

Specification includes a Sequence Listing.

(56) References Cited

OTHER PUBLICATIONS

Kavšček, et al., "Optimization of lipid production with a genome-scale model of Yarrowia lipolytica." BMC Systems Biology (2015); 9: 72; pp. 1-13.
Lin and McAlister-Henn, "Homologous binding sites in yeast isocitrate dehydrogenase for cofactor (NAD+) and allosteric activator (AMP)", J Biol Chem (Apr. 11, 2003); 278(15): 12864-12872. Epub Jan. 31, 2003.
Maniatis, et al,. "Regulation of inducible and tissue-specific gene expression" Science (1987); 236 (4806): 1237-1245.
Mauersberger, et al., "Insertional Mutagenesis in the n-Alkane-Assimilating Yeast *Yarrowia lipolytica*: Generation of Tagged Mutations in Genes Involved in Hydrophobic Substrate Utilization." J. Bacteriology (2001); 183 (17): 5102-5109.
Morin, et al., "Transcriptomic Analyses during the Transition from Biomass Production to Lipid Accumulation in the Oleaginous Yeast *Yarrowia lipolytica*." PLoS ONE (Nov. 2011); (11): e27966, pp. 1-13. Epub Nov. 22, 2011.
Q8GAXO_ACITH. UniProtKB/TrEMBL Database. Mar. 15, 2017.
Rutter and Rao, "Production of 1-decanol by metabolically engineered Yarrowia lipolytica". Metabolic Engineering (Nov. 2016); 38: 139-147. Epub Jul. 26, 2016.
Stelinski, et al., "Sprayable microencapsulated sex pheromone formulations for mating disruption of four tortricid species: effects of application height, rate, frequency, and sticker adjuvant" J Econ. Entomol. (2007); 100(4): 1360-1369.
Studer, et al., "Residue mutations and their impact on protein structure and function: detecting beneficial and pathogenic changes", Biochem J. (Feb. 1, 2013); 449(3): 581-594.
Tang, et al., "Metabolic engineering for enhanced fatty acids synthesis in *Saccharomyces cerevisiae*", Metabolic Engineering (Mar. 2012); 16: 95-102. Epub Jan. 23, 2013.
Wasylenko, et al., "The oxidative pentose phosphate pathway is the primary source of NADPH for lipid overproduction from glucose in Yarrowia lipolytica", Metabolic Engineering (Jul. 2015); 30: 27-39.
Zhang, et al., "Enhanced lipid accumulation in the yeast *Yarrowia lipolytica* by over-expression of ATP:citrate lyase from Mus musculus." Journal of Biotechnology (Dec. 20, 2014); 192 Pt A: 78-84. Epub Oct. 16, 2014.
Zhu and Jackson, "Metabolic engineering of Yarrowia lipolytica for industrial applications", Current Opinion in Biotechnology (Dec. 2015); 36: 65-72.

* cited by examiner

FIG. 11

```
        (SEQ ID NO: 50)ACACA_RAT    MDEPSPLAKTLELNQHSRFIIGSVSEDNSEDEISNLVKLD-LEEKEGSLSPASVSSDTLS
       (SEQ ID NO: 51)|ACACA_MOUSE   MDEPSPLAKTLELNQHSRFIIGSVSEDNSEDEISNLVKLD-LEEKEGSLSPASVSSDTLS
        (SEQ ID NO: 52)|ACAC_YEAST   ------------------------------------------------------------M
       (SEQ ID NO: 53)|ACACA_HUMAN   ------------------------------------------------------------
       (SEQ ID NO: 54)|ACACA_HUMAN   MDEPSPLAQPLELNQHSRFIIGSVSEDNSEDEISNLVKLDLLEEKEGSLSPASVGSDTLS
    (SEQ ID NO: 55)|A0A0H3VB41_LIPST  ------------------------------------------------------------
        (SEQ ID NO: 56)|F2QLC7_KOMPC  ------------------------------------------------------------
        (SEQ ID NO: 57)|Q6CC91_YARLI  -------------------------------------------------MRLQLRTLT (SEQ ID NO: 50)ACACA_RAT    DLGISALQDGLAFHMRSSMSGLHLVKQGRDRKKIDSQRDFTVASPAEFVTRFGGNKVIEK
       (SEQ ID NO: 51)|ACACA_MOUSE   DLGISGLQDGLAFHMRSSMSGLHLVKQGRDRKKIDSQRDFTVASPAEFVTRFGGNKVIEK
        (SEQ ID NO: 52)|ACAC_YEAST   SEESLFESSPQKMEYEITNYSERHTELFGHFIGLNTVDKLEESFLRDFVKSHGGHTVISK
       (SEQ ID NO: 53)|ACACA_HUMAN   ------------------MSGLHLVKQGRDRKKIDSQRDFTVASPAEFVTRFGGNKVIEK
       (SEQ ID NO: 54)|ACACA_HUMAN   DLGISSLQDGLALHIPSSMSGLHLVKQGRDPKKIDSQRDFTVASPAEFVTRFGGNKVIEK
    (SEQ ID NO: 55)|A0A0H3VB41_LIPST  ----------------MSAAASSLPSHFIGLNTVDVAANSPVKDFVQNHGGHTVITS
        (SEQ ID NO: 56)|F2QLC7_KOMPC  ---------------MSSVNHSLPHSKLPPHFLGLNSVEVAAPSKVRDFVRDHGGHSVITR
        (SEQ ID NO: 57)|Q6CC91_YARLI  RRFFSMASGSSTPDVAPLVDPNIHKGLASHFFGLNSVHTAKPSKVKEFVASHGGHTVINK (SEQ ID NO: 50)ACACA_RAT    VLIANNGIAAVKCMRSIPPWSYEMFPNERAIRFVVMVTPEDLEANAEYIKMADHYVPVPG
       (SEQ ID NO: 51)|ACACA_MOUSE   VLIANNGIAAVKCMRSIPPWSYEMFPNERAIRFVVMVTPEDLEANAEYIKMADHYVPVPG
        (SEQ ID NO: 52)|ACAC_YEAST   ILIANNGIAAVKEIRSVPEWAYETFGDDRTVQFVAMATPEDLEANAEYIRMADQYIEVPG
       (SEQ ID NO: 53)|ACACA_HUMAN   VLIANNGIAAVKCMRSIPPWSYEMFPNERAIRFVVMVTPEDLEANAEYIKMADHYVPVPG
       (SEQ ID NO: 54)|ACACA_HUMAN   VLIANNGIAAVKCMRSIPPWSYEMFPNERAIRFVVMVTPEDLEANAEYIKMADHYVPVPG
    (SEQ ID NO: 55)|A0A0H3VB41_LIPST  VLIANNGIAAVKEIRSVPEWAYETFGDERAISFTVMATPEDLEANADYIRMADQYVMVPG
        (SEQ ID NO: 56)|F2QLC7_KOMPC  VLIANNGIAAVKEIRSVRFWAYETFGNDRAIQFIVMATPEDLEANAEYIRMADQYVMVPG
        (SEQ ID NO: 57)|Q6CC91_YARLI  VLIANNGIAAVKEIRSVRFWAYETFGDERAISFTVMATPEDLAANADYIRMADQYEVPG (SEQ ID NO: 50)ACACA_RAT    GANNNNYANVELILDIAKRIPVQAVWAGWGHASENPKLPELLLKN---GIAFMGPPSQAMW
       (SEQ ID NO: 51)|ACACA_MOUSE   GPNNNNYANVELILDIAKRIPVQAVWAGWGHASENPKLPELLLKN---GIAFMGPPSQAMW
        (SEQ ID NO: 52)|ACAC_YEAST   GTNNNNYANVDLIVDIAERADVDAVWAGWGHASENPLLPEKLSQSKPKVIFIGPPGNAMR
       (SEQ ID NO: 53)|ACACA_HUMAN   GPNNNNYANVELILDIAKRIPVQAVWAGWGHASENPKLPELLLKN---GIAFMGPPSQAMW
       (SEQ ID NO: 54)|ACACA_HUMAN   GPNNNNYANVELILDIAKRIPVQAVWAGWGHASENPKLPELLLKN---GIAFNGPPSQAMW
    (SEQ ID NO: 55)|A0A0H3VB41_LIPST  GTNNNNYANVELIVDIAERMNVHAVWAGWGHASENPKLPESLAQSPEKIVFIGPPGGSAMR
        (SEQ ID NO: 56)|F2QLC7_KOMPC  GTANNNYANVDLIVEIAESTDAHAVWAGWGFASENPHLPEQLAASPEKIIFIGPPSAMR
        (SEQ ID NO: 57)|Q6CC91_YARLI  GTNNNNYANVELIVDVAERFGVDAVWAGWGHASENPLLPESLAASPPKIVFIGPPGAAMR (SEQ ID NO: 50)ACACA_RAT    ALGDKIASSIVAQTAGIPTLFWSGSGLRVDWQENDFSKRILNVPQDLYEKGYVKDVDDGL
       (SEQ ID NO: 51)|ACACA_MOUSE   ALGDKIASSIVAQTAGIPTLFWSGSGLRVDWQENDFSKRILNVPQDLYEKGYVKDVDDGL
        (SEQ ID NO: 52)|ACAC_YEAST   SLGDKISSTIVAQSAKVPCIFWSGTG--VDTVHVDEKTGLVSVDDDIYQKGCCTSPEDGL
       (SEQ ID NO: 53)|ACACA_HUMAN   ALGDKIASSIVAQTAGIPTLFWSGSGLRVDWQENDFSKRILNVPQDLYEKGYVKDVDDGL
       (SEQ ID NO: 54)|ACACA_HUMAN   ALGDKIASSIVAQTAGIPTLFWSGSGLRVDWQENDFSKRILNVPQDLYEKGYVKDVDDGL
    (SEQ ID NO: 55)|A0A0H3VB41_LIPST  SLGDKISSTIVAQRHKVPCIFWSGTG--VDEVQIDSVSGLVTVSDEIYAKGCTPSTAEEAL
        (SEQ ID NO: 56)|F2QLC7_KOMPC  SLGDKISSTIVAQHAKVPCIFWSGTG--VQQVIIDEVSNLVSVSDEETYAKGCCSDPQDGL
        (SEQ ID NO: 57)|Q6CC91_YARLI  SLGDKISSTIVAQHAKVPCIFWSGTG--VDEVVVDKSTNLVSVSEEVYTKGCTTGPKQGL (SEQ ID NO: 50)ACACA_RAT    KAAEEVGYPVMIKASEGGGGKGIRKVNNADDFPNLFRQVQAEVPGSPIFVMRLAKQSRHL
       (SEQ ID NO: 51)|ACACA_MOUSE   KAAEEVGYPVMIKASEGGGGKGIRKVNNADDFPNLFRQVQAEVPGSPIFVMRLAKQSRHL
        (SEQ ID NO: 52)|ACAC_YEAST   QKAKRIGFPVMIKASEGGGGKGIRQVEREEDFIALYHQAANEIPGSPIFIMKLAGRARHL
       (SEQ ID NO: 53)|ACACA_HUMAN   QAAEEVGYPVMIKASEGGGGKGIRKVNNADDFPNLFRQVQAEVPGSPIFVMRLAKQSRHL
       (SEQ ID NO: 54)|ACACA_HUMAN   QAAEEVGYPVMIKASEGGGGKGIRKVNNADDFPNLFRQVQAEVPGSPIFVMRLAKQSRHL
    (SEQ ID NO: 55)|A0A0H3VB41_LIPST  EKARIIGFPVMIKASEGGGGKGIRKVESEINFRSLYDQVANEVPGSPIFVMKLAGNARHL
        (SEQ ID NO: 56)|F2QLC7_KOMPC  AKAKAIGFPVMIKASEGGGGKGIRKVD-REEDFLSLYDQAANEIPGSPIFIMKLAGDARHL
        (SEQ ID NO: 57)|Q6CC91_YARLI  EKAKQIGFPVMIKASEGGGGKGIRKVEREEDFEAAYHQVEGEIPGSPIFIMQLAGNARHL (SEQ ID NO: 50)ACACA_RAT    EVQILADQYGNAISLFGRDCSVQRRHQKIIEEAPAAIATPAVFEHMEQCAVKLAKMVGYV
       (SEQ ID NO: 51)|ACACA_MOUSE   EVQILADQYGNAISLFGRDCSVQRRHQKIIEEAPAAIATPAVFEHMEQCAVKLAKMVGYV
        (SEQ ID NO: 52)|ACAC_YEAST   EVQLLADQYGTNISLFGRDCSVQRRHQKIIEEAPVTIAKAETFHEMEKAAVRLGKLVGYV
       (SEQ ID NO: 53)|ACACA_HUMAN   EVQILADQYGNAISLFGRDCSVQRRHQKIIEEAPATIATPAVFEHMEQCAVKLAKMVGYV
       (SEQ ID NO: 54)|ACACA_HUMAN   EVQILADQYGNAISLFGRDCSVQRRHQKIIEEAPATIATPAVFEHMEQCAVKLAKMVGYV
    (SEQ ID NO: 55)|A0A0H3VB41_LIPST  EVQLLADQYGNNISLFGRDCSVQRRHQKIIEEAPVTVANPATFSAMEHAAVRLGQLVGYV
        (SEQ ID NO: 56)|F2QLC7_KOMPC  EVQLLADQYGTNISLFGRDCSVQRRHQKIIEEAPVTIAKQDTFRQMEQAAVRLGQLVGYV
        (SEQ ID NO: 57)|Q6CC91_YARLI  EVQLLADQYGNNISLFGRDCSVQRRHQKIIEEAPVTVAGQQTFTAMEKAAVRLGKLVGYV (SEQ ID NO: 50)ACACA_RAT    SAGTVEYLYSQ-DGSFYFLELNPRLQVEHPCTEMVADVNLPAAQLQIAMGIPLFRIKDIR
       (SEQ ID NO: 51)|ACACA_MOUSE   SAGTVEYLYSQ-DGSFYFLELNPRLQVEHPCTEMVADVNLPAAQLQIAMGIPLFRIKDIR
        (SEQ ID NO: 52)|ACAC_YEAST   SAGTVEYLYSHDDGKFYFLELNPRLQVEHPTTEMVSGVNLPAAQLQIAMGIPMHRISDIR
       (SEQ ID NO: 53)|ACACA_HUMAN   SAGTVEYLYSQ-DGSFYFLELNPRLQVEHPCTEMVADVNLPAAQLQIAMGIPLYRIKDIR
       (SEQ ID NO: 54)|ACACA_HUMAN   SAGTVEYLYSQ-DGSFYFLELNPRLQVEHPCTEMVADVNLPAAQLQIAMGIPLYRIKDIR
    (SEQ ID NO: 55)|A0A0H3VB41_LIPST  SAGTVEYLYSHDDDKFYFLELNPRLQVEHPTTEMVTGVNLPAAQLQIAMGVSLHRIRDIR
        (SEQ ID NO: 56)|F2QLC7_KOMPC  SAGTVEYLYSHAEDKFYFLELNPRLQVEHPTTEMATGVNLPVAQLLIAMGIPLNRIRDIR
        (SEQ ID NO: 57)|Q6CC91_YARLI  SAGTVEYLYSHEDDKFYFLELNPRLQVEHPTTEMVTGVNLPAAQLQIAMGIPLDRIKDIR
```

FIG. 11 (continued)

```
            (SEQ ID NO: 50)ACACA_RAT    MMYGVSPWGDAPIDFE--------NSAHVPCPRGHVIAARITSENPDEGFKPSSGTVQELN
          (SEQ ID NO: 51)|ACACA_MOUSE   MMYGVSPWGDAPIDFE--------NSAHVPCPRGHVIAARITSENPDEGFKPSSGTVQELN
           (SEQ ID NO: 52)|ACAC_YEAST   TLYGMNPHSASEIDFEFKTQDATKKQRRPIPKGHCTACRITSEDPNDGFKPSSGGTLHELN
          (SEQ ID NO: 53)|ACACA_HUMAN   MMYGVSPWGDSPIDFE--------DSAHVPCPRGHVIAARITSENPDEGFKPSSGTVQELN
          (SEQ ID NO: 54)|ACACA_HUMAN   MMYGVSPWGDSPIDFED-------SAHVPCPRGHVIAARITSENPDEGFKPSSGTVQELN
      (SEQ ID NO: 55)|A0A0H3VB41_LIPST  LFYGVDPHTSTEIDFDFSKEGSLQTQRRPVPKGHTTACRITSEDPGEGFKPSSGVMHELN
          (SEQ ID NO: 56)|F2QLC7_KOMPC   VLYGLEPNGATEIDFEFKTEESLKSQRKPIPKGHTIACRITSEDPGEGFKPSGGALYELN
          (SEQ ID NO: 57)|Q6CC91_YARLI   LFYGVNPHTTTPIDFDFSGEDADKTQRRPVPRGHTTACRITSEDPGEGFKPSGGTMHELN (SEQ ID NO: 50)ACACA_RAT    FRSNKNVWGYFSVAAAGGLHEFADSQFGHCFSWGENREEAISNMVVALKELSIRGDFRTT
          (SEQ ID NO: 51)|ACACA_MOUSE   FRSNKNVWGYFSVAAAGGLHEFADSQFGHCFSWGENREEAISNMVVALKELSIRGDFRTT
           (SEQ ID NO: 52)|ACAC_YEAST   FRSSSNVWGYFSVGNRGNIHSFSDSQFGHIFAFGENRQASPKHMVVALKELSIRGDFRTT
          (SEQ ID NO: 53)|ACACA_HUMAN   FRSNKNVWGYFSVAAAGGLHEFADSQFGHCFSWGENREEAISNMVVALKELSIRGDFPTT
          (SEQ ID NO: 54)|ACACA_HUMAN   FRSNKNVWGYFSVAAAGGLHEFADSQFGHCFSWGENREEAISNMVVALKELSIRGDFPTT
      (SEQ ID NO: 55)|A0A0H3VB41_LIPST  FRSSSNVWGYFSVGNQGGIHSFSDSQFGHIFAFGENRSASPKHMVVALKELSIRGDFPTT
          (SEQ ID NO: 56)|F2QLC7_KOMPC   FRSSSSVWGYFSVGNKSSIHSFSDSQFGHIFSFGENRQIAPKHMVVALKELSIRGDFPTT
          (SEQ ID NO: 57)|Q6CC91_YARLI   FPSSSNVWGYFSVGNQGGIHSFSDSQFGHIFAFGENRSASPKHMVVALKELSIRGDFPTT (SEQ ID NO: 50)ACACA_RAT    VEYLIKLLETESFQLNRIDTGWLDRLIAEKVQAERPDTMLGVVCGALHVADVNLRNSISN
          (SEQ ID NO: 51)|ACACA_MOUSE   VEYLIKLLETESFQLNRIDTGWLDRLIAEKVQAERPDTMLGVVCGALHVADVSLRNSISN
           (SEQ ID NO: 52)|ACAC_YEAST   VEYLIKLLETEDFEDNTITTGWLDDLITHKMTAEKPDFTLAVICGAATKAFLASEEARHK
          (SEQ ID NO: 53)|ACACA_HUMAN   VEYLIKLLETESFQMNRIDTGWLDRLIAEKVQAERPDTMLGVVCGALHVADVSLRNSVSN
          (SEQ ID NO: 54)|ACACA_HUMAN   VEYLIKLLETESFQMNRIDTGWLDRLIAEKVQAERPDTMLGVVCGALHVADVSLRNSVSN
      (SEQ ID NO: 55)|A0A0H3VB41_LIPST  VEYLIKLLETPDFESNKITTGWLDELISEKLTAERPDFVVAVVCGAVTKAHLASEACFQE
          (SEQ ID NO: 56)|F2QLC7_KOMPC   IEYLIKLLETADFEDNTITTGWLDELISFKLTAERPDETTAILCGAVTKAYIQWDLCRKE
          (SEQ ID NO: 57)|Q6CC91_YARLI   VEYLIKLLETPDFEDNTITTGWLDELISNKLTAERPDSFLAVVCGAATKAHRASEDSIAT (SEQ ID NO: 50)ACACA_RAT    FLRSLERGQVLPAHTLLNTVDVELIYEGIKYVLKVTRQSPNSYVVIMNGSCVEVDVHRLS
          (SEQ ID NO: 51)|ACACA_MOUSE   FLRSLERGQVLPAHTLLNTVDVELIYEGIKVVLKVTRQSPNSYVVIMNGSCVEVDVHRLS
           (SEQ ID NO: 52)|ACAC_YEAST   YIESLQKGQVLSKDLLQTMFPVDFIHEGKRYHFTVAKSGNDRYTLFINGSKCDIILPQLS
          (SEQ ID NO: 53)|ACACA_HUMAN   FLRSLERGQVLPAHTLLNTVDVELIYEGVKYVLKVTRQSPNSYVVIMNGSCVEVDVHRLS
          (SEQ ID NO: 54)|ACACA_HUMAN   FLRSLERGQVLPAHTLLNTVDVELIYEGVKYVLKVTRQSPNSYVVIMNGSCVEVDVHRLS
      (SEQ ID NO: 55)|A0A0H3VB41_LIPST  YKNSLEKGQVPSKDILFTLFPVDFIYEGSRYHFTVTRSSMDLYQIFINGSKCLVGVESLS
          (SEQ ID NO: 56)|F2QLC7_KOMPC   YVASLEKGQIPGKELLPTIFPIEFIYEGKKYHFTVVQAAFDKYNVFVNGCMITVSVTHLK
          (SEQ ID NO: 57)|Q6CC91_YARLI   YMASLEKGQVPARDILFTLFPVDFIYEGQRYHFTATRSSEDSYTLFINGSRCDIGVPPLS (SEQ ID NO: 50)ACACA_RAT    DGGLLLSYDGSSYTTY-MKEEVDRYRITIGNKTCVFEKENDPSVMRSPSAGKLIQYIVED
          (SEQ ID NO: 51)|ACACA_MOUSE   DGGLLLSYDGSSYTTY-MKEEVDRYRITIGNKTCVFEKENDPSVMRSPSAGKLIQYIVED
           (SEQ ID NO: 52)|ACAC_YEAST   DGGLLIAIGGKSHTIY-WKEEVAATRLSVDSMTTLLEVENDPTQLRTPSPGKLVKFLVEH
          (SEQ ID NO: 53)|ACACA_HUMAN   DGGLLLSYDGSSYTTY-MKEEVDRYRITIGNKTCVFEKENDPSVMRSPSAGKLIQYIVED
          (SEQ ID NO: 54)|ACACA_HUMAN   DGGLLLSYDGSSYTTY-MKEEVDRYRITIGNKTCVFEKENDPSVMRSPSAGKLIQYIVED
      (SEQ ID NO: 55)|A0A0H3VB41_LIPST  DGGLLVLLGGKSHNVY-WKDEVGTTRLSVDSKTCLLEQENDPTQLRTPSPGKLVKFLVEN
          (SEQ ID NO: 56)|F2QLC7_KOMPC   DGSLLVALDGKSHSVYYLQEEVGNTRLSVDGKSCILEVEREPTELRTPSPGKLIKYLVEH
          (SEQ ID NO: 57)|Q6CC91_YARLI   DGGILCLVGGRSHNVY-WKEEVGATRLSVDSKTCLLEVENDPTQLRSPSPGKLVKFLVEN (SEQ ID NO: 50)ACACA_RAT    GGRVFAGQCYAEIEVMKMVMTLTAVESGCIHYVKRPGAALDPGCVIAKMQLDNPSKVQQA
          (SEQ ID NO: 51)|ACACA_MOUSE   GGRVFAGQCYAEIEVMKMVMTLTAVESGCIHYVKRPGAALDPGCVIAKMQLDNPSKVQQA
           (SEQ ID NO: 52)|ACAC_YEAST   GERIIKGQPYAEIEVMKMQMPLVSQENGIVQLLRQPGSTIVAGDIMAIMTLDDPSKVKRA
          (SEQ ID NO: 53)|ACACA_HUMAN   GGRVFAGQCYAEIEVMKMVMTLTAVESGCIHYVKRPGAALDPGCVIAKMQLDNPSKVQQA
          (SEQ ID NO: 54)|ACACA_HUMAN   GGRVFAGQCYAEIEVMKMVMTLTAVESGCIHYVKRPGAALDPGCVIAKMQLDNPSKVQQA
      (SEQ ID NO: 55)|A0A0H3VB41_LIPST  GERVKTGQPFAEVEVMKMYMPLYAQEDGIVQLINQPGATLEAGDILGILALDDPSRVKRA
          (SEQ ID NO: 56)|F2QLC7_KOMPC   GDRVKIGQPYAEVEMKMCMPLVSQENGTIRLLNQPGSSVAAGDILAILALDDPSKVKRA
          (SEQ ID NO: 57)|Q6CC91_YARLI   GDRVRANQPYAEIEVMKMYMTLTAQEDGIVQLMKQPGSTIEAGDILGILALDDPSKVRRA (SEQ ID NO: 50)ACACA_RAT    ELHTGSLPQIQSTALRGEKLHRVFHYVLDNLVNVMNGYCLPDPFFSSKVKDWVERLMKTL
          (SEQ ID NO: 51)|ACACA_MOUSE   ELHTGSLPQIQSTALRGEKLHRVFHYVLDNLVNVMNGYCLPDPFFSSKVKDWVERLMKTL
           (SEQ ID NO: 52)|ACAC_YEAST   LPFEGMLPDFGSPVIEGTKPAYKFKSLVSTLENILKGY---DN--QVIMNASLQQLIEVL
          (SEQ ID NO: 53)|ACACA_HUMAN   ELHTGSLPRIQSTALRGEKLHRVFHYVLDNLVNVMNGYCLPDPFFSSKVKDWVERLMKTL
          (SEQ ID NO: 54)|ACACA_HUMAN   ELHTGSLPRIQSTALRGEKLHRVFHYVLDNLVNVMNGYCLPDPFFSSKVKDWVERLMKTL
      (SEQ ID NO: 55)|A0A0H3VB41_LIPST  KPFEGQLPDFGSPLVLGSKPSQRENILLSTLRNILAGF----DN--QVLLASTLRDLSQVL
          (SEQ ID NO: 56)|F2QLC7_KOMPC   LPFDGTIPDMKQPFIHSNKPVYKFISLLSVLKNILAGY----DN--QVVMNDTLQSLLDVL
          (SEQ ID NO: 57)|Q6CC91_YARLI   KPFEGQLPELGPPTLSGNKPBQRYEHCQNVLRNILLGF----DN--QVVMKSTLQEMYGLL (SEQ ID NO: 50)ACACA_RAT    RDPSLPLLELQDIMTSVSGRIPLNVEKSIKKEMAQYASNITSVLCQFPSQQIANILDSHA
          (SEQ ID NO: 51)|ACACA_MOUSE   RDPSLPLLELQDIMTSVSGRIPLNVEKSIKKEMAQYASNITSVLCQFPSQQIANILDSHA
           (SEQ ID NO: 52)|ACAC_YEAST   RNPKLPYSEWKLHISALHSRLPAKLDEQMEELVARSLPRG----AVFPARQLSKLIDM-A
          (SEQ ID NO: 53)|ACACA_HUMAN   RDPSLPLLELQDIMTSVSGRIPPNVEKSIKKEMAQYASNITSVLCQFPSQQIANILDSHA
          (SEQ ID NO: 54)|ACACA_HUMAN   RDPSLPLLELQDIMTSVSGRIPPNVEKSIKKEMAQYASNITSVLCQFPSQQIANILDSHA
      (SEQ ID NO: 55)|A0A0H3VB41_LIPST  KDDALPYSEWNAQFSALHRSKIPQKLDATLSSLIERSKSKD----AEFPAKLLPAIERFA
          (SEQ ID NO: 56)|F2QLC7_KOMPC   RNPELPYSEWMRSISALHSRLPIHLDEQLTSLIERSHQRG----ADFPAKRLLKLLDKEQ
          (SEQ ID NO: 57)|Q6CC91_YARLI   RNPELPYLQWAKQVSSLHTRMSAKLDATLAGLIDKAKQRGG----EFPAKQLLRALEKEA
```

FIG. 11 (continued)

```
      (SEQ ID NO: 50)ACACA_RAT          ATLNRKSEREVFFMNTQSIVQLVQRYRSGIRGHMKAVVMDLLRQYLRVETQF--QNGHYD
      (SEQ ID NO: 51)|ACACA_MOUSE        ATLNRKSEREVFFMNTQSIVQLVQRYRSGIRGHMKAVVMDLLRQYLRVETQF--QNGHYD
      (SEQ ID NO: 52)|ACAC_YEAST         VKNSEYNPDKLLGAVVEPLADIAHKYSNGLEAHEKSIFVHFPLESYYEVEKLFNGPHVREE
      (SEQ ID NO: 53)|ACACA_HUMAN        ATLNRKSEREVFFMNTQSIVQLVQRYRSGIRGHMKAVVMDLLRQYLRVETQF--QNGHYD
      (SEQ ID NO: 54)|ACACA_HUMAN        ATLNRKSEREVFFMNTQSIVQLVQRYRSGIRGHMKAVVMDLLRQYLRVETQF--QNGHYD
(SEQ ID NO: 55)|A0A0H3VB41_LIPST         EEFIQPQDLFVFKQQVEPLVTIATRYQAGLKAHEYGVIAELLEQYLAVEKLFSGAHIRDE
      (SEQ ID NO: 56)|F2QLC7_KOMPC       AV-----NPDPLFSQVIAPLTAVAKSYEHGLEVHEHNVFADLITQYYDIESLF---ADKREE
      (SEQ ID NO: 57)|Q6CC91_YARLI       SS---GEVDALFQQTLAPLFDLAREYQDGLAIHELQVAAGLLQAYYDSEARFCGPHVRDE (SEQ ID NO: 50)ACACA_RAT          KCVFALREENKSDMNTVLNYIFSHAQVTKKNLLVTMLIDQL--C---GRDPT-----LTD
      (SEQ ID NO: 51)|ACACA_MOUSE        KCVFALREENKSDMNTVLNYIFSHAQVTKKNLLVTMLIDQL--C---GRDPT-----LTD
      (SEQ ID NO: 52)|ACAC_YEAST         NIILKLRDENPKDLDKVALTVLSHSKVSAKNNLILAILKHY--QPLCKLSSK-----VSA
      (SEQ ID NO: 53)|ACACA_HUMAN        KCVFALREENKSDMNTVLNYIFSHAQVTKKNLLVTMLIDQL--C---GRDPT-----LTD
      (SEQ ID NO: 54)|ACACA_HUMAN        KCVFALREENKSDMNTVLNYIFSHAQVTKKNLLVTMLIDQL--C---GRDPT-----LTD
(SEQ ID NO: 55)|A0A0H3VB41_LIPST         DVFLRLRDENKDDIFKVVMTVFSKGRVGAKNNLILAILAAL---RSDRSEVSE-----VAK
      (SEQ ID NO: 56)|F2QLC7_KOMPC       DVILQLRDENKSSLDKVIDVVLSHSRVGAKNNHLIRAILEIY--QTICQNDLQ-----AAT
      (SEQ ID NO: 57)|Q6CC91_YARLI       DVILKLREENRDSLRKVVMAQLSHSRVGAKNNLVLALLDEYKVADQAGTDSPASNVHVAK (SEQ ID NO: 50)ACACA_RAT          ELLNILTELTQLSKTTNAKVALRARQVLIASHLPSYDVRHNQVESIFLSAI--DMYGRQF
      (SEQ ID NO: 51)|ACACA_MOUSE        ELLNILTELTQLSKTTNAKVALRARQVLIASHLPSYELRHNQVESIFLSAI--DMYGRQF
      (SEQ ID NO: 52)|ACAC_YEAST         IFSTPLQHIVELESKATAKVALQAREILIQGALPSVKERTEQIEHILKSSVVKVAYGSS-
      (SEQ ID NO: 53)|ACACA_HUMAN        ELLNILTELTQLSKTTNAKVALRARQVLIASHLPSYELRHNQVESIFLSAI--DMYGRQF
      (SEQ ID NO: 54)|ACACA_HUMAN        ELLNILTELTQLSKTTNAKVALRARQVLIASHLPSYELRHNQVESIFLSAI--DMYGRQF
(SEQ ID NO: 55)|A0A0H3VB41_LIPST         YLRPALKTLTELDSGVTAPVALKARELLIQCALPSLEEFTAQLEHILRSSVVESRYGEV-
      (SEQ ID NO: 56)|F2QLC7_KOMPC       ILKKFLKKIVELDSRFTAKVSLKAREILIQCSLPSIKERSDQLEHILRSSVVQTQYGESF
      (SEQ ID NO: 57)|Q6CC91_YARLI       YLRPVLRKIVELESPASAKVSLKAREILIQCALPSLKERTDQLEHILRSSVVESRYGEV- (SEQ ID NO: 50)ACACA_RAT          CIEN-------LQKLILSETSIFDVLPNFFYHSNQVVRMAALEVYVRRAYIAYELNSVQH
      (SEQ ID NO: 51)|ACACA_MOUSE        CIEN-------LQKLILSETSIFDVLPNFFYHSNQVVRMAALEVYVRRAYIAYELNSVQH
      (SEQ ID NO: 52)|ACAC_YEAST         NPKRSEPDLNILKDLIDSNYVVFDVLLQFLTHQDPVVTAAAQVYIRRAYRAYTIGDIRV
      (SEQ ID NO: 53)|ACACA_HUMAN        CIEN-------LQKLILSETSIFDVLPNFFYHSNQVVRMAALEVYVRRAYIAYELNSVQH
      (SEQ ID NO: 54)|ACACA_HUMAN        CIEN-------LQKLILSETSIFDVLPNFFYHSNQVVRMAALEVYVRRAYIAYELNSVQH
(SEQ ID NO: 55)|A0A0H3VB41_LIPST         GFERSAPRIDVLKEVIDSQYIVFDVLPKFFAHSDRYVTLAALELYVRRAYRAYNVMSMEY
      (SEQ ID NO: 56)|F2QLC7_KOMPC       NGNYKLPNLDVIQDVIDSKYIVFDVLTQFVVSPNKYIFAAAAEVYLRRAYRAYSVREVKH
      (SEQ ID NO: 57)|Q6CC91_YARLI       GLEHRTPRADYLKEVVDSKYIVFDVLAQFFAHDDPWIVLAALELYIRRACKAYSILDINY (SEQ ID NO: 50)ACACA_RAT          RQLKDNTC-VVEFQFMLPTSHFNRGNIPTLNRMSFASNLNHYGMTHVASVSDV-LLDNAF
      (SEQ ID NO: 51)|ACACA_MOUSE        RQLKDNTC-VVEFQFMLPTSHFNRGNIPTLNRMSFASNLNHYGMTHVASVSDV-LLDNAF
      (SEQ ID NO: 52)|ACAC_YEAST         HE--GVTVPIVEWKFQLPSAAFS----------TFPTVKSKMGMNPAVSVSDLSYVANSQ
      (SEQ ID NO: 53)|ACACA_HUMAN        RQLKDNTC-VVEFQFMLPTSHFNRGNIPTLNRMSFSSNLNHYGMTHVASVSDV-LLDNSF
      (SEQ ID NO: 54)|ACACA_HUMAN        RQLKDNTC-VVEFQFMLPTSHFNRGNIPTLNRMSFSSNLNHYGMTHVASVSDV-LLDNSF
(SEQ ID NO: 55)|A0A0H3VB41_LIPST         HNEGDLV-PVVTFKFLLAAIGNPAYNIVG---QGAPSGDSRIDFQRAASVSDLTFMMSKS
      (SEQ ID NO: 56)|F2QLC7_KOMPC       HFVGDSALPIVEWKFQLPLLSTAAYNSVPEAMRNSSSNRSSISMDRAVSVSDLTFMINKN
      (SEQ ID NO: 57)|Q6CC91_YARLI       HQDSDLP-PVISWEFRLPTMSSALYNSVV---SSGSKTPTSPSVSRADSVSDFSYTVERD (SEQ ID NO: 50)ACACA_RAT          TPPCQRMGGMVSFRTFEDFVRIFDEVMGCFCDSPPQ-SPTFPESGHT---SLYDEDKVPR
      (SEQ ID NO: 51)|ACACA_MOUSE        TPPCQRMGGMVSFRTFEDFVRIFDEIMGCFCDSPPQ-SPTFPESGHT---SLYDEDKVPR
      (SEQ ID NO: 52)|ACAC_YEAST         SSP-LREGILMAVDHLDDVDEILSQSLEVIPRHQ--------SSSNG---PAPDRSGSSA
      (SEQ ID NO: 53)|ACACA_HUMAN        TPPCQRMGGMVSFRTFEDFVRIFDEVMGCFCDSPPQ-SPTFPEAGHT---SLYDEDKVPR
      (SEQ ID NO: 54)|ACACA_HUMAN        TPPCQRMGGMVSFRTFEDFVRIFDEVMGCFCDSPPQ-SPTFPEAGHT---SLYDEDKVPR
(SEQ ID NO: 55)|A0A0H3VB41_LIPST         DSESLRSGVIVFVADIADIDEVLPRADLYLPQRAGAGSGGFSFSAKS---DL-DSKRRPA
      (SEQ ID NO: 56)|F2QLC7_KOMPC       DSQFLRTGIIIPTNHLDDIEESLSSAIDVFPKRP---------RNNG---PAPDRTNVAP
      (SEQ ID NO: 57)|Q6CC91_YARLI       SAPA-RTGAIVAVPHLDDLEDALTRVLENLPKRGAGLAISVGASNKSAAASARDAAAAAA (SEQ ID NO: 50)ACACA_RAT          DE----PIHILNVAI-KTDGDIEDDRLAAMFREFTQQNKATLVEHGIRRPLTFLVAQKDFR
      (SEQ ID NO: 51)|ACACA_MOUSE        DE----PIHILNVAI-KTDGDIEDDRLAAMFREFTQQNKATLVEHGIRRPLTFLVAQKDFR
      (SEQ ID NO: 52)|ACAC_YEAST         S-----LSNVANVCVASTEGFESEEEILVRELREILDLNKQELINASIRKRITFMFGFKD--
      (SEQ ID NO: 53)|ACACA_HUMAN        DE----PIHILNVAI-KTDCDIEDDRLAAMFREFTQQNKATLVDHGIRRPLTFLVAQKDFR
      (SEQ ID NO: 54)|ACACA_HUMAN        DE----PIHILNVAI-KTDCDIEDDRLAAMFREFTQQNKATLVDHGIRRPLTFLVAQKDFR
(SEQ ID NO: 55)|A0A0H3VB41_LIPST         PPKPESLSNICNVLIRKT-AKTDDAALVSDIKFIVDEYKEEFLLRSIRRVTFVCGRED--
      (SEQ ID NO: 56)|F2QLC7_KOMPC       EQ----PTNVCNVFIANVSGYNSEAEIVDKISSVLSELKDDLRASGVRRVTFVLGDKV--
      (SEQ ID NO: 57)|Q6CC91_YARLI       SSVDTGLSNICNVMIGRVDESDDDDTLIARISQVIEDFKEDPEACSLRRITFSFGNSR--

(SEQ ID NO: 50)ACACA_RAT          KQVNCEVDQRFHREFPKFFTFRARDKFEEDRIYRHLEPALAFQLELNRMRNFDLTAIPCA
      (SEQ ID NO: 51)|ACACA_MOUSE        KQVNCEVDQRFHREFPKFFTFRARDKFEEDRIYRHLEPALAFQLELNRMRNFDLTAIPCA
      (SEQ ID NO: 52)|ACAC_YEAST         -------------GSYPKYYTFNGPN-YNENETIRHIEPALAFQLELGRLSNFNIKPFSTD
      (SEQ ID NO: 53)|ACACA_HUMAN        KQVNYEVDRRFHREFPKFFTFRARDKFEEDRIYRHLEPALAFQLELNRMRNFDLTAIPCA
      (SEQ ID NO: 54)|ACACA_HUMAN        KQVNYEVDRRFHREFPKFFTFRARDKFEEDRIYRHLEPALAFQLELNRMRNFDLTAIPCA
(SEQ ID NO: 55)|A0A0H3VB41_LIPST         -------------GSYPGYFTFRGPD-YVEDESIRHIEPALAYQLELGRLSNFNYKPIFTD
      (SEQ ID NO: 56)|F2QLC7_KOMPC       -------------GTYPKYYTFKFPD-YFEDETIRHIEPALAFQLELRRLSNFNIKPVPTE
      (SEQ ID NO: 57)|Q6CC91_YARLI       -------------GTYPKYFTFRGPA-YEEDPTIRHIEPALAFQLELARLSNFDIKPVHTD
```

FIG. 11 (continued)

```
        (SEQ ID NO: 50)ACACA_RAT        NHKMHLYLGAAKVEVGTEVTDYRFFVRAIIRHSDLVTKEASFEYLQNEGERLLLEAMDEL
        (SEQ ID NO: 51)|ACACA_MOUSE     NHKMHLYLGAAKVEVGTEVTDYRFFVRAIIRHSDLVTKEASFEYLQNEGERLLLEAMDEL
        (SEQ ID NO: 52)|ACAC_YEAST      NRNIHVYEAVSK-----TSPLDKRFFTRGIIRTGHIRDDISIQEYLTSEANRLMSDILDNL
        (SEQ ID NO: 53)|ACACA_HUMAN     NHKMHLYLGAAKVEVGTEVTDYRFFVRAIIRHSDLVTKEASFEYLQNEGERLLLEAMDEL
        (SEQ ID NO: 54)|ACACA_HUMAN     NHKMHLYLGAAKVEVGTEVTDYRFFVRAIIRHSDLVTKEASFEYLQNEGERLLLEAMDEL
        (SEQ ID NO: 55)|A0A0H3VB41_LIPST NRNIHVYQAIGK-----DVPSDKRFFVRGIVRPGRLRDEIPTSEYLISETDRLMSDILDAL
        (SEQ ID NO: 56)|F2QLC7_KOMPC    NRNIHVYEAVAK----NTSCIDKRFFTRGIRTSRIREDVTISEYLISEANRLMSDILDAL
        (SEQ ID NO: 57)|Q6CC91_YARLI    NRNIHVYEATGK-----NAASDKRFFTRGIVRPGRLRENIPTSEYLISEADRLMSDILDAL (SEQ ID NO: 50)ACACA_RAT        EVAFNNTNVRTDCNHIFLNFVPTVIMDPSKIEESVRSMVMRYGSRLWKLRVLQAELKINI
        (SEQ ID NO: 51)|ACACA_MOUSE     EVAFNNTNVRTDCNHIFLNFVPTVIMDPSKIEESVRSMVMRYGSRLWKLRVLQAELKINI
        (SEQ ID NO: 52)|ACAC_YEAST      EV-TDTSN--SDLNHIFINFIAVFDISPEDVEAAFGGFLERFGKRLLRLFVSSAEIRIII
        (SEQ ID NO: 53)|ACACA_HUMAN     EVAFNNTNVRTDCNHIFLNFVPTVIMDPSKIEESVRSMVMRYGSRLWKLRVLQAELKINI
        (SEQ ID NO: 54)|ACACA_HUMAN     EVAFNNTNVRTDCNHIFLNFVPTVIMDPSKIEESVRSMVMRYGSRLWKLRVLQAELKINI
        (SEQ ID NO: 55)|A0A0H3VB41_LIPST EV-IGPNN---TDMNRIFINFSPIFHLVPEEVEAAFGGFLERFGRRLWRLRVTGAEIRIMC
        (SEQ ID NO: 56)|F2QLC7_KOMPC    EI-IDTSN---TDLNRIFINFSAVFNVTPDDVEAAFGGFLERFGRRLWRLRVSSAEIRIMC
        (SEQ ID NO: 57)|Q6CC91_YARLI    EV-IGTTN--SDLNHIFINFSAVFALKPEEVEAAFGGFLERFGRRLWRLRVTGAEIRMMV (SEQ ID NO: 50)ACACA_RAT        RLTTTGKAIPIRLFLTNESGYYLDISLYKEVTDSRTAQIMFQAYGDKQGPLHGMLINTPY
        (SEQ ID NO: 51)|ACACA_MOUSE     RLTTTGKAIPIRLFLTNESGYYLDISLYKEVTDSRTAQIMFQAYGDKQGPLHGMLINTPY
        (SEQ ID NO: 52)|ACAC_YEAST      KDPQTGAPVPLRALINNVSGYVIKTEMYTEVNKAK-GEWVFKSLGK-PGSMHLRPIATPY
        (SEQ ID NO: 53)|ACACA_HUMAN     RLTPTGKAIPIRLFLTNESGYYLDISLYKEVTDSRTAQIMFQAYGDKQGPLHGMLINTPY
        (SEQ ID NO: 54)|ACACA_HUMAN     RLTPTGKAIPIRLFLTNESGYYLDISLYKEVTDSRTAQIMFQAYGDKQGPLHGMLINTPY
        (SEQ ID NO: 55)|A0A0H3VB41_LIPST TDPETNVPYPLRAIITNVSGYVVQSELYTEVNDK-GQWVFKSLGK-PGNMHLRSITTPY
        (SEQ ID NO: 56)|F2QLC7_KOMPC    TDPETGIPFPLRALIHNVSGYVVKSEMYQEVKNDR-GEWVPKSLGPTPGSMHLRPISTPY
        (SEQ ID NO: 57)|Q6CC91_YARLI    SDPETGSAFPLRAMINNVSGYVVQSELYAEAKNDK-GQWIFKSLGK-PGSMHMRSINTPY (SEQ ID NO: 50)ACACA_RAT        VTKDLLQSKRFQAQSLGTTYIYDIPEMFRQSLIKLWESMSTQAFLPSPPLPSD-ILTYTEL
        (SEQ ID NO: 51)|ACACA_MOUSE     VTKDLLQSKRFQAQSLGTTYIYDIPEMFRQSLIKLWESMSTQAFLPSPPLPSD-ILTYTEL
        (SEQ ID NO: 52)|ACAC_YEAST      PVKEWLQPKRYKAHLMGTTYVYDFPELFRQASSSQWKNFSADV------KLTDDFFISNEL
        (SEQ ID NO: 53)|ACACA_HUMAN     VTKDLLQSKRFQAQSLGTTYIYDIPEMFRQSLIKLWESMSTQAFLPSPPLPSDMLTYTEL
        (SEQ ID NO: 54)|ACACA_HUMAN     VTKDLLQSKRFQAQSLGTTYIYDIPEMFRQSLIKLWESMSTQAFLPSPPLPSDMLTYTEL
        (SEQ ID NO: 55)|A0A0H3VB41_LIPST ATKEWLQPKRYKAHLMGTTFVYDFPELFNQAIRASWRAAQQQS--------PENVLTYKEL
        (SEQ ID NO: 56)|F2QLC7_KOMPC    PTKEWLQPERYKAHLMGTTYVYDFPELFRQATLSQWKKYSPTA-----RVPSDVFVANEL
        (SEQ ID NO: 57)|Q6CC91_YARLI    PTKEWLQPERYKAHLMGTTYCYDFPELFRQSIESDWKKYDGKA--------PDDLMTCNEL (SEQ ID NO: 50)ACACA_RAT        VLD-DQGQLVHMNRLPGGNEIGMVAWKMSLKSPEYPDGRDVIVIGNDITYRIGSFGPQED
        (SEQ ID NO: 51)|ACACA_MOUSE     VLD-DQGQLVHMNRLPGGNEIGMVAWKMSLKSPEYPDGRDIIVIGNDITYRIGSFGPQED
        (SEQ ID NO: 52)|ACAC_YEAST      IED-ENGELTEVERSPGANAIGMVAFKITVKTPEYPRGRQFVVVANDITFKIGSFGPQED
        (SEQ ID NO: 53)|ACACA_HUMAN     VLD-DQGQLVHMNRLPGGNEIGMVAWKMTFKSPEYPEGRDIIVIGNDITYRIGSFGPQED
        (SEQ ID NO: 54)|ACACA_HUMAN     VLD-DQGQLVHMNRLPGGNEIGMVAWKMTFKSPEYPEGRDIIVIGNDITYRIGSFGPQED
        (SEQ ID NO: 55)|A0A0H3VB41_LIPST IMD-DSGELSEVSREPGANTCGMVAWLFTALTPEYPTGRQFIVVANDITYKIGSFGPQED
        (SEQ ID NO: 56)|F2QLC7_KOMPC    IVD-DSGELTEVSREPGANWVGMVAFKVTAKTPEYPRGRHFIIIANDITFKIGSFGPQED
        (SEQ ID NO: 57)|Q6CC91_YARLI    ILDEDSGELQEVNRSPGANHVGMVAWKFEAKTPEYPRGRSFIVVANDITFQIGSFGPAED (SEQ ID NO: 50)ACACA_RAT        LLFLRASELARAEGIPRIYVAANSGARIGLAEEIRHMFHVAWVDSEDPYKGYKYLYLTPQ
        (SEQ ID NO: 51)|ACACA_MOUSE     LLFLRASELARAEGIPRIYVAANSGARIGLAEEIRHMFHVAWVDPEDPYKGYKYLYLTPQ
        (SEQ ID NO: 52)|ACAC_YEAST      EFFNKVTEYARKRGIPRIYLAANSGARIGMAEEIVPLFQVAWNDAANPDKGFQYLYLTSE
        (SEQ ID NO: 53)|ACACA_HUMAN     LLFLRASELARAEGIPRIYVSANSGARIGLAEEIRHMFHVAWVDPEDPYKGYRYLYLTPQ
        (SEQ ID NO: 54)|ACACA_HUMAN     LLFLRASELARAEGIPRIYVSANSGARIGLAEEIRHMFHVAWVDPEDPYKGYRYLYLTPQ
        (SEQ ID NO: 55)|A0A0H3VB41_LIPST KYFRTVTQLAVKLGIPRIYLSANSGARIGVADEFVSLFSVAWNDSSNPEKGFKYLYLTPA
        (SEQ ID NO: 56)|F2QLC7_KOMPC    EYFNKATQLARKLGIPRIYLSANSGARIGVAEELLPLFKVAWKSEGKPSKGFEYLYLTSE
        (SEQ ID NO: 57)|Q6CC91_YARLI    QFFFKVTELARKLGIPRIYLSANSGARIGIADELVGKYKVAWNDETDPSKGFKYLYPTPE (SEQ ID NO: 50)ACACA_RAT        DYKRVS---ALNSVHCEHVEDEGESPYKITDIIGKEEGLGAENLRGSGMIAGESSLAYDE
        (SEQ ID NO: 51)|ACACA_MOUSE     DYKRVS---ALNSVHCEHVEDEGESPYKITDIIGKEEGLGAENLRGSGMIAGESSLAYDE
        (SEQ ID NO: 52)|ACAC_YEAST      GMETLKKFDKENSVLTERTVINGEERFVIKTIIGSEDGLGVECLRGSGLIAGATSRAYHD
        (SEQ ID NO: 53)|ACACA_HUMAN     DYKRVS---ALNSVHCEHVEDEGESPYKITDIIGKEEGIGPENLRGSGMIAGESSLAYNE
        (SEQ ID NO: 54)|ACACA_HUMAN     DYKRVS---ALNSVHCEHVEDEGESPYKITDIIGKEEGIGPENLRGSGMIAGESSLAYNE
        (SEQ ID NO: 55)|A0A0H3VB41_LIPST IYNGLSD--AAKKTVLTERIVEEGEERPYVITTIIGAEDGLGVECLRGSGLIAGATSKAYKD
        (SEQ ID NO: 56)|F2QLC7_KOMPC    DLTLLEKSGKSNSVPTQRIVEEGEERHVITAIIGASDGLGVECLRGSGLIAGATSRAYKD
        (SEQ ID NO: 57)|Q6CC91_YARLI    SLATLRPDTVVTTEIEEEGPNGVEKRHVIDYIVGERDGLGVECLRGSGLIAGATSRAYKD (SEQ ID NO: 50)ACACA_RAT        IITISLVTCRAIGIGAYLVRLGQRTIQVENSHLILTGAGALNKVLGREVYTSNNQLGGIQ
        (SEQ ID NO: 51)|ACACA_MOUSE     VITISLVTCRAIGIGAYLVRLGQRTIQVENSHLILTGAGALNKVLGREVYTSNNQLGGIQ
        (SEQ ID NO: 52)|ACAC_YEAST      IFTITLVTCRSVGIGAYLVRLGQRAIQVEGQPIILTGAPAINKMLGREVYTSNLQLGGTQ
        (SEQ ID NO: 53)|ACACA_HUMAN     IITISLVTCRAIGIGAYLVRLGQRTIQVENSHLILTGAGALNKVLGREVYTSNNQLGGIQ
        (SEQ ID NO: 54)|ACACA_HUMAN     IITISLVTCRAIGIGAYLVRLGQRTIQVENSHLILTGAGALNKVLGREVYTSNNQLGGIQ
        (SEQ ID NO: 55)|A0A0H3VB41_LIPST IFTITLVTCRSVGIGAYLVRLGQRAIQIEGQPIILTGAPAINKLLGREVYSSNLQLGGTQ
        (SEQ ID NO: 56)|F2QLC7_KOMPC    IFTITLVTCRSVGIGAYLVRLGQRAIQIEGQPIILTGAPAINKLLGREVYSSNLQLGGTQ
        (SEQ ID NO: 57)|Q6CC91_YARLI    IFTLTLVTCRSVGIGAYLVRLGQRAIQIEGQPIILTGAPAINKLLGREVYSSNLQLGGTQ
```

FIG. 11 (continued)

```
      (SEQ ID NO: 50)ACACA_RAT         IMHNNGVTHCTVCDDFEGVFTVLHWLSYMPKNVHSSVPLLNS-KDPIDRIIEFVPTK-AP
      (SEQ ID NO: 51)|ACACA_MOUSE      IMHNNGVTHSTVCDDFEGVFTVLHWLSYMPKSVHSSVPLLNS-KDPIDRIIEFVPTK-AP
      (SEQ ID NO: 52)|ACAC_YEAST       IMYNNGVSHLTAVDDLAGVEKIVEWMSYVPAKRNMFVPILET-KDTWDRPVDFTPTNDET
      (SEQ ID NO: 53)|ACACA_HUMAN      IMHNNGVTHCTVCDDFEGVFTVLHWLSYMPKSVHSSVPLLNS-KDPIDRIIEFVPTK-TP
      (SEQ ID NO: 54)|ACACA_HUMAN      IMHNNGVTHCTVCDDFEGVFTVLHWLSYMPKSVHSSVPLLNS-KDPIDRIIEFVPTK-TP
  (SEQ ID NO: 55)|A0A0H3VB41_LIPST     IMYKNGVSHLTANDDLAGVMKIIEWMSYVPYKKGGQLPIYPS-SDTWDRDVTYTPPKQVE
      (SEQ ID NO: 56)|F2QLC7_KOMPC     IMYKNGVSHLTANDDLAGVEKIMDWLAYVPAKRNMFVPILESLHD-KWDRDVDYKPTRNEE
      (SEQ ID NO: 57)|Q6CC91_YARLI     IMYNNGVSHLTARDDLNGVRKIMQWLSYIPASRGLEVPVLPHKTD-VWDRDVTFQPVRGEQ (SEQ ID NO: 50)ACACA_RAT         YDPRWMLAGEPHPTQKGQWLSGFFDYGSFSEIMQPWAQTVVGRARLGGIPVGVVAVETR
      (SEQ ID NO: 51)|ACACA_MOUSE      YDPRWMLAGEPHPTQKGQWLSGFFDYGSFSEIMQPWAQTVVGRARLGGIPVGVVAVETR
      (SEQ ID NO: 52)|ACAC_YEAST       YDVRWMIEGRE--TESG-FEYGLFDKGSFFEETLSGWAKGVVVGRARLGGIPLGVIGVETR
      (SEQ ID NO: 53)|ACACA_HUMAN      YDPRWMLAGEPHPTQKGQWLSGFFDYGSFSEIMQPWAQTVVGRARLGGIPVGVVAVETR
      (SEQ ID NO: 54)|ACACA_HUMAN      YDPRWMLAGEPHPTQKGQWLSGFFDYGSFSEIMQPWAQTVVGRARLGGIPVGVVAVETR
  (SEQ ID NO: 55)|A0A0H3VB41_LIPST     YDVRWLIAGRE--DEEGGFEYGLFDKDSFQETLSGWARTVVGRARLGGIPVGVIGVEVR
      (SEQ ID NO: 56)|F2QLC7_KOMPC     YDVRWMISGRE--TPDGEFESGLFDSGSFTETLSGWAKGVVVGRARLGGIPMGVIGVETR
      (SEQ ID NO: 57)|Q6CC91_YARLI     YDVRWLISGRT-LEDGAFESGLFDKDSFQETLSGWAKGVVVGRARLGGIPFGVIGVETA (SEQ ID NO: 50)ACACA_RAT         TVELSVPADPANLDSEAKIIQQAGQVWFPDSAFKTYQAIKDFNR-EGLPLMVFANWRGFS
      (SEQ ID NO: 51)|ACACA_MOUSE      TVELSIPADPANLDSEAKIIQQAGQVWFPDSAFKTYQAIKDFNR-EGLPLMVFANWRGFS
      (SEQ ID NO: 52)|ACAC_YEAST       TVENLIPADPANFNSAETLIQEPGQVWHPNSAFKTAQAINDFNNGEQLPMMILANWRGFS
      (SEQ ID NO: 53)|ACACA_HUMAN      TVELSIPADPANLDSEAKIIQQAGQVWFPDSAFKTYQAIKDFNR-EGLPLMVFANWRGFS
      (SEQ ID NO: 54)|ACACA_HUMAN      TVELSIPADPANLDSEAKIIQQAGQVWFPDSAFKTYQAIKDFNR-EGLPLMVFANWRGFS
  (SEQ ID NO: 55)|A0A0H3VB41_LIPST     SVENIFPADPANPDSTEMVVQEAGQVWYPNSAFKTAQAINDFNHGEELPLVILANWRGFS
      (SEQ ID NO: 56)|F2QLC7_KOMPC     VTENLIPADPANPDSTEMMIQEAGQVWYPNSAFKTAQAINDFNNGEQLPLMILANWRGFS
      (SEQ ID NO: 57)|Q6CC91_YARLI     TVDNTTPADPANPDSIEMSTSEAGQVWYPNSAFKTSQAINDFNHGEALPLMILANWRGFS (SEQ ID NO: 50)ACACA_RAT         GGMKDMYDQVLKFGAYIVDGLRECSQPVMVYIPPQAELRGGSWVVIDPTINPRHMEMYAD
      (SEQ ID NO: 51)|ACACA_MOUSE      GGMKDMYDQVLKFGAYIVDGLRECSQPVMVYIPPQAELRGGSWVVIDPTINPRHMEMYAD
      (SEQ ID NO: 52)|ACAC_YEAST       GGQRDMFNEVLKYGSFIVDALVDYKQPTIIYIPPTGELRGGSWVVVDPTINADQMEMYAD
      (SEQ ID NO: 53)|ACACA_HUMAN      GGMKDMYDQVLKFGAYIVDGLRECCQPVLVYIPPQAELRGGSWVVIDSSINPRHMEMYAD
      (SEQ ID NO: 54)|ACACA_HUMAN      GGMKDMYDQVLKFGAYIVDGLRECCQPVLVYIPPQAELRGGSWVVIDSSINPRHMEMYAD
  (SEQ ID NO: 55)|A0A0H3VB41_LIPST     GGQRDMYNEVLKYGSFIVDALVGYKQPIFVYIPPHAELRGGSWVVIDPTINSDQMEMYAD
      (SEQ ID NO: 56)|F2QLC7_KOMPC     GGQRDMYNEVLKYGSFIVDALVDFKQPIFTYIPPTAELRGGSWVVVDPTINEDMMEMYAD
      (SEQ ID NO: 57)|Q6CC91_YARLI     GGQRDMYNEVLKYGSFIVDALVDYKQPIMVYIPPTGELRGGSWVVVDPTINSDMMEMYAD (SEQ ID NO: 50)ACACA_RAT         RESRGSVLEPEGTVEIKFRKKDLVKTMRPVDPVYIRLAERLGTPELSPTERKELESKLKE
      (SEQ ID NO: 51)|ACACA_MOUSE      RESRGSVLEPEGTVEIKFRKKDLVKTMRPVDPVYIRLAERLGTPELSPTERKELESKLKE
      (SEQ ID NO: 52)|ACAC_YEAST       VNARAGVLEPQGMVGIKFRREKLLDTMNRLDDKYRELRSQLSNKSLAPEVHQQISKQLAD
      (SEQ ID NO: 53)|ACACA_HUMAN      RESRGSVLEPEGTVEIKFRKKDLVKTMRPVDPVYIHLAERLGTPELSTAERKELENKLKE
      (SEQ ID NO: 54)|ACACA_HUMAN      RESRGSVLEPEGTVEIKFRKKDLVKTMRPVDPVYIHLAERLGTPELSTAERKELENKLKE
  (SEQ ID NO: 55)|A0A0H3VB41_LIPST     DEARAGVLEPEGMVGIKYRRDRLLETMTPLDPVYASLKRQADKKDLAPAIAQDLKVKLSE
      (SEQ ID NO: 56)|F2QLC7_KOMPC     VESRAGVLEPEGMVGIKYRRDKLLATMEPLDAKYAELKSKVSDTSLSEKDVSEIKKQISQ
      (SEQ ID NO: 57)|Q6CC91_YARLI     VESRKGVLEPEGMVGIKYRRDKLLDTMARLDPEYSSLKKQL---EESP-DSEELKVKLSV (SEQ ID NO: 50)ACACA_RAT         PEEFLIPIYHQVAVQFADLHDTPGRMQEKGVINDILDWKTSRTFFYWRLRRLLEDLVKK
      (SEQ ID NO: 51)|ACACA_MOUSE      PEEFLIPIYHQVAVQFADLHDTPGRMQEKGVINDILDWKTSRTFFYWRLRRLLEDLVKK
      (SEQ ID NO: 52)|ACAC_YEAST       PERELLPIYGQISLQFADLHDRESPMVAKGVISKELEWTEARFFFWRLPRRLNEEYLIK
      (SEQ ID NO: 53)|ACACA_HUMAN      PEEFLIPIYHQVAVQFADLHDTPGRMQEKGVISDILDWKTSRTFFYWRLRRLLEDLVKK
      (SEQ ID NO: 54)|ACACA_HUMAN      PEEFLIPIYHQVAVQFADLHDTPGRMQEKGVISDILDWKTSRTFFYWRLRRLLEDLVKK
  (SEQ ID NO: 55)|A0A0H3VB41_LIPST     PESTLMPIYRQISLQFADLHDRAGPMKAKGTIPEVLHWREARFFFWRVPRRVGESYILR
      (SEQ ID NO: 56)|F2QLC7_KOMPC     PEKQLLPIYAQISIQFADLHDRSGPMLAKGVIFKELEWVNSPRFFFWRVPRRLNEEYLIK
      (SEQ ID NO: 57)|Q6CC91_YARLI     PEKSLMPIYQQISVQFADLHDRAGPMEAKGVIPEALVWKDAPRFFFWRIPRRLVEEYLIT (SEQ ID NO: 50)ACACA_RAT         KIHS-ANPELTDGQIQAMLRPWFVEVEGTVKAYVWDNNKDLVEWLEKQLTEEDGVRSVIE
      (SEQ ID NO: 51)|ACACA_MOUSE      KIHN-ANPELTDGQIQAMLRPWFVEVEGTVKAYVWDNNKDLVEWLEKQLTEEDGVRSVIE
      (SEQ ID NO: 52)|ACAC_YEAST       RLSHQVG-EASPLEKIARIRSWYPA-------SVDHEDDRQVATWIEEN-------YKTLD
      (SEQ ID NO: 53)|ACACA_HUMAN      KIHN-ANPELTDGQIQAMLRPWFVEVEGTVKAYVWDNNKDLAEWLEKQLTEEDGVRSVIE
      (SEQ ID NO: 54)|ACACA_HUMAN      KIHN-ANPELTDGQIQAMLRPWFVEVEGTVKAYVWDNNKDLAEWLEKQLTEEDGVRSVIE
  (SEQ ID NO: 55)|A0A0H3VB41_LIPST     DLEA-ANPKSTRLERVARLKSWYAEA-----GINESSDADVASWIEKS-------GAAIT
      (SEQ ID NO: 56)|F2QLC7_KOMPC     RITEFLSASATRLDKISRINSWLPT------SIDLEDDQKVAIWLEEN-------RKALD
      (SEQ ID NO: 57)|Q6CC91_YARLI     KINSIL-PSCTRLECLARIKSWKPA------TLDQGSDRGVAEWFDEN-------SDAVS (SEQ ID NO: 50)ACACA_RAT         ENIKYISPDYVLKQIPSLVQANPEVAMDSIVHMTQRISPTQRAEVVRILSTMDSPST
      (SEQ ID NO: 51)|ACACA_MOUSE      ENIKYISPDYVLKQIPSLVQANPEVAMDSIVHMTQRISPTQRAEVVRILSTMDSPST
      (SEQ ID NO: 52)|ACAC_YEAST       DKLKGLKLESSFAQDLAFKIRSDHDNAIDGLSEVIKMLSTDDKEKLLKTLK-------
      (SEQ ID NO: 53)|ACACA_HUMAN      ENIKCISPDYVLKQIPSLVQANPEVAMDSIIHMTQRISPTQRAEVIRILSTMDSPST
      (SEQ ID NO: 54)|ACACA_HUMAN      ENIKCISPDYVLKQIPSLVQANPEVAMDSIIHMTQRISPTQRAEVIRILSTMDSPST
  (SEQ ID NO: 55)|A0A0H3VB41_LIPST     SKVKQVREDAKIQDLLALVRADKDVALQGLVESLKALSTEERDAIFKQASN------
      (SEQ ID NO: 56)|F2QLC7_KOMPC     ANIKELRAEHVRRTLATLVRTDMDTTSKSLAELINLLPETEKESILSKIKS------
      (SEQ ID NO: 57)|Q6CC91_YARLI     ARLSELKKDASAQSFASQLRKDRQGTLQGMKQALASLSEAEPAELLKGL---------
```

MULTI-SUBSTRATE METABOLISM FOR IMPROVING BIOMASS AND LIPID PRODUCTION

CROSS REFERENCE TO RELATED APPLICATIONS

This application is a divisional of U.S. patent application Ser. No. 16/401,690, filed May 2, 2019, which issued on Jan. 11, 2022 as U.S. Pat. No. 11,220,675, and which claims priority to U.S. Provisional Patent Application No. 62/665,809, filed on May 2, 2018, each of which is incorporated by reference herein in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVI_019_03US_SeqList_ST25.txt, date recorded: Dec. 2, 2021, file size 325 kilobytes).

TECHNICAL FIELD

This application relates to recombinant microorganisms useful in the biosynthesis of biomass or one or more lipid from one or more fatty acid and one or more simple carbon co-substrate. The one or more lipid can be unsaturated C6-C24 fatty acids, fatty alcohols, aldehydes, and acetates which may be useful as final products or precursors to insect pheromones, fragrances, flavors, and polymer intermediates. The application further relates to methods to improve biomass or lipid production in a microorganism from one or more fatty acid and one or more simple carbon co-substrate. The application also relates to methods of producing one or more lipid using the recombinant microorganisms, as well as compositions comprising the recombinant microorganisms and/or optionally one or more of the product lipid.

BACKGROUND

Derivatives of microbial lipids can be harnessed as precursors of fuels, and as chemicals used in detergent formulation, fragrances, and insect control agents. By applying metabolic engineering strategies to increase lipid content in some microbes, several microbial oleochemicals have been produced at commercial scale. A pathway to produce lipids from simple carbon sources such as glucose, fructose, and glycerol is referred to as a de novo pathway.

De novo lipid biosynthetic pathways rely on several key enzymes, such as fatty acid synthase. De novo pathways yield a broad range of fatty acid moieties with differing chain lengths and unsaturation. Engineering microbial de novo pathways for the purpose of enriching certain lipid species is challenging. De novo lipid pathways also require reducing equivalents. Biosynthetic pathways, such as an insect fatty alcohol pathway to generate pheromone precursors, require NADPH and NADH. Therefore, an improvement in reducing equivalent pool is needed to achieve high level lipid production.

Furthermore, in the presence of multiple substrates, metabolic regulations prevent the full utilization of biosynthetic pathways for the formation of lipids and biomass. The present disclosure addresses these challenges with the development of microorganisms modified to improve production of valuable products such as lipids from multiple substrates while maintaining or increasing biomass of the microorganism. Products produced by these modified microorganisms can include a wide-range of unsaturated $C_6$-$C_{24}$ fatty acids, fatty alcohols, aldehydes, and acetates including insect pheromones.

SUMMARY OF THE DISCLOSURE

The present application relates to microorganisms modified to improve production of valuable products such as lipids from one or more fatty acids and one or more simple carbon co-substrates while maintaining or increasing biomass of the microorganism. The recombinant microorganisms described herein may be used for the production of at least one compound, such as an insect pheromone, a fragrance, or a flavoring agent. In some embodiments, at least one compound comprise unsaturated $C_6$-$C_{24}$ fatty acids, fatty alcohols, aldehydes, and acetates.

In one aspect, the application relates to a recombinant microorganism having improved production of biomass or improved production of one or more lipid from one or more fatty acids and one or more simple carbon co-substrates, wherein the recombinant microorganism comprises one or more modifications associated with: tricarboxylic acid cycle; lipid synthesis; reducing equivalent availability; metabolic intermediates availability; and/or increased product purity, wherein the recombinant microorganism has improved production of biomass or improved production of one or more lipids compared to a microorganism without the same modifications.

In some embodiments, the one or more modifications associated with comprising tricarboxylic acid cycle comprises the overexpression of at least one endogenous and/or exogenous nucleic acid molecule encoding an AMP-insensitive isocitrate dehydrogenase (IDH) variant in the recombinant microorganism. In certain embodiments, the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans,* or *Yarrowia lipolytica.* In further embodiments, the at least one nucleic acid molecule is from *Yarrowia lipolytica* and comprises isoleucine to alanine substitutions at amino acid positions 279 and 280 of XP_503571.2 (SEQ ID NO: 30). In some embodiments, the one or more modifications associated with tricarboxylic acid cycle results in extended activation of the tricarboxylic acid cycle.

In some embodiments, the one or more modifications associated with tricarboxylic acid cycle or one or more metabolic intermediates availability comprises the overexpression of at least one endogenous and/or exogenous nucleic acid molecule encoding a pyruvate transporter in the recombinant microorganism. In other embodiments, the one or more metabolic intermediates availability comprises mitochondrial pyruvate availability. In certain embodiments, the at least one nucleic acid molecule encodes for a protein that has at least 70% sequence identity, at least 80% sequence identity, or at least 90% sequence identity to pyruvate transporter from *Saccharomyces cerevisiae, Hanseniaspora osmophila, Yarrowia lipolytica,* or *Talaromyces marneffei* PM1. In further embodiments, the pyruvate transporter is selected from *Saccharomyces cerevisiae* mpc1, *Saccharomyces cerevisiae* mpc3 (NP_011759.1—SEQ ID NO: 31), *Hanseniaspora osmophila* mpc3 (OEJ86292.1), *Yarrowia lipolytica* mpc, and *Talaromyces marneffei* PM1 mpc3 (KFX48982.1), or homolog thereof. In yet a further embodiment, the recombinant microorganism is *Saccharo-*

*myces cerevisiae* comprising a deletion, disruption, or loss of function mutation in a gene encoding an mpc2 pyruvate transporter. In some embodiments, the recombinant microorganism is *Yarrowia lipolytica*.

In some embodiments, the one or more modifications associated with lipid synthesis comprises alleviation of acetyl-CoA carboxylase (ACC) inhibition. In certain embodiments, alleviation of ACC inhibition comprises the replacement of the endogenous ACC, or overexpression of at least one endogenous and/or exogenous nucleic acid molecule encoding a feedback-insensitive ACC variant in the recombinant microorganism. In further embodiments, the at least one nucleic acid molecule encodes for a protein that has at least 70% sequence identity, at least 80% sequence identity, or at least 90% sequence identity to ACC from *Mus musculus, Rattus norvegicus*, or *Homo sapiens*.

In some embodiments, the one or more modifications associated with reducing equivalent availability comprises the overexpression of at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica*. In further embodiments, the IDH is selected from *Escherichia coli* Idh (WP_000444484.1—SEQ ID NO: 21), *Mycobacterium smegmatis* Icd2 (WP_011727802.1—SEQ ID NO: 23), *Acidithiobacillus thiooxidans* Idh (PDB: 2D4V_A—SEQ ID NO: 22), and *Yarrowia lipolytica* Idh1 (XP_503571.2—SEQ ID NO: 20 for mutant, or SEQ ID NO: 30 for wild type), or homolog thereof.

In some embodiments, the one or more modifications associated with reducing equivalent availability further comprises the overexpression of at least one endogenous and/or exogenous nucleic acid encoding an aconitase in the cytosol of the recombinant microorganism. In certain embodiments, the at least one endogenous and/or exogenous nucleic acid molecule encoding the IDH and the at least one endogenous and/or exogenous nucleic acid molecule encoding the aconitase lack a sequence encoding a mitochondrial-targeting peptide.

In some embodiments, the one or more modifications associated with reducing equivalent availability or one or more metabolic intermediates availability comprises the overexpression of at least one endogenous or exogenous nucleic acid encoding a citrate transporter in the recombinant microorganism. In certain embodiments, the one or more intermediate comprises cytosolic citrate/isocitrate. In further embodiments, the at least one nucleic acid molecule encodes for a protein that has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

In some embodiments, the one or more modifications associated with reducing equivalent availability comprises the overexpression of at least one exogenous nucleic acid molecule encoding a decarboxylating malic enzyme in the recombinant microorganism. In certain embodiments, the at least one nucleic acid molecule encodes for a protein that has at least 70% sequence identity, at least 80% sequence identity, or at least 90% sequence identity to a decarboxylating malic enzyme from *Arabidopsis thaliana, Amaranthus hypochondriacus, Rhizobium meliloti, Solanum tuberosum, Homo sapiens*, or *Escherichia coli*. In further embodiments, the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof. In yet a further embodiment, the decarboxylating malic enzyme lacks a sequence encoding a mitochondrial-targeting peptide.

In some embodiments, the one or more modifications associated with one or more metabolic intermediates availability comprises the overexpression of at least one endogenous and/or exogenous nucleic acid encoding an ATP-citrate lyase in the recombinant microorganism. In certain embodiments, the one or more intermediates availability comprises cytosolic oxaloacetate availability. In further embodiments, the at least one nucleic acid molecule encodes for a protein that has at least 70% sequence identity, at least 80% sequence identity, or at least 90% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

In some embodiments, the one or more modifications associated with comprising reducing equivalent availability comprises one or more modifications in the pentose phosphate pathway (PPP) in the recombinant microorganism. In certain embodiments, the one or more modifications in the PPP comprises one or more of: downregulation of hexose kinase activity; upregulation of one or more oxidative PPP enzyme activity; downregulation of fructose-6-phosphate kinase activity; and/or expression of one or more oxidative PPP enzyme variant. In further embodiments, the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1). In yet a further embodiment, the downregulation of hexose kinase activity and/or fructose-6-phosphate kinase activity comprises deletion, disruption, and/or mutation of one or more endogenous gene encoding one or more hexose kinase enzyme and/or fructose-6-phosphate kinase enzyme. In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70% sequence identity, at least 80% sequence identity, or at least 90% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70% sequence identity, at least 80% sequence identity, or at least 90% sequence identity to an NAD-dependent 6-phosphogluconate dehydrogenase (GND1) from *Bradyrhizobium* or

*Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an NADPH-dependent mannitol dehydrogenase and/or an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g, or homolog thereof.

In some embodiments, the one or more modifications associated with reducing equivalent availability comprises decoupling and increasing glucose uptake in the recombinant microorganism. In certain embodiments, decoupling and increasing glucose uptake comprises: upregulation of hexose transporter activity; and/or downregulation of hexose kinase activity. In further embodiments, the upregulation of one or more hexose transporter activity comprises the overexpression of one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70% sequence identity, at least 80% sequence identity, or at least 90% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof. In some embodiments, the downregulation of hexose kinase activity comprises deletion, disruption, and/or mutation of one or more endogenous gene encoding one or more hexose kinase enzyme.

In some embodiments, the one or more modifications associated with reducing equivalent availability, one or more metabolic intermediates availability, or increased product purity comprises downregulation or inhibition of acetyl-CoA carboxylase (ACC) activity in the recombinant microorganism. In certain embodiments, the downregulation or inhibition of ACC activity comprises deletion, disruption, and/or mutation of one or more endogenous gene encoding one or more ACC enzyme.

In some embodiments of a recombinant microorganism having improved production of biomass or improved production of one or more lipid from one or more fatty acid and one or more simple carbon co-substrates, the one or more fatty acid co-substrate is a saturated fatty acid. In some embodiments of a recombinant microorganism having improved production of biomass or improved production of one or more lipid from one or more fatty acid and one or more simple carbon co-substrates, the one or more simple carbon co-substrate is selected from glucose, fructose, and glycerol.

In some embodiments of a recombinant microorganism having improved production of biomass or improved production of one or more lipid from one or more fatty acid and one or more simple carbon co-substrates, the improved production of one or more lipid comprises improved production of one or more mono- or poly-unsaturated $C_6$-$C_{24}$ fatty acid, fatty alcohol, aldehyde, or acetate. In certain embodiments, the one or more mono- or poly-unsaturated $C_6$-$C_{24}$ fatty acid, fatty alcohol, aldehyde, or acetate is an insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In some embodiments of a recombinant microorganism having improved production of biomass or improved production of one or more lipid from one or more fatty acid and one or more simple carbon co-substrates, the recombinant microorganism is a eukaryotic microorganism. In certain embodiments, the eukaryotic microorganism is a yeast. In further embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*. In yet a further embodiment, the yeast is an oleaginous yeast. In some embodiments, the oleaginous yeast is a member of a genus selected from the group consisting of *Yarrowia, Candida, Rhodotorula, Rhodosporidium, Cryptococcus, Trichosporon*, and *Lipomyces*. In certain embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis*, and *R. graminis*.

In another aspect, the present application provides methods of producing one or more lipid using a recombinant microorganism as described herein. In one embodiment, the method includes cultivating the recombinant microorganism in a culture medium containing a feedstock providing one or more simple carbon and one or more fatty acid co-substrates until the one or more lipid is produced.

In another aspect, the present application provides methods of producing a recombinant microorganism having improved production of biomass or improved production of one or more lipid from one or more fatty acid and one or more simple carbon co-substrates, comprising introducing into a microorganism one or more modifications associated with: tricarboxylic acid cycle; lipid synthesis; reducing equivalent availability; one or more metabolic intermediates availability; and/or increased product purity, wherein the introducing one or more modifications yields a recombinant microorganism having improved production of biomass or improved production of one or more lipid compared to a microorganism not comprising the same modifications.

In yet another aspect, the present application provides compositions comprising one or more of the recombinant microorganisms described herein. In certain embodiments, the composition may further comprise one or more lipid produced by the recombinant microorganism. In some embodiments, the composition may further comprise one or more mono- or poly-unsaturated $C_6$-$C_{24}$ fatty acid, fatty alcohol, aldehyde, or acetate produced by the recombinant microorganism. In some embodiments, the composition may further comprise one or more insect pheromone produced by the recombinant microorganism.

BRIEF DESCRIPTION OF DRAWINGS

Illustrative embodiments of the disclosure are illustrated in the drawings, in which:

FIG. 11 shows the alignment of feedback insensitive acetyl-CoA carboxylase (ACC) enzymes of the present disclosure.

DETAILED DESCRIPTION

Definitions

Figure 1A:
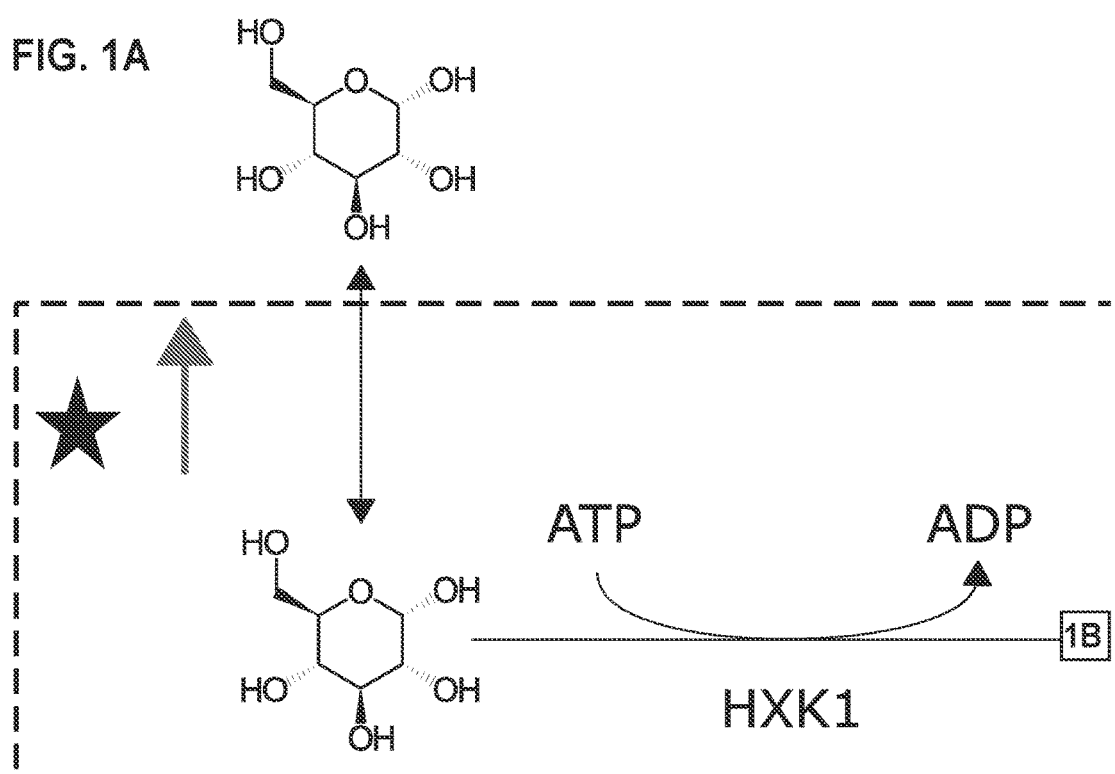
FIG. 1A, FIG. 1B, FIG. 1C, FIG. 1D, FIG. 1E, FIG. 1F, FIG. 1G, FIG. 1H, FIG. 1I, FIG. 1J, FIG. 1K, FIG. 1L, and FIG. 1M show a lipid biosynthetic pathway showing genetic modifications of the present disclosure. Enzymes with stars are identified as candidates for increasing de novo lipid synthesis or lipid synthesis from fatty acid precursors.
Figure 1B:
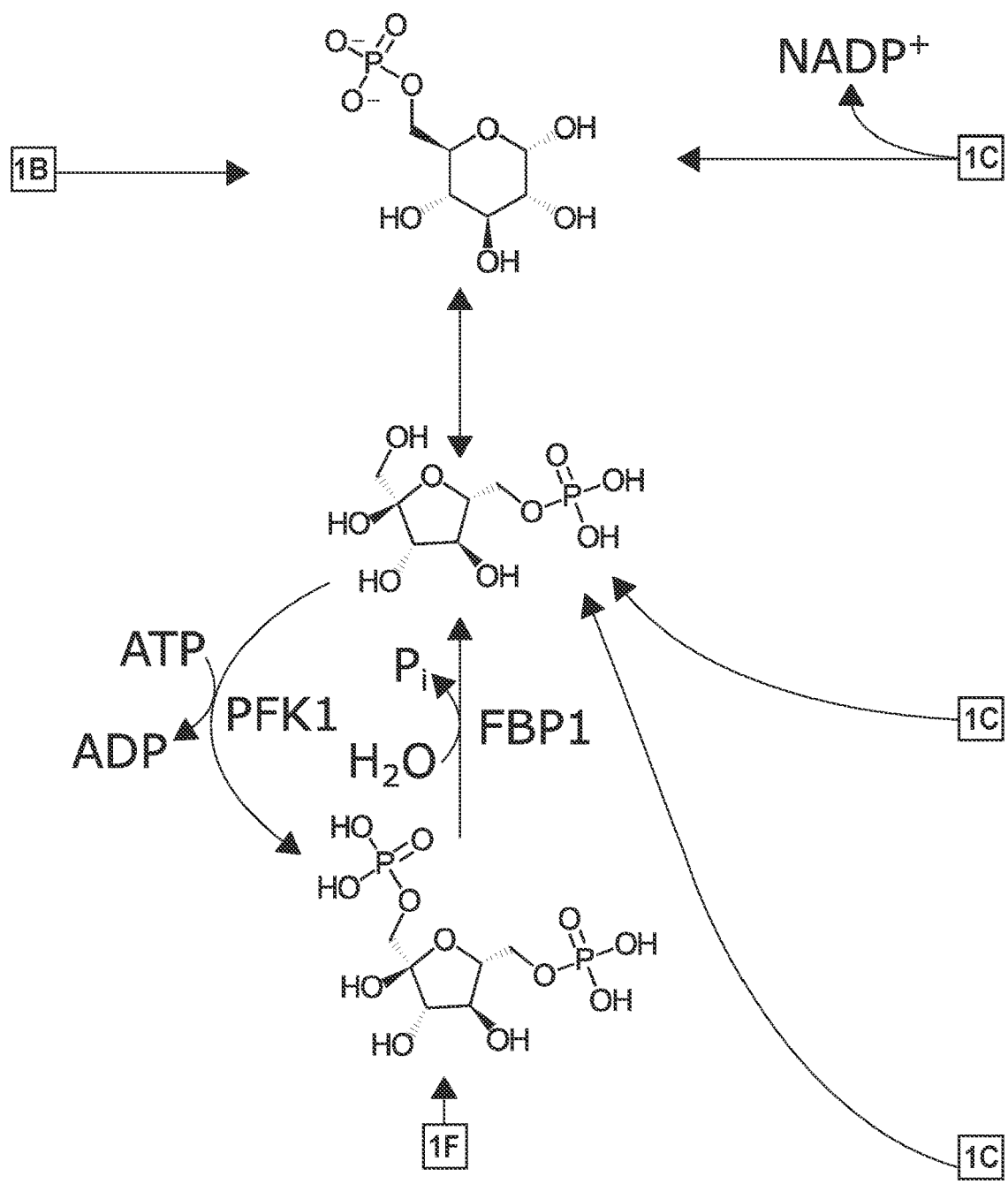
Figure 1C:
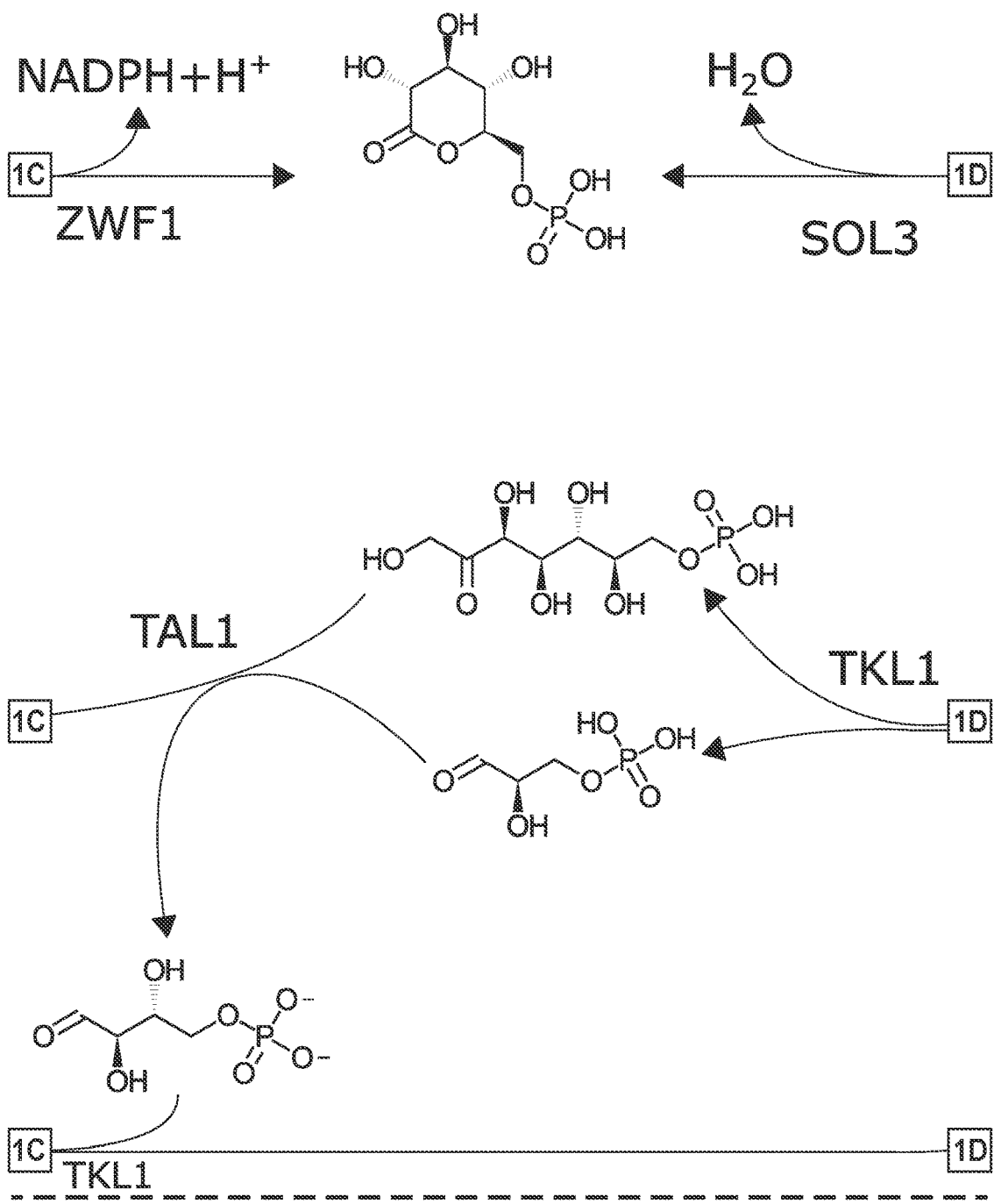
Figure 1D:
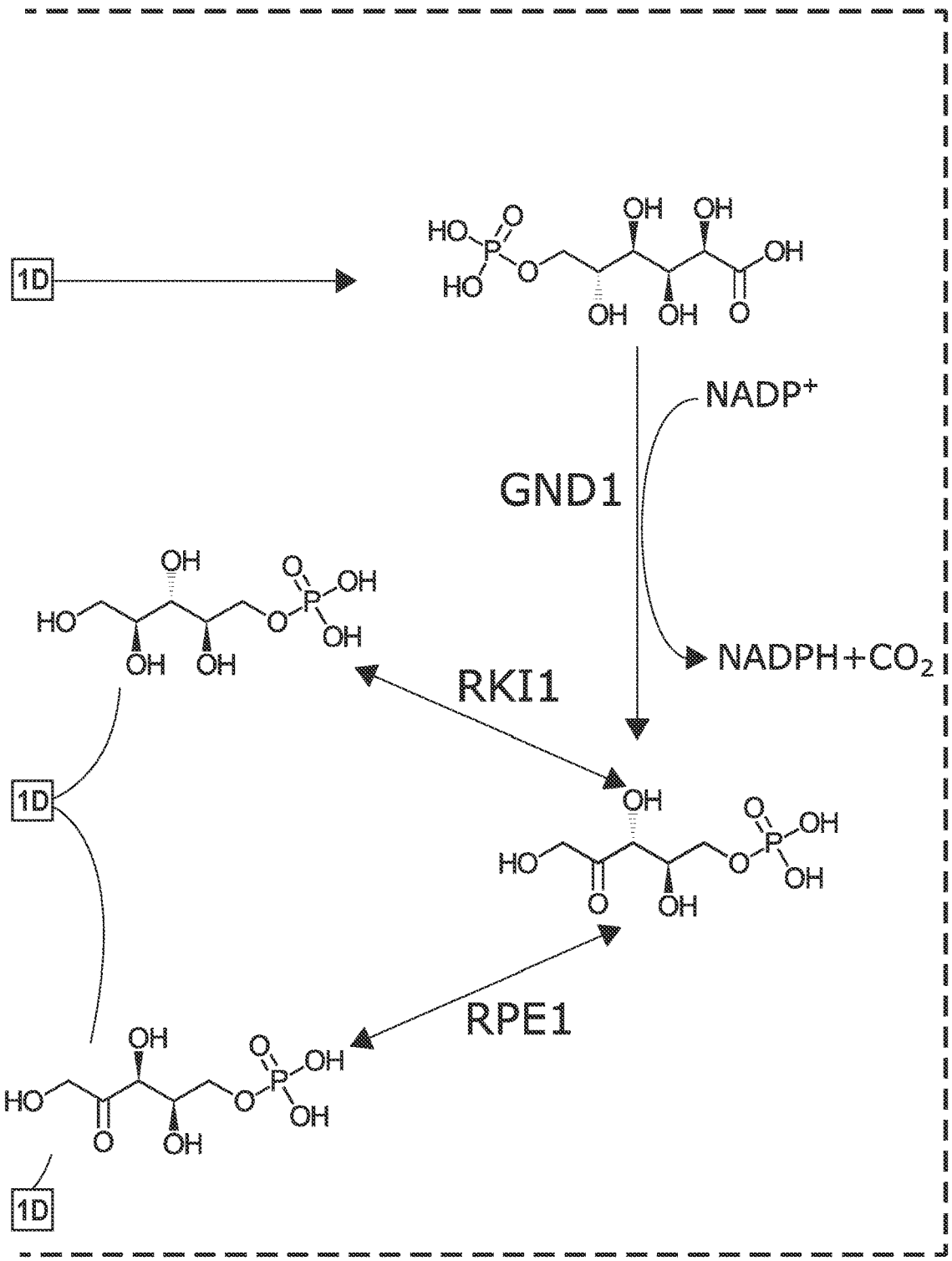
Figure 1E:
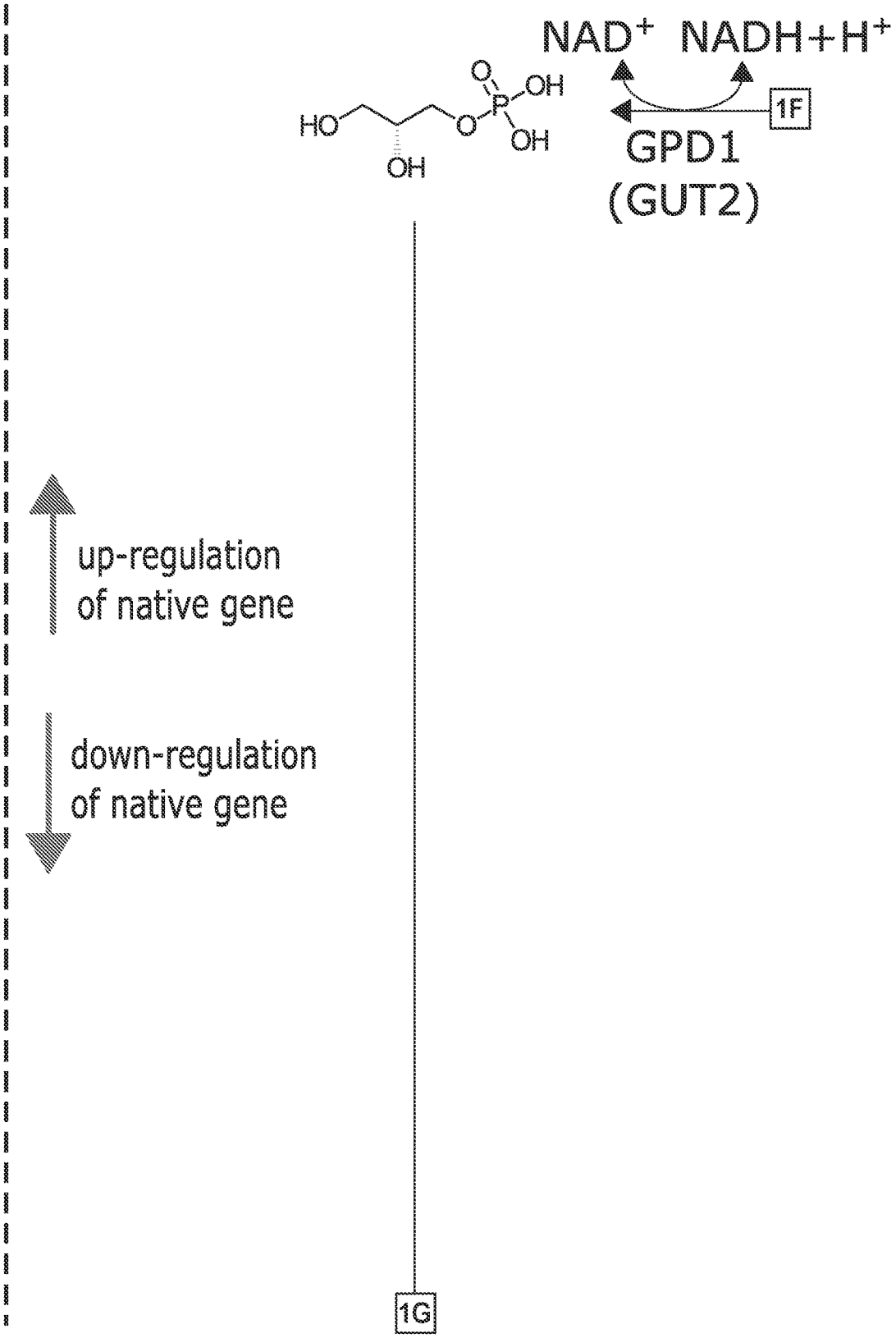
Figure 1F:
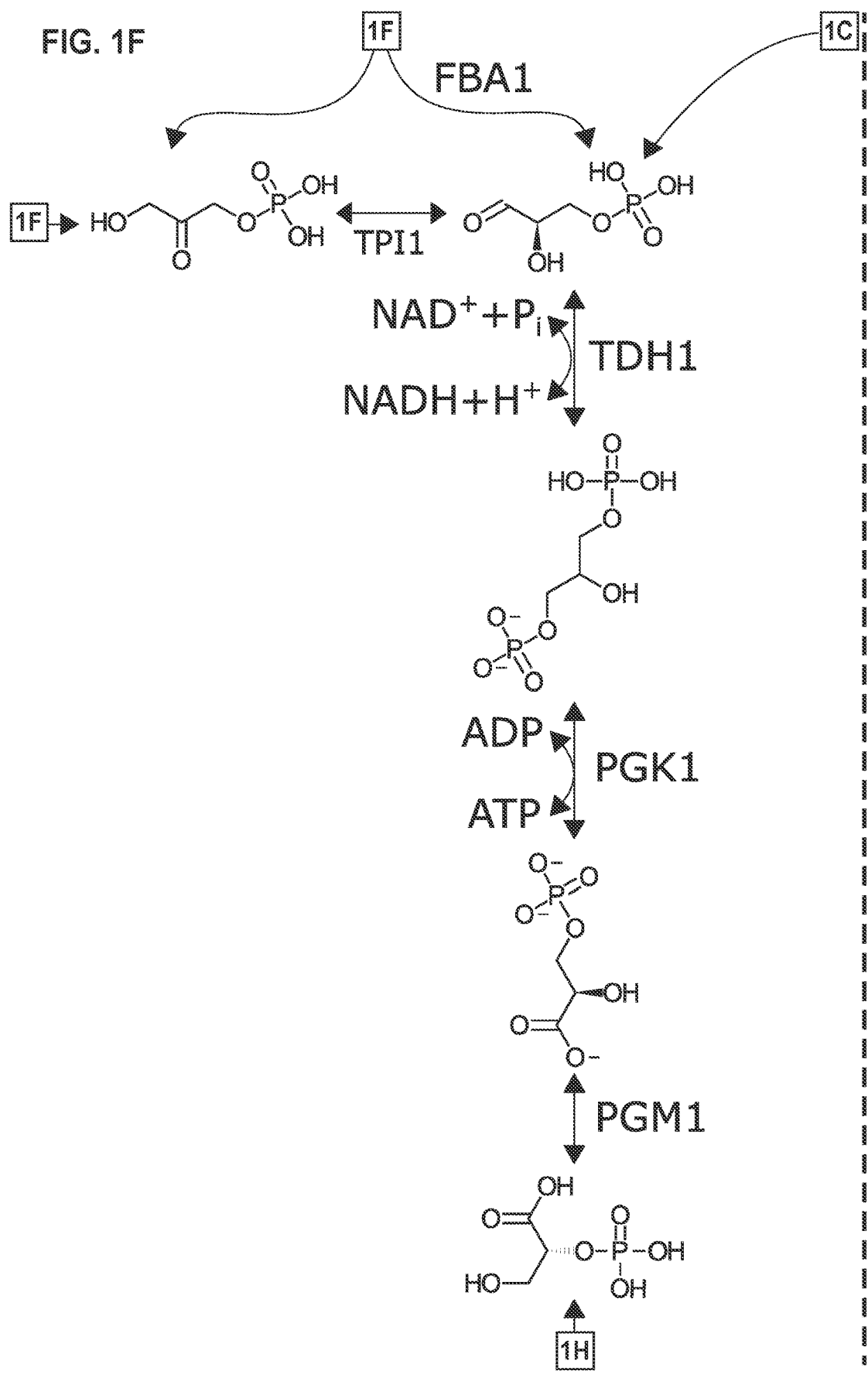
Figure 1G:
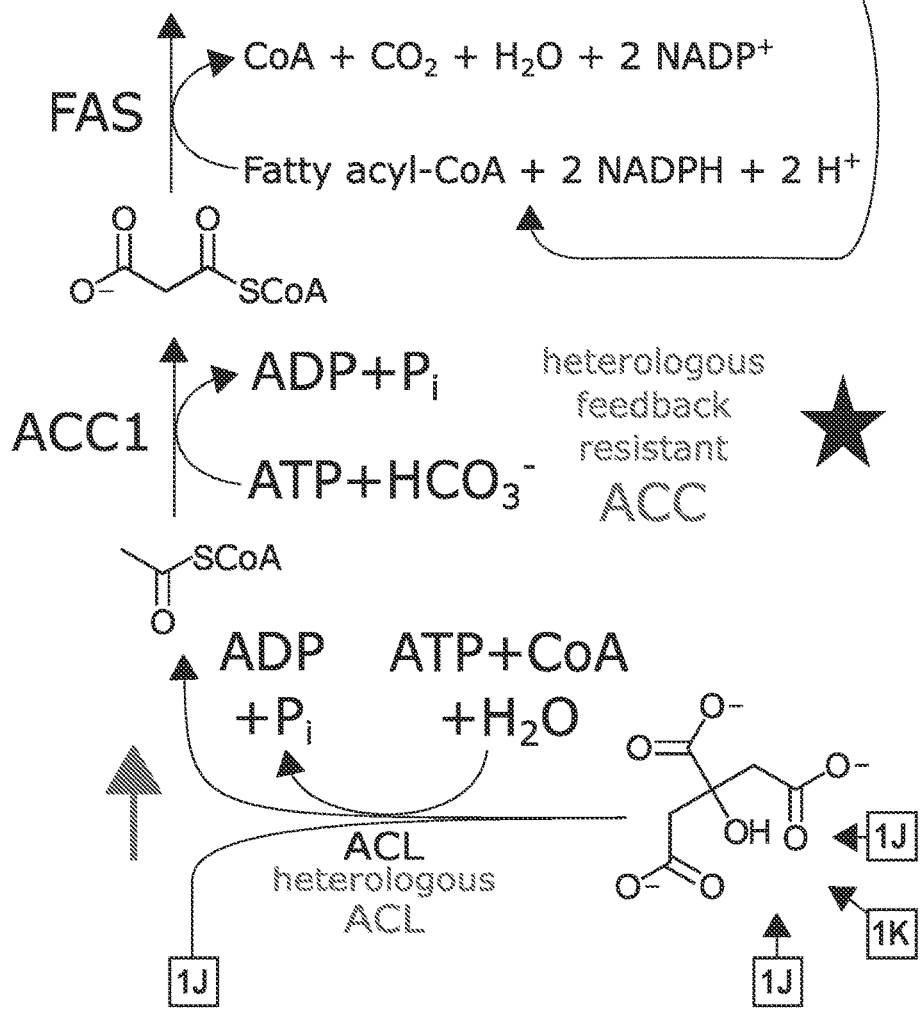
Figure 1H:
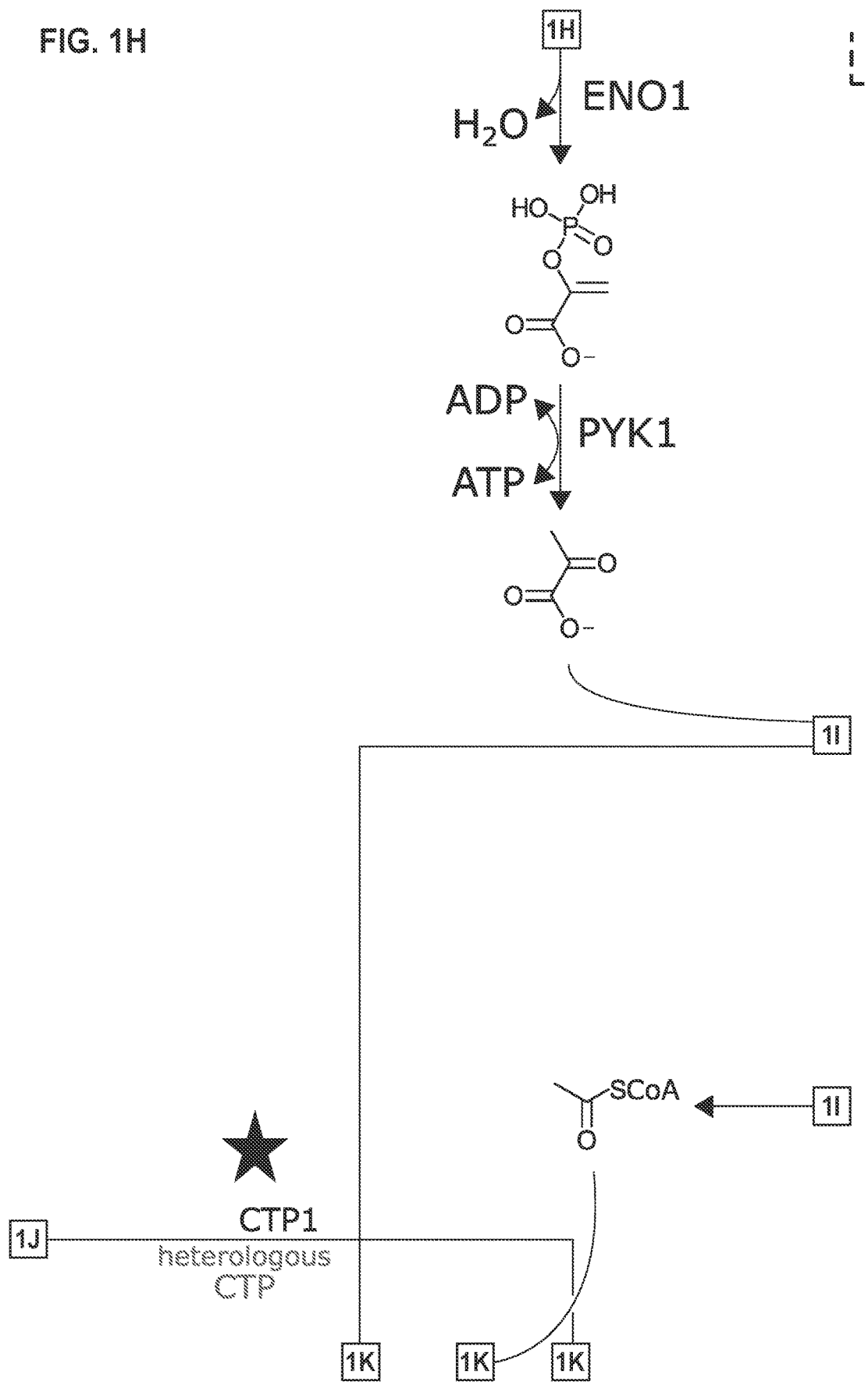
Figure 1I:
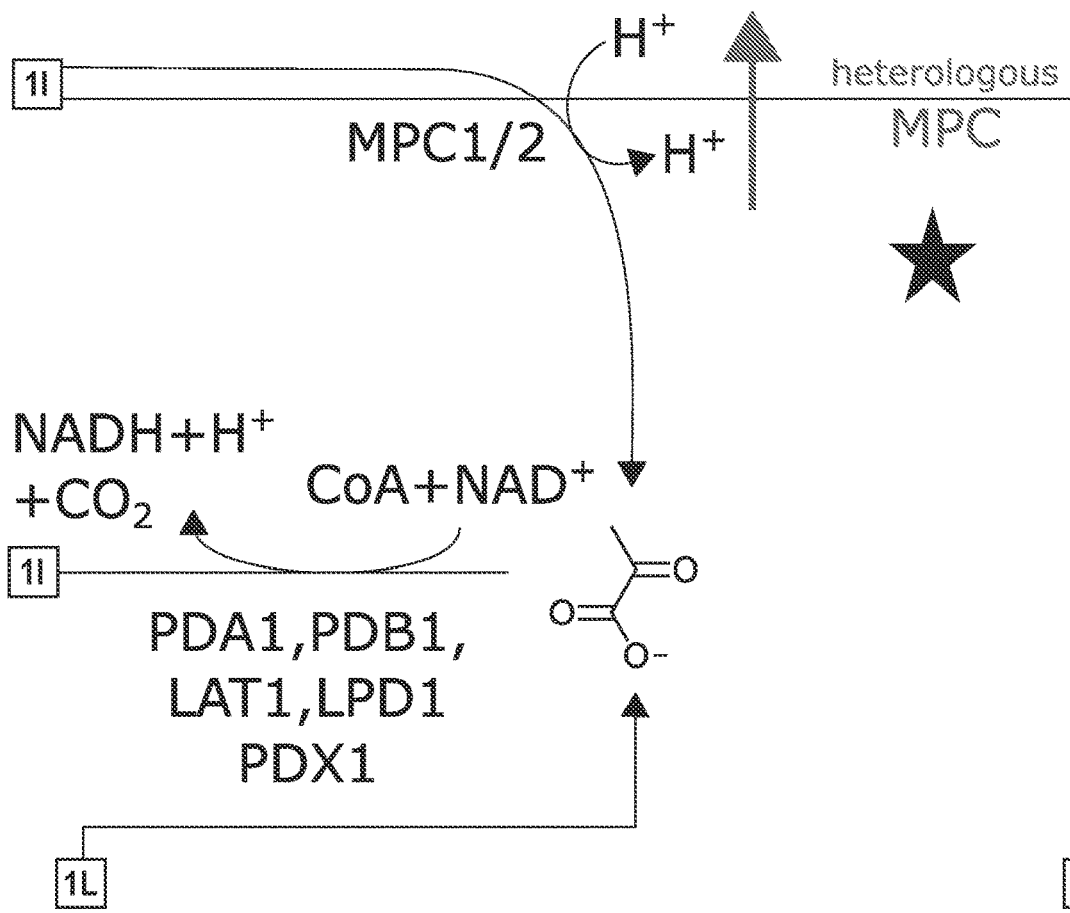
Figure 1J:
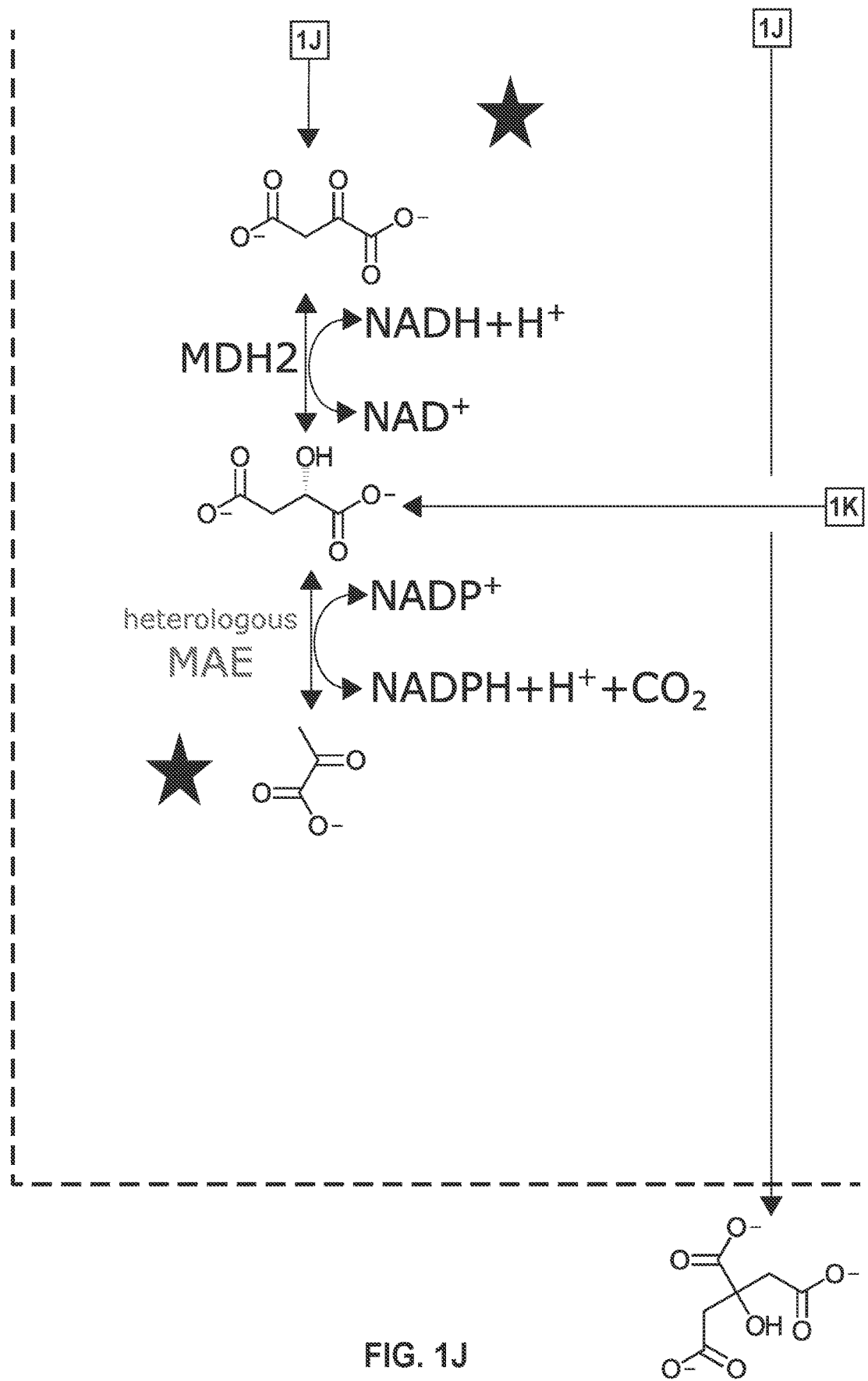
Figure 1K:
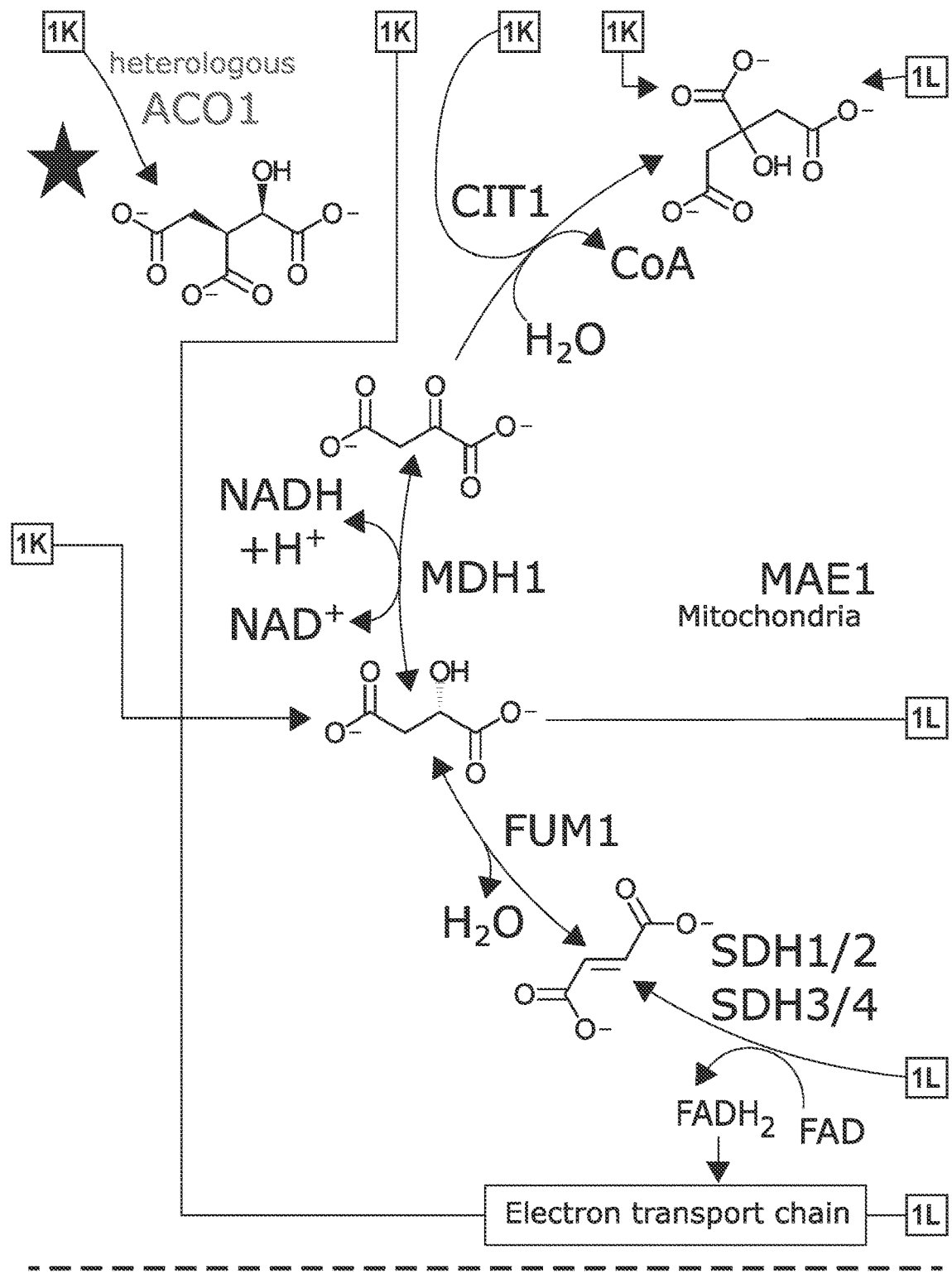
Figure 1L:
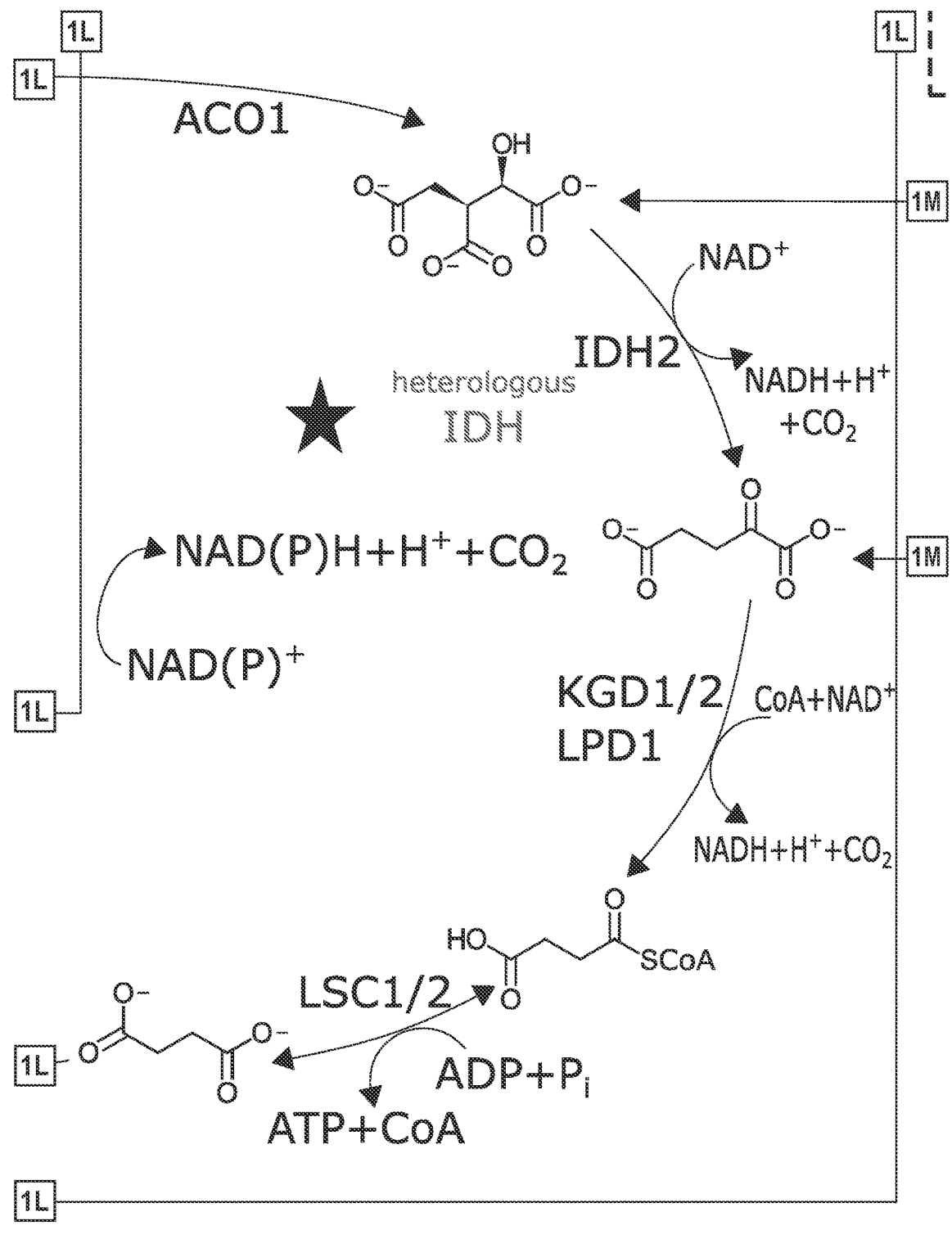
Figure 1M:
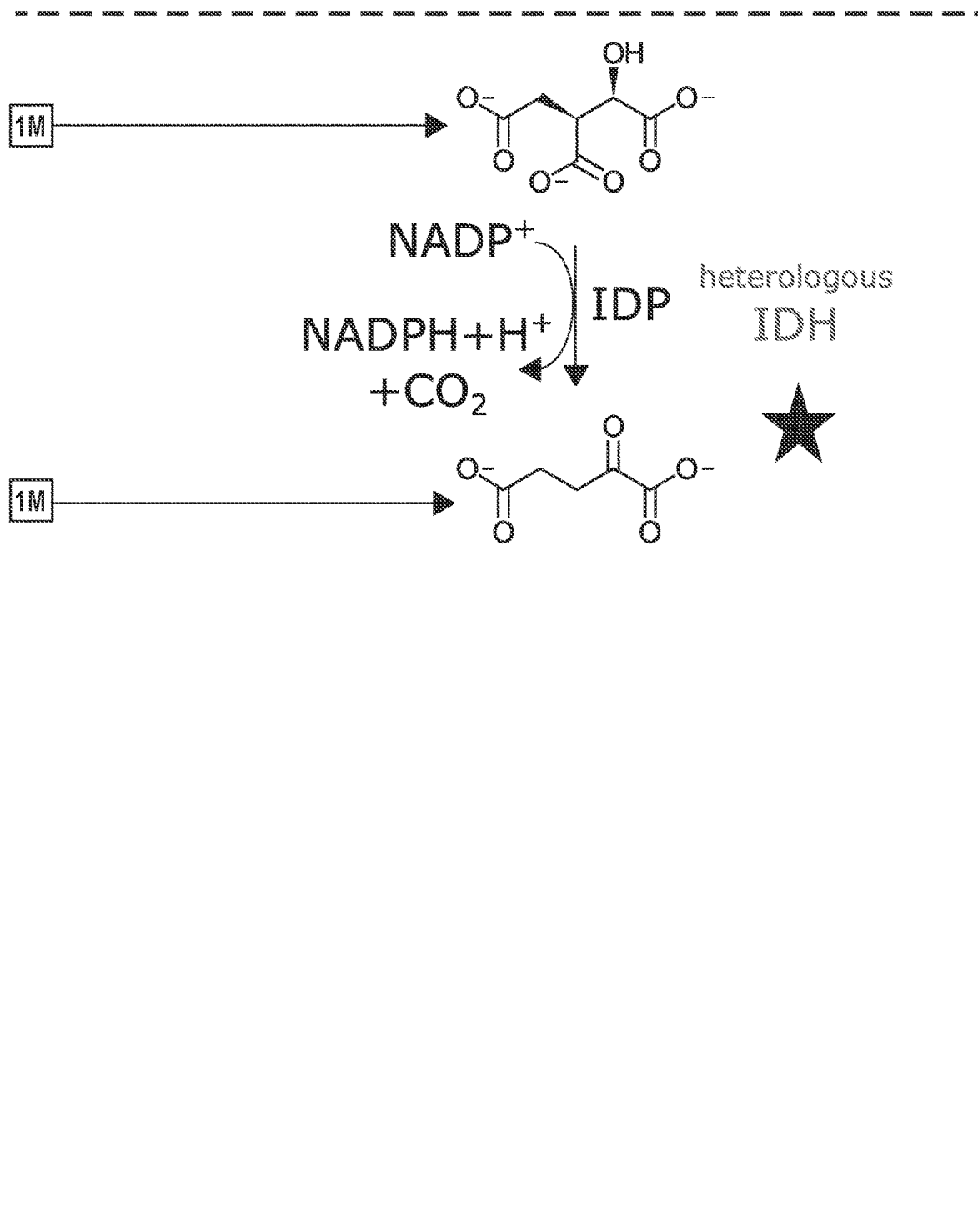
Figure 2A:
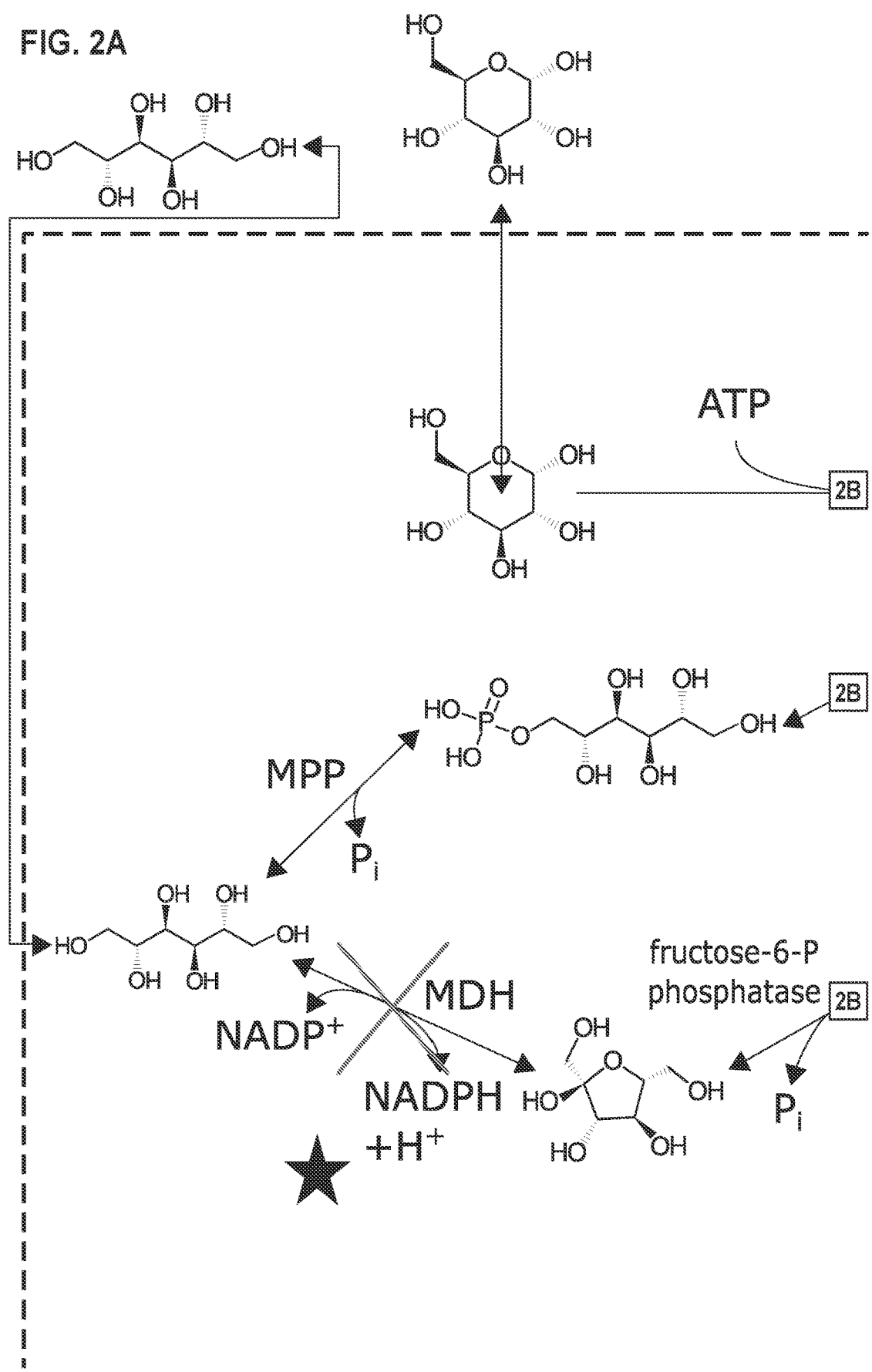
FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, and FIG. 2M show a lipid biosynthetic pathway showing genetic modifications of the present disclosure. Enzymes with stars are identified as candidates for increasing cofactors important for lipid synthesis.
Figure 2B:
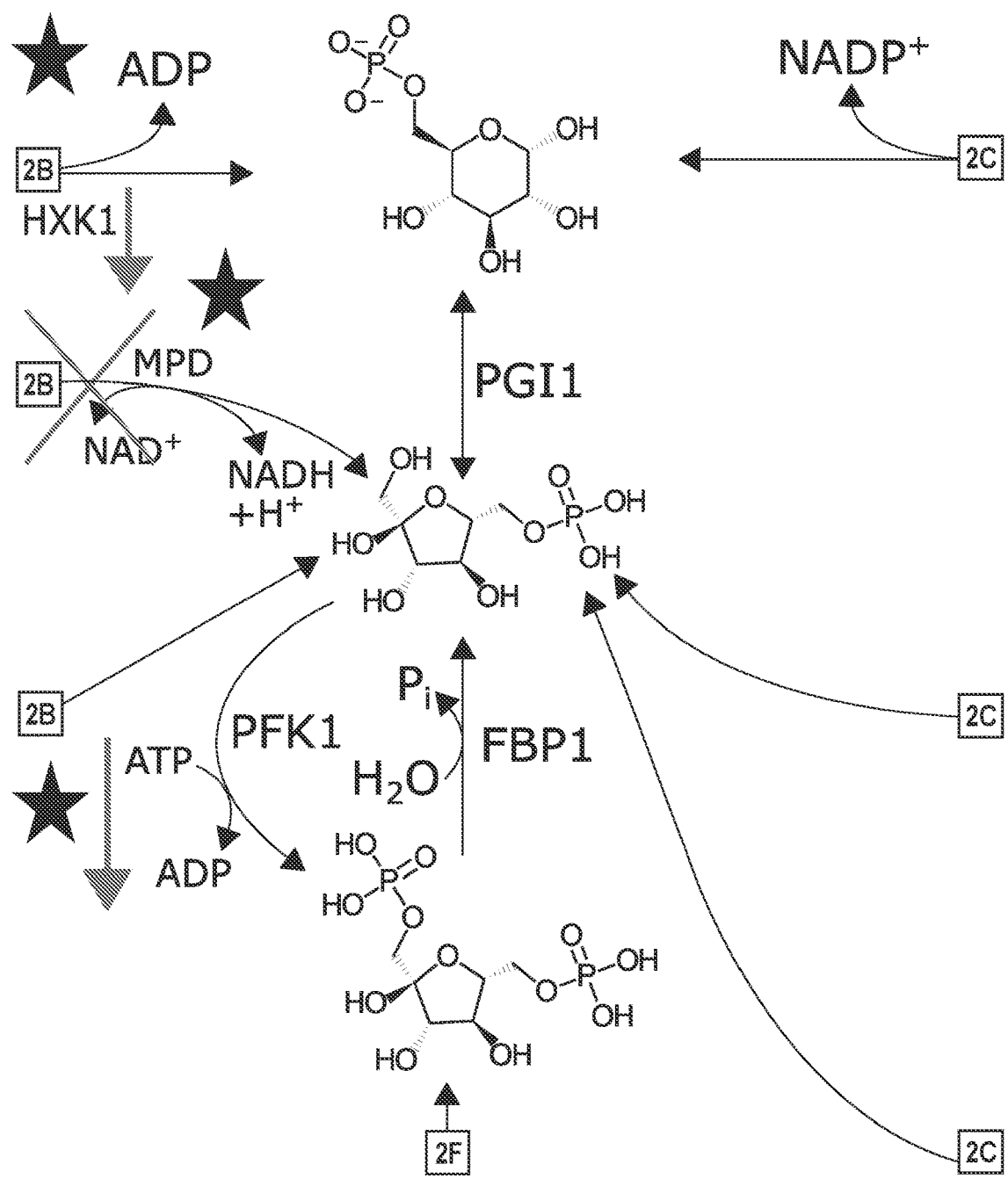
Figure 2C:
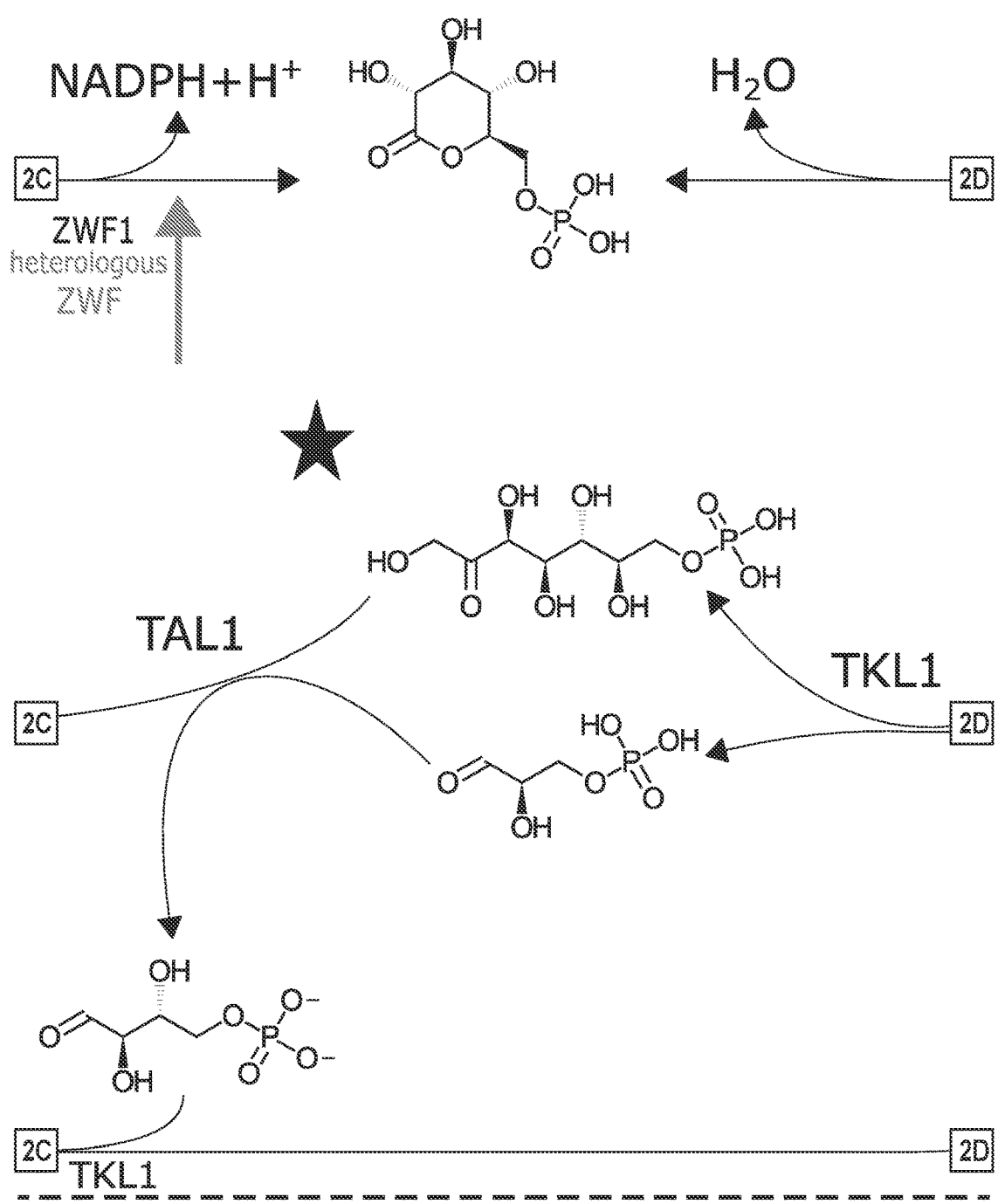
Figure 2D:
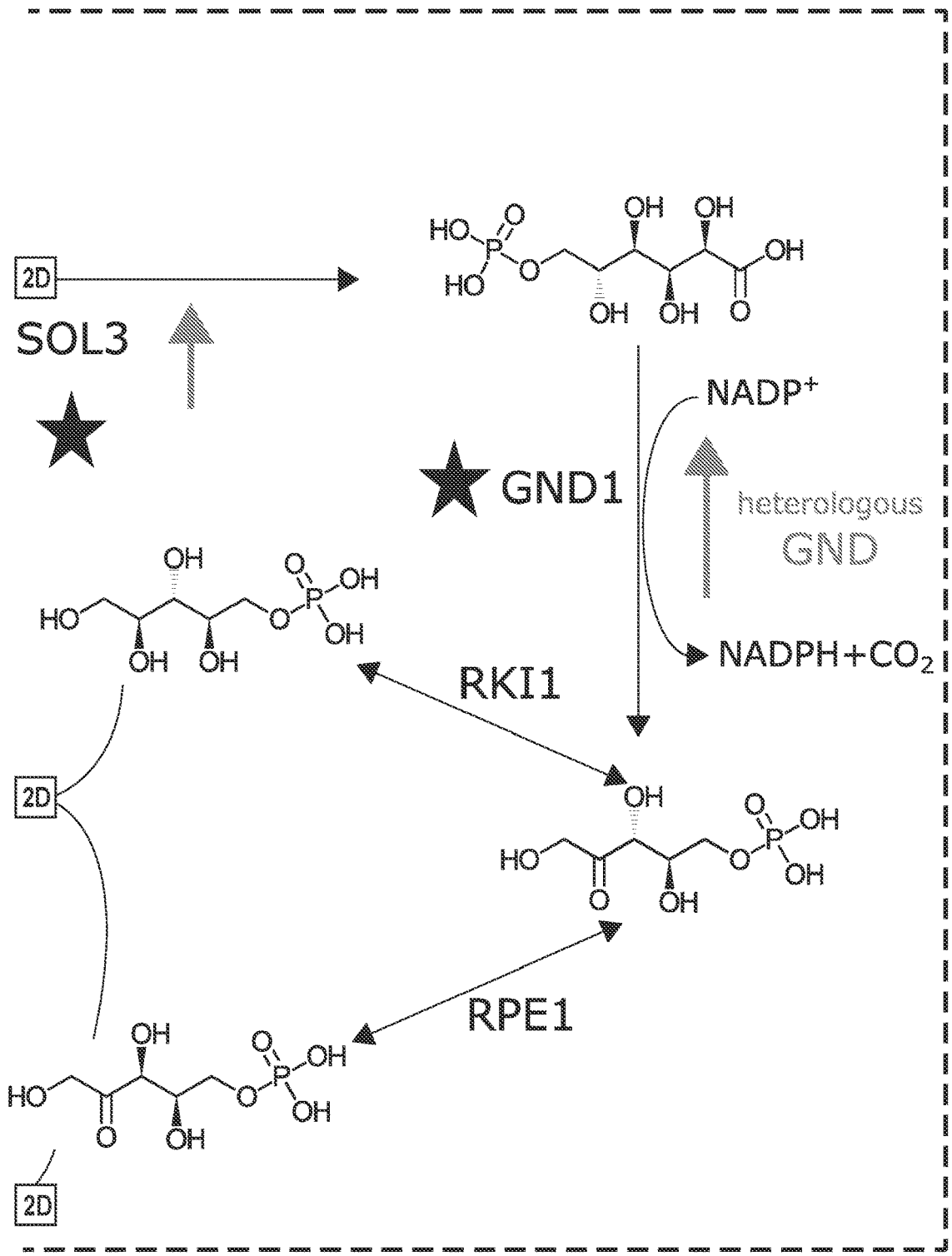
Figure 2E:
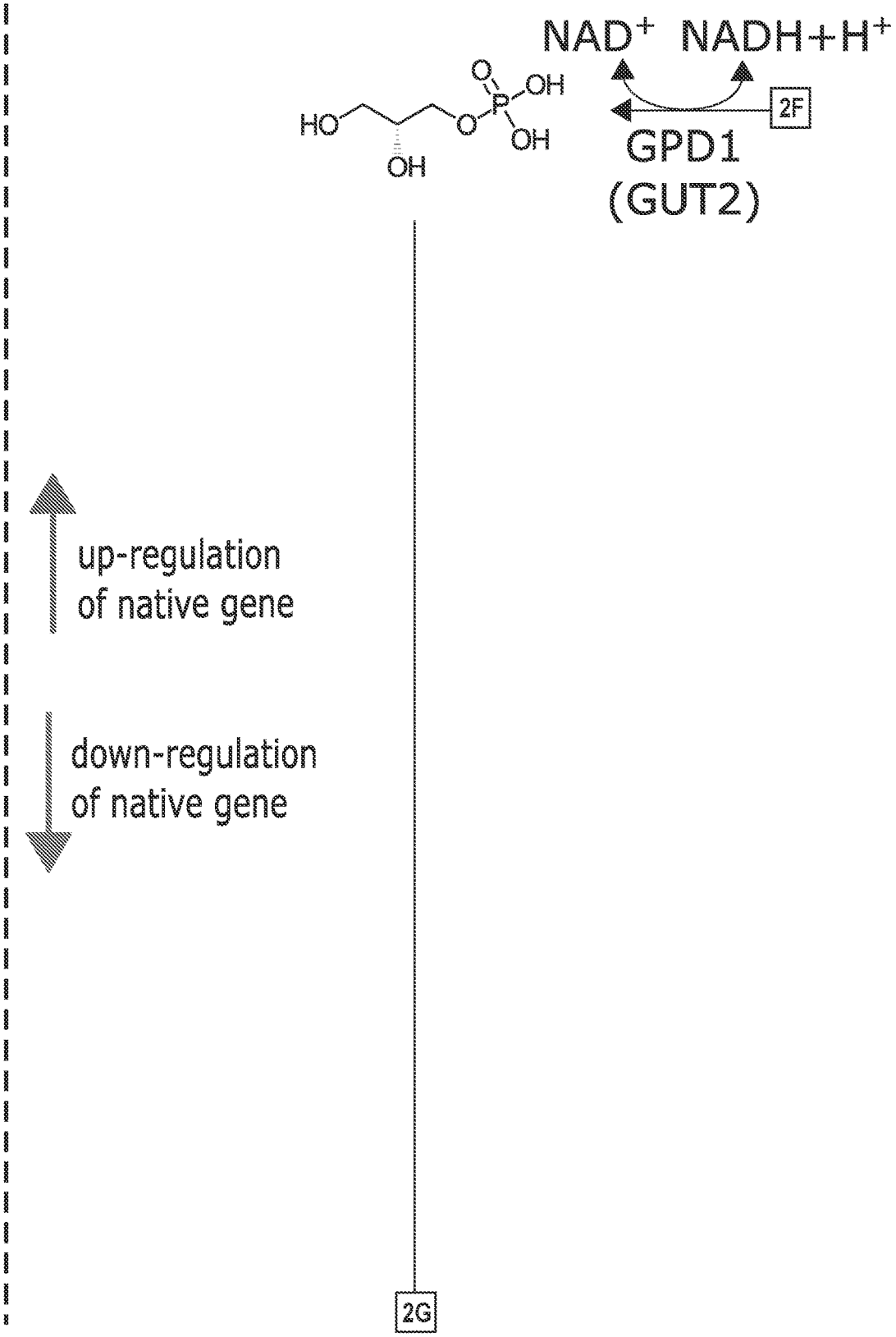
Figure 2F:
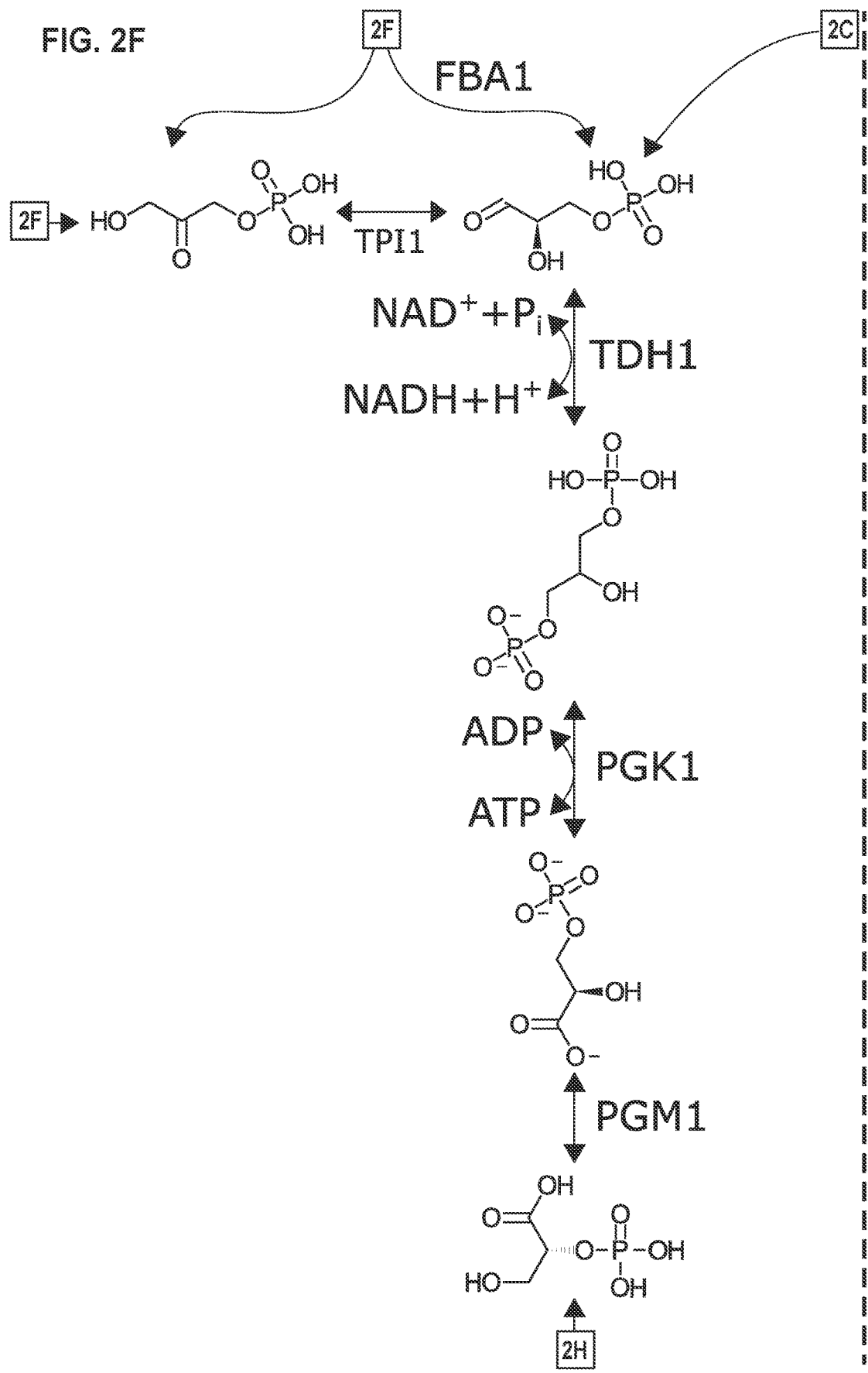
Figure 2G:
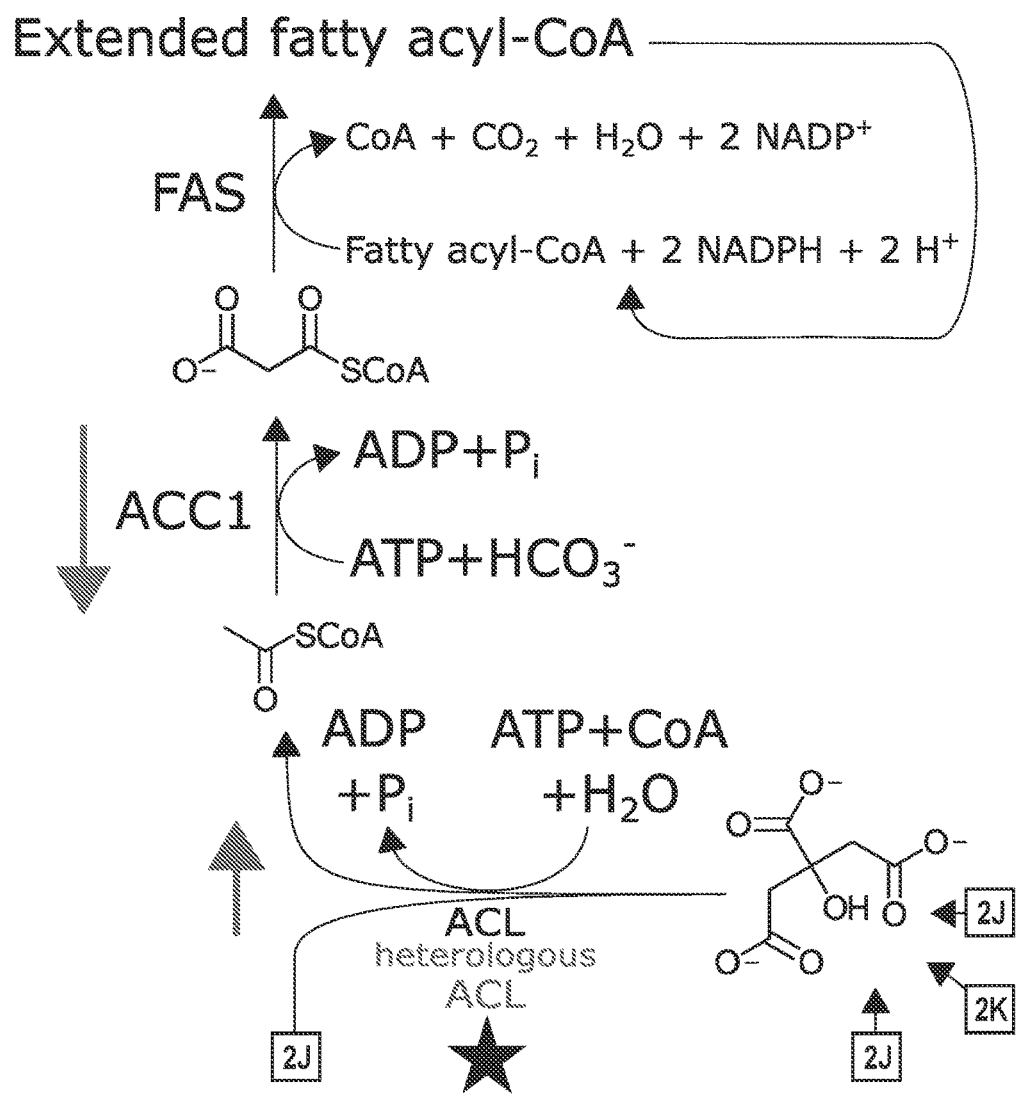
Figure 2H:
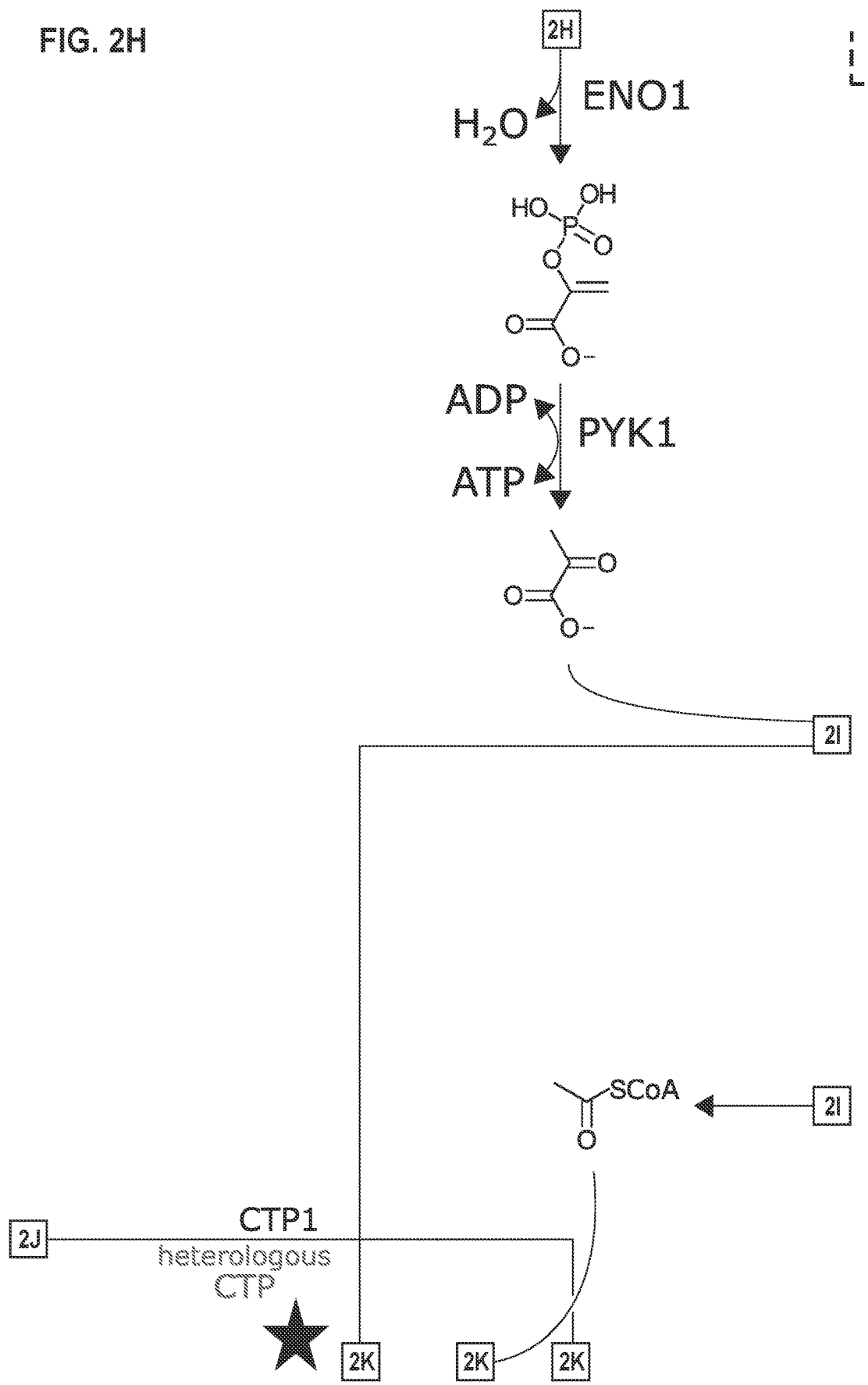
Figure 2I:
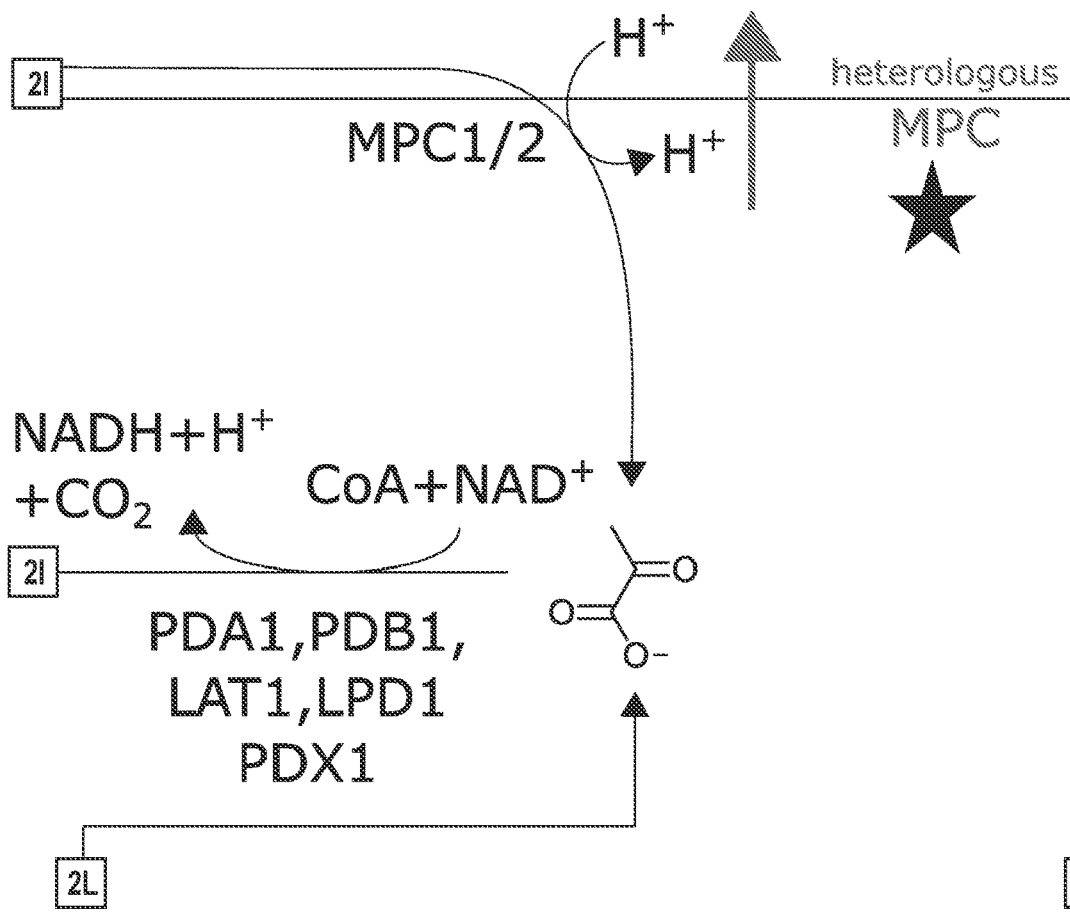
Figure 2J:
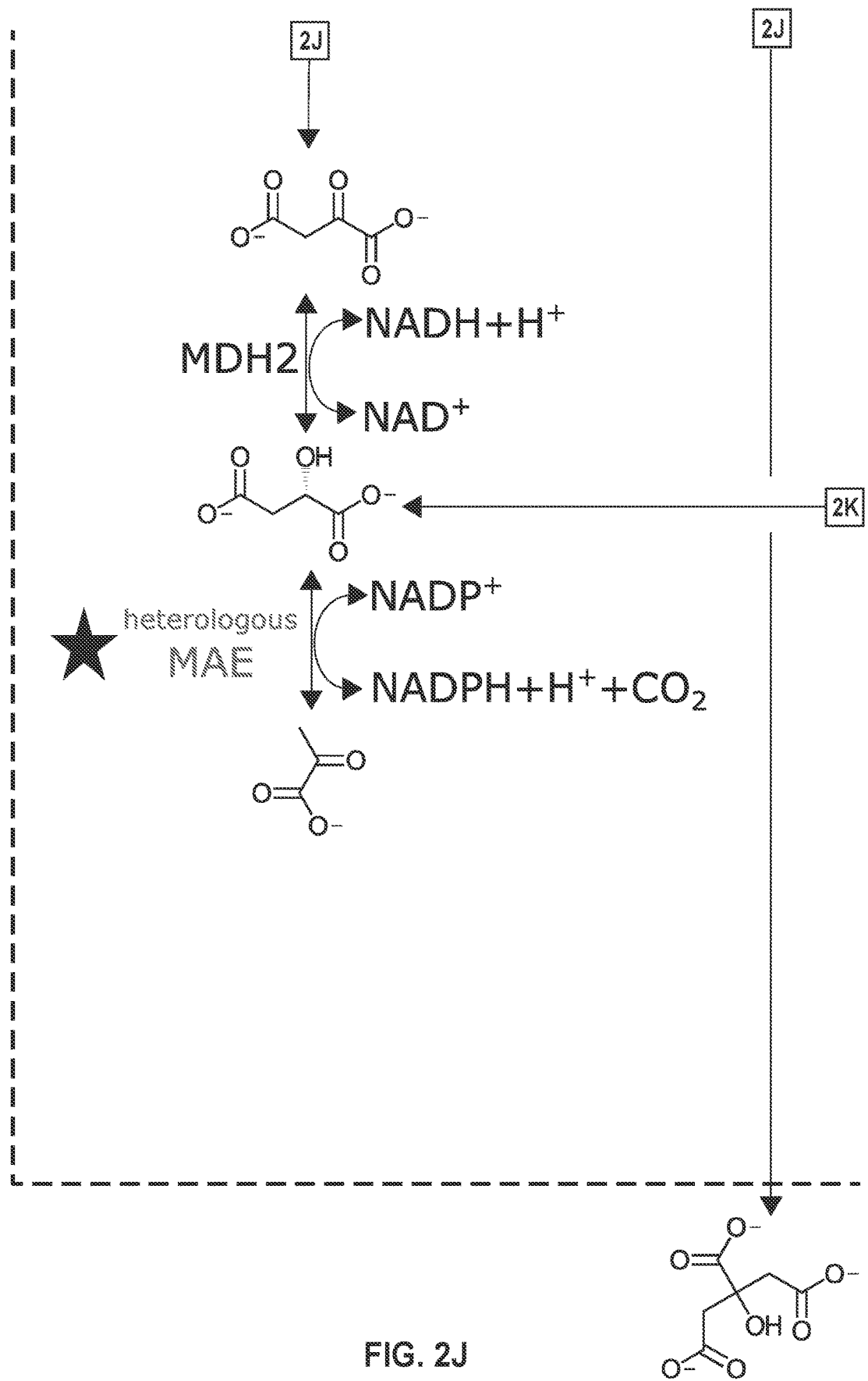
Figure 2K:
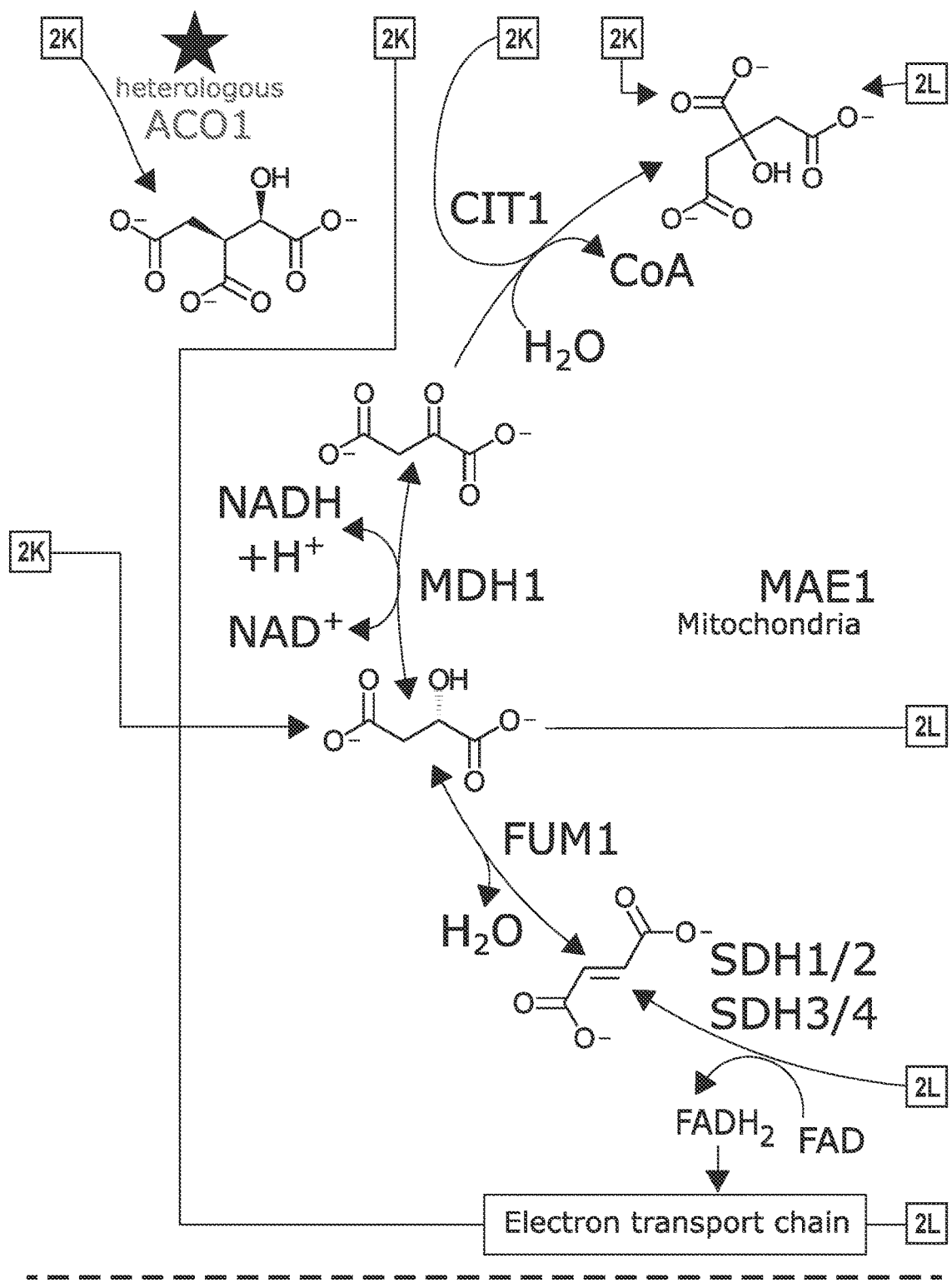
Figure 2L:
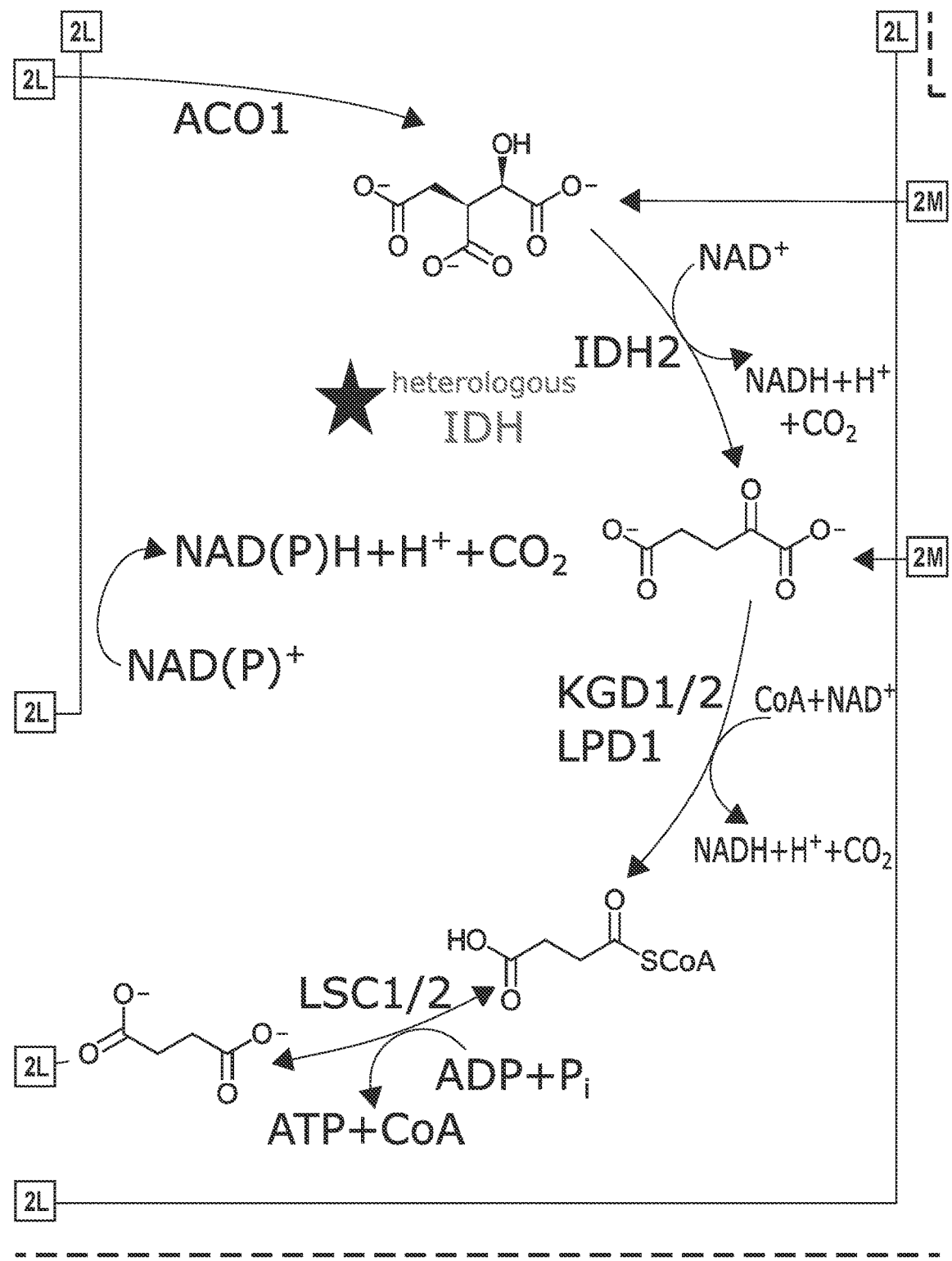
Figure 2M:
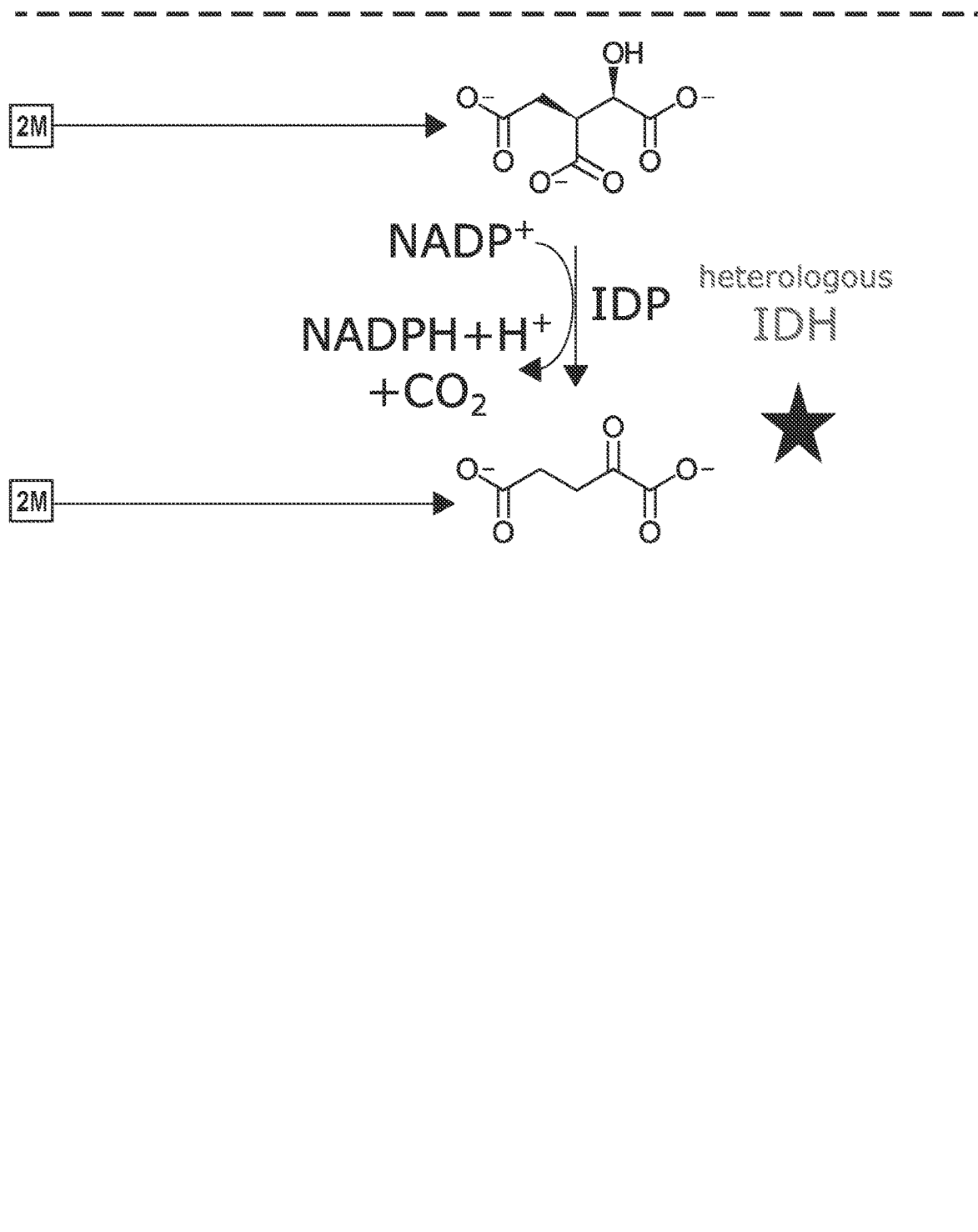

The following definitions and abbreviations are to be used for the interpretation of the disclosure.

As used herein and in the appended claims, the singular forms "a," "an," and "the" include plural referents unless the context clearly dictates otherwise. Thus, for example, reference to "a pheromone" includes a plurality of such pheromones and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s).

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution.

The term "fatty acid" as used herein refers to a compound of structure R—COOH, wherein R is a $C_6$ to $C_{24}$ saturated, unsaturated, linear, branched or cyclic hydrocarbon and the carboxyl group is at position 1. In a particular embodiment, R is a $C_6$ to $C_{24}$ saturated or unsaturated linear hydrocarbon and the carboxyl group is at position 1.

The term "fatty alcohol" as used herein refers to an aliphatic alcohol having the formula R—OH, wherein R is a $C_6$ to $C_{24}$ saturated, unsaturated, linear, branched or cyclic hydrocarbon. In a particular embodiment, R is a $C_6$ to $C_{24}$ saturated or unsaturated linear hydrocarbon.

The term "fatty acyl-CoA" refers to a compound having the structure R—(CO)—S—$R_1$, wherein $R_1$ is Coenzyme A, and the term "fatty acyl-ACP" refers to a compound having the structure R—(CO)—S—$R_1$, wherein $R_1$ is an acyl carrier protein ACP.

The term "one or more modifications associated with . . ." refer to one or more modifications in, for example: a biochemical pathway; biological process; growth; cell division; tricarboxylic acid cycle; lipid synthesis; the availability of cofactors, reducing equivalents or metabolic intermediates; and/or product purity in a microorganism or microbial host. The one or more modifications can include, but is not limited to: expression or overexpression of genes or gene variants; deletion, disruption or downregulation of genes; increasing or decreasing activities of gene products; altered localization of a protein within the microorganism, for example, from mitochondria to cytosol or vice versa; alleviation of enzyme feedback inhibition; uptake or secretion of compounds, nutrients, or molecules.

The term "Z11-16 acid selectivity" refers to the degree to which the recombinant microorganism produces Z11-16 acid from palmitate substrate over other lipid variants. Microorganisms that produce higher relative levels of Z11-16 acid over other C6-C24 carbon chain lipids are considered to have higher Z11-16 acid selectivity. Z11-16 acid selectivity can be calculated as done in Example 2, by the formula=[Z11-16Acid]/([Z9-16Acid]+[Z11-16Acid]+[18Acid]+[Z9-18Acid]+[Z11-18Acid]+[Z13-18Acid]+[Z9Z12-18Acid].

The term reduced or eliminated activity refers to enzymes which are either expressed at lower rates than their wild type counterparts, or have been somehow modified to exhibit less enzymatic activity when compared to similarly expressed wild type versions of the enzyme. The reduction in the activity of proteins can be achieved by various methods known to the person skilled in the art such as, for example: (i) through the inhibition or reduction in the expression of the gene coding for the target enzyme; (ii) by partial or complete deletion of the genes coding for the target enzyme, (iii) by expression of non-functional genes that compete against the functional native target enzyme; and/or by inhibition or reduction in the activity of the expressed genes. The inhibition or reduction of the expression of a gene coding for a protein can, for example, be accomplished by inhibition or reduction of the transcription of the coding gene or the translation of the mRNA formed. The deletion of the coding genes can be performed, for example, by a removal of the genes by means of deletion cassettes. The expression of a dysfunctional or activity-reduced gene product can be accomplished, for example, by insertion, substitution or point mutation in the gene coding for the protein. In some embodiments, the deletion of a coding gene is a reduction in activity.

The term "control microorganism" refers to a microorganism that is substantially identical to the referenced recombinant microorganism except for the referenced genetic alteration. References to improvements of the recombinant microorganisms, such as improved lipid production, improved Z11-16 acid selectivity, or improved biomass, should be understood as improvements over a control microorganism lacking the referenced genetic change.

As used herein, the term "bypass pathway culture" refers to a dual substrate culture comprising growth media with a fatty acid precursor substrate and a simple carbon co-substrate. Bypass pathway cultures are designed to bypass de novo lipid synthesis by providing a fatty acid precursor that a microorganism can convert to the final desired desaturated lipid. The simple carbon co-substrate provides the energy input required to maintain the culture, allowing the fatty acid precursor to be used in the final steps of the desired lipid biosynthesis.

Introduction

The present disclosure addresses the need for novel technologies for improved production of biomass or one or more lipid from multiple substrates. The present disclosure solves the problem of carbon utilization to unwanted metabolites in an engineered microbial system. The present disclosure solves the problem of insufficient reducing equivalent pool for high lipid production. Specifically, the present inventors have addressed these problems with the development of recombinant microorganisms having one or more modifications associated with: tricarboxylic acid cycle; lipid synthesis; reducing equivalent availability; one or more metabolic intermediates availability; and/or increased product purity.

In one embodiment, the one or more lipid can be unsaturated $C_6$-$C_{24}$ fatty acids, alcohols, aldehydes, and acetates including final products or fatty acid precursors of insect pheromones, fragrances, flavors, and polymer intermediates produced from one or more fatty acid and one or more simple carbon co-substrates. Thus, aspects of the disclosure are based on the inventors' discovery that recombinant microorganisms can be engineered to improve production of valuable products such as lipids from one or more fatty acid and one or more simple carbon co-substrates while maintaining or increasing biomass of the recombinant microorganism.

Derivatives of microbial lipids can be harnessed as precursors of fuels, and as chemicals used in detergent formulation, fragrances, and insect control agents. By applying metabolic engineering strategies to increase lipid content in some microbes, several microbial oleochemicals have been produced at commercial scale. Lipid biosynthetic pathways from simple carbon sources such as glucose, fructose, and glycerol (de novo pathway) generate a mixture of fatty acids with different chain lengths and degrees of unsaturation. For certain commercial applications, however, increasing biosynthetic selectivity towards one or a group of some fatty acid species is desirable.

De novo lipid biosynthetic pathways rely on several key enzymes. Fatty acid synthase is a cytosolic enzyme ensemble which catalyzes the polymerization of acyl-CoA with malonyl-CoA. At a certain length, elongation of fatty acyl-ACP polymers is terminated by transacylase activity to produce fatty acyl-CoAs, the precursors of lipids used in diverse functions (e.g. membrane building blocks such as phospholipid, and sphingolipid, or energy storage in the form of mono-, di-, triglycerides, and sterol esters). Prior to conversion into membrane lipid bilayers and storage lipids, fatty acyl-CoAs are processed in the endoplasmic reticulum to undergo desaturations or further elongation. De novo pathways yield a broad range of fatty acid moieties with differing chain lengths and unsaturation. Engineering microbial de novo pathways for the purpose of enriching certain lipid species is challenging, and may compromise host viability because of the interconnectivity of fatty acid enzyme complexes (especially in eukaryotic cells such as yeasts) and the importance of certain fatty acid species on cellular function. De novo lipid pathways are also NADPH intensive. Biosynthetic pathways, such as an insect fatty alcohol pathway to generate pheromone precursors, require NADPH and NADH. Therefore, an improvement in reducing equivalent pool is needed to achieve high level lipid production.

To bypass the limitations in de novo pathway engineering, a strategy was developed to utilize inexpensive plant derived saturated fatty acids in addition to sugar as bioconversion co-substrates to enrich the synthesis of select unsaturated lipid species (bypass pathway). In the presence of multiple substrates, however, metabolic regulations prevent the full utilization of both de novo and bypass pathways for the formation of lipids and biomass. Under a nitrogen-starved and glucose-rich environment, low levels of intracellular AMP reduce the activity of isocitrate dehydrogenase (IDH), a key allosteric enzyme in the TCA cycle in yeast mitochondria. The reduction of IDH activity slows the TCA cycle used for synthesis of biomass and reducing equivalents, and accumulates citrate (the equilibrium form of isocitrate). Build-up of isocitrate in mitochondria creates citrate overflow to the cytosolic compartment. This cytosolic citrate is cleaved into oxaloacetate and acetyl-CoA, the committed precursor of fatty acid synthesis, eliciting lipogenesis and reducing growth. High citrate accumulation has been observed in oleagenic yeast cultivation under nitrogen-limited conditions. Therefore, it is desirable to engineer an oleochemical production host to repurpose citrate for improvement in biomass generation. This can be achieved by an extended activation of the TCA cycle during lipogenesis, while increasing the malonyl-CoA pool, the lipid precursor. Additionally, the number of malonyl-CoA generated for every molecule of glucose consumed can be reduced by the existence of the mannitol synthesis pathway. The NADPH required for 18-carbon triacylglyceride synthesis is balanced if 0.35 moles of mannitol is generated for every mole of glucose consumed resulting in 0.92 moles of malonyl-CoA, 0.04 moles glycerol, and 1.65 moles of NADPH. Alternative sources of NADPH may reduce the required flux through the mannitol pathway and balance NADPH generation. Therefore, in some embodiments, the deletion of the mannitol synthesis pathway can be used to enhance generation of reducing equivalents and improve glucose yields to support production of fatty acid derived products.

Another aspect of the invention relates to increasing the availability of reducing equivalents in the cytosolic compartment. Many heterologous proteins are expressed in the cytosol, or with an active site that is exposed to the cytosol. Of interest is a system which expresses insect desaturases and alcohol forming reductases to generate insect pheromone fatty alcohol precursors. These desaturases and reductases are bound to the endoplasmic reticulum membrane with active sites facing the cytosol. They require cytosolic NADH and NADPH as cofactors to transform a fatty acid precursor into an unsaturated fatty acid, and subsequently into a fatty alcohol. Glycolysis and the pentose phosphate pathway can provide the necessary reducing equivalents. The majority of NADPH required for de novo or bypass fatty acid synthesis in $Y.$ $lipolytica$ comes from the oxidative branch of the pentose phosphate pathway. Under growth conditions which elicit fatty acid synthesis and lipid storage, the majority of glucose flux can be funneled through the pentose phosphate pathway in order to supply the NADPH required for fatty acid synthesis. Depending on various factors such as feeding strategy and cultivation conditions, however, the pool of reducing equivalents in the cytosol may not be sufficient to support heterologous high fatty alcohol production. Therefore, it is desirable to engineer an oleochemical production host with high cytosolic pool of reducing equivalents to allow high level synthesis of lipid products.

Overall, the disclosure describes methods to engineer oleagenic microbes to maximize the conversion efficiency of carbons derived from simple carbons in conjunction with fatty acids for improved microbial production of chemicals such as lipids and fatty acid derivatives by re-directing biosynthetic pathways for reducing overflow metabolites, rebalancing and increasing reducing equivalent, and increasing lipid precursor metabolite.

In one aspect, methods for increasing biomass and precursors of lipid synthesis and microorganisms capable of improved production of biomass and one or more lipid are disclosed.

In some embodiments, microorganisms are modified to alleviate inhibition of isocitrate dehydrogenase (IDH) in the TCA cycle. Specifically, in some embodiments, the locus which corresponds to IDH is replaced with a sequence of an AMP-insensitive IDH variant. Examples of AMP-insensitive IDH variants can be sourced from multiple organisms (Table 1). AMP-insensitive IDH variant can also be engineered in Y. lipolytica IDH1 by mutations of I279A and I280A (Table 1). An AMP-insensitive IDH variant can also be introduced in addition to the native IDH variant to achieve a similar phenotype.

TABLE 1

Exemplary isocitrate dehydrogenase (IDH) enzymes

| Species | Enzyme | Gene ID/Protein ID | co-factor | Inhibition |
|---|---|---|---|---|
| Escherichia coli | Idh | WP_000444484.1 (SEQ ID NO: 21) | NADP | phosphorylation (inhibiting via AceK) |
| Mycobacterium smegmatis | Icd2 | WP_011727802.1 (SEQ ID NO: 23) | NADP | feedback via glyoxylate (activating) |
| Acidithiobacillus thiooxidans | Idh | PDB: 2D4V_A (SEQ ID NO: 22) | NAD | likely phosphorylation |
| Yarrowia lipolytica | Idh1 | XP_503571.2 (SEQ ID NO: 30) AMP-insensitive variant in (SEQ ID NO: 20) | NAD | AMP |

In some embodiments, microorganisms are modified to increase mitochondrial pyruvate pool. Pyruvate is a precursor of multiple enzymes involved in the TCA cycle used for biomass and reducing equivalent generation. To increase pyruvate pool in mitochondria, pyruvate flux from cytosol is enhanced by overexpressing select pyruvate transporter proteins. In Saccharomyces cerevisiae, this is achieved via deletion or truncation of mpc2 gene locus, and overexpression of mpc1, and mpc3 loci. In Y. lipolytica, overexpression of the endogenous mpc genes, co-expression or replacement with heterologous mpc genes can achieve a similar phenotype. Heterologous mpc genes can be sourced from multiple organisms (Table 2).

TABLE 2

Exemplary pyruvate transporters (MPC)

| Species | Enzyme | Gene ID/Protein ID |
|---|---|---|
| Saccharomyces cerevisiae | mpc | NP_011759.1 |
| Hanseniaspora osmophila | mpc3 | OEJ86292.1 |
| Talaromyces marneffei PM1 | mpc3 | KFX48982.1 |

In some embodiments, microorganisms are modified to alleviate inhibition of lipid synthesis by removing acetyl-CoA carboxylase (ACC) regulation. Inclusion of a fatty acid as a co-substrate in addition to simple carbon sources (glucose, fructose, etc.) may inhibit de novo lipid biosynthesis due to excess fatty acyl-CoA. A key enzyme in de novo lipid pathway is ACC, an allosterically regulated enzyme to convert acetyl-CoA into malonyl-CoA (lipid precursor). To relieve ACC inhibition, the native gene locus in Y. lipolytica which encodes for ACC is replaced by or co-expressed with a non-native gene fragment that encodes for a feedback-insensitive ACC variant. Heterologous feedback-insensitive ACC genes can be sourced from multiple organisms (Table 3).

TABLE 3

Exemplary acetyl-CoA carboxylases (ACC)

| Species | Enzyme | Gene ID/Protein ID |
|---|---|---|
| Mus musculus | ACC1 | Q5SWU9 |
| Mus musculus | ACC2 | E9Q4Z2 |
| Rattus norvegicus | ACC1 | P11497 |
| Rattus norvegicus | ACC2 | P11497 |
| Homo sapiens | ACC | Q13085 |
| Homo sapiens | ACC2 | O00763 |

In another aspect, methods for increasing and balancing reducing equivalents and microorganisms capable of increasing and balancing reducing equivalents are disclosed.

In some embodiments, microorganisms are engineered to assimilate cytosolic citrate or isocitrate into alpha-ketoglutarate, and generation of reducing equivalents. In certain embodiments, an NADP/NAD-dependent IDH is functionally expressed in the cytosol alone or together with an aconitase. To functionally express aconitase and NADP/NAD-linked IDH, a variety of yeast promoter sequences can be used. To redirect expression into the cytosolic compartment, the mitochondrial-targeting peptide of respective enzymes are removed. In the case of NAD/NADP-specific IDHs, cytosolic bacterial proteins can be utilized (Table 1).

In some embodiments, the citrate/isocitrate pool in the cytosol is increased by overexpression of citrate transporter protein in a microorganism to increase and/or rebalance reducing equivalent. In certain embodiments, one or more copies of citrate transporter genes are introduced into a microorganism. Citrate transporter sequences include, but are not limited to, Yarrowia lipolytica YALI0F26323p, Saccharomyces cerevisiae AAC48984.1, Rattus norvegicus AAA18899.1, Caenorhabditis elegans P34519.1, and Caliqus clemensi ACO14982.1.

In some embodiments, microorganisms are engineered to express a decarboxylating malic enzyme to generate reducing equivalent in the cytosol from citrate. An ATP-dependent citrate lyase cleaves cytosolic citrate into acetyl-CoA and oxaloacetate. Subsequently, an NADPH-dependent malate dehydrogenase converts oxaloacetate into malate, a metabolite which is transported back into the mitochondria to enter the TCA cycle. A heterologous decarboxylating malic enzyme is expressed to convert malate into pyruvate and $CO_2$ while generating a reducing equivalent either in the form of NADH or NADPH. To redirect expression into the cytosolic compartment, the mitochondrial-targeting peptide of the malate dehydrogenase is removed. Examples of gene sequences which encode decarboxylating malic enzymes include *Arabidopsis thaliana* Q9SIU0 (SEQ ID NO: 34), *Amaranthus hypochondriacus* P37224 (SEQ ID NO: 35), *Rhizobium meliloti* 030807 (SEQ ID NO: 36), *Solanum tuberosum* P37221 (SEQ ID NO: 37), *Homo sapiens* Q16798 (SEQ ID NO: 38), and *Escherichia coli* P26616 (SEQ ID NO: 29).

In some embodiments, the oxaloacetate pool in the cytosol is increased by upregulation of ATP-citrate lyase to increase and/or rebalance reducing equivalent. Further improvement of reducing equivalent by expressing a malic enzyme is gained by improving oxaloacetate (malic enzyme precursor) via upregulation of ATP-citrate lyase. In some embodiments, upregulation of ATP-citrate lyase in a microorganism comprises replacing the native promoter sequence of the endogenous ATP-citrate lyase with a strong promoter sequence such as one derived from a transaldolase gene. In other embodiments, the activity of ATP-citrate lyase is increased by introducing additional sequences which encode the enzyme. Native or heterologous ATP-citrate lyase sequences such as *Mus musculus* NP_001186225.1, *Mus musculus* NP_598798.1, *Aspergillus niger* XP_001394055.1, and *Aspergillus niger* XP_001394057.1 can be used for this purpose.

In some embodiments, flux through the pentose phosphate pathway (PPP) is increased upon entering lipogenesis and lipid storage phase after biomass synthesis to increase and/or rebalance reducing equivalent. Several strategies are utilized to funnel carbon into PPP. In some embodiments, hexose kinase activity is downregulated to limit flux of glucose to glucose-6-phosphate. In other embodiments, independent from or in concert with hexose kinase downregulation, the activity of glucose-6-phosphate dehydrogenase (ZWF1), 6-phosphogluconolactonase (SOL3), and 6-phosphogluconate dehydrogenase (GND1) is increased to draw down the pool of glucose-6-phosphate and pull additional fructose-6-phosphate to enter the oxidative pentose phosphate pathway. In certain embodiments, fructose-6-phosphate kinase is downregulated to reduce flux through upper glycolysis. In another aspect, native glucose-6-phosphate dehydrogenase (ZWF1) or 6-phosphogluconate dehydrogenase (GND1) is replaced with recombinant or engineered variants which use NAD+ in place of NADP+ producing NADH instead of NADPH to match cofactor requirements of recombinant pathways. Examples of suitable NAD-dependent variants of GND include *Bradyrhizobium* WP_012029377.1, *Bradyrhizobium* A4YZZ8, *Methylobacillus* AAF34407.1, and *Methylobacillus* Q9L9P8. Examples of suitable NAD-dependent ZWF include *Leuconostoc* AAA25265.1 and *Leuconostoc* P11411.

In some embodiments, deletion or downregulation of mannitol synthesis pathway can increase and/or rebalance reducing equivalent. In certain embodiments, downregulation of mannitol synthesis pathway comprises deletion, disruption, and/or mutation of one or more gene encoding an NADPH-dependent mannitol dehydrogenase and/or an aldo-keto reductase. In some embodiments, the NADPH-dependent mannitol dehydrogenase is selected from YALI0B16192g, YALI0D18964g, and YALI0E12463g. In other embodiments, the aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g.

In some embodiments, reducing equivalent can be increased and/or rebalanced by decoupling and increasing glucose uptake via amplifying the activity of both high and low affinity hexose transporters. Yeasts possess several variants of hexose transporters that are distinguished based on their specificity and mode of activation. It is desirable to optimize biomass and lipid synthesis regardless of glucose concentration and media composition throughout the fermentation period. It was shown that under distinct fermentation conditions such as nitrogen limitation, glucose uptake rates drop significantly. Thus, glucose depletion might diminish the pool of reducing equivalents necessary for lipid synthesis, desaturation of fatty acids and reduction of fatty acids to fatty alcohols. In some embodiments, hexokinase deletion or downregulation increases both high and low affinity hexose transporters in yeasts such as *Saccharomyces cerevisiae* and *Yarrowia lipolytica*. The deletion of a hexokinase variant leads to an increase in pyruvate, a precursor of the TCA cycle used for biomass and reducing equivalent generation. An alternative strategy involves the expression of specific glucose transporters using heterologous promoters. The use of heterologous promoters achieves a decoupling of hexose transporter expression from cellular regulation. In some embodiments, a microorganism can be modified to overexpress *Yarrowia lipolytica* hexose transporter genes selected from YALI0A14212g, YALI0D01111g, YALI0D00363g, YALI0C16522g and YALI0F25553g.

In another aspect, methods of increasing product purity, reducing equivalents, and pathway intermediates and microorganisms capable of increasing product purity, reducing equivalents, and pathway intermediates are disclosed.

In some embodiments, downregulation or inhibition of ACC activity during conversion phase to reduce flux to 18 carbon fatty acids increases product purity, available NADPH, and acetyl-CoA units as potential building blocks for fatty esters or for NADH generation via respiration.

In some embodiments, the recombinant microorganisms of the disclosure can be used to synthesize mono- or poly-unsaturated $C_6$-$C_{24}$ fatty acids. In other embodiments, the recombinant microorganisms of the disclosure can be used to synthesize mono- or poly-unsaturated $C_6$-$C_{24}$ fatty alcohols. Mono- or poly-unsaturated $C_6$-$C_{24}$ fatty alcohols can be further converted into the corresponding aldehydes or acetates. Thus, various embodiments of the present disclosure can be used to synthesize a variety of insect pheromones selected from fatty alcohols, aldehydes, and acetates. Additionally, embodiments described herein can also be used for the synthesis of fragrances, flavors, and polymer intermediates.

Pheromones

As described above, embodiments of the disclosure provide for the production of one or more insect pheromones using a recombinant microorganism of the disclosure. A pheromone is a volatile chemical compound that is secreted by a particular insect for the function of chemical communication within the species. That is, a pheromone is secreted or excreted chemical factor that triggers a social response in members of the same species. There are, inter alia, alarm pheromones, food trail pheromones, sex pheromones, aggregation pheromones, epideictic pheromones, releaser pheromones, primer pheromones, and territorial pheromones, that affect behavior or physiology.

Non-limiting examples of insect pheromones which can be produced using the recombinant microorganisms and methods disclosed herein include linear alcohols, aldehydes, and acetates listed in Table 4.

TABLE 4

| $C_6$-$C_{20}$ Linear Pheromones | |
|---|---|
| Name | Name |
| (E)-2-Decen-1-ol | (E,E)-10,12-Tetradecadien-1-ol |
| (E)-2-Decenyl acetate | (E,E)-10,12-Tetradecadienyl acetate |
| (E)-2-Decenal | (E,E)-10,12-Tetradecadienal |
| (Z)-2-Decen-1-ol | (E,Z)-10,12-Tetradecadienyl acetate |
| (Z)-2-Decenyl acetate | (Z,E)-10,12-Tetradecadienyl acetate |
| (Z)-2-Decenal | (Z,Z)-10,12-Tetradecadien-1-ol |
| (E)-3-Decen-1-ol | (Z,Z)-10,12-Tetradecadienyl acetate |
| (Z)-3-Decenyl acetate | (E,Z,Z)-3,8,11-Tetradecatrienyl acetate |
| (Z)-3-Decen-1-ol | (E)-8-Pentadecen-1-ol |
| (Z)-4-Decen-1-ol | (E)-8-Pentadecenyl acetate |
| (E)-4-Decenyl acetate | (Z)-8-Pentadecen-1-ol |
| (Z)-4-Decenyl acetate | (Z)-8-Pentadecenyl acetate |
| (Z)-4-Decenal | (Z)-9-Pentadecenyl acetate |
| (E)-5-Decen-1-ol | (E)-9-Pentadecenyl acetate |
| (E)-5-Decenyl acetate | (Z)-10-Pentadecenyl acetate |
| (Z)-5-Decen-1-ol | (Z)-1O-P entadecenal |
| (Z)-5-Decenyl acetate | (E)-12-Pentadecenyl acetate |
| (Z)-5-Decenal | (Z)-12-Pentadecenyl acetate |
| (E)-7-Decenyl acetate | (Z,Z)-6,9-Pentadecadien-1-ol |
| (Z)-7-Decenyl acetate | (Z,Z)-6,9-Pentadecadienyl acetate |
| (E)-8-Decen-1-ol | (Z,Z)-6,9-Pentadecadienal |
| (E,E)-2,4-Decadienal | (E,E)-8,10-Pentadecadienyl acetate |
| (E,Z)-2,4-Decadienal | (E,Z)-8,10-Pentadecadien-1-ol |
| (Z,Z)-2,4-Decadienal | (E,Z)-8,10-Pentadecadienyl acetate |
| (E,E)-3,5-Decadienyl acetate | (Z,E)-8,10-Pentadecadienyl acetate |
| (Z,E)-3,5-Decadienyl acetate | (Z,Z)-8,10-Pentadecadienyl acetate |
| (Z,Z)-4,7-Decadien-1-ol | (E,Z)-9,11-Pentadecadienal |
| (Z,Z)-4,7-Decadienyl acetate | (Z,Z)-9,11-Pentadecadienal |
| (E)-2-Undecenyl acetate | (Z)-3-Hexadecenyl acetate |
| (E)-2-Undecenal | (E)-5-Hexadecen-1-ol |
| (Z)-5-Undecenyl acetate | (E)-5-Hexadecenyl acetate |
| (Z)-7-Undecenyl acetate | (Z)-5-Hexadecen-1-ol |
| (Z)-8-Undecenyl acetate | (Z)-5-Hexadecenyl acetate |
| (Z)-9-Undecenyl acetate | (E)-6-Hexadecenyl acetate |
| (E)-2-Dodecenal | (E)-7-Hexadecen-1-ol |
| (Z)-3-Dodecen-1-ol | (E)-7-Hexadecenyl acetate |
| (E)-3-Dodecenyl acetate | (E)-7-Hexadecenal |
| (Z)-3-Dodecenyl acetate | (Z)-7-Hexadecen-1-ol |
| (E)-4-Dodecenyl acetate | (Z)-7-Hexadecenyl acetate |
| (E)-5-Dodecen-1-ol | (Z)-7-Hexadecenal |
| (E)-5-Dodecenyl acetate | (E)-8-Hexadecenyl acetate |
| (Z)-5-Dodecen-1-ol | (E)-9-Hexadecen-1-ol |
| (Z)-5-Dodecenyl acetate | (E)-9-Hexadecenyl acetate |
| (Z)-5-Dodecenal | (E)-9-Hexadecenal |
| (E)-6-Dodecen-1-ol | (Z)-9-Hexadecen-1-ol |
| (Z)-6-Dodecenyl acetate | (Z)-9-Hexadecenyl acetate |
| (E)-6-Dodecenal | (Z)-9-Hexadecenal |
| (E)-7-Dodecen-1-ol | (E)-10-Hexadecen-1-ol |
| (E)-7-Dodecenyl acetate | (E)-10-Hexadecenal |
| (E)-7-Dodecenal | (Z)-10-Hexadecenyl acetate |
| (Z)-7-Dodecen-1-ol | (Z)-10-Hexadecenal |
| (Z)-7-Dodecenyl acetate | (E)-11-Hexadecen-1-ol |
| (Z)-7-Dodecenal | (E)-11-Hexadecenyl acetate |
| (E)-8-Dodecen-1-ol | (E)-11-Hexadecenal |
| (E)-8-Dodecenyl acetate | (Z)-11-Hexadecen-1-ol |
| (E)-8-Dodecenal | (Z)-11-Hexadecenyl acetate |
| (Z)-8-Dodecen-1-ol | (Z)-11-Hexadecenal |
| (Z)-8-Dodecenyl acetate | (Z)-12-Hexadecenyl acetate |
| (E)-9-Dodecen-1-ol | (Z)-12-Hexadecenal |
| (E)-9-Dodecenyl acetate | (E)-14-Hexadecenal |
| (E)-9-Dodecenal | (Z)-14-Hexadecenyl acetate |
| (Z)-9-Dodecen-1-ol | (E,E)-1,3-Hexadecadien-1-ol |
| (Z)-9-Dodecenyl acetate | (E,Z)-4,6-Hexadecadien-1-ol |
| (Z)-9-Dodecenal | (E,Z)-4,6-Hexadecadienyl acetate |
| (E)-10-Dodecen-1-ol | (E,Z)-4,6-Hexadecadienal |
| (E)-10-Dodecenyl acetate | (E,Z)-6,11-Hexadecadienyl acetate |
| (E)-10-Dodecenal | (E,Z)-6,11-Hexadecadienal |
| (Z)-10-Dodecen-1-ol | (Z,Z)-7,10-Hexadecadien-1-ol |
| (Z)-10-Dodecenyl acetate | (Z,Z)-7,10-Hexadecadienyl acetate |
| (E,Z)-3,5-Dodecadienyl acetate | (Z,E)-7,11-Hexadecadien-1-ol |
| (Z,E)-3,5-Dodecadienyl acetate | (Z,E)-7,11-Hexadecadienyl acetate |
| (Z,Z)-3,6-Dodecadien-1-ol | (Z,E)-7,11-Hexadecadienal |
| (E,E)-4,10-Dodecadienyl acetate | (Z,Z)-7,11-Hexadecadien-1-ol |
| (E,E)-5,7-Dodecadien-1-ol | (Z,Z)-7,11-Hexadecadienyl acetate |
| (E,E)-5,7-Dodecadienyl acetate | (Z,Z)-7,11-Hexadecadienal |
| (E,Z)-5,7-Dodecadien-1-ol | (Z,Z)-8,10-Hexadecadienyl acetate |

TABLE 4-continued

$C_6$-$C_{20}$ Linear Pheromones

| Name | Name |
|---|---|
| (E,Z)-5,7-Dodecadienyl acetate | (E,Z)-8,11-Hexadecadienal |
| (E,Z)-5,7-Dodecadienal | (E,E)-9,11-Hexadecadienal |
| (Z,E)-5,7-Dodecadien-1-ol | (E,Z)-9,11-Hexadecadienyl acetate |
| (Z,E)-5,7-Dodecadienyl acetate | (E,Z)-9,11-Hexadecadienal |
| (Z,E)-5,7-Dodecadienal | (Z,E)-9,11-Hexadecadienal |
| (Z,Z)-5,7-Dodecadienyl acetate | (Z,Z)-9,11-Hexadecadienal |
| (Z,Z)-5,7-Dodecadienal | (E,E)-10,12-Hexadecadien-1-ol |
| (E,E)-7,9-Dodecadienyl acetate | (E,E)-10,12-Hexadecadienyl acetate |
| (E,Z)-7,9-Dodecadien-1-ol | (E,E)-10,12-Hexadecadienal |
| (E,Z)-7,9-Dodecadienyl acetate | (E,Z)-10,12-Hexadecadien-1-ol |
| (E,Z)-7,9-Dodecadienal | (E,Z)-10,12-Hexadecadienyl acetate |
| (Z,E)-7,9-Dodecadien-1-ol | (E,Z)-10,12-Hexadecadienal |
| (Z,E)-7,9-Dodecadienyl acetate | (Z,E)-10,12-Hexadecadienyl acetate |
| (Z,Z)-7,9-Dodecadien-1-ol | (Z,E)-10,12-Hexadecadienal |
| (Z,Z)-7,9-Dodecadienyl acetate | (Z,Z)-10,12-Hexadecadienal |
| (E,E)-8,10-Dodecadien-1-ol | (E,E)-11,13-Hexadecadien-1-ol |
| (E,E)-8,10-Dodecadienyl acetate | (E,E)-11,13-Hexadecadienyl acetate |
| (E,E)-8,10-Dodecadienal | (E,E)-11,13-Hexadecadienal |
| (E,Z)-8,10-Dodecadien-1-ol | (E,Z)-11,13-Hexadecadien-1-ol |
| (E,Z)-8,10-Dodecadienyl acetate | (E,Z)-11,13-Hexadecadienyl acetate |
| (E,Z)-8,10-Dodecadienal | (E,Z)-11,13-Hexadecadienal |
| (Z,E)-8,10-Dodecadien-1-ol | (Z,E)-11,13-Hexadecadien-1-ol |
| (Z,E)-8,10-Dodecadienyl acetate | (Z,E)-11,13-Hexadecadienyl acetate |
| (Z,E)-8,10-Dodecadienal | (Z,E)-11,13-Hexadecadienal |
| (Z,Z)-8,10-Dodecadien-1-ol | (Z,Z)-11,13-Hexadecadien-1-ol |
| (Z,Z)-8,10-Dodecadienyl acetate | (Z,Z)-11,13-Hexadecadienyl acetate |
| (Z,E,E)-3,6,8-Dodecatrien-1-ol | (Z,Z)-11,13-Hexadecadienal |
| (Z,Z,E)-3,6,8-Dodecatrien-1-ol | (E,E)-10,14-Hexadecadienal |
| (E)-2-Tridecenyl acetate | (Z,E)-11,14-Hexadecadienyl acetate |
| (Z)-2-Tridecenyl acetate | (E,E,Z)-4,6,10-Hexadecatrien-1-ol |
| (E)-3-Tridecenyl acetate | (E,E,Z)-4,6,10-Hexadecatrienyl acetate |
| (E)-4-Tridecenyl acetate | (E,Z,Z)-4,6,10-Hexadecatrien-1-ol |
| (Z)-4-Tridecenyl acetate | (E,Z,Z)-4,6,10-Hexadecatrienyl acetate |
| (Z)-4-Tridecenal | (E,E,Z)-4,6,11-Hexadecatrienyl acetate |
| (E)-6-Tridecenyl acetate | (E,E,Z)-4,6,11-Hexadecatrienal |
| (Z)-7-Tridecenyl acetate | (Z,Z,E)-7,11,13-Hexadecatrienal |
| (E)-8-Tridecenyl acetate | (E,E,E)-10,12,14-Hexadecatrienyl acetate |
| (Z)-8-Tridecenyl acetate | (E,E,E)-10,12,14-Hexadecatrienal |
| (E)-9-Tridecenyl acetate | (E,E,Z)-10,12,14-Hexadecatrienyl acetate |
| (Z)-9-Tridecenyl acetate | (E,E,Z)-10,12,14-Hexadecatrienal |
| (Z)-10-Tridecenyl acetate | (E,E,Z,Z)-4,6,11,13-Hexadecatetraenal |
| (E)-11-Tridecenyl acetate | (E)-2-Heptadecenal |
| (Z)-11-Tridecenyl acetate | (Z)-2-Heptadecenal |
| (E,Z)-4,7-Tridecadienyl acetate | (E)-8-Heptadecen-1-ol |
| (Z,Z)-4,7-Tridecadien-1-ol | (E)-8-Heptadecenyl acetate |
| (Z,Z)-4,7-Tridecadienyl acetate | (Z)-8-Heptadecen-1-ol |
| (E,Z)-5,9-Tridecadienyl acetate | (Z)-9-Heptadecenal |
| (Z,E)-5,9-Tridecadienyl acetate | (E)-10-Heptadecenyl acetate |
| (Z,Z)-5,9-Tridecadienyl acetate | (Z)-11-Heptadecen-1-ol |
| (Z,Z)-7,11-Tridecadienyl acetate | (Z)-11-Heptadecenyl acetate |
| (E,Z,Z)-4,7,10-Tridecatrienyl acetate | (E,E)-4,8-Heptadecadienyl acetate |
| (E)-3-Tetradecen-1-ol | (Z,Z)-8,10-Heptadecadienyl acetate |
| (E)-3-Tetradecenyl acetate | (Z,Z)-8,11-Heptadecadienyl acetate |
| (Z)-3-Tetradecen-1-ol | (E)-2-Octadecenyl acetate |
| (Z)-3-Tetradecenyl acetate | (E)-2-Octadecenal |
| (E)-5-Tetradecen-1-ol | (Z)-2-Octadecenyl acetate |
| (E)-5-Tetradecenyl acetate | (Z)-2-Octadecenal |
| (E)-5-Tetradecenal | (E)-9-Octadecen-1-ol |
| (Z)-5-Tetradecen-1-ol | (E)-9-Octadecenyl acetate |
| (Z)-5-Tetradecenyl acetate | (E)-9-Octadecenal |
| (Z)-5-Tetradecenal | (Z)-9-Octadecen-1-ol |
| (E)-6-Tetradecenyl acetate | (Z)-9-Octadecenyl acetate |
| (Z)-6-Tetradecenyl acetate | (Z)-9-Octadecenal |
| (E)-7-Tetradecen-1-ol | (E)-11-Octadecen-1-ol |
| (E)-7-Tetradecenyl acetate | (E)-11-Octadecenal |
| (Z)-7-Tetradecen-1-ol | (Z)-11-Octadecen-1-ol |
| (Z)-7-Tetradecenyl acetate | (Z)-11-Octadecenyl acetate |
| (Z)-7-Tetradecenal | (Z)-11-Octadecenal |
| (E)-8-Tetradecenyl acetate | (E)-13-Octadecenyl acetate |
| (Z)-8-Tetradecen-1-ol | (E)-13-Octadecenal |
| (Z)-8-Tetradecenyl acetate | (Z)-13-Octadecen-1-ol |
| (Z)-8-Tetradecenal | (Z)-13-Octadecenyl acetate |
| (E)-9-Tetradecen-1-ol | (Z)-13-Octadecenal |
| (E)-9-Tetradecenyl acetate | (E)-14-Octadecenal |
| (Z)-9-Tetradecen-1-ol | (E,Z)-2,13-Octadecadien-1-ol |
| (Z)-9-Tetradecenyl acetate | (E,Z)-2,13-Octadecadienyl acetate |

TABLE 4-continued

C$_6$-C$_{20}$ Linear Pheromones

| Name | Name |
|---|---|
| (Z)-9-Tetradecenal | (E,Z)-2,13-Octadecadienal |
| (E)-10-Tetradecenyl acetate | (Z,E)-2,13-Octadecadienyl acetate |
| (Z)-10-Tetradecenyl acetate | (Z,Z)-2,13-Octadecadien-1-ol |
| (E)-11-Tetradecen-1-ol | (Z,Z)-2,13-Octadecadienyl acetate |
| (E)-11-Tetradecenyl acetate | (E,E)-3,13-Octadecadienyl acetate |
| (E)-11-Tetradecenal | (E,Z)-3,13-Octadecadienyl acetate |
| (Z)-11-Tetradecen-1-ol | (E,Z)-3,13-Octadecadienal |
| (Z)-11-Tetradecenyl acetate | (Z,E)-3,13-Octadecadienyl acetate |
| (Z)-11-Tetradecenal | (Z,Z)-3,13-Octadecadienyl acetate |
| (E)-12-Tetradecenyl acetate | (Z,Z)-3,13-Octadecadienal |
| (Z)-12-Tetradecenyl acetate | (E,E)-5,9-Octadecadien-1-ol |
| (E,E)-2,4-Tetradecadienal | (E,E)-5,9-Octadecadienyl acetate |
| (E,E)-3,5-Tetradecadienyl acetate | (E,E)-9,12-Octadecadien-1-ol |
| (E,Z)-3,5-Tetradecadienyl acetate | (Z,Z)-9,12-Octadecadienyl acetate |
| (Z,E)-3,5-Tetradecadienyl acetate | (Z,Z)-9,12-Octadecadienal |
| (E,Z)-3,7-Tetradecadienyl acetate | (Z,Z)-11,13-Octadecadienal |
| (E,Z)-3,8-Tetradecadienyl acetate | (E,E)-11,14-Octadecadienal |
| (E,Z)-4,9-Tetradecadienyl acetate | (Z,Z)-13,15-Octadecadienal |
| (E,Z)-4,9-Tetradecadienal | (Z,Z,Z)-3,6,9-Octadecatrienyl acetate |
| (E,Z)-4,10-Tetradecadienyl acetate | (E,E,E)-9,12,15-Octadecatrien-1-ol |
| (E,E)-5,8-Tetradecadienal | (Z,Z,Z)-9,12,15-Octadecatrienyl acetate |
| (Z,Z)-5,8-Tetradecadien-1-ol | (Z,Z,Z)-9,12,15-Octadecatrienal |
| (Z,Z)-5,8-Tetradecadienyl acetate | (Z,E)-9,11-Tetradecadien-1-ol |
| (Z,Z)-5,8-Tetradecadienal | (Z,E)-9,11-Tetradecadienyl acetate |
| (E,E)-8,10-Tetradecadien-1-ol | (Z,E)-9,11-Tetradecadienal |
| (E,E)-8,10-Tetradecadienyl acetate | (Z,Z)-9,11-Tetradecadien-1-ol |
| (E,E)-8,10-Tetradecadienal | (Z,Z)-9,11-Tetradecadienyl acetate |
| (E,Z)-8,10-Tetradecadienyl acetate | (Z,Z)-9,11-Tetradecadienal |
| (E,Z)-8,10-Tetradecadienal | (E,E)-9,12-Tetradecadienyl acetate |
| (Z,E)-8,10-Tetradecadien-1-ol | (Z,E)-9,12-Tetradecadien-1-ol |
| (Z,E)-8,10-Tetradecadienyl acetate | (Z,E)-9,12-Tetradecadienyl acetate |
| (Z,Z)-8,10-Tetradecadienal | (Z,E)-9,12-Tetradecadienal |
| (E,E)-9,11-Tetradecadienyl acetate | (Z,Z)-9,12-Tetradecadien-1-ol |
| (E,Z)-9,11-Tetradecadienyl acetate | (Z,Z)-9,12-Tetradecadienyl acetate |

In some aspects, one or more pheromones that can be produced using a recombinant microorganism of the disclosure include at least one pheromone listed in Table 5 to modulate the behavior of an insect listed in Table 5. In other aspects, non-limiting examples of insect pheromones which can be produced using the recombinant microorganisms and methods disclosed herein include alcohols, aldehydes, and acetates listed in Table 5. However, the microorganisms described herein are not limited to the production of C$_6$-C$_{20}$ pheromones listed in Table 4 and Table 5. Rather, the disclosed microorganisms can also be utilized in the synthesis of various C$_6$-C$_{24}$ mono- or poly-unsaturated fatty acids, alcohols, aldehydes, and acetates, including fragrances, flavors, and polymer intermediates.

TABLE 5

Exemplary pheromones that can be produced using recombinant microorganisms and methods of the present disclosure.

| Name | Structure | Example of Biological importance |
|---|---|---|
| (Z)-3-hexen-1-ol | HO∼∼=∼ | See, Sugimoto et al. (2014) |
| (Z)-3-nonen-1-ol | HO∼∼=∼∼∼ | West Indian Fruity Fly male sex pheromone |
| (Z)-5-decen-1-ol | HO∼∼∼=∼∼ | |
| (Z)-5-decenyl acetate | AcO∼∼∼=∼∼ | *Agrotis segetum* sex pheromone component |
| (E)-5-decen-1-ol | HO∼∼∼=∼∼ | *Anarsia lineatella* sex pheromone component |
| (E)-5-decenyl acetate | AcO∼∼∼=∼∼ | *Anarsia lineatella* sex pheromone component |
| (Z)-7-dodecen-1-ol | HO∼∼∼∼=∼∼ | |

TABLE 5-continued

Exemplary pheromones that can be produced using recombinant microorganisms and methods of the present disclosure.

| Name | Structure | Example of Biological importance |
|---|---|---|
| (Z)-7-dodecenyl acetate | 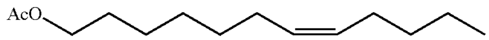 | *Pseudoplusia includens* sex pheromone<br>*Agrotis segetum* sex pheromone component |
| (E)-8-dodecen-1-ol | 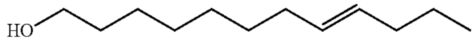 | Citrus Fruit Moth sex pheromone |
| (E)-8-dodecenyl acetate | 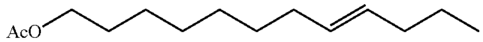 [SMILES: CCC/C=C/CCCCCCCOC(C)=O] | *Grapholitha molesta, Ecdytolopha aurantiana* sex pheromone component |
| (Z)-8-dodecen-1-ol | 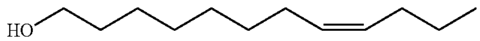 | *Grapholitha molesta, Ecdytolopha aurantiana* sex pheromone component |
| (Z)-8-dodecenyl acetate | 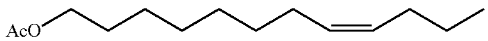 [SMILES: CCC/C=C\CCCCCCCOC(C)=O] | *Grapholitha molesta* sex pheromone component |
| (Z)-9-dodecen-1-ol | 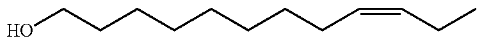 | |
| (Z)-9-dodecenyl acetate | 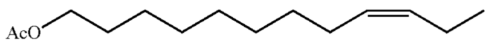 [SMILES: CC/C=C\CCCCCCCCOC(C)=O] | *Eupoecilia ambiguella* sex pheromone |
| (E,E)-8,10-dodecadien-l-ol | 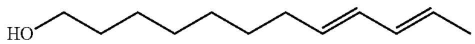 | *Cydia pomonella* |
| (7E,9Z)-dodecadienyl acetate | 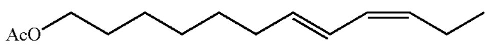 [SMILES: CC/C=C\C=C\CCCCCCOC(C)=O] | *Lobesia botrana* |
| (Z)-9-tetradecen-1-ol | 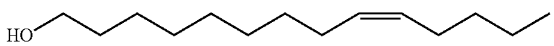 | |
| (Z)-9-tetradecenyl acetate | 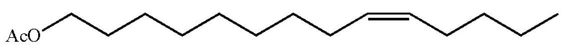 [SMILES: CCCC/C=C\CCCCCCCCOC(C)=O] | *Pandemis pyrusana, Naranga aenescens, Agrotis segetum* sex pheromone component |
| (Z)-11-tetradecen-l-ol | 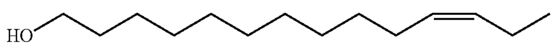 | |
| (Z)-11-tetradecenyl acetate | 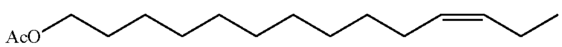 [SMILES: CC/C=C\CCCCCCCCCCOC(C)=O] | *Pandemis pyrusana, Choristoneura roseceana* sex pheromone component |
| (E)-11-tetradecen-l-ol | 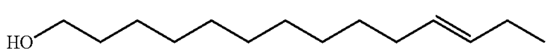 | |
| (E)-11-tetradecenyl acetate | 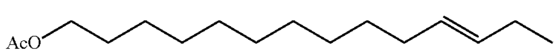 [SMILES: CC/C=C/CCCCCCCCCCOC(C)=O] | *Choristoneura roseceana, Crocidolomia pavonana* sex pheromone component |
| (Z)-7-hexadecen-1-ol | 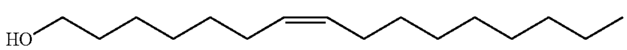 | |
| (Z)-7-hexadecenal | 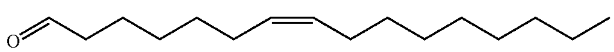 [SMILES: CCCCCCCC/C=C\CCCCCC=O] | *Diatraea considerata* sex pheromone component |
| (Z)-9-hexadecen-1-ol | 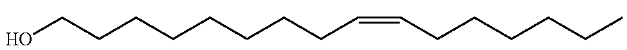 | |
| (Z)-9-hexadecenal | 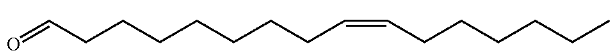 [SMILES: CCCCCC/C=C\CCCCCCCC=O] | *Helicoverpa zea, Helicoverpa armigera,* Heliothis virescens sex pheromone component |
| (Z)-9-hexadecenyl acetate | 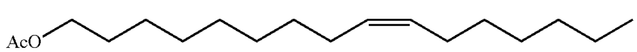 [SMILES: CCCCCC/C=C\CCCCCCCCOC(C)=O] | *Naranga aenescens* sex pheromone component |
| (Z)-11-hexadecen-l-ol | 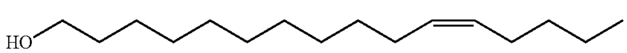 [SMILES: CCCC/C=C\CCCCCCCCCCO] | |

TABLE 5-continued

Exemplary pheromones that can be produced using recombinant microorganisms and methods of the present disclosure.

| Name | Structure | Example of Biological importance |
|---|---|---|
| (Z)-11-hexadecenal | 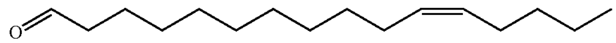 [SMILES: CCCC/C=C\CCCCCCCCCC=O] | *Platyptila carduidactyla, Heliothis virescens* sex pheromone *Helicoverpa zea, Helicoverpa armigera, Plutella xylostella, Diatraea considerate, Diatraea grandiosella, Diatraea saccharalis, Acrolepiopsis assectella* sex pheromone component |
| (Z)-11-hexadecenyl acetate | 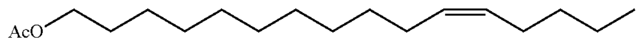 [SMILES: CCCC/C=C\CCCCCCCCCCOC(C)=O] | *Discestra trifolii* sex pheromone *Heliothis virescens, Plutella xylostella, Acrolepiopsis assectella, Crocidolomia pavonana, Naranga aenescens* sex pheromone component |
| (Z,Z)-11,13-hexadecadienal | 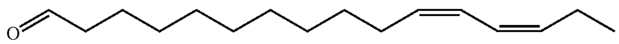 [SMILES: CC/C=C\C=C/CCCCCCCCCC=O] | *Amyelosis transitella* |
| (Z,Z)-11,13-hexadecadien-1-ol | | *Amyelosis transitella* |
| (11Z,13E)-hexadecadien-1-ol | | *Amyelosis transitella* |
| (9Z,11E)-hexadecadienal | 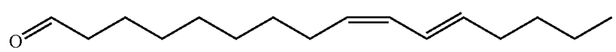 [SMILES: CCCC/C=C/C=C\CCCCCCCC=O] | |
| (Z)-13-octadecen-1-ol | 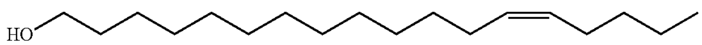 [SMILES: CCCC/C=C\CCCCCCCCCCCCO] | |
| (Z)-13-octadecenal | 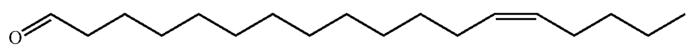 [SMILES: CCCC/C=C\CCCCCCCCCCCC=O] | *Diatraea considerata, Diatraea grandiosella* sex pheromone component |
| (Z,Z,Z,Z,Z)-3,6,9,12,15-tricosapentaene | 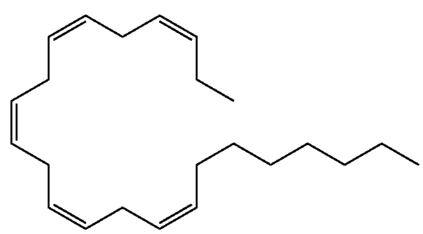 [SMILES: CC/C=C\C/C=C\C/C=C\C/C=C\C/C=C\CCCCCCC] | *Amyelosis transitella* |

Most pheromones comprise a hydrocarbon skeleton with the terminal hydrogen substituted by a functional group (Ryan MF (2002). Insect Chemoreception. Fundamental and Applied. Kluwer Academic Publishers). Table 6 shows some common functional groups, along with their formulas, prefixes and suffixes. The presence of one or more double bonds, generated by the loss of hydrogens from adjacent carbons, determines the degree of unsaturation of the molecule and alters the designation of a hydrocarbon from -ane (no multiple bonds) to -ene. The presence of two and three double bonds is indicated by ending the name with -diene and -triene, respectively. The position of each double bond is represented by a numeral corresponding to that of the carbon from which it begins, with each carbon numbered from that attached to the functional group. The carbon to which the functional group is attached is designated -1-. Pheromones may have, but are not limited to, hydrocarbon chain lengths numbering 10 (deca-), 12 (dodeca-), 14 (tetradeca-), 16 (hexadeca-), or 18 (octadeca-) carbons long. The presence of a double bond has another effect. It precludes rotation of the molecule by fixing it in one of two possible configurations, each representing geometric isomers that are different molecules. These are designated either E (from the German word Entgegen, opposite) or Z (Zusammen, together), when the carbon chains are connected on the opposite (trans) or same (cis) side, respectively, of the double bond.

TABLE 6

Prefixes and suffixes for common functional groups

| Functional group | Formula | Prefix | Suffix |
|---|---|---|---|
| Alcohol | —OH | Hydroxy- | -ol |
| Aldehyde | —CH=O | Formyl- | -al |
| Amine | —NH$_2$ | Amino- | -amine |
| Carboxylic acid | —COOH | Carboxy- | -oic acid |
| Ester | —COOR | R-oxycarbonyl- | -R-oate |
| Ketone | >C=O | Oxo- | -one| |

From Howse, PE, Stevens, IDR and Jones, OT (1998). Insect pheromones and their use in pest management. London: Chapman and Hall.

Pheromones described herein can be referred to using IUPAC nomenclature or various abbreviations or variations known to one skilled in the art. For example, (11Z)-hexadecen-1-al, can also be written as Z-11-hexadecen-1-al, Z-11-hexadecenal, or Z-x-y:Ald, wherein x represents the position of the double bond and y represents the number of carbons in the hydrocarbon skeleton. Abbreviations used herein and known to those skilled in the art to identify functional groups on the hydrocarbon skeleton include "Ald," indicating an aldehyde, "OH," indicating an alcohol, and "Ac," indicating an acetyl. Also, the number of carbons in the chain can be indicated using numerals rather than using the written name. Thus, as used herein, an unsaturated carbon chain comprised of sixteen carbons can be written as hexadecene or 16.

Similar abbreviation and derivations are used herein to describe pheromone precursors. For example, the fatty acyl-CoA precursors of (11Z)-hexadecen-1-al can be identified as (11Z)-hexadecenyl-CoA or Z-11-16:Acyl-CoA.

The present disclosure relates to recombinant microorganisms expressing one or more enzyme or transporter that contributes to improved production of biomass or one or more lipid. The present disclosure also relates to recombinant microorganisms comprising downregulation of one or more enzyme in one or more pathways that contributes to improved production of biomass or one or more lipid.

Isocitrate Dehydrogenase

In some embodiments, the present disclosure teaches microorganisms comprising an AMP-deficient isocitrate dehydrogenase (IDH). IDH catalyzes the oxidation of iso-citrate to oxalosuccinate in the TCA pathway. In many microorganisms, including *Y. lipolytica*, IDH is an allosteric enzyme, sensitive to AMP levels. Under non-optimal growTH conditions, such as nitrogen deprivation, AMP levels are reduced by AMP deaminase (AMD1), thus reducing IDH activity. IDH enzymes produce NADPH/NADH, which are important for native fatty acid synthesis and for methyl palmitate desaturation. Thus in some embodiments, the recombinant microorganisms of the present disclosure exhibit improved lipid production from fatty acid precursors, in part, because they comprise a nucleic acid encoding for an AMP-deficient IDH enzyme.

The present disclosure describes enzymes that catalyze the oxidative decarboxylation of isocitrate, producing alpha-ketoglutarate (α-ketoglutarate) and $CO_2$. This is a two-step process, which involves oxidation of isocitrate (a secondary alcohol) to oxalosuccinate (a ketone), followed by the decarboxylation of the carboxyl group beta to the ketone, forming alpha-ketoglutarate.

Isocitrate dehydrogenase can catalyze the following reactions:

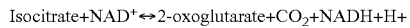

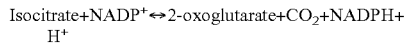

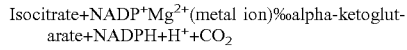

The isocitrate dehydrogenase (IDH) enzyme structure in *Escherichia coli* was the first structure to be elucidated and understood. Most isocitrate dehydrogenases are dimers, to be specific, homodimers (two identical monomer subunits forming one dimeric unit).

Isocitrate dehydrogenase is the first bacterial enzyme shown to be regulated by phosphorylation/dephosphorylation. The modulation of this key enzyme activity enables *E. coli* to make rapid shifts between TCA and glyoxalate bypass pathways. Fluxes and intercellular concentrations for this junction have been determined. The state of phosphorylation of isocitrate dehydrogenase determines its activity.

There are marked differences in the properties of enzymes from different sources. The *E. coli* enzyme is not an allosteric protein as isocitrate dehydrogenases from other sources are, and it is cold sensitive. IcdA is observed to have several distinct isoforms. Phosphorylation of the enzyme on a serine residue by isocitrate dehydrogenase kinase/phosphatase inactivates it, and dephosphorylation by the phosphatase reactivates it. Phosphorylation affects the binding of NADP. The enzyme shows allosteric inhibition by phosphoenolpyruvate.

In some embodiments, the one or more modifications associated with tricarboxylic acid cycle comprises the overexpression of at least one endogenous and/or exogenous nucleic acid molecule encoding an AMP-insensitive isocitrate dehydrogenase (IDH) variant in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli*, *Mycobacterium smegmatis*, *Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2. In some embodiments, the one or more modifications associated with tricarboxylic acid cycle results in extended activation of the tricarboxylic acid cycle.

In some embodiments, the one or more modifications associated with reducing equivalent availability comprises the overexpression of at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli*, *Mycobacterium smegmatis*, *Acidithiobacillus thiooxidans*, or *Yarrowia lipolytica*. In further embodiments, the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

Pyruvate Transporter

Pyruvate is the end-product of glycolysis, a major substrate for oxidative metabolism, and a branching point for glucose, lactate, fatty acid and amino acid synthesis. The mitochondrial enzymes that metabolize pyruvate are physically separated from cytosolic pyruvate pools and rely on a membrane transport system to shuttle pyruvate across the impermeable inner mitochondrial membrane (IMM). Two proteins, mitochondrial pyruvate carriers MPC1 and MPC2, form a hetero-oligomeric complex in the IMM to facilitate pyruvate transport.

In some embodiments, the one or more modifications associated with comprising tricarboxylic acid cycle or one or more metabolic intermediates availability comprises the overexpression of at least one endogenous and/or exogenous nucleic acid molecule encoding a pyruvate transporter in the recombinant microorganism. In other embodiments, the one or more metabolic intermediates availability comprises mitochondrial pyruvate availability. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to pyruvate transporter from *Saccharomyces cerevisiae, Hanseniaspora osmophila, Yarrowia lipolytica*, or *Talaromyces marneffei* PM1. In further embodiments, the pyruvate transporter is selected from *Saccharomyces cerevisiae* mpc1, *Saccharomyces cerevisiae* mpc3 (NP_011759.1), *Hanseniaspora osmophila* mpc3 (OEJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia lipolytica*.

Aconitase

Aconitase (aconitate hydratase) is an enzyme that catalyzes the stereo-specific isomerization of citrate to isocitrate via cis-aconitate in the tricarboxylic acid cycle, a non-redox-active process.

Aconitase has two slightly different structures, depending on whether it is activated or inactivated. In the inactive form, its structure is divided into four domains. Counting from the N-terminus, only the first three of these domains are involved in close interactions with the [3Fe-4S] cluster, but the active site consists of residues from all four domains, including the larger C-terminal domain. The Fe—S cluster and a $SO_4^{2-}$ anion also reside in the active site. When the enzyme is activated, it gains an additional iron atom, creating a [4Fe-4S] cluster. However, the structure of the rest of the enzyme is nearly unchanged.

In contrast with the majority of iron-sulfur proteins that function as electron carriers, the iron-sulfur cluster of aconitase reacts directly with an enzyme substrate. Aconitase has an active [Fe4S4]2+ cluster, which may convert to an inactive [Fe3S4]+ form. Three cysteine (Cys) residues have been shown to be ligands of the [Fe4S4] center. In the active state, the labile iron ion of the [Fe4S4] cluster is not coordinated by Cys but by water molecules.

The iron-responsive element-binding protein (IRE-BP) and 3-isopropylmalate dehydratase (α-isopropylmalate isomerase), an enzyme catalyzing the second step in the biosynthesis of leucine, are known aconitase homologues. Iron regulatory elements (IREs) constitute a family of 28-nucleotide, non-coding, stem-loop structures that regulate iron storage, heme synthesis and iron uptake. They also participate in ribosome binding and control the mRNA turnover (degradation). The specific regulator protein, the IRE-BP, binds to IREs in both 5' and 3' regions, but only to RNA in the apo form, without the Fe—S cluster. Expression of IRE-BP in cultured cells has revealed that the protein functions either as an active aconitase, when cells are iron-replete, or as an active RNA-binding protein, when cells are iron-depleted. Mutant IRE-BPs, in which any or all of the three Cys residues involved in Fe—S formation are replaced by serine, have no aconitase activity, but retain RNA-binding properties.

Aconitase is inhibited by fluoroacetate, therefore fluoroacetate is poisonous. Fluoroacetate, in the citric acid cycle, can innocently enter as fluorocitrate. However, aconitase cannot bind this substrate and thus the citric acid cycle is halted. The iron sulfur cluster is highly sensitive to oxidation by superoxide.

In some embodiments, the one or more modifications associated with reducing equivalent availability further comprises the overexpression of at least one endogenous and/or exogenous nucleic acid encoding an aconitase in the cytosol of the recombinant microorganism. In certain embodiments, the at least one endogenous and/or exogenous nucleic acid molecule encoding the aconitase lack a sequence encoding a mitochondrial-targeting peptide.

Citrate Transporter

Citrate is a key intermediate in both catabolism and anabolism and thus occupies a prominent position in eukaryotic energy metabolism. When the cell has excess energy, citrate is transported out of the mitochondrial matrix across the inner membrane via the mitochondrial citrate transport protein (CTP). Citrate can then passively diffuse through an anion selective channel across the outer mitochondrial membrane into the cytoplasm. Once in the cytoplasm, citrate is broken down to acetyl CoA and oxaloacetate, the former providing the immediate carbon source to fuel fatty acid, triacylglycerol, and cholesterol biosyntheses.

The mitochondrial CTP catalyzes an obligatory exchange of tricarboxylates (i.e., citrate, isocitrate) either for each other or for the dicarboxylate malate or for phosphoenolpyruvate. In higher eukaryotes the transporter catalyzes citrate/malate exchange with citrate moving outwardly across the inner membrane. In yeast, the CTP is thought to catalyze a citrate/isocitrate exchange. In both cases, the CTP catalyzes a facilitated-diffusion with dianions being the transported species. The CTP is a member of the mitochondrial transporter family. Most members of this family display several common characteristics including: a size of approximately 300 amino acids and a basic isoelectric point, the presence of 3 homologous sequence domains, and a signature sequence motif of Px(D,E)x(V,I,A,M)(K,R)x(R,K,Q,A)(L,M,F,I) which repeats two-three times.

In some embodiments, the one or more modifications associated with reducing equivalent availability or one or more metabolic intermediates availability comprises the overexpression of at least one endogenous and/or exogenous nucleic acid encoding a citrate transporter in the recombinant microorganism. In certain embodiments, the one or more metabolic intermediates availability comprises cytosolic citrate/isocitrate. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a citrate transporter from *Yarrowia lipolytica, Saccharomyces cerevisiae, Rattus norvegicus, Caenorhabditis elegans*, or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

Decarboxylating Malic Enzyme

In some embodiments, the present disclosure teaches recombinant microorganisms comprising a nucleic acid encoding for a heterologous malic enzyme. In some embodiments, the recombinant microorganisms of the present disclosure exhibit improved production of lipids from fatty acid substrates. In some embodiments, the recombinant microorganisms of the present disclosure exhibit improved Z11-16 acid selectivity.

Figure 4:
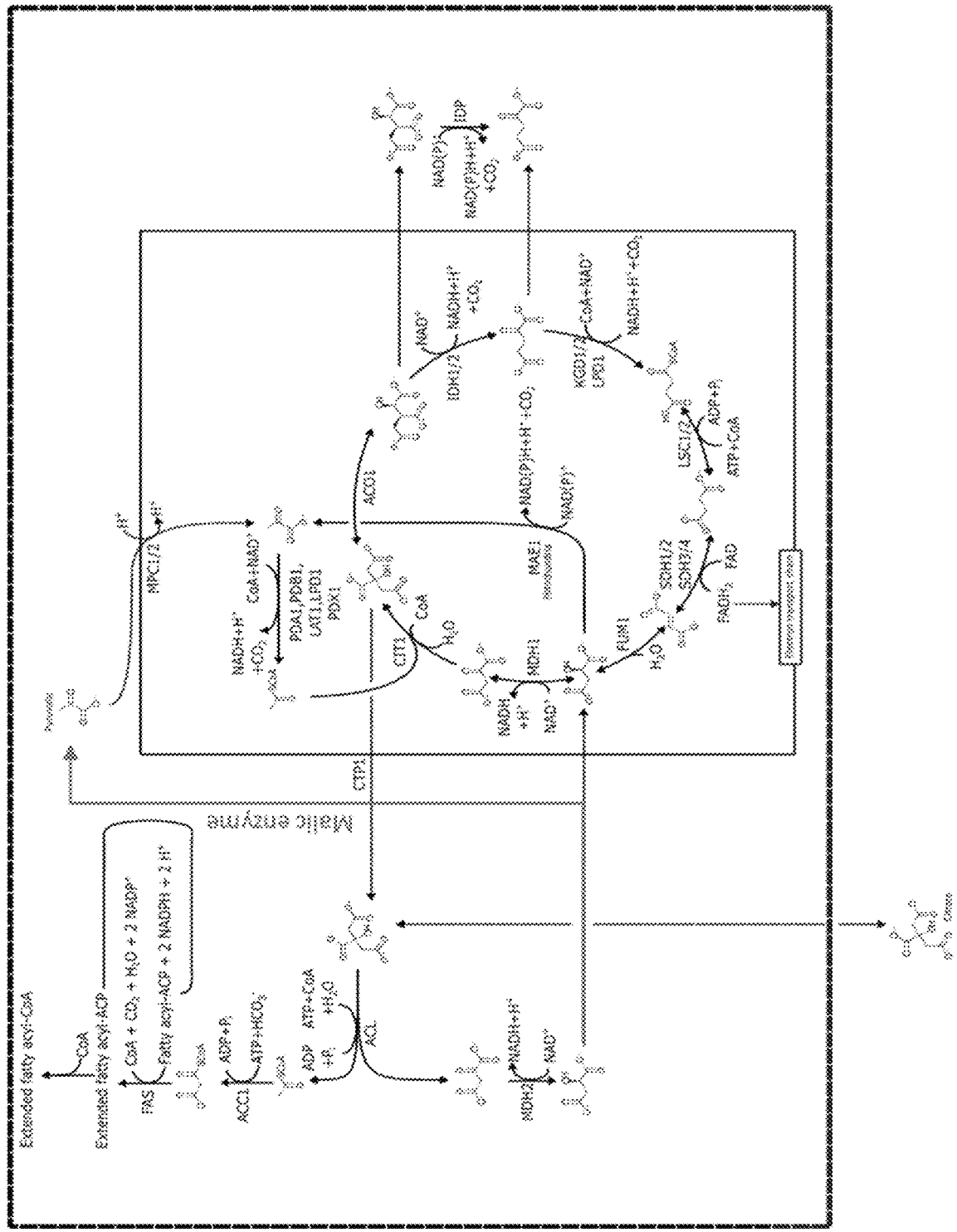
FIG. 4 shows a TCA cycle, citrate shuttle, and FAS pathway diagram. Citrate overflow from the TCA cycle is transported into the cytoplasm and ultimately from the cell. Overexpression of cytosolic decarboxylating malic enzyme can harness citrate derived s-malate to produce pyruvate while supplying cofactor for lipogenesis (NADP$^+$ dependent malic enzyme) or desaturation (NAD$^+$ dependent malic enzyme).

Microorganisms of the present disclosure produce citrate as co-product under nitrogen-limited conditions. This is because during nitrogen starvation many organisms, including *Y. lipolytica* down-regulate respiration to divert carbon/energy storage via lipid synthesis. Citrate is first exported from mitochondria into the cytosol and subsequently from the cell. Exported citrate can be re-assimilated, especially when alternative carbon sources are scarce. Alternatively, the combination of the enzymes ATP citrate lyase (ACL), malate dehydrogenase (e.g., MDH2) and cytosolic malic enzyme can turn cytosolic citrate into pyruvate, to feed back into the TCA cycle to feed further lipid synthesis (FIG. 4). Many organisms, including *Y. lipolytica* however, do not express a cytosolic malic enzyme.

The inventors further hypothesized that expression of a heterologous NADP+ dependent cytosolic malic enzyme may increase fatty acid production if the primary rate limitation is cofactor supply. Surprisingly, the inventors also discovered that expression of a heterologous malic enzyme improved the Z11-16 acid selectivity of the recombinant microorganisms.

Malate dehydrogenase (decarboxylating) or NAD-malic enzyme (NAD-ME) is an enzyme that catalyzes the chemical reaction:

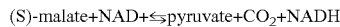

(S)-malate+NAD+⇌pyruvate+$CO_2$+NADH

Thus, the two substrates of this enzyme are (S)-malate and NAD+, whereas its three products are pyruvate, $CO_2$, and NADH. Malate is oxidized to pyruvate and $CO_2$, and NAD+ is reduced to NADH.

This enzyme belongs to the family of oxidoreductases, to be specific, those acting on the CH—OH group of donor with NAD+ or NADP+ as acceptor. The systematic name of this enzyme class is (S)-malate:NAD+ oxidoreductase (decarboxylating). This enzyme participates in pyruvate metabolism and carbon fixation. NAD-malic enzyme is one of three decarboxylation enzymes used in the inorganic carbon concentrating mechanisms of C4 and CAM plants. The others are NADP-malic enzyme and PEP carboxykinase.

In some embodiments, the one or more modifications associated with reducing equivalent availability comprises the overexpression of at least one exogenous nucleic acid molecule encoding a decarboxylating malic enzyme in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a decarboxylating malic enzyme from *Arabidopsis thaliana, Amaranthus hypochondriacus, Rhizobium meliloti, Solanum tuberosum, Homo sapiens*, or *Escherichia coli*. In further embodiments, the decarboxylating malic enzyme is selected from *Arabidopsis thaliana* Q9SIU0, *Amaranthus hypochondriacus* P37224, *Rhizobium meliloti* O30807, *Solanum tuberosum* P37221, *Homo sapiens* Q16798, and *Escherichia coli* P26616, or homolog thereof. In yet a further embodiment, the decarboxylating malic enzyme lacks a sequence encoding a mitochondrial-targeting peptide.

ATP-Citrate Lyase

ATP citrate lyase is an enzyme that represents an important step in fatty acid biosynthesis. ATP citrate lyase is important in that, by converting citrate to acetyl CoA, it links the metabolism of carbohydrates, which yields citrate as an intermediate, and the production of fatty acids, which requires acetyl CoA. ATP-citrate lyase is responsible for catalyzing the conversion of citrate and CoA into acetyl-CoA and oxaloacetate, along with the hydrolysis of ATP.

ATP citrate lyase is the primary enzyme responsible for the synthesis of cytosolic acetyl-CoA in many tissues. The enzyme is a tetramer of apparently identical subunits. The product, acetyl-CoA, serves several important biosynthetic pathways, including lipogenesis and cholesterogenesis. It is activated by insulin.

In some embodiments, the one or more modifications associated with one or more metabolic intermediates availability comprises the overexpression of at least one endogenous and/or exogenous nucleic acid encoding an ATP-citrate lyase in the recombinant microorganism. In certain embodiments, the one or more metabolic intermediates availability comprises cytosolic oxaloacetate availability. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

Hexose Transporter

The hexose transporters belong to a transporter superfamily termed the major facilitator superfamily. The members of this superfamily include a variety of sugar transporters and transporters of other carbon compounds in eukaryotes as well as prokaryotes. The yeast hexose transporters form a subfamily. Twenty hexose transporter proteins are found in *S. cerevisiae*.

Glucose-dependent modulation of the affinity of glucose transport in wild-type cells can depend upon a number of factors, including the regulation of expression of various sets of Hxtp proteins with significantly different affinities to the sugar, the removal and inactivation of transporter proteins under certain conditions, the modulation of the affinity of specific transporters and, possibly, interactions between the different transporter proteins.

In some embodiments, the one or more modifications associated with reducing equivalent availability comprises decoupling and increasing glucose uptake in the recombinant microorganism. In certain embodiments, decoupling and increasing glucose uptake comprises: upregulation of hexose transporter activity. In further embodiments, the upregulation of one or more hexose transporter activity comprises the overexpression of one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof.

Acetyl-CoA Carboxylase

Acetyl-CoA carboxylase 1 catalyzes the carboxylation of acetyl-CoA to malonyl-CoA, the first committed and rate-limiting step in de novo fatty acid biosynthesis. Malonyl-CoA is used as a building block to extend the chain length of fatty acids by fatty acid synthase.

Two isoforms exist in mammals, acetyl-CoA carboxylase 1 and acetyl-CoA carboxylase 2. Both are dimeric, multifunctional enzymes composed of four distinct domains; a biotin carboxylase (BC) domain, a biotin carboxyl carrier protein (BCCP) domain, the ACC central region, and a carboxyltransferase (CT) domain.

The function of ACC is to regulate the metabolism of fatty acids. When the enzyme is active, the product, malonyl-CoA, is produced which is a building block for new fatty acids and can inhibit the transfer of the fatty acyl group from acyl CoA to carnitine with carnitine acyltransferase, which inhibits the beta-oxidation of fatty acids in the mitochondria.

The regulation of mammalian ACC is complex, in order to control two distinct pools of malonyl CoA that direct either the inhibition of beta oxidation or the activation of lipid biosynthesis.

Mammalian ACC1 and ACC2 are regulated transcriptionally by multiple promoters which mediate ACC abundance in response to the cells nutritional status. Activation of gene expression through different promoters results in alternative splicing. The sensitivity to nutritional status results from the control of these promoters by transcription factors such as SREBP1c, controlled by insulin at the transcriptional level, and ChREBP, which increases in expression with high carbohydrates diets.

Through a feedforward loop, citrate allosterically activates ACC. Citrate may increase ACC polymerization to increase enzymatic activity. Other allosteric activators include glutamate and other dicarboxylic acids. Long and short chain fatty acyl CoAs are negative feedback inhibitors of ACC.

Phosphorylation can result when the hormones glucagon or epinephrine bind to cell surface receptors, but the main cause of phosphorylation is due to a rise in AMP levels when the energy status of the cell is low, leading to the activation of the AMP-activated protein kinase (AMPK). AMPK is the main kinase regulator of ACC, able to phosphorylate a number of serine residues on both isoforms of ACC. On ACC1, AMPK phosphorylates Ser79, Ser1200, and Ser1215. Protein kinase A also has the ability to phosphorylate ACC, with a much greater ability to phosphorylate ACC2 than ACC1. Researchers hypothesize there are other ACC kinases important to its regulation as there are many other possible phosphorylation sites on ACC.

When insulin binds to its receptors on the cellular membrane, it activates a phosphatase enzyme called protein phosphatase 2A (PP2A) to dephosphorylate the enzyme, thereby removing the inhibitory effect. Furthermore, insulin induces a phosphodiesterase that lowers the level of cAMP in the cell, thus inhibiting PKA, and also inhibits AMPK directly.

In some embodiments, the one or more modifications associated with lipid synthesis comprises alleviation of acetyl-CoA carboxylase (ACC) inhibition. In certain embodiments, alleviation of ACC inhibition comprises the replacement of the endogenous ACC, or overexpression of at least one endogenous and/or exogenous nucleic acid molecule encoding a feedback-insensitive ACC variant in the recombinant microorganism. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to ACC from *Mus musculus*, *Rattus norvegicus*, or *Homo sapiens*.

In some embodiments, the one or more modifications associated with reducing equivalent availability, one or more metabolic intermediates availability, or increased product purity comprises downregulation or inhibition of acetyl-CoA carboxylase (ACC) activity in the recombinant microorganism. In certain embodiments, the downregulation or inhibition of ACC activity comprises deletion, disruption, and/or mutation of one or more endogenous gene encoding one or more ACC enzyme.

Hexose Kinase

A hexose kinase is an enzyme that phosphorylates hexoses (six-carbon sugars), forming hexose phosphate. In most organisms, glucose is the most important substrate of hexose kinases, and glucose-6-phosphate is the most important product. Hexose kinase also possesses the ability of transferring an inorganic phosphate group from ATP to a substrate.

They are categorized as actin fold proteins, sharing a common ATP binding site core that is surrounded by more variable sequences which determine substrate affinities and other properties.

Most bacterial hexose kinases are approximately 50 kD in size. Multicellular organisms such as plants and animals often have more than one hexose kinase isoform. Most are about 100 kD in size and consist of two halves (N and C terminal), which share much sequence homology.

By catalyzing the phosphorylation of glucose to yield glucose 6-phosphate, hexose kinases maintain the downhill concentration gradient that favors the facilitated transport of glucose into cells. This reaction also initiates all physiologically relevant pathways of glucose utilization, including glycolysis and the pentose phosphate pathway. The addition of a charged phosphate group at the 6-position of hexoses also ensures 'trapping' of glucose and 2-deoxyhexose glucose analogs (e.g. 2-deoxyglucose, and 2-fluoro-2-deoxyglucose) within cells, as charged hexose phosphates cannot easily cross the cell membrane.

In some embodiments, the one or more modifications associated with reducing equivalent availability comprises one or more modifications in the pentose phosphate pathway (PPP) in the recombinant microorganism. In certain embodiments, one or more modifications in the PPP comprises downregulation of hexose kinase activity. In yet a further embodiment, the downregulation of hexose kinase activity comprises deletion, disruption, and/or mutation of one or more endogenous gene encoding one or more hexose kinase enzyme.

In some embodiments, the one or more modifications associated with reducing equivalent availability comprises decoupling and increasing glucose uptake in the recombinant microorganism. In certain embodiments, decoupling and increasing glucose uptake comprises downregulation of hexose kinase activity. In some embodiments, the downregulation of hexose kinase activity comprises deletion, disruption, and/or mutation of one or more endogenous gene encoding one or more hexose kinase enzyme.

Fructose-6-Phosphate Kinase

Fructose-6-phosphate kinase (phosphofructokinase) is a kinase enzyme that phosphorylates fructose 6-phosphate in glycolysis.

The enzyme-catalyzed transfer of a phosphoryl group from ATP is an important reaction in a wide variety of biological processes. Fructose-6-phosphate kinase (PFK) catalyzes the phosphorylation of fructose-6-phosphate to fructose-1,6-bisphosphate, a key regulatory step in the glycolytic pathway. It is allosterically inhibited by ATP and allosterically activated by AMP, thus indicating the cell's energetic needs when it undergoes the glycolytic pathway. PFK exists as a homotetramer in bacteria and mammals (where each monomer possesses 2 similar domains) and as an octamer in yeast (where there are 4 alpha-(PFK1) and 4 beta-chains (PFK2), the latter, like the mammalian monomers, possessing 2 similar domains). This protein may use the morpheein model of allosteric regulation.

PFK is about 300 amino acids in length, and structural studies of the bacterial enzyme have shown it comprises two similar (alpha/beta) lobes: one involved in ATP binding and the other housing both the substrate-binding site and the allosteric site.

In some embodiments, the one or more modifications associated with reducing equivalent availability comprises one or more modifications in the pentose phosphate pathway (PPP) in the recombinant microorganism. In certain embodiments, the one or more modifications in the PPP comprises downregulation of fructose-6-phosphate kinase activity. In yet a further embodiment, the downregulation of fructose-6-phosphate kinase activity comprises deletion, disruption, and/or mutation of one or more endogenous gene encoding one or more fructose-6-phosphate kinase enzyme.

NADPH-Dependent Mannitol Dehydrogenase

Mannitol 2-dehydrogenase (NADP+) is an enzyme that catalyzes the chemical reaction:

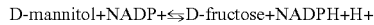

Thus, the two substrates of this enzyme are D-mannitol and NADP+, whereas its 3 products are D-fructose, NADPH, and H+.

This enzyme belongs to the family of oxidoreductases, specifically those acting on the CH—OH group of donor with NAD+ or NADP+ as acceptor. The systematic name of this enzyme class is D-mannitol:NADP+2-oxidoreductase. This enzyme is also called mannitol 2-dehydrogenase (NADP+). This enzyme participates in fructose and mannose metabolism.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an NADPH-dependent mannitol dehydrogenase. In further embodiments, the one or more gene encoding an NADPH-dependent mannitol dehydrogenase is selected from YALI0B16192g, YALI0D18964g, and YALI0E12463g, or homolog thereof Aldo-Keto Reductase Aldo-keto reductases (AKR) comprise a superfamily of structurally-similar proteins that catalyze the NADPH-dependent conversion of various carbonyl compounds into their corresponding alcohol products.

The mannitol synthesis pathway comprises three unique enzymatic steps: (a) isomerization of fructose-6-phosphate to mannose-6-phosphate by mannose-6-phosphate isomerase; (b) reduction of mannose-6-phosphate to mannitol-1-phosphate by mannose-6-phosphate reductase; and (c) dephosphorylation of mannitol-1-phosphate to mannitol by mannitol-1-phosphate phosphatase. Radiotracer studies and kinetic analyses suggest that mannose-6-phosphate reductase, an aldo-keto reductase, plays a regulatory role in this pathway. In *Yarrowia*, a fructose-6-phosphate phosphatase produces fructose which is reduced by mannitol dehydrogenase into mannitol, and NADP.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0000319g, and YALI0A19910g, or homolog thereof.

Pentose Phosphate Pathway

The pentose phosphate pathway (PPP) is a central and widely conserved metabolic pathway of carbohydrate metabolism located in the cytoplasm in eukaryotic cells. This pathway serves two major functions: production of precursors for biosynthesis of macromolecules and production of reducing equivalents in the form of NADPH. Accordingly, these two roles are reflected in the two major phases of the PPP: in the "oxidative phase," glucose 6-phosphate (G6P) is converted into ribulose 5-phosphate (RuSP) through the sequential action of: glucose-6-phosphate dehydrogenase (ZWF1) which converts G6P to 6-phospho D-glucono-1,5-lactone with generation of NADPH; 6-phosphogluconolactonase (SOL3, SOL4) which converts 6-phospho D-glucono-1,5-lactone to D-gluconate 6-phosphate; 6-phosphogluconate dehydrogenase (GND1, GND2) which converts D-gluconate 6-phosphate to RuSP with generation of NADPH. The "non-oxidative phase" carries out the isomerization of RuSP to ribose 5-phosphate (R5P), the epimerization of RuSP to xylulose 5-phosphate (X5P) and, through the actions of transketolase (TKL1, TKL2) and transaldolase (TAL1, NQM1), a series of carbon skeleton transfers that can interconvert pentose phosphate into fructose 6-phosphate (F6P) and glyceraldehyde 3-phosphate (GAP)—both glycolytic intermediates—and erythrose 4-phosphate (E4P). The net effect of the non-oxidative phase is to produce an equilibrium between the pentoses needed for biosynthesis of macromolecules and the hexoses needed for energy management, allowing the two pools of sugars easily to interconvert.

The oxidative branch is considered to be largely irreversible under normal cellular conditions, whilst the non-oxidative branch is reversible. The PPP is not a simple linear pathway since several carbon atoms are recycled back into glycolysis. Furthermore, the enzyme transketolase catalyses two different reactions in the pathway, resulting in the substrates of these reactions being competitive inhibitors of one another. The PPP has three main products: reduced equivalents in the form of NADPH, produced in the oxidative phase, needed in biosynthetic pathways and for maintenance of the oxidative level of cells; RSP, for the biosynthesis of all nucleic acids; and E4P, for biosynthesis of the three aromatic amino acids. Different physiological states require operation of this biochemical network in different modes: in actively growing cells, such as during culture growth in reactors, the pathway must produce a sufficient amount of all three products, since all are required in the construction of new cells. Under stress conditions growth slows and the only product in considerable demand is NADPH.

The inventors hypothesized that the recombinant microorganism's lipid production could further be increased by overexpressing the genes of the upper (oxidative) pentose phosphate pathway (ZWF1, SOL3, and GND1), to increase NADPH supply for fatty acid biosynthesis. Surprisingly, the inventors discovered that upregulation of ZWF1, SOL3, and/or GND1 resulted in improved Z11-16 selectivity in recombinant microorganisms.

Enzymes to Express to Increase Levels of One or More Coenzymes

Nicotinamide adenine dinucleotide (NAD, including NAD+ and NADH) and nicotinamide adenine dinucleotide phosphate (NADP, including NADP+ and NADPH) belong to the fundamental common mediators of various biological processes, including energy metabolism, mitochondrial functions, calcium homeostasis, antioxidation/generation of oxidative stress, gene expression, immunological functions, aging, and cell death: NAD mediates energy metabolism and mitochondrial functions; NADPH is a key component in cellular antioxidation systems; NADH-dependent reactive oxygen species (ROS) generation from mitochondria and NADPH oxidase-dependent ROS generation are two critical mechanisms of ROS generation; cyclic ADP-ribose and several other molecules that are generated from NAD and NADP could mediate calcium homeostasis; NAD and NADP modulate multiple key factors in cell death, such as mitochondrial permeability transition, energy state, poly (ADP-ribose) polymerase-1, and apoptosis-inducing factor; and NAD and NADP profoundly affect aging-influencing factors such as oxidative stress and mitochondrial activities, and NAD-dependent sirtuins also mediate the aging process. Additionally, the in situ regeneration of reduced nicotinamide cofactors (NAD(P)H) is necessary for practical synthesis of many important chemicals in recombinant microorganisms.

In some embodiments, the one or more modifications associated with reducing equivalent availability comprises one or more modifications in the pentose phosphate pathway (PPP) in the recombinant microorganism. In certain embodiments, the one or more modifications in the PPP comprises upregulation of one or more oxidative PPP enzyme activity. In certain embodiments, the one or more modifications in the PPP comprises expression of one or more oxidative PPP enzyme variant. In further embodiments, the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1).

In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent 6-phosphogluconate dehydrogenase (GND1) from *Bradyrhizobium* or *Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

Dehydrogenase

In some embodiments, the recombinant microorganisms of the present disclosure are engineered to reduce or eliminate expression of one or more endogenous fatty alcohol dehydrogenases (i.e. FADH, ADH1, ADH2, ADH3, ADH4, ADH5, ADH6, and ADH7). In some embodiments, the recombinant microorganisms of the present disclosure are engineered comprise deletions of one or more endogenous fatty alcohol dehydrogenases (i.e. FADH, ADH1, ADH2, ADH3, ADH4, ADH5, ADH6, and ADH7). For example, in some embodiments, the recombinant microorganism is a *Y. lipolytica* strain, wherein the recombinant microorganism comprises reduced or eliminated activities of relevant (fatty) alcohol dehydrogenases selected from FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g and/or ADH7: YALI0E07766g.

The present disclosure describes enzymes that catalyze the conversion of a fatty aldehyde to a fatty alcohol in various organisms. In some embodiments, an alcohol dehydrogenase (ADH, Table 6.1) is used to catalyze the conversion of a fatty aldehyde to a fatty alcohol. A number of ADHs identified from alkanotrophic organisms, *Pseudomonas fluorescens* NRRL B-1244 (Hou et al. 1983), *Pseudomonas butanovora* ATCC 43655 (Vangnai and Arp 2001), and *Acinetobacter* sp. strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length Cm and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-ω-fatty acids has been observed (Lu et al. 2010). Recently, two ADHs were characterized from *Geobacillus thermodenitrificans* NG80-2, an organism that degrades $C_{15}$ to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from *Lactobacillus brevis* and coupled cofactor regeneration with isopropanol, Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained *S. cerevisiae* for the conversion of hexanol to hexanal (Presecki et al. 2012) and 2-heptanol to 2-heptanone (Cappaert and Larroche 2004).

TABLE 6.1

Exemplary alcohol dehydrogenase enzymes.

| Organism | Gene Name | Accession No. |
| --- | --- | --- |
| *Bactrocera oleae* (Olive fruit fly) (*Dacus oleae*) | ADH | Q9NAR7 |
| *Cupriavidus necator* (*Alcaligenes eutrophus*) (*Ralstonia eutropha*) | adh | P14940 |
| *Drosophila adiastola* (Fruit fly) (*Idiomyia adiastola*) | Adh | Q00669 |
| *Drosophila affinidisjuncta* (Fruit fly) (*Idiomyia affini disjuncta*) | Adh | P21518 |
| *Drosophila ambigua* (Fruit fly) | Adh | P25139 |
| *Drosophila borealis* (Fruit fly) | Adh | P48584 |
| *Drosophila differens* (Fruit fly) | Adh | P22245 |
| *Drosophila equinoxialis* (Fruit fly) | Adh | Q9NG42 |
| *Drosophila flavomontana* (Fruit fly) | Adh | P48585 |
| *Drosophila guanche* (Fruit fly) | Adh | Q09009 |
| *Drosophila hawaiiensis* (Fruit fly) | Adh | P51549 |
| *Drosophila heteroneura* (Fruit fly) | Adh | P21898 |
| *Drosophila immigrans* (Fruit fly) | Adh | Q07588 |
| *Drosophila insularis* (Fruit fly) | Adh | Q9NG40 |
| *Drosophila lebanonensis* (Fruit fly) (*Scaptodrosophila lebanonensis*) | Adh | P10807 |
| *Drosophila mauritiana* (Fruit fly) | Adh | P07162 |
| *Drosophila madeirensis* (Fruit fly) | Adh | Q09010 |
| *Drosophila mimica* (Fruit fly) (*Idiomyia mimica*) | Adh | Q00671 |
| *Drosophila nigra* (Fruit fly) (*Idiomyia nigra*) | Adh | Q00672 |
| *Drosophila orena* (Fruit fly) | Adh | P07159 |
| *Drosophila pseudoobscura bogotana* (Fruit fly) | Adh | P84328 |
| *Drosophila picticomis* (Fruit fly) (*Idiomyia picticomis*) | Adh | P23361 |
| *Drosophila planitibia* (Fruit fly) | Adh | P23277 |
| *Drosophila paulistorum* (Fruit fly) | Adh | Q9U8S9 |
| *Drosophila silvestris* (Fruit fly) | Adh | P23278 |
| *Drosophila subobscura* (Fruit fly) | Adh | Q03384 |
| *Drosophila teissieri* (Fruit fly) | Adh | P28484 |
| *Drosophila tsacasi* (Fruit fly) | Adh | P51550 |
| *Fragaria ananassa* (Strawberry) | ADH | P17648 |
| *Malus domestica* (Apple) (*Pyrus malus*) | ADH | P48977 |
| *Scaptomyza albovittata* (Fruit fly) | Adh | P25988 |
| *Scaptomyza crassifemur* (Fruit fly) (*Drosophila crassifemur*) | Adh | Q00670 |
| *Sulfolobus* sp. (strain RC3) | adh | P50381 |
| *Zaprionus tuberculatus* (Vinegar fly) | Adh | P51552 |
| *Geobacillus stearothermophilus* (*Bacillus stearothermophilus*) | adh | P42327 |
| *Drosophila mayaguana* (Fruit fly) | Adh, Adh2 | P25721 |
| *Drosophila melanogaster* (Fruit fly) | Adh, CG3481 | P00334 |
| *Drosophila pseudoobscura pseudoobscura* (Fruit fly) | Adh, GA17214 | Q6LCE4 |
| *Drosophila simulans* (Fruit fly) | Adh, GD23968 | Q24641 |
| *Drosophila yakuba* (Fruit fly) | Adh, GE19037 | P26719 |
| *Drosophila ananassae* (Fruit fly) | Adh, GF14888 | Q50L96 |
| *Drosophila erecta* (Fruit fly) | Adh, GG25120 | P28483 |
| *Drosophila grimshawi* (Fruit fly) (*Idiomyia grimshawi*) | Adh, GH13025 | P51551 |
| *Drosophila willistoni* (Fruit fly) | Adh, GK18290 | Q05114 |
| *Drosophila persimilis* (Fruit fly) | Adh, GL25993 | P37473 |
| *Drosophila sechellia* (Fruit fly) | Adh, GM15656 | Q9GN94 |
| *Cupriavidus necator* (strain ATCC 17699 / H16 / DSM 428 / Stanier 337) (*Ralstonia eutropha*) | adh, H16_A0757 | Q0KDL6 |
| *Mycobacterium tuberculosis* (strain CDC 1551 / Oshkosh) | adh, MT1581 | P9WQC2 |
| *Staphylococcus aureus* (strain MW2) | adh, MW0568 | Q8NXU1 |
| *Mycobacterium tuberculosis* (strain ATCC 25618 / H37Rv) | adh, Rv1530 | P9WQC3 |
| *Staphylococcus aureus* (strain N315) | adh, SA0562 | Q7A742 |
| *Staphylococcus aureus* (strain bovine RF122 / ET3-1) | adh, SAB0557 | Q2YSX0 |
| *Sulfolobus acidocaldarius* (strain ATCC 33909 / DSM 639 / JCM 8929 / NBRC 15157 / NCIMB 11770) | adh, Saci_2057 | Q4J781 |
| *Staphylococcus aureus* (strain COL) | adh, SACOL0660 | Q5HI63 |
| *Staphylococcus aureus* (strain NCTC 8325) | adh, SAOUHSC_00608 | Q2G0G1 |
| *Staphylococcus aureus* (strain MRSA252) | adh, SAR0613 | Q6GJ63 |
| *Staphylococcus aureus* (strain MSSA476) | adh, SAS0573 | Q6GBM4 |
| *Staphylococcus aureus* (strain USA300) | adh, SAUSA300_0594 | Q2FJ31 |

TABLE 6.1-continued

Exemplary alcohol dehydrogenase enzymes.

| Organism | Gene Name | Accession No. |
|---|---|---|
| *Staphylococcus aureus* (strain Mu50 / ATCC 700699) | adh, SAV0605 | Q99W07 |
| *Staphylococcus epidermidis* (strain ATCC 12228) | adh, SE_0375 | Q8CQ56 |
| *Staphylococcus epidermidis* (strain ATCC 35984 / RP62A) | adh, SERP0257 | Q5HRD6 |
| *Sulfolobus solfataricus* (strain ATCC 35092 / DSM 1617 /JCM 11322/P2) | adh, SSO2536 | P39462 |
| *Sulfolobus tokodaii* (strain DSM 16993 / JCM 10545 / NBRC 100140 / 7) | adh, STK_25770 | Q96XE0 |
| *Anas platyrhynchos* (Domestic duck) (*Anas boschas*) | ADH1 | P30350 |
| *Apteryx australis* (Brown kiwi) | ADH1 | P49645 |
| *Ceratitis capitata* (Mediterranean fruit fly) (*Tephritis capitata*) | ADH1 | P48814 |
| *Ceratitis cosyra* (Mango fruit fly) (*Trypeta cosyra*) | ADH1 | Q7OUN9 |
| *Gallus gallus* (Chicken) | ADH1 | P23991 |
| *Columba livia* (Domestic pigeon) | ADH1 | P86883 |
| *Coturnix coturnix japonica* (Japanese quail) (*Coturnix japonica*) | ADH1 | P19631 |
| *Drosophila hydei* (Fruit fly) | Adhl | P23236 |
| *Drosophila montana* (Fruit fly) | Adhl | P48586 |
| *Drosophila mettleri* (Fruit fly) | Adhl | P22246 |
| *Drosophila mulleri* (Fruit fly) | Adhl | P07161 |
| *Drosophila navojoa* (Fruit fly) | Adhl | P12854 |
| *Geomys attwateri* (Attwater's pocket gopher) (*Geomys bursarius attwateri*) | ADH1 | Q9Z2M2 |
| *Geomys bursarius* (Plains pocket gopher) | ADH1 | Q64413 |
| *Geomys knoxjonesi* (Knox Jones's pocket gopher) | ADH1 | Q64415 |
| *Hordeum vulgare* (Barley) | ADH1 | P05336 |
| *Kluyveromyces marxianus* (Yeast) (*Candida kefyr*) | ADH1 | Q07288 |
| *Zea mays* (Maize) | ADH1 | P00333 |
| *Mesocricetus auratus* (Golden hamster) | ADH1 | P86885 |
| *Pennisetum americanum* (Pearl millet) (*Pennisetum glaucum*) | ADH1 | P14219 |
| *Petunia hybrida* (Petunia) | ADH1 | P25141 |
| *Oryctolagus cuniculus* (Rabbit) | ADH1 | Q03505 |
| *Solanum tuberosum* (Potato) | ADH1 | P14673 |
| *Struthio camelus* (Ostrich) | ADH1 | P80338 |
| *Trifolium repens* (Creeping white clover) | ADH1 | P13603 |
| *Zea luxurians* (Guatemalan teosinte) (*Euchlaena luxurians*) | ADH1 | Q07264 |
| *Saccharomyces cerevisiae* (strain ATCC 204508 / S288c) (Baker's yeast) | ADH1, ADC1, YOL086C, O0947 | P00330 |
| *Arabidopsis thaliana* (Mouse-ear cress) | ADH1, ADH, At1g77120, F22K20.19 | P06525 |
| *Schizosaccharomyces pombe* (strain 972 / ATCC 24843) (Fission yeast) | adhl, adh, SPCC13B11.01 | P00332 |
| *Drosophila lacicola* (Fruit fly) | Adhl, Adh-1 | Q27404 |
| *Mus musculus* (Mouse) | Adhl, Adh-1 | P00329 |
| *Peromyscus maniculatus* (North American deer mouse) | ADH1, ADH-1 | P41680 |
| *Rattus norvegicus* (Rat) | Adhl, Adh-1 | P06757 |
| *Drosophila virilis* (Fruit fly) | Adhl, Adh-1, GJ18208 | B4M8Y0 |
| *Scheffersomyces stipitis* (strain ATCC 58785 / CBS 6054 / NBRC 10063 / NRRL Y-11545) (Yeast) (*Pichia stipitis*) | ADH1, ADH2, PICST_68558 | O00097 |
| *Aspergillus flavus* (strain ATCC 200026 / FGSC A1120 / NRRL 3357 / JCM 12722 / SRRC 167) | adhl, AFLA_048690 | P41747 |
| *Neurospora crassa* (strain ATCC 24698 / 74-OR23-1A / CBS 708.71 / DSM 1257 / FGSC 987) | adh-1, B17C10.210, NCU01754 | Q9P6C8 |
| *Candida albicans* (Yeast) | ADH1, CAD | P43067 |
| *Oryza sativa* subsp. *japonica* (Rice) | ADH1, DUPR11.3, Os11g0210300, LOC_Os11g10480, OsJ_032001 | Q2R8Z5 |
| *Drosophila mojavensis* (Fruit fly) | Adhl, GI17644 | P09370 |
| *Kluyveromyces lactis* (strain ATCC 8585 / CBS 2359 / DSM 70799 / NBRC 1267 / NRRL Y-1140 / WM37) (Yeast) (*Candida sphaerica*) | ADH1, KLLA0F21010g | P20369 |
| *Oryza sativa* subsp. *indica* (Rice) | ADH1, OsI_034290 | Q75ZX4 |

TABLE 6.1-continued

Exemplary alcohol dehydrogenase enzymes.

| Organism | Gene Name | Accession No. |
|---|---|---|
| *Pongo abelii* (Sumatran orangutan) (*Pongo pygmaeus abelii*) | ADH1A | Q5RBP7 |
| *Homo sapiens* (Human) | ADH1A, ADH1 | P07327 |
| *Macaca mulatta* (Rhesus macaque) | ADH1A, ADH1 | P28469 |
| *Pan troglodytes* (Chimpanzee) | ADH1B | Q5R1W2 |
| *Papio hamadryas* (Hamadryas baboon) | ADH1B | P14139 |
| *Homo sapiens* (Human) | ADH1B, ADH2 | P00325 |
| *Homo sapiens* (Human) | ADH1C, ADH3 | P00326 |
| *Papio hamadryas* (Hamadryas baboon) | ADH1C, ADH3 | O97959 |
| *Ceratitis capitata* (Mediterranean fruit fly) (*Tephritis capitata*) | ADH2 | P48815 |
| *Ceratitis cosyra* (Mango fruit fly) (*Trypeta cosyra*) | ADH2 | Q7OUP5 |
| *Ceratitis rosa* (Natal fruit fly) (*Pterandrus rosa*) | ADH2 | Q7OUP6 |
| *Drosophila arizonae* (Fruit fly) | Adh2 | P27581 |
| *Drosophila buzzatii* (Fruit fly) | Adh2 | P25720 |
| *Drosophila hydei* (Fruit fly) | Adh2 | P23237 |
| *Drosophila montana* (Fruit fly) | Adh2 | P48587 |
| *Drosophila mulleri* (Fruit fly) | Adh2 | P07160 |
| *Drosophila wheeleri* (Fruit fly) | Adh2 | P24267 |
| *Entamoeba histolytica* | ADH2 | Q24803 |
| *Hordeum vulgare* (Barley) | ADH2 | P10847 |
| *Kluyveromyces marxianus* (Yeast) (*Candida kefyr*) | ADH2 | Q9P4C2 |
| *Zea mays* (Maize) | ADH2 | P04707 |
| *Oryza sativa* subsp. *indica* (Rice) | ADH2 | Q4R1E8 |
| *Solanum lycopersicum* (Tomato) (*Lycopersicon esculentum*) | ADH2 | P28032 |
| *Solanum tuberosum* (Potato) | ADH2 | P14674 |
| *Scheffersomyces stipitis* (strain ATCC 58785 / CBS 6054 / NBRC 10063 / NRRL Y-11545) (Yeast) (*Pichia stipitis*) | ADH2, ADH1, PICST_27980 | O13309 |
| *Arabidopsis thaliana* (Mouse-ear cress) | ADH2, ADHIII, FDH1, At5g43940, MRH10.4 | Q96533 |
| *Saccharomyces cerevisiae* (strain ATCC 204508 / S288c) (Baker's yeast) | ADH2, ADR2, YMR303C, YM9952.05C | P00331 |
| *Candida albicans* (strain SC5314 / ATCC MYA-2876) (Yeast) | ADH2, Ca41C10.04, CaO19.12579, CaO19.5113 | O94038 |
| *Oryza sativa* subsp. *japonica* (Rice) | ADH2, DUPR11.1, Os11g0210500, LOC Os11g10510 | Q0ITW7 |
| *Drosophila mojavensis* (Fruit fly) | Adh2, GI17643 | P09369 |
| *Kluyveromyces lactis* (strain ATCC 8585 / CBS 2359 / DSM 70799 / NBRC 1267 / NRRL Y-1140 / WM37) (Yeast) (*Candida sphaerica*) | ADH2, KLLA0F18260g | P49383 |
| *Oryctolagus cuniculus* (Rabbit) | ADH2-1 | O46649 |
| *Oryctolagus cuniculus* (Rabbit) | ADH2-2 | O46650 |
| *Hordeum vulgare* (Barley) | ADH3 | P10848 |
| *Solanum tuberosum* (Potato) | ADH3 | P14675 |
| *Kluyveromyces lactis* (strain ATCC 8585 / CBS 2359 / DSM 70799 / NBRC 1267 / NRRL Y-1140 / WM37) (Yeast) (*Candida sphaerica*) | ADH3, KLLA0B09064g | P49384 |
| *Saccharomyces cerevisiae* (strain ATCC 204508 / S288c) (Baker's yeast) | ADH3, YMR083W, YM9582.08 | P07246 |
| *Homo sapiens* (Human) | ADH4 | P08319 |
| *Mus musculus* (Mouse) | Adh4 | Q9QYY9 |
| *Rattus norvegicus* (Rat) | Adh4 | Q64563 |
| *Struthio camelus* (Ostrich) | ADH4 | P80468 |
| *Kluyveromyces lactis* (strain ATCC 8585 / CBS 2359 / DSM 70799 / NBRC 1267 / NRRL Y-1140 / WM37) (Yeast) (*Candida sphaerica*) | ADH4, KLLA0F13530g | P49385 |
| *Schizosaccharomyces pombe* (strain 972 / ATCC 24843) (Fission yeast) | adh4, SPAC5H10.06c | Q09669 |
| *Saccharomyces cerevisiae* (strain YJM789) (Baker's yeast) | ADH4, ZRG5, SCY_1818 | A6ZTT5 |
| *Saccharomyces cerevisiae* (strain ATCC 204508 / S288c) (Baker's yeast) | ADH4, ZRG5, YGL256W, NRC465 | P10127 |
| *Saccharomyces pastorianus* (Lager yeast) (*Saccharomyces cerevisiae* x *Saccharomyces eubayanus*) | ADH5 | Q6XQ67 |
| *Bos taurus* (Bovine) | ADH5 | Q3ZC42 |
| *Equus caballus* (Horse) | ADH5 | P19854 |

TABLE 6.1-continued

Exemplary alcohol dehydrogenase enzymes.

| Organism | Gene Name | Accession No. |
|---|---|---|
| *Mus musculus* (Mouse) | Adh5, Adh-2, Adh2 | P28474 |
| *Rattus norvegicus* (Rat) | Adh5, Adh-2, Adh2 | P12711 |
| *Oryctolagus cuniculus* (Rabbit) | ADH5, ADH3 | O19053 |
| *Homo sapiens* (Human) | ADH5, ADHX' FDH | P11766 |
| *Dictyostelium discoideum* (Slime mold) | adh5, DDB_G0281865 | Q54TC2 |
| *Saccharomyces cerevisiae* (strain ATCC 204508 / S288c) (Baker's yeast) | ADH5, YBR145W, YBR1122 | P38113 |
| *Homo sapiens* (Human) | ADH6 | P28332 |
| *Peromyscus maniculatus* (North American deer mouse) | ADH6 | P41681 |
| *Pongo abelii* (Sumatran orangutan) (*Pongo pygmaeus abelii*) | ADH6 | Q5R7Z8 |
| *Rattus norvegicus* (Rat) | Adh6 | Q5XI95 |
| *Homo sapiens* (Human) | ADH7 | P40394 |
| *Rattus norvegicus* (Rat) | Adh7 | P41682 |
| *Mus musculus* (Mouse) | Adh7, Adh-3, Adh3 | Q64437 |
| *Mycobacterium tuberculosis* (strain CDC 1551 / Oshkosh) | adhA, MT1911 | P9WQC0 |
| *Rhizobium meliloti* (strain 1021) (*Ensifer meliloti*) (*Sinorhizobium meliloti*) | adhA, RA0704 SMa1296 | O31186 |
| *Mycobacterium tuberculosis* (strain ATCC 25618 / H37Rv) | adhA, Rv1862 | P9WQC1 |
| *Zymomonas mobilis* subsp. *mobilis* (strain ATCC 31821 / ZM4 / CP4) | adhA, ZMO1236 | P20368 |
| *Mycobacterium bovis* (strain ATCC BAA-935 / AF2122/97) | adhB, Mb0784c | Q7U1B9 |
| *Mycobacterium tuberculosis* (strain CDC 1551 / Oshkosh) | adhB, MT0786 | P9WQC6 |
| *Mycobacterium tuberculosis* (strain ATCC 25618 / H37Rv) | adhB, Rv0761c, MTCY369.06c | P9WQC7 |
| *Zymomonas mobilis* subsp. *mobilis* (strain ATCC 31821 / ZM4 / CP4) | adhB, ZMO1596 | P0DJA2 |
| *Zymomonas mobilis* subsp. *mobilis* (strain ATCC 10988 / DSM 424 / LMG 404 / NCIMB 8938 / NRRL B-806 / ZM1) | adhB, Zmob_1541 | F8DVL8 |
| *Mycobacterium tuberculosis* (strain CDC 1551 / Oshkosh) | adhD, MT3171 | P9WQB8 |
| *Mycobacterium tuberculosis* (strain ATCC 25618 / H37Rv) | adhD, Rv3086 | P9WQB9 |
| *Clostridium acetobutylicum* (strain ATCC 824 / DSM 792 / JCM 1419 / LMG 5710 / VKM B-1787) | adhE, aad, CA_P0162 | P33744 |
| *Escherichia coli* (strain K12) | adhE, ana, b1241, JW1228 | P0A9Q7 |
| *Escherichia coli* O157:H7 | adhE, Z2016, ECs1741 | P0A9Q8 |
| *Rhodobacter sphaeroides* (strain ATCC 17023 / 2.4.1 / NCIB 8253 / DSM 158) | adhI, RHOS4_11650, RSP_2576 | P72324 |
| *Oryza sativa* subsp. *indica* (Rice) | ADHIII, OsI_009236 | A2XAZ3 |
| *Escherichia coli* (strain K12) | adhP, yddN, b1478, JW1474 | P39451 |
| *Geobacillus stearothermophilus* (*Bacillus stearothermophilus*) | adhT | P12311 |
| *Emericella nidulans* (strain FGSC A4 / ATCC 38163 /CBS 112.46 / NRRL 194 / M139) (*Aspergillus nidulans*) | alcA, AN8979 | P08843 |
| *Emericella nidulans* (strain FGSC A4 / ATCC 38163 / CBS 112.46 / NRRL 194 / M139) (*Aspergillus nidulans*) | alc, AN3741 | P54202 |
| *Emericella nidulans* (strain FGSC A4 / ATCC 38163 / CBS 112.46 / NRRL 194 /M139) (*Aspergillus nidulans*) | alcC, adh3, AN2286 | P07754 |
| *Arabidopsis thaliana* (Mouse-ear cress) | At1g22430, F12K8.22 | Q95K86 |
| *Arabidopsis thaliana* (Mouse-ear cress) | At1g22440, F12K8.21 | Q95K87 |
| *Arabidopsis thaliana* (Mouse-ear cress) | At1g32780, F6N18.16 | A1L4Y2 |

TABLE 6.1-continued

Exemplary alcohol dehydrogenase enzymes.

| Organism | Gene Name | Accession No. |
|---|---|---|
| Arabidopsis thaliana (Mouse-ear cress) | At1g64710, F13O11.3 | Q8VZ49 |
| Arabidopsis thaliana (Mouse-ear cress) | At4g22110, F1N20.210 | Q0V7W6 |
| Arabidopsis thaliana (Mouse-ear cress) | At5g24760, T4C12_30 | Q8LEB2 |
| Arabidopsis thaliana (Mouse-ear cress) | At5g42250, K5J14.5 | Q9FH04 |
| Zea mays (Maize) | FDH | P93629 |
| Drosophila melanogaster (Fruit fly) | Fdh, gfd, ODH, CG6598 | P46415 |
| Bacillus subtilis (strain 168) | gbsB, BSU31050 | P71017 |
| Caenorhabditis elegans | H24K24.3 | Q17335 |
| Oryza sativa subsp. japonica (Rice) | Os02g0815500, LOC_Os02g57040, OsJ_008550, P0643F09.4 | Q0DWH1 |
| Mycobacterium tuberculosis (strain ATCC 25618 / H37Rv) | Rv1895 | O07737 |
| Caenorhabditis elegans | sodh-1, K12G11.3 | Q17334 |
| Caenorhabditis elegans | sodh-2, K12G11.4 | O45687 |
| Pseudomonas sp. | terPD | P33010 |
| Escherichia coli (strain K12) | yiaY, b3589, JW5648 | P37686 |
| Moraxella sp. (strain TAE123) | | P81786 |
| Alligator mississippiensis (American alligator) | | P80222 |
| Catharanthus roseus (Madagascar periwinkle) (Vinca rosea) | | P85440 |
| Gadus morhua subsp. callarias (Baltic cod) (Gadus callarias) | | P26325 |
| Naja naja (Indian cobra) | | P80512 |
| Pisum sativum (Garden pea) | | P12886 |
| Pelophylax perezi (Perez's frog) (Rana perezi) | | P22797 |
| Saara hardwickii (Indian spiny-tailed lizard) (Uromastyx hardwickii) | | P25405 |
| Saara hardwickii (Indian spiny-tailed lizard) (Uromastyx hardwickii) | | P25406 |
| Equus caballus (Horse) | | P00327 |
| Equus caballus (Horse) | | P00328 |
| Geobacillus stearothermophilus (Bacillus stearothermophilus) | | P42328 |
| Gadus morhua (Atlantic cod) | | P81600 |
| Gadus morhua (Atlantic cod) | | P81601 |
| Myxine glutinosa (Atlantic hagfish) | | P80360 |
| Octopus vulgaris (Common octopus) | | P81431 |
| Pisum sativum (Garden pea) | | P80572 |
| Saara hardwickii (Indian spiny-tailed lizard) (Uromastyx hardwickii) | | P80467 |
| Scyliorhinus canicula (Small-spotted catshark) (Squalus canicula) | | P86884 |
| Sparus aurata (Gilthead sea bream) | | P79896 |

Acyl-CoA Oxidases

In some embodiments, the present disclosure teaches recombinant microorganisms that are engineered to reduce or eliminate the expression or activity of one or more of the endogenous acyl-CoA oxidases (i.e. POX1, POX2, POX3, POX4, POX5, and POX6). In some embodiments, recombinant microorganisms of the present disclosure are engineered to comprise deletions of endogenous acyl-CoA oxidases (i.e. POX1, POX2, POX3, POX4, POX5, and POX6). For example, in some embodiments, the recombinant microorganism is a Y. lipolytica strain exhibiting a reduction in the activities of acyl-CoA oxidases (namely POX1: YALI0E32835g, POX2: YALI0F10857g, POX3: YALI0D24750g, POX4: YALI0E27654g, POX5: YALI0C23859g, POX6: YALI0E06567g).

Alcohol Oxidase

In some embodiments, the present disclosure teaches recombinant microorganisms that are engineered to reduce or eliminate the expression or activity of endogenous fatty alcohol oxidase (FAO1). In some embodiments, recombinant microorganisms of the present disclosure are engineered to comprise deletions of of endogenous fatty alcohol oxidase (FAO1). For example, in some embodiments, the recombinant microorganism is Y. lipolytica, and the microorganism comprises reduced activity of relevant (fatty) alcohol oxidases, namely FAO1: YALI0B14014g).

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some members of these four groups are better suited than others as candidates for evaluation.

Short chain alcohol oxidases (including but not limited to those currently classified as EC 1.1.3.13, Table 6.2) catalyze the oxidation of lower chain length alcohol substrates in the range of C1-C8 carbons (van der Klei et al. 1991) (Ozimek et al. 2005). Aliphatic alcohol oxidases from methylotrophic yeasts such as *Candida boidinii* and *Komagataella pastoris* (formerly *Pichia pastoris*) catalyze the oxidation of primary alkanols to the corresponding aldehydes with a preference for unbranched short-chain aliphatic alcohols. The most broad substrate specificity is found for alcohol oxidase from the *Pichia pastoris* including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using *Pichia pastoris* alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from *Pichia pastoris* was able to oxidize aliphatic alcohols of C6 to C11 when used biphasic organic reaction system (Murray and Duff 1990). Methods for using alcohol oxidases in a biphasic system according to (Karra-Chaabouni et al. 2003) and (Murray and Duff 1990) are incorporated by reference in their entirety.

Long chain alcohol oxidases (including but not limited to those currently classified as EC 1.1.3.20; Table 6.3) include fatty alcohol oxidases, long chain fatty acid oxidases, and long chain fatty alcohol oxidases that oxidize alcohol substrates with carbon chain length of greater than six (Goswami et al. 2013). Banthorpe et al. reported a long chain alcohol oxidase purified from the leaves of *Tanacetum vulgare* that was able to oxidize saturated and unsaturated long chain alcohol substrates including hex-trans-2-en-1-ol and octan-1-ol (Banthorpe 1976) (Cardemil 1978). Other plant species, including *Simmondsia chinensis* (Moreau, R. A., Huang 1979), *Arabidopsis thaliana* (Cheng et al. 2004), and *Lotus japonicas* (Zhao et al. 2008) have also been reported as sources of long chain alcohol oxidases. Fatty alcohol oxidases are mostly reported from yeast species (Hommel and Ratledge 1990) (Vanhanen et al. 2000) (Hommel et al. 1994) (Kemp et al. 1990) and these enzymes play an important role in long chain fatty acid metabolism (Cheng et al. 2005). Fatty alcohol oxidases from yeast species that degrade and grow on long chain alkanes and fatty acid catalyze the oxidation of fatty alcohols. Fatty alcohol oxidase from *Candida tropicalis* has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{16}$ with reported KM in the 10-50 µM range (Eirich et al. 2004). Alcohol oxidases described may be used for the conversion of medium chain aliphatic alcohols to aldehydes as described, for example, for whole-cells *Candida boidinii* (Gabelman and Luzio 1997), and *Pichia pastoris* (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from *Lotus japonicas* has been heterologously expressed in *E. coli* and exhibited broad substrate specificity for alcohol oxidation including 1-dodecanol and 1-hexadecanol (Zhao et al. 2008).

TABLE 6.2

Alcohol oxidase enzymes capable of oxidizing short chain alcohols (EC 1.1.3.13)

| Organism | Gene names | Accession No. |
|---|---|---|
| *Komagataella pastoris* (strain ATCC 76273 / CBS 7435 / CECT 11047 / NRRL Y-11430 / Wegner 21-1) (Yeast) (*Pichia pastoris*) | AOX1 PP7435_Chr4-0130 | F2QY27 |
| *Komagataella pastoris* (strain GS115 / ATCC 20864) (Yeast) (*Pichia pastoris*) | AOX1 PAS_chr4_0821 | P04842 |
| *Komagataella pastoris* (strain ATCC 76273 / CBS 7435 / CECT 11047 / NRRL Y-11430 / Wegner 21-1) (Yeast) (*Pichia pastoris*) | AOX2 PP7435_Chr4-0863 | F2R038 |
| *Komagataella pastoris* (strain GS115 / ATCC 20864) (Yeast) (*Pichia pastoris*) | AOX2 PAS_chr4_0152 | C4R702 |
| *Candida boidinii* (Yeast) | AOD1 | Q00922 |
| *Pichia angusta* (Yeast) (*Hansenula polymorpha*) | MOX | P04841 |
| *Thanatephorus cucumeris* (strain AG1-IB / isolate 7/3/14) (Lettuce bottom rot fungus) (*Rhizoctonia solani*) | AOD1 BN14_10802 | M5CC52 |
| *Thanatephorus cucumeris* (strain AG1-IB / isolate 7/3/14) (Lettuce bottom rot fungus) (*Rhizoctonia solani*) | MOX BN14_12214 | M5CF32 |
| *Thanatephorus cucumeris* (strain AG1-IB / isolate 7/3/14) (Lettuce bottom rot fungus) (*Rhizoctonia solani*) | AOD1 BN14_10691 | M5CAV1 |
| *Thanatephorus cucumeris* (strain AG1-IB / isolate 7/3/14) (Lettuce bottom rot fungus) (*Rhizoctonia solani*) | AOD1 BN14_09479 | M5C7F4 |
| *Thanatephorus cucumeris* (strain AG1-IB / isolate 7/3/14) (Lettuce bottom rot fungus) (*Rhizoctonia solani*) | AOD1 BN14_10803 | M5CB66 |
| *Thanatephorus cucumeris* (strain AG1-IB / isolate 7/3/14) (Lettuce bottom rot fungus) (*Rhizoctonia solani*) | AOD1 BN14_09900 | M5C9N9 |
| *Thanatephorus cucumeris* (strain AG1-IB / isolate 7/3/14) (Lettuce bottom rot fungus) (*Rhizoctonia solani*) | AOD1 BN14_08302 | M5C2L8 |
| *Thanatephorus cucumeris* (strain AG1-IB / isolate 7/3/14) (Lettuce bottom rot fungus) (*Rhizoctonia solani*) | MOX BN14_09408 | M5C784 |

TABLE 6.2-continued

Alcohol oxidase enzymes capable of oxidizing short chain alcohols (EC 1.1.3.13)

| Organism | Gene names | Accession No. |
|---|---|---|
| *Thanatephorus cucumeris* (strain AG1-IB / isolate 7/3/14) (Lettuce bottom rot fungus) (*Rhizoctonia solani*) | MOX BN14_09478 | M5C8F8 |
| *Thanatephorus cucumeris* (strain AG1-IB / isolate 7/3/14) (Lettuce bottom rot fungus) (*Rhizoctonia solani*) | AOD1 BN14_11356 | M5CH40 |
| *Ogataea henricii* | AOD1 | A5LGF0 |
| *Candida methanosorbosa* | AOD1 | A5LGE5 |
| *Candida methanolovescens* | AOD1 | A5LGE4 |
| *Candida succiphila* | AOD1 | A5LGE6 |
| *Aspergillus niger* (strain CBS 513.88 / FGSC A1513) | An15g02200 | A2R501 |
| *Aspergillus niger* (strain CBS 513.88 / FGSC A1513) | An18g05480 | A2RB46 |
| *Moniliophthora perniciosa* (Witches'-broom disease fungus) (*Marasmius perniciosus*) | | I7CMK2 |
| *Candida cariosilignicola* | AOD1 | A5LGE3 |
| *Candida pignaliae* | AOD1 | A5LGE1 |
| *Candida pignaliae* | AOD2 | A5LGE2 |
| *Candida sonorensis* | AOD1 | A5LGD9 |
| *Candida sonorensis* | AOD2 | A5LGE0 |
| *Pichia naganishii* | AOD1 | A5LGF2 |
| *Ogataea minuta* | AOD1 | A5LGF1 |
| *Ogataea philodendra* | AOD1 | A5LGF3 |
| *Ogataea wickerhamii* | AOD1 | A5LGE8 |
| *Kuraishia* capsulate | AOD1 | A5LGE7 |
| *Talaromyces stipitatus* (strain ATCC 10500 / CBS 375.48 / QM 6759 / NRRL 1006) (*Penicillium stipitatum*) | TSTA_021940 | B8MHF8 |
| *Talaromyces stipitatus* (strain ATCC 10500 / CBS 375.48 / QM 6759 / NRRL 1006) (*Penicillium stipitatum*) | TSTA_065150 | B8LTH7 |
| *Talaromyces stipitatus* (strain ATCC 10500 / CBS 375.48 / QM 6759 / NRRL 1006) (*Penicillium stipitatum*) | TSTA_065150 | B8LTH8 |
| *Talaromyces stipitatus* (strain ATCC 10500 / CBS 375.48 / QM 6759 / NRRL 1006) (*Penicillium stipitatum*) | TSTA_000410 | B8MSB1 |
| *Ogataea glucozyma* | AOD1 | A5LGE9 |
| *Ogataea parapolymorpha* (strain DL-1 / ATCC 26012 / NRRL Y-7560) (Yeast) (*Hansenula polymorpha*) | HPODL_03886 | W1QCJ3 |
| *Gloeophyllum trabeum* (Brown rot fungus) | AOX | A8DPS4 |
| *Pichia angusta* (Yeast) (*Hansenula polymorpha*) | mox1 | A6PZG8 |
| *Pichia trehalophila* | AOD1 | A5LGF4 |
| *Pichia angusta* (Yeast) (*Hansenula polymorpha*) | mox1 | A6PZG9 |
| *Pichia angusta* (Yeast) (*Hansenula polymorpha*) | mox1 | A6PZG7 |
| *Ixodes scapularis* (Black-legged tick) (Deer tick) | IscW_ISCW017898 | B7PIZ7 |

TABLE 6.3

Alcohol oxidase enzymes capable of oxidizing long chain alcohols including fatty alcohols (EC 1.1.3.20)

| Organism | Gene names | Accession No. |
|---|---|---|
| *Lotus japonicus* (*Lotus corniculatus* var. *japonicus*) | FAO1 | B5WWZ8 |
| *Arabidopsis thaliana* (Mouse-ear cress) | FAO1 At1g03990 F21M11.7 | Q9ZWB9 |
| *Lotus japonicus* (*Lotus corniculatus* var. *japonicus*) | FAO2 | B5WWZ9 |
| *Arabidopsis thaliana* (Mouse-ear cress) | FAO3 At3g23410 MLM24.14 MLM24.23 | Q9LW56 |
| *Arabidopsis thaliana* (Mouse-ear cress) | FAO4A At4g19380 T5K18.160 | O65709 |
| *Arabidopsis thaliana* (Mouse-ear cress) | FAO4B At4g28570 T5F17.20 | Q94BP3 |
| *Microbotryum violaceum* (strain p1A1 Lamole) (Anther smut fungus) (*Ustilago violacea*) | MVLG_06864 | U5HIL4 |
| *Ajellomyces dermatitidis* ATCC 26199 | BDFG_03507 | T5BNQ0 |
| *Gibberella zeae* (strain PH-1 / ATCC MYA-4620 / FGSC 9075 / NRRL 31084) (Wheat head blight fungus) (*Fusarium graminearum*) | FG06918.1 FGSG_06918 | I1RS14 |
| *Pichia sorbitophila* (strain ATCC MYA-4447 / BCRC 22081 / CBS 7064 / NBRC 10061 / NRRL Y-12695) (Hybrid yeast) | Piso0_004410 GNLVRS01_PISO0K16268g GNLVRS01_PISO0L16269g | G8Y5E1 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Emericella nidulans* (strain FGSC A4 / ATCC 38163 / CBS 112.46 /NRRL 194 / M139) (*Aspergillus nidulans*) | AN0623.2 ANIA_00623 | Q5BFQ7 |
| *Pyrenophora tritici-repentis* (strain Pt-1C-BFP) (Wheat tan spot *fungus*) (*Drechslera tritici-repentis*) | PTRG_10154 | B2WJW5 |
| *Paracoccidioides lutzii* (strain ATCC MYA-826 / Pb01) (*Paracoccidioides brasiliensis*) | PAAG_09117 | C1HEC6 |
| *Candida parapsilosis* (strain CDC 317 / ATCC MYA-4646) (Yeast) (*Monilia parapsilosis*) | CPAR2_204420 | G8BG15 |
| *Pseudozyma brasiliensis* (strain GHG001) (Yeast) | PSEUBRA_SCAF2g03010 | V5GPS6 |
| *Candida parapsilosis* (strain CDC 317 / ATCC MYA-4646) (Yeast) (*Monilia parapsilosis*) | CPAR2_204430 | G8BG16 |
| *Sclerotinia borealis* F-4157 | SBOR_5750 | W9CDE2 |
| *Sordaria macrospora* (strain ATCC MYA-333 / DSM 997 / K(L3346) / K-hell) | SMAC_06361 | F7W6K4 |
| *Sordaria macrospora* (strain ATCC MYA-333 / DSM 997 / K(L3346) / K-hell) | SMAC_01933 | F7VSA1 |
| *Meyerozyma guilliermondii* (strain ATCC 6260 / CBS 566 / DSM 6381 / JCM 1539 / NBRC 10279 / NRRL Y-324) (Yeast) (*Candida guilliermondii*) | PGUG_03467 | A5DJL6 |
| *Trichophyton rubrum* CBS 202.88 | H107_00669 | A0A023ATC5 |
| *Arthrobotrys oligospora* (strain ATCC 24927 / CBS 115.81 / DSM 1491) (*Nematode-trapping fungus*) (*Didymozoophaga oligospora*) | AOL_s00097g516 | G1XJI9 |
| *Scheffersomyces stipitis* (strain ATCC 58785 / CBS 6054 / NBRC 10063 / NRRL Y-11545) (Yeast) (*Pichia stipitis*) | FAO1 PICST_90828 | A3LYX9 |
| *Scheffersomyces stipitis* (strain ATCC 58785 / CBS 6054 / NBRC 10063 / NRRL Y-11545) (Yeast) (*Pichia stipitis*) | FAO2 PICST_32359 | A3LW61 |
| *Aspergillus oryzae* (strain 3.042) (Yellow koji mold) | Ao3042_09114 | I8TL25 |
| *Fusarium oxysporum* (strain Fo5176) (*Fusarium vascular wilt*) | FOXB_17532 | F9GFU8 |
| *Rhizopus delemar* (strain RA 99-880 / ATCC MYA-4621 / FGSC 9543 / NRRL 43880) (*Mucormycosis* agent) (*Rhizopus arrhizus* var. delemar) | RO3G_08271 | I1C536 |
| *Rhizopus delemar* (strain RA 99-880 / ATCC MYA-4621 / FGSC 9543 / NRRL 43880) (*Mucormycosis* agent) (*Rhizopus arrhizus* var. delemar) | RO3G_00154 | I1BGX0 |
| *Fusarium oxysporum* (strain Fo5176) (*Fusarium vascular wilt*) | FOXB_ 07532 | F9FMA2 |
| *Penicillium roqueforti* | PROQFM164_S02g001772 | W6QPY1 |
| *Aspergillus clavatus* (strain ATCC 1007 / CBS 513.65 / DSM 816 /NCTC 3887 / NRRL 1) | ACLA_018400 | A1CNB5 |
| *Arthroderma otae* (strain ATCC MYA-4605 / CBS 113480) (*Microsporum canis*) | MCYG_08732 | C5G1B0 |
| *Trichophyton tonsurans* (strain CBS 112818) (Scalp ringworm *fungus*) | TESG_07214 | F2SI12 |
| *Colletotrichum higginsianum* (strain IMI 349063) (*Crucifer anthracnose fungus*) | CH063_13441 | H1VUE7 |
| *Ajellomyces capsulatus* (strain H143) (*Darling's disease fungus*) (*Histoplasma capsulatum*) | HCDG_07658 | C6HN77 |
| *Trichophyton rubrum* (strain ATCC MYA-4607 / CBS 118892) (Athlete's foot *fungus*) | TERG_08235 | F2T096 |
| *Cochliobolus heterostrophus* (strain C5 / ATCC 48332 / race 0) (Southern corn leaf blight *fungus*) (*Bipolaris maydis*) | COCHEDRAFT_1201414 | M2UMT9 |
| *Candida orthopsilosis* (strain 90-125) (Yeast) | CORT_0D04510 | H8X643 |
| *Candida orthopsilosis* (strain 90-125) (Yeast) | CORT_0D04520 | H8X644 |
| *Candida orthopsilosis* (strain 90-125) (Yeast) | CORT_0D04530 | H8X645 |
| *Pseudozyma aphidis* DSM 70725 | PaG_03027 | W3VP49 |
| *Coccidioides posadasii* (strain C735) (*Valley fever fungus*) | CPC735_000380 | C5P005 |
| *Magnaporthe oryzae* (strain P131) (Rice blast *fungus*) (*Pyricularia oryzae*) | OOW_P131scaffold01214g15 | L7IZ92 |
| *Neurospora tetrasperma* (strain FGSC 2508 / ATCC MYA-4615 / P0657) | NEUTE1DRAFT_82541 | F8MKD1 |
| *Hypocrea virens* (strain Gv29-8 / FGSC 10586) (*Gliocladium virens*) (*Trichoderma virens*) | TRIVIDRAFT_54537 | G9MMY7 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| Hypocrea virens (strain Gv29-8 / FGSC 10586) (Gliocladium virens) (Trichoderma virens) | TRIVIDRAFT_53801 | G9MT89 |
| Aspergillus niger (strain CBS 513.88 / FGSC A1513) | An01g09620 | A2Q9Z3 |
| Verticillium dahliae (strain VdLs.17 / ATCC MYA-4575 / FGSC 10137) (Verticillium wilt) | VDAG_05780 | G2X6J8 |
| Ustilago maydis (strain 521 / FGSC 9021) (Corn smut fungus) | UM02023.1 | Q4PCZ0 |
| Fusarium oxysporum f. sp. lycopersici MN25 | FOWG_13006 | W9LNI9 |
| Fusarium oxysporum f. sp. lycopersici MN25 | FOWG_02542 | W9N9Z1 |
| Candida tropicalis (Yeast) | FAO1 | Q6QIR6 |
| Magnaporthe oryzae (strain 70-15 / ATCC MYA-4617 / FGSC 8958) (Rice blast fungus) (Pyricularia oryzae) | MGG 11317 | G4MVK1 |
| Candida tropicalis (Yeast) | faot | Q9P8D9 |
| Candida tropicalis (Yeast) | FAO2a | Q6QIR5 |
| Phaeosphaeria nodorum (strain SN15 / ATCC MYA-4574 / FGSC 10173) (Glume blotch fungus) (Septoria nodorum) | SNOG_02371 | Q0V0U3 |
| Candida tropicalis (Yeast) | FAO2b | Q6QIR4 |
| Pestalotiopsis fici W106-1 | PFICI_11209 | W3WU04 |
| Magnaporthe oryzae (strain Y34) (Rice blast fungus) (Pyricularia oryzae) | OOU_Y34scaffold00240g57 | L7IFT5 |
| Pseudogymnoascus destructans (strain ATCC MYA-4855 / 20631-21) (Bat white-nose syndrome fungus) (Geomyces destructans) | GMDG_01756 | L8G0G6 |
| Pseudogymnoascus destructans (strain ATCC MYA-4855 / 20631-21) (Bat white-nose syndrome fungus) (Geomyces destructans) | GMDG_04950 | L8GCY2 |
| Mycosphaerella fijiensis (strain CIRAD86) (Black leaf streak disease fungus) (Pseudocercospora fijiensis) | MYCFIDRAFT_52380 | M2Z831 |
| Bipolaris oryzae ATCC 44560 | COCMIDRAFT_84580 | W7A0I8 |
| Cladophialophora psammophila CBS 110553 | A1O5_08147 | W9WTM9 |
| Fusarium oxysporum f. sp. melonis 26406 | FOMG_05173 | X0AEE6 |
| Fusarium oxysporum f. sp. melonis 26406 | FOMG_17829 | W9ZBB7 |
| Cyphellophora europaea CBS 101466 | HMPREF1541_02174 | W252S5 |
| Aspergillus kawachii (strain NBRC 4308) (White koji mold) (Aspergillus awamori var. kawachi) | AKAW_00147 | G7X626 |
| Aspergillus terreus (strain NIH 2624 / FGSC A1156) | ATEG_05086 | Q0CMJ8 |
| Coccidioides immitis (strain RS) (Valley fever fungus) | CIMG_02987 | J3KAI8 |
| Ajellomyces dermatitidis (strain ER-3 / ATCC MYA-2586) (Blastomyces dermatitidis) | BDCG_04701 | C5GLS5 |
| Fusarium oxysporum f. sp. cubense (strain race 1) (Panama disease fungus) | FOC1_g10013865 | N4U732 |
| Rhodotorula glutinis (strain ATCC 204091 / IIP 30 / MTCC 1151) (Yeast) | RTG_00643 | G0SVU8 |
| Aspergillus niger (strain ATCC 1015 / CBS 113.46 / FGSC A1144 / LSHB Ac4 / NCTC 3858a/ NRRL 328 / USDA 3528.7) | ASPNIDRAFT_35778 | G3XTM6 |
| Candida cloacae | fao1 | Q9P8D8 |
| Candida cloacae | fao2 | Q9P8D7 |
| Fusarium oxysporum f. sp. cubense (strain race 1) (Panama disease fungus) | FOC1_g10006358 | N4TUH3 |
| Candida albicans (strain 5C5314 / ATCC MYA-2876) (Yeast) | FAO1 CaO19.13562 orf19.13562 | Q59RS8 |
| Candida albicans (strain 5C5314 / ATCC MYA-2876) (Yeast) | FAO1 Ca019.6143 orf19.6143 | Q59RP0 |
| Chaetomium thermophilum (strain DSM 1495 / CBS 144.50 / IMI 039719) | CTHT_0018560 | G0S2U9 |
| Mucor circinelloides f. circinelloides (strain 1006PhL) (Mucormycosis agent) (Calyptromyces circinelloides) | HMPREF1544_05296 | S2JDN0 |
| Mucor circinelloides f. circinelloides (strain 1006PhL) (Mucormycosis agent) (Calyptromyces circinelloides) | HMPREF1544_05295 | S2JYP5 |
| Mucor circinelloides f. circinelloides (strain 1006PhL) (Mucormycosis agent) (Calyptromyces circinelloides) | HMPREF1544_06348 | S2JVK9 |
| Botryotinia fuckeliana (strain BcDW1) (Noble rot fungus) (Botrytis cinerea) | BcDW1_6807 | M7UD26 |
| Podospora anserina (strain S / ATCC MYA-4624 / DSM 980 / FGSC 10383) (Pleurage anserina) | PODANS_5_13040 | B2AFD8 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Neosartorya fumigata* (strain ATCC MYA-4609 / Af293 / CBS 101355 / FGSC A1100) (*Aspergillus fumigatus*) | AFUA_1G17110 | Q4WR91 |
| *Fusarium oxysporum f. sp. vasinfectum* 25433 | FOTG_00686 | X0MEE6 |
| *Fusarium oxysporum f. sp. vasinfectum* 25433 | FOTG_12485 | X0LE98 |
| *Trichophyton interdigitale* H6 | H101_06625 | A0A022U717 |
| *Beauveria bassiana* (strain ARSEF 2860) (*White muscardine disease fungus*) (*Tritirachium shiotae*) | BBA_04100 | J4UNY3 |
| *Fusarium oxysporum f. sp. radicis-lycopersici* 26381 | FOCG_00843 | X0GQ62 |
| *Fusarium oxysporum f. sp. radicis-lycopersici* 26381 | FOCG_15170 | X0F4T1 |
| *Neurospora tetrasperma* (strain FGSC 2509 / P0656) | NEUTE2DRAFT_88670 | G4UNN6 |
| *Pseudozyma hubeiensis* (strain SY62) (Yeast) | PHSY_000086 | R9NVU1 |
| *Lodderomyces elongisporus* (strain ATCC 11503 / CBS 2605 / JCM 1781 / NBRC 1676 / NRRL YB-4239) (Yeast) (*Saccharomyces elongisporus*) | LELG_03289 | A5E102 |
| *Malassezia globosa* (strain ATCC MYA-4612 / CBS 7966) (Dandruff-associated *fungus*) | MGL_3855 | A8QAY8 |
| *Byssochlamys spectabilis* (strain No. 5 / NBRC 109023) (*Paecilomyces variotii*) | PVAR5_7014 | V5GBL6 |
| *Ajellomyces capsulatus* (strain H88) (*Darling's disease fungus*) (*Histoplasma capsulatum*) | HCEG_03274 | F0UF47 |
| *Trichosporon asahii* var. *asahii* (strain ATCC 90039 / CBS 2479 / JCM 2466 / KCTC 7840 / NCYC 2677 / UAMH 7654) (Yeast) | A1Q1_03669 | J6FBP4 |
| *Penicillium oxalicum* (strain 114-2 / CGMCC 5302) (*Penicillium decumbens*) | PDE_00027 | S7Z8U8 |
| *Fusarium oxysporum f. sp. conglutinans* race 2 54008 | FOPG_02304 | X0IBE3 |
| *Fusarium oxysporum f. sp. conglutinans* race 2 54008 | FOPG_13066 | X0H540 |
| *Fusarium oxysporum f. sp. raphani* 54005 | FOQG_00704 | X0D1G8 |
| *Fusarium oxysporum f. sp. raphani* 54005 | FOQG_10402 | X0C482 |
| *Metarhizium acridum* (strain CQMa 102) | MAC_03115 | E9DZR7 |
| *Arthroderma benhamiae* (strain ATCC MYA-4681 / CBS 112371) (*Trichophyton mentagrophytes*) | ARB_02250 | D4B1C1 |
| *Fusarium oxysporum f. sp. cubense* tropical race 4 54006 | FOIG_12161 | X0JFI6 |
| *Fusarium oxysporum f. sp. cubense* tropical race 4 54006 | FOIG_12751 | X0JDU5 |
| *Cochliobolus heterostrophus* (strain C4 / ATCC 48331 / race T) (*Southern corn leaf blight fungus*) (*Bipolaris maydis*) | COCC4DRAFT_52836 | N4WZZ0 |
| *Trichosporon asahii* var. *asahii* (strain CBS 8904) (Yeast) | A1Q2_00631 | K1YZW1 |
| *Mycosphaerella graminicola* (strain CBS 115943 / IPO323) (*Speckled leaf blotch fungus*) (*Septoria tritici*) | MYCGRDRAFT_37086 | F9X375 |
| *Botryotinia fuckeliana* (strain T4) (*Noble rot fungus*) (*Botrytis cinerea*) | BofuT4_P072020.1 | G2XQ18 |
| *Metarhizium anisopliae* (strain ARSEF 23 / ATCC MYA-3075) | MAA_05783 | E9F0I4 |
| *Cladophialophora carrionii* CBS 160.54 | G647_05801 | V9DAR1 |
| *Coccidioides posadasii* (strain RMSCC 757 / Silveira) (*Valley fever fungus*) | CPSG_09174 | E9DH75 |
| *Rhodosporidium toruloides* (strain NP11) (Yeast) (*Rhodotorula gracilis*) | RHTO_06879 | M7X159 |
| *Puccinia graminis f. sp. tritici* (strain CRL 75-36-700-3 / race SCCL) (*Black stem rust fungus*) | PGTG_10521 | E3KIL8 |
| *Trichophyton rubrum* CBS 288.86 | H103_00624 | A0A022WG28 |
| *Colletotrichum fioriniae* PJ7 | CFIO01_08202 | A0A010RKZ4 |
| *Trichophyton rubrum* CBS 289.86 | H104_00611 | A0A022XB46 |
| *Cladophialophora yegresii* CBS 114405 | A1O7_02579 | W9WC55 |
| *Colletotrichum orbiculare* (strain 104-T / ATCC 96160 / CBS 514.97 / LARS 414 / MAFF 240422) (Cucumber *anthracnose fungus*) (*Colletotrichum lagenarium*) | Cob_10151 | N4VFP3 |
| *Drechslerella stenobrocha* 248 | DRE_03459 | W7IDL6 |
| *Neosartorya fumigata* (strain CEA10 / CBS 144.89 / FGSC A1163) (*Aspergillus fumigatus*) | AFUB_016500 | B0XP90 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Thielavia terrestris* (strain ATCC 38088 / NRRL 8126) (*Acremonium alabamense*) | THITE_2117674 | G2R8H9 |
| *Gibberella fujikuroi* (strain CBS 195.34 / IMI 58289 / NRRL A-6831) (*Bakanae and foot rot disease fungus*) (*Fusarium fujikuroi*) | FFUJ_02948 | S0DZP7 |
| *Gibberella fujikuroi* (strain CBS 195.34 / IMI 58289 / NRRL A-6831) (*Bakanae and foot rot disease fungus*) (*Fusarium fujikuroi*) | FFUJ_12030 | S0EMC6 |
| *Aspergillus flavus* (strain ATCC 200026 / FGSC A1120 / NRRL 3357 / JCM 12722 / SRRC 167) | AFLA_109870 | B8N941 |
| *Togninia minima* (strain UCR-PA7) (*Esca disease fungus*) (*Phaeoacremonium aleophilum*) | UCRPA7_1719 | R8BTZ6 |
| *Ajellomyces dermatitidis* (strain ATCC 18188 / CBS 674.68) (*Blastomyces dermatitidis*) | BDDG_09783 | F2TUC0 |
| *Macrophomina phaseolina* (strain M56) (*Charcoal rot fungus*) | MPH_10582 | K2RHA5 |
| *Neurospora crassa* (strain ATCC 24698 / 74-OR23-1A / CBS 708.71 / DSM 1257 / FGSC 987) | NCU08977 | Q752Z2 |
| *Neosartorya fischeri* (strain ATCC 1020 / DSM 3700 / FGSC A1164 / NRRL 181) (*Aspergillus fischerianus*) | NFIA_008260 | A1D156 |
| *Fusarium pseudograminearum* (strain C53096) (*Wheat and barley crown-rot fungus*) | FPSE_11742 | K3U9J5 |
| *Spathaspora passalidarum* (strain NRRL Y-27907 / 11-Y1) | SPAPADRAFT_54193 | G3AJP0 |
| *Spathaspora passalidarum* (strain NRRL Y-27907 / 11-Y1) | SPAPADRAFT_67198 | G3ANX7 |
| *Trichophyton verrucosum* (strain HKI 0517) | TRV_07960 | D4DL86 |
| *Arthroderma gypseum* (strain ATCC MYA-4604 / CBS 118893) (*Microsporum gypseum*) | MGYG_07264 | E4V2J0 |
| *Hypocrea jecorina* (strain QM6a) (*Trichoderma reesei*) | TRIREDRAFT_43893 | G0R7P8 |
| *Trichophyton rubrum* MR1448 | H110_00629 | A0A022Z1G4 |
| *Aspergillus ruber* CBS 135680 | EURHEDRAFT_512125 | A0A0175PR0 |
| *Glarea lozoyensis* (strain ATCC 20868 / MF5171) | GLAREA_04397 | S3D6C1 |
| *Setosphaeria turcica* (strain 28A) (*Northern leaf blight fungus*) (*Exserohilum turcicum*) | SETTUDRAFT_20639 | R0K6H8 |
| *Paracoccidioides brasiliensis* (strain Pb18) | PADG_06552 | C1GH16 |
| *Fusarium oxysporum* Fo47 | FOZG_13577 | W9JPG9 |
| *Fusarium oxysporum* Fo47 | FOZG_05344 | W9KPH3 |
| *Trichophyton rubrum* MR1459 | H113_00628 | A0A022ZY09 |
| *Penicillium marneffei* (strain ATCC 18224 / CBS 334.59 / QM 7333) | PMAA_075740 | B6QBY3 |
| *Sphaerulina musiva* (strain SO2202) (*Poplar stem canker fungus*) (*Septoria musiva*) | SEPMUDRAFT_154026 | M3DAK6 |
| *Gibberella moniliformis* (strain M3125 / FGSC 7600) (*Maize ear and stalk rot fungus*) (*Fusarium verticillioides*) | FVEG_10526 | W7N4P8 |
| *Gibberella moniliformis* (strain M3125 / FGSC 7600) (*Maize ear and stalk rot fungus*) (*Fusarium verticillioides*) | FVEG_08281 | W7MVR9 |
| *Pseudozyma antarctica* (strain T-34) (Yeast) (*Candida antarctica*) | PANT_22d00298 | M9MGF2 |
| *Paracoccidioides brasiliensis* (strain Pb03) | PABG_07795 | C0SJD4 |
| *Rhizophagus irregularis* (strain DAOM 181602 / DAOM 197198 / MUCL 43194) (*Arbuscular mycorrhizal fungus*) (*Glomus intraradices*) | GLOINDRAFT_82554 | U9TF61 |
| *Penicillium chrysogenum* (strain ATCC 28089 / DSM 1075 / Wisconsin 54-1255) (*Penicillium notatum*) | Pc21g23700 PCH_Pc21g23700 | B6HJ58 |
| *Baudoinia compniacensis* (strain UAMH 10762) (*Angels' share fungus*) | BAUCODRAFT_274597 | M2M6Z5 |
| *Hypocrea atroviridis* (strain ATCC 20476 / IMI 206040) (*Trichoderma atroviride*) | TRIATDRAFT_280929 | G9NJ32 |
| *Colletotrichum gloeosporioides* (strain Cg-14) (*Anthracnose fungus*) (*Glomerella cingulata*) | CGLO_06642 | T0LPH0 |
| *Cordyceps militaris* (strain CM01) (*Caterpillar fungus*) | CCM_02665 | G3JB34 |
| *Pyronema omphalodes* (strain CBS 100304) (*Pyronema confluens*) | PCON_13062 | U4LKE9 |
| *Colletotrichum graminicola* (strain M1.001 / M2 / FGSC 10212) (*Maize anthracnose fungus*) (*Glomerella graminicola*) | GLRG_08499 | E3QR67 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Glarea lozoyensis* (strain ATCC 74030 / MF5533) | M7I_2117 | H0EHX4 |
| *Fusarium oxysporum f. sp. cubense* (strain race 4) (*Panama disease fungus*) | FOC4_g10002493 | N1S969 |
| *Fusarium oxysporum f. sp. cubense* (strain race 4) (*Panama disease fungus*) | FOC4_g10011461 | N1RT80 |
| *Cochliobolus sativus* (strain ND90Pr / ATCC 201652) (*Common root rot and spot blotch fungus*) (*Bipolaris sorokiniana*) | COCSADRAFT_295770 | M2TBE4 |
| *Mixia osmundae* (strain CBS 9802 / IAM 14324 / JCM 22182 / KY 12970) | Mo05571 E5Q_05571 | G7E7S3 |
| *Mycosphaerella pini* (strain NZE10 / CBS 128990) (*Red band needle blight fungus*) (*Dothistroma septosporum*) | DOTSEDRAFT_69651 | N1PXR0 |
| *Grosmarmia clavigera* (strain kw1407 / UAMH 11150) (*Blue stain fungus*) (*Graphiocladiella clavigera*) | CMQ_1113 | F0XC64 |
| *Fusarium oxysporum* FOSC 3-a | FOYG_03004 | W9IUE5 |
| *Fusarium oxysporum* FOSC 3-a | FOYG_16040 | W9HNP0 |
| *Fusarium oxysporum* FOSC 3-a | FOYG_17058 | W9HB31 |
| *Nectria haematococca* (strain 77-13-4 / ATCC MYA-4622 / FGSC 9596 / MPVI) (*Fusarium solani subsp. pisi*) | NECHADRAFT_37686 | C7YQL1 |
| *Nectria haematococca* (strain 77-13-4 / ATCC MYA-4622 / FGSC 9596 / MPVI) (*Fusarium solani subsp. pisi*) | NECHADRAFT_77262 | C7ZJI0 |
| *Tuber melanosporum* (strain Me128) (*Perigord black truffle*) | GSTUM_00010376001 | D5GLS0 |
| *Ajellomyces dermatitidis* (strain SLH14081) (*Blastomyces dermatitidis*) | BDBG_07633 | C5JYI9 |
| *Chaetomium globosum* (strain ATCC 6205 / CBS 148.51 / DSM 1962 / NBRC 6347 / NRRL 1970) (*Soil fungus*) | CHGG_09885 | Q2GQ69 |
| *Candida tenuis* (strain ATCC 10573 / BCRC 21748 / CBS 615 / JCM 9827 / NBRC 10315 / NRRL Y-1498 / VKM Y-70) (*Yeast*) | CANTEDRAFT_108652 | G3B9Z1 |
| *Trichophyton rubrum* CBS 100081 | H102_00622 | A0A022VKY4 |
| *Pyrenophora teres f. teres* (strain 0-1) (*Barley net blotch fungus*) (*Drechslera teres f. teres*) | PTT_09421 | E3RLZ3 |
| *Colletotrichum gloeosporioides* (strain Nara gc5) (*Anthracnose fungus*) (*Glomerella cingulata*) | CGGC5_4608 | L2GB29 |
| *Gibberella zeae* (*Wheat head blight fungus*) (*Fusarium graminearum*) | FG05_06918 | A0A016PCS4 |
| *Trichophyton soudanense* CBS 452.61 | H105_00612 | A0A022Y6A6 |
| *Sclerotinia sclerotiorum* (strain ATCC 18683 / 1980 / Ss-1) (*White mold*) (*Whetzelinia sclerotiorum*) | SS1G_07437 | A7EQ37 |
| *Fusarium oxysporum f. sp. pisi* HDV247 | FOVG_14401 | W9NWU8 |
| *Fusarium oxysporum f. sp. pisi* HDV247 | FOVG_02874 | W9Q5V3 |
| *Ustilago hordei* (strain Uh4875-4) (*Barley covered smut fungus*) | UHOR_03009 | I2G1Z4 |
| *Sporisorium reilianum* (strain SRZ2) (*Maize head smut fungus*) | sr12985 | E6ZYF7 |
| *Bipolaris zeicola* 26-R-13 | COCCADRAFT_81154 | W6YIP8 |
| *Melampsora larici-populina* (strain 98AG31 / pathotype 3-4-7) (*Poplar leaf rust fungus*) | MELLADRAFT_78490 | F4RUZ8 |
| *Fusarium oxysporum f. sp. lycopersici* (strain 4287 / CBS 123668 / FGSC 9935 / NRRL 34936) (*Fusarium vascular wilt of tomato*) | FOXG_01901 | J9MG95 |
| *Fusarium oxysporum f. sp. lycopersici* (strain 4287 / CBS 123668 / FGSC 9935 / NRRL 34936) (*Fusarium vascular wilt of tomato*) | FOXG_11941 | J9N954 |
| *Bipolaris victoriae* FI3 | COCVIDRAFT_39053 | W7EMJ8 |
| *Debaryomyces hansenii* (strain ATCC 36239 / CBS 767 / JCM 1990 / NBRC 0083 / IGC 2968) (*Yeast*) (*Torulaspora hansenii*) | DEHA2E04268g | Q6BQL4 |
| *Clavispora lusitaniae* (strain ATCC 42720) (*Yeast*) (*Candida lusitaniae*) | CLUG_01505 | C4XZX3 |
| *Candida albicans* (strain WO-1) (*Yeast*) | CAWG_02023 | C4YME4 |
| *Trichophyton rubrum* MR850 | H100_00625 | A0A022U0Q2 |
| *Candida dubliniensis* (strain CD36 / ATCC MYA-646 / CBS 7987 / NCPF 3949 / NRRL Y-17841) (*Yeast*) | CD36_32890 | B9WMC7 |

TABLE 6.3-continued

Alcohol oxidase enzymes capable of oxidizing long chain alcohols including fatty alcohols (EC 1.1.3.20)

| Organism | Gene names | Accession No. |
| --- | --- | --- |
| *Starmerella bombicola* | AOX1 | A0A024FB95 |
| *Thielavia heterothallica* (strain ATCC 42464 / BCRC 31852 / DSM 1799) (*Myceliophthora thermophila*) | MYCTH_103590 | G2QJL7 |
| *Claviceps purpurea* (strain 20.1) (*Ergot fungus*) (*Sphacelia segetum*) | CPUR_07614 | M1WFI4 |
| *Aspergillus oryzae* (strain ATCC 42149 / RIB 40) (Yellow koji mold) | AO090023000571 | Q2UH61 |
| *Dictyostelium discoideum* (Slime mold) | DDB_0184181 DDB_G0292042 | Q54DT6 |
| *Triticum urartu* (Red wild einkorn) (*Crithodium urartu*) | TRIUR3_22733 | M7YME5 |
| *Solanum tuberosum* (Potato) | PGSC0003DMG400017211 | M1BG07 |
| *Oryza sativa* subsp. *japonica* (Rice) | OSJNBb0044B19.5 LOC_Os10g33540 | Q8W5P8 |
| *Oryza sativa* subsp. *japonica* (Rice) | OJ1234_B11.20 Os02g0621800 | Q6K9N5 |
| *Oryza sativa* subsp. *japonica* (Rice) | OSJNBa0001K12.5 LOC_Os10g33520 | Q8W5P3 |
| *Zea mays* (Maize) | ZEAMMB73_809149 | C0P3J6 |
| *Citrus clementina* | CICLE_v10011111mg | V4S9P4 |
| *Citrus clementina* | CICLE_v10018992mg | V4U4C9 |
| *Citrus clementina* | CICLE_v10004405mg | V4S9D3 |
| *Citrus clementina* | CICLE_v10004403mg | V4RZZ6 |
| *Morus notabilis* | L484_011703 | W9RIK0 |
| *Morus notabilis* | L484_005930 | W9RET7 |
| *Medicago truncatula* (Barrel medic) (*Medicago tribuloides*) | MTR_1g075650 | G7I4U3 |
| *Arabidopsis thaliana* (Mouse-ear cress) | | Q8LDP0 |
| *Medicago truncatula* (Barrel medic) (*Medicago tribuloides*) | MTR_4g081080 | G7JF07 |
| *Simmondsia chinensis* (Jojoba) (*Buxus chinensis*) | | L7VFV2 |
| *Prunus persica* (Peach) (*Amygdalus persica*) | PRUPE_ppa018458mg | M5VXL1 |
| *Aphanomyces astaci* | H257_07411 | W4GI89 |
| *Aphanomyces astaci* | H257_07412 | W4GI44 |
| *Aphanomyces astaci* | H257_07411 | W4GKE3 |
| *Aphanomyces astaci* | H257_07411 | W4GK29 |
| *Aphanomyces astaci* | H257_07411 | W4GJ79 |
| *Aphanomyces astaci* | H257_07411 | W4GI38 |
| *Phaeodactylum tricornutum* (strain CCAP 1055/1) | PHATRDRAFT_48204 | B7G6C1 |
| *Hordeum vulgare* var. *distichum* (Two-rowed barley) | | F2E4R4 |
| *Hordeum vulgare* var. *distichum* (Two-rowed barley) | | F2DZG1 |
| *Hordeum vulgare* var. *distichum* (Two-rowed barley) | | M0YPG7 |
| *Hordeum vulgare* var. *distichum* (Two-rowed barley) | | M0YPG6 |
| *Hordeum vulgare* var. *distichum* (Two-rowed barley) | | F2CUY4 |
| *Ricinus communis* (Castor bean) | RCOM_0867830 | B9S1S3 |
| *Brassica rapa* subsp. *pekinensis* (Chinese cabbage) (*Brassica pekinensis*) | BRA014947 | M4DEM5 |
| *Ricinus communis* (Castor bean) | RCOM_0258730 | B9SV13 |
| *Brassica rapa* subsp. *pekinensis* (Chinese cabbage) (*Brassica pekinensis*) | BRA001912 | M4CCI2 |
| *Brassica rapa* subsp. *pekinensis* (Chinese cabbage) (*Brassica pekinensis*) | BRA012548 | M4D7T8 |
| *Brassica rapa* subsp. *pekinensis* (Chinese cabbage) (*Brassica pekinensis*) | BRA024190 | M4E5Y6 |
| *Brassica rapa* subsp. *pekinensis* (Chinese cabbage) (*Brassica pekinensis*) | BRA015283 | M4DFL0 |
| *Ricinus communis* (Castor bean) | RCOM_1168730 | B9SS54 |
| *Zea mays* (Maize) | | C4J691 |
| *Oryza glaberrima* (African rice) | | I1P2B7 |
| *Zea mays* (Maize) | | B6SXM3 |
| *Zea mays* (Maize) | | C0HFU4 |
| *Aegilops tauschii* (Tausch's goatgrass) (*Aegilops squarrosa*) | F775_19577 | R7W4J3 |
| *Solanum habrochaites* (Wild tomato) (*Lycopersicon hirsutum*) | | R9R6T0 |
| *Physcomitrella patens* subsp. *patens* (Moss) | PHYPADRAFT_124285 | A9S535 |
| *Physcomitrella patens* subsp. *patens* (Moss) | PHYPADRAFT_113581 | A9RG13 |
| *Physcomitrella patens* subsp. *patens* (Moss) | PHYPADRAFT_182504 | A9S9A5 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| Solanum pennellii (Tomato) (Lycopersicon pennellii) | | R9R6Q1 |
| Vitis vinifera (Grape) | VIT_02s0087g00630 | F6HJ27 |
| Vitis vinifera (Grape) | VIT_07s0005g03780 | F6HZM3 |
| Vitis vinifera (Grape) | VIT_05s0049g01400 | F6H8T4 |
| Vitis vinifera (Grape) | VITISV_019349 | A5AH38 |
| Capsella rubella | CARUB_v10013046mg | R0HIT3 |
| Capsella rubella | CARUB_v10004212mg | R0GUX4 |
| Capsella rubella | CARUB_v10004208mg | R0F3X6 |
| Capsella rubella | CARUB_v10012453mg | R0ILD0 |
| Capsella rubella | CARUB_v10004208mg | R0GUX1 |
| Eutrema salsugineum (Saltwater cress) (Sisymbrium salsugineum) | EUTSA_v10024496mg | V4MD54 |
| Eutrema salsugineum (Saltwater cress) (Sisymbrium salsugineum) | EUTSA_v10020141mg | V4NM59 |
| Eutrema salsugineum (Saltwater cress) (Sisymbrium salsugineum) | EUTSA_v10024496mg | V4LUR9 |
| Eutrema salsugineum (Saltwater cress) (Sisymbrium salsugineum) | EUTSA_v10024528mg | V4P767 |
| Eutrema salsugineum (Saltwater cress) (Sisymbrium salsugineum) | EUTSA_v10006882mg | V4L2P6 |
| Selaginella moellendorffii (Spikemoss) | SELMODRAFT_87684 | D8R6Z6 |
| Selaginella moellendorffii (Spikemoss) | SELMODRAFT_87621 | D8R6Z5 |
| Selaginella moellendorffii (Spikemoss) | SELMODRAFT_74601 | D8QN81 |
| Selaginella moellendorffii (Spikemoss) | SELMODRAFT_73531 | D8QN82 |
| Sorghum bicolor (Sorghum) (Sorghum vulgare) | Sb04g026390 SORBIDRAFT_04g026390 | C5XXS4 |
| Sorghum bicolor (Sorghum) (Sorghum vulgare) | 5b04g026370 SORBIDRAFT_04g026370 | C5XXS1 |
| Sorghum bicolor (Sorghum) (Sorghum vulgare) | 5b01g019470 SORBIDRAFT_01g019470 | C5WYH6 |
| Sorghum bicolor (Sorghum) (Sorghum vulgare) | 5b01g019480 SORBIDRAFT_01g019480 | C5WYH7 |
| Sorghum bicolor (Sorghum) (Sorghum vulgare) | 5b01g019460 SORBIDRAFT_01g019460 | C5WYH5 |
| Solanum pimpinellifolium (Currant tomato) (Lycopersicon pimpinellifolium) | | R9R6J2 |
| Phaseolus vulgaris (Kidney bean) (French bean) | PHAVU_007G124200g | V7BGM7 |
| Phaseolus vulgaris (Kidney bean) (French bean) | PHAVU_011G136600g | V7AI35 |
| Phaseolus vulgaris (Kidney bean) (French bean) | PHAVU_001G162800g | V7D063 |
| Solanum tuberosum (Potato) | PG5C0003DMG400024294 | M1C923 |
| Solanum tuberosum (Potato) | PGSC0003DMG400018458 | M1BKV4 |
| Solanum tuberosum (Potato) | PGSC0003DMG400018458 | M1BKV3 |
| Glycine max (Soybean) (Glycine hispida) | | K7LK61 |
| Glycine max (Soybean) (Glycine hispida) | | K7KXQ9 |
| Populus trichocarpa (Western balsam poplar) (Populus balsamifera subsp. trichocarpa) | POPTR_0008s16920g | B9HKS3 |
| Picea sitchensis (Sitka spruce) (Pinus sitchensis) | | B8LQ84 |
| Populus trichocarpa (Western balsam poplar) (Populus balsamifera subsp. trichocarpa) | POPTR_0004s24310g | U5GKQ5 |
| Populus trichocarpa (Western balsam poplar) (Populus balsamifera subsp. trichocarpa) | POPTR_0010507980g | B9HSG9 |
| Glycine max (Soybean) (Glycine hispida) | | I1N9S7 |
| Glycine max (Soybean) (Glycine hispida) | | I1LSK5 |
| Setaria italica (Foxtail millet) (Panicum italicum) | Si034362m.g | K4A658 |
| Solanum lycopersicum (Tomato) (Lycopersicon esculentum) | Solyc09g072610.2 | K4CUT7 |
| Setaria italica (Foxtail millet) (Panicum italicum) | Si016380m.g | K3YQ38 |
| Solanum lycopersicum (Tomato) (Lycopersicon esculentum) | | R9R6I9 |
| Solanum lycopersicum (Tomato) (Lycopersicon esculentum) | Solyc09g090350.2 | K4CW61 |
| Solanum lycopersicum (Tomato) (Lycopersicon esculentum) | Solyc08g005630.2 | K4CI54 |
| Solanum lycopersicum (Tomato) (Lycopersicon esculentum) | Solyc08g075240.2 | K4CMP1 |
| Setaria italica (Foxtail millet) (Panicum italicum) | Si034359m.g | K4A655 |
| Setaria italica (Foxtail millet) (Panicum italicum) | Si034354m.g | K4A650 |
| Mimulus guttatus (Spotted monkey flower) (Yellow monkey flower) | MIMGU_mgvla001896mg | A0A022PU07 |
| Mimulus guttatus (Spotted monkey flower) (Yellow monkey flower) | MIMGU_mgv1a022390mg | A0A022RAV4 |
| Mimulus guttatus (Spotted monkey flower) (Yellow monkey flower) | MIMGU_mgvla001868mg | A0A02252E6 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Mimulus guttatus* (Spotted monkey flower) (Yellow monkey flower) | MIMGU_mgvla001883mg | A0A0225275 |
| *Mimulus guttatus* (Spotted monkey flower) (Yellow monkey flower) | MIMGU_mgv1a001761mg | A0A022QNF0 |
| *Musa acuminata subsp. malaccensis* (Wild banana) (*Musa malaccensis*) | | M0SNA8 |
| *Musa acuminata subsp. malaccensis* (Wild banana) (*Musa malaccensis*) | | M0RUT7 |
| *Musa acuminata subsp. malaccensis* (Wild banana) (*Musa malaccensis*) | | M0RUK3 |
| *Saprolegnia diclina* V520 | SDRG_10901 | T0RG89 |
| *Brachypodium distachyon* (Purple false brome) (*Trachynia distachya*) | BRADI3G49085 | I1IBP7 |
| *Brachypodium distachyon* (Purple false brome) (*Trachynia distachya*) | BRADI3G28677 | I1I4N2 |
| *Brachypodium distachyon* (Purple false brome) (*Trachynia distachya*) | BRADI3G28657 | I1I4N0 |
| *Oryza sativa subsp. indica* (Rice) | OsI_34012 | B8BHG0 |
| *Oryza sativa subsp. indica* (Rice) | OsI_08118 | B8AFT8 |
| *Oryza sativa subsp. indica* (Rice) | OsI_34008 | A2Z8H1 |
| *Oryza sativa subsp. indica* (Rice) | OsI_34014 | B8BHG1 |
| *Oryza sativa subsp. japonica* (Rice) | LOC_Os10g33460 | Q7XDG3 |
| *Oryza sativa subsp. japonica* (Rice) | Os10g0474800 | Q0IX12 |
| *Oryza sativa subsp. japonica* (Rice) | Os10g0474966 | C7J7R1 |
| *Oryza sativa subsp. japonica* (Rice) | OSJNBa0001K12.13 | Q8W5N7 |
| *Oryza sativa subsp. japonica* (Rice) | OsJ_31873 | B9G683 |
| *Oryza sativa subsp. japonica* (Rice) | OsJ_31875 | B9G684 |
| *Oryza sativa subsp. japonica* (Rice) | OSJNBa0001K12.3 | Q8W5P5 |
| *Arabidopsis lyrata subsp. lyrata* (Lyre-leaved rock-cress) | ARALYDRAFT_470376 | D7KDA3 |
| *Arabidopsis lyrata subsp. lyrata* (Lyre-leaved rock-cress) | ARALYDRAFT_479855 | D7L3B6 |
| *Arabidopsis lyrata subsp. lyrata* (Lyre-leaved rock-cress) | ARALYDRAFT_491906 | D7MDA9 |
| *Arabidopsis lyrata subsp. lyrata* (Lyre-leaved rock-cress) | ARALYDRAFT_914728 | D7MGS9 |

Desaturase

The present disclosure describes enzymes that desaturate fatty acyl substrates to corresponding unsaturated fatty acyl substrates.

In some embodiments, a desaturase is used to catalyze the conversion of a fatty acyl-CoA or acyl-ACP to a corresponding unsaturated fatty acyl-CoA or acyl-ACP. A desaturase is an enzyme that catalyzes the formation of a carbon-carbon double bond in a saturated fatty acid or fatty acid derivative, e.g., fatty acyl-CoA or fatty acyl-ACP (collectively referred to herein as "fatty acyl"), by removing at least two hydrogen atoms to produce a corresponding unsaturated fatty acid/acyl. Desaturases are classified with respect to the ability of the enzyme to selectively catalyze double bond formation at a subterminal carbon relative to the methyl end of the fatty acid/acyl or a subterminal carbon relative to the carbonyl end of the fatty acid/acyl. Omega ($\omega$) desaturases catalyze the formation of a carbon-carbon double bond at a fixed subterminal carbon relative to the methyl end of a fatty acid/acyl. For example, an $\omega^3$ desaturase catalyzes the formation of a double bond between the third and fourth carbon relative the methyl end of a fatty acid/acyl. Delta ($\Delta$) desaturases catalyze the formation of a carbon-carbon double bond at a specific position relative to the carboxyl group of a fatty acid or the carbonyl group of a fatty acyl CoA. For example, a $\Delta^9$ desaturase catalyzes the formation of a double bond between the $C_9$ and $C_{10}$ carbons with respect to the carboxyl end of the fatty acid or the carbonyl group of a fatty acyl CoA.

As used herein, a desaturase can be described with reference to the location in which the desaturase catalyzes the formation of a double bond and the resultant geometric configuration (i.e., E/Z) of the unsaturated hydrocarbon. Accordingly, as used herein, a Z9 desaturase refers to a $\Delta$ desaturase that catalyzes the formation of a double bond between the $C_9$ and $C_{10}$ carbons with respect to the carbonyl end of a fatty acid/acyl, thereby orienting two hydrocarbons on opposing sides of the carbon-carbon double bonds in the cis or Z configuration. Similarly, as used herein, a Z11 desaturase refers to a $\Delta$ desaturase that catalyzes the formation of a double bond between the $C_{11}$ and $C_{12}$ carbons with respect to the carbonyl end of a fatty acid/acyl.

Desaturases have a conserved structural motif. This sequence motif of transmembrane desaturases is characterized by [HX3-4HX7-41(3 non-His)HX2-3(1 nonHis) HHX61-189(40 non-His)HX2-3(1 non-His)HH]. The sequence motif of soluble desaturases is characterized by two occurrences of [D/EEXXH].

In some embodiments, the desaturase is a fatty acyl-CoA desaturase that catalyzes the formation of a double bond in a fatty acyl-CoA. In some such embodiments, the fatty acyl-CoA desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl desaturase described herein is capable of catalyzing the formation of a double bond at a desired carbon relative to the terminal CoA on the unsaturated fatty acyl-CoA. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-CoA.

In some embodiments, the fatty acyl desaturase described herein is capable of catalyzing the formation of a double bond in a saturated fatty acyl-CoA such that the resultant unsaturated fatty acyl-CoA has a cis or trans (i.e., Z or E) geometric configuration.

In some embodiments, the desaturase is a fatty acyl-ACP desaturase that catalyzes the formation of a double bond in a fatty acyl-ACP. In some embodiments, the fatty acyl-ACP desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl-ACP desaturase described herein is capable of catalyzing the formation of a double bond at a desired carbon relative to the terminal carbonyl on the unsaturated fatty acyl-ACP. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-ACP.

In some embodiments, the fatty acyl desaturase described herein is capable of catalyzing the formation of a double bond in a saturated fatty acyl-CoA such that the resultant unsaturated fatty acyl-ACP has a cis or trans (i.e., Z or E) geometric configuration.

In one embodiment, the fatty acyl desaturase is a Z11 desaturase. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana* is codon optimized. In some embodiments, the Z11 desaturase comprises a sequence set forth in SEQ ID NO: 32 or 33 from *Helicoverpa zea.*

Fatty Acyl Reductase

The present disclosure describes enzymes that reduce fatty acyl substrates to corresponding fatty alcohols or aldehydes.

In some embodiments, a fatty alcohol forming fatty acyl-reductase is used to catalyze the conversion of a fatty acyl-CoA to a corresponding fatty alcohol. In some embodiments, a fatty aldehyde forming fatty acyl-reductase is used to catalyze the conversion of a fatty acyl-ACP to a corresponding fatty aldehyde. A fatty acyl reductase is an enzyme that catalyzes the reduction of a fatty acyl-CoA to a corresponding fatty alcohol or the reduction of a fatty acyl-ACP to a corresponding fatty aldehyde. A fatty acyl-CoA and fatty acyl-ACP has a structure of R—(CO)—S—$R_1$, wherein R is a $C_6$ to $C_{24}$ saturated, unsaturated, linear, branched or cyclic hydrocarbon, and $R_1$ represents CoA or ACP. In a particular embodiment, R is a $C_6$ to $C_{24}$ saturated or unsaturated linear hydrocarbon. "CoA" is a non-protein acyl carrier group involved in the synthesis and oxidation of fatty acids. "ACP" is an acyl carrier protein, i.e., a polypeptide or protein subunit, of fatty acid synthase used in the synthesis of fatty acids.

Thus, in some embodiments, the disclosure provides for a fatty alcohol forming fatty acyl-reductase which catalyzes the reduction of a fatty acyl-CoA to the corresponding fatty alcohol. For example, R—(CO)—S-CoA is converted to R—$CH_2OH$ and CoA-SH when two molecules of NAD(P)H are oxidized to NAD(P)$^+$. Accordingly, in some such embodiments, a recombinant microorganism described herein can include a heterologous fatty alcohol forming fatty acyl-reductase, which catalyzes the reduction a fatty acyl-CoA to the corresponding fatty alcohol. In an exemplary embodiment, a recombinant microorganism disclosed herein includes at least one exogenous nucleic acid molecule encoding a fatty alcohol forming fatty-acyl reductase which catalyzes the conversion of a mono- or poly-unsaturated $C_6$-$C_{24}$ fatty acyl-CoA into the corresponding mono- or poly-unsaturated $C_6$-$C_{24}$ fatty alcohol.

In other embodiments, the disclosure provides for a fatty aldehyde forming fatty acyl-reductase which catalyzes the reduction of a fatty acyl-ACP to the corresponding fatty aldehyde. For example, R—(CO)—S-ACP is converted to R—(CO)—H and ACP-SH when one molecule of NAD(P)H is oxidized to NAD(P)$^+$. In some such embodiments, a recombinant microorganism described herein can include a heterologous fatty aldehyde forming fatty acyl-reductase, which catalyzes the reduction a fatty acyl-ACP to the corresponding fatty aldehyde. In an exemplary embodiment, a recombinant microorganism disclosed herein includes at least one exogenous nucleic acid molecule encoding a fatty aldehyde forming fatty-acyl reductase which catalyzes the conversion of a mono- or poly-unsaturated $C_6$-$C_{24}$ fatty acyl-ACP into the corresponding mono- or poly-unsaturated $C_6$-$C_{24}$ fatty aldehyde.

In some embodiments, a nucleic acid sequence encoding a fatty-acyl reductase from organisms of the species *Agrotis segetum, Spodoptera littoralis,* or *Helicoverpa amigera* is codon optimized.

Acyl-ACP Synthetase

The present disclosure describes enzymes that ligate a fatty acid to the corresponding fatty acyl-ACP.

In some embodiments, an acyl-ACP synthetase is used to catalyze the conversion of a fatty acid to a corresponding fatty acyl-ACP. An acyl-ACP synthetase is an enzyme capable of ligating a fatty acid to ACP to produce a fatty acid acyl-ACP. In some embodiments, an acyl-ACP synthetase can be used to catalyze the conversion of a fatty acid to a corresponding fatty acyl-ACP. In some embodiments, the acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms. In one such embodiment, a recombinant microorganism described herein can include a heterologous acyl-ACP synthetase, which catalyzes the conversion of a fatty acid to a corresponding fatty acyl-ACP. In an exemplary embodiment, a recombinant microorganism disclosed herein includes at least one exogenous nucleic acid molecule which encodes an acyl-ACP synthetase that catalyzes the conversion of a saturated $C_6$-$C_{24}$ fatty acid to a corresponding saturated $C_6$-$C_{24}$ fatty acyl-ACP.

Improved Production of Biomass and One or More Lipid Using a Recombinant Microorganism As discussed above, in a first aspect, the present disclosure relates to a recombinant microorganism having improved production of biomass or improved production of one or more lipid from one or more fatty acid and one or more simple carbon co-substrates, wherein the recombinant microorganism comprises one or more modifications associated with: tricarboxylic acid cycle; lipid synthesis; reducing equivalent availability; one or more metabolic intermediates availability; and/or increased product purity, wherein the recombinant microorganism has improved production of biomass or improved production of one or more lipid compared to a microorganism without the same modifications.

In some embodiments, the one or more modifications associated with tricarboxylic acid cycle comprises the overexpression of at least one endogenous and/or exogenous nucleic acid molecule encoding an AMP-insensitive isocitrate dehydrogenase (IDH) variant in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to AMP-insensitive IDH from *Escherichia coli*, *Mycobacterium smegmatis*, *Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2. In some embodiments, the one or more modifications associated with tricarboxylic acid cycle results in extended activation of the tricarboxylic acid cycle.

In some embodiments, the one or more modifications associated with tricarboxylic acid cycle or one or more metabolic intermediates availability comprises the overexpression of at least one endogenous and/or exogenous nucleic acid molecule encoding a pyruvate transporter in the recombinant microorganism. In other embodiments, the one or more metabolic intermediates availability comprises mitochondrial pyruvate availability. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to pyruvate transporter from *Saccharomyces cerevisiae*, *Hanseniaspora osmophila*, *Yarrowia lipolytica*, or *Talaromyces marneffei* PM1. In further embodiments, the pyruvate transporter is selected from *Saccharomyces cerevisiae* mpc1, *Saccharomyces cerevisiae* mpc3 (NP_011759.1), *Hanseniaspora osmophila* mpc3 (OEJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia lipolytica*.

In some embodiments, the one or more modifications associated with lipid synthesis comprises alleviation of acetyl-CoA carboxylase (ACC) inhibition. In certain embodiments, alleviation of ACC inhibition comprises the replacement of the endogenous ACC, or overexpression of at least one endogenous and/or exogenous nucleic acid molecule encoding a feedback-insensitive ACC variant in the recombinant microorganism. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to ACC from *Mus musculus*, *Rattus norvegicus*, or *Homo sapiens*.

In some embodiments, the one or more modifications associated with reducing equivalent availability comprises the overexpression of at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli*, *Mycobacterium smegmatis*, *Acidithiobacillus thiooxidans*, or *Yarrowia lipolytica*. In further embodiments, the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

In some embodiments, the one or more modifications associated with reducing equivalent availability further comprises the overexpression of at least one endogenous and/or exogenous nucleic acid encoding an aconitase in the cytosol of the recombinant microorganism. In certain embodiments, the at least one endogenous and/or exogenous nucleic acid molecule encoding the IDH and the at least one endogenous and/or exogenous nucleic acid molecule encoding the aconitase lack a sequence encoding a mitochondrial-targeting peptide.

In some embodiments, the one or more modifications associated with reducing equivalent availability or one or more metabolic intermediates availability comprises the overexpression of at least one endogenous or exogenous nucleic acid encoding a citrate transporter in the recombinant microorganism. In certain embodiments, the one or more intermediate comprises cytosolic citrate/isocitrate. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a citrate transporter from *Yarrowia lipolytica*, *Saccharomyces cerevisiae*, *Rattus norvegicus*, *Caenorhabditis elegans*, or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

In some embodiments, the one or more modifications associated with reducing equivalent availability comprises the overexpression of at least one exogenous nucleic acid molecule encoding a decarboxylating malic enzyme in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a decarboxylating malic enzyme from *Arabidopsis thaliana*, *Amaranthus hypochondriacus*, *Rhizobium meliloti*, *Solanum tuberosum*, *Homo sapiens*, or *Escherichia coli*. In further embodiments, the decarboxylating malic enzyme is selected from *Arabidopsis thaliana* Q9SIU0 (SEQ ID NO: 34), *Amaranthus hypochondriacus* P37224 (SEQ ID NO: 35), *Rhizobium meliloti* O30807 (SEQ ID NO: 36), *Solanum tuberosum* P37221 (SEQ ID NO: 37), *Homo sapiens* Q16798 (SEQ ID NO: 38), and *Escherichia coli* P26616 (SEQ ID NO: 29), or homolog thereof. In yet a further embodiment, the decarboxylating malic enzyme lacks a sequence encoding a mitochondrial-targeting peptide.

In some embodiments, the one or more modifications associated with one or more metabolic intermediates availability comprises the overexpression of at least one endogenous and/or exogenous nucleic acid encoding an ATP-citrate lyase in the recombinant microorganism. In certain embodiments, the one or more intermediates availability comprises cytosolic oxaloacetate availability. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

In some embodiments, the one or more modifications associated with reducing equivalent availability comprises one or more modifications in the pentose phosphate pathway (PPP) in the recombinant microorganism. In certain embodiments, the one or more modifications in the PPP comprises one or more of: downregulation of hexose kinase activity; upregulation of one or more oxidative PPP enzyme activity; downregulation of fructose-6-phosphate kinase activity; and/or expression of one or more oxidative PPP enzyme variant. In further embodiments, the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1). In yet a further embodiment, the downregulation of hexose kinase activity and/or fructose-6-phosphate kinase activity comprises deletion, disruption, and/or mutation of one or more endogenous gene encoding one or more hexose kinase enzyme and/or fructose-6-phosphate kinase enzyme. In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent 6-phosphogluconate dehydrogenase (GND1) from *Bradyrhizobium* or *Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an NADPH-dependent mannitol dehydrogenase and/or an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g, or homolog thereof.

In some embodiments, the one or more modifications associated with reducing equivalent availability comprises decoupling and increasing glucose uptake in the recombinant microorganism. In certain embodiments, decoupling and increasing glucose uptake comprises: upregulation of hexose transporter activity; and/or downregulation of hexose kinase activity. In further embodiments, the upregulation of one or more hexose transporter activity comprises the overexpression of one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof. In some embodiments, the downregulation of hexose kinase activity comprises deletion, disruption, and/or mutation of one or more endogenous gene encoding one or more hexose kinase enzyme.

In some embodiments, the one or more modifications associated with reducing equivalent availability, one or more metabolic intermediates availability, or increased product purity comprises downregulation or inhibition of acetyl-CoA carboxylase (ACC) activity in the recombinant microorganism. In certain embodiments, the downregulation or inhibition of ACC activity comprises deletion, disruption, and/or mutation of one or more endogenous gene encoding one or more ACC enzyme.

In some embodiments of a recombinant microorganism having improved production of biomass or improved production of one or more lipid from one or more fatty acid and one or more simple carbon co-substrates, the one or more fatty acid co-substrate is a saturated fatty acid. In some embodiments of a recombinant microorganism having improved production of biomass or improved production one or more lipid from one or more fatty acid and one or more simple carbon co-substrates, the one or more simple carbon co-substrate is selected from glucose, fructose, and glycerol.

In some embodiments of a recombinant microorganism having improved production of biomass or improved production of one or more lipid from one or more fatty acid and one or more simple carbon co-substrates, the improved production of one or more lipid comprises improved production of one or more mono- or poly-unsaturated $C_6$-$C_{24}$ fatty acid, fatty alcohol, aldehyde, or acetate. In certain embodiments, the one or more mono- or poly-unsaturated $C_6$-$C_{24}$ fatty acid, fatty alcohol, aldehyde, or acetate is an insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In some embodiments of a recombinant microorganism having improved production of biomass or improved production of one or more lipid from one or more fatty acid and one or more simple carbon co-substrates, the recombinant microorganism is a eukaryotic microorganism. In certain embodiments, the eukaryotic microorganism is a yeast. In further embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula,* and *Myxozyma*. In yet a further embodiment, the yeast is an oleaginous yeast. In some embodiments, the oleaginous yeast is a member of a genus selected from the group consisting of *Yarrowia, Candida, Rhodotorula, Rhodosporidium, Cryptococcus, Trichosporon,* and *Lipomyces*. In certain embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis,* and *R. graminis*.

Recombinant Microorganism

The disclosure provides microorganisms modified to have improved production of biomass or valuable products, such as one or more lipids or metabolic intermediates. In one embodiment, the valuable product is one or more lipids. In some embodiments, the valuable product is fatty acid, fatty alcohol, fatty aldehyde, and/or fatty acetate. In some embodiments, the valuable product is one or more pheromones. In some embodiments, the valuable product is one or more fatty acid precursors of one or more pheromones.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula,* and *Myxozyma*.

The present inventors have discovered that oleaginous yeast, such as *Candida* and *Yarrowia*, have a surprisingly high tolerance to the $C_6$-$C_{24}$ fatty alcohol substrates and products. Accordingly, in one such exemplary embodiment, the recombinant microorganism of the invention is an oleaginous yeast. In further embodiments, the oleaginous yeast is a member of a genus selected from the group consisting of *Yarrowia, Candida, Rhodotorula, Rhodosporidium, Cryptococcus, Trichosporon,* and *Lipomyces*. In even further embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis,* and *R. graminis*.

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium*.

In some embodiments, the recombinant microorganism is used to produce a mono- or poly-unsaturated $C_6$-$C_{24}$ fatty acid, alcohol, aldehyde, or acetate disclosed herein.

Accordingly, in another aspect, the present disclosure provides a method of producing one or more lipid using a recombinant microorganism described herein. In one embodiment, the method comprises cultivating the recombinant microorganism in a culture medium containing a feedstock providing one or more carbon source until the one or more lipid is produced. In some embodiments, the one or more lipid comprises one or more mono- or poly-unsaturated $C_6$-$C_{24}$ fatty acid, alcohol, aldehyde, or acetate. In further embodiments, the one or more mono- or poly-unsaturated $C_6$-$C_{24}$ fatty acid, alcohol, aldehyde, or acetate is one or more insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal. In a further embodiment, the one or more lipid is recovered. Recovery can be by methods known in the art, such as distillation, membrane-based separation gas stripping, solvent extraction, and expanded bed adsorption.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In a further embodiment, the sugar is selected from the group consisting of glucose, fructose, and sucrose. In some embodiments, the one or more carbon source comprises one or more simple carbon and one or more fatty acid. In certain embodiments, the one or more simple carbon is selected from glucose, fructose and glycerol.

In some embodiments, the recombinant microorganism is a microalgae. Non-limiting examples of microalgae that can be used with the methods and compositions of the disclosure are members of the following divisions: cyanobacteria (Cyanophyceae), green algae (Chlorophyceae), diatoms (Bacillariophyceae), yellow green algae (Xanthophyceae), golden algae (Chrysophyceae), red algae (Rhodophyceae), brown algae (Phaeophyceae), dinoflagellates (Dinophyceae), and "pico-plankton" (Prasinophyceae and Eustigmatophyceae). In some embodiments, the preferred algae for use in connection with the production of Fas are green algae (fresh water), Cyanobacteria, and Diotoms (Marine). In certain embodiments, the microalgae used with the methods of the disclosure are members of one of the following classes: Bacillariophyceae, Eustigmatophyceae, and Chrysophyceae. In certain embodiments, the microalgae used with the methods of the disclosure are members of one of the following genera: *Nannochloropsis, Chlorella, Dunaliella, Scenedesmus, Selenastrum, Oscillatoria, Phormidium, Spirulina, Amphora,* and *Ochromonas*.

Non-limiting examples of microalgae species that can be used in connection with the present disclosure include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorelladesiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorellaluteoviridis* var. *aureoviridis, Chlorella luteoviridis* var. *lutescens, Chlorella miniata, Chlorella minutissima, Chlorella mutabilis, Chlorella noctuma, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorellasaccharophila* var. *ellipsoidea, Chlorella salina, Chlorella simplex, Chlorella sorokiniana, Chlorella* sp., *Chlorella sphaerica, Chlorellastigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliellapeircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis off galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carter ae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana*.

Methods of Producing a Recombinant Microorganism Having Improved Production of Biomass and One or More Lipid As discussed above, in another aspect, the present disclosure relates to a method of producing a recombinant microorganism having improved production of biomass or improved production of one or more lipid from one or more fatty acid and one or more simple carbon co-substrates, comprising introducing into a microorganism one or more modifications associated with: tricarboxylic acid cycle; lipid synthesis; reducing equivalent availability; one or more metabolic intermediates availability; and/or increased product purity, wherein the introducing one or more modifications yields a recombinant microorganism having improved production of biomass or improved production of one or more lipid compared to a microorganism not comprising the same modifications.

In some embodiments, the introducing one or more modifications associated with tricarboxylic acid cycle comprises introducing into and/or overexpressing in the recombinant microorganism at least one endogenous and/or exogenous nucleic acid molecule encoding an AMP-insensitive isocitrate dehydrogenase (IDH) variant. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2. In some embodiments, the one or more modifications associated with tricarboxylic acid cycle results in extended activation of the tricarboxylic acid cycle.

In some embodiments, the introducing one or more modifications associated with tricarboxylic acid cycle or one or more metabolic intermediates availability comprises introducing into and/or overexpressing in the recombinant microorganism at least one endogenous and/or exogenous nucleic acid molecule encoding a pyruvate transporter. In other embodiments, the one or more metabolic intermediates availability comprises mitochondrial pyruvate availability. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to pyruvate transporter from *Saccharomyces cerevisiae, Hanseniaspora osmophila, Yarrowia lipolytica,* or *Talaromyces marneffei* PM1. In further embodiments, the pyruvate transporter is selected from *Saccharomyces cerevisiae* mpc1, *Saccharomyces cerevisiae* mpc3 (NP_011759.1), *Hanseniaspora osmophila* mpc3 (OEJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia lipolytica*.

In some embodiments, the introducing one or more modifications associated with lipid synthesis comprises alleviation of acetyl-CoA carboxylase (ACC) inhibition. In certain embodiments, alleviation of ACC inhibition comprises introducing into and/or overexpressing in the recombinant microorganism at least one endogenous and/or exogenous nucleic acid molecule encoding a feedback-insensitive ACC variant in the recombinant microorganism. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to ACC from *Mus musculus, Rattus norvegicus,* or *Homo sapiens*.

In some embodiments, the introducing one or more modifications associated with reducing equivalent availability comprises introducing into and/or overexpressing in the recombinant microorganism at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans,* or *Yarrowia lipolytica*. In further embodiments, the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

In some embodiments, the introducing one or more modifications associated with reducing equivalent availability further comprises introducing into and/or overexpressing in the recombinant microorganism at least one endogenous and/or exogenous nucleic acid encoding an aconitase in the cytosol of the recombinant microorganism. In certain embodiments, the at least one endogenous and/or exogenous nucleic acid molecule encoding the IDH and the at least one endogenous and/or exogenous nucleic acid molecule encoding the aconitase lack a sequence encoding a mitochondrial-targeting peptide.

In some embodiments, the introducing one or more modifications associated with reducing equivalent availability or one or more metabolic intermediates availability comprises introducing into and/or overexpressing in the recombinant microorganism at least one endogenous and/or exogenous nucleic acid encoding a citrate transporter in the recombinant microorganism. In certain embodiments, the one or more intermediate comprises cytosolic citrate/isocitrate. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a citrate transporter from *Yarrowia lipolytica, Saccharomyces cerevisiae, Rattus norvegicus, Caenorhabditis elegans,* or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

In some embodiments, the introducing one or more modifications associated with reducing equivalent availability comprises introducing into and/or overexpressing in the recombinant microorganism at least one exogenous nucleic acid molecule encoding a decarboxylating malic enzyme in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a decarboxylating malic enzyme from *Arabidopsis thaliana, Amaranthus hypochondriacus, Rhizobium meliloti, Solanum tuberosum, Homo sapiens,* or *Escherichia coli*. In further embodiments, the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof. In yet a further embodiment, the decarboxylating malic enzyme lacks a sequence encoding a mitochondrial-targeting peptide.

In some embodiments, the introducing one or more modifications associated with one or more metabolic intermediates availability comprises introducing into and/or overexpressing in the recombinant microorganism at least one endogenous and/or exogenous nucleic acid encoding an ATP-citrate lyase in the recombinant microorganism. In certain embodiments, the one or more metabolic intermediates availability comprises cytosolic oxaloacetate availability. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an ATP-citrate lyase from *Saccharomyces cerevisiae, Yarrowia lipolytica, Mus musculus,* and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

In some embodiments, the introducing one or more modifications associated with reducing equivalent availability comprises one or more modifications in the pentose phosphate pathway (PPP) in the recombinant microorganism. In certain embodiments, the one or more modifications in the PPP comprises one or more of: downregulation of hexose kinase activity; upregulation of one or more oxidative PPP enzyme activity; downregulation of fructose-6-phosphate kinase activity; and/or expression of one or more oxidative PPP enzyme variant. In further embodiments, the upregulation of one or more oxidative PPP enzyme activity comprises introducing into and/or overexpressing in the recombinant microorganism one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1). In yet a further embodiment, the downregulation of hexose kinase activity and/or fructose-6-phosphate kinase activity comprises introducing into the recombinant microorganism a deletion, disruption, and/or mutation of one or more endogenous gene encoding one or more hexose kinase enzyme and/or fructose-6-phosphate kinase enzyme. In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent glucose-6-phosphate dehydrogenase (ZWF1) from $Leuconostoc$. In further embodiments, the NAD-dependent glucose-6-phosphate dehydrogenase (ZWF1) is selected from $Leuconostoc$ AAA25265.1 and $Leuconostoc$ P11411, or homolog thereof. In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent 6-phosphogluconate dehydrogenase (GND1) from $Bradyrhizobium$ or $Methylobacillus$. In further embodiments, the NAD-dependent 6-phosphogluconate dehydrogenase (GND1) is selected from $Bradyrhizobium$ WP_012029377.1, $Bradyrhizobium$ A4YZZ8, $Methylobacillus$ AAF34407.1, and $Methylobacillus$ Q9L9P8, or homolog thereof.

In some embodiments, the introducing one or more modifications associated with reducing equivalent availability comprises downregulation of mannitol synthesis pathway in the recombinant microorganism. In certain embodiments, downregulation of mannitol synthesis pathway comprises introducing into the recombinant microorganism a deletion, disruption, and/or mutation of one or more gene encoding an NADPH-dependent mannitol dehydrogenase and/or an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0C00319g, and YALI0A19910g, or homolog thereof.

In some embodiments, the introducing one or more modifications associated with reducing equivalent availability comprises decoupling and increasing glucose uptake in the recombinant microorganism. In certain embodiments, decoupling and increasing glucose uptake comprises: upregulation of hexose transporter activity; and/or downregulation of hexose kinase activity. In further embodiments, the upregulation of one or more hexose transporter activity comprises introducing into and/or overexpressing in the recombinant microorganism one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a hexose transporter from $Yarrowia$ $lipolytica$. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof. In some embodiments, the downregulation of hexose kinase activity comprises introducing into the recombinant microorganism a deletion, disruption, and/or mutation of one or more endogenous gene encoding one or more hexose kinase enzyme.

In some embodiments, the introducing one or more modifications associated with reducing equivalent availability, one or more metabolic intermediates availability, and/or increased product purity comprises downregulation or inhibition of acetyl-CoA carboxylase (ACC) activity in the recombinant microorganism. In certain embodiments, the downregulation or inhibition of ACC activity comprises introducing into the recombinant microorganism a deletion, disruption, and/or mutation of one or more endogenous gene encoding one or more ACC enzyme.

In some embodiments of a method of producing a recombinant microorganism having improved production of biomass or improved production of one or more lipid from one or more fatty acid and one or more simple carbon co-substrates, the one or more fatty acid co-substrate is a saturated fatty acid. In some embodiments of a method of producing a recombinant microorganism having improved production of biomass or improved production of one or more lipid from one or more fatty acid and one or more simple carbon co-substrates, the one or more simple carbon co-substrate is selected from glucose, fructose, and glycerol.

In some embodiments of a method of producing a recombinant microorganism having improved production of biomass or improved production of one or more lipid from one or more fatty acid and one or more simple carbon co-substrates, the improved production of one or more lipid comprises improved production of one or more mono- or poly-unsaturated $C_6$-$C_{24}$ fatty acid, alcohol, aldehyde, or acetate. In certain embodiments, the one or more mono- or poly-unsaturated $C_6$-$C_{24}$ fatty acid, alcohol, aldehyde, or acetate is an insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In some embodiments of a method of producing a recombinant microorganism having improved production of biomass or improved production of one or more lipid from one or more fatty acid and one or more simple carbon co-substrates, the recombinant microorganism is a eukaryotic microorganism. In certain embodiments, the eukaryotic microorganism is a yeast. In further embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*. In yet a further embodiment, the yeast is an oleaginous yeast. In some embodiments, the oleaginous yeast is a member of a genus selected from the group consisting of *Yarrowia, Candida, Rhodotorula, Rhodosporidium, Cryptococcus, Trichosporon*, and *Lipomyces*. In certain embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis*, and *R. graminis*.

Enzyme Engineering

The enzymes in the recombinant microorganism can be engineered to improve one or more aspects of the substrate to product conversion. Non-limiting examples of enzymes that can be further engineered for use in methods of the disclosure include an isocitrate dehydrogenase, a pyruvate transporter, an acetyl-CoA carboxylase, an aconitase, a citrate transporter, a decarboxylating malic enzyme, an ATP-citrate lyase, a glucose-6-phosphate dehydrogenase, a 6-phosphogluconolactonase, a 6-phosphogluconate dehydrogenase, a hexose transporter and combinations thereof. These enzymes can be engineered for improved catalytic activity, improved selectivity, improved stability, improved tolerance to various fermentations conditions (temperature, pH, etc.), altered selectivity of one or more substrate, altered selectivity of one or more co-factor, altered cellular localization, or improved tolerance to various metabolic substrates, products, by-products, intermediates, etc.

In some embodiments, an isocitrate dehydrogenase (IDH) enzyme can be engineered for insensitivity to AMP. Under a nitrogen-starved and glucose-rich environment, low levels of intracellular AMP reduce the activity of isocitrate dehydrogenase (IDH), a key allosteric enzyme in the TCA cycle in yeast mitochondria. The reduction of IDH activity slows the TCA cycle used for synthesis of biomass and reducing equivalents, and accumulates citrate (the equilibrium form of isocitrate). Therefore, in some embodiments, it is desirable to engineer an oleochemical production host to repurpose citrate for improvement in biomass generation. In certain embodiments, the AMP-insensitive IDH is from *Yarrowia lipolytica* and comprises isoleucine to alanine substitutions at amino acid positions 279 and 280 of XP_503571.2. In further non-limiting examples, an IDH can be engineered to lack a sequence encoding a mitochondrial-targeting peptide. In some embodiments, the IDH lacking a mitochondrial-targeting peptide localizes to the cytosol of a cell. In a further example, an aconitase can be engineered to lack a sequence encoding a mitochondrial-targeting peptide. In some embodiments, the aconitase lacking a mitochondrial-targeting peptide localizes to the cytosol of a cell. In a further example, a malate dehydrogenase can be engineered to lack a sequence encoding a mitochondrial-targeting peptide. In some embodiments, the malate dehydrogenase lacking a mitochondrial-targeting peptide localizes to the cytosol of a cell. In a further example, an acetyl-CoA carboxylase (ACC) enzyme can be engineered to be feedback-insensitive. In some embodiments, the feedback-insensitive ACC leads to increased lipid biosynthesis. In a further example, glucose-6-phosphate dehydrogenase (ZWF1) can be engineered to use NAD+ in place of NADP+ producing NADH instead of NADPH to match cofactor requirements of recombinant biosynthesis pathways. In a further example, 6-phosphogluconate dehydrogenase (GND1) can be engineered to use NAD+ in place of NADP+ producing NADH instead of NADPH to match cofactor requirements of recombinant biosynthesis pathways.

The term "improved catalytic activity" as used herein with respect to a particular enzymatic activity refers to a higher level of enzymatic activity than that measured relative to a comparable non-engineered enzyme, such as a non-engineered isocitrate dehydrogenase, an acetyl-CoA carboxylase, an aconitase, a decarboxylating malic enzyme, an ATP-citrate lyase, a glucose-6-phosphate dehydrogenase, a 6-phosphogluconolactonase, or a 6-phosphogluconate dehydrogenase. For example, overexpression of a specific enzyme can lead to an increased level of activity in the cells for that enzyme. Mutations can be introduced into an isocitrate dehydrogenase, an acetyl-CoA carboxylase, an aconitase, a decarboxylating malic enzyme, an ATP-citrate lyase, a glucose-6-phosphate dehydrogenase, a 6-phosphogluconolactonase, or a 6-phosphogluconate dehydrogenase enzyme resulting in engineered enzymes with improved catalytic activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the KM for the substrate, or by directed evolution. See, e.g., Methods in Molecular Biology (vol. 231), ed. Arnold and Georgiou, Humana Press (2003).

Metabolic Engineering—Enzyme Overexpression and Gene Deletion/Downregulation for Increased Pathway Flux In various embodiments described herein, the exogenous and endogenous enzymes in the recombinant microorganism participating in the pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 25%, 35%, 45%, 55%, 65%, 75%, 85%, 95%, 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, it may be useful to increase the expression of endogenous or exogenous isocitrate dehydrogenase enzymes to extend activation of the tricarboxylic acid (TCA) cycle and increase flux from citrate, thereby resulting in increased biomass generation. In some embodiments, extended activation of the tricarboxylic acid cycle comprises the overexpression of at least one endogenous and/or exogenous nucleic acid molecule encoding an AMP-insensitive isocitrate dehydrogenase (IDH) variant in the recombinant microorganism. In some embodiments, the overexpression of an NADP/NAD-dependent isocitrate dehydrogenase (IDH) in the cytosol of the recombinant microorganism increases the availability or amount of reducing equivalents.

In some embodiments, it may be useful to increase the expression of endogenous or exogenous pyruvate transporters to enhance pyruvate flux from the cytosol to the mitochondria. In some embodiments, it may be useful to increase the expression of endogenous or exogenous pyruvate transporters to increase the mitochondrial pyruvate pool. In some embodiments, one or more modifications associated with tricarboxylic acid cycle and/or one or more metabolic intermediates availability comprises the overexpression of a pyruvate transporter in the recombinant microorganism. In other embodiments, the one or more metabolic intermediates availability comprises mitochondrial pyruvate availability.

In some embodiments, it may be useful to increase the expression of endogenous or exogenous acetyl-CoA carboxylase enzymes to increase lipid synthesis. In some embodiments, it may be useful to increase the expression of endogenous or exogenous acetyl-CoA carboxylase feedback-insensitive variant enzymes to alleviate inhibition of lipid synthesis.

In some embodiments, it may be useful to increase the expression of endogenous or exogenous aconitase enzymes to increase and/or rebalance reducing equivalents. In further embodiments, the overexpression of an aconitase in the cytosol of the recombinant microorganism increases and/or rebalances reducing equivalents.

In some embodiments, it may be useful to increase the expression of endogenous or exogenous citrate transporters to increase and/or rebalance reducing equivalents. In some embodiments, it may be useful to increase the expression of endogenous or exogenous citrate transporters to increase the amount of one or more metabolic intermediate. In certain embodiments, the one or more intermediate comprises cytosolic citrate/isocitrate.

In some embodiments, it may be useful to increase the expression of endogenous or exogenous decarboxylating malic enzymes to increase and/or rebalance reducing equivalents. In one embodiment, the malic enzyme is NAD+ dependent. In another embodiment, the malic enzyme is NADP+ dependent. In yet a further embodiment, it may be useful to increase the expression of endogenous or exogenous malate dehydrogenases in the cytosol of a recombinant microorganism.

In some embodiments, it may be useful to increase the expression of endogenous or exogenous ATP-citrate lyase to increase the amount of one or more metabolic intermediate. In certain embodiments, the one or more intermediate comprises cytosolic oxaloacetate.

In some embodiments, it may be useful to increase the expression of endogenous or exogenous oxidative pentose phosphate pathway (PPP) enzymes to increase flux through the PPP. In some embodiments, increasing the expression of oxidative PPP enzymes draws down the pool of glucose-6-phosphate and pulls additional fructose-6-phosphate to enter the oxidative PPP. In certain embodiments, increasing the flux through the PPP increases and/or rebalances reducing equivalents. In further embodiments, the upregulation of one or more oxidative PPP enzyme activity comprises the overexpression of a glucose-6-phosphate dehydrogenase (ZWF1), a 6-phosphogluconolactonase (SOL3), or a 6-phosphogluconate dehydrogenase (GND1). In some embodiments, it may be useful to increase the expression of endogenous or exogenous PPP enzyme variants which use NAD+ in place of NADP+ producing NADH instead of NADPH to match cofactor requirements of recombinant pathways. In some embodiments, the one or more oxidative PPP enzyme variant comprises an NAD-dependent glucose-6-phosphate dehydrogenase (ZWF1) and/or an NAD-dependent 6-phosphogluconate dehydrogenase (GND1).

In some embodiments, it may be useful to increase the expression of endogenous or exogenous hexose transporters to increase and/or rebalance reducing equivalents. In certain embodiments, the hexose transporter is high affinity. In some embodiments, the hexose transporter is low affinity.

Improved biomass or lipid production can be accomplished by, for example, overexpression of nucleic acids encoding one or more of the above-described enzymes or transporters. Overexpression of the above-described enzymes or proteins can occur, for example, through increased expression of an endogenous gene or genes, or through the expression, or increased expression, of an exogenous gene or genes. Therefore, naturally occurring organisms can be readily modified to generate non-natural microorganisms having improved biomass and lipid production through overexpression of one or more nucleic acid molecules encoding, for example, an isocitrate dehydrogenase, a pyruvate transporter, an acetyl-CoA carboxylase, an aconitase, a citrate transporter, a decarboxylating malic enzyme, an ATP-citrate lyase, a glucose-6-phosphate dehydrogenase, a 6-phosphogluconolactonase, a 6-phosphogluconate dehydrogenase, a hexose transporter, or combination thereof.

In addition, a non-naturally occurring organism can be generated by mutagenesis of an endogenous gene that results in an increase in activity of an enzyme or transporter as described herein.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding an enzyme or transporter described herein in sufficient amounts to produce lipid and generate biomass.

Methods for constructing and testing the expression levels of a non-naturally occurring lipid and biomass-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more enzyme or transporter encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes to increase and/or rebalance reducing equivalents. In some embodiments, the recombinant microorganism is manipulated to delete, disrupt, mutate, and/or reduce the activity of one or more endogenous enzymes to increase product purity. In some embodiments, the recombinant microorganism is manipulated to delete, disrupt, mutate, and/or reduce the activity of one or more endogenous enzymes to modify availability of metabolic intermediates.

In some embodiments, the recombinant microorganism is manipulated to delete, disrupt, mutate, and/or reduce the activity of one or more endogenous enzymes that catalyzes the conversion of glucose to glucose-6-phosphate. In some such embodiments, the enzymes that catalyze the conversion of glucose to glucose-6-phosphate are hexose kinases. In some embodiments, the deletion, disruption, mutation, and/or reduction in activity of one or more hexose kinase decouples and increases glucose uptake. In some embodiments, the deletion, disruption, mutation, and/or reduction in activity of one or more hexose kinase increases and/or rebalances reducing equivalents.

In other embodiments, the recombinant microorganism is manipulated to delete, disrupt, mutate, and/or reduce the activity of one or more endogenous enzymes that catalyzes the conversion of fructose-6-phosphate to fructose-1,6-bisphosphate to reduce flux through upper glycolysis. In some such embodiments, the enzymes that catalyze the conversion of fructose-6-phosphate to fructose-1,6-bisphosphate are fructose-6-phosphate kinases. In some embodiments, the deletion, disruption, mutation, and/or reduction in activity of one or more fructose-6-phosphate kinase increases and/or rebalances reducing equivalents.

In some embodiments, the recombinant microorganism is manipulated to delete, disrupt, mutate, and/or reduce the activity of one or more enzymes involved in the mannitol synthesis pathway. In some embodiments, disruption of the mannitol synthesis pathway can be used to enhance generation of reducing equivalents and improve glucose yields to support production of fatty acid derived products. In certain embodiments, the one or more enzyme involved in the mannitol synthesis pathway is an NADPH-dependent mannitol dehydrogenase. In certain embodiments, the NADPH-dependent mannitol dehydrogenase is selected from the group consisting of YALI0B16192g, YALI0D18964g, and YALI0E12463g, or homologs thereof. In certain embodiments, the one or more enzyme involved in the mannitol synthesis pathway is an aldo-keto reductase. In certain embodiments, the aldo-keto reductase is selected from the group consisting of YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0000319g, YALI0A19910g, or homologs thereof.

In some embodiments, the recombinant microorganism is manipulated to delete, disrupt, mutate, and/or reduce the activity of one or more endogenous enzymes that catalyzes carboxylation of acetyl-CoA to malonyl-CoA. In one embodiment, the one or more endogenous enzymes comprise one or more acetyl-CoA carboxylase. In some embodiments, the deletion, disruption, mutation, and/or reduction in activity of one or more acetyl-CoA carboxylase increases availability or amount of reducing equivalents, increases amount of one or more metabolic intermediate, and/or increases product purity.

Pheromone Compositions and Uses Thereof

As described above, products made via the methods described herein may be pheromones. Pheromones prepared according to the methods of the invention can be formulated for use as insect control compositions. The pheromone compositions can include a carrier, and/or be contained in a dispenser. The carrier can be, but is not limited to, an inert liquid or solid. In some embodiments, the pheromone composition is combined with an active chemical agent such that a synergistic effect results. In some embodiments, the pheromone composition can include one or more insecticides, one or more solubilizing agents, one or more fillers, one or more solvents, one or more solubilizing agents, one or more binders, one or more surface-active agents, one or more wetting agents, one or more dispersing agents, one or more polymeric surfactants, one or more emulsifying agents, one or more gelling agents, one or more anti-foam agents, and/or one or more preservative. According to another embodiment of the disclosure, the pheromone composition may include one or more insect feeding stimulants. According to another embodiment of the disclosure, the pheromone composition may include one or more insect growth regulators ("IGRs"). According to another embodiment of the disclosure, the attractant-composition may include one or more insect sterilants that sterilize the trapped insects or otherwise block their reproductive capacity, thereby reducing the population in the following generation.

In some embodiments, the pheromone compositions disclosed herein can be formulated as a sprayable composition (i.e., a sprayable pheromone composition). In some embodiments, the pheromone compositions disclosed herein can be formulated as a microencapsulated pheromone, such as disclosed in Ill'lchev, A L et al., *J. Econ. Entomol.* 2006; 99(6):2048-54; and Stelinki, L L et al., *J. Econ. Entomol.* 2007; 100(4):1360-9. Pheromone compositions can be formulated so as to provide slow release into the atmosphere, and/or so as to be protected from degradation following release. The pheromone compositions of the disclosure may be used in traps or lures. Pheromone compositions of the present disclosure can be used in conjunction with a dispenser for release of the composition in a particular environment.

Pheromone compositions prepared according to the methods disclosed herein can be used to control or modulate the behavior of insects. Thus, in some embodiments, the pheromones can be used to attract insects away from vulnerable crop areas. Pheromones prepared according to the methods of the disclosure can also be used to disrupt mating. Mating disruption is a pest management technique designed to control insect pests by introducing artificial stimuli (e.g., a pheromone composition as disclosed herein) that confuses the insects and disrupts mating localization and/or courtship, thereby preventing mating and blocking the reproductive cycle. In some embodiments, the pheromone compositions may be used in attract and kill. The attract and kill method utilizes an attractant, such as a sex pheromone, to lure insects of the target species to an insecticidal chemical, surface, device, etc., for mass-killing and ultimate population suppression.

Thus, in some embodiments, the present disclosure teaches edibles produced from the Specialty Cannabis and/or cannabinoid compositions disclosed herein.

This invention is further illustrated by the following examples, which should not be construed as limiting. The contents of all references, patents and published patent applications cited throughout this application, as well as the Figures and the Sequence Listing, are incorporated herein by reference.

EXAMPLES

Example 1. Improving Lipid Production By Alleviating AMP Allosteric Inhibition Background and Rationale Many microorganisms down-regulate respiration under non-optimal growth conditions to encourage carbon/energy storage via citrate and lipid synthesis. Under nitrogen limited conditions, intracellular AMP levels are depleted by an AMP deaminase (AMD1). Reduced AMP levels in these microorganisms, inactivate the mitochondrial isocitrate dehydrogenase complex (IDH1/2) through allosteric regulation, which results in accumulation of isocitrate, and reduced TCA cycle throughput.

Both native fatty acid synthesis, and the bypass methyl palmitate based synthesis of Z11-16 acid, require reducing equivalents in the form of NADPH and NADH. The inventors hypothesized that increasing the oxidation rate of citrate (through IDH activation) could increase the available reduced cofactor pool leading to increased production of unsaturated fatty acids.

Experimental Design

Figure 3:
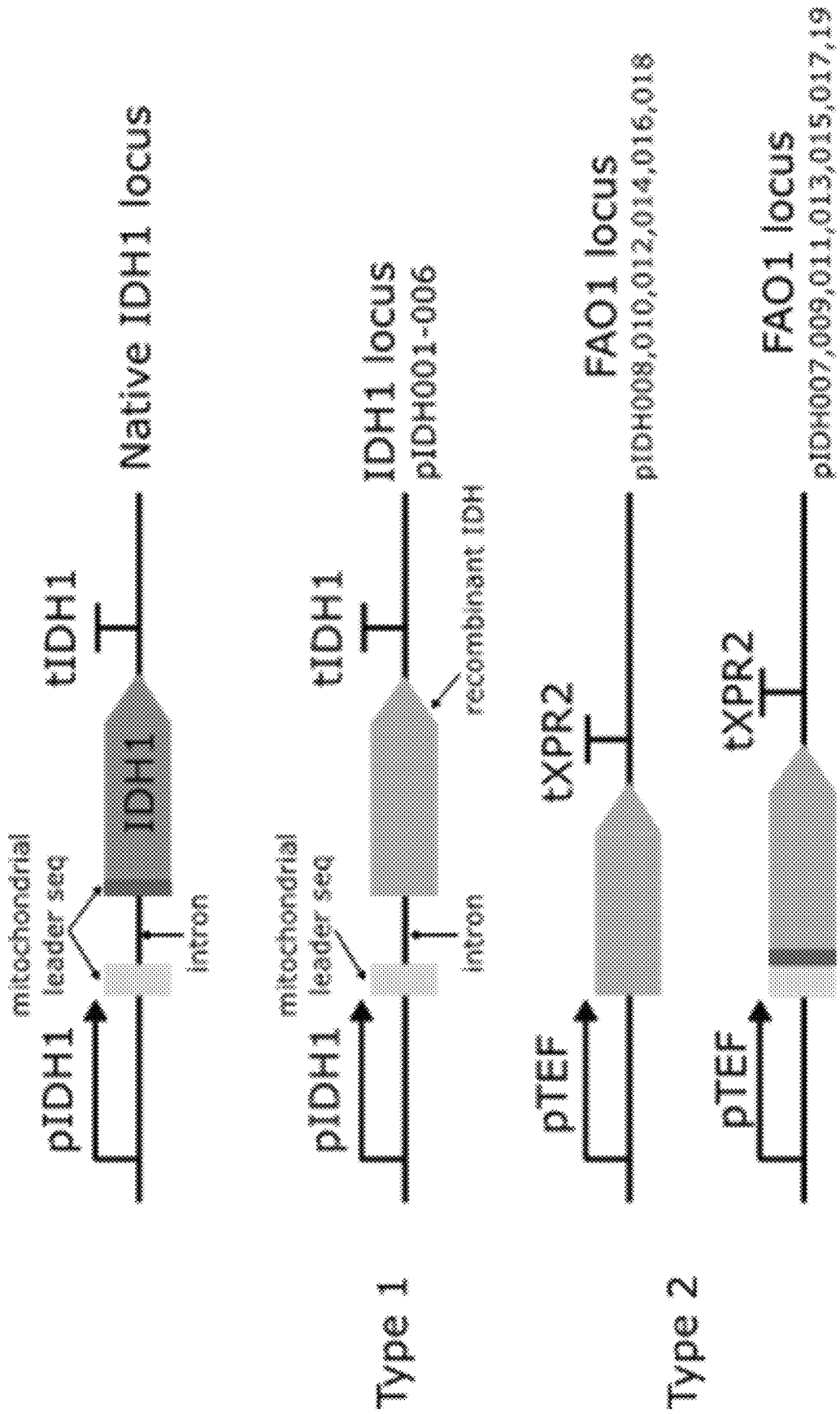
FIG. 3 shows IDH expression cassette architectures. The native IDH1 coding sequence is split by a single intron near the 5' end (Top). A mitochondrial targeting sequence at the 5' end of the coding sequence continues briefly after the intron. Three different expression cassettes were used for recombinant IDH expression. Each IDH was cloned into an IDH1 targeting vector which utilized the native promoter sequence (2nd from the top). Constructs were also cloned in a FAO1 targeting cassette either with or without the *Y. lipolytica* IDH1 mitochondrial targeting sequence (3rd and 4th from the top).

Two different loci were targeted to test the impact of individual IDHs on glucose consumption, growth, citrate, and fatty acid production. One cassette was designed to target the *Y. lipolytica* IDH1 locus replacing the native IDH1 variant with recombinant AMP-insensitive IDH enzymes (FIG. 3). This cassette takes advantage of the native intron promoter to drive expression of the alterative IDH genes (FIG. 3). Both native and codon optimized sequences were tested for the *Y. lipolytica* IDH1 D279A, I280A double mutant, but only codon optimized bacterial IDHs were used in this Example. In addition, one construct replaced the native IDH with a GFP gene to serve as a negative control and to evaluate the IDH promoter.

A second cassette was designed to add a recombinant copy of IDH while retaining the wild type *Y. lipolytica* IDH1 copy. This cassette targets the FAO1 locus and uses the constitutive TEF promoter to drive expression (FIG. 3). The native sequence of the *Y. lipolytica* IDH1 D279A, I280A mutant and four variants of each bacterial IDH were integrated using the FAO1 cassette. Both native source sequences and codon optimized sequences of bacterial IDHs were cloned either with or without the *Y. lipolytica* IDH1 mitochondrial targeting sequence. These designs tested the effects of compartmental targeting and codon optimization. Table 7 compiles the 19 constructs that were tested.

The 19 constructs described above were transformed into SPV739, a marker rescued descendent of SPV458. SPV458 was created by integrating a single copy of the *H. zea* Z11 desaturase into the XPR2 locus of SPV300 (H222 Δpox1 Δpox2 Δpox3 Δpox4 Δpox5 Δpox6 Δadh1 Δadh2 Δadh3 Δadh4 Δadh5 Δadh6 Δadh7 Δfao1 Δura3, herein also referred to as "H222 ΔP ΔA ΔF ura3"). H222 corresponds *Y. lipolytica* H222 (Mauersberger, S., H. J. Wang, et al. (2001), J Bacteriol 183(17): 5102-5109), according to Barth and Gaillardin (Barth G & Gaillardin C (1996) *Yarrowia lipolytica*. Springer-Verlag, Berlin, Heidelberg, New York).

TABLE 7

Constructs used in Example 1

| Source organism | Cassette type | Promoter | Localization | Codon optimization | IDH plasmid ID | IDH1 KO |
|---|---|---|---|---|---|---|
| *Y. Lipolytica* IDH1 (D279A, I280A) (SEQ ID NO: 20) | Type 1 | *Y. lipolytica* IDH1 | mitochondria | none | pIDH001 (SEQ ID NO: 1) Full Plasmid | Yes |
| | | | | *H. sapiens* | pIDH002 (SEQ ID NO: 2) Insert | Yes |
| | Type 2 | *Y. lipolytica* pTEF | mitochondria | none | pIDH007 (SEQ ID NO: 7) Insert | No |
| *E. Coli* IDH (NADPH) (SEQ ID NO: 21) | Type 1 | *Y. lipolytica* IDH1 | unknown | *H. sapiens* | pIDH003 (SEQ ID NO: 3) Insert | Yes |
| | Type 2 | *Y. lipolytica* pTEF | cytosol | *H. sapiens* | pIDH008 (SEQ ID NO: 8) Insert | No |
| | | | mitochondria | *H. sapiens* | pIDH009 (SEQ ID NO: 9) Insert | No |

TABLE 7-continued

Constructs used in Example 1

| Source organism | Cassette type | Promoter | Localization | Codon optimization | IDH plasmid ID | IDH1 KO |
|---|---|---|---|---|---|---|
| | | | cytosol | none | pIDH014 (SEQ ID NO: 14) Insert | No |
| | | | mitochondria | none | pIDH015 (SEQ ID NO: 15) Insert | No |
| A. Thiooxidans IDH (NADH) (SEQ ID NO: 22) | Type 1 | Y. lipolytica IDH1 | unknown | H. sapiens | pIDH004 (SEQ ID NO: 4) Insert | Yes |
| | Type 2 | Y. lipolytica pTEF | cytosol | H. sapiens | pIDH010 (SEQ ID NO: 10) Insert | No |
| | | | mitochondria | H. sapiens | pIDH011 (SEQ ID NO: 11) Insert | No |
| | | | cytosol | none | pIDH016 (SEQ ID NO: 16) Insert | No |
| | | | mitochondria | none | pIDH017 (SEQ ID NO: 17) Insert | No |
| M. smegmatis IDH (NADPH) (SEQ ID NO: 23) | Type 1 | Y. lipolytica IDH1 | unknown | H. sapiens | pIDH005 (SEQ ID NO: 5) Insert | Yes |
| | Type 2 | Y. lipolytica pTEF | cytosol | H. sapiens | pIDH012 (SEQ ID NO: 12) Insert | No |
| | | | mitochondria | H. sapiens | pIDH013 (SEQ ID NO: 13) Insert | No |
| | | | cytosol | none | pIDH018 (SEQ ID NO: 18) Insert | No |
| | | | mitochondria | none | pIDH019 (SEQ ID NO: 19) Insert | No |
| R. reniformis GFP | Type 1 | Y. lipolytica IDH1 | unknown | H. sapiens | pIDH006 (SEQ ID NO: 6) Insert | Yes |

Four clonal isolates of each construct were selected for screening in a 24-deepwell plate assay (76 strains total) (See Materials and Methods for full description of protocol). Initial seeds were grown in YPD medium before transfer to a nitrogen limited medium supplemented with methyl palmitate as a saturated fatty acid substrate. To evaluate the impact of each IDH, extracellular glucose and citrate and fatty acid content were quantified (See Materials and Methods for sampling procedures).

Experimental Results

Analysis of Strains with Type 1 Cassettes (Single IDH Copy, Replaced Native IDH1)

Fatty Acid Analysis

Strain IDH002 (Y. lipolytica IDH1 D279A, I280A codon optimized), displayed increased OD-normalized Z11-16Acid titer at both 48 hours (~40%) and 72 hours (~20%). In addition, IDH002 produced increased titers of other native Y. lipolytica fatty acids including the major native fatty acid Z9-18Acid. Two other constructs, IDH001 (Y. lipolytica IDH1 D279A, I280A native sequence) and IDH004 (A. thiooxidans IDH) produced increased titers of other native Y. lipolytica fatty acids. As expected, the idh1::GFP knockout strains (IDH006) produced less fatty acids generally and ~50% less Z11-16Acid.

Glucose Analysis

In agreement with increased TCA cycle flux, IDH001 and IDH002 also demonstrated increased glucose consumption over the 72-hour assay. IDH004 consumed an equivalent quantity of glucose to the SPV458 control. Two constructs which displayed the largest increase in fatty acid production also showed increased glucose consumption at 48 and 72 hours (IDH002, IDH011). The idh1::GFP knockout (IDH006) displayed reduced glucose consumption at both 48 and 72 hours. Initial concentration of 60 g/L glucose.

Citrate Analysis

Citrate titers followed multiple trends depending on the IDH variant. Y. lipolytica IDH1 D279A, I280A constructs (IDH001, IDH002) did not display reduced citrate titer (g/L-OD). The A. thiooxidans IDH construct, IDH004 however, displayed lower normalized citrate titer at 72.

Analysis of Strains with Type 2 Cassettes (Native+Recombinant IDH at FAO1 Locus)

Fatty Acid Analysis

Two FAO1 cassette constructs, IDH011 (A. thiooxidans IDH, mitochondria targeted, codon optimized) and IDH012 (M. smegmatis IDH, cytosol targeted, codon optimized), produced increased Z11-16 acid titer and OD-normalized titer at 48 hours. Increases were 20% for IDH011 and 10% for IDH012. Both these constructs also produced higher titers of native fatty acid species.

Increased native fatty acid titers were also observed for three other FAO1 cassette constructs: native coded E. coli constructs which were targeted to either the cytosol (IDH014) or mitochondria (IDH015) and codon optimized

*M. smegmatis* IDH targeted to the mitochondria (IDH013). Of the two *E. coli* constructs, IDH014 (cytosol) sustained the increase in fatty acid production at the 72-hour time point while titers were stagnant for IDH015 (mitochondria).

Glucose Analysis

IDH009 (*E. coli* IDH, mitochondria targeted, codon optimized), IDH010 (*A. thiooxidans* IDH, cytosol targeted, codon optimized), IDH0011 (*A. thiooxidans* IDH, mitochondria targeted, codon optimized) and IDH019 (*M. smegmatis* IDH, mitochondira targeted, native sequence) displayed increased glucose consumption.

Citrate Analysis

As with IDH1 cassettes, citrate titers followed multiple trends depending on the IDH variant. Of the *E. coli* IDH constructs, only IDH009 produced less citrate than the SPV458. Both *A. thiooxidans* IDH constructs which consumed additional glucose, IDH010, and IDH011, also produced less citrate. *M. smegmatis* constructs which either showed increased fatty acid production (IDH012, IDH013) or increased glucose consumption (IDH019) also produced less citrate. Of the *M. smegmatis* constructs, the most significant reduction in citrate was observed for IDH019.

Summary of the 24 Well Assay

An additional trend emerges when citrate titers are examined as a function of expression cassette design for each of the recombinant IDHs. IDH1 targeted cassettes with the IDH1 promoters produced the highest citrate titers while FAO1 cassettes with the TEF promoter and the *Y. lipolytica* IDH1 mitochondrial targeting sequence produced the lowest citrate titers. This dependence on cassette design is consistent with high mitochondrial expression of IDH leading to increased TCA cycle flux. Finally, as expected, the IDH006 strains (idh1::GFP) grew slowly and produced the highest normalized citrate titers (g/L-OD). The increase was especially noticeable at 48 hours. This increase in citrate titer confirms the negative control hypothesis that reduced TCA cycle flux in the mitochondria leads to further accumulation of citrate.

Strains expressing codon optimized *A. thiooxidans* IDH using the TEF promoter and targeted to the mitochondria showed reduced citrate titer (g/L) and specific citrate production (g/L-OD) at 72 hours in the 24-deepwell plate assay. Cell density, as measured by OD600, increased by ~35% at 72 hours. Fatty acid titers were increased over the SPV458 control as follows:

Z11-16Acid: ~20% at 48 hours and 0% at 72 hours.
  Z9-16Acid: ~130% at 48 hours and ~100% at 72 hours.
  Z9-18Acid: ~80% at 48 hours and ~60% at 72 hours.
  Z9Z12-18Acid: ~20% at 48 hours and ~50% at 72 hours Strains expressing a copy of the *Y. lipolytica* IDH1 mutant D279, I280A under the TEF promoter did not display reduced citrate titer or increased cell density in the 24-deepwell plate assay, but did produce increased fatty acid titers as follows:

Z11-16Acid: ~15% at 48 hours and ~20% at 72 hours
  Z9-16Acid: 0% at 48 and 72 hours
  Z9-18Acid: ~30% at 48 hours and ~40% at 72 hours
  Z9Z12-18Acid ~30 at 48 hours and ~50% at 72 hours Materials & Methods HSD035 24-Deepwell Assay For each construct 4 clonal isolates were inoculated in 1 ml of YPD seed culture in 24-deepwell plates for 24 hours at 28° C. and 1000 rpm (Infors plate incubator). Seed cultures were pelleted and supernatant removed before resuspension in 2 ml of S2 medium. After cell pellets were resuspended, 24 µl of 37° C. methyl palmitate was added to each well (~10 g/L final concentration). The plates were then incubated for 48 hours at 28° C. and 1000 rpm (Infors plate incubator) before 250 µl samples were transferred to glass, crimp-top GC vials. Plates were incubated an additional 24 hours and a second set of 250 µl samples were taken at 72 hours. Vials were frozen at −80° C. before further processing. Cell density was measured with a Tecan M200 Pro plate reader at each sampling.

GC Sample Processing-Lyophilized Samples 250 uL of culture were lyophilized in open glass crimp top vials for at least 3 hours. 500 uL of TMSH were added to the vials and sealed with a crimp cap. These vials were arrayed in racks, which were placed in a 28° C. plate shaker for 2 hours at 250 rpm. After mixing these dried cells with the derivatizing agent, the vials were incubated in a heat block for 1 hour at 85° C. to lyse the cell membranes. Finally, the liquid portion of the methylated sample was transferred to a clean GC vial with glass insert to prevent solid debris from clogging the column during GC analysis. Samples were run on GC-FID.

Example 2. Improving Lipid Production and Z11-16 Selectivity Through Expression of Decarboxylating Malic Enzyme and/or Oxidative Pentose Phosphate Pathway Enzymes (PPP)

Background and Rationale

Microorganisms of the present disclosure produce citrate as co-product under nitrogen-limited conditions. This is because during nitrogen starvation many organisms, including *Y. lipolytica* down-regulate respiration to divert carbon/energy storage via lipid synthesis. Citrate is first exported from mitochondria into the cytosol and subsequently from the cell. Exported citrate can be re-assimilated, especially when alternative carbon sources are scarce. Alternatively, the combination of the enzymes ATP citrate lyase (ACL), malate dehydrogenase (e.g., MDH2) and cytosolic malic enzyme can turn cytosolic citrate into pyruvate, to feed back into the TCA cycle to power further lipid synthesis (FIG. 4). Many organisms, including *Y. lipolytica* however, do not express a cytosolic malic enzyme.

The inventors further hypothesized that expression of a heterologous $NADP^+$ dependent cytosolic malic enzyme may increase fatty acid production if the primary rate limitation is cofactor supply.

In many organisms, including *Y. lipolytica*, the pentose phosphate pathway (PPP) is the primary source of NADPH reducing equivalents for fatty acid synthesis. The inventors hypothesized that the recombinant microorganisms lipid production and selectivity could further be increased by overexpressing the genes of the upper (oxidative) pentose phosphate pathway (ZWF1, SOL3, and GND1), potentially offering another route to increase biomass and/or fatty acid synthesis.

Experimental Design

Nucleic acids encoding for heterologous malic enzymes, and overexpressing endogenous PPP enzymes, ZWF1, GND1, and SOL3, were introduced into a *Y. lipolytica* microorganism. Three or four clonal isolates of each construct were characterized in a 24-well bioconversion assay, feeding co-substrates glucose/glycerol and methyl palmitate. Fatty acid profiles for all constructs were quantified using GC analysis. Measurements for initial biomass in YPD and final biomass in nitrogen-limited media were taken. Growth of each microorganism was tracked and analyzed for fatty acid profiles in nitrogen-limited media with Solulys95 to confirm that access to methyl palmitate as a co-substrate is necessary to realize improvements in Z11-

16Acid selectivity, total fatty acid production, and/or biomass generation. Table 8 provides a summary of the recombinant microorganisms tested. Note that the *L. starkeyi* construct was excluded from the bioconversion results due to technical issues during the experiment resulting in no growth of the microorganism.

7). When the strains were tested in lipid-accumulating media without adding substrate, all strains produced Z11-16Acid titers within the margin of error of our SPV458 control. This indicates the dual-substrate approach led to the benefits observed with overexpression of *L. starkeyi* and *M. musculus* malic enzymes and GND1.

TABLE 8

Enzyme expression constructs in microorganisms: All constructs were integrated at the AXP locus.

| Source organism | Gene | Promoter | Cofactor | Cellular location | Modification | Codon optimization | Plasmid ID |
|---|---|---|---|---|---|---|---|
| *L. starkeyi* | ME | TEF | NAD | Mitochondria | Truncation* Unmodified enzyme-(SEQ ID NO: 24) | human | pPV1279 |
| *R. toruloides* | ME | TEF | NAD | Mitochondria | Truncation* (SEQ ID NO: 25) | human | pPV1280 |
| *M. musculus* | ME | TEF | NADP | Cytosol | (SEQ ID NO: 28) | human | pPV1281 |
| *R. norvegicus* | ME | TEF | NADP | Cytosol | (SEQ ID NO: 27) | human | pPV1282 |
| *H. sapiens* | ME | TEF | NAD | Mitochondria | Truncation* (SEQ ID NO: 26) | human | pPV1283 |
| *E. coli* | ME | TEF | NAD | Cytosol | (SEQ ID NO: 29) | human | pPV1284 |
| *Y. lipolytica* | ZWF1 | TEF | NADP | Cytosol | YALI0E22649g DNA-(SEQ ID NO 39) Prot-(SEQ ID NO 40) | NA | pPV1285 |
| *Y. lipolytica* | GND1 | TEF | NADP | Cytosol | YALI0B15598g DNA-(SEQ ID NO: 41) Prot-(SEQ ID NO: 42) | NA | pPV1286 |
| *Y. lipolytica* | SOL3 | TEF | None | Cytosol | YALI0_E11671g DNA-(SEQ ID NO: 43) Prot-(SEQ ID NO: 44) | NA | pPV1287 |

*Truncation of the mitochondrial targeting sequence. Malic enzyme sequences were analyzed using the TargetP 1.1 server. (Predicting subcellular localization of proteins based on their N-terminal amino acid sequence. Olof Emanuelsson, Henrik Nielsen, Soren Brunak and Gunnar von Heijne. J. Mol. Biol., 300: 1005-1016, 2000.) The predicted mitochondrial targeting sequence of the respective enzymes was removed to direct the enzyme to the cytosol.

Three or four clonal isolates of each construct were selected for screening in a 24-deepwell plate assay (See Materials and Methods for full description of protocol). Initial seeds were grown in YPD medium before transfer to a nitrogen limited medium supplemented with methyl palmitate as a saturated FAME substrate. To evaluate the impact of malic enzyme and PPP overexpression, fatty acid content and biomass generation were quantified (See Materials and Methods).

Experimental Results

Figure 5:
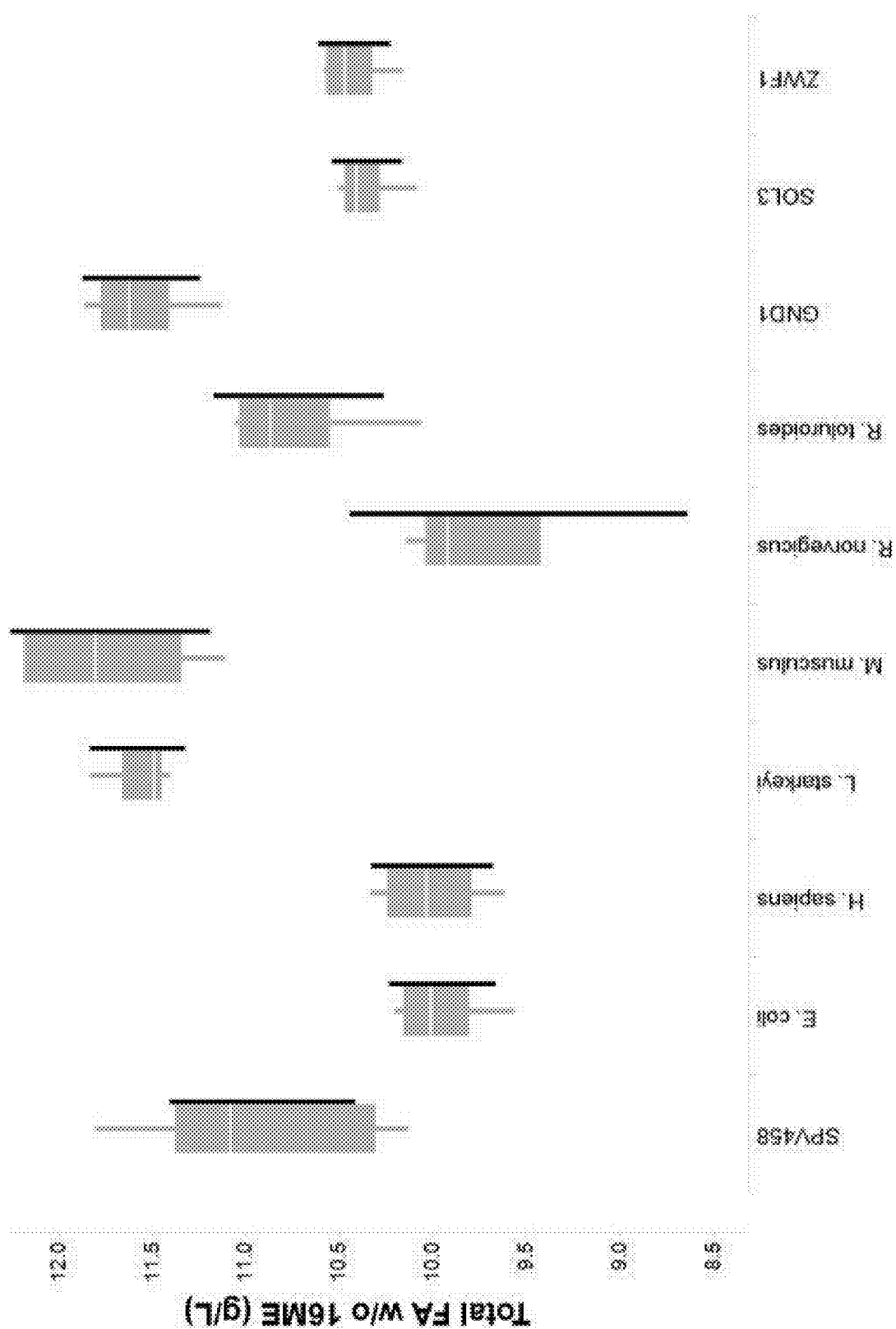
FIG. 5 shows the total fatty acid content of malic enzyme and PPP recombinant microorganisms. Methyl palmitate was fed to recombinant microrganisms comprising heterologous malic enzyme or upregulated PPP enzymes. The results show a spike in fatty acid production for the GND1, *L. starkeyi*, and *M. musculus* recombinant microorganisms. A Box plot with 95% confidence interval denoted by vertical bar on the right side of each result.

Overexpression of the NADP+ dependent *L. starkeyi* and *M. musculus* cytosolic malic enzyme, as well as the PPP gene GND1, led to increased titers of total fatty acid compared to the reference strain SPV458 when feeding glucose/glycerol and methyl palmitate co-substrates after 42 hours of bioconversion (FIG. 5). All samples were analyzed for the following fatty acids which were derivatized as fatty acid methyl esters: Z9-16Acid, Z11-16Acid, 18Acid, Z9-18Acid, Z11-18Acid, Z13-18Acid, Z9Z12-18Acid.

Figure 6:
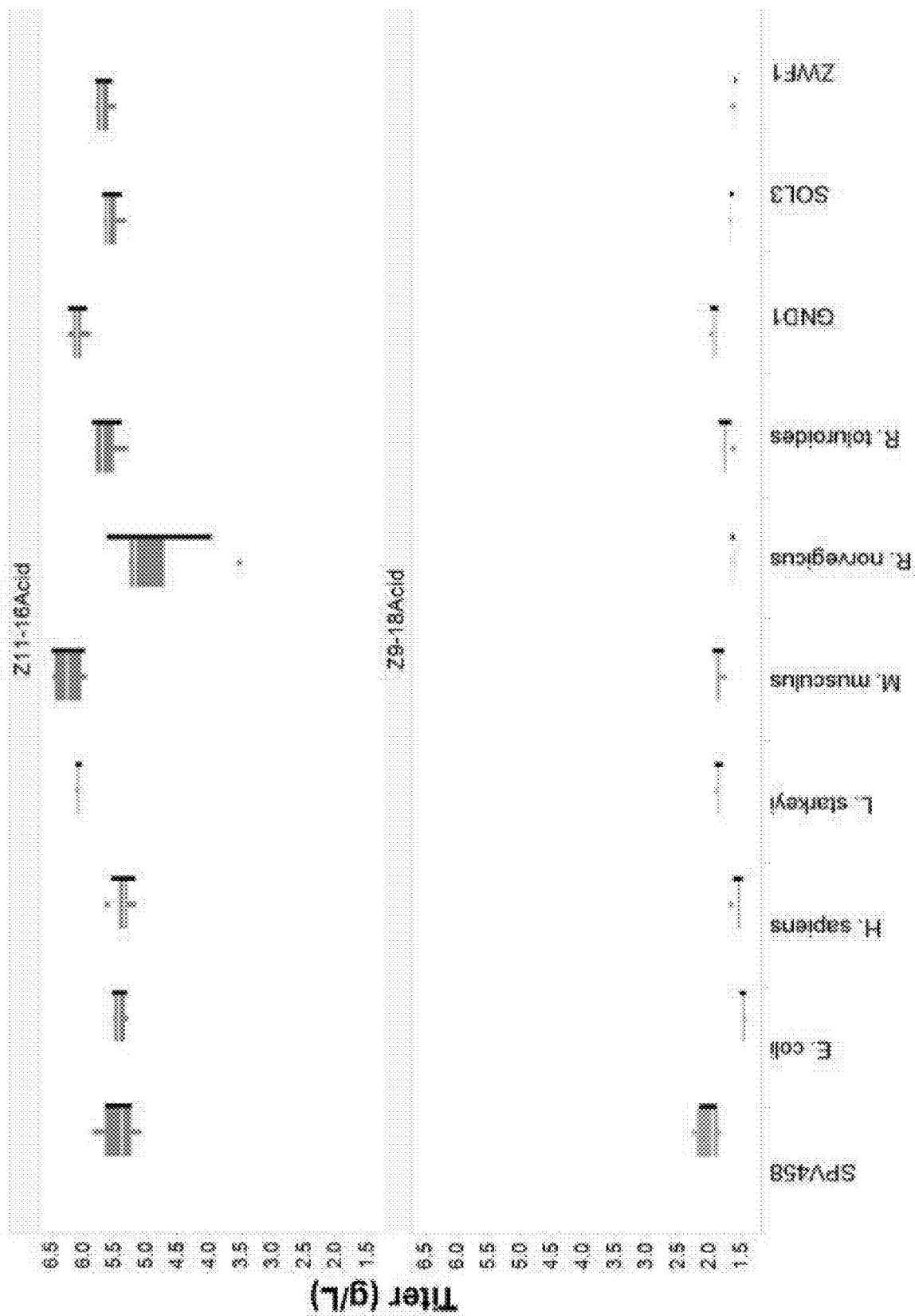
FIG. 6 shows Z11-16 acid and Z9-18 acid titer of malic enzyme and PPP recombinant microorganisms. The increase in Z11-16 acid in GND1, *L. staryeki*, and *M. musculus* expressing strains compared to the SPV458 control reveals that most of the increase in total fatty acid production is from increased Z11-16Acid. These three strains do not produce additional Z9-18Acid compared to the control. Box plot with 95% confidence interval denoted by vertical bar on the side of each result.

FIG. 6 shows the specific results for Z11-16 Acid and Z9-18 Acid. These results show that the boost in total fatty acid accumulated in the three improved strains is mostly accounted for by the increase in Z11-16Acid.

Figure 7:
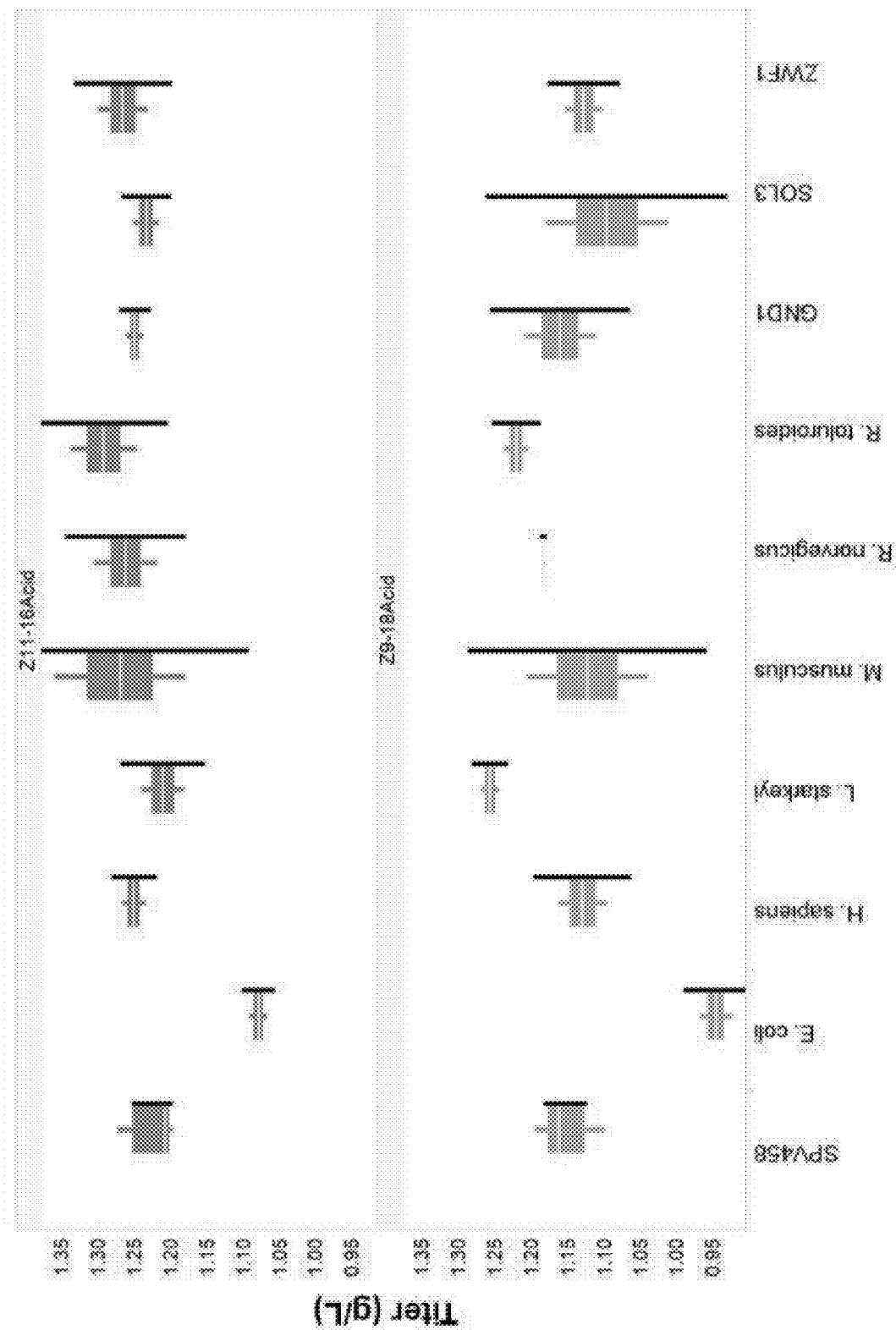
FIG. 7 shows de novo fatty acid production of malic enzyme and PPP recombinant microorganisms. Recombinant microorganisms cultured in bioprocess media without methyl palmitate substrate do not demonstrate a significant improvement in Z11-16 acid productivity over the control strain. Box plot with 95% confidence interval denoted by vertical bar on the right side of each result.

While three strains produced higher Z11-16Acid titer when fed methyl palmitate, the strains did not exhibit significant improvements in de novo lipid production (FIG. 7).

Figure 8:
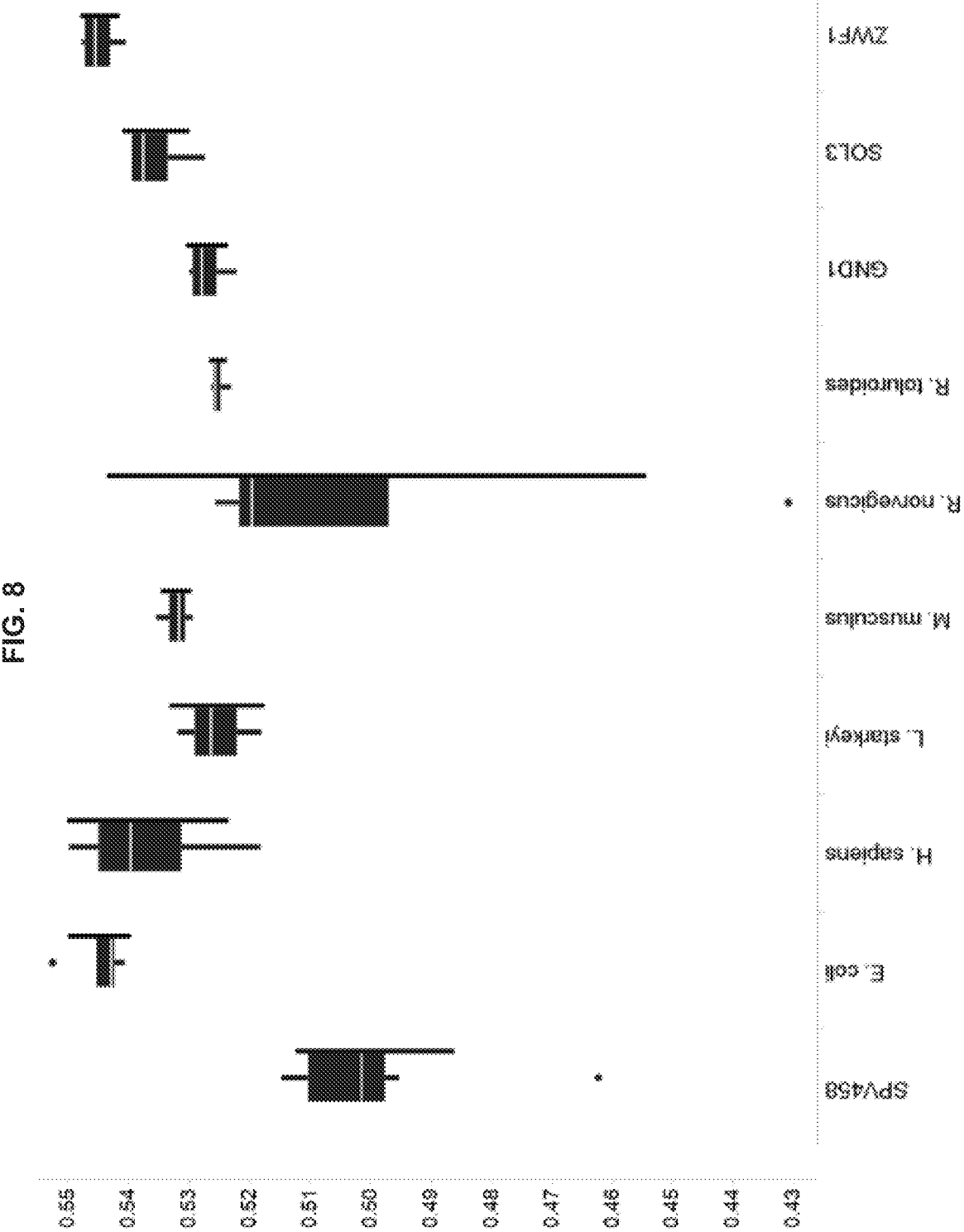
FIG. 8 shows Z11-16 acid selectivity of malic enzyme and PPP recombinant microorganisms. All modifications demonstrated improvements in Z11-16 acid selectivity over the SPV458 control when fed methyl palmitate in standard bioconversion assays. Box plot with 95% confidence interval denoted by vertical bar on the side of each result.

Surprisingly, all tested strains exhibited an improvement in Z11-16Acid selectivity (FIG. 8). All tested malic enzyme and PPP enzyme-containing microorganisms yielded average Z11-16Acid selectivities greater than the 50% found in SPV458, the highest being overexpression of ZWF1 yielding 55% Z11-16Acid. Of the 3 strains that yielded the highest Z11-16Acid titers, *M. musculus* had the highest selectivity, while GND1 was second, both rounding to 53%.

Figure 9:
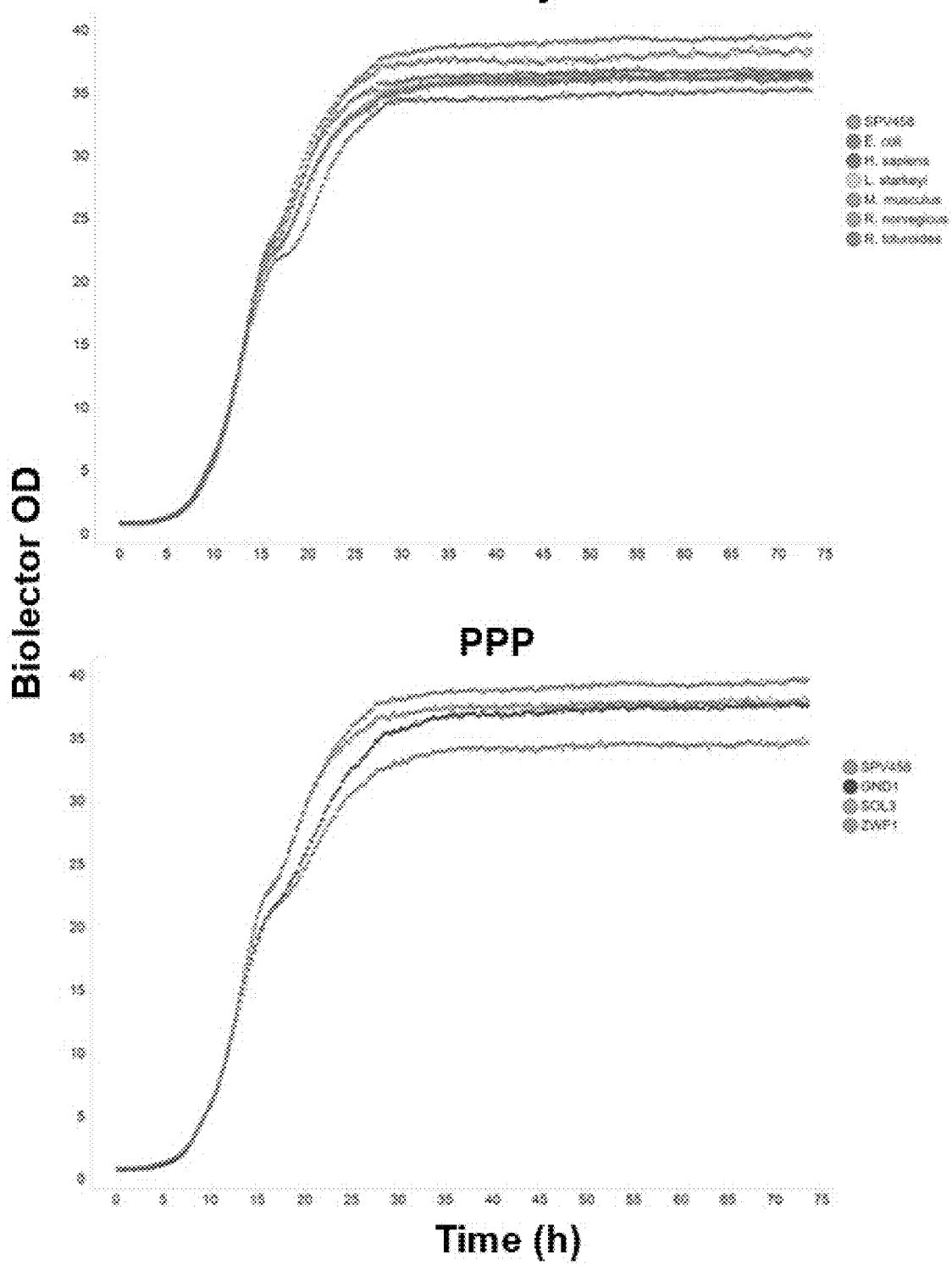
FIG. 9 shows the biomass of malic enzyme and PPP recombinant microorganisms. In bioprocess media with excess ammonium sulfate and using glucose as the carbon source, the malic enzyme and PPP recombinant microorganisms of Example 2 grow to a stationary phase between 33 and 38 hours.
Figure 10:
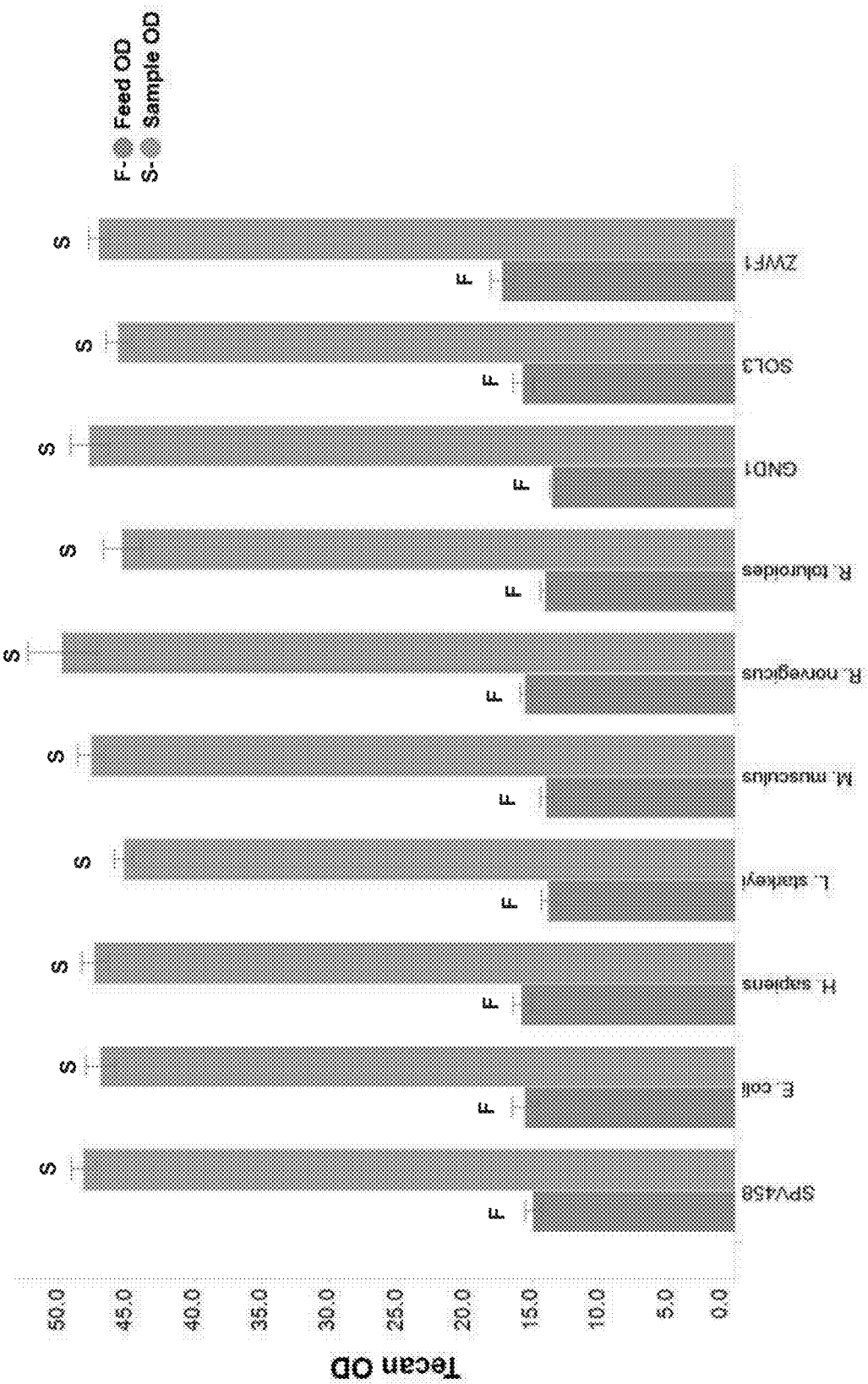
FIG. 10 shows OD600 readings from Tecan reader in standard bioconversion assay of malic enzyme and PPP recombinant microorganisms. Feed OD is after 24 h growth in YPD and 6 h growth in FERMI media, prior to methyl palmitate feed. Sample OD after an additional 42 h bioconversion in FERMI media, after methyl palmitate feed.

We tested the strains in bioprocess media with glucose and excess nitrogen to assess differences in growth and lean biomass accumulation. As seen in FIG. 9, all strains grow very similarly between 0 and 15 hours during the exponential phase, followed by a change in growth rate in the linear phase. All constructs did accumulate slightly less lean biomass than the SPV458 control.

The bioconversion assay did not uncover a significant increase in biomass production for any of our strains either, further corroborating the hypothesis that improved Z11-16Acid production and selectivity is not a related to increased biomass generation, but primarily to increased bioconversion rate and/or efficiency.

Materials & Methods

24-Deepwell Assay

For each construct three or four clonal isolates were inoculated in 1 ml of YPD seed culture in 17 mm glass vials in 24-deepwell plates for 24 hours at 28° C. and 1000 rpm (Infors plate incubator). Seed cultures were pelleted and supernatant removed before resuspension in 1 mL FERMI media. Cultures were incubated at 28° C. and 1000 rpm (Infors plate shaker) for an additional 6 hours in FERMI media. Then, methyl palmitate was added at 20 g/L with a P200 multi-channel. After an additional 42 hours of bioconversion (72 hours total), 250 μl sample was transferred to a crimp-top GC vial for analysis. Vials were frozen at −80° C. before further processing. Cell density was measured with a Tecan M200 Pro plate reader at feeding and at sampling.

Biolector Growth Assay

For each construct three or four clonal isolates were inoculated in 2 ml of YPD seed culture in 24-deepwell plates for 24 hours at 28° C. and 1000 rpm (Infors plate incubator). 7-8 uL of each seed culture were used to inoculate 750 uL of Bioprocess media in each Biolector plate well. Cultures were incubated at 32° C. and 1500 rpm (Biolector) for an additional 72 hours in Bioprocess media, either with excess nitrogen (10 g/L) or limited nitrogen (2 g/L). After 72 hours of growth, 250 μl sample for the nitrogen-limited condition was transferred to a crimp-top GC vial for analysis. Vials were frozen at −80° C. before further processing. Cell density was measured with a Tecan M200 Pro plate reader at feeding and at sampling. Growth curves for the excess nitrogen condition were assessed to compare lean biomass generation for each strain.

GC Sample Work-up 250 uL of culture were lyophilized in open glass crimp top vials for at least 3 hours. 500 uL of methanol was added to the vials followed by addition of 35 ul 10M potassium hydroxide. Vials were then sealed with a crimp cap, arrayed in 54-well racks, mixed for 10 minutes at 2000 RPM using a Mixmate plate shaker, and heated at 60 C for 40 minutes in a convection oven. Vials were cooled to room temperature and decapped. 29 ul 24N sulfuric acid was added to vials. Vials were then sealed with a crimp cap, arrayed in 54-well racks, mixed for 2 minutes at 2000 RPM using a Mixmate plate shaker, and heated at 60 C for 40 minutes in a convection oven. Vials were cooled to room temperature and decapped. 1 ml hexanes was added to vials. Vials were then sealed with a crimp cap, arrayed in 54-well racks, and mixed for 10 minutes at 2000 RPM using a Mixmate plate shaker. Vials then spun down for 5 minutes at 1000 RPM using an Avanti centrifuge. Vials were run on GC-FID.

Example 3. Improving Lipid Production Through Expression of Acetyl-CoA Carboxylase (ACC) Enzymes that are Modified to Prevent Regulatory Inhibition Via Phosphorylation. (PROPHETIC)

Background and Rationale

ACC catalyzes the irreversible conversion of acetyl-CoA to malonyl-CoA, one of the key substrates in lipid biosynthesis. To regulate lipid biosynthesis, kinases inhibit ACC via post-translational modifications. Kinases phosphorylate ACC serine residues, which, when phosphorylated, interact with two downstream arginine residues to inhibit the activity. In order to counteract the microorganism's native regulation of lipid biosynthesis, a few engineering approaches can be taken to increase lipid accumulation in the microorganism, aided by the fact that neither of the residues involved in ACC inhibition are also involved in the conversion of acetyl-CoA to malonyl-CoA. The first approach is to overexpress heterologous ACC variants which may not be phosphorylated by host kinases and are thus not inhibited by a phosphorylated serine. To further improve lipid production, the heterologous ACC variants are further engineered by eliminating key serine residues through replacement with alternative amino acids. The serine residue is replaced by either a point mutation or through replacement of a loop region of the amino acid sequence which contains the key serine residue. In another strategy to further improve lipid synthesis, the heterologous ACC is mutated by replacing the arginine residues involved in inhibiting ACC with a residue, like alanine, that does not interact with phosphorylated serine to deactivate the enzyme. In addition to overexpression of heterologous feedback-resistant ACC variants, the host's native ACC can be deleted or down-regulated. The overexpression of modified ACC variants relieved of post-translational phosphorylation is expected to lead to enhanced flux towards malonyl-CoA and enhanced fatty acid production.

Experimental Design

An expression cassette containing the nucleic acid encoding select heterologous acetyl-CoA carboxylase (see sequences below) will be introduced into the chromosome of the *Y. lipolytica* host that has been previously engineered to produce insect fatty acid pheromone precursors. Expression of the ACC gene variant will be mediated by a strong promoter such as the yeast trancription elongation factor promoter sequence. In the alternative, ACC variants will be expressed by the microorganism's native ACC promoter sequence. Each transformed gene will contain at least one of the three modifications:

(a) Replacement of the portion of the gene that encodes for an amino acid sequence containing a serine residue targeted for phosphorylation with a glycine linker of 4 to 34 amino acids. (Replaced region from position 1,219 to 1,262 in the alignment of FIG. 11)

(b) Replacement the key serine residue (position that is targeted for phosphorylation with a residue that cannot be phosphorylated. (Position 1249 of the alignment of FIG. 11, residue 1157 of *S. cerevisiae* Acc1p)

(c) Replacement the arginine residues at positions 1,266 and 1,369 in the alignment of FIG. 11 with a residue that will not interact with phosphorylated serine to inactivate ACC.

Genome integration of the cassette will utilize homologous recombination methods used in Examples 1 and 2. Inclusion of an amino acid biosynthetic or antibiotic resistance gene in the cassette allows selection of colonies harboring the cassette by plating on selective agar media. Successful integration of the cassette is verified via PCR and sequencing. Three or four positive clonal isolates harboring each heterologous ACC construct will be characterized in a 24-well bioconversion assay, feeding co-substrates glucose/glycerol and methyl palmitate. Fatty acid profiles for all constructs will be quantified using GC analysis. Measurements for initial biomass in YPD and final biomass in nitrogen-limited media will be taken. Growth of each microorganism will be tracked and analyzed for fatty acid profiles in nitrogen-limited media with Solulys95 to confirm that access to methyl palmitate as a co-substrate is necessary to realize improvements in Z11-16Acid selectivity, total fatty acid production, and/or biomass generation.

Experimental Results

Expression of the heterologous ACC genes including the mutations described above are expected to increase accumulation of total fatty acids. All samples will be analyzed for the following fatty acids: Z9-16Acid, Z11-16Acid, 18Acid, Z9-18Acid, Z11-18Acid, Z13-18Acid, Z9Z12-18Acid.

Numbered Embodiments of the Disclosure

Particular subject matter contemplated by the present disclosure is set out in the below numbered embodiments.

1. A recombinant microorganism having improved production of biomass or improved production of one or more lipids from one or more fatty acid and one or more simple carbon co-substrates, wherein the recombinant microorganism comprises one or more modifications in one or more fields comprising:
   tricarboxylic acid cycle;
   lipid synthesis;
   reducing equivalent availability;
   one or more metabolic intermediates availability; and/or
   increased product purity,
   wherein the recombinant microorganism has improved production of biomass or improved production of one or more lipids compared to a microorganism without the same modifications.

2. The recombinant microorganism of embodiment 1, wherein the one or more modifications in one or more fields comprising tricarboxylic acid cycle comprises the overexpression of at least one endogenous and/or exogenous nucleic acid molecule encoding an AMP-insensitive isocitrate dehydrogenase (IDH) variant in the recombinant microorganism.

3. The recombinant microorganism of embodiment 2, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica*.

4. The recombinant microorganism of embodiment 2, wherein the at least one nucleic acid molecule is from *Yarrowia lipolytica* and comprises isoleucine to alanine substitutions at amino acid positions 279 and 280 of XP_503571.2.

5. The recombinant microorganism of embodiment 1, wherein the one or more modifications in one or more fields comprising tricarboxylic acid cycle and one or more metabolic intermediates availability comprises the overexpression of at least one endogenous and/or exogenous nucleic acid molecule encoding a pyruvate transporter in the recombinant microorganism.

6. The recombinant microorganism of embodiment 5, wherein the one or more metabolic intermediates availability comprises mitochondrial pyruvate availability.

7. The recombinant microorganism of embodiment 5, wherein the at least one nucleic acid molecule encodes for a protein that has at least 70% sequence identity, at least 80% sequence identity, or at least 90% sequence identity to pyruvate transporter from *Saccharomyces cerevisiae, Hanseniaspora osmophila, Yarrowia lipolytica*, or *Talaromyces marneffei* PM1.

8. The recombinant microorganism of embodiment 5, wherein the pyruvate transporter is selected from *Saccharomyces cerevisiae* mpc1, *Saccharomyces cerevisiae* mpc3 (NP_011759.1), *Hanseniaspora osmophila* mpc3 (OEJ86292.1), *Yarrowia lipolytica* mpc, and *Talaromyces marneffei* PM1 mpc3 (KFX48982.1), or homolog thereof.

9. The recombinant microorganism of embodiment 5, wherein the recombinant microorganism is *Saccharomyces cerevisiae* comprising a deletion, disruption, or loss of function mutation in a gene encoding an mpc2 pyruvate transporter.

10. The recombinant microorganism of embodiment 5, wherein the recombinant microorganism is *Yarrowia lipolytica*.

11. The recombinant microorganism of embodiment 1, wherein the one or more modifications in one or more fields comprising lipid synthesis comprises alleviation of acetyl-CoA carboxylase (ACC) inhibition.

12. The recombinant microorganism of embodiment 11, wherein alleviation of ACC inhibition comprises the replacement of endogenous ACC or overexpression of at least one exogenous nucleic acid molecule encoding a feedback-insensitive ACC variant in the recombinant microorganism.

13. The recombinant microorganism of embodiment 11, wherein the at least one nucleic acid molecule encodes for a protein that has at least 70% sequence identity, at least 80% sequence identity, or at least 90% sequence identity to ACC from *Mus musculus, Rattus norvegicus*, or *Homo sapiens*.

14. The recombinant microorganism of embodiment 1, wherein the one or more modifications in one or more fields comprising reducing equivalent availability comprises the overexpression of at least one endogenous and/or exogenous nucleic acid molecule encoding an NADP/NAD-dependent isocitrate dehydrogenase (IDH) in the cytosol of the recombinant microorganism to increase the availability of reducing equivalents.

15. The recombinant microorganism of embodiment 14, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica*.

16. The recombinant microorganism of embodiment 14, wherein the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

17. The recombinant microorganism of embodiment 14, wherein the one or more modifications in one or more fields comprising reducing equivalent availability further comprises the overexpression of at least one endogenous and/or exogenous nucleic acid encoding an aconitase in the cytosol of the recombinant microorganism.

18. The recombinant microorganism of embodiment 17, wherein the at least one endogenous and/or exogenous nucleic acid molecule encoding the IDH and the at least one endogenous and/or exogenous nucleic acid molecule encoding the aconitase lack a sequence encoding a mitochondrial-targeting peptide.

19. The recombinant microorganism of embodiment 1, wherein the one or more modifications in one or more fields comprising reducing equivalent availability or one or more metabolic intermediates availability comprise the overexpression of at least one endogenous and/or exogenous nucleic acid encoding a citrate transporter in the recombinant microorganism.

20. The recombinant microorganism of embodiment 19, wherein the one or more metabolic intermediates availability comprises cytosolic citrate/isocitrate availability.

21. The recombinant microorganism of embodiment 19, wherein the at least one nucleic acid molecule encodes for a protein that has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus clemensi*.

22. The recombinant microorganism of embodiment 19, wherein the citrate transporter is selected from *Yarrowia lipolytica* YALI0F26323p, *Saccharomyces cerevisiae*

AAC48984.1, *Rattus norvegicus* AAA18899.1, *Caenorhabditis elegans* P34519.1, and *Caliqus clemensi* ACO14982.1, or homolog thereof.

23. The recombinant microorganism of embodiment 1, wherein the one or more modifications in one or more fields comprising reducing equivalent availability comprises the overexpression of at least one exogenous nucleic acid molecule encoding a decarboxylating malic enzyme in the recombinant microorganism.

24. The recombinant microorganism of embodiment 23, wherein the at least one nucleic acid molecule encodes for a protein that has at least 70% sequence identity, at least 80% sequence identity, or at least 90% sequence identity to a decarboxylating malic enzyme from *Arabidopsis thaliana*, *Amaranthus hypochondriacus*, *Rhizobium meliloti*, *Solanum tuberosum*, *Homo sapiens*, or *Escherichia coli*.

25. The recombinant microorganism of embodiment 23, wherein the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof.

26. The recombinant microorganism of embodiment 23, wherein the decarboxylating malic enzyme lacks a sequence encoding a mitochondrial-targeting peptide.

27. The recombinant microorganism of embodiment 1, wherein the one or more modifications in one or more fields comprising one or more metabolic intermediates availability comprises the overexpression of at least one endogenous and/or exogenous nucleic acid encoding an ATP-citrate lyase in the recombinant microorganism.

28. The recombinant microorganism of embodiment 27, wherein the one or more metabolic intermediate availability comprises cytosolic oxaloacetate availability.

29. The recombinant microorganism of embodiment 27, wherein the at least one nucleic acid molecule encodes for a protein that has at least 70% sequence identity, at least 80% sequence identity, or at least 90% sequence identity to an ATP-citrate lyase from *Saccharomyces cerevisiae, Yarrowia lipolytica, Mus musculus*, and *Aspergillus niger*.

30. The recombinant microorganism of embodiment 27, wherein the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

31. The recombinant microorganism of embodiment 1, wherein the one or more modifications in one or more fields comprising reducing equivalent availability comprises one or more modifications in the pentose phosphate pathway (PPP) in the recombinant microorganism.

32. The recombinant microorganism of embodiment 31, wherein the one or more modifications in the PPP comprises one or more of:
 downregulation of hexose kinase activity;
 upregulation of one or more oxidative PPP enzyme activity;
 downregulation of fructose-6-phosphate kinase activity; and/or
 expression of one or more oxidative PPP enzyme variant.

33. The recombinant microorganism of embodiment 32, wherein the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1).

34. The recombinant microorganism of embodiment 32, wherein the downregulation of hexose kinase activity and/or fructose-6-phosphate kinase activity comprises deletion, disruption, and/or mutation of one or more endogenous gene encoding one or more hexose kinase enzyme and/or fructose-6-phosphate kinase enzyme.

35. The recombinant microorganism of embodiment 32, wherein the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1).

36. The recombinant microorganism of embodiment 35, wherein the one or more nucleic acid molecule encodes for a protein that has at least 70% sequence identity, at least 80% sequence identity, or at least 90% sequence identity to an NAD-dependent glucose-6-phosphate dehydrogenase (ZWF1) from *Leuconostoc*.

37. The recombinant microorganism of embodiment 35, wherein the one or more nucleic acid molecule encodes for a protein that has at least 70% sequence identity, at least 80% sequence identity, or at least 90% sequence identity to an NAD-dependent 6-phosphogluconate dehydrogenase (GND1) from *Bradyrhizobium* or *Methylobacillus*.

38. The recombinant microorganism of embodiment 35, wherein the NAD-dependent glucose-6-phosphate dehydrogenase (ZWF1) is selected from *Leuconostoc* AAA25265.1 and *Leuconostoc* P11411, or homolog thereof.

39. The recombinant microorganism of embodiment 35, wherein the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

40. The recombinant microorganism of embodiment 1, wherein the one or more modifications in one or more fields comprising reducing equivalent availability comprises downregulation of mannitol synthesis pathway in the recombinant microorganism.

41. The recombinant microorganism of embodiment 40, wherein downregulation of mannitol synthesis pathway comprises deletion, disruption, and/or mutation of one or more gene encoding an NADPH-dependent mannitol dehydrogenase and/or an aldo-keto reductase.

42. The recombinant microorganism of embodiment 41, wherein the one or more gene encoding an NADPH-dependent mannitol dehydrogenase is selected from YALI0B16192g, YALI0D18964g, and YALI0E12463g, or homolog thereof.

43. The recombinant microorganism of embodiment 41, wherein the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g, or homolog thereof.

44. The recombinant microorganism of embodiment 1, wherein the one or more modifications in one or more fields comprising reducing equivalent availability comprises decoupling and increasing glucose uptake in the recombinant microorganism.

45. The recombinant microorganism of embodiment 44, wherein decoupling and increasing glucose uptake comprises:
 upregulation of hexose transporter activity; and/or
 downregulation of hexose kinase activity.

46. The recombinant microorganism of embodiment 45, wherein the upregulation of one or more hexose transporter activity comprises the overexpression of one or more endogenous and/or exogenous nucleic acid molecule encoding a hexose transporter operably linked to one or more heterologous promoters.

47. The recombinant microorganism of embodiment 46, wherein the one or more endogenous and/or exogenous nucleic acid molecule encodes for a protein that encodes for a protein that has at least 70% sequence identity, at least 80% sequence identity, or at least 90% sequence identity to a hexose transporter from *Yarrowia lipolytica*.

48. The recombinant microorganism of embodiment 46, wherein the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof.

49. The recombinant microorganism of embodiment 45, wherein the downregulation of hexose kinase activity comprises deletion, disruption, and/or mutation of one or more endogenous gene encoding one or more hexose kinase enzyme.

50. The recombinant microorganism of embodiment 1, wherein the one or more modifications in one or more fields comprising reducing equivalent availability, one or more metabolic intermediates availability, or increased product purity comprises downregulation or inhibition of acetyl-CoA carboxylase (ACC) activity in the recombinant microorganism.

51. The recombinant microorganism of embodiment 50, wherein the downregulation or inhibition of ACC activity comprises deletion, disruption, and/or mutation of one or more endogenous gene encoding one or more ACC enzyme.

52. The recombinant microorganism of embodiment 1, wherein the one or more fatty acid co-substrate is a saturated fatty acid.

53. The recombinant microorganism of embodiment 1, wherein the one or more simple carbon co-substrate is selected from glucose, fructose, and glycerol.

54. The recombinant microorganism of embodiment 1, wherein the improved production of one or more lipid comprises improved production of one or more mono- or poly-unsaturated $C_6$-$C_{24}$ fatty acid, fatty alcohol, aldehyde, or acetate.

55. The recombinant microorganism of embodiment 54, wherein the one or more mono- or poly-unsaturated $C_6$-$C_{24}$ fatty acid, fatty alcohol, aldehyde, or acetate is an insect pheromone.

56. The recombinant microorganism of embodiment 55, wherein the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

57. The recombinant microorganism of any of the preceding embodiments, wherein the recombinant microorganism is a eukaryotic microorganism.

58. The recombinant microorganism of embodiment 57, wherein the eukaryotic microorganism is a yeast.

59. The recombinant microorganism of embodiment 58, wherein the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula,* and *Myxozyma*.

60. The recombinant microorganism of embodiment 58, wherein the yeast is an oleaginous yeast.

61. The recombinant microorganism of embodiment 60, wherein the oleaginous yeast is a member of a genus selected from the group consisting of *Yarrowia, Candida, Rhodotorula, Rhodosporidium, Cryptococcus, Trichosporon,* and *Lipomyces*.

62. The recombinant microorganism of embodiment 61, wherein the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis,* and *R. graminis*.

63. A method of producing one or more lipid using a recombinant microorganism of any of the preceding embodiments, wherein the method comprises cultivating the recombinant microorganism in a culture medium containing a feedstock providing one or more simple carbon and one or more fatty acid until the one or more lipid is produced.

64. A method of producing a recombinant microorganism having improved production of biomass or improved production of one or more lipid from one or more fatty acid and one or more simple carbon co-substrates, comprising modifying a microorganism in one or more fields comprising:
   tricarboxylic acid cycle;
   lipid synthesis;
   reducing equivalent availability;
   one or more metabolic intermediates availability; and/or
   increased product purity,
   wherein the modifying yields a recombinant microorganism having improved production of biomass or improved production of one or more lipid compared to a microorganism not comprising the same modifications.

65. The method of embodiment 64, wherein the modifying in one or more fields comprising tricarboxylic acid cycle comprises introducing into and/or overexpressing in the recombinant microorganism at least one endogenous and/or exogenous nucleic acid molecule encoding an AMP-insensitive isocitrate dehydrogenase (IDH) variant.

66. The method of embodiment 65, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans,* or *Yarrowia lipolytica*.

67. The method of embodiment 65, wherein the at least one nucleic acid molecule is from *Yarrowia lipolytica* and comprises isoleucine to alanine substitutions at amino acid positions 279 and 280 of XP_503571.2, or homolog thereof.

68. The method of embodiment 64, wherein the modifying in one or more fields comprising tricarboxylic acid cycle or one or more metabolic intermediates availability comprises introducing into or overexpressing in the recombinant microorganism at least one endogenous and/or exogenous nucleic acid molecule encoding a pyruvate transporter.

69. The method of embodiment 68, wherein the one or more metabolic intermediates availability comprises mitochondrial pyruvate availability.

70. The method of embodiment 68, wherein the at least one nucleic acid molecule encodes for a protein that has at least 70% sequence identity, at least 80% sequence identity, or at least 90% sequence identity to pyruvate transporter from *Saccharomyces cerevisiae*, *Hanseniaspora osmophila*, *Yarrowia lipolytica*, or *Talaromyces marneffei* PM1.

71. The method of embodiment 68, wherein the pyruvate transporter is selected from *Saccharomyces cerevisiae* mpc1, *Saccharomyces cerevisiae* mpc3 (NP_011759.1), *Hanseniaspora osmophila* mpc3 (OEJ86292.1), *Yarrowia lipolytica* mpc, and *Talaromyces marneffei* PM1 mpc3 (KFX48982.1), or homolog thereof.

72. The method of embodiment 68, wherein the recombinant microorganism is *Saccharomyces cerevisiae* comprising a deletion, disruption, or loss of function mutation in a gene encoding an mpc2 pyruvate transporter.

73. The method of embodiment 68, wherein the recombinant microorganism is *Yarrowia lipolytica*.

74. The method of embodiment 64, wherein the modifying in one or more fields comprising lipid synthesis comprises alleviation of acetyl-CoA carboxylase (ACC) inhibition.

75. The method of embodiment 74, wherein alleviation of ACC inhibition comprises introducing into and/or overexpressing in the recombinant microorganism at least one endogenous and/or exogenous nucleic acid molecule encoding a feedback-insensitive ACC variant.

76. The method of embodiment 74, wherein the at least one nucleic acid molecule encodes for a protein that has at least 70% sequence identity, at least 80% sequence identity, or at least 90% sequence identity to ACC from *Mus musculus*, *Rattus norvegicus*, or *Homo sapiens*.

77. The method of embodiment 64, wherein the modifying in one or more fields comprising reducing equivalent availability comprises introducing into and/or overexpressing in the recombinant microorganism at least one endogenous and/or exogenous nucleic acid molecule encoding an NADP/NAD-dependent isocitrate dehydrogenase (IDH) targeted to the cytosol.

78. The method of embodiment 77, wherein the at least one nucleic acid molecule encodes for a protein that has at least 70% sequence identity, at least 80% sequence identity, or at least 90% sequence identity to IDH from *Escherichia coli*, *Mycobacterium smegmatis*, *Acidithiobacillus thiooxidans*, or *Yarrowia lipolytica*.

79. The method of embodiment 77, wherein the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

80. The method of embodiment 77, wherein the method further comprises introducing into or overexpressing in the recombinant microorganism at least one endogenous and/or exogenous nucleic acid encoding an aconitase targeted to the cytosol.

81. The method of embodiment 80, wherein the at least one endogenous and/or exogenous nucleic acid molecule encoding the IDH and the at least one endogenous and/or exogenous nucleic acid molecule encoding the aconitase lack a sequence encoding a mitochondrial-targeting peptide.

82. The method of embodiment 64, wherein the modifying in one or more fields comprising reducing equivalent availability or one or more metabolic intermediates availability comprises introducing into and/or overexpressing in the recombinant microorganism at least one endogenous and/or exogenous nucleic acid encoding a citrate transporter.

83. The method of embodiment 82, wherein the one or more metabolic intermediates comprises cytosolic citrate/isocitrate availability.

84. The method of embodiment 82, wherein the at least one nucleic acid molecule encodes for a protein that has at least 70% sequence identity, at least 80% sequence identity, or at least 90% sequence identity to a citrate transporter from *Yarrowia lipolytica*, *Saccharomyces cerevisiae*, *Rattus norvegicus*, *Caenorhabditis elegans*, or *Caliqus clemensi*.

85. The method of embodiment 82, wherein the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

86. The method of embodiment 64, wherein the modifying in one or more fields comprising reducing equivalent availability comprises introducing into and/or overexpressing in the recombinant microorganism at least one exogenous nucleic acid molecule encoding a decarboxylating malic enzyme.

87. The method of embodiment 86, wherein the at least one nucleic acid molecule encodes for a protein that has at least 70% sequence identity, at least 80% sequence identity, or at least 90% sequence identity to a decarboxylating malic enzyme from *Arabidopsis thaliana*, *Amaranthus hypochondriacus*, *Rhizobium meliloti*, *Solanum tuberosum*, *Homo sapiens*, or *Escherichia coli*.

88. The method of embodiment 86, wherein the decarboxylating malic enzyme is selected from *Arabidopsis thaliana* Q9SIU0, *Amaranthus hypochondriacus* P37224, *Rhizobium meliloti* O30807, *Solanum tuberosum* P37221, *Homo sapiens* Q16798, and *Escherichia coli* P26616, or homolog thereof.

89. The method of embodiment 86, wherein the decarboxylating malic enzyme lacks a sequence encoding a mitochondrial-targeting peptide.

90. The method of embodiment 64, wherein the modifying in one or more fields comprising one or more metabolic intermediates availability comprises introducing into and/or overexpressing in the recombinant microorganism at least one endogenous and/or exogenous nucleic acid encoding an ATP-citrate lyase.

91. The method of embodiment 90, wherein the one or more metabolic intermediates availability comprises cytosolic oxaloacetate availability.

92. The method of embodiment 90, wherein the at least one nucleic acid molecule encodes for a protein that has at least 70% sequence identity, at least 80% sequence identity, or at least 90% sequence identity to an ATP-citrate lyase from *Saccharomyces cerevisiae*, *Yarrowia lipolytica*, *Mus musculus*, and *Aspergillus niger*.

93. The method of embodiment 90, wherein the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof 94. The method of embodiment 64, wherein of the modifying in one or more fields comprising reducing equivalent availability comprises modifications in the pentose phosphate pathway (PPP) in the recombinant microorganism.

95. The method of embodiment 94, wherein modifications in the PPP comprises one or more of:
- downregulation of hexose kinase activity;
- upregulation of one or more oxidative PPP enzyme activity;
- downregulation of fructose-6-phosphate kinase activity; and/or
- expression of one or more oxidative PPP enzyme variant.

96. The method of embodiment 95, wherein the upregulation of one or more oxidative PPP enzyme activity comprises introducing into and/or overexpressing in the recombinant microorganism one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1).

97. The method of embodiment 95, wherein the downregulation of hexose kinase activity and/or fructose-6-phosphate kinase activity comprises introducing into the recombinant microorganism a deletion, disruption, and/or mutation of one or more endogenous gene encoding one or more hexose kinase enzyme and/or fructose-6-phosphate kinase enzyme.

98. The method of embodiment 95, wherein the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1).

99. The method of embodiment 98, wherein the one or more nucleic acid molecule encodes for a protein that has at least 70% sequence identity, at least 80% sequence identity, or at least 90% sequence identity to an NAD-dependent glucose-6-phosphate dehydrogenase (ZWF1) from *Leuconostoc*.

100. The method of embodiment 98, wherein the one or more nucleic acid molecule encodes for a protein that has at least 70% sequence identity, at least 80% sequence identity, or at least 90% sequence identity to an NAD-dependent 6-phosphogluconate dehydrogenase (GND1) from *Bradyrhizobium* or *Methylobacillus*.

101. The method of embodiment 98, wherein the NAD-dependent glucose-6-phosphate dehydrogenase (ZWF1) is selected from *Leuconostoc* AAA25265.1 and *Leuconostoc* P11411, or homolog thereof.

102. The method of embodiment 98, wherein the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

103. The method of embodiment 64, wherein the modifying in one or more fields comprising reducing equivalent availability comprises downregulation of mannitol synthesis pathway in the recombinant microorganism.

104. The method of embodiment 103, wherein downregulation of mannitol synthesis pathway comprises introducing into the recombinant microorganism a deletion, disruption, and/or mutation of one or more gene encoding an NADPH-dependent mannitol dehydrogenase and/or an aldo-keto reductase.

105. The method of embodiment 104, wherein the one or more gene encoding an NADPH-dependent mannitol dehydrogenase is selected from YALI0B16192g, YALI0D18964g, and YALI0E12463g, or homolog thereof.

106. The method of embodiment 104, wherein the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g, or homolog thereof.

107. The method of embodiment 64, wherein the modifying in one or more fields comprising reducing equivalent availability comprises decoupling and increasing glucose uptake in the recombinant microorganism.

108. The method of embodiment 107, wherein decoupling and increasing glucose uptake comprises:
- upregulation of hexose transporter activity; and/or
- downregulation of hexose kinase activity.

109. The method of embodiment 108, wherein the upregulation of one or more hexose transporter activity comprises introducing into and/or overexpressing in the recombinant microorganism one or more endogenous and/or exogenous nucleic acid molecule encoding a hexose transporter operably linked to one or more heterologous promoters.

110. The method of embodiment 109, wherein the one or more endogenous and/or exogenous nucleic acid molecule encodes for a protein that has at least 70% sequence identity, at least 80% sequence identity, or at least 90% sequence identity to a hexose transporter from *Yarrowia lipolytica*.

111. The method of embodiment 109, wherein the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof.

112. The method of embodiment 108, wherein the downregulation of hexose kinase activity comprises introducing into the recombinant microorganism a deletion, disruption, and/or mutation of one or more endogenous gene encoding one or more hexose kinase enzyme.

113. The method of embodiment 64, wherein the modifying in one or more fields comprising reducing equivalent availability, one or more metabolic intermediates availability, and/or increased product purity comprises downregulation or inhibition of acetyl-CoA carboxylase (ACC) activity in the recombinant microorganism.

114. The method of embodiment 113, wherein the downregulation or inhibition of ACC activity comprises introducing into the recombinant microorganism a deletion, disruption, and/or mutation of one or more endogenous gene encoding one or more ACC enzyme.

115. The method of embodiment 64, wherein the one or more fatty acid co-substrate is a saturated fatty acid.

116. The method of embodiment 64, wherein the one or more simple carbon co-substrate is selected from glucose, fructose, and glycerol.

117. The method of embodiment 64, wherein the improved production of one or more lipid comprises improved production of one or more mono- or poly-unsaturated $C_6$-$C_{24}$ fatty acid, alcohol, aldehyde, or acetate.

118. The method of embodiment 117, wherein the one or more mono- or poly-unsaturated $C_6$-$C_{24}$ fatty acid, alcohol, aldehyde, or acetate is an insect pheromone or fatty acid precursor of an insect pheromone.

119. The method of embodiment 118, wherein the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetradecen-1-ol, (Z)-11-tetraceden-1-ol, (Z)-11-tetracedenyl acetate, (E)-11-tetradecen-1-ol, (E)-11- tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

120. The method of any one of embodiments 64-119, wherein the recombinant microorganism is a eukaryotic microorganism.

121. The method of embodiment 120, wherein the eukaryotic microorganism is a yeast.

122. The method of embodiment 121, wherein the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

123. The method of embodiment 121, wherein the yeast is an oleaginous yeast.

124. The method of embodiment 123, wherein the oleaginous yeast is a member of a genus selected from the group consisting of *Yarrowia, Candida, Rhodotorula, Rhodosporidium, Cryptococcus, Trichosporon*, and *Lipomyces*.

125. The method of embodiment 124, wherein the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis*, and *R. graminis*.

Further Embodiments of the Invention

Other subject matter contemplated by the present disclosure is set out in the following numbered embodiments:

1. A recombinant microorganism with improved lipid production from one or more fatty acid, and one or more simple carbon co-substrates, wherein the recombinant microorganism comprises:
   a) a nucleic acid encoding a heterologous AMP-insensitive isocitrate dehydrogenase (IDH) enzyme;
wherein the recombinant microorganism has improved production of one or more lipids compared to a control microorganism without a).

2. The recombinant microorganism of embodiment 1, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

2.1 The recombinant microorganism of embodiment 1, wherein the recombinant microorganism is further engineered to comprise deletions of one or more of the endogenous acyl-CoA oxidases selected from the group consisting of: POX1, POX2, POX3, POX4, POX5, and POX6.

3. The recombinant microorganism of any one of embodiments 1-2.1, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

3.1 The recombinant microorganism of any one of embodiments 1-2.1, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

4. The recombinant microorganism of any one of embodiments 1-3.1, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

4.1 The recombinant microorganism of embodiment 4, wherein the fatty acyl desaturase is a Z11 desaturase.

4.2 The recombinant microorganism of embodiment 4.1, wherein the fatty acyl desaturase is has at least 70% sequence identity, at least 80% sequence identity, or at least 90% sequence identity to an amino acid sequence encoded by SEQ ID NO. 32 or 33.

5. The recombinant microorganism of any one of embodiments 1-4.2, wherein the recombinant microorganism is engineered to reduce or eliminate the expression or activity of endogenous fatty alcohol oxidase (FAO1).

5.1. The recombinant microorganism of any one of embodiments 1-4.2, wherein the recombinant microorganism is engineered to comprise a deletion of endogenous fatty alcohol oxidase (FAO1).

6. The recombinant microorganism of any one of embodiments 1-5.1, wherein the IDH enzyme has at least 70% sequence identity, at least 80% sequence identity, or at least 90% sequence identity to an IDH from *Escherichia coli, Mycobacterium smegmatis, Acidithiobacillus thiooxidans*, and/or *Yarrowia lipolytica*.

7. The recombinant microorganism of any one of embodiments 1-5.1, wherein the IDH enzyme has at least 70% sequence identity, at least 80% sequence identity, or at least 90% sequence identity with a sequence selected from the group consisting of SEQ ID 20, 21, 22, and 23.

8. The recombinant microorganism of any one of embodiments 1-7, wherein the recombinant microorganism is *Yarrowia lipolytica*.

9. The recombinant microorganism of any one of embodiments 1-8, wherein the recombinant microorganism comprises an nucleic acid molecule encoding a heterologous decarboxylating malic enzyme.

10. The recombinant microorganism of embodiment 9, wherein the decarboxylating malic enzyme has at least 70% sequence identity, at least 80% sequence identity, or at least 90% sequence identity to a decarboxylating malic enzyme from *Escherichia coli, Hominidae sapiens, Lypomyces starkeyi, Mus musculus*, and *Rattus novegicus*, and/or *Rhodosporidium toruloides*.

11. The recombinant microorganism of embodiment 9, wherein the decarboxylating malic enzyme has at least 70% sequence identity, at least 80% sequence identity, or at least 90% sequence identity with a sequence selected from the group consisting of SEQ ID NO. 24, 25, 26, 27, 28, and 29.

12. The recombinant microorganism of any one of embodiments 1-11, wherein the recombinant microorganism comprises one or more modification(s) to the pentose phosphate pathway (PPP).

13. The recombinant microorganism of embodiment 12, wherein the one or more modification(s) to the PPP pathway is the upregulation of one or more enzymes exhibiting oxidative PPP activity.

14. The recombinant microorganism of embodiment 12, wherein the recombinant microorganism is engineered to overexpress one or more endogenous and/or exogenous enzymes selected from the group consisting of: a glucose- 6-phosphate dehydrogenase (ZWF1), a 6-phosphoglucono-lactonase (SOL3), or a 6-phosphogluconate dehydrogenase (GND1).

15. The recombinant microorganism of embodiment 12, wherein the recombinant microorganism is engineered to overexpress one or more endogenous and/or exogenous enzyme(s) exhibiting at least 70% sequence identity, at least 80% sequence identity, or at least 90% sequence identity with a sequence selected from the group consisting of SEQ ID NO. 40, 42, and 44.

16. A recombinant microorganism with improved Z11-16 acid selectivity, said recombinant microorganism comprising:
   a) a nucleic acid encoding a heterologous decarboxylating malic enzyme; and/or
   b) a genetic modification overexpressing an enzyme exhibiting oxidative PPP activity;
wherein the recombinant microorganism has improved Z11-16 acid selectivity compared to a control microorganism without a) and/or b).

17. A recombinant microorganism with improved lipid production from one or more fatty acid, and one or more simple carbon co-substrates, said recombinant microorganism comprising:
   a) a nucleic acid encoding a heterologous decarboxylating malic enzyme from *Lypomyces starkeyi* and/or *Mus musculus*; and/or
   b) a genetic modification overexpressing a 6-phosphogluconate dehydrogenase (GND1) enzyme;
wherein the recombinant microorganism has improved lipid production compared to a control microorganism without a) and/or b).

18. The recombinant microorganism of embodiment 17, wherein the decarboxylating malic enzyme has at least 70% sequence identity, at least 80% sequence identity, or at least 90% sequence identity with a sequence selected from the group consisting of SEQ ID NO. 24, 25, 26, 27, 28, and 29.

19. The recombinant microorganism of embodiment 17, wherein the GND1 enzyme has at least 70% sequence identity, at least 80% sequence identity, or at least 90% sequence identity with SEQ ID NO. 42.

20. The recombinant microorganism of any one of embodiments 16-19, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

20.1 The recombinant microorganism of any one of embodiments 16-19, wherein the recombinant microorganism is further engineered to comprise deletions of one or more of the endogenous acyl-CoA oxidases selected from the group consisting of: POX1, POX2, POX3, POX4, POX5, and POX6.

21. The recombinant microorganism of any one of embodiments 16-20, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

21.1 The recombinant microorganism of any one of embodiments 16-20, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

22. The recombinant microorganism of any one of embodiments 16-21, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

22.1 The recombinant microorganism of embodiment 22, wherein the fatty acyl desaturase is a Z11 desaturase.

22.2 The recombinant microorganism of embodiment 22.1, wherein the fatty acyl desaturase comprises an amino acid sequence encoded by SEQ ID NO. 32 or 33.

23. The recombinant microorganism of any one of embodiments 16-22.2, wherein the recombinant microorganism is engineered to reduce or eliminate the expression or activity of endogenous fatty alcohol oxidase (FAO1).

23.1 The recombinant microorganism of any one of embodiments 16-22.2, wherein the recombinant microorganism is engineered to comprise a deletion of endogenous fatty alcohol oxidase (FAO1).

24. The recombinant microorganism of any one of embodiments 16 or 20-23.1, wherein the decarboxylating malic enzyme has at least 70% sequence identity, at least 80% sequence identity, or at least 90% sequence identity to a decarboxylating malic enzyme from *Escherichia coli*, *Hominidae sapiens*, *Lypomyces starkeyi*, *Mus musculus*, and *Rattus novegicus*, and/or *Rhodosporidium toruloides*.

25. The recombinant microorganism of any one of embodiments 16 or 20-23.1, wherein the decarboxylating malic enzyme has at least 70% sequence identity, at least 80% sequence identity, or at least 90% sequence identity with a sequence selected from the group consisting of SEQ ID NO. 24, 25, 26, 27, 28, and 29.

26. The recombinant microorganism of any one of embodiments 16 or 20-25, wherein the enzyme exhibiting oxidative PPP activity is selected from the group consisting of glucose-6-phosphate dehydrogenase (ZWF1), a 6-phosphogluconolactonase (SOL3), and a 6-phosphogluconate dehydrogenase (GND1).

27. The recombinant microorganism of embodiments 16 or 20-25, wherein the enzyme exhibiting oxidative PPP activity exhibits at least 70% sequence identity, at least 80% sequence identity, or at least 90% sequence identity with a sequence selected from the group consisting of SEQ ID NO. 40, 42, and 44.

28. The recombinant microorganism of any one of embodiments 16-27, wherein the recombinant microorganism comprises a nucleic acid encoding a heterologous AMP-insensitive isocitrate dehydrogenase (IDH) enzyme.

29. The recombinant microorganism of embodiment 28, wherein the IDH enzyme has at least 70% sequence identity, at least 80% sequence identity, or at least 90% sequence identity to an IDH from *Escherichia coli*, *Mycobacterium smegmatis*, *Acidithiobacillus thiooxidans*, and/or *Yarrowia lipolytica*.

30. The recombinant microorganism of embodiment 28, wherein the IDH enzyme has at least 70% sequence identity, at least 80% sequence identity, or at least 90% sequence identity with a sequence selected from the group consisting of SEQ ID 20, 21, 22, and 23.

31. The recombinant microorganism of any one of embodiments 16-30, wherein the recombinant microorganism is *Yarrowia lipolytica*.

32. The recombinant microorganism of any one of embodiments 1-31, wherein the recombinant microorganism comprises a nucleic acid encoding a feedback-insensitive acetyl-CoA carboxylase (ACC) enzyme.

33. The recombinant microorganism of embodiment 32, wherein the ACC enzyme has at least 70% sequence identity, at least 80% sequence identity, or at least 90% sequence identity to ACC from *Mus musculus, Rattus norvegicus*, or *Homo sapiens*.

34. The recombinant microorganism of any one of embodiments 1-33, wherein the recombinant microorganism is modified to overexpress an endogenous aconitase gene and/or comprises an exogenous nucleic acid encoding an aconitase enzyme.

35. The recombinant microorganism of any one of embodiments 1-34, wherein the recombinant microorganism is modified to overexpress an endogenous citrate transporter gene and/or comprises an exogenous nucleic acid encoding a citrate transporter.

36. The recombinant microorganism of embodiment 35, wherein the citrate transporter has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus clemensi*.

37. The recombinant microorganism of embodiment 35, wherein the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

38. The recombinant microorganism of any one of embodiments 1-37, wherein the recombinant microorganism is modified to overexpress an endogenous hexose transporter gene and/or comprises an exogenous nucleic acid encoding a hexose transporter.

39. The recombinant microorganism of embodiment 38, wherein the hexose transporter has at least 70% sequence identity, at least 80% sequence identity, or at least 90% sequence identity to a hexose transporter from *Yarrowia lipolytica*.

40. The recombinant microorganism of embodiment 38, wherein the hexose transporter is selected from the group consisting of: YALI0A14212g, YALI0D01111g, YALI0D00363g, YALI0C16522g, and YALI0F25553g, or homolog thereof.

41. The recombinant microorganism of any one of embodiments 1-40, wherein the one or more fatty acid co-substrate is a saturated fatty acid.

42. The recombinant microorganism of any one of embodiments 1-41, wherein the one or more simple carbon co-substrate is selected from glucose, fructose, and glycerol.

43. The recombinant microorganism of any one of embodiments 1-42, wherein the oleaginous yeast is a member of a genus selected from the group consisting of *Yarrowia, Candida, Rhodotorula, Rhodosporidium, Cryptococcus, Trichosporon*, and *Lipomyces*.

44. The recombinant microorganism of any one of embodiments 1-43, wherein the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis*, and *R. graminis*.

44.1 A composition comprising:
 a) the recombinant microorganism of any one of embodiments 1-44; and
 b) a dual-substrate culture medium comprising:
  i) a fatty acid precursor substrate; and
  ii) a simple carbon co-substrate.

44.2 The composition of embodiment 44.1, wherein the fatty acid precursor substrate is a C6-C24 saturated fatty acid.

44.3. The composition of embodiment 44.2, wherein the fatty acid precursor substrate is derived from a plant.

44.4. The composition of embodiment 44.1, wherein the fatty acid precursor substrate is methyl palmitate.

44.5. The composition of any one of embodiments 44.1-44.4, wherein the simple carbon co-substrate is glycerol and/or glucose.

45. A method of producing one or more lipid using a recombinant microorganism of any of the preceding embodiments, wherein the method comprises cultivating the recombinant microorganism in a culture medium containing a feedstock providing one or more simple carbon and one or more fatty acid until the one or more lipid is produced.

45.1 A method for increasing the production of non-native unsaturated fatty acids from a recombinant microorganism in a bypass pathway culture, said method comprising the steps of:
 a) providing a recombinant microorganism comprising a modification to the:
  i) Tricarboxylic acid cycle;
  ii) Lipid synthesis;
  iii) One or more metabolic intermediates; and/or
  iv) Reducing equivalents; and
 b) contacting said recombinant microorganism with a dual-substrate culture medium comprising:
  i) a fatty acid precursor substrate; and
  ii) a simple carbon co-substrate;
wherein the recombinant microorganism exhibits improved production of non-native unsaturated fatty acids compared to a control microorganism without the modification(s) of a). The inventors intend that embodiments 46-117 can be presented as dependent embodiments from embodiment 45.1.

46. A method for increasing the production of fatty acids from a recombinant microorganism in a bypass pathway culture, said method comprising the steps of:
 a) providing a recombinant microorganism comprising a nucleic acid encoding a heterologous AMP-insensitive isocitrate dehydrogenase (IDH) enzyme capable of catalyzing the oxidation of isocitrate to oxalosuccinate; and
 b) contacting said recombinant microorganism with a dual-substrate culture medium comprising:
  i) a fatty acid precursor substrate; and
  ii) a simple carbon co-substrate;
wherein the recombinant microorganism exhibits improved fatty acid production compared to a control microorganism without the nucleic acid encoding the IDH enzyme.

46.1 The method of embodiment 46, wherein the microorganism exhibits improved production of non-native unsaturated fatty acids.

47. The method of embodiment 46 or 46.1, wherein the fatty acid precursor substrate is a C6-C24 saturated fatty acid.

48. The method of embodiment 47, wherein the fatty acid precursor substrate is derived from a plant.

49. The method of embodiment 46 or 46.1, wherein the fatty acid precursor substrate is methyl palmitate.

50. The method of any one of embodiments 46-49, wherein the simple carbon co-substrate is glycerol and/or glucose.

51. The method of any one of embodiments 46-50, wherein the IDH enzyme has at least 70% sequence identity, at least 80% sequence identity, or at least 90% sequence identity to an IDH from *Escherichia coli, Mycobacterium smegmatis, Acidithiobacillus thiooxidans*, or *Yarrowia lipolytica*.

52. The method of any one of embodiments 46-50, wherein the IDH enzyme has at least 70% sequence identity, at least 80% sequence identity, or at least 90% sequence identity with a sequence selected from the group consisting of SEQ ID 20, 21, 22, and 23.

53. The method of any one of embodiments 46-52, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

54. The method of any one of embodiments 46-52, wherein the recombinant microorganism is further engineered to comprise deletions of one or more of the endogenous acyl-CoA oxidases selected from the group consisting of: POX1, POX2, POX3, POX4, POX5, and POX6.

55. The method of any one of embodiments 46-54, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

56. The method of any one of embodiments 46-54, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

57. The method of any one of embodiments 46-55, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

58. The method of embodiment 57, wherein the fatty acyl desaturase is a Z11 desaturase.

59. The method of any one of embodiments 46-58, wherein the recombinant microorganism is *Yarrowia lipolytica*.

60. A method for improving the Z11-16 acid selectivity of a recombinant microorganism in a bypass pathway culture, said method comprising the steps of:
   a) providing a recombinant microorganism comprising a nucleic acid encoding a heterologous decarboxylating malic enzyme capable of catalyzing the oxidation of malate to pyruvate; and
   b) contacting said recombinant microorganism with a dual-substrate culture medium comprising:
      i) a fatty acid precursor substrate; and
      ii) a simple carbon co-substrate;
wherein the recombinant microorganism exhibits improved Z11-16 acid selectivity compared to a control microorganism without the nucleic acid encoding the heterologous decarboxylating malic enzyme.

61. The method of embodiment 60, wherein the fatty acid precursor substrate is a C6-C24 saturated fatty acid.

62. The method of embodiment 61, wherein the fatty acid precursor substrate is derived from a plant.

63. The method of embodiment 60, wherein the fatty acid precursor substrate is methyl palmitate.

64. The method of any one of embodiments 60-63, wherein the simple carbon co-substrate is glycerol and/or glucose.

65. The method of any one of embodiments 60-64, wherein the decarboxylating malic enzyme has at least 70% sequence identity, at least 80% sequence identity, or at least 90% sequence identity with a decarboxylating malic enzyme from *Escherichia coli*, *Hominidae sapiens*, *Lypomyces starkeyi*, *Mus musculus*, *Rattus novegicus*, or *Rhodosporidium toruloides*.

66. The method of any one of embodiments 60-64, wherein the heterologous decarboxylating malic enzyme has at least 70% sequence identity, at least 80% sequence identity, or at least 90% sequence identity with SEQ ID NO. 24, 25, 26, 27, 28, and 29.

67. The method of any one of embodiments 60-66, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

68. The method of any one of embodiments 60-66, wherein the recombinant microorganism is further engineered to comprise deletions of one or more of the endogenous acyl-CoA oxidases selected from the group consisting of: POX1, POX2, POX3, POX4, POX5, and POX6.

69. The method of any one of embodiments 60-68, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

70. The method of any one of embodiments 60-68, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

71. The method of any one of embodiments 60-70, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

72. The method of embodiment 71, wherein the fatty acyl desaturase is a Z11 desaturase.

72. The method of any one of embodiments 60-72, wherein the recombinant microorganism is *Yarrowia lipolytica*.

73. A method for improving the Z11-16 acid selectivity of a recombinant microorganism in a bypass pathway culture, said method comprising the steps of:
   a) providing a recombinant microorganism comprising a genetic modification overexpressing an enzyme exhibiting oxidative pentose phosphate pathway (PPP) activity; and
   b) contacting said recombinant microorganism with a dual-substrate culture medium comprising:
      i) a fatty acid precursor substrate; and
      ii) a simple carbon co-substrate;
wherein the recombinant microorganism exhibits improved Z11-16 acid selectivity compared to a control microorganism without the genetic modification overexpressing the enzyme exhibiting oxidative PPP activity.

74. The method of embodiment 73, wherein the fatty acid precursor substrate is a C6-C24 saturated fatty acid.

75. The method of embodiment 74, wherein the fatty acid precursor substrate is derived from a plant.

76. The method of embodiment 73, wherein the fatty acid precursor substrate is methyl palmitate.

77. The method of any one of embodiments 73-76, wherein the simple carbon co-substrate is glycerol and/or glucose.

78. The method of any one of embodiments 73-77, wherein the enzyme exhibiting oxidative PPP activity is selected from the group consisting of: a glucose-6-phosphate dehydrogenase (ZWF1), a 6-phosphogluconolactonase (SOL3), or a 6-phosphogluconate dehydrogenase (GND1).

79. The method of any one of embodiments 73-77, wherein the enzyme exhibiting oxidative PPP activity has at least 70% sequence identity, at least 80% sequence identity, or at least 90% sequence identity with SEQ ID NOs. 40, 42, or 44.

80. The method of any one of embodiments 73-79, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

81. The method of any one of embodiments 73-79, wherein the recombinant microorganism is further engineered to comprise deletions of one or more of the endogenous acyl-CoA oxidases selected from the group consisting of: POX1, POX2, POX3, POX4, POX5, and POX6.

82. The method of any one of embodiments 73-81, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

83. The method of any one of embodiments 73-81, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

84. The method of any one of embodiments 73-83, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

85. The method of embodiment 84, wherein the fatty acyl desaturase is a Z11 desaturase.

86. The method of any one of embodiments 73-85, wherein the recombinant microorganism is *Yarrowia lipolytica*.

87. A method for improving the fatty acid production of a recombinant microorganism in a bypass pathway culture, said method comprising the steps of:
   a) providing a recombinant microorganism comprising:
      i) a genetic modification overexpressing an enzyme exhibiting oxidative pentose phosphate pathway (PPP) activity; and/or
      ii) a nucleic acid encoding a heterologous decarboxylating malic enzyme; and
   b) contacting said recombinant microorganism with a dual-substrate culture medium comprising:
      i) a fatty acid precursor substrate; and
      ii) a simple carbon co-substrate;
   wherein the recombinant microorganism exhibits improved fatty acid production compared to a control microorganism without the genetic modification or nucleic acid of a).

87.1 The method claim 87, wherein the microorganism exhibits improved production of non-native unsaturated fatty acids.

88. The method of embodiment 87 or 87.1, wherein the fatty acid precursor substrate is a C6-C24 saturated fatty acid.

89. The method of embodiment 88, wherein the fatty acid precursor substrate is derived from a plant.

90. The method of embodiment 87 or 87.1, wherein the fatty acid precursor substrate is methyl palmitate.

91. The method of any one of embodiments 87-89, wherein the simple carbon co-substrate is glycerol and/or glucose.

92. The method of any one of embodiments 87-91, wherein the enzyme exhibiting oxidative PPP activity is a 6-phosphogluconate dehydrogenase (GND) enzyme.

93. The method of any one of embodiments 87-91, wherein the enzyme exhibiting oxidative PPP activity has at least 70% sequence identity, at least 80% sequence identity, or at least 90% sequence identity with SEQ ID NO. 42.

94. The method of any one of embodiments 87-93, wherein the decarboxylating malic enzyme has at least 70% sequence identity, at least 80% sequence identity, or at least 90% sequence identity with a decarboxylating malic enzyme from *Lypomyces starkeyi* or *Mus musculus*.

95. The method of any one of embodiments 87-93, wherein the heterologous decarboxylating malic enzyme has at least 70% sequence identity, at least 80% sequence identity, or at least 90% sequence identity with SEQ ID NO. 24 or 28.

96. The method of any one of embodiments 87-95, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

97. The method of any one of embodiments 87-95, wherein the recombinant microorganism is further engineered to comprise deletions of one or more of the endogenous acyl-CoA oxidases selected from the group consisting of: POX1, POX2, POX3, POX4, POX5, and POX6.

98. The method of any one of embodiments 87-97, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

99. The method of any one of embodiments 87-97, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

100. The method of any one of embodiments 87-99, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

101. The method of embodiment 100, wherein the fatty acyl desaturase is a Z11 desaturase.

102. The method of any one of embodiments 87-101, wherein the recombinant microorganism is *Yarrowia lipolytica*.

103. A method for improving the fatty acid production of a recombinant microorganism in a bypass pathway culture, said method comprising the steps of:
   a) providing a recombinant microorganism comprising:
      i) a genetic modification overexpressing an endogenous feedback insensitive acetyl-CoA carboxylase (ACC) enzyme; or
      ii) a nucleic acid encoding a heterologous feedback-insensitive ACC enzyme; and b) contacting said recombinant microorganism with a dual-substrate culture medium comprising:
   i) a fatty acid precursor substrate; and
   ii) a simple carbon co-substrate;
wherein the recombinant microorganism exhibits improved fatty acid production compared to a control microorganism without the genetic modification or nucleic acid of a).

104. The method of embodiment 103, wherein the heterologous feedback-insensitive ACC has at least 70% sequence identity, at least 80% sequence identity, or at least 90% sequence identity to ACC from *Mus musculus, Rattus norvegicus*, or *Homo sapiens*.

105. The method of embodiment 103 or 104, wherein the fatty acid precursor substrate is a C6-C24 saturated fatty acid.

106. The method of embodiment 105, wherein the fatty acid precursor substrate is derived from a plant.

107. The method of embodiment 103 or 104, wherein the fatty acid precursor substrate is methyl palmitate.

108. The method of any one of embodiments 103-107, wherein the simple carbon co-substrate is glycerol and/or glucose.

109. The method of any one of embodiments 103-108, wherein the ACC enzyme has at least 70% sequence identity, at least 80% sequence identity, or at least 90% sequence identity with a decarboxylating malic enzyme from *Rattus norvegicus, Mus musculus, Saccharomyces cerevisiae, Homo sapiens, Lipomyces* starkeyi, *Komagataella phaffii*, or *Yarrowia lipolytica*.

110. The method of any one of embodiments 103-108, wherein the ACC enzyme has at least 70% sequence identity, at least 80% sequence identity, or at least 90% sequence identity with SEQ ID NO. 50, 51, 52, 53, 54, 55, 56, or 57.

110.1 The method of embodiments of any one of embodiments 103-110, wherein the ACC enzyme:
   a) comprises a replacement of a serine residue targeted for phosphorylation with a glycine linker of 4 to 34 amino acids; and/or
   b) comprises a replacement of the serine residue targeted for phosphorylation with a residue that cannot be phosphorylated; and/or
   c) comprises a replacement of argenine residues at positions 1266 and 1369 of the alignment of FIG. 11 with a residue that will not interact with the serine residue after phosphorylation to inactivate ACC.

111. The method of any one of embodiments 103-110.1, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

112. The method of any one of embodiments 103-110.1, wherein the recombinant microorganism is further engineered to comprise deletions of one or more of the endogenous acyl-CoA oxidases selected from the group consisting of: POX1, POX2, POX3, POX4, POX5, and POX6.

113. The method of any one of embodiments 103-112, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

114. The method of any one of embodiments 110-112, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

115. The method of any one of embodiments 110-114, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

116. The method of embodiment 115, wherein the fatty acyl desaturase is a Z11 desaturase.

117. The method of any one of embodiments 110-116, wherein the recombinant microorganism is *Yarrowia lipolytica*.

118. A a recombinant microorganism having improved production of non-native unsaturated fatty acids from one or more fatty acids and one or more simple carbon co-substrates wherein said recombinant microorganism comprises:
   a) a genetic modification overexpressing an endogenous feedback insensitive acetyl-CoA carboxylase (ACC) enzyme; and/or
   b) a nucleic acid encoding a heterologous feedback-insensitive ACC enzyme;
wherein the recombinant microorganism exhibits improved fatty acid production compared to a control microorganism without the genetic modification or nucleic acid of a).

119. The recombinant microorganism of embodiment 118, wherein the ACC enzyme has at least 70% sequence identity, at least 80% sequence identity, or at least 90% sequence identity with a decarboxylating malic enzyme from *Rattus norvegicus, Mus musculus, Saccharomyces cerevisiae, Homo sapiens, Lipomyces* starkeyi, *Komagataella phaffii*, or *Yarrowia lipolytica*.

120. The recombinant microorganism of any one of embodiments 118-119, wherein the ACC enzyme has at least 70% sequence identity, at least 80% sequence identity, or at least 90% sequence identity with SEQ ID NO. 50, 51, 52, 53, 54, 55, 56, or 57.

121 The recombinant microorganism of any one of embodiments 118-120, wherein the ACC enzyme:
   a) comprises a replacement of an serine residue targeted for phosphorylation with a glycine linker of 4 to 34 amino acids; and/or
   b) comprises a replacement of the serine residue targeted for phosphorylation with a residue that cannot be phosphorylated; and/or
   c) comprises a replacement of the argenine residues at positions 1266 and 1369 of the alignment of FIG. 11 with a residue that will not interact with the serine residue after phosphorylation to inactivate ACC.

122. The recombinant microorganism of any one of embodiments 118-121, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

123. The recombinant microorganism of any one of embodiments 118-121, wherein the recombinant microorganism is further engineered to comprise deletions of one or more of the endogenous acyl-CoA oxidases selected from the group consisting of: POX1, POX2, POX3, POX4, POX5, and POX6.

124. The recombinant microorganism of any one of embodiments 118-123, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

125. The recombinant microorganism of any one of embodiments 118-123, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

126. The recombinant microorganism of any one of embodiments 118-125, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

127. The recombinant microorganism of embodiment 126, wherein the fatty acyl desaturase is a Z11 desaturase.

128. The recombinant microorganism of any one of embodiments 118-126, wherein the recombinant microorganism is *Yarrowia lipolytica*.

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

REFERENCES

1. Zhang, H. et. al. Enhanced lipid accumulation in the yeast *Yarrowia lipolytica* by overexpression of ATP:citrate lyase from *Mus musculus*. J Biotechnol. 2014 Dec. 20; 192.
2. Halperin, M. L. et. al. Effects of Palmitoyl CoA on Citrate and Malate Transport by Rat Liver Mitochondria. Proc Natl Acad Sci USA. 1972 April; 69(4): 1003-1007.
3. Dulermo, T. et. al. Analysis of ATP-citrate lyase and malic enzyme mutants of *Yarrowia lipolytica* points out the importance of mannitol metabolism in fatty acid synthesis. Biochim Biophys Acta. 2015 September; 1851(9): 1107-17. doi: 10.1016/j.bbalip.2015.04.007. Epub 2015 May 8.
4. Morin, N. et. al. Transcriptomic analyses during the transition from biomass production to lipid accumulation in the oleaginous yeast *Yarrowia lipolytica*. PLoS One. 2011; 6(11):e27966. doi: 10.1371/journal.pone.0027966. Epub 2011 Nov. 22.
5. Kavšček, M., Bhutada, G., Madl, T. & Natter, K. Optimization of lipid production with a genome-scale model of *Yarrowia lipolytica*. BMC Syst. Biol. 9, 72 (2015).

| LISTING OF SEQUENCES | |
|---|---|
| SEQ ID | Description of Sequence |
| SEQ ID NO: 1 | Full IDH001 plasmid sequence |
| SEQ ID NO: 2 | IDH002 insert sequence |
| SEQ ID NO: 3 | IDH003 insert sequence |
| SEQ ID NO: 4 | IDH004 insert sequence |
| SEQ ID NO: 5 | IDH005 insert sequence |
| SEQ ID NO: 6 | IDH006 insert sequence |
| SEQ ID NO: 7 | IDH007 plasmid sequence |
| SEQ ID NO: 8 | IDH008 insert sequence |
| SEQ ID NO: 9 | IDH009 insert sequence |
| SEQ ID NO: 10 | IDH010 insert sequence |
| SEQ ID NO: 11 | IDH011 insert sequence |
| SEQ ID NO: 12 | IDH012 insert sequence |
| SEQ ID NO: 13 | IDH013 insert sequence |
| SEQ ID NO: 14 | IDH014 insert sequence |
| SEQ ID NO: 15 | IDH015 insert sequence |
| SEQ ID NO: 16 | IDH016 insert sequence |
| SEQ ID NO: 17 | IDH017 insert sequence |
| SEQ ID NO: 18 | IDH018 insert sequence |
| SEQ ID NO: 19 | IDH019 insert sequence |
| SEQ ID NO: 20 | *Y. lipolytica* IDH1 D279A, I280A amino acid sequence |
| SEQ ID NO: 21 | *E. coli* IDH amino acid sequence WP_000444484.1 |
| SEQ ID NO: 22 | *A. thiooxidans* IDH amino acid sequence PDB: 2D4V_A |
| SEQ ID NO: 23 | *M. smegmatis* IDH amino acid sequence WP_011727802.1 |
| SEQ ID NO: 24 | *L. starkeyi* malic enzyme amino acid sequence (mitochondrial, NAD+, unmodified) |
| SEQ ID NO: 25 | *R. toruloides* malic enzyme amino acid sequence (mitochondrial, NAD+, mitochondrial targeting sequence truncated) |
| SEQ ID NO: 26 | *H. sapiens* malic enzyme amino acid sequence (mitochondrial, NAD+, mitochondrial targeting sequence truncated) |
| SEQ ID NO: 27 | *R. norvegicus* malic enzyme amino acid sequence (cytoplasm, NADP+, unmodified) |
| SEQ ID NO: 28 | *M. musculus* malic enzyme amino acid sequence (cytoplasm, NADP+, unmodified) |
| SEQ ID NO: 29 | *E. coli* malic enzyme amino acid sequence (NAD+, unmodified) P26616 |
| SEQ ID NO: 30 | IDH from *Y. lipolytica* XP_503571.2 |
| SEQ ID NO: 31 | mpc3 Pyruvate Transporter from *Saccharomyces cerevisiae* NP_011759.1 |

LISTING OF SEQUENCES

| SEQ ID | Description of Sequence |
|---|---|
| SEQ ID NO: 32 | *Helicoverpa zea* Z11 desaturase |
| SEQ ID NO: 33 | *Helicoverpa zea* Z11 desaturase |
| SEQ ID NO: 34 | Malic Enzyme from *Arabidopsis* Q9SIU0 |
| SEQ ID NO: 35 | Malic Enzyme from *Amaranthus hypochondriacus* P37224 |
| SEQ ID NO: 36 | Malic Enzyme from *Rhizobium meliloti* O30807 |
| SEQ ID NO: 37 | Malic Enzyme from *Solanum tuberosum* P37221 |
| SEQ ID NO: 38 | Malic Enzyme from *Homo sapiens* Q16798 |
| SEQ ID NO: 39 | ZWF1 from *Y. Lipolytica* YALI0E22649g |
| SEQ ID NO: 40 | ZWF1 from *Y. Lipolytica* YALI0E22649g protein |
| SEQ ID NO: 41 | GND1 from *Y. Lipolytica* YALI0B15598g |
| SEQ ID NO: 42 | GND1 from *Y. Lipolytica* YALI0B15598g protein |
| SEQ ID NO: 43 | SOL3 from *Y. Lipolytica* YALI0_E11671g |
| SEQ ID NO: 44 | SOL3 from *Y. Lipolytica* YALI0_E11671g |
| SEQ ID NO: 45 | KFX48982.1 Mitochondrial pyruvate carrier 3 [*Talaromyces marneffei* PM1] |
| SEQ ID NO: 46 | OEJ86292.1 Mitochondrial pyruvate carrier 3 [*Hanseniaspora osmophila*] |
| SEQ ID NO: 47 | NP_721100.1 isocitrate dehydrogenase [*Streptococcus mutans* UA159] |
| SEQ ID NO: 48 | WP_003229433.1 MULTISPECIES: NADP-dependent isocitrate dehydrogenase [*Bacillales*] AMP-insensitive |
| SEQ ID NO: 49 | *Bacillus subtilis* IDH S104A mutant, AMP-insensitive |
| SEQ ID NO: 50 | sp|P11497|ACACA_RAT Acetyl-CoA carboxylase 1 OS=*Rattus norvegicus* OX=10116 GN=Acaca PE=1 SV=1 |
| SEQ ID NO: 51 | sp|Q5SWU9|ACACA_MOUSE Acetyl-CoA carboxylase 1 OS=Mus musculus OX=10090 GN=Acaca PE=1 SV=1 |
| SEQ ID NO: 52 | sp|Q00955|ACAC_YEAST Acetyl-CoA carboxylase OS=*Saccharomyces cerevisiae* (strain ATCC 204508 / 5288c) OX=559292 GN=ACC1 PE=1 SV=2 |
| SEQ ID NO: 53 | sp|Q13085-3|ACACA_HUMAN Isoform 3 of Acetyl-CoA carboxylase 1 OS=*Homo sapiens* OX=9606 GN=ACACA |
| SEQ ID NO: 54 | sp|Q13085|ACACA_HUMAN Acetyl-CoA carboxylase 1 OS=*Homo sapiens* OX=9606 GN=ACACA PE=1 SV=2 |
| SEQ ID NO: 55 | tr|A0A0H3VB41|A0A0H3VB41_LIPST Acetyl-CoA carboxylase OS=*Lipomyces starkeyi* OX=29829 GN=ACC1 PE=4 SV=1 |
| SEQ ID NO: 56 | tr|F2QLC7|F2QLC7_KOMPC Acetyl-CoA carboxylase OS=*Komagataella phaffii* (strain ATCC 76273 / CBS 7435 / CECT 11047 / NRRL Y-11430 / Wegner 21-1) OX=981350 GN=ACC1 PE=4 SV=1 |
| SEQ ID NO: 57 | tr|Q6CC91|Q6CC91_YARLI YALI0C11407p OS=*Yarrowia lipolytica* (strain CUB 122 / E 150) OX=284591 GN=YALI0_C11407g PE=4 SV=1 |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A method for increasing the selectivity of methyl palmitate conversion to a Z11-16 non-native unsaturated fatty acid over conversion to other lipid variants in a recombinant *Yarrowia lipolytica* microorganism, said method comprising the steps of:
   a) oxidizing cytosolic malate to pyruvate in the recombinant *Yarrowia lipolytica* microorganism; wherein the oxidizing step is carried out by a heterologous decarboxylating malic enzyme from an organism selected from the group consisting of *Escherichia coli, Hominidae sapiens, Lypomyces starkeyi, Mus musculus, Rattus novegicus,* and *Rhodosporidium toruloides*; and
   b) culturing said recombinant *Yarrowia lipolytica* microorganism in medium comprising a simple carbon substrate and methyl palmitate;
   wherein the recombinant *Yarrowia lipolytica* microorganism exhibits increased selectivity in the conversion of methyl palmitate to the Z11-16 non-native unsaturated fatty acid compared to a control *Yarrowia lipolytica* microorganism in which the oxidizing step of (a) is not carried out.

2. The method of claim 1, wherein the Z11-16 non-native unsaturated fatty acid selectivity is greater than about 50% by molarity compared to other lipid variants converted from the methyl palmitate.

3. The method of claim 1, wherein the heterologous decarboxylating malic enzyme comprises a sequence selected from the group consisting of SEQ ID NOs: 24, 25, 26, 27, 28, and 29.

4. The method of claim 1, wherein the heterologous decarboxylating malic enzyme is an NAD+ dependent or NADP+ dependent decarboxylating malic enzyme.

5. The method of claim 1, wherein the recombinant *Yarrowia lipolytica* microorganism has been engineered to reduce or eliminate the expression or activity of one or more endogenous acyl-CoA oxidases selected from the group consisting of: POX1, POX2, POX3, POX4, POX5, and POX6.

6. The method of claim 1, wherein the recombinant *Yarrowia lipolytica* microorganism has been engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

7. The method of claim 1, wherein the recombinant *Yarrowia lipolytica* microorganism comprises a heterologous fatty acyl desaturase that catalyzes the conversion of a saturated C6-C24 fatty acyl-CoA to a corresponding mono- or poly-unsaturated C6-C24 fatty acyl-CoA.

8. The method of claim 7, wherein the fatty acyl desaturase is a Z11 desaturase.

9. The method of claim 1, wherein the simple carbon substrate comprises glycerol and/or glucose.

* * * * *

SEQUENCE LISTING

```
<160> NUMBER OF SEQ ID NOS: 57

<210> SEQ ID NO 1
<211> LENGTH: 5860
<212> TYPE: DNA
<213> ORGANISM: Artificial Sequence
<220> FEATURE:
<223> OTHER INFORMATION: Full IDH001 plasmid sequence

<400> SEQUENCE: 1
tcgcgcgttt cggtgatgac ggtgaaaacc tctgacacat gcagctcccg gagcccagag      60
agccattgac gttctttcta atttggaccg atagccgtat agtccagtct atctataagt     120
tcaactaact cgtaactatt accataacat atacttcact gccccagata aggttccgat     180
aaaaagttct gcagactaaa tttatttcag tctcctcttc accaccaaaa tgccctccta     240
```

-continued

```
cgaagctcga gctaacgtcc acaagtccgc ctttgccgct cgagtgctca agctcgtggc    300
agccaagaaa accaacctgt gtgcttctct ggatgttacc accaccaagg agctcattga    360
gcttgccgat aaggtcggac cttatgtgtg catgatcaag acccatatcg acatcattga    420
cgacttcacc tacgccggca ctgtgctccc cctcaaggaa cttgctctta agcacggttt    480
cttcctgttc gaggacagaa agttcgcaga tattggcaac actgtcaagc accagtacaa    540
gaacggtgtc taccgaatcg ccgagtggtc cgatatcacc aacgcccacg gtgtacccgg    600
aaccggaatc attgctggcc tgcgagctgg tgccgaggaa actgtctctg aacagaagaa    660
ggaggacgtc tctgactacg agaactccca gtacaaggag ttcctggtcc cctctcccaa    720
cgagaagctg gccagaggtc tgctcatgct ggccgagctg tcttgcaagg gctctctggc    780
cactggcgag tactccaagc agaccattga gcttgcccga tccgaccccg agtttgtggt    840
tggcttcatt gcccagaacc gacctaaggg cgactctgag gactggctta ttctgacccc    900
cggggtgggt cttgacgaca agggagacgc tctcggacag cagtaccgaa ctgttgagga    960
tgtcatgtct accggaacgg atatcataat tgtcggccga ggtctgtacg ccagaaccg    1020 agatcctatt gaggaggcca agcgatacca gaaggctggc tgggaggctt accagaagat    1080
taactgttag aggttagact atggatatgt aatttaactg tgtatataga gagcgtgcaa    1140
gtatggagcg cttgttcagc ttgtatgatg gtcagacgac ctgtctgatc gagtatgtat    1200
gatactgcac aacctgtgta tccgcatatc ttccaatggg gcatgttgtt gtgttcataa    1260
cttcgtatag catacattat acgaagttat ggccagacgg ccagacaggc caaacctgca    1320
gggtaataat gtgccatgct gtataacaat cgccttccg cagctgtatc tatgggtatg    1380
attaactctg atgatccgga gataaactaa tcttaaccac tgtacgatac atatactgta    1440
agatggcacc ctgtggttta acccttgtag caatgtgttt aagcaaggga atattgtgat    1500
agagaagtgt atttgaagta tgtggctggt acggtacttg tacgagtgtg tttgtgtatt    1560
ctaaagatgg acattccaca tattcgctgg tcaaggtgtt ttgtttgagg attcagtgag    1620
gcatatttct tcactgggtg tgatggagtt gggtaaggtt ataggttttt accagaactt    1680
gtacttgtag aaatactgaa caactatatc accgtgataa agagtgcata agaaggtgcg    1740
ttgaacatga tgtttcggcg cgcaaaatcg agaatttcaa gttttttggt cggtacttgc    1800
gataagatga gtccaactaa aatgttagat tttcaatacc gctcaaattg cgtgtttatg    1860
agacttcttg aagccgtgat tctcccagct ctccgaact ctacaaggtt cataccgaga    1920
tttggtgatg agtggcaata ggagtgcagc ggttcattga gggcgaaata tcagaagaat    1980
gagaagatgt agttatttca acagtgcaca atgatattat atgctcacgg gactctgaaa    2040
agcctttgaa cgccatattt cagcccaatc acgtttaaac ctcgccgtcc ttaatttcgt    2100
aaaagctttt tttgcatcct cccacataaa actctctctc tctctcttct ttaactagga    2160
cacctttggg caacatcttg tcgtctaatc gaaaacatat ccacatccac aatgcttcga    2220
accgcctacc tggctaaggt gagtactccg ggcgagtcaa tggaggtgac tcaaggtgca    2280
atggaagcac cgctccatgg cacagcgatg cgcgctacat gaccgacgac atctgtgtac    2340
aacccataac atttttctcgg aaacaacaac agcatcacag acagagactc ggggcagggg    2400
aagacgccat tgagaccaat ggctagtgta tgtcgcaact ccggcgccga ttgctccaca    2460
gtctcctact ttggtcctgt ccacgtcacc accaccccg gaacatctat gcgtgtattt    2520
attttccctc cactatttt tttcctgcat gtgctacgga gaaaaatagt agcgggcagt    2580
agcacactgt gtggggacag gggaatggag aacaattgag gcgatgcgga tacgaagaca    2640
```

```
cctgtttacg ttgttgtcgc acgccgctgc tgttgctggt gtgttttgtg ttaattgccg    2700
cacaccacaa taactatcat cgacaccaaa acattaggat aacatactaa cccaggccgc    2760
ctcggctctc cccaagcgaa ccctcgctac caacgctcga accatgttcc agcccaagga    2820
gtacggatcc aagtacaccg tcaccctcat ccccggtgat ggtatcggta acgagattac    2880
tgacgctgtc aagaccatct tcaagactat ctccgtcccc attgactggg aggttgtcaa    2940
tgtcaccggt gttggcgaga accatctcga cggctacgag gaggccattc gatccatcaa    3000
ccgaaacaag gttgccatca agggtatcct ccacaccccc gttgagaagc acggtcacac    3060
ttctttcaac gttgccctgc gacgagagct cgacatttttt gcttctctcg ttctcatcaa    3120
gaacatcccc ggtgtccaga cccgactcga cggcattgac atggctctga tccgagagaa    3180
cactgagggt gagtactccg gtctggagca ctcccctgtc cccggtgttg ttgagtccat    3240
caaggtcatc accaagcgaa agtccgagcg aattgcccga tttgcctttg actttgctct    3300
caagaacaac cgacacaagg tcactgccat ccacaaggcc aacattatga agcttgccga    3360
tggtctgttc cgaaacacct gtaaggaggt ctccgccgag taccccgaga tccagtacgg    3420
cgacatgatt gtcgacaacg cctccatgca ggccgtctct tggccccagc agtttgacgt    3480
tctcgtcacc cctaaccttt acggaaccat tctgtctaac attggtgccg gtcttgttgg    3540
aggccccggt ctcgtccctg tgtcaacct gggtaccgag cacgccgttt cgagcccgg    3600 ttgccgacac gtcggtcttg ccgctaaggg ccgaggtacc gctaaccccca ccgccatgat    3660 tctgtcttcc gccatgcttc tgcgacacct caacctcgat gacttcgctg acgtcatctc    3720
caaggctacc tacgacgttc ttgctgaggg ccaggtccga acccccgatc ttggcggcaa    3780
ctccactact gacgagttca ccatggctgt tatcaacaag ctccagtaag cggccgctta    3840
tgtatgattt agatgatatt atgacattga acgaattatt gatgagtagt gggtgtgatg    3900
gatttagtgt ggatgtacac ggttcttggc catataggcc aggccataac ttcgtatagc    3960
atacattata cgaagttata catgtgagca aaaggccagc aaaaggccag gaaccgtaaa    4020
aaggccgcgt tgctggcgtt tttccatagg ctccgccccc ctgacgagca tcacaaaaat    4080
cgacgctcaa gtcagaggtg gcgaaacccg acaggactat aaagatacca ggcgtttccc    4140
cctggaagct ccctcgtgcg ctctcctgtt ccgaccctgc cgcttaccgg atacctgtcc    4200
gcctttctcc cttcgggaag cgtggcgctt tctcatagct cacgctgtag gtatctcagt    4260
tcggtgtagg tcgttcgctc caagctgggc tgtgtgcacg aaccccccgt tcagcccgac    4320
cgctgcgcct tatccggtaa ctatcgtctt gagtccaacc cggtaagaca cgacttatcg    4380
ccactggcag cagccactgg taacaggatt agcagagcga ggtatgtagg cggtgctaca    4440
gagttcttga agtggtggcc taactacggc tacactagaa gaacagtatt tggtatctgc    4500
gctctgctga agccagttac cttcggaaaa agagttggta gctcttgatc cggcaaacaa    4560
accaccgctg gtagcggtgg tttttttgtt tgcaagcagc agattacgcg cagaaaaaaa    4620
ggatctcaag aagatccttt gatcttttct acggggtctg acgctcagtg aacgaaaac    4680 tcacgttaag ggattttggt catgagatta tcaaaaagga tcttcaccta gatcctttta    4740
aattaaaaat gaagttttaa atcaatctaa agtatatatg agtaaacttg gtctgacagt    4800
taccaatgct taatcagtga ggcacctatc tcagcgatct gtctatttcg ttcatccata    4860
gttgcctgac tccccgtcgt gtagataact acgatacggg agggcttacc atctggcccc    4920
agtgctgcaa tgataccgcg agacccacgc tcaccggctc cagatttatc agcaataaac    4980
```

|  |  |  |  |  |
|---|---|---|---|---|
| cagccagccg | gaagggccga | gcgcagaagt | ggtcctgcaa | ctttatccgc | ctccatccag | 5040 |
| tctattaatt | gttgccggga | agctagagta | agtagttcgc | cagttaatag | tttgcgcaac | 5100 |
| gttgttgcca | ttgctacagg | catcgtggtg | tcacgctcgt | cgtttggtat | ggcttcattc | 5160 |
| agctccggtt | cccaacgatc | aaggcgagtt | acatgatccc | ccatgttgtg | caaaaaagcg | 5220 |
| gttagctcct | tcggtcctcc | gatcgttgtc | agaagtaagt | tggccgcagt | gttatcactc | 5280 |
| atggttatgg | cagcactgca | taattctctt | actgtcatgc | catccgtaag | atgcttttct | 5340 |
| gtgactggtg | agtactcaac | caagtcattc | tgagaatagt | gtatgcggcg | accgagttgc | 5400 |
| tcttgcccgg | cgtcaatacg | ggataatacc | gcgccacata | gcagaacttt | aaaagtgctc | 5460 |
| atcattggaa | aacgttcttc | ggggcgaaaa | ctctcaagga | tcttaccgct | gttgagatcc | 5520 |
| agttcgatgt | aacccactcg | tgcacccaac | tgatcttcag | catcttttac | tttcaccagc | 5580 |
| gtttctgggt | gagcaaaaac | aggaaggcaa | aatgccgcaa | aaaagggaat | aagggcgaca | 5640 |
| cggaaatgtt | gaatactcat | actcttcctt | tttcaatatt | attgaagcat | ttatcagggt | 5700 |
| tattgtctca | tgagcggata | catatttgaa | tgtatttaga | aaaataaaca | aatagggggtt | 5760 |
| ccgcgcacat | ttccccgaaa | agtgccacct | gacgtctaag | aaaccattat | tatcatgaca | 5820 |
| ttaacctata | aaaataggcg | tatcacgagg | ccctttcgtc |  | 5860 |

<210> SEQ ID NO 2
<211> LENGTH: 1228
<212> TYPE: DNA
<213> ORGANISM: Artificial Sequence
<220> FEATURE:
<223> OTHER INFORMATION: IDH002 insert sequence

<400> SEQUENCE: 2

|  |  |  |  |  |  |
|---|---|---|---|---|---|
| caattgaggc | gatgcggata | cgaagacacc | tgtttacgtt | gttgtcgcac | gccgctgctg | 60 |
| ttgctggtgt | gttttgtgtt | aattgccgca | caccacaata | actatcatcg | acaccaaaac | 120 |
| attaggataa | catactaacc | caggccgcct | cggctctccc | caagcgaacc | ctcatggcca | 180 |
| ccaacgccag | gacaatgttt | cagcccaagg | agtacggcag | caagtatacc | gtgacactga | 240 |
| tccctggcga | cggcatcggc | aatgagatca | ccgatgccgt | gaagaccatc | ttcaagacaa | 300 |
| tcagcgtgcc | catcgactgg | gaggtggtga | acgtgacagg | cgtgggcgag | aatcacctgg | 360 |
| atggctacga | ggaggccatc | cggtccatca | acagaaataa | ggtggccatc | aagggcatcc | 420 |
| tgcacacccc | tgtggagaag | cacggccaca | catcttttaa | cgtggccctg | cggagagagc | 480 |
| tggacatctt | cgccagcctg | gtgctgatca | agaatatccc | aggcgtgcag | acccggctgg | 540 |
| acggaatcga | tatggccctg | atcagagaga | acacagaggg | cgagtattct | ggcctggagc | 600 |
| acagccccgt | gcctggcgtg | gtggagagca | tcaaagtgat | caccaagagg | aagtccgaga | 660 |
| ggatcgcccg | cttcgccttt | gacttcgccc | tgaagaacaa | tcgccacaag | gtgaccgcca | 720 |
| tccacaaggc | caacatcatg | aagctggccg | atggcctgtt | tcggaataca | tgcaaggagg | 780 |
| tgtctgccga | gtaccccgag | atccagtatg | gcgacatgat | cgtggataac | gcctccatgc | 840 |
| aggccgtgtc | ttggcctcag | cagttcgatg | tgctggtgac | cccaaacctg | tacggcacaa | 900 |
| tcctgtccaa | tatcggagca | ggactggtgg | gaggcccagg | cctggtgccc | ggcgtgaatc | 960 |
| tgggcaccga | gcacgccgtg | tttgagccag | gctgtaggca | cgtgggactg | gcagcaaagg | 1020 |
| gaagggggcac | cgccaacccc | acagccatga | tcctgagcag | cgccatgctg | ctgcggcacc | 1080 |
| tgaatctgga | cgatttttgcc | gacgtgatct | ccaaggccac | ctatgatgtg | ctggccgagg | 1140 |
| gccaggtgag | aacacctgac | ctgggcggca | actctaccac | agatgagttc | acaatggccg | 1200 | tgatcaacaa gctgcagtga gcggccgc                                              1228

<210> SEQ ID NO 3
<211> LENGTH: 1432
<212> TYPE: DNA
<213> ORGANISM: Artificial Sequence
<220> FEATURE:
<223> OTHER INFORMATION: IDH003 insert sequence

<400> SEQUENCE: 3

| | | |
|---|---|---|
| caattgaggc gatgcggata cgaagacacc tgtttacgtt gttgtcgcac gccgctgctg | 60 |
| ttgctggtgt gttttgtgtt aattgccgca caccacaata actatcatcg acaccaaaac | 120 |
| attaggataa catactaacc caggccgcct cggctctccc caagcgaacc ctcatggaga | 180 |
| gcaaggtggt ggtgccagcc cagggcaaga agatcaccct gcagaacggc aagctgaatg | 240 |
| tgccagagaa ccccatcatc ccttacatcg agggcgacgg catcggcgtg gatgtgacac | 300 |
| cagcaatgct gaaggtggtg gacgcagcag tggagaaggc ctataagggc gagaggaaga | 360 |
| tctcttggat ggagatctac accggcgaga agagcacaca ggtgtatgga caggacgtgt | 420 |
| ggctgcctgc agagaccctg gatctgatcc gggagtacag agtggccatc aagggaccac | 480 |
| tgaccacacc agtgggagga ggcatcaggt ctctgaatgt ggccctgcgc caggagctgg | 540 |
| atctgtatat ctgcctgagg cctgtgcgct actatcaggg caccccagcc ctgtgaagc | 600 |
| acccagagct gacagacatg gtcatcttcc gggagaactc cgaggacatc tacgccggca | 660 |
| tcgagtggaa ggccgactct gccgatgccg agaaagtgat caagttcctg cgggaggaga | 720 |
| tgggcgtgaa gaagatcaga tttcccgagc actgcggcat cggcatcaag ccttgtagcg | 780 |
| aggagggcac caagcggctg gtgagagcag ccatcgagta cgccatcgcc aatgacaggg | 840 |
| attccgtgac cctggtgcac aagggcaaca tcatgaagtt cacagagggc gcctttaagg | 900 |
| actgggggcta tcagctggcc cgcgaggagt tcggaggaga gctgatcgat ggaggacctt | 960 |
| ggctgaaggt gaagaaccca atacaggca aggagatcgt gatcaaggac gtgatcgccg | 1020 |
| atgccttct gcagcagatc ctgctgagc cagcagagta cgacgtgatc gcatgcatga | 1080 |
| acctgaatgg cgactatatc tccgatgcac tggcagcaca agtgggagga atcggaatcg | 1140 |
| cccctggcgc caatatcggc gacgagtgtg ccctgtttga ggccacccac ggcacagcac | 1200 |
| caaagtacgc aggacaggat aaggtgaacc ccggcagcat catcctgtcc gccgagatga | 1260 |
| tgctgaggca catgggatgg accgaggcag cagacctgat cgtgaagggc atggagggcg | 1320 |
| ccatcaatgc caagaccgtg acctacgact cgagagact gatggatggc gccaagctgc | 1380 |
| tgaagtgttc tgagtttggc gatgccatca tcgagaacat gtgagcggcc gc | 1432 |

<210> SEQ ID NO 4
<211> LENGTH: 1471
<212> TYPE: DNA
<213> ORGANISM: Artificial Sequence
<220> FEATURE:
<223> OTHER INFORMATION: IDH004 insert sequence

<400> SEQUENCE: 4

| | | |
|---|---|---|
| caattgaggc gatgcggata cgaagacacc tgtttacgtt gttgtcgcac gccgctgctg | 60 |
| ttgctggtgt gttttgtgtt aattgccgca caccacaata actatcatcg acaccaaaac | 120 |
| attaggataa catactaacc caggccgcct cggctctccc caagcgaacc ctcatgacca | 180 |
| cacacatcca gaagccagca accggctccc ctctgacact gctgaacggc gtgctgcagg | 240 |

| | |
|---|---|
| tgccagacca gcccatcatc cctttcatcg agggcgacgg aatcggatgc gatgtgaccc | 300 |
| ctgccatgcg ctctgtggtg gatgcagcag tggcaaaggt gtacggagga cagaggcaga | 360 |
| tcgcatggat ggagctgttt gcaggacaga aggcagtgca gctgtacgga gagggccagt | 420 |
| atctgccaga cgacaatg gccgccatcc gggagtataa ggtggccatc aagggaccac | 480 |
| tggagacacc agtgggagga ggcatccgca gcctgaacgt ggccatgcgg caggacctgg | 540 |
| atctgtacgt gtgcctgcgg cccgtgagat atttcgaggg caccccctcc cctatgagac | 600 |
| accctgagaa ggtggacatg gtcatcttcc gggagaacag cgaggacatc tacgcaggaa | 660 |
| tcgagtggcc tgcaggcagc ccagaggccg agaagatcat caggttcctg cgcgaggaga | 720 |
| tgggcgtgac aaagatcaga tttccagaca gctccgccat cggcatcaag cccgtgagca | 780 |
| ccgagggctc cgagaggctg atccggagaa caatccagta cgccctggag cacggcaagc | 840 |
| catccgtgtc tctggtgcac aagggcaaca tcatgaagtt caccgagggc ggctttcgcg | 900 |
| attggggata tgcactggca gagagggagt cgcaggaag agtgtttaca tggaggcaga | 960 |
| aggccgccat cagcaaggca gagggcaagg cagcaggaca gaaggcagag cagcaggcca | 1020 |
| tcgccgacgg caagctgatc atcaaggacg tgatcgccga taatttcctg cagcagatcc | 1080 |
| tgctgcggcc agaggattac tccgtggtgg ccacccctgaa cctgaatggc gactacgtga | 1140 |
| gcgatgcact ggcagcagaa gtgggaggaa tcggaatggc ccctggcgcc aacctgtctg | 1200 |
| acacacacgc catctttgag gccacccacg gcacagcacc tgacatcgca ggacagggca | 1260 |
| aggcaaatcc atctagcctg atcctgagcg ccgtgatgat gctggagcac ctgggatggg | 1320 |
| gagaggcagc acaggccatc gtggcagcaa tgaatgcaac catcgccgca ggagaggtga | 1380 |
| caggcgacct ggccgccctg agaggcgatg tgcctgccct gtccaccaca gagttcaccg | 1440 |
| ccgcccctgat caggcgcttt tgagcggccg c | 1471 |

<210> SEQ ID NO 5
<211> LENGTH: 2413
<212> TYPE: DNA
<213> ORGANISM: Artificial Sequence
<220> FEATURE:
<223> OTHER INFORMATION: IDH005 insert sequence

<400> SEQUENCE: 5

| | |
|---|---|
| caattgaggc gatgcggata cgaagacacc tgtttacgtt gttgtcgcac gccgctgctg | 60 |
| ttgctggtgt gttttgtgtt aattgccgca caccacaata actatcatcg acaccaaaac | 120 |
| attaggataa catactaacc caggccgcct cggctctccc caagcgaacc ctcatgagcg | 180 |
| cccagcagcc caccatcatc tataccctga cagatgaggc cccactgctg gccacatacg | 240 |
| ccttcctgcc cgtggtgagg aagtttgccg aggccgccgg catcgatgtg aagaccagcg | 300 |
| acatctccgt ggccgccaga atcctggccg agttcggcga tcacctgacc gaggagcaga | 360 |
| gagtgcctga caacctggga gagctgggcg ccctgacaca ggacccatcc gccaacatca | 420 |
| tcaagctgcc taatatcagc gcctccgtgc acagctgct ggcagccatc aaggagctgc | 480 |
| agggcaaggg ctataacgtg ccagattacc ccgccaatcc taagaccgac gatgagaaga | 540 |
| agatcaagga cagatacgcc aagatcctgg gctctgccgt gaaccctgtg ctgcgcgagg | 600 |
| gcaatagcga tcggagagcc ccaaaggccg tgaaggagta tgcaaggaag cacccacaca | 660 |
| gcatgggcga gtggtctcag gccagcagaa cccacgtggc caccatgaag acaggcgact | 720 |
| tctaccacgg cgagaagtct atgaccctgg accgcgatag gcgcgtgaag atggtgctga | 780 |
| agacaaagag cggcgaggag atcgtgctga agcccgaggt gaagctggac gccggcgaca | 840 |

```
tcatcgacag catgtacatg tccaagaagg ccctgatcgc cttctatgag gagcagatcg      900
aggacgccta caagaccggc gtgatgtttt ccctgcacgt gaaggccaca atgatgaagg      960
tgtctcaccc tatcgtgttc ggccacgccg tgaaggtgtt ctacaaggat gcctttgcca     1020
agcacgagaa gctgtttgac gagctgggcg tgaacgtgaa caatggcctg agcgatctgt     1080
atgacaagat cgaggccctg ccagcatccc agagggagga gatcatcgag gatctgcaca     1140
agtgccacga gcacaggcca gagctggcta tggtggactc cgccaagggc atctctaatt     1200
tccactctcc tagcgatgtg atcgtggacg cctccatgcc agccatgatc aggctgggcg     1260
gcaagatgta tggcgccgat ggccgcacca aggacacaaa ggccgtgaac ccagagtcca     1320 cctttttctag gatgtaccag gagatgatca atttctgtaa gacccacggc cagtttgatc     1380
ccaccacaat gggcacagtg cctaacgtgg gcctgatggc ccagaaggcc gaggagtacg     1440
gctcccacga caagacattc gagatccccg aggatggcgt ggccgacatc gtggacatcg     1500
ataccggcga ggtgctgctg acacagaatg tggaggaggg cgacatctgg cggatgccaa     1560
tcgtgaagga tgcccccatc agagactggg tgaagctggc agtgaccagg gcccgcctgt     1620
ctggcatgcc cgtggtgttt tggctggaca cagagaggcc tcacgaggtg gagctgcgca     1680
agaaggtgaa ggagtatctg aaggaccacg ataccgaggg cctgaagatc cagatcatgc     1740
ctcaagtgtg ggccatgcgg tacacactgg agcgggtggt gagaggcaag gataccatcg     1800
ccgccacagg caacatcctg agagattatc tgaccgacct gttccccatc ctggagctgg     1860
gcacaagcgc caagatgctg tccatcgtgc ctctgatggc aggaggagga ctgtatgaga     1920
ccggagcagg aggcagcgcc ccaaagcacg tgcaccagct ggtggaggag aatcacctgc     1980
ggtgggatag cctgggagag tttctggccc tgggagcctc cctggaggac atgggcaaca     2040
agacaggcaa tgagaaggcc aaggtgctgg ccaaggccct ggataccgcc acaggcaagc     2100
tgctggagga gaacaagtcc ccttctcgga gaaccggcga gctggacaat agggctctc     2160 agttctacct gagcctgttt tgggcacagg ccctggcaga gcagacagag gacgcagagc     2220
tggcagagcg gttcaagcca ctggcaaagg ccctggcaga gcaggaggag gccatcgtgt     2280
ctgagctgaa cagcgtgcag ggcaagaccg tggacatcgg cggctactat taccccgacc     2340
ctgagaagac ctccgaagtg atgagaccct taagaccttt caacaccaca ctggagtccg     2400
tgtgagcggc cgc                                                        2413
```

<210> SEQ ID NO 6
<211> LENGTH: 901
<212> TYPE: DNA
<213> ORGANISM: Artificial Sequence
<220> FEATURE:
<223> OTHER INFORMATION: IDH006 insert sequence

<400> SEQUENCE: 6

```
caattgaggc gatgcggata cgaagacacc tgtttacgtt gttgtcgcac gccgctgctg       60
ttgctggtgt gttttgtgtt aattgccgca caccacaata actatcatcg acaccaaaac      120
attaggataa catactaacc caggccgcct cggctctccc caagcgaacc ctcatggtga      180
gcaagcagat cctgaagaac accggcctgc aggagatcat gagcttcaag gtgaacctgg      240
agggcgtggt gaacaaccac gtgttcacca tggagggctg cggcaagggc aacatcctgt      300
tcggcaacca gctggtgcag atccgcgtga ccaagggcgc ccccctgccc ttcgccttcg      360
acatcctgag cccccgcctt cagtacggca accgcacctt caccaagtac cccgaggaca      420
```

```
tcagcgactt cttcatccag agcttccccg ccggcttcgt gtacgagcgc accctgcgct    480
acgaggacgg cggcctggtg gagatccgca gcgacatcaa cctgatcgag agatgttcg     540 tgtaccgcgt ggagtacaag ggccgcaact cccccaacga cggccccgtg atgaagaaga    600
ccatcaccgg cctgcagccc agcttcgagg tggtgtacat gaacgacggc gtgctggtgg    660
gccaggtgat cctggtgtac cgcctgaaca gcggcaagtt ctacagctgc acatgcgca    720 ccctgatgaa gagcaagggc gtggtgaagg acttccccga gtaccacttc atccagcacc    780
gcctggagaa gacctacgtg gaggacggcg gcttcgtgga gcagcacgag accgccatcg    840
cccagctgac cagcctgggc aagcccctgg gcagcctgca cgagtgggtg taagcggccg    900
c                                                                    901
```

<210> SEQ ID NO 7
<211> LENGTH: 6774
<212> TYPE: DNA
<213> ORGANISM: Artificial Sequence
<220> FEATURE:
<223> OTHER INFORMATION: IDH007 plasmid sequence
<400> SEQUENCE: 7

```
tcgcgcgttt cggtgatgac ggtgaaaacc tctgacacat gcagctcccg gagcccagag     60
agccattgac gttctttcta atttggaccg atagccgtat agtccagtct atctataagt    120
tcaactaact cgtaactatt accataacat atacttcact gccccagata aggttccgat    180
aaaaagttct gcagactaaa tttatttcag tctcctcttc accaccaaaa tgccctccta    240
cgaagctcga gctaacgtcc acaagtccgc ctttgccgct cgagtgctca agctcgtggc    300
agccaagaaa accaacctgt gtgcttctct ggatgttacc accaccaagg agctcattga    360
gcttgccgat aagtcggac cttatgtgtg catgatcaag acccatatcg acatcattga    420
cgacttcacc tacgccggca ctgtgctccc cctcaaggaa cttgctctta agcacggttt    480
cttcctgttc gaggacagaa agttcgcaga tattggcaac actgtcaagc accagtacaa    540
gaacggtgtc taccgaatcg ccgagtggtc cgatatcacc aacgcccacg gtgtacccgg    600
aaccggaatc attgctggcc tgcgagctgg tgccgaggaa actgtctctg aacagaagaa    660
ggaggacgtc tctgactacg agaactccca gtacaaggag ttcctggtcc cctctcccaa    720
cgagaagctg gccagaggtc tgctcatgct ggccgagctg tcttgcaagg gctctctggc    780
cactggcgag tactccaagc agaccattga gcttgcccga tccgacccg agtttgtggt    840 tggcttcatt gcccagaacc gacctaaggg cgactctgag gactggctta ttctgaccccc    900 cggggtgggt cttgacgaca agggagacgc tctcggacag cagtaccgaa ctgttgagga   960
tgtcatgtct accggaacgg atatcataat tgtcggccga ggtctgtacg gccgaaccg    1020 agatcctatt gaggagcca agcgatacca gaaggctggc tgggaggctt accagaagat    1080
taactgttag aggttagact atggatatgt aatttaactg tgtatataga gagcgtgcaa    1140
gtatggagcg cttgttcagc ttgtatgatg gtcagacgac ctgtctgatc gagtatgtat    1200
gatactgcac aacctgtgta tccgcatatc ttccaatggg gcatgttgtt gtgttcataa    1260
cttcgtatag catacattat acgaagttat ggccagacag gccaaacctg cagggctgag    1320
cacgcgagta caccccctca agtacagtag ctatatattg gggtatgtac tgtacatact    1380
gtacagacat acagatagat agatacaagt acaaacccaa gtacaagtac cggtactcta    1440
cacgcctcgt actcgaatgc tcatcacgga gtggttaaac tcatgctcac taatcagagg    1500
ccgatctcga tgcccttca tacaccacca ataactcaat gagctaaaaa atgcggcatt    1560
```

```
ttttcatttc ttcaaattac ttgccacaag cacttacatt ttttctttcc ccgattctct    1620
gatgtgcaca tcgctactgt tttttcttat tggctcgtat ttcgatcagt cgatttatgg    1680
gttgcctaaa cgaagctaat acccgtaaca cactacaagg aactaacaca agattgttat    1740
aattatatat atactccagt agaaagccac gatatgataa gatagcgcag aagccactgg    1800
atgttaaagg tgctgccgta tacatgattc tctgcctcgc ttaagcggtc agtccagtat    1860
tacgtatgtg cagcacttcc gcgctgtagg gtaattaaca cacgaccatc gtcacctcgc    1920
tcataataat ggtttgtcca caagagcaat atatcgccta tacccaacaa gagaaaacgg    1980
ttcaacacgc acactaattg tattaacgcg ccccagacct gtcagtgttc cctagacacc    2040
acacaaaacc aaaccgccga cgaaaactac cgctcttatc atgaatatca taacttataa    2100
tatgtaaggt cagaatgagt tgttgtgtgc catacatttc tctgaccgaa ttaatggatg    2160
ccagactcac gtcgtccttc cacgggtaaa aacgtcatgc caaaaccatg cccttcattt    2220
cagttcctcc ttggtcaatc tccttagttg tacgacagat cgtttaaact cgccacctgt    2280
ccacgtctcg gaacacgccc ctacaaactt gtagggtttg tgcggctcgg gatctcgtgc    2340
tctagtctcg gtggcggatc aagtgcagat catcttatga agcggaggaa gtgggtgaga    2400
ataaaggatg taaatagttt catattgaga gatatttgat atttcaccgg gagaagttgt    2460
agaaataatt ctagtctaaa tttgagtata ttgatccatt gatagtcctc aaaacacact    2520
atcaatcatc caggtatgct gatgacttat cctcccgacg atcttagttt ctgttttca    2580 cgtttcaccc caacaacctt agacaccaac ggctgcatgt gtgacgctag gtgggtttgc    2640
aacgtgtgga gaaatgtggt acgattcagc gggtttatca ggcgattaat gctatcatat    2700
gtaggatggg tggcaaaagt atgtggcatt tcattcacat gtttgcacgt gacgtttcca    2760
gctctgtcgc gagctgcagg tacaacatta gcgtctgctg ttctgacgtc tgtcttatta    2820
attagtgggg tggtaaccac atgctacata ttggtctatt agtagcacga tcacgtgtct    2880
accgttgcca ccggtttcag tgtaatatat accctcttac aagtactcta caattgctct    2940
ctaacatctg tcgtatttct gttattattc tcggaaatgc aacggcatta ttatcaactc    3000 cccccagat tgcatacaga gccaagaagt gcatgatagg cgttggggga ggattgcgat    3060
ggggcggaga gcgtgataat aggcctgaca aaataaattt ctttgtctca tctactgtac    3120
ttcagaaaaa atagactgta tgcatgggct catcctcttg acgtgtcctt ctcaccacac    3180
gtcgcttcgc ttaattaaga gaccggggttg gcggcgcatt tgtgtcccaa aaaacagccc    3240
caattgcccc aaattgaccc aaattgaccc agtagcgggc caacccccgg cgagagcccc    3300
cttctcccca catatcaaac ctcccccggt tcccacactt gccgttaagg gcgtagggta    3360
ctgcagtctg gaatctacgc ttgttcagac tttgtactag tttcttttgtc tggccatccg    3420 ggtaacccat gccggacgca aaatagacta ctgaaaattt ttttgctttg tggttgggac    3480
tttagccaag ggtataaaag accaccgtcc ccgaattacc tttcctcttc ttttctctct    3540
ctccttgtca actcacaccc gaaatcgtta agcatttcct tctgagtata agaatcattc    3600
aaaatgcttc gaaccgccta cctggctaag gccgcctcgg ctctcccccaa gcgaaccctc    3660 gctaccaacg ctcgaaccat gttccagccc aaggagtacg gatccaagta caccgtcacc    3720
ctcatccccg gtgatggtat cggtaacgag attactgacg ctgtcaagac catcttcaag    3780
actatctccg tccccattga ctgggaggtt gtcaatgtca ccggtgttgg cgagaaccat    3840
ctcgacggct acgaggaggc cattcgatcc atcaaccgaa acaaggttgc catcaagggt    3900
```

| | |
|---|---|
| atcctccaca ccccgttga gaagcacggt cacacttctt tcaacgttgc cctgcgacga | 3960 |
| gagctcgaca tttttgcttc tctcgttctc atcaagaaca tccccggtgt ccagacccga | 4020 |
| ctcgacggca ttgacatggc tctgatccga gagaacactg agggtgagta ctccggtctg | 4080 |
| gagcactccc ctgtcccgg tgttgttgag tccatcaagg tcatcaccaa gcgaaagtcc | 4140 |
| gagcgaattg cccgatttgc cttttgacttt gctctcaaga acaaccgaca caaggtcact | 4200 |
| gccatccaca aggccaacat tatgaagctt gccgatggtc tgttccgaaa cacctgtaag | 4260 |
| gaggtctccg ccgagtaccc cgagatccag tacggcgaca tgattgtcga caacgcctcc | 4320 |
| atgcaggccg tctcttggcc ccagcagttt gacgttctcg tcaccctaa cctttacgga | 4380 |
| accattctgt ctaacattgg tgccggtctt gttggaggcc ccggtctcgt ccctggtgtc | 4440 |
| aacctgggta ccgagcacgc cgttttcgag cccggttgcc gacacgtcgg tcttgccgct | 4500 |
| aagggccgag gtaccgctaa ccccaccgcc atgattctgt cttccgccat gcttctgcga | 4560 |
| cacctcaacc tcgatgactt cgctgacgtc atctccaagg ctacctacga cgttcttgct | 4620 |
| gagggccagg tccgaacccc cgatcttggc ggcaactcca ctactgacga gttcaccatg | 4680 |
| gctgttatca acaagctcca gtaagcggcc gcaaattaac agatagtttg ccggtgataa | 4740 |
| ttctcttaac ctcccacact cctttgacat aacgatttat gtaacgaaac tgaaatttga | 4800 |
| ccagatattg ttgtaaatag aaaatctggc ttgtaggtgg caaatcccg tctttgttca | 4860 |
| taacttcgta tagcatacat tatacgaagt tatacatgtg agcaaaaggc cagcaaaagg | 4920 |
| ccaggaaccg taaaaaggcc gcgttgctgg cgttttccca taggctccgc cccctgacg | 4980 |
| agcatcacaa aaatcgacgc tcaagtcaga ggtggcgaaa cccgacagga ctataaagat | 5040 |
| accaggcgtt ccccctgga agctccctcg tgcgctctcc tgttccgacc ctgccgctta | 5100 |
| ccggatacct gtccgccttt ctcccttcgg aagcgtggc gctttctcat agctcacgct | 5160 |
| gtaggtatct cagttcggtg taggtcgttc gctccaagct gggctgtgtg cacgaacccc | 5220 |
| ccgttcagcc cgaccgctgc gccttatccg gtaactatcg tcttgagtcc aacccggtaa | 5280 |
| gacacgactt atcgccactg gcagcagcca ctggtaacag gattagcaga gcgaggtatg | 5340 |
| taggcggtgc tacagagttc ttgaagtggt ggcctaacta cggctacact agaagaacag | 5400 |
| tatttggtat ctgcgctctg ctgaagccag ttaccttcgg aaaaagagtt ggtagctctt | 5460 |
| gatccggcaa acaaaccacc gctggtagcg gtggtttttt tgtttgcaag cagcagatta | 5520 |
| cgcgcagaaa aaaggatct caagaagatc ctttgatctt ttctacgggg tctgacgctc | 5580 |
| agtggaacga aaactcacgt taagggattt tggtcatgag attatcaaaa aggatcttca | 5640 |
| cctagatcct tttaaattaa aaatgaagtt ttaaatcaat ctaaagtata tatgagtaaa | 5700 |
| cttggtctga cagttaccaa tgcttaatca gtgaggcacc tatctcagcg atctgtctat | 5760 |
| ttcgttcatc catagttgcc tgactccccg tcgtgtagat aactacgata cgggagggct | 5820 |
| taccatctgg ccccagtgct gcaatgatac cgcgagaccc acgctcaccg gctccagatt | 5880 |
| tatcagcaat aaaccagcca gccggaaggg ccgagcgcag aagtggtcct gcaactttat | 5940 |
| ccgcctccat ccagtctatt aattgttgcc gggaagctag agtaagtagt tcgccagtta | 6000 |
| atagtttgcg caacgttgtt gccattgcta caggcatcgt ggtgtcacgc tcgtcgtttg | 6060 |
| gtatggcttc attcagctcc ggttcccaac gatcaaggcg agttacatga tcccccatgt | 6120 |
| tgtgcaaaaa agcggttagc tccttcggtc ctccgatcgt tgtcagaagt aagttggccg | 6180 |
| cagtgttatc actcatggtt atggcagcac tgcataattc tcttactgtc atgccatccg | 6240 |
| taagatgctt ttctgtgact ggtgagtact caaccaagtc attctgagaa tagtgtatgc | 6300 |

```
ggcgaccgag ttgctcttgc ccggcgtcaa tacgggataa taccgcgcca catagcagaa    6360
ctttaaaagt gctcatcatt ggaaaacgtt cttcggggcg aaaactctca aggatcttac    6420
cgctgttgag atccagttcg atgtaaccca ctcgtgcacc caactgatct tcagcatctt    6480
ttactttcac cagcgtttct gggtgagcaa aaacaggaag gcaaaatgcc gcaaaaaagg    6540
gaataagggc gacacggaaa tgttgaatac tcatactctt ccttttcaa tattattgaa     6600 gcatttatca gggttattgt ctcatgagcg gatacatatt tgaatgtatt tagaaaaata    6660
aacaaatagg ggttccgcgc acatttcccc gaaaagtgcc acctgacgtc taagaaacca    6720
ttattatcat gacattaacc tataaaaata ggcgtatcac gaggcccttt cgtc          6774

<210> SEQ ID NO 8
<211> LENGTH: 1467
<212> TYPE: DNA
<213> ORGANISM: Artificial Sequence
<220> FEATURE:
<223> OTHER INFORMATION: IDH008 insert sequence

<400> SEQUENCE: 8
actagtttct tgtctggcc atccgggtaa cccatgccgg acgcaaaata gactactgaa       60
aatttttttg ctttgtggtt gggactttag ccaagggtat aaaagaccac cgtccccgaa     120 ttaccttttcc tcttcttttc tctctctcct tgtcaactca cacccgaaat cgttaagcat    180
ttccttctga gtataagaat cattcaaaat ggagagcaag gtggtggtgc cagcccaggg    240
caagaagatc accctgcaga acggcaagct gaatgtgcca gagaaccca tcatccctta     300 catcgagggc gacggcatcg cgtggatgt gacaccagca atgctgaagg tggtggacgc    360
agcagtggag aaggcctata agggcgagag gaagatctct tggatggaga tctacaccgg   420
cgagaagagc acacaggtgt atggacagga cgtgtggctg cctgcagaga ccctggatct    480
gatccgggag tacagagtgg ccatcaaggg accactgacc acaccagtgg gaggaggcat   540
caggtctctg aatgtggccc tgcgccagga gctggatctg tatatctgcc tgaggcctgt   600
gcgctactat cagggcaccc ccagccctgt gaagcaccca gagctgacag acatggtcat   660
cttccgggag aactccgagg acatctacgc cggcatcgag tggaaggccg actctgccga   720
tgccagaaaa gtgatcaagt tcctgcggga ggagatgggc gtgaagaaga tcagatttcc    780
cgagcactgc ggcatcggca tcaagccttg tagcgaggag ggcaccaagc ggctggtgag    840
agcagccatc gagtacgcca tcgccaatga cagggattcc gtgaccctgg tgcacaaggg    900
caacatcatg aagttcacag agggcgccctt taaggactgg ggctatcagc tggcccgcga    960
ggagttcgga ggagagctga tcgatggagg accttggctg aaggtgaaga acccaaatac   1020
aggcaaggag atcgtgatca aggacgtgat cgccgatgcc tttctgcagc agatcctgct   1080
gaggccagca gagtacgacg tgatcgcatg catgaacctg aatggcgact atatctccga   1140
tgcactggca gcacaagtgg gaggaatcgg aatcgcccct ggcgccaata tcggcgacga   1200
gtgtgccctg tttgaggcca cccacggcac agcaccaaag tacgcaggac aggataaggt   1260 gaacccccggc agcatcatcc tgtccgccga gatgatgctg aggcacatgg gatggaccga   1320
ggcagcagac ctgatcgtga agggcatgga gggcgccatc aatgccaaga ccgtgaccta   1380
cgacttcgag agactgatgg atggcgccaa gctgctgaag tgttctgagt ttggcgatgc   1440
catcatcgag aacatgtgag cggccgc                                        1467

<210> SEQ ID NO 9
```

<211> LENGTH: 1521
<212> TYPE: DNA
<213> ORGANISM: Artificial Sequence
<220> FEATURE:
<223> OTHER INFORMATION: IDH009 insert sequence

<400> SEQUENCE: 9

```
actagtttct tgtctggcc atccgggtaa cccatgccgg acgcaaaata gactactgaa      60
aattttttg ctttgtggtt gggactttag ccaagggtat aaaagaccac cgtccccgaa     120
ttacctttcc tcttcttttc tctctctcct tgtcaactca cacccgaaat cgttaagcat    180
ttccttctga gtataagaat cattcaaaat gctgaggacc gcatacctgg caaaggcagc    240
atctgccctg cctaagcgca cactggagag caaggtggtg gtgccagccc agggcaagaa    300
gatcaccctg cagaacggca agctgaatgt gccagagaac cccatcatcc cttacatcga    360
gggcgacggc atcggcgtgg atgtgacacc tgccatgctg aaggtggtgg acgccgccgt    420
ggagaaggcc tataagggcg agcggaagat ctcctggatg gagatctaca ccggcgagaa    480
gtctacacag gtgtatggac aggacgtgtg gctgccagca gagaccctgg atctgatccg    540
ggagtacaga gtggccatca agggaccact gaccacacca gtgggaggag catcaggtc     600
cctgaatgtg gccctgcgcc aggagctgga tctgtatatc tgcctgaggc ccgtgcgcta    660
ctatcagggc accccctctc ctgtgaagca ccctgagctg acagacatgg tcatcttccg    720
ggagaacagc gaggacatct acgcaggaat cgagtgaaag gcagactccg ccgatgccga    780
gaaagtgatc aagttcctgc gggaggagat gggcgtgaag aagatcagat tccccgagca    840
ctgcggcatc ggcatcaagc cttgttctga ggagggcacc aagcggctgg tgagagcagc    900
catcgagtac gccatcgcca tgaccgggga tagcgtgacc ctggtgcaca agggcaacat    960
catgaagttc acagagggcg cctttaagga ctggggctat cagctggcca gagaggagtt    1020
cggaggagag ctgatcgatg gaggaccttg gctgaaggtg aagaacccaa atacaggcaa    1080
ggagatcgtg atcaaggacg tgatcgccga tgccttttg cagcagatcc tgctgcggcc    1140
agccgagtac gacgtgatcg cctgcatgaa cctgaatggc gactatatca gcgatgcact    1200
ggcagcacaa gtgggaggaa tcggaatcgc ccctggcgcc aatatcggcg acgagtgtgc    1260
cctgtttgag gccacccacg gcacagcacc aaagtacgca ggacaggata aggtgaaccc    1320
cggcagcatc atcctgtccg ccgagatgat gctgaggcac atgggatgga ccgaggcagc    1380
agacctgatc gtgaagggca tggagggcgc catcaatgcc aagaccgtga cctacgactt    1440
cgagcgcctg atggatggcg ccaagctgct gaagtgttcc gagtttggcg atgccatcat    1500
cgagaacatg tgagcggccg c                                             1521
```

<210> SEQ ID NO 10
<211> LENGTH: 1506
<212> TYPE: DNA
<213> ORGANISM: Artificial Sequence
<220> FEATURE:
<223> OTHER INFORMATION: IDH010 insert sequence

<400> SEQUENCE: 10

```
actagtttct tgtctggcc atccgggtaa cccatgccgg acgcaaaata gactactgaa      60
aattttttg ctttgtggtt gggactttag ccaagggtat aaaagaccac cgtccccgaa     120
ttacctttcc tcttcttttc tctctctcct tgtcaactca cacccgaaat cgttaagcat    180
ttccttctga gtataagaat cattcaaaat gaccacacac atccgaaagc cagcaaccgg    240
ctcccctctg acactgctga acggcgtgct gcaggtgcca gaccagccca tcatcccttt    300
```

```
catcgagggc gacggaatcg gatgcgatgt gaccccctgcc atgcgctctg tggtggatgc    360
agcagtggca aaggtgtacg gaggacagag gcagatcgca tggatggagc tgtttgcagg    420
acagaaggca gtgcagctgt acggagaggg ccagtatctg ccagacgaga caatggccgc    480
catccgggag tataaggtgg ccatcaaggg accactggag acaccagtgg gaggaggcat    540
ccgcagcctg aacgtggcca tgcggcagga cctggatctg tacgtgtgcc tgcggcccgt    600
gagatatttc gagggcaccc cctcccctat gagacaccct gagaaggtgg acatggtcat    660
cttccgggag aacagcgagg acatctacgc aggaatcgag tggcctgcag gcagcccaga    720
ggccgagaag atcatcaggt tcctgcgcga ggagatgggc gtgacaaaga tcagatttcc    780
agacagctcc gccatcggca tcaagcccgt gagcaccgag ggctccgaga ggctgatccg    840
gagaacaatc cagtacgccc tggagcacgg caagccatcc gtgtctctgg tgcacaaggg    900
caacatcatg aagttcaccg agggcggctt tcgcgattgg ggatatgcac tggcagagag    960
ggagttcgca ggaagagtgt ttacatggag gcagaaggcc gccatcagca aggcagaggg   1020
caaggcagca ggacagaagg cagagcagca ggcaatcgca gacggcaagc tgatcatcaa   1080
ggacgtgatc gccgataatt tcctgcagca gatcctgctg cggccagagg attactccgt   1140
ggtggccacc ctgaacctga atggcgacta cgtgagcgat gcactggcag cagaagtggg   1200
aggaatcgga atggcccctg cgccaacct gtctgacaca cacgccatct ttgaggccac   1260
ccacggcaca gcacctgaca tcgcaggaca gggcaaggca aatccatcta gcctgatcct   1320
gagcgccgtg atgatgctgg agcacctggg atggggagag gcagcacagg ccatcgtggc   1380
agcaatgaat gcaaccatcg cagcaggaga ggtgacaggc gacctggccg ccctgagagg   1440
cgatgtgcct gccctgtcca ccacagagtt caccgccgcc ctgatcaggc gcttttgagc   1500
ggccgc                                                              1506
```

<210> SEQ ID NO 11
<211> LENGTH: 1560
<212> TYPE: DNA
<213> ORGANISM: Artificial Sequence
<220> FEATURE:
<223> OTHER INFORMATION: IDH011 insert sequence

<400> SEQUENCE: 11

```
actagtttct ttgtctggcc atccgggtaa cccatgccgg acgcaaaata gactactgaa     60
aatttttttg ctttgtggtt gggactttag ccaagggtat aaaagaccac cgtccccgaa    120
ttacctttcc tcttcttttc tctctctcct tgtcaactca cacccgaaat cgttaagcat    180
ttccttctga gtataagaat cattcaaaat gctgcgcacc gcatacctgg caaaggcagc    240
aagcgccctg cccaagcgga cactgaccac acacatccag aagccagcaa ccggctcccc    300
tctgacactg ctgaacggcg tgctgcaggt gccagaccag cccatcatcc ctttcatcga    360
gggcgacgga atcggatgcg atgtgacccc tgccatgaga agcgtggtgg atgcagcagt    420
ggcaaaggtg tacggaggac agaggcagat cgcctggatg gagctgtttg caggacagaa    480
ggcagtgcag ctgtacggag agggccagta tctgccagac gagacaatgg ccgccatccg    540
cgagtataag gtggccatca agggaccact ggagacacca gtgggaggag gcatccgctc    600
tctgaacgtg gccatgcggc aggacctgga tctgtacgtg tgcctgcggc ccgtgagata    660
tttcgagggc accccagcc ctatgagaca ccctgagaag gtggacatgg tcatcttccg    720
ggagaacagc gaggacatct acgcaggaat cgagtggcct gcaggcagcc cagaggccga    780
```

| | |
|---|---|
| gaagatcatc aggttcctgc gcgaggagat gggcgtgaca agatccgct ttccagacag | 840 |
| ctccgccatc ggcatcaagc ccgtgagcac cgagggctcc gagcggctga tccggagaac | 900 |
| aatccagtac gccctggagc acggcaagcc atccgtgtct ctggtgcaca agggcaacat | 960 |
| catgaagttc accgagggcg gctttagaga ttggggctat gcactggcag agagggagtt | 1020 |
| cgcaggaaga gtgtttacat ggaggcagaa ggccgccatc agcaaggcag agggcaaggc | 1080 |
| agcaggacag aaggcagagc agcaggcaat cgcagacggc aagctgatca tcaaggacgt | 1140 |
| gatcgccgat aatttcctgc agcagatcct gctgaggcca gaggattact ccgtggtggc | 1200 |
| caccctgaac ctgaatggcg actacgtgag cgatgcactg gcagcagaag tgggaggaat | 1260 |
| cggaatggcc cctggcgcaa acctgtccga cacacacgcc atctttgagg ccacccacgg | 1320 |
| cacagcacct gacatcgcag gacagggcaa ggcaaatcca tctagcctga tcctgtctgc | 1380 |
| cgtgatgatg ctggagcacc tgggatgggg agaggcagca caggccatcg tggcagcaat | 1440 |
| gaatgcaacc atcgcagcag agaggtgac aggcgacctg gccgccctga ggggcgatgt | 1500 |
| gcctgccctg tccaccacag agttcaccgc cgccctgatc aggcgctttt gagcggccgc | 1560 |

<210> SEQ ID NO 12
<211> LENGTH: 2448
<212> TYPE: DNA
<213> ORGANISM: Artificial Sequence
<220> FEATURE:
<223> OTHER INFORMATION: IDH012 insert sequence

<400> SEQUENCE: 12

| | |
|---|---|
| actagtttct tgtctggcc atccgggtaa cccatgccgg acgcaaaata gactactgaa | 60 |
| aatttttttg ctttgtggtt gggactttag ccaagggtat aaaagaccac cgtccccgaa | 120 |
| ttaccttttcc tcttcttttc tctctctcct tgtcaactca cacccgaaat cgttaagcat | 180 |
| ttccttctga gtataagaat cattcaaaat gagcgcccag cagcccacca tcatctatac | 240 |
| cctgacagat gaggccccac tgctggccac atacgccttc ctgcccgtgg tgaggaagtt | 300 |
| tgccgaggcc gccggcatcg atgtgaagac cagcgacatc tccgtggccg ccagaatcct | 360 |
| ggccgagttc ggcgatcacc tgaccgagga gcagagagtg cctgacaacc tgggagagct | 420 |
| gggcgccctg acacaggacc catccgccaa catcatcaag ctgcctaata tcagcgcctc | 480 |
| cgtgccacag ctgctggcag ccatcaagga gctgcagggc aagggctata acgtgccaga | 540 |
| ttaccccgcc aatcctaaga ccgacgatga aagaagatc aaggacagat acgccaagat | 600 |
| cctgggctct gccgtgaacc ctgtgctgcg cgagggcaat agcgatcgga gagccccaaa | 660 |
| ggccgtgaag gagtatgcaa ggaagcaccc acacagcatg ggcgagtggt ctcaggccag | 720 |
| cagaacccac gtggccacca tgaagacagg cgacttctac cacggcgaga agtctatgac | 780 |
| cctggaccgc gataggcgcg tgaagatggt gctgaagaca aagagcggcg aggagatcgt | 840 |
| gctgaagccc gaggtgaagc tggacgccgg cgacatcatc gacagcatgt acatgtccaa | 900 |
| gaaggccctg atcgccttct atgaggagca gatcgaggac gcctacaaga ccggcgtgat | 960 |
| gttttcccctg cacgtgaagg ccacaatgat gaaggtgtct caccctatcg tgttcggcca | 1020 |
| cgccgtgaag gtgttctaca aggatgcctt tgccaagcac gagaagctgt ttgacgagct | 1080 |
| gggcgtgaac gtgaacaatg gcctgagcga tctgtatgac aagatcgagg ccctgccagc | 1140 |
| atcccgagg gaggagatca tcgaggatct gcacaagtgc cacgagcaca ggccagagct | 1200 |
| ggctatggtg gactccgcca agggcatctc taatttccac tctcctagcg atgtgatcgt | 1260 |
| ggacgcctcc atgccagcca tgatcaggct gggcggcaag atgtatggcg ccgatggccg | 1320 |

```
caccaaggac acaaaggccg tgaacccaga gtccaccttt tctaggatgt accaggagat    1380
gatcaatttc tgtaagaccc acggccagtt tgatcccacc acaatgggca cagtgcctaa    1440
cgtgggcctg atggcccaga aggccgagga gtacggctcc cacgacaaga cattcgagat    1500 cccccgaggat ggcgtggccg acatcgtgga catcgatacc ggcgaggtgc tgctgacaca   1560
gaatgtggag gagggcgaca tctggcggat gccaatcgtg aaggatgccc ccatcagaga    1620
ctgggtgaag ctggcagtga ccagggcccg cctgtctggc atgcccgtgg tgttttggct    1680
ggacacagag aggcctcacg aggtggagct gcgcaagaag gtgaaggagt atctgaagga    1740
ccacgatacc gagggcctga agatccgat catgcctcaa gtgtgggcca tgcggtacac     1800
actggagcgg tggtgagag gcaaggatac catcgccgcc acaggcaaca tcctgagaga     1860
ttatctgacc gacctgttcc ccatcctgga gctgggcaca agcgccaaga tgctgtccat    1920
cgtgcctctg atggcaggag gaggactgta tgagaccgga gcaggaggca gcgccccaaa    1980
gcacgtgcac cagctggtgg aggagaatca cctgcggtgg atagcctgg gagagtttct    2040 ggccctggga gcctccctgg aggacatggg caacaagaca ggcaatgaga aggccaaggt    2100
gctggccaag gccctggata ccgccacagg caagctgctg gaggagaaca agtcccccttc   2160 tcggagaacc ggcgagctgg acaataggg ctctcagttc tacctgagcc tgttttgggc    2220
acaggccctg gcagagcaga cagaggacgc agagctggca gagcggttca agccactggc    2280
aaaggccctg gcagagcagg aggaggcaat cgtgtctgag ctgaacagcg tgcagggcaa    2340
gaccgtggac atcggcggct actattaccc cgaccctgag aagacctccg aagtgatgag    2400
accctctaag accttcaaca ccacactgga gtccgtgtga gcggccgc                 2448
```

<210> SEQ ID NO 13
<211> LENGTH: 2502
<212> TYPE: DNA
<213> ORGANISM: Artificial Sequence
<220> FEATURE:
<223> OTHER INFORMATION: IDH013 insert sequence

<400> SEQUENCE: 13

```
actagtttct ttgtctggcc atccgggtaa cccatgccgg acgcaaaata gactactgaa     60
aatttttttg ctttgtggtt gggactttag ccaagggtat aaaagaccac cgtccccgaa    120
ttacctttcc tcttctttc tctctctcct tgtcaactca cacccgaaat cgttaagcat    180
ttccttctga gtataagaat cattcaaaat gctgcggacc gcatacctgg caaaggcagc    240
aagcgccctg ccaaagagaa ccctgtccgc ccagcagccc acaatcatct ataccctgac    300
agatgaggcc cctctgctgg ccacctacgc cttcctgcca gtggtgcgga gtttgcaga    360 ggcagcagga atcgatgtga agacaagcga catctccgtg gccgccagaa tcctggccga    420
gttcggcgat cacctgaccg aggagcagcg cgtgcccgac aacctgggag agctgggcgc    480
cctgacacag gaccccttctg ccaacatcat caagctgcct aatatcagcg cctccgtgcc    540
acagctgctg gcagccatca ggagctgca gggcaagggc tataacgtgc cagattaccc    600
cgccaatcct aagaccgacg atgagaagaa gatcaaggac cggtacgcca agatcctggg    660
ctccgccgtg aaccccgtgc tgagagaggg caattctgat cggagagccc taaggccgt    720 gaaggagtat gccaggaagc acccacacag catgggcgag tggtctcagg ccagccgcac    780
ccacgtggca accatgaaga caggcgactt ctaccgggc gagaagtcca tgaccctgga    840
cagagatagg cgcgtgaaga tggtgctgaa gacaaagtct ggcgaggaga tcgtgctgaa    900
```

```
gccagaggtg aagctggacg ccggcgacat catcgacagc atgtatatgt ccaagaaggc    960
cctgatcgcc ttctatgagg agcagatcga ggacgcctac aagaccggcg tgatgtttag   1020
cctgcacgtg aaggccacaa tgatgaaggt gtcccacccc atcgtgttcg ccacgccgt    1080
gaaggtgttc tacaaggatg cctttgccaa gcacgagaag ctgtttgacg agctgggcgt   1140
gaacgtgaac aatggcctgt ctgatctgta tgacaagatc gaggccctgc ctgcaagcca   1200
gagggaggag atcatcgagg atctgcacaa gtgccacgag cacagaccag agctggctat   1260
ggtggactcc gccaagggca tctctaattt ccactctccc agcgatgtga tcgtggacgc   1320
cagcatgcct gccatgatca ggctgggcgg caagatgtat ggcgccgatg ccgcaccaa    1380
ggacacaaag gccgtgaacc ctgagtccac cttttctcgg atgtaccagg agatgatcaa   1440
tttctgtaag acccacggcc agtttgatcc caccacaatg gcacagtgc ctaacgtggg    1500
cctgatggcc cagaaggccg aggagtacgg cagccacgac aagacattcg agatcccaga   1560
ggatggcgtg gccgacatcg tggacatcga taccggcgag gtgctgctga cacagaatgt   1620
ggaggagggc gacatctggc ggatgccaat cgtgaaggat gcccccatca gagactgggt   1680
gaagctggca gtgaccaggg cccgcctgtc cggcatgcca gtggtgtttt ggctggacac   1740
agagaggccc cacgaggtgg agctgcgcaa gaaggtgaag gagtatctga aggaccacga   1800
taccgagggc ctgaagatcc agatcatgcc ccaagtgtgg gccatgaggt acacactgga   1860
gcgggtggtg agaggcaagg ataccatcgc cgccacaggc aacatcctgc gcgattatct   1920
gaccgacctg ttcccaatcc tggagctggg cacaagcgcc aagatgctgt ccatcgtgcc   1980
actgatggca ggaggaggac tgtatgagac cggagcagga ggcagcgccc taagcacgt    2040
gcaccagctg gtggaggaga atcacctgag atgggattct ctgggagagt ttctggccct   2100
gggagccagc ctggaggaca tgggcaacaa gacaggcaat gagaaggcca aggtgctggc   2160
caaggccctg gataccgcca caggcaagct gctggaggag aacaagtccc cctctcggag   2220
aaccggcgag ctggacaatc ggggctctca gttctacctg agcctgtttt gggcacaggc   2280
cctggcagag cagacagagg acgcagagct ggccgagaga ttcaagcctc tggcaaaggc   2340
cctggcagag caggaggagg caatcgtgtc tgagctgaac agcgtgcagg caagaccgt    2400
ggacatcggc ggctactatt accccgaccc tgagaagacc tccgaagtga tgcgcccctc   2460
taagaccttc aacaccacac tggagtccgt gtgagcggcc gc                      2502
```

<210> SEQ ID NO 14
<211> LENGTH: 1467
<212> TYPE: DNA
<213> ORGANISM: Artificial Sequence
<220> FEATURE:
<223> OTHER INFORMATION: IDH014 insert sequence

<400> SEQUENCE: 14

```
actagtttct tgtctggcc atccgggtaa cccatgccgg acgcaaaata gactactgaa     60
aatttttttg ctttgtggtt gggactttag ccaagggtat aaaagaccac cgtccccgaa   120
ttacctttcc tcttcttttc tctctctcct tgtcaactca caccccgaaat cgttaagcat   180
ttccttctga gtataagaat cattcaaaat ggaaagtaaa gtagttgttc cggcacaagg   240
caagaagatc accctgcaaa acggcaaact caacgttcct gaaaatccga ttatccctta   300
cattgaaggt gatggaatcg gtgtagatgt aaccccagcc atgctgaaag tggtcgacgc   360
tgcagtcgag aaagcctata aaggcgagcg taaaatctcc tggatggaaa tttcacccgg   420
tgaaaaatcc acacaggttt atggtcagga cgtctggctg cctgctgaaa ctcttgatct   480
```

```
gattcgtgaa tatcgcgttg ccattaaagg tccgctgacc actccggttg gtggcggtat      540
tcgctctctg aacgttgccc tgcgccagga actggatctc tacatctgcc tgcgtccggt      600
acgttactat cagggcactc caagcccggt taaacaccct gaactgaccg atatggttat      660
cttccgtgaa aactcggaag acattttatgc gggtatcgaa tggaaagcag actctgccga     720
cgccgagaaa gtgattaaat tcctgcgtga agagatgggg gtgaagaaaa ttcgcttccc      780
ggaacattgt ggtatcggta ttaagccgtg ttcggaagaa ggcaccaaac gtctggttcg      840
tgcagcgatc gaatacgcaa ttgctaacga tcgtgactct gtgactctgg tgcacaaagg      900
caacatcatg aagttcaccg aaggagcgtt taaagactgg ggctaccagc tggcgcgtga      960
agagtttggc ggtgaactga tcgacggtgg cccgtggctg aaagttaaaa acccgaacac     1020
tggcaaagag atcgtcatta aagacgtgat tgctgatgca ttcctgcaac agatcctgct     1080
gcgtccggct gaatatgatg ttatcgcctg tatgaacctg aacggtgact acatttctga     1140
cgccctggca gcgcaggttg gcggtatcgg tatcgcccct ggtgcaaaca tcggtgacga     1200
atgcgccctg tttgaagcca cccacggtac tgcgccgaaa tatgccggtc aggacaaagt     1260
aaatcctggc tctattattc tctccgctga gatgatgctg cgccacatgg gttggaccga     1320
agcggctgac ttaattgtta aaggtatgga aggcgcaatc aacgcgaaaa ccgtaaccta     1380
tgacttcgag cgtctgatgg atggcgctaa actgctgaaa tgttcagagt ttggtgacgc     1440
gatcatcgaa aacatgtaag cggccgc                                        1467

<210> SEQ ID NO 15
<211> LENGTH: 1521
<212> TYPE: DNA
<213> ORGANISM: Artificial Sequence
<220> FEATURE:
<223> OTHER INFORMATION: IDH015 insert sequence

<400> SEQUENCE: 15
actagtttct ttgtctggcc atccgggtaa cccatgccgg acgcaaaata gactactgaa       60
aatttttttg ctttgtggtt gggactttag ccaagggtat aaaagaccac cgtccccgaa      120 ttaccttttcc tcttcttttc tctctctcct tgtcaactca cacccgaaat cgttaagcat     180
ttccttctga gtataagaat cattcaaaat gcttcgaacc gcctacctgg ctaaggccgc      240
ctcggctctc cccaagcgaa ccctcgaaag taaagtagtt gttccggcac aaggcaagaa      300
gatcaccctg caaaacggca aactcaacgt tcctgaaaat ccgattatcc cttacattga      360
aggtgatgga atcggtgtag atgtaaccccc agccatgctg aaagtggtcg acgctgcagt      420
cgagaaagcc tataaaggcg agcgtaaaat ctcctggatg gaaatttaca ccggtgaaaa     480
atccacacag gttatggtca aggacgtctg gctgcctgct gaaactcttg atctgattcg      540
tgaatatcgc gttgccatta aggtccgct gaccactccg gttggtggcg gtattcgctc      600
tctgaacgtt gccctgcgcc aggaactgga tctctacatc tgcctgcgtc cggtacgtta      660
ctatcagggc actccaagcc cggttaaaca ccctgaactg accgatatgg ttatcttccg      720
tgaaaactcg gaagacattt atgcgggtat cgaatggaaa gcagactctg ccgacgccga      780
gaaagtgatt aaattcctgc gtgaagagat ggggtgaag aaaattcgct tcccggaaca      840
ttgtggtatc ggtattaagc cgtgttcgga agaaggcacc aaacgtctgg ttcgtgcagc      900
gatcgaatac gcaattgcta acgatcgtga ctctgtgact ctggtgcaca aaggcaacat      960
catgaagttc accgaaggag cgtttaaaga ctggggctac cagctggcgc gtgaagagtt     1020
```

| | |
|---|---:|
| tggcggtgaa ctgatcgacg gtggcccgtg gctgaaagtt aaaaacccga acactggcaa | 1080 |
| agagatcgtc attaaagacg tgattgctga tgcattcctg caacagatcc tgctgcgtcc | 1140 |
| ggctgaatat gatgttatcg cctgtatgaa cctgaacggt gactacattt ctgacgccct | 1200 |
| ggcagcgcag gttggcggta tcggtatcgc ccctggtgca acatcggtg acgaatgcgc | 1260 |
| cctgtttgaa gccacccacg gtactgcgcc gaaatatgcc ggtcaggaca agtaaatcc | 1320 |
| tggctctatt attctctccg ctgagatgat gctgcgccac atgggttgga ccgaagcggc | 1380 |
| tgacttaatt gttaaaggta tggaaggcgc aatcaacgcg aaaaccgtaa cctatgactt | 1440 |
| cgagcgtctg atggatggcg ctaaaactgc tgaaatgttca gagtttggtg acgcgatcat | 1500 |
| cgaaaacatg taagcggccg c | 1521 |

<210> SEQ ID NO 16
<211> LENGTH: 1506
<212> TYPE: DNA
<213> ORGANISM: Artificial Sequence
<220> FEATURE:
<223> OTHER INFORMATION: IDH016 insert sequence

<400> SEQUENCE: 16

| | |
|---|---:|
| actagtttct ttgtctggcc atccgggtaa cccatgccgg acgcaaaata gactactgaa | 60 |
| aatttttttg ctttgtggtt gggactttag ccaagggtat aaaagaccac cgtccccgaa | 120 |
| ttacctttcc tcttcttttc tctctctcct tgtcaactca cacccgaaat cgttaagcat | 180 |
| ttccttctga gtataagaat cattcaaaat gacgacccat attcagaaac cgcaacagg | 240 |
| cagtccctta acactgctga atggggtgtt gcaggtgcct gatcaaccca ttattcccctt | 300 |
| cattgaaggc gacggaattg gttgtgatgt aaccccggcc atgcgcagtg tggtggatgc | 360 |
| ggcagtggcc aaagtctatg gaggacagcg gcagattgcc tggatggagt tgtttgcagg | 420 |
| tcagaaggcc gtgcaactgt atggtgaagg gcagtatttg cccgatgaga ccatggccgc | 480 |
| cattcgggaa tataaagtcg ccatcaaagg tcctctggaa actccggtgg gcggggggat | 540 |
| tcgtagcctg aatgtggcca tgcgtcagga tcttgatttg tatgtctgcc tccggccggt | 600 |
| gcgttatttt gaggggacgc ccagccccat gcggcatccg gaaaaagtgg atatggtcat | 660 |
| ttttcgcgaa aactccgagg acatttacgc cggtattgaa tggcctgcgg gtagtcccga | 720 |
| agcagaaaaa atcatccgtt ttctgcggga agaaatgggc gtcacaaaaa tccgcttttcc | 780 |
| cgacagctct gccattggca tcaaacccgt atcgacggaa ggttcggaac gtctgatccg | 840 |
| gcgtaccatt caatacgctc tggaacatgg caagccctct gtgagtctgg tgcacaaggg | 900 |
| taatatcatg aaattcaccg aaggcggttt ccgtgactgg ggttatgccc tggcggagcg | 960 |
| ggagttcgcc ggtcgggtgt ttacctgag gcaaaaggcc gccatcagca aggcagaggg | 1020 |
| taaggcggca gggcagaaag ccgagcagca ggccattgcc gacgggaagc tgatcatcaa | 1080 |
| ggacgtgatt gccgataatt ttctgcagca gattttgctg cgcccggaag attactctgt | 1140 |
| ggttgccacg ctgaacttga atggtgacta tgtttctgat gccctggccg cagaagtagg | 1200 |
| gggtattggt atggcacccg gtgccaacct ttctgatacc cacgcgattt ttgaagctac | 1260 |
| ccatggtacg gcaccggata ttgccgggca gggcaaagcc aacccagct cgctgatttt | 1320 |
| gtcggctgtc atgatgctgg agcatctggg ctggggagaa gctgctcagg cgattgtggc | 1380 |
| ggccatgaat gccaccattg cggctggtga agtcaccggt gatctggcgg ccttgcgggg | 1440 |
| tgatgtgccg gcactgagca ccacagagtt tacggcagca ctgatccggc gttttttaagc | 1500 |
| ggccgc | 1506 |

<210> SEQ ID NO 17
<211> LENGTH: 1560
<212> TYPE: DNA
<213> ORGANISM: Artificial Sequence
<220> FEATURE:
<223> OTHER INFORMATION: IDH017 insert sequence

<400> SEQUENCE: 17

```
actagtttct tgtctggcc atccgggtaa cccatgccgg acgcaaaata gactactgaa      60 aattttttg ctttgtggtt gggactttag ccaagggtat aaaagaccac cgtccccgaa     120
ttacctttcc tcttcttttc tctctctcct tgtcaactca cacccgaaat cgttaagcat     180
ttccttctga gtataagaat cattcaaaat gcttcgaacc gcctacctgg ctaaggccgc     240
ctcggctctc cccaagcgaa ccctcacgac ccatattcag aaacccgcaa caggcagtcc     300
cttaacactg ctgaatgggg tgttgcaggt gcctgatcaa cccattattc ccttcattga     360
aggcgacgga attggttgtg atgtaacccc ggccatgcgc agtgtggtgg atgcggcagt     420
ggccaaagtc tatggaggac agcggcagat tgcctggatg gagttgtttg caggtcagaa     480
ggccgtgcaa ctgtatggtg aagggcagta tttgcccgat gagaccatgg ccgccattcg     540
ggaatataaa gtcgccatca aggtcctct ggaaactccg gtgggcgggg ggattcgtag      600
cctgaatgtg gccatgcgtc aggatcttga tttgtatgtc tgcctccggc cggtgcgtta     660
ttttgagggg acgcccagcc ccatgcggca tccggaaaaa gtggatatgg tcattttcg      720 cgaaaactcc gaggacattt acgccggtat tgaatggcct gcgggtagtc ccgaagcaga     780
aaaaatcatc cgttttctgc gggaagaaat gggcgtcaca aaaatccgct ttcccgacag     840
ctctgccatt ggcatcaaac ccgtatcgac ggaaggttcg gaacgtctga tccggcgtac     900
cattcaatac gctctggaac atggcaagcc ctctgtgagt ctggtgcaca agggtaatat     960
catgaaattc accgaaggcg gtttccgtga ctgggggtat gccctggcgg agcgggagtt    1020
cgccggtcgg gtgtttacct ggaggcaaaa ggccgccatc agcaaggcag agggtaaggc    1080
ggcagggcag aaagccgagc agcaggccat gccgacggg aagctgatca tcaaggacgt     1140
gattgccgat aatttttctgc agcagatttt gctgcgcccg gaagattact ctgtggttgc    1200
cacgctgaac ttgaatggtg actatgtttc tgatgccctg gccgcagaag taggggtat    1260 tggtatggca cccggtgcca ccttttctga taccacgcg atttttgaag ctacccatgg    1320
tacggcaccg gatattgccg ggcagggcaa agccaacccc agctcgctga ttttgtcggc    1380
tgtcatgatg ctggagcatc tgggctgggg agaagctgct caggcgattg tggcggccat    1440
gaatgccacc attgcggctg gtgaagtcac cggtgatctg gcggccttgc ggggtgatgt    1500
gccggcactg agcaccacag agtttacggc agcactgatc cggcgttttt aagcggccgc    1560
```

<210> SEQ ID NO 18
<211> LENGTH: 2448
<212> TYPE: DNA
<213> ORGANISM: Artificial Sequence
<220> FEATURE:
<223> OTHER INFORMATION: IDH018 insert sequence

<400> SEQUENCE: 18

```
actagtttct tgtctggcc atccgggtaa cccatgccgg acgcaaaata gactactgaa      60 aattttttg ctttgtggtt gggactttag ccaagggtat aaaagaccac cgtccccgaa     120
ttacctttcc tcttcttttc tctctctcct tgtcaactca cacccgaaat cgttaagcat     180
```

```
ttccttctga gtataagaat cattcaaaat gagcgcccag cagccgacca tcatctacac     240
gctgaccgac gaggcgccgc tgcttgcgac ctatgccttc ttgccggtgg tacggaaatt     300
cgccgaagcg gcaggcatcg acgtcaaaac cagcgacatc tcggttgcgg cccgcatcct     360
ggccgagttc ggggatcacc tgaccgagga gcagcgggtc ccggacaacc tgggtgagct     420
gggcgcgctg acgcaggacc ccagcgccaa catcatcaag ctgccgaaca tcagcgcttc     480
ggtgccgcag ctgctcgcgg cgatcaagga gctgcagggc aaggggtaca acgtgccgga     540
ttacccggcc aacccgaaga ccgacgacga agaagatc aaggaccgct acgccaagat       600
cctcggcagc gcggtgaacc ccgttctgcg cgaaggcaac tcggaccgcc gcgcacccaa     660
ggcggtcaag gagtacgcgc gcaagcaccc gcacagcatg ggtgagtgga gccaggcgtc     720
gcgcacccac gtcgcgacca tgaagaccgg cgacttctac cacggcgaga agtcgatgac     780
gctggaccgc gaccgccgcg tcaagatggt gctcaagacc aagagcggcg aggagatcgt     840
cctcaagccc gaggtcaagc tcgacgcggg cgacatcatc gactcgatgt acatgagcaa     900
gaaggcgctc atcgcgttct acgaggagca gatcgaggac gcctacaaga ccggcgtcat     960
gttcagcctt cacgtcaagg cgaccatgat gaaggtgtcg cacccatcg tgttcggcca      1020 cgcggtcaag gtcttctaca aggacgcgtt cgccaagcac gagaagctgt tcgacgagct     1080
cggtgtcaac gtcaacaacg gtctgtccga tctgtacgac aagatcgagg cgctgcccgc     1140
gtcgcagcgc gaggagatca tcgaggatct gcacaagtgc cacgagcacc ggccggagct     1200
cgcgatggtc gactcggcca agggcatctc gaacttccac tcgccgtccg acgtcatcgt     1260
cgacgcctcg atgcccgcga tgatccgcct cggcggcaag atgtacgcg cagacggccg      1320 caccaaggac accaaggccg tcaacccgga gtcgaccttc tcccgcatgt accaggagat     1380
gatcaacttc tgcaagacgc acggccagtt cgatcccacc accatgggca cggtgccgaa     1440
cgtcggactg atggcgcaga aggccgagga gtacggcagc cacgacaaga ccttcgagat     1500
ccccgaggac ggcgtcgccg acatcgtcga catcgacacc ggtgaggtgc tgctcaccca     1560
gaacgtcgaa gagggcgata tctggcgcat gccgatcgtc aaggacgcgc cgatccgcga     1620
ctgggtcaag ctggccgtca cgcgcgctcg gctgtccggc atgcccgtgg tgttctggct     1680
cgacaccgag cgtccgcacg aggtcgagct gcgcaagaag gtcaaggagt acctcaagga     1740
ccacgacacc gaaggcctga aaatccagat catgccgcag gtgtgggcca tgcggtacac     1800
gctggagcgg gtcgtccgcg gcaaggacac catcgccgcg accggcaaca tcctgcgcga     1860
ctacctcacc gacctgttcc cgatcctgga gctgggcacc agcgccaaga tgctgtcgat     1920
cgtgccgctg atggccggcg gcggtctgta cgagaccggg gcgggcggct cggcgcccaa     1980
gcatgtgcac cagctcgtcg aggagaacca cctgcggtgg gattcgctgg gtgagttcct     2040
cgcactcggc gccagccttg aggacatggg caacaagacc ggcaacgaga aggccaaggt     2100
gctggccaag gcgctcgaca ccgcgaccgg aaagttgttg gaggagaaca agagcccgtc     2160
gcgtcgtacc ggtgagctgg acaaccgcgg cagccagttc tacctgtcgc tgttctgggc     2220
ccaggccctg gccgagcaga ccgaggacgc cgaactcgcc gagcgcttca gccgctggc      2280 caaggcgctc gccgagcagg aggaggccat cgtctccgag ctgaactcgg tgcagggcaa     2340
gacggtcgac atcggcggtt actactaccc ggatccggag aagacctccg aggtgatgcg     2400
tccgagcaag acgttcaaca ccacgctcga atcggtgtaa gcggccgc                  2448
```

<210> SEQ ID NO 19
<211> LENGTH: 2502

```
<212> TYPE: DNA
<213> ORGANISM: Artificial Sequence
<220> FEATURE:
<223> OTHER INFORMATION: IDH019 insert sequence

<400> SEQUENCE: 19
actagtttct ttgtctggcc atccgggtaa cccatgccgg acgcaaaata gactactgaa      60
aatttttttg ctttgtggtt gggactttag ccaagggtat aaaagaccac cgtccccgaa     120
ttaccttttcc tcttcttttc tctctctcct tgtcaactca cacccgaaat cgttaagcat    180
ttccttctga gtataagaat cattcaaaat gcttcgaacc gcctacctgg ctaaggccgc     240
ctcggctctc cccaagcgaa ccctcagcgc cagcagccg accatcatct acacgctgac      300
cgacgaggcg ccgctgcttg cgacctatgc cttcttgccg gtggtacgga aattcgccga    360
agcggcagga atcgacgtca aaaccagcga catctcggtt gcggcccgca tcctggccga    420
gttcggggat cacctgaccg aggagcagcg ggtcccggac aacctgggtg agctgggcgc    480
gctgacgcag gaccccagcg ccaacatcat caagctgccg aacatcagcg cttcggtgcc    540
gcagctgctc gcggcgatca aggagctgca gggcaagggg tacaacgtgc cggattaccc    600
ggccaacccg aagaccgacg acgagaagaa gatcaaggac cgctacgcca agatcctcgg    660
cagcgcggtg aaccccgttc tgcgcgaagg caactcggac cgccgcgcac ccaaggcggt   720
caaggagtac gcgcgcaagc acccgcacag catgggtgag tggagccagg cgtcgcgcac    780
ccacgtcgcg accatgaaga ccggcgactt ctaccacggc gagaagtcga tgacgctgga    840
ccgcgaccgc cgcgtcaaga tggtgctcaa gaccaagagc ggcgaggaga tcgtcctcaa    900
gcccgaggtc aagctcgacg cgggcgacat catcgactcg atgtacatga gcaagaaggc    960
gctcatcgcg ttctacgagg agcagatcga ggacgcctac aagaccggcg tcatgttcag   1020
ccttcacgtc aaggcgacca tgatgaaggt gtcgcacccc atcgtgttcg ccacgcggt   1080
caaggtcttc tacaaggacg cgttcgccaa gcacagagaag ctgttcgacg agctcggtgt   1140
caacgtcaac aacggtctgt ccgatctgta cgacaagatc gaggcgctgc ccgcgtcgca    1200
gcgcgaggag atcatcgagg atctgcacaa gtgccacgag caccggccgg agctcgcgat   1260
ggtcgactcg gccaagggca tctcgaactt ccactcgccg tccgacgtca tcgtcgacgc    1320
ctcgatgccc gcgatgatcc gcctcggcgg caagatgtac ggcgcagacg gccgcaccaa    1380
ggacaccaag gccgtcaacc cggagtcgac ctttctcccgc atgtaccagg agatgatcaa   1440
cttctgcaag acgcacggcc agttcgatcc caccaccatg ggcacggtgc cgaacgtcgg    1500
actgatggcg cagaaggccg aggagtacgg cagccacgac aagaccttcg agatccccga   1560
ggacggcgtc gccgacatcg tcgacatcga caccggtgag gtgctgctca cccagaacgt    1620
cgaagagggc gatatctggc gcatgccgat cgtcaaggac gcgccgatcc gcgactgggt    1680
caagctggcc gtcacgcgcg ctcggctgtc cggcatgccc gtggtgttct ggctcgacac    1740
cgagcgtccg cacgaggtcg agctgcgcaa aaggtcaag gagtacctca aggaccacga   1800
caccgaaggc ctgaaaatcc agatcatgcc gcaggtgtgg gccatgcggt acacgctgga   1860
gcgggtcgtc cgcggcaagg acaccatcgc cgcgaccggc aacatcctgc gcgactacct    1920
caccgacctg ttcccgatcc tggagctggg caccagcgcc aagatgctgt cgatcgtgcc    1980
gctgatggcc ggcggcgtc tgtacgagac cggggcgggc ggctcggcgc ccaagcatgt    2040
gcaccagctc gtcgaggaga accacctgcg gtgggattcg ctgggtgagt tcctcgcact   2100
cggcgccagc cttgaggaca tgggcaacaa gaccggcaac gagaaggcca aggtgctggc   2160
```

-continued

```
caaggcgctc gacaccgcga ccggaaagtt gttggaggag aacaagagcc cgtcgcgtcg    2220
taccggtgag ctggacaacc gcggcagcca gttctacctg tcgctgttct gggcccaggc    2280
cctggccgag cagaccgagg acgccgaact cgccgagcgc ttcaagccgc tggccaaggc    2340
gctcgccgag caggaggagg ccatcgtctc cgagctgaac tcggtgcagg caagacggt     2400 cgacatcggc ggttactact acccggatcc ggagaagacc tccgaggtga tgcgtccgag    2460
caagacgttc aacaccacgc tcgaatcggt gtaagcggcc gc                       2502
```

<210> SEQ ID NO 20
<211> LENGTH: 366
<212> TYPE: PRT
<213> ORGANISM: Yarrowia lipolytica

<400> SEQUENCE: 20

```
Met Leu Arg Thr Ala Tyr Leu Ala Lys Ala Ala Ser Ala Leu Pro Lys
1               5                   10                  15

Arg Thr Leu Ala Thr Asn Ala Arg Thr Met Phe Gln Pro Lys Glu Tyr
            20                  25                  30

Gly Ser Lys Tyr Thr Val Thr Leu Ile Pro Gly Asp Gly Ile Gly Asn
        35                  40                  45

Glu Ile Thr Asp Ala Val Lys Thr Ile Phe Lys Thr Ile Ser Val Pro
    50                  55                  60

Ile Asp Trp Glu Val Val Asn Val Thr Gly Val Gly Glu Asn His Leu
65                  70                  75                  80

Asp Gly Tyr Glu Glu Ala Ile Arg Ser Ile Asn Arg Asn Lys Val Ala
                85                  90                  95

Ile Lys Gly Ile Leu His Thr Pro Val Glu Lys His Gly His Thr Ser
            100                 105                 110

Phe Asn Val Ala Leu Arg Arg Glu Leu Asp Ile Phe Ala Ser Leu Val
        115                 120                 125

Leu Ile Lys Asn Ile Pro Gly Val Gln Thr Arg Leu Asp Gly Ile Asp
    130                 135                 140

Met Ala Leu Ile Arg Glu Asn Thr Glu Gly Glu Tyr Ser Gly Leu Glu
145                 150                 155                 160

His Ser Pro Val Pro Gly Val Val Glu Ser Ile Lys Val Ile Thr Lys
                165                 170                 175

Arg Lys Ser Glu Arg Ile Ala Arg Phe Ala Phe Asp Phe Ala Leu Lys
            180                 185                 190

Asn Asn Arg His Lys Val Thr Ala Ile His Lys Ala Asn Ile Met Lys
        195                 200                 205

Leu Ala Asp Gly Leu Phe Arg Asn Thr Cys Lys Glu Val Ser Ala Glu
    210                 215                 220

Tyr Pro Glu Ile Gln Tyr Gly Asp Met Ile Val Asp Asn Ala Ser Met
225                 230                 235                 240

Gln Ala Val Ser Trp Pro Gln Gln Phe Asp Val Leu Val Thr Pro Asn
                245                 250                 255

Leu Tyr Gly Thr Ile Leu Ser Asn Ile Gly Ala Gly Leu Val Gly Gly
            260                 265                 270

Pro Gly Leu Val Pro Gly Val Asn Leu Gly Thr Glu His Ala Val Phe
        275                 280                 285

Glu Pro Gly Cys Arg His Val Gly Leu Ala Ala Lys Gly Arg Gly Thr
    290                 295                 300

Ala Asn Pro Thr Ala Met Ile Leu Ser Ser Ala Met Leu Leu Arg His
305                 310                 315                 320
```

```
Leu Asn Leu Asp Asp Phe Ala Asp Val Ile Ser Lys Ala Thr Tyr Asp
            325                 330                 335

Val Leu Ala Glu Gly Gln Val Arg Thr Pro Asp Leu Gly Gly Asn Ser
            340                 345                 350

Thr Thr Asp Glu Phe Thr Met Ala Val Ile Asn Lys Leu Gln
            355                 360                 365

<210> SEQ ID NO 21
<211> LENGTH: 416
<212> TYPE: PRT
<213> ORGANISM: Escherichia coli

<400> SEQUENCE: 21

Met Glu Ser Lys Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
            20                  25                  30

Glu Gly Asp Gly Ile Gly Val Asp Val Thr Pro Ala Met Leu Lys Val
            35                  40                  45

Val Asp Ala Ala Val Glu Lys Ala Tyr Lys Gly Glu Arg Lys Ile Ser
        50                  55                  60

Trp Met Glu Ile Tyr Thr Gly Glu Lys Ser Thr Gln Val Tyr Gly Gln
65              70                  75                  80

Asp Val Trp Leu Pro Ala Glu Thr Leu Asp Leu Ile Arg Glu Tyr Arg
            85                  90                  95

Val Ala Ile Lys Gly Pro Leu Thr Thr Pro Val Gly Gly Gly Ile Arg
            100                 105                 110

Ser Leu Asn Val Ala Leu Arg Gln Glu Leu Asp Leu Tyr Ile Cys Leu
            115                 120                 125

Arg Pro Val Arg Tyr Tyr Gln Gly Thr Pro Ser Pro Val Lys His Pro
        130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
            165                 170                 175

Lys Phe Leu Arg Glu Glu Met Gly Val Lys Lys Ile Arg Phe Pro Glu
            180                 185                 190

His Cys Gly Ile Gly Ile Lys Pro Cys Ser Glu Glu Gly Thr Lys Arg
            195                 200                 205

Leu Val Arg Ala Ala Ile Glu Tyr Ala Ile Ala Asn Asp Arg Asp Ser
        210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
            245                 250                 255

Leu Ile Asp Gly Gly Pro Trp Leu Lys Val Lys Asn Pro Asn Thr Gly
            260                 265                 270

Lys Glu Ile Val Ile Lys Asp Val Ile Ala Asp Ala Phe Leu Gln Gln
            275                 280                 285

Ile Leu Leu Arg Pro Ala Glu Tyr Asp Val Ile Ala Cys Met Asn Leu
        290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
```

```
                     325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
            355                 360                 365

Trp Thr Glu Ala Ala Asp Leu Ile Val Lys Gly Met Glu Gly Ala Ile
            370                 375                 380

Asn Ala Lys Thr Val Thr Tyr Asp Phe Glu Arg Leu Met Asp Gly Ala
385                 390                 395                 400

Lys Leu Leu Lys Cys Ser Glu Phe Gly Asp Ala Ile Ile Glu Asn Met
                405                 410                 415

<210> SEQ ID NO 22
<211> LENGTH: 429
<212> TYPE: PRT
<213> ORGANISM: Acidithiobacillus thiooxidans

<400> SEQUENCE: 22

Met Thr Thr His Ile Gln Lys Pro Ala Thr Gly Ser Pro Leu Thr Leu
1               5                   10                  15

Leu Asn Gly Val Leu Gln Val Pro Asp Gln Pro Ile Ile Pro Phe Ile
            20                  25                  30

Glu Gly Asp Gly Ile Gly Cys Asp Val Thr Pro Ala Met Arg Ser Val
        35                  40                  45

Val Asp Ala Ala Val Ala Lys Val Tyr Gly Gly Gln Arg Gln Ile Ala
    50                  55                  60

Trp Met Glu Leu Phe Ala Gly Gln Lys Ala Val Gln Leu Tyr Gly Glu
65                  70                  75                  80

Gly Gln Tyr Leu Pro Asp Glu Thr Met Ala Ala Ile Arg Glu Tyr Lys
                85                  90                  95

Val Ala Ile Lys Gly Pro Leu Glu Thr Pro Val Gly Gly Gly Ile Arg
            100                 105                 110

Ser Leu Asn Val Ala Met Arg Gln Asp Leu Asp Leu Tyr Val Cys Leu
        115                 120                 125

Arg Pro Val Arg Tyr Phe Glu Gly Thr Pro Ser Pro Met Arg His Pro
    130                 135                 140

Glu Lys Val Asp Met Val Ile Phe Arg Glu Asn Ser Glu Asp Ile Tyr
145                 150                 155                 160

Ala Gly Ile Glu Trp Pro Ala Gly Ser Pro Glu Ala Glu Lys Ile Ile
                165                 170                 175

Arg Phe Leu Arg Glu Glu Met Gly Val Thr Lys Ile Arg Phe Pro Asp
            180                 185                 190

Ser Ser Ala Ile Gly Ile Lys Pro Val Ser Thr Glu Gly Ser Glu Arg
        195                 200                 205

Leu Ile Arg Arg Thr Ile Gln Tyr Ala Leu Glu His Gly Lys Pro Ser
    210                 215                 220

Val Ser Leu Val His Lys Gly Asn Ile Met Lys Phe Thr Glu Gly Gly
225                 230                 235                 240

Phe Arg Asp Trp Gly Tyr Ala Leu Ala Glu Arg Glu Phe Ala Gly Arg
                245                 250                 255

Val Phe Thr Trp Arg Gln Lys Ala Ala Ile Ser Lys Ala Glu Gly Lys
            260                 265                 270

Ala Ala Gly Gln Lys Ala Glu Gln Gln Ala Ile Ala Asp Gly Lys Leu
        275                 280                 285
```

```
Ile Ile Lys Asp Val Ile Ala Asp Asn Phe Leu Gln Gln Ile Leu Leu
            290                 295                 300

Arg Pro Glu Asp Tyr Ser Val Ala Thr Leu Asn Leu Asn Gly Asp
305                 310                 315                 320

Tyr Val Ser Asp Ala Leu Ala Ala Glu Val Gly Gly Ile Gly Met Ala
                    325                 330                 335

Pro Gly Ala Asn Leu Ser Asp Thr His Ala Ile Phe Glu Ala Thr His
                    340                 345                 350

Gly Thr Ala Pro Asp Ile Ala Gly Gln Gly Lys Ala Asn Pro Ser Ser
                355                 360                 365

Leu Ile Leu Ser Ala Val Met Met Leu Glu His Leu Gly Trp Gly Glu
370                 375                 380

Ala Ala Gln Ala Ile Val Ala Ala Met Asn Ala Thr Ile Ala Ala Gly
385                 390                 395                 400

Glu Val Thr Gly Asp Leu Ala Ala Leu Arg Gly Asp Val Pro Ala Leu
                    405                 410                 415

Ser Thr Thr Glu Phe Thr Ala Ala Leu Ile Arg Arg Phe
                420                 425

<210> SEQ ID NO 23
<211> LENGTH: 743
<212> TYPE: PRT
<213> ORGANISM: Mycobacterium smegmatis

<400> SEQUENCE: 23

Met Ser Ala Gln Gln Pro Thr Ile Ile Tyr Thr Leu Thr Asp Glu Ala
1               5                   10                  15

Pro Leu Leu Ala Thr Tyr Ala Phe Leu Pro Val Val Arg Lys Phe Ala
                20                  25                  30

Glu Ala Ala Gly Ile Asp Val Lys Thr Ser Asp Ile Ser Val Ala Ala
            35                  40                  45

Arg Ile Leu Ala Glu Phe Gly Asp His Leu Thr Glu Glu Gln Arg Val
50                  55                  60

Pro Asp Asn Leu Gly Glu Leu Gly Ala Leu Thr Gln Asp Pro Ser Ala
65                  70                  75                  80

Asn Ile Ile Lys Leu Pro Asn Ile Ser Ala Ser Val Pro Gln Leu Leu
                85                  90                  95

Ala Ala Ile Lys Glu Leu Gln Gly Lys Gly Tyr Asn Val Pro Asp Tyr
                100                 105                 110

Pro Ala Asn Pro Lys Thr Asp Asp Glu Lys Lys Ile Lys Asp Arg Tyr
            115                 120                 125

Ala Lys Ile Leu Gly Ser Ala Val Asn Pro Val Leu Arg Glu Gly Asn
130                 135                 140

Ser Asp Arg Arg Ala Pro Lys Ala Val Lys Glu Tyr Ala Arg Lys His
145                 150                 155                 160

Pro His Ser Met Gly Glu Trp Ser Gln Ala Ser Arg Thr His Val Ala
                165                 170                 175

Thr Met Lys Thr Gly Asp Phe Tyr His Gly Glu Lys Ser Met Thr Leu
            180                 185                 190

Asp Arg Asp Arg Arg Val Lys Met Val Leu Lys Thr Lys Ser Gly Glu
        195                 200                 205

Glu Ile Val Leu Lys Pro Glu Val Lys Leu Asp Ala Gly Asp Ile Ile
    210                 215                 220

Asp Ser Met Tyr Met Ser Lys Lys Ala Leu Ile Ala Phe Tyr Glu Glu
225                 230                 235                 240
```

```
Gln Ile Glu Asp Ala Tyr Lys Thr Gly Val Met Phe Ser Leu His Val
            245                 250                 255

Lys Ala Thr Met Met Lys Val Ser His Pro Ile Val Phe Gly His Ala
        260                 265                 270

Val Lys Val Phe Tyr Lys Asp Ala Phe Ala Lys His Glu Lys Leu Phe
    275                 280                 285

Asp Glu Leu Gly Val Asn Val Asn Asn Gly Leu Ser Asp Leu Tyr Asp
290                 295                 300

Lys Ile Glu Ala Leu Pro Ala Ser Gln Arg Glu Ile Ile Glu Asp
305                 310                 315                 320

Leu His Lys Cys His Glu His Arg Pro Glu Leu Ala Met Val Asp Ser
                325                 330                 335

Ala Lys Gly Ile Ser Asn Phe His Ser Pro Ser Asp Val Ile Val Asp
            340                 345                 350

Ala Ser Met Pro Ala Met Ile Arg Leu Gly Gly Lys Met Tyr Gly Ala
        355                 360                 365

Asp Gly Arg Thr Lys Asp Thr Lys Ala Val Asn Pro Glu Ser Thr Phe
    370                 375                 380

Ser Arg Met Tyr Gln Glu Met Ile Asn Phe Cys Lys Thr His Gly Gln
385                 390                 395                 400

Phe Asp Pro Thr Thr Met Gly Thr Val Pro Asn Val Gly Leu Met Ala
                405                 410                 415

Gln Lys Ala Glu Glu Tyr Gly Ser His Asp Lys Thr Phe Glu Ile Pro
            420                 425                 430

Glu Asp Gly Val Ala Asp Ile Val Asp Ile Asp Thr Gly Glu Val Leu
        435                 440                 445

Leu Thr Gln Asn Val Glu Glu Gly Asp Ile Trp Arg Met Pro Ile Val
    450                 455                 460

Lys Asp Ala Pro Ile Arg Asp Trp Val Lys Leu Ala Val Thr Arg Ala
465                 470                 475                 480

Arg Leu Ser Gly Met Pro Val Val Phe Trp Leu Asp Thr Glu Arg Pro
                485                 490                 495

His Glu Val Glu Leu Arg Lys Lys Val Lys Glu Tyr Leu Lys Asp His
            500                 505                 510

Asp Thr Glu Gly Leu Lys Ile Gln Ile Met Pro Gln Val Trp Ala Met
        515                 520                 525

Arg Tyr Thr Leu Glu Arg Val Val Arg Gly Lys Asp Thr Ile Ala Ala
    530                 535                 540

Thr Gly Asn Ile Leu Arg Asp Tyr Leu Thr Asp Leu Phe Pro Ile Leu
545                 550                 555                 560

Glu Leu Gly Thr Ser Ala Lys Met Leu Ser Ile Val Pro Leu Met Ala
                565                 570                 575

Gly Gly Gly Leu Tyr Glu Thr Gly Ala Gly Gly Ser Ala Pro Lys His
            580                 585                 590

Val His Gln Leu Val Glu Glu Asn His Leu Arg Trp Asp Ser Leu Gly
        595                 600                 605

Glu Phe Leu Ala Leu Gly Ala Ser Leu Glu Asp Met Gly Asn Lys Thr
    610                 615                 620

Gly Asn Glu Lys Ala Lys Val Leu Ala Lys Ala Leu Asp Thr Ala Thr
625                 630                 635                 640

Gly Lys Leu Leu Glu Glu Asn Lys Ser Pro Ser Arg Arg Thr Gly Glu
                645                 650                 655
```

```
Leu Asp Asn Arg Gly Ser Gln Phe Tyr Leu Ser Leu Phe Trp Ala Gln
                660                 665                 670

Ala Leu Ala Glu Gln Thr Glu Asp Ala Glu Leu Ala Glu Arg Phe Lys
            675                 680                 685

Pro Leu Ala Lys Ala Leu Ala Glu Gln Glu Glu Ala Ile Val Ser Glu
        690                 695                 700

Leu Asn Ser Val Gln Gly Lys Thr Val Asp Ile Gly Gly Tyr Tyr Tyr
705                 710                 715                 720

Pro Asp Pro Glu Lys Thr Ser Glu Val Met Arg Pro Ser Lys Thr Phe
                725                 730                 735

Asn Thr Thr Leu Glu Ser Val
            740

<210> SEQ ID NO 24
<211> LENGTH: 572
<212> TYPE: PRT
<213> ORGANISM: Lipomyces starkeyi

<400> SEQUENCE: 24

Met Ala Pro Lys Ser Ser Thr Arg Val Pro Leu Ser Val Lys Gly Pro
1               5                   10                  15

Ile Asp Cys Pro Tyr Glu Gly Lys Glu Met Leu Asn Leu Pro Gln Phe
            20                  25                  30

Asn Arg Gly Thr Ala Phe Thr Ala Glu Glu Arg Asp Leu Phe Asn Leu
        35                  40                  45

Val Gly Asn Leu Pro Ala Ala Leu Gln Thr Leu Gln Asn Gln Val Asp
    50                  55                  60

Arg Ala Tyr Asp Gln Tyr Ser Ser Ile Ser Thr Ala Leu Gly Lys Asn
65                  70                  75                  80

Thr Phe Leu Met Ser Leu Lys Val Gln Asn Glu Val Leu Tyr Phe Lys
                85                  90                  95

Leu Leu Gln Asp His Leu Lys Glu Met Phe Ser Ile Ile Tyr Thr Pro
            100                 105                 110

Thr Glu Ser Glu Ala Ile Glu His Tyr Ser Arg Leu Phe Arg Arg Pro
        115                 120                 125

Glu Gly Cys Phe Leu Asn Ile Asn His Pro Glu Tyr Ile Glu Arg Ser
    130                 135                 140

Leu Ala Ala Trp Gly Thr Glu Glu Asp Ile Asp Tyr Ile Ile Val Ser
145                 150                 155                 160

Asp Gly Glu Glu Ile Leu Gly Ile Gly Asp Gln Gly Val Gly Ala Ile
                165                 170                 175

Gly Ile Ser Ser Ala Lys Ala Val Leu Met Thr Leu Cys Ala Gly Val
            180                 185                 190

His Pro Ser Arg Cys Ile Pro Val Ala Leu Asp Val Gly Thr Asp Asn
        195                 200                 205

Glu Gln Leu Leu Glu Asp Glu Leu Tyr Leu Gly Asn Arg His Asn Arg
    210                 215                 220

Val Arg Gly Gly Arg Tyr Asp Lys Phe Val Asp Phe Val Gln Cys
225                 230                 235                 240

Val Lys Lys Leu Tyr Pro Arg Ala Val Leu His Phe Glu Asp Phe Gly
                245                 250                 255

Leu Pro Asn Ala Arg Arg Leu Leu Asp Thr Tyr Arg Pro Arg Leu Ala
            260                 265                 270

Cys Phe Asn Asp Asp Val Gln Gly Thr Gly Ala Val Thr Leu Ala Ala
        275                 280                 285
```

```
Leu Ser Ser Ala Val Arg Val Ala Gly Ile Asp Phe Arg Asp Leu Arg
            290                 295                 300

Thr Val Ile Phe Gly Ala Gly Thr Ala Gly Thr Gly Ile Ala Asp Gln
305                 310                 315                 320

Leu Arg Asp Phe Leu Asn Thr Gln Gly Ile Ser Lys Gln Gln Val Ile
                325                 330                 335

Asp His Ile Trp Leu Val Asp Lys Pro Gly Leu Leu Leu Lys Ser Met
                340                 345                 350

His Asp Lys Leu Thr Ser Ala Gln Arg Pro Tyr Ala Ala Ser Asp Asp
            355                 360                 365

Arg Trp Lys Glu Ile Asp Thr Lys Ser Leu Ser Glu Ile Val Lys Lys
370                 375                 380

Val Lys Pro His Val Leu Ile Gly Cys Ser Thr Lys Pro Lys Ala Phe
385                 390                 395                 400

Asn Glu Ala Val Leu Arg Glu Met Ala Lys His Val Glu Arg Pro Ile
                405                 410                 415

Val Phe Pro Leu Ser Asn Pro Thr Arg Leu His Glu Ala Thr Pro Ala
                420                 425                 430

Glu Ile Phe Lys Tyr Thr Asp Gly Lys Ala Leu Val Ala Thr Gly Ser
            435                 440                 445

Pro Phe Asp Pro Val Asp Gly Lys Glu Ile Ala Glu Asn Asn Asn Cys
450                 455                 460

Phe Val Tyr Pro Gly Ile Gly Met Gly Ser Ile Leu Ser Arg Ala Asp
465                 470                 475                 480

Arg Val Thr Glu Thr Met Ile Ala Ala Val Val Lys Glu Leu Ala Ser
                485                 490                 495

Leu Ala Pro Ser Glu Lys Asp Pro Thr Gly Ala Leu Leu Pro Asp Val
            500                 505                 510

Ala Asp Ile Arg Asp Ile Ser Ala Lys Ile Ala Thr Ala Val Val Leu
            515                 520                 525

Gln Ala Leu Glu Glu Gly Thr Ala Arg Val Glu Ile Glu Gly Ile
            530                 535                 540

Lys Val Pro Arg Asp Arg Asp His Cys Leu Glu Trp Val Lys Glu Gln
545                 550                 555                 560

Met Trp Lys Pro Glu Tyr Arg Pro Leu Arg Lys Val
                565                 570

<210> SEQ ID NO 25
<211> LENGTH: 599
<212> TYPE: PRT
<213> ORGANISM: Rhodosporidium toruloides

<400> SEQUENCE: 25

Met Asn Lys Leu Arg Leu Gln Ala Lys Asp Ala Asp Glu Glu Gly Ala
1               5                   10                  15

Ala Leu His Asp Ser Thr Ile Ser Asn Lys Glu Tyr Leu Gln His Ser
            20                  25                  30

Lys Asn Glu Arg Pro Ile Trp Thr Ala Leu Arg Gly Arg Ala Leu Leu
        35                  40                  45

Asn Glu Pro Ala Leu Asn Lys Gly Ala Gly Phe Thr Pro Glu Glu Arg
    50                  55                  60

Asp Thr Phe Gly Leu Thr Gly Leu Leu Pro His Glu Val His Ser Leu
65                  70                  75                  80

Asp Gln Gln Cys Lys Arg Ala Tyr Ser Gln Leu Gln Glu Arg Pro Ser
```

```
            85                  90                  95
Ala Leu Ala Lys Tyr Thr Phe Leu Ser Ser Leu Arg Asp Gln Asn Ile
            100                 105                 110
Ile Leu Phe Tyr Ala Leu Cys Leu Arg His Leu Asn Glu Leu Leu Pro
            115                 120                 125
Val Ile Tyr Thr Pro Thr Val Gly Glu Ala Ile Gln Lys Tyr Ser Thr
            130                 135                 140
Ile Trp Arg Arg Pro Asp Gly Leu Phe Leu Ser Tyr Ala His Arg His
145                 150                 155                 160
Lys Met Arg Glu Met Met Met Gln Ala Lys Arg Pro Lys Asp Val Asp
            165                 170                 175
Leu Val Ile Val Thr Asp Ser Glu Gly Ile Leu Gly Ile Gly Asp Gln
            180                 185                 190
Gly Val Gly Gly Ile Leu Ile Ala Gln Gly Lys Ala Asn Leu Tyr Thr
            195                 200                 205
Leu Gly Ala Gly Ile Asp Pro Ser Arg Ile Leu Ser Val Val Leu Asp
            210                 215                 220
Val Gly Thr Asp Asn Ser Ala Leu Leu Asn Asp Pro Leu Tyr Leu Gly
225                 230                 235                 240
Leu Arg Arg Lys Arg Val Arg Gly Ala Glu Tyr Asp Lys Phe Val Asp
            245                 250                 255
Arg Phe Cys Glu Leu Val Arg Glu Glu Tyr Pro Gln Ala Leu Leu His
            260                 265                 270
Phe Glu Asp Phe Gly Val Ser Asn Ala Ser Lys Ile Leu Thr Thr Tyr
            275                 280                 285
Arg Asn Lys Gln Ser Val Phe Asn Asp Asp Met Gln Gly Thr Ala Ala
            290                 295                 300
Val Val Leu Ala Ala Leu Leu Ser Ala Val Lys Val Thr Lys Ser Glu
305                 310                 315                 320
Leu Lys Asp Gln Arg Ile Val Val Phe Gly Phe Gly Thr Ala Gly Tyr
            325                 330                 335
Gly Ile Ala Asp Gly Ile Arg Asn Ala Leu Met Leu Glu Ala Gly Leu
            340                 345                 350
Ser Ser Glu Glu Val Arg Lys Ile Phe Trp Cys Val Asp Arg Pro Gly
            355                 360                 365
Leu Leu Thr Thr Glu His Ser Pro Thr Leu Arg Pro Gly Gln Glu His
            370                 375                 380
Phe Ile Arg Asp Ala Ser Glu Val Ser Ser Trp Glu Arg Asp Ala Glu
385                 390                 395                 400
Gly Arg Ile Ser Leu Leu Glu Val Val Lys Gln Ala Lys Pro Thr Ile
            405                 410                 415
Leu Val Gly Cys Ser Thr Met Ser Gly Ala Phe Asp Glu Glu Val Val
            420                 425                 430
Arg Glu Met Ala Lys His Val Glu Arg Pro Ile Val Phe Pro Leu Ser
            435                 440                 445
Asn Pro Thr Lys Leu Ala Glu Ala Asp Pro Ala Asp Ile Asn Glu Trp
            450                 455                 460
Thr Asn Gly Leu Ala Leu Met Ala Thr Gly Ser Pro Phe Pro Pro Val
465                 470                 475                 480
Lys Thr Pro Arg Gly Lys Glu His Lys Ile Ala Glu Ala Asn Asn Gly
            485                 490                 495
Leu Leu Tyr Pro Gly Leu Gly Leu Gly Val Val Val Ser Arg Ala Ser
            500                 505                 510
```

```
Phe Leu Thr Glu Lys Met Ile Thr Ala Gly Val Ala Ala Leu Ala Arg
        515                 520                 525

Met Ala Pro Ala Leu Asp Asp Pro Asp Glu Ser Leu Leu Pro Pro Leu
        530                 535                 540

Ser Asp Leu Arg His Val Ser Val Lys Val Ala Thr Ala Val Ala Asn
545                 550                 555                 560

Ala Ala Lys Glu Glu Gly Val Ser Gln Ile Lys Arg Asp Asp Pro Phe
                565                 570                 575

Ser Glu Asp Glu Val Arg Ala Ala Gln Trp Asp Pro Val Tyr Arg Pro
                580                 585                 590

Leu Glu Leu Val Asp Arg His
        595

<210> SEQ ID NO 26
<211> LENGTH: 567
<212> TYPE: PRT
<213> ORGANISM: Homo sapiens

<400> SEQUENCE: 26

Met Leu His Ile Lys Glu Lys Gly Lys Pro Leu Met Leu Asn Pro Arg
1               5                   10                  15

Thr Asn Lys Gly Met Ala Phe Thr Leu Gln Glu Arg Gln Met Leu Gly
            20                  25                  30

Leu Gln Gly Leu Leu Pro Pro Lys Ile Glu Thr Gln Asp Ile Gln Ala
        35                  40                  45

Leu Arg Phe His Arg Asn Leu Lys Lys Met Thr Ser Pro Leu Glu Lys
    50                  55                  60

Tyr Ile Tyr Ile Met Gly Ile Gln Glu Arg Asn Glu Lys Leu Phe Tyr
65                  70                  75                  80

Arg Ile Leu Gln Asp Asp Ile Glu Ser Leu Met Pro Ile Val Tyr Thr
                85                  90                  95

Pro Thr Val Gly Leu Ala Cys Ser Gln Tyr Gly His Ile Phe Arg Arg
            100                 105                 110

Pro Lys Gly Leu Phe Ile Ser Ile Ser Asp Arg Gly His Val Arg Ser
        115                 120                 125

Ile Val Asp Asn Trp Pro Glu Asn His Val Lys Ala Val Val Val Thr
    130                 135                 140

Asp Gly Glu Arg Ile Leu Gly Leu Gly Asp Leu Gly Val Tyr Gly Met
145                 150                 155                 160

Gly Ile Pro Val Gly Lys Leu Cys Leu Tyr Thr Ala Cys Ala Gly Ile
                165                 170                 175

Arg Pro Asp Arg Cys Leu Pro Val Cys Ile Asp Val Gly Thr Asp Asn
            180                 185                 190

Ile Ala Leu Leu Lys Asp Pro Phe Tyr Met Gly Leu Tyr Gln Lys Arg
        195                 200                 205

Asp Arg Thr Gln Gln Tyr Asp Asp Leu Ile Asp Glu Phe Met Lys Ala
    210                 215                 220

Ile Thr Asp Arg Tyr Gly Arg Asn Thr Leu Ile Gln Phe Glu Asp Phe
225                 230                 235                 240

Gly Asn His Asn Ala Phe Arg Phe Leu Arg Lys Tyr Arg Glu Lys Tyr
                245                 250                 255

Cys Thr Phe Asn Asp Asp Ile Gln Gly Thr Ala Ala Val Ala Leu Ala
            260                 265                 270

Gly Leu Leu Ala Ala Gln Lys Val Ile Ser Lys Pro Ile Ser Glu His
```

```
                 275                 280                 285

Lys Ile Leu Phe Leu Gly Ala Gly Glu Ala Ala Leu Gly Ile Ala Asn
        290                 295                 300

Leu Ile Val Met Ser Met Val Glu Asn Gly Leu Ser Glu Gln Glu Ala
    305                 310                 315                 320

Gln Lys Lys Ile Trp Met Phe Asp Lys Tyr Gly Leu Leu Val Lys Gly
                    325                 330                 335

Arg Lys Ala Lys Ile Asp Ser Tyr Gln Glu Pro Phe Thr His Ser Ala
                340                 345                 350

Pro Glu Ser Ile Pro Asp Thr Phe Glu Asp Ala Val Asn Ile Leu Lys
                355                 360                 365

Pro Ser Thr Ile Ile Gly Val Ala Gly Ala Gly Arg Leu Phe Thr Pro
        370                 375                 380

Asp Val Ile Arg Ala Met Ala Ser Ile Asn Glu Arg Pro Val Ile Phe
    385                 390                 395                 400

Ala Leu Ser Asn Pro Thr Ala Gln Ala Glu Cys Thr Ala Glu Glu Ala
                    405                 410                 415

Tyr Thr Leu Thr Glu Gly Arg Cys Leu Phe Ala Ser Gly Ser Pro Phe
                420                 425                 430

Gly Pro Val Lys Leu Thr Asp Gly Arg Val Phe Thr Pro Gly Gln Gly
                435                 440                 445

Asn Asn Val Tyr Ile Phe Pro Gly Val Ala Leu Ala Val Ile Leu Cys
        450                 455                 460

Asn Thr Arg His Ile Ser Asp Ser Val Phe Leu Glu Ala Ala Lys Ala
    465                 470                 475                 480

Leu Thr Ser Gln Leu Thr Asp Glu Glu Leu Ala Gln Gly Arg Leu Tyr
                    485                 490                 495

Pro Pro Leu Ala Asn Ile Gln Glu Val Ser Ile Asn Ile Ala Ile Lys
                500                 505                 510

Val Thr Glu Tyr Leu Tyr Ala Asn Lys Met Ala Phe Arg Tyr Pro Glu
                515                 520                 525

Pro Glu Asp Lys Ala Lys Tyr Val Lys Glu Arg Thr Trp Arg Ser Glu
                530                 535                 540

Tyr Asp Ser Leu Leu Pro Asp Val Tyr Glu Trp Pro Glu Ser Ala Ser
    545                 550                 555                 560

Ser Pro Pro Val Ile Thr Glu
                565

<210> SEQ ID NO 27
<211> LENGTH: 572
<212> TYPE: PRT
<213> ORGANISM: Rattus norvegicus

<400> SEQUENCE: 27

Met Asp Pro Arg Ala Pro Arg Arg His Thr His Gln Arg Gly Tyr
    1               5                   10                  15

Leu Leu Thr Arg Asp Pro His Leu Asn Lys Asp Leu Ala Phe Thr Leu
                    20                  25                  30

Glu Glu Arg Gln Gln Leu Lys Ile His Gly Leu Leu Pro Pro Cys Ile
                35                  40                  45

Val Asn Gln Glu Ile Gln Val Leu Arg Val Ile Lys Asn Phe Glu Arg
        50                  55                  60

Leu Asn Ser Asp Phe Asp Arg Tyr Leu Leu Leu Met Asp Leu Gln Asp
    65                  70                  75                  80
```

```
Arg Asn Glu Lys Leu Phe Tyr Ser Val Leu Met Ser Asn Val Glu Lys
                85                  90                  95

Phe Met Pro Ile Val Tyr Thr Pro Thr Val Gly Leu Ala Cys Gln Gln
            100                 105                 110

Tyr Ser Leu Ala Phe Arg Lys Pro Arg Gly Leu Phe Ile Ser Ile His
        115                 120                 125

Asp Lys Gly His Ile Ala Ser Val Leu Asn Ala Trp Pro Glu Asp Val
    130                 135                 140

Val Lys Ala Ile Val Val Thr Asp Gly Glu Arg Ile Leu Gly Leu Gly
145                 150                 155                 160

Asp Leu Gly Cys Asn Gly Met Gly Ile Pro Val Gly Lys Leu Ala Leu
                165                 170                 175

Tyr Thr Ala Cys Gly Gly Val Asn Pro Gln Gln Cys Leu Pro Ile Thr
            180                 185                 190

Leu Asp Val Gly Thr Glu Asn Glu Glu Leu Leu Lys Asp Pro Leu Tyr
        195                 200                 205

Ile Gly Leu Arg His Arg Arg Val Arg Gly Pro Glu Tyr Asp Ala Phe
    210                 215                 220

Leu Asp Glu Phe Met Glu Ala Ala Ser Ser Lys Tyr Gly Met Asn Cys
225                 230                 235                 240

Leu Ile Gln Phe Glu Asp Phe Ala Asn Leu Asn Ala Phe Arg Leu Leu
                245                 250                 255

Asn Lys Tyr Arg Asn Lys Tyr Cys Thr Phe Asn Asp Asp Ile Gln Gly
            260                 265                 270

Thr Ala Ser Val Ala Val Ala Gly Leu Leu Ala Ala Leu Arg Ile Thr
        275                 280                 285

Lys Asn Lys Leu Ser Asp Gln Thr Val Leu Phe Gln Gly Ala Gly Glu
    290                 295                 300

Ala Ala Leu Gly Ile Ala His Leu Ile Val Met Ala Met Glu Lys Glu
305                 310                 315                 320

Gly Leu Ser Lys Glu Lys Ala Arg Gln Lys Ile Trp Leu Val Asp Ser
                325                 330                 335

Lys Gly Leu Ile Val Lys Gly Arg Ala Ser Leu Thr Glu Glu Lys Glu
            340                 345                 350

Val Phe Ala His Glu His Glu Glu Met Lys Asn Leu Glu Ala Ile Val
        355                 360                 365

Gln Lys Ile Lys Pro Thr Ala Leu Ile Gly Val Ala Ala Ile Gly Gly
    370                 375                 380

Ala Phe Thr Glu Gln Ile Leu Lys Asp Met Ala Ala Phe Asn Glu Arg
385                 390                 395                 400

Pro Ile Ile Phe Ala Leu Ser Asn Pro Thr Ser Lys Ala Glu Cys Ser
                405                 410                 415

Ala Glu Glu Cys Tyr Lys Val Thr Lys Gly Arg Ala Ile Phe Ala Ser
            420                 425                 430

Gly Ser Pro Phe Asp Pro Val Thr Leu Pro Asp Gly Arg Thr Leu Phe
        435                 440                 445

Pro Gly Gln Gly Asn Asn Ser Tyr Val Phe Pro Gly Val Ala Leu Gly
    450                 455                 460

Val Val Ala Cys Gly Leu Arg His Ile Asn Asp Ser Val Phe Leu Thr
465                 470                 475                 480

Thr Ala Glu Val Ile Ser Gln Gln Val Ser Asp Lys His Leu Glu Glu
                485                 490                 495

Gly Arg Leu Tyr Pro Pro Leu Asn Thr Ile Arg Asp Val Ser Leu Lys
```

```
            500                 505                 510
Ile Ala Val Lys Ile Val Gln Asp Ala Tyr Lys Glu Lys Met Ala Thr
            515                 520                 525
Val Tyr Pro Glu Pro Gln Asn Lys Glu Glu Phe Val Ser Ser Gln Met
            530                 535                 540
Tyr Ser Thr Asn Tyr Asp Gln Ile Leu Pro Asp Cys Tyr Ser Trp Pro
545                 550                 555                 560
Glu Glu Val Gln Lys Ile Gln Thr Lys Val Asn Gln
                565                 570

<210> SEQ ID NO 28
<211> LENGTH: 572
<212> TYPE: PRT
<213> ORGANISM: Mus musculus

<400> SEQUENCE: 28

Met Glu Pro Arg Ala Pro Arg Arg His Thr His Gln Arg Gly Tyr
1               5                   10                  15
Leu Leu Thr Arg Asp Pro His Leu Asn Lys Asp Leu Ala Phe Thr Leu
                20                  25                  30
Glu Glu Arg Gln Gln Leu Asn Ile His Gly Leu Leu Pro Pro Cys Ile
            35                  40                  45
Ile Ser Gln Glu Leu Gln Val Leu Arg Ile Ile Lys Asn Phe Glu Arg
50                  55                  60
Leu Asn Ser Asp Phe Asp Arg Tyr Leu Leu Leu Met Asp Leu Gln Asp
65                  70                  75                  80
Arg Asn Glu Lys Leu Phe Tyr Ser Val Leu Met Ser Asp Val Glu Lys
                85                  90                  95
Phe Met Pro Ile Val Tyr Thr Pro Thr Val Gly Leu Ala Cys Gln Gln
                100                 105                 110
Tyr Ser Leu Ala Phe Arg Lys Pro Arg Gly Leu Phe Ile Ser Ile His
            115                 120                 125
Asp Lys Gly His Ile Ala Ser Val Leu Asn Ala Trp Pro Glu Asp Val
130                 135                 140
Val Lys Ala Ile Val Val Thr Asp Gly Glu Arg Ile Leu Gly Leu Gly
145                 150                 155                 160
Asp Leu Gly Cys Asn Gly Met Gly Ile Pro Val Gly Lys Leu Ala Leu
                165                 170                 175
Tyr Thr Ala Cys Gly Gly Val Asn Pro Gln Gln Cys Leu Pro Ile Thr
            180                 185                 190
Leu Asp Val Gly Thr Glu Asn Glu Glu Leu Leu Lys Asp Pro Leu Tyr
            195                 200                 205
Ile Gly Leu Arg His Arg Arg Val Arg Gly Pro Glu Tyr Asp Ala Phe
        210                 215                 220
Leu Asp Glu Phe Met Glu Ala Ala Ser Ser Lys Tyr Gly Met Asn Cys
225                 230                 235                 240
Leu Ile Gln Phe Glu Asp Phe Ala Asn Arg Asn Ala Phe Arg Leu Leu
                245                 250                 255
Asn Lys Tyr Arg Asn Lys Tyr Cys Thr Phe Asn Asp Asp Ile Gln Gly
            260                 265                 270
Thr Ala Ser Val Ala Val Ala Gly Leu Leu Ala Ala Leu Arg Ile Thr
        275                 280                 285
Lys Asn Lys Leu Ser Asp Gln Thr Val Leu Phe Gln Gly Ala Gly Glu
        290                 295                 300
```

Ala Ala Leu Gly Ile Ala His Leu Val Val Met Ala Met Glu Lys Glu
305                 310                 315                 320

Gly Leu Ser Lys Glu Asn Ala Arg Lys Lys Ile Trp Leu Val Asp Ser
            325                 330                 335

Lys Gly Leu Ile Val Lys Gly Arg Ala Ser Leu Thr Glu Glu Lys Glu
                340                 345                 350

Val Phe Ala His Glu His Glu Glu Met Lys Asn Leu Glu Ala Ile Val
                355                 360                 365

Gln Lys Ile Lys Pro Thr Ala Leu Ile Gly Val Ala Ala Ile Gly Gly
370                 375                 380

Ala Phe Thr Glu Gln Ile Leu Lys Asp Met Ala Ala Phe Asn Glu Arg
385                 390                 395                 400

Pro Ile Ile Phe Ala Leu Ser Asn Pro Thr Ser Lys Ala Glu Cys Ser
                405                 410                 415

Ala Glu Gln Cys Tyr Lys Val Thr Lys Gly Arg Ala Ile Phe Ala Ser
                420                 425                 430

Gly Ser Pro Phe Asp Pro Val Thr Leu Pro Asp Gly Arg Thr Leu Phe
                435                 440                 445

Pro Gly Gln Gly Asn Asn Ser Tyr Val Phe Pro Gly Val Ala Leu Gly
450                 455                 460

Val Val Ala Cys Gly Leu Arg His Ile Asp Asp Lys Val Phe Leu Thr
465                 470                 475                 480

Thr Ala Glu Val Ile Ser Gln Gln Val Ser Asp Lys His Leu Gln Glu
                485                 490                 495

Gly Arg Leu Tyr Pro Pro Leu Asn Thr Ile Arg Gly Val Ser Leu Lys
                500                 505                 510

Ile Ala Val Lys Ile Val Gln Asp Ala Tyr Lys Glu Lys Met Ala Thr
515                 520                 525

Val Tyr Pro Glu Pro Gln Asn Lys Glu Glu Phe Val Ser Ser Gln Met
530                 535                 540

Tyr Ser Thr Asn Tyr Asp Gln Ile Leu Pro Asp Cys Tyr Pro Trp Pro
545                 550                 555                 560

Ala Glu Val Gln Lys Ile Gln Thr Lys Val Asn Gln
                565                 570

<210> SEQ ID NO 29
<211> LENGTH: 565
<212> TYPE: PRT
<213> ORGANISM: Escherichia coli

<400> SEQUENCE: 29

Met Glu Pro Lys Thr Lys Lys Gln Arg Ser Leu Tyr Ile Pro Tyr Ala
1               5                   10                  15

Gly Pro Val Leu Leu Glu Phe Pro Leu Leu Asn Lys Gly Ser Ala Phe
                20                  25                  30

Ser Met Glu Glu Arg Arg Asn Phe Asn Leu Leu Gly Leu Leu Pro Glu
            35                  40                  45

Val Val Glu Thr Ile Glu Glu Gln Ala Glu Arg Ala Trp Ile Gln Tyr
        50                  55                  60

Gln Gly Phe Lys Thr Glu Ile Asp Lys His Ile Tyr Leu Arg Asn Ile
65                  70                  75                  80

Gln Asp Thr Asn Glu Thr Leu Phe Tyr Arg Leu Val Asn Asn His Leu
                85                  90                  95

Asp Glu Met Met Pro Val Ile Tyr Thr Pro Thr Val Gly Ala Ala Cys
                100                 105                 110

```
Glu Arg Phe Ser Glu Ile Tyr Arg Arg Ser Arg Gly Val Phe Ile Ser
            115                 120                 125

Tyr Gln Asn Arg His Asn Met Asp Asp Ile Leu Gln Asn Val Pro Asn
        130                 135                 140

His Asn Ile Lys Val Ile Val Val Thr Asp Gly Glu Arg Ile Leu Gly
145                 150                 155                 160

Leu Gly Asp Gln Gly Ile Gly Gly Met Gly Ile Pro Ile Gly Lys Leu
                    165                 170                 175

Ser Leu Tyr Thr Ala Cys Gly Gly Ile Ser Pro Ala Tyr Thr Leu Pro
                180                 185                 190

Val Val Leu Asp Val Gly Thr Asn Asn Gln Gln Leu Leu Asn Asp Pro
            195                 200                 205

Leu Tyr Met Gly Trp Arg Asn Pro Arg Ile Thr Asp Asp Glu Tyr Tyr
        210                 215                 220

Glu Phe Val Asp Glu Phe Ile Gln Ala Val Lys Gln Arg Trp Pro Asp
225                 230                 235                 240

Val Leu Leu Gln Phe Glu Asp Phe Ala Gln Lys Asn Ala Met Pro Leu
                245                 250                 255

Leu Asn Arg Tyr Arg Asn Glu Ile Cys Ser Phe Asn Asp Asp Ile Gln
                260                 265                 270

Gly Thr Ala Ala Val Thr Val Gly Thr Leu Ile Ala Ala Ser Arg Ala
            275                 280                 285

Ala Gly Gly Gln Leu Ser Glu Lys Lys Ile Val Phe Leu Gly Ala Gly
        290                 295                 300

Ser Ala Gly Cys Gly Ile Ala Glu Met Ile Ile Ser Gln Thr Gln Arg
305                 310                 315                 320

Glu Gly Leu Ser Glu Glu Ala Ala Arg Gln Lys Val Phe Met Val Asp
                325                 330                 335

Arg Phe Gly Leu Leu Thr Asp Lys Met Pro Asn Leu Leu Pro Phe Gln
                340                 345                 350

Thr Lys Leu Val Gln Lys Arg Glu Asn Leu Ser Asp Trp Asp Thr Asp
        355                 360                 365

Ser Asp Val Leu Ser Leu Leu Asp Val Val Arg Asn Val Lys Pro Asp
370                 375                 380

Ile Leu Ile Gly Val Ser Gly Gln Thr Gly Leu Phe Thr Glu Glu Ile
385                 390                 395                 400

Ile Arg Glu Met His Lys His Cys Pro Arg Pro Ile Val Met Pro Leu
                405                 410                 415

Ser Asn Pro Thr Ser Arg Val Glu Ala Thr Pro Gln Asp Ile Ile Ala
            420                 425                 430

Trp Thr Glu Gly Asn Ala Leu Val Ala Thr Gly Ser Pro Phe Asn Pro
        435                 440                 445

Val Val Trp Lys Asp Lys Ile Tyr Pro Ile Ala Gln Cys Asn Asn Ala
450                 455                 460

Phe Ile Phe Pro Gly Ile Gly Leu Gly Val Ile Ala Ser Gly Ala Ser
465                 470                 475                 480

Arg Ile Thr Asp Glu Met Leu Met Ser Ala Ser Glu Thr Leu Ala Gln
                485                 490                 495

Tyr Ser Pro Leu Val Leu Asn Gly Glu Gly Met Val Leu Pro Glu Leu
                500                 505                 510

Lys Asp Ile Gln Lys Val Ser Arg Ala Ile Ala Phe Ala Val Gly Lys
        515                 520                 525
```

```
Met Ala Gln Gln Gln Gly Val Ala Val Lys Thr Ser Ala Glu Ala Leu
            530                 535                 540

Gln Gln Ala Ile Asp Asp Asn Phe Trp Gln Ala Glu Tyr Arg Asp Tyr
545                 550                 555                 560

Arg Arg Thr Ser Ile
                565

<210> SEQ ID NO 30
<211> LENGTH: 366
<212> TYPE: PRT
<213> ORGANISM: Yarrowia lipolytica

<400> SEQUENCE: 30

Met Leu Arg Thr Ala Tyr Leu Ala Lys Ala Ala Ser Ala Leu Pro Lys
1               5                   10                  15

Arg Thr Leu Ala Thr Asn Ala Arg Thr Met Phe Gln Pro Lys Glu Tyr
            20                  25                  30

Gly Ser Lys Tyr Thr Val Thr Leu Ile Pro Gly Asp Gly Ile Gly Asn
        35                  40                  45

Glu Ile Thr Asp Ala Val Lys Thr Ile Phe Lys Thr Ile Ser Val Pro
50                  55                  60

Ile Asp Trp Glu Val Val Asn Val Thr Gly Val Gly Glu Asn His Leu
65                  70                  75                  80

Asp Gly Tyr Glu Glu Ala Ile Arg Ser Ile Asn Arg Asn Lys Val Ala
                85                  90                  95

Ile Lys Gly Ile Leu His Thr Pro Val Glu Lys His Gly His Thr Ser
            100                 105                 110

Phe Asn Val Ala Leu Arg Arg Glu Leu Asp Ile Phe Ala Ser Leu Val
        115                 120                 125

Leu Ile Lys Asn Ile Pro Gly Val Gln Thr Arg Leu Asp Gly Ile Asp
130                 135                 140

Met Ala Leu Ile Arg Glu Asn Thr Glu Gly Glu Tyr Ser Gly Leu Glu
145                 150                 155                 160

His Ser Pro Val Pro Gly Val Val Glu Ser Ile Lys Val Ile Thr Lys
                165                 170                 175

Arg Lys Ser Glu Arg Ile Ala Arg Phe Ala Phe Asp Phe Ala Leu Lys
            180                 185                 190

Asn Asn Arg His Lys Val Thr Ala Ile His Lys Ala Asn Ile Met Lys
        195                 200                 205

Leu Ala Asp Gly Leu Phe Arg Asn Thr Cys Lys Glu Val Ser Ala Glu
210                 215                 220

Tyr Pro Glu Ile Gln Tyr Gly Asp Met Ile Val Asp Asn Ala Ser Met
225                 230                 235                 240

Gln Ala Val Ser Trp Pro Gln Gln Phe Asp Val Leu Val Thr Pro Asn
                245                 250                 255

Leu Tyr Gly Thr Ile Leu Ser Asn Ile Gly Ala Gly Leu Val Gly Gly
            260                 265                 270

Pro Gly Leu Val Pro Gly Val Asn Leu Gly Thr Glu His Ala Val Phe
        275                 280                 285

Glu Pro Gly Cys Arg His Val Gly Leu Asp Ile Lys Gly Arg Gly Thr
290                 295                 300

Ala Asn Pro Thr Ala Met Ile Leu Ser Ser Ala Met Leu Leu Arg His
305                 310                 315                 320

Leu Asn Leu Asp Asp Phe Ala Asp Val Ile Ser Lys Ala Thr Tyr Asp
                325                 330                 335
```

Val Leu Ala Glu Gly Gln Val Arg Thr Pro Asp Leu Gly Gly Asn Ser
            340                 345                 350

Thr Thr Asp Glu Phe Thr Met Ala Val Ile Asn Lys Leu Gln
        355                 360                 365

<210> SEQ ID NO 31
<211> LENGTH: 146
<212> TYPE: PRT
<213> ORGANISM: Saccharomyces cerevisiae

<400> SEQUENCE: 31

Met Ser Ala Ser Ala Phe Asn Phe Ala Phe Arg Arg Phe Trp Asn Ser
1               5                   10                  15

Glu Thr Gly Pro Lys Thr Val His Phe Trp Ala Pro Thr Leu Lys Trp
            20                  25                  30

Gly Leu Val Phe Ala Gly Leu Asn Asp Ile Lys Arg Pro Val Glu Lys
        35                  40                  45

Val Ser Gly Ala Gln Asn Leu Ser Leu Leu Ala Thr Ala Leu Ile Trp
    50                  55                  60

Thr Arg Trp Ser Phe Val Ile Lys Pro Lys Asn Tyr Leu Leu Ala Ser
65                  70                  75                  80

Val Asn Phe Phe Leu Gly Cys Thr Ala Gly Tyr His Leu Thr Arg Ile
                85                  90                  95

Ala Asn Phe Arg Ile Arg Asn Gly Asp Ser Phe Lys Gln Val Ile His
            100                 105                 110

Tyr Ile Ile Lys Gly Glu Thr Pro Ala Ala Val Ala Ala Lys Gln Thr
        115                 120                 125

Ala Ser Thr Ser Met Asn Lys Gly Val Ile Gly Thr Asn Pro Pro Ile
    130                 135                 140

Thr His
145

<210> SEQ ID NO 32
<211> LENGTH: 338
<212> TYPE: PRT
<213> ORGANISM: Helicoverpa zea

<400> SEQUENCE: 32

Met Ala Gln Ser Tyr Gln Ser Thr Thr Val Leu Ser Glu Glu Lys Glu
1               5                   10                  15

Leu Thr Leu Gln His Leu Val Pro Gln Ala Ser Pro Arg Lys Tyr Gln
            20                  25                  30

Ile Val Tyr Pro Asn Leu Ile Thr Phe Gly Tyr Trp His Ile Ala Gly
        35                  40                  45

Leu Tyr Gly Leu Tyr Leu Cys Phe Thr Ser Ala Lys Trp Ala Thr Ile
    50                  55                  60

Leu Phe Ser Tyr Ile Leu Phe Val Leu Ala Glu Ile Gly Ile Thr Ala
65                  70                  75                  80

Gly Ala His Arg Leu Trp Ala His Lys Thr Tyr Lys Ala Lys Leu Pro
                85                  90                  95

Leu Glu Ile Leu Leu Met Val Phe Asn Ser Ile Ala Phe Gln Asn Ser
            100                 105                 110

Ala Ile Asp Trp Val Arg Asp His Arg Leu His His Lys Tyr Ser Asp
        115                 120                 125

Thr Asp Ala Asp Pro His Asn Ala Ser Arg Gly Phe Phe Tyr Ser His
    130                 135                 140

```
Val Gly Trp Leu Leu Val Arg Lys His Pro Glu Val Lys Arg Gly
145                 150                 155                 160

Lys Glu Leu Asn Met Ser Asp Ile Tyr Asn Asn Pro Val Leu Arg Phe
                165                 170                 175

Gln Lys Lys Tyr Ala Ile Pro Phe Ile Gly Ala Val Cys Phe Ala Leu
            180                 185                 190

Pro Thr Met Ile Pro Val Tyr Phe Trp Gly Glu Thr Trp Ser Asn Ala
            195                 200                 205

Trp His Ile Thr Met Leu Arg Tyr Ile Met Asn Leu Asn Val Thr Phe
        210                 215                 220

Leu Val Asn Ser Ala Ala His Ile Trp Gly Asn Lys Pro Tyr Asp Ala
225                 230                 235                 240

Lys Ile Leu Pro Ala Gln Asn Val Ala Val Ser Val Ala Thr Gly Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Leu Thr Thr Lys Phe Ile Asp
            275                 280                 285

Leu Phe Ala Ala Ile Gly Trp Ala Tyr Asp Leu Lys Thr Val Ser Glu
        290                 295                 300

Asp Met Ile Lys Gln Arg Ile Lys Arg Thr Gly Asp Gly Thr Asp Leu
305                 310                 315                 320

Trp Gly His Glu Gln Asn Cys Asp Glu Val Trp Asp Val Lys Asp Lys
                325                 330                 335

Ser Ser

<210> SEQ ID NO 33
<211> LENGTH: 353
<212> TYPE: PRT
<213> ORGANISM: Helicoverpa zea

<400> SEQUENCE: 33

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Pro Val Gln Lys
                20                  25                  30

Ala Asp Asn Arg Pro Lys Gln Leu Val Trp Arg Asn Ile Leu Leu Phe
            35                  40                  45

Ala Tyr Leu His Leu Ala Ala Leu Tyr Gly Gly Tyr Leu Phe Leu Phe
        50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Arg Val Ile Leu Val Ile Phe Asn
                100                 105                 110

Thr Val Ala Phe Gln Asp Ala Ala Met Asp Trp Ala Arg Asp His Arg
            115                 120                 125

Met His His Lys Tyr Ser Glu Thr Asp Ala Asp Pro His Asn Ala Thr
        130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175
```

Ala Asp Pro Ile Leu Arg Phe Gln Lys Lys Tyr Tyr Leu Ile Leu Met
            180                 185                 190

Pro Leu Ala Cys Phe Val Met Pro Thr Val Ile Pro Val Tyr Phe Trp
            195                 200                 205

Gly Glu Thr Trp Thr Asn Ala Phe Phe Val Ala Ala Met Phe Arg Tyr
            210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Leu
                245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Leu Gly Asn Asn Lys Leu
            275                 280                 285

Asn Phe Thr Thr Thr Phe Ile Asn Phe Phe Ala Lys Ile Gly Trp Ala
            290                 295                 300

Tyr Asp Leu Lys Thr Val Ser Asp Asp Ile Val Lys Asn Arg Val Lys
305                 310                 315                 320

Arg Thr Gly Asp Gly Ser His His Leu Trp Gly Trp Gly Asp Glu Asn
                325                 330                 335

Gln Ser Lys Glu Glu Ile Asp Ala Ala Ile Arg Ile Asn Pro Lys Asp
            340                 345                 350

Asp

<210> SEQ ID NO 34
<211> LENGTH: 623
<212> TYPE: PRT
<213> ORGANISM: Arabidopsis thaliana

<400> SEQUENCE: 34

Met Gly Ile Ala Asn Lys Leu Arg Leu Ser Ser Ser Ser Leu Ser Arg
1               5                   10                  15

Ile Leu His Arg Arg Ile Leu Tyr Ser Ser Ala Val Arg Ser Phe Thr
            20                  25                  30

Thr Ser Glu Gly His Arg Pro Thr Ile Val His Lys Gln Gly Leu Asp
        35                  40                  45

Ile Leu His Asp Pro Trp Phe Asn Lys Gly Thr Ala Phe Thr Met Thr
    50                  55                  60

Glu Arg Asn Arg Leu Asp Leu Arg Gly Leu Leu Pro Pro Asn Val Met
65                  70                  75                  80

Asp Ser Glu Gln Gln Ile Phe Arg Phe Met Thr Asp Leu Lys Arg Leu
                85                  90                  95

Glu Glu Gln Ala Arg Asp Gly Pro Ser Asp Pro Asn Ala Leu Ala Lys
            100                 105                 110

Trp Arg Ile Leu Asn Arg Leu His Asp Arg Asn Glu Thr Met Tyr Tyr
            115                 120                 125

Lys Val Leu Ile Asn Asn Ile Glu Glu Tyr Ala Pro Ile Val Tyr Thr
        130                 135                 140

Pro Thr Val Gly Leu Val Cys Gln Asn Tyr Ser Gly Leu Phe Arg Arg
145                 150                 155                 160

Pro Arg Gly Met Tyr Phe Ser Ala Glu Asp Arg Gly Glu Met Met Ser
                165                 170                 175

Met Val Tyr Asn Trp Pro Ala Glu Gln Val Asp Met Ile Val Val Thr
            180                 185                 190

```
Asp Gly Ser Arg Ile Leu Gly Leu Gly Asp Leu Gly Val His Gly Ile
        195                 200                 205
Gly Ile Ala Val Gly Lys Leu Asp Leu Tyr Val Ala Ala Gly Ile
    210                 215                 220
Asn Pro Gln Arg Val Leu Pro Val Met Ile Asp Val Gly Thr Asn Asn
225                 230                 235                 240
Glu Lys Leu Arg Asn Asp Pro Met Tyr Leu Gly Leu Gln Gln Arg Arg
                245                 250                 255
Leu Glu Asp Asp Asp Tyr Ile Asp Val Ile Asp Glu Phe Met Glu Ala
            260                 265                 270
Val Tyr Thr Arg Trp Pro His Val Ile Val Gln Phe Glu Asp Phe Gln
        275                 280                 285
Ser Lys Trp Ala Phe Lys Leu Leu Gln Arg Tyr Arg Cys Thr Tyr Arg
    290                 295                 300
Met Phe Asn Asp Asp Val Gln Gly Thr Ala Gly Val Ala Ile Ala Gly
305                 310                 315                 320
Leu Leu Gly Ala Val Arg Ala Gln Gly Arg Pro Met Ile Asp Phe Pro
                325                 330                 335
Lys Met Lys Ile Val Val Ala Gly Ala Gly Ser Ala Gly Ile Gly Val
            340                 345                 350
Leu Asn Ala Ala Arg Lys Thr Met Ala Arg Met Leu Gly Asn Thr Glu
        355                 360                 365
Thr Ala Phe Asp Ser Ala Gln Ser Gln Phe Trp Val Asp Ala Gln
    370                 375                 380
Gly Leu Ile Thr Glu Gly Arg Glu Asn Ile Asp Pro Glu Ala Gln Pro
385                 390                 395                 400
Phe Ala Arg Lys Thr Lys Glu Met Glu Arg Gln Gly Leu Lys Glu Gly
                405                 410                 415
Ala Thr Leu Val Glu Val Val Arg Glu Val Lys Pro Asp Val Leu Leu
            420                 425                 430
Gly Leu Ser Ala Val Gly Gly Leu Phe Ser Lys Glu Val Leu Glu Ala
        435                 440                 445
Met Lys Gly Ser Thr Ser Thr Arg Pro Ala Ile Phe Ala Met Ser Asn
    450                 455                 460
Pro Thr Lys Asn Ala Glu Cys Thr Pro Gln Asp Ala Phe Ser Ile Leu
465                 470                 475                 480
Gly Glu Asn Met Ile Phe Ala Ser Gly Ser Pro Phe Lys Asn Val Glu
                485                 490                 495
Phe Gly Asn Gly His Val Gly His Cys Asn Gln Gly Asn Asn Met Tyr
            500                 505                 510
Leu Phe Pro Gly Ile Gly Leu Gly Thr Leu Leu Ser Gly Ala Pro Ile
        515                 520                 525
Val Ser Asp Gly Met Leu Gln Ala Ala Ser Glu Cys Leu Ala Ala Tyr
    530                 535                 540
Met Ser Glu Glu Glu Val Leu Glu Gly Ile Ile Tyr Pro Pro Ile Ser
545                 550                 555                 560
Arg Ile Arg Asp Ile Thr Lys Arg Ile Ala Ala Val Ile Lys Glu
                565                 570                 575
Ala Ile Glu Glu Asp Leu Val Glu Gly Tyr Arg Glu Met Asp Ala Arg
            580                 585                 590
Glu Ile Gln Lys Leu Asp Glu Glu Gly Leu Met Glu Tyr Val Glu Asn
        595                 600                 605
```

```
Asn Met Trp Asn Pro Glu Tyr Pro Thr Leu Val Tyr Lys Asp Asp
    610                 615                 620

<210> SEQ ID NO 35
<211> LENGTH: 623
<212> TYPE: PRT
<213> ORGANISM: Amaranthus hypochondriacus

<400> SEQUENCE: 35

Met Leu Val Leu Cys Ser Arg Ser Arg Leu Thr Ser Ser Leu Ile Arg
1               5                   10                  15

Arg Leu Lys Asp Gln Ile Ala Asn Val Ser Asn His Arg Ser Phe Ala
            20                  25                  30

Thr Ser Glu Gly His Arg Leu Ala Ile Val Asn Lys Arg Ser Leu Asp
        35                  40                  45

Ile Leu Gln Asp Pro Trp Phe Asn Lys Gly Thr Ala Phe Ser Met Thr
    50                  55                  60

Glu Arg Asp Arg Leu Asp Leu Arg Gly Leu Leu Pro Pro Asn Val Met
65                  70                  75                  80

Thr Thr Glu Gln Gln Ile Glu Arg Phe Thr Ala Asp Leu Arg Val Leu
                85                  90                  95

Glu Leu Thr Thr Lys Asp Gly Pro Ser Asp Thr Tyr Asp Leu Ala Lys
            100                 105                 110

Trp Arg Ile Leu Asn Arg Leu His Asp Arg Asn Glu Thr Met Phe Phe
        115                 120                 125

Lys Val Leu Ile Glu Asn Ile Glu Glu Tyr Ala Pro Ile Val Ser Thr
    130                 135                 140

Pro Thr Val Gly Leu Val Cys Gln Lys Phe Ser Gly Leu Tyr Arg Arg
145                 150                 155                 160

Pro Arg Gly Met Tyr Phe Ser Ser Asp Asp Arg Gly Glu Met Met Ser
                165                 170                 175

Met Val Tyr Asn Trp Pro Ala Glu Gln Val Asp Met Ile Val Val Thr
            180                 185                 190

Asp Gly Ser Arg Ile Leu Gly Leu Gly Asp Leu Gly Val His Gly Ile
        195                 200                 205

Gly Val Ala Ile Gly Lys Leu Asp Leu Tyr Val Ala Ala Ala Gly Ile
    210                 215                 220

Asn Pro Gln Arg Val Leu Pro Val Met Ile Asp Val Gly Thr Asn Asn
225                 230                 235                 240

Glu Asp Leu Leu Lys Asn Pro Leu Tyr Leu Gly Leu Gln Lys Lys Arg
                245                 250                 255

Leu Asp Gly Glu Glu Tyr Leu Ala Val Met Asp Glu Phe Met Glu Ala
            260                 265                 270

Val Phe Thr Arg Trp Pro Asn Val Ile Val Gln Phe Glu Asp Ile Gln
        275                 280                 285

Asn Lys Trp Ala Leu Thr Leu Leu Gln Arg Tyr Arg His Lys Tyr Arg
    290                 295                 300

Thr Phe Asn Val Asp Val Gln Gly Thr Ser Gly Val Ala Ile Ala Gly
305                 310                 315                 320

Leu Leu Gly Ala Val Arg Ala Gln Gly Arg Pro Met Ile Asp Phe Pro
                325                 330                 335

Lys Gln Lys Ile Val Val Ala Gly Ala Gly Ser Ser Gly Val Gly Val
            340                 345                 350

Leu Asn Ala Ala Arg Lys Thr Met Ala Arg Met Leu Gly Asn Asp Glu
        355                 360                 365
```

```
Ser Ala Phe Asp Arg Ala Arg Ser Gln Phe Trp Val Val Asp Asp Lys
    370                 375                 380

Gly Leu Ile Thr Glu Lys Arg Ala Asn Leu Asp Pro Glu Val Gln Pro
385                 390                 395                 400

Phe Ala Trp Lys Glu Asn Glu Ile Ser Leu Gln Gly Leu Asn Glu Gly
                405                 410                 415

Ala Lys Leu Val Glu Val Val Arg Gln Val Lys Pro Asp Val Leu Leu
                420                 425                 430

Gly Leu Ser Ala Tyr Gly Gly Leu Phe Ser Lys Glu Val Leu Glu Ala
                435                 440                 445

Leu Lys Asp Ser Thr Ser Thr Arg Pro Ala Ile Phe Ala Met Ser Asn
    450                 455                 460

Pro Thr Lys Asn Ala Glu Cys Thr Pro Glu Glu Ala Phe Ser Ile Val
465                 470                 475                 480

Gly Asp His Val Val Tyr Ala Ser Gly Ser Pro Phe Lys Asp Val Asp
                485                 490                 495

Leu Gly Asn Gly Lys Ile Gly His Val Asn Gln Gly Asn Asn Met Tyr
                500                 505                 510

Leu Phe Pro Gly Ile Gly Leu Gly Val Leu Leu Ser Gly Ser Arg Ile
                515                 520                 525

Ile Ser Asp Ser Met Phe Gln Ala Ala Ala Glu Arg Leu Ala Gly Tyr
    530                 535                 540

Met Thr Asp Glu Glu Val Ile Asn Gly Val Ile Tyr Pro Ser Ile Ser
545                 550                 555                 560

Arg Ile Arg Asp Ile Thr Lys Glu Val Ala Ala Val Ile Lys Glu
                565                 570                 575

Ala Val Glu Glu Asp Leu Ala Glu Gly Tyr Arg Asp Met Asp Ala Arg
                580                 585                 590

Glu Leu Gln Lys Leu Asn Glu Glu Gln Ile Leu Glu Tyr Ile Glu Lys
                595                 600                 605

Asn Met Trp Asn Pro Glu Tyr Pro Thr Leu Val Tyr Lys Lys Arg
    610                 615                 620

<210> SEQ ID NO 36
<211> LENGTH: 770
<212> TYPE: PRT
<213> ORGANISM: Rhizobium meliloti

<400> SEQUENCE: 36

Met Asn Thr Gly Asp Lys Ala Lys Ser Gln Ala Val Pro Ala Ser Gly
1               5                   10                  15

Asp Ile Asp Gln Gln Ala Leu Phe Phe His Arg Tyr Pro Arg Pro Gly
                20                  25                  30

Lys Leu Glu Ile Gln Pro Thr Lys Pro Leu Gly Asn Gln Arg Asp Leu
            35                  40                  45

Ala Leu Ala Tyr Ser Pro Gly Val Ala Ala Pro Cys Leu Ala Ile Lys
    50                  55                  60

Asp Asn Pro Glu Thr Ala Ala Asp Phe Thr Ala Arg Ala Asn Leu Val
65                  70                  75                  80

Ala Val Val Ser Asn Gly Thr Ala Val Leu Gly Leu Gly Asn Ile Gly
                85                  90                  95

Pro Leu Ala Ser Lys Pro Val Met Glu Gly Lys Ala Val Leu Phe Lys
                100                 105                 110

Lys Phe Ala Gly Ile Asp Val Phe Asp Ile Glu Ile Asp Ala Pro Thr
```

```
            115                 120                 125
Val Asp Arg Met Val Asp Val Ile Ser Ala Leu Glu Pro Thr Phe Gly
130                 135                 140

Gly Ile Asn Leu Glu Asp Ile Lys Ala Pro Glu Cys Phe Glu Val Glu
145                 150                 155                 160

Arg Arg Leu Arg Glu Lys Met Glu Ile Pro Val Phe His Asp Asp Gln
                165                 170                 175

His Gly Thr Ala Ile Ile Val Ala Ala Ala Val Leu Asn Gly Leu Glu
            180                 185                 190

Leu Ala Gly Lys Asp Ile Ala Glu Ala Lys Ile Val Ala Ser Gly Ala
        195                 200                 205

Gly Ala Ala Ala Leu Ala Cys Leu Asn Leu Leu Val Thr Leu Gly Ala
210                 215                 220

Arg Arg Glu Asn Ile Trp Val His Asp Ile Gly Leu Val Tyr Lys
225                 230                 235                 240

Gly Arg Glu Ala Leu Met Asp Glu Trp Lys Ala Val Tyr Ala Gln Glu
                245                 250                 255

Ser Asp Asn Arg Val Leu Ala Asp Ser Ile Gly Gly Ala Asp Val Phe
            260                 265                 270

Leu Gly Leu Ser Ala Ala Gly Val Leu Lys Pro Glu Leu Leu Ala Arg
        275                 280                 285

Met Ala Glu Lys Pro Leu Ile Met Ala Leu Ala Asn Pro Thr Pro Glu
290                 295                 300

Ile Met Pro Glu Val Ala Arg Ala Ala Arg Pro Asp Ala Met Ile Cys
305                 310                 315                 320

Thr Gly Arg Ser Asp Phe Pro Asn Gln Val Asn Asn Val Leu Cys Phe
                325                 330                 335

Pro His Ile Phe Arg Gly Ala Leu Asp Cys Gly Ala Arg Thr Ile Asn
            340                 345                 350

Glu Glu Met Lys Met Ala Ala Val Arg Ala Ile Ala Gly Leu Ala Arg
        355                 360                 365

Glu Glu Pro Ser Asp Val Ala Ala Arg Ala Tyr Ser Gly Glu Thr Pro
370                 375                 380

Val Phe Gly Pro Asp Tyr Leu Ile Pro Ser Pro Phe Asp Gln Arg Leu
385                 390                 395                 400

Ile Leu Arg Ile Ala Pro Ala Val Ala Lys Ala Ala Glu Ser Gly
                405                 410                 415

Val Ala Thr Arg Pro Ile Gln Asp Phe Asp Ala Tyr Leu Asp Lys Leu
            420                 425                 430

Asn Arg Phe Val Phe Arg Ser Gly Phe Ile Met Lys Pro Val Phe Ala
        435                 440                 445

Ala Ala Lys Asn Ala Lys Asn Arg Val Ile Phe Ala Glu Gly Glu
450                 455                 460

Asp Glu Arg Val Leu Arg Ala Ala Gln Val Leu Leu Glu Glu Gly Thr
465                 470                 475                 480

Ala Lys Pro Ile Leu Ile Gly Arg Pro Gln Ile Ile Glu Thr Arg Leu
                485                 490                 495

Arg Arg Tyr Gly Leu Arg Ile Arg Pro Asp Val Asp Phe Glu Val Val
            500                 505                 510

Asn Pro Glu Gly Asp Pro Arg Tyr Arg Asp Tyr Val Asp Asp Tyr Phe
        515                 520                 525

Ala Leu Val Gly Arg Leu Gly Val Ile Pro Glu Ala Ala Arg Thr Ile
530                 535                 540
```

```
Val Arg Thr Asn Thr Thr Val Ile Gly Ala Leu Ala Val Lys Arg Gly
545                 550                 555                 560

Glu Ala Asp Ala Leu Ile Cys Gly Val Glu Gly Arg Tyr Ser Arg His
                565                 570                 575

Leu Arg Asp Val Ser Gln Ile Ile Gly Lys Arg Ser Gly Val Leu Asp
                580                 585                 590

Phe Ser Ala Leu Ser Leu Ile Ser Gln Arg Gly Ala Thr Phe Phe
                595                 600                 605

Thr Asp Thr Tyr Val Ser Phe Ser Pro Ser Ala Glu Glu Ile Ala Gln
                610                 615                 620

Thr Thr Val Met Ala Ala Asn Glu Ile Arg Arg Phe Gly Ile Thr Pro
625                 630                 635                 640

Arg Ala Ala Leu Val Ser His Ser Asn Phe Gly Ser Arg Asp Ser Glu
                645                 650                 655

Ser Ala Phe Lys Met Arg Thr Ala Leu Gln Leu Val Arg Glu Leu Ala
                660                 665                 670

Pro Asp Leu Glu Val Asp Gly Glu Met His Gly Asp Ser Ala Ile Ser
                675                 680                 685

Glu Val Leu Arg Gln Arg Val Met Pro Asp Ser Thr Leu Asn Gly Glu
                690                 695                 700

Ala Asn Leu Leu Val Phe Pro Asn Leu Asp Ala Ala Asn Ile Thr Leu
705                 710                 715                 720

Gly Val Val Lys Thr Met Thr Asp Ser Leu His Val Gly Pro Ile Leu
                725                 730                 735

Leu Gly Ser Ala Leu Pro Ala His Ile Leu Ser Pro Ser Val Thr Ser
                740                 745                 750

Arg Gly Val Val Asn Met Ala Ala Leu Ala Val Val Glu Ser Ser His
                755                 760                 765

Pro Val
    770

<210> SEQ ID NO 37
<211> LENGTH: 626
<212> TYPE: PRT
<213> ORGANISM: Solanum tuberosum

<400> SEQUENCE: 37

Met Ala Ile Phe Ser Asn Gln Met Arg Leu Ser Ser Thr Leu Leu Lys
1               5                   10                  15

Arg Leu His Gln Arg Val Ala Ala Val Asn Ser Ser Ser Arg
                20                  25                  30

Asn Phe Thr Thr Thr Glu Gly His Arg Pro Thr Ile Val His Lys Arg
                35                  40                  45

Ser Leu Asp Ile Leu His Asp Pro Trp Phe Asn Lys Gly Thr Ala Phe
50                  55                  60

Ser Phe Thr Glu Arg Asp Arg Leu His Ile Arg Gly Leu Leu Pro Pro
65                  70                  75                  80

Asn Val Met Ser Phe Glu Gln Gln Ile Ala Arg Phe Met Ala Asp Leu
                85                  90                  95

Lys Arg Leu Glu Val Gln Ala Arg Asp Gly Pro Ser Asp Pro Tyr Val
                100                 105                 110

Leu Ala Lys Trp Arg Ile Leu Asn Arg Leu His Asp Arg Asn Glu Thr
                115                 120                 125

Leu Tyr Tyr Lys Val Leu Met Glu Asn Ile Glu Glu Tyr Ala Pro Ile
```

```
            130                 135                 140
Val Tyr Thr Pro Thr Val Gly Leu Val Cys Gln Lys Tyr Ser Gly Leu
145                 150                 155                 160

Phe Arg Arg Pro Arg Gly Met Tyr Phe Ser Ala Glu Asp Arg Gly Glu
                165                 170                 175

Met Met Ser Met Val Tyr Asn Trp Pro Ala Asp Gln Val Asp Met Ile
                180                 185                 190

Val Val Thr Asp Gly Ser Arg Ile Leu Gly Leu Gly Asp Leu Gly Ile
                195                 200                 205

Gln Gly Ile Gly Ile Ala Ile Gly Lys Leu Asp Leu Tyr Val Ala Ala
210                 215                 220

Ala Gly Ile Asn Pro Gln Arg Val Leu Pro Val Met Ile Asp Val Gly
225                 230                 235                 240

Thr Asp Asn Glu Asn Leu Leu Lys Asp Pro Leu Tyr Leu Gly Leu Gln
                245                 250                 255

Asp His Arg Leu Asp Gly Glu Glu Tyr Ile Glu Val Ile Asp Glu Phe
                260                 265                 270

Met Glu Ala Val Phe Thr Arg Trp Pro His Val Ile Val Gln Phe Glu
                275                 280                 285

Asp Phe Gln Ser Lys Trp Ala Phe Lys Leu Leu Gln Arg Tyr Arg Asn
                290                 295                 300

Asn Tyr Arg Met Phe Asn Asp Asp Ile Gln Gly Thr Ala Gly Val Ala
305                 310                 315                 320

Ile Ala Gly Leu Leu Gly Ala Val Arg Ala Gln Gly Arg Pro Met Ile
                325                 330                 335

Asp Phe Pro Lys Met Lys Ile Val Val Ala Gly Ala Gly Ser Ala Gly
                340                 345                 350

Ile Gly Val Leu Asn Ala Ala Arg Lys Thr Met Ala Arg Met Leu Gly
                355                 360                 365

Asn Thr Glu Ile Ala Phe Glu Ser Ala Arg Ser Gln Phe Trp Val Val
                370                 375                 380

Asp Ala Lys Gly Leu Ile Thr Glu Ala Arg Glu Asn Val Asp Pro Asp
385                 390                 395                 400

Ala Arg Pro Phe Ala Arg Lys Ile Lys Glu Ile Glu Arg Gln Gly Leu
                405                 410                 415

Ser Glu Gly Ala Thr Leu Ala Glu Val Val Arg Glu Val Lys Pro Asp
                420                 425                 430

Val Leu Leu Gly Leu Ser Ala Cys Gly Gly Leu Phe Ser Lys Glu Val
                435                 440                 445

Leu Glu Ala Leu Lys His Ser Thr Ser Thr Arg Pro Ala Ile Phe Pro
450                 455                 460

Met Ser Asn Pro Thr Arg Asn Ala Glu Cys Thr Pro Glu Glu Ala Phe
465                 470                 475                 480

Ser Ile Leu Gly Glu Asn Ile Ile Phe Ala Ser Gly Ser Pro Phe Lys
                485                 490                 495

Asp Val Asp Leu Gly Asn Gly His Val Gly His Cys Asn Gln Ala Asn
                500                 505                 510

Asn Met Phe Leu Phe Pro Gly Ile Gly Leu Gly Thr Leu Leu Ser Gly
                515                 520                 525

Ser Arg Ile Val Ser Asp Gly Met Leu Gln Ala Ala Ala Glu Cys Leu
                530                 535                 540

Ala Ala Tyr Ile Thr Glu Glu Val Leu Lys Gly Ile Ile Tyr Pro
545                 550                 555                 560
```

-continued

Ser Ile Ser Arg Ile Arg Asp Ile Thr Lys Glu Val Ala Ala Val
                565                 570             575

Val Lys Glu Ala Ile Glu Glu Asp Leu Ala Glu Gly Tyr Arg Glu Met
            580                 585                 590

Asp Ser Arg Glu Leu Arg Lys Leu Asp Glu Ala Gln Ile Ser Glu Phe
        595                 600                 605

Val Glu Asn Asn Met Trp Ser Pro Asp Tyr Pro Thr Leu Val Tyr Lys
    610                 615                 620

Lys Asp
625

<210> SEQ ID NO 38
<211> LENGTH: 604
<212> TYPE: PRT
<213> ORGANISM: Homo sapiens

<400> SEQUENCE: 38

Met Gly Ala Ala Leu Gly Thr Gly Thr Arg Leu Ala Pro Trp Pro Gly
1               5                   10                  15

Arg Ala Cys Gly Ala Leu Pro Arg Trp Thr Pro Thr Ala Pro Ala Gln
            20                  25                  30

Gly Cys His Ser Lys Pro Gly Pro Ala Arg Pro Val Pro Leu Lys Lys
        35                  40                  45

Arg Gly Tyr Asp Val Thr Arg Asn Pro His Leu Asn Lys Gly Met Ala
    50                  55                  60

Phe Thr Leu Glu Glu Arg Leu Gln Leu Gly Ile His Gly Leu Ile Pro
65                  70                  75                  80

Pro Cys Phe Leu Ser Gln Asp Val Gln Leu Leu Arg Ile Met Arg Tyr
                85                  90                  95

Tyr Glu Arg Gln Gln Ser Asp Leu Asp Lys Tyr Ile Ile Leu Met Thr
            100                 105                 110

Leu Gln Asp Arg Asn Glu Lys Leu Phe Tyr Arg Val Leu Thr Ser Asp
        115                 120                 125

Val Glu Lys Phe Met Pro Ile Val Tyr Thr Pro Thr Val Gly Leu Ala
    130                 135                 140

Cys Gln His Tyr Gly Leu Thr Phe Arg Arg Pro Arg Gly Leu Phe Ile
145                 150                 155                 160

Thr Ile His Asp Lys Gly His Leu Ala Thr Met Leu Asn Ser Trp Pro
                165                 170                 175

Glu Asp Asn Ile Lys Ala Val Val Val Thr Asp Gly Glu Arg Ile Leu
            180                 185                 190

Gly Leu Gly Asp Leu Gly Cys Tyr Gly Met Gly Ile Pro Val Gly Lys
        195                 200                 205

Leu Ala Leu Tyr Thr Ala Cys Gly Gly Val Asn Pro Gln Gln Cys Leu
    210                 215                 220

Pro Val Leu Leu Asp Val Gly Thr Asn Asn Glu Glu Leu Leu Arg Asp
225                 230                 235                 240

Pro Leu Tyr Ile Gly Leu Lys His Gln Arg Val His Gly Lys Ala Tyr
                245                 250                 255

Asp Asp Leu Leu Asp Glu Phe Met Gln Ala Val Thr Asp Lys Phe Gly
            260                 265                 270

Ile Asn Cys Leu Ile Gln Phe Glu Asp Phe Ala Asn Ala Asn Ala Phe
        275                 280                 285

Arg Leu Leu Asn Lys Tyr Arg Asn Lys Tyr Cys Met Phe Asn Asp Asp

```
        290                 295                 300
Ile Gln Gly Thr Ala Ser Val Ala Val Ala Gly Ile Leu Ala Ala Leu
305                 310                 315                 320

Arg Ile Thr Lys Asn Lys Leu Ser Asn His Val Phe Val Phe Gln Gly
                325                 330                 335

Ala Gly Glu Ala Ala Met Gly Ile Ala His Leu Leu Val Met Ala Leu
                340                 345                 350

Glu Lys Glu Gly Val Pro Lys Ala Glu Ala Thr Arg Lys Ile Trp Met
                355                 360                 365

Val Asp Ser Lys Gly Leu Ile Val Lys Gly Arg Ser His Leu Asn His
370                 375                 380

Glu Lys Glu Met Phe Ala Gln Asp His Pro Glu Val Asn Ser Leu Glu
385                 390                 395                 400

Glu Val Val Arg Leu Val Lys Pro Thr Ala Ile Ile Gly Val Ala Ala
                405                 410                 415

Ile Ala Gly Ala Phe Thr Glu Gln Ile Leu Arg Asp Met Ala Ser Phe
                420                 425                 430

His Glu Arg Pro Ile Ile Phe Ala Leu Ser Asn Pro Thr Ser Lys Ala
                435                 440                 445

Glu Cys Thr Ala Glu Lys Cys Tyr Arg Val Thr Glu Gly Arg Gly Ile
                450                 455                 460

Phe Ala Ser Gly Ser Pro Phe Lys Ser Val Thr Leu Glu Asp Gly Lys
465                 470                 475                 480

Thr Phe Ile Pro Gly Gln Gly Asn Asn Ala Tyr Val Phe Pro Gly Val
                485                 490                 495

Ala Leu Gly Val Ile Ala Gly Gly Ile Arg His Ile Pro Asp Glu Ile
                500                 505                 510

Phe Leu Leu Thr Ala Glu Gln Ile Ala Gln Glu Val Ser Glu Gln His
                515                 520                 525

Leu Ser Gln Gly Arg Leu Tyr Pro Pro Leu Ser Thr Ile Arg Asp Val
530                 535                 540

Ser Leu Arg Ile Ala Ile Lys Val Leu Asp Tyr Ala Tyr Lys His Asn
545                 550                 555                 560

Leu Ala Ser Tyr Tyr Pro Glu Pro Lys Asp Lys Glu Ala Phe Val Arg
                565                 570                 575

Ser Leu Val Tyr Thr Pro Asp Tyr Asp Ser Phe Thr Leu Asp Ser Tyr
                580                 585                 590

Thr Trp Pro Lys Glu Ala Met Asn Val Gln Thr Val
                595                 600

<210> SEQ ID NO 39
<211> LENGTH: 1497
<212> TYPE: DNA
<213> ORGANISM: Yarrowia lipolytica

<400> SEQUENCE: 39
atgactggca ccttacccaa gttcggcgac ggaaccacca ttgtggttct tggagcctcc      60
ggcgacctcg ctaagaagaa gaccttcccc gccctcttcg cctttaccg aaacggcctg     120 ctgcccaaaa atgttgaaat catcggctac gcacggtcga aatgactca ggaggagtac     180 cacgagcgaa tcagccacta cttcaagacc ccgacgacc agtccaagga gcaggccaag     240
aagttccttg agaacacctg ctacgtccag ggccttacg acggtgccga gggctaccag     300
cgactgaatg aaaagattga ggagtttgag aagaagaagc ccgagcccca ctaccgtctt     360
```

```
ttctacctgg ctctgccccc cagcgtcttc cttgaggctg ccaacggtct gaagaagtat      420
gtctaccccg gcgagggcaa ggcccgaatc atcatcgaga agccctttgg ccacgacctg      480
gcctcgtcac gagagctcca ggacggcctt gctcctctct ggaaggagtc tgagatcttc      540
cgaatcgacc actacctcgg aaaggagatg gtcaagaacc tcaacattct gcgatttggc      600
aaccagttcc tgtccgccgt gtgggacaag aacaccattt ccaacgtcca gatctccttc      660
aaggagccct ttggcactga gggccgaggt ggatacttca cgacattgg aatcatccga       720
gacgttattc agaaccatct gttgcaggtt ctgtccattc tagccatgga gcgacccgtc      780
actttcggcg ccgaggacat tcgagatgag aaggtcaagg tgctccgatg tgtcgacatt      840
ctcaacattg acgacgtcat tctcggccag tacggcccct ctgaagacgg aaagaagccc      900
ggatacaccg atgacgatgg cgttcccgat gactcccgag ctgtgacctt tgctgctctc      960
catctccaga tccacaacga cagatgggag ggtgttcctt tcatcctccg agccggtaag     1020
gctctggacg agggcaaggt cgagatccga gtgcagttcc gagacgtgac caagggcgtt     1080
gtggaccatc tgcctcgaaa tgagctcgtc atccgaatcc agccctccga gtccatctac     1140
atgaagatga actccaagct gcctggcctt actgccaaga acattgtcac cgacctggat     1200
ctgacctaca accgacgata tcggacgtg cgaatccctg aggcttacga gtctctcatt      1260
ctggactgcc tcaagggtga ccacaccaac tttgtgcgaa cgacgagct ggacatttcc      1320
tggaagattt tcaccgatct gctgcacaag attgacgagg acaagagcat tgtgcccgag     1380
aagtacgcct acggctctcg tggccccgag cgactcaagc agtggctccg agaccgaggc     1440
tacgtgcgaa acggcaccga gctgtaccaa tggcctgtca ccaagggctc ctcgtga       1497
```

<210> SEQ ID NO 40
<211> LENGTH: 498
<212> TYPE: PRT
<213> ORGANISM: Yarrowia lipolytica

<400> SEQUENCE: 40

```
Met Thr Gly Thr Leu Pro Lys Phe Gly Asp Gly Thr Thr Ile Val Val
1               5                   10                  15

Leu Gly Ala Ser Gly Asp Leu Ala Lys Lys Thr Phe Pro Ala Leu
            20                  25                  30

Phe Gly Leu Tyr Arg Asn Gly Leu Leu Pro Lys Asn Val Glu Ile Ile
        35                  40                  45

Gly Tyr Ala Arg Ser Lys Met Thr Gln Glu Glu Tyr His Glu Arg Ile
    50                  55                  60

Ser His Tyr Phe Lys Thr Pro Asp Asp Gln Ser Lys Glu Gln Ala Lys
65                  70                  75                  80

Lys Phe Leu Glu Asn Thr Cys Tyr Val Gln Gly Pro Tyr Asp Gly Ala
                85                  90                  95

Glu Gly Tyr Gln Arg Leu Asn Glu Lys Ile Glu Glu Phe Glu Lys Lys
            100                 105                 110

Lys Pro Glu Pro His Tyr Arg Leu Phe Tyr Leu Ala Leu Pro Pro Ser
        115                 120                 125

Val Phe Leu Glu Ala Ala Asn Gly Leu Lys Lys Tyr Val Tyr Pro Gly
    130                 135                 140

Glu Gly Lys Ala Arg Ile Ile Ile Glu Lys Pro Phe Gly His Asp Leu
145                 150                 155                 160

Ala Ser Ser Arg Glu Leu Gln Asp Gly Leu Ala Pro Leu Trp Lys Glu
                165                 170                 175
```

```
Ser Glu Ile Phe Arg Ile Asp His Tyr Leu Gly Lys Glu Met Val Lys
            180                 185                 190

Asn Leu Asn Ile Leu Arg Phe Gly Asn Gln Phe Leu Ser Ala Val Trp
        195                 200                 205

Asp Lys Asn Thr Ile Ser Asn Val Gln Ile Ser Phe Lys Glu Pro Phe
    210                 215                 220

Gly Thr Glu Gly Arg Gly Gly Tyr Phe Asn Asp Ile Gly Ile Ile Arg
225                 230                 235                 240

Asp Val Ile Gln Asn His Leu Leu Gln Val Leu Ser Ile Leu Ala Met
                245                 250                 255

Glu Arg Pro Val Thr Phe Gly Ala Glu Asp Ile Arg Asp Glu Lys Val
            260                 265                 270

Lys Val Leu Arg Cys Val Asp Ile Leu Asn Ile Asp Asp Val Ile Leu
        275                 280                 285

Gly Gln Tyr Gly Pro Ser Glu Asp Gly Lys Lys Pro Gly Tyr Thr Asp
    290                 295                 300

Asp Asp Gly Val Pro Asp Asp Ser Arg Ala Val Thr Phe Ala Ala Leu
305                 310                 315                 320

His Leu Gln Ile His Asn Asp Arg Trp Glu Gly Val Pro Phe Ile Leu
                325                 330                 335

Arg Ala Gly Lys Ala Leu Asp Glu Gly Lys Val Glu Ile Arg Val Gln
            340                 345                 350

Phe Arg Asp Val Thr Lys Gly Val Asp His Leu Pro Arg Asn Glu
        355                 360                 365

Leu Val Ile Arg Ile Gln Pro Ser Glu Ser Ile Tyr Met Lys Met Asn
370                 375                 380

Ser Lys Leu Pro Gly Leu Thr Ala Lys Asn Ile Val Thr Asp Leu Asp
385                 390                 395                 400

Leu Thr Tyr Asn Arg Arg Tyr Ser Asp Val Arg Ile Pro Glu Ala Tyr
                405                 410                 415

Glu Ser Leu Ile Leu Asp Cys Leu Lys Gly Asp His Thr Asn Phe Val
            420                 425                 430

Arg Asn Asp Glu Leu Asp Ile Ser Trp Lys Ile Phe Thr Asp Leu Leu
        435                 440                 445

His Lys Ile Asp Glu Asp Lys Ser Ile Val Pro Glu Lys Tyr Ala Tyr
    450                 455                 460

Gly Ser Arg Gly Pro Glu Arg Leu Lys Gln Trp Leu Arg Asp Arg Gly
465                 470                 475                 480

Tyr Val Arg Asn Gly Thr Glu Leu Tyr Gln Trp Pro Val Thr Lys Gly
                485                 490                 495

Ser Ser

<210> SEQ ID NO 41
<211> LENGTH: 1470
<212> TYPE: DNA
<213> ORGANISM: Yarrowia lipolytica

<400> SEQUENCE: 41
atgactgaca cttcaaacat caagcctgtc gctgacattg ccctcatcgg tctcgccgtc    60
atgggccaga acctgatcct caacatggcc gaccacggct acgaggttgt tgcctacaac   120
cgaaccacct ccaaggtcga ccacttcctc gagaacgagg ccaagggaaa gtccattatt   180
ggtgctcact ctatcaagga gctgtgtgct ctgctgaagc gaccccgacg aatcattctg   240
ctcgttaagg ccggtgctgc tgtcgattct ttcatcgaac agctcctgcc ctatctcgat   300
```

-continued

```
aagggtgata tcatcattga cggtggtaac tcccacttcc ccgactccaa ccgacgatac    360
gaggagctta acgagaaggg aatcctcttt gttggttccg gtgtttccgg cggtgaggag    420
ggtgcccgat acggtccctc catcatgccc ggtggaaaca aggaggcctg gccccacatt    480
aagaagattt tccaggacat ctctgctaag gctgatggtg agccctgctg tgactgggtc    540
ggtgacgctg gtgccggcca ctttgtcaag atggttcaca acggtattga gtatggtgac    600
atgcagctta tctgcgaggc ttacgacctc atgaagcgag gtgctggttt caccaatgag    660
gagattggag acgttttcgc caagtggaac aacggtatcc tcgactcctt cctcattgag    720
atcacccgag acatcttcaa gtacgacgac ggctctggaa ctcctctcgt tgagaagatc    780
tccgacactg ctggccagaa gggtactgga agtggaccg ctatcaacgc tcttgacctt    840
ggtatgcccg tcaccctgat cggtgaggcc gtcttcgctc gatgcctttc tgccctcaag    900
caggagcgtg tccgagcttc caaggttctt gatggccccg agcccgtcaa gttcactggt    960
gacaagaagg agtttgtcga ccagctcgag caggcccttt acgcctccaa gatcatctct   1020
tacgcccagg gtttcatgct tatccgagag gccgccaaga cctacggctg ggagctcaac   1080
aacgccggta ttgccctcat gtggcgaggt ggttgcatca tccgatccgt cttccttgct   1140
gacatcacca aggcttaccg acaggacccc aacctcgaga acctgctgtt caacgacttc   1200
ttcaagaacg ccatctccaa ggccaacccc tcttggcgag ctaccgtggc caaggctgtc   1260
acctggggtg ttcccactcc cgcctttgcc tcggctctgg ctttctacga cggttaccga   1320
tctgccaagc tccccgctaa cctgctccag gcccagcgag actacttcgg cgcccacacc   1380
taccagctcc tcgatggtga tggaaagtgg atccacacca actggaccgg ccgaggtggt   1440
gaggtttctt cttccactta cgatgcttaa                                    1470
```

<210> SEQ ID NO 42
<211> LENGTH: 489
<212> TYPE: PRT
<213> ORGANISM: Yarrowia lipolytica

<400> SEQUENCE: 42

```
Met Thr Asp Thr Ser Asn Ile Lys Pro Val Ala Asp Ile Ala Leu Ile
1               5                   10                  15

Gly Leu Ala Val Met Gly Gln Asn Leu Ile Leu Asn Met Ala Asp His
            20                  25                  30

Gly Tyr Glu Val Val Ala Tyr Asn Arg Thr Thr Ser Lys Val Asp His
        35                  40                  45

Phe Leu Glu Asn Glu Ala Lys Gly Lys Ser Ile Ile Gly Ala His Ser
    50                  55                  60

Ile Lys Glu Leu Cys Ala Leu Leu Lys Arg Pro Arg Arg Ile Ile Leu
65                  70                  75                  80

Leu Val Lys Ala Gly Ala Ala Val Asp Ser Phe Ile Glu Gln Leu Leu
                85                  90                  95

Pro Tyr Leu Asp Lys Gly Asp Ile Ile Ile Asp Gly Gly Asn Ser His
            100                 105                 110

Phe Pro Asp Ser Asn Arg Arg Tyr Glu Glu Leu Asn Glu Lys Gly Ile
        115                 120                 125

Leu Phe Val Gly Ser Gly Val Ser Gly Gly Glu Glu Gly Ala Arg Tyr
    130                 135                 140

Gly Pro Ser Ile Met Pro Gly Gly Asn Lys Glu Ala Trp Pro His Ile
145                 150                 155                 160
```

Lys Lys Ile Phe Gln Asp Ile Ser Ala Lys Ala Asp Gly Glu Pro Cys
                165                 170                 175

Cys Asp Trp Val Gly Asp Ala Gly Ala Gly His Phe Val Lys Met Val
            180                 185                 190

His Asn Gly Ile Glu Tyr Gly Asp Met Gln Leu Ile Cys Glu Ala Tyr
        195                 200                 205

Asp Leu Met Lys Arg Gly Ala Gly Phe Thr Asn Glu Glu Ile Gly Asp
    210                 215                 220

Val Phe Ala Lys Trp Asn Gly Ile Leu Asp Ser Phe Leu Ile Glu
225                 230                 235                 240

Ile Thr Arg Asp Ile Phe Lys Tyr Asp Asp Gly Ser Gly Thr Pro Leu
                245                 250                 255

Val Glu Lys Ile Ser Asp Thr Ala Gly Gln Lys Gly Thr Gly Lys Trp
            260                 265                 270

Thr Ala Ile Asn Ala Leu Asp Leu Gly Met Pro Val Thr Leu Ile Gly
        275                 280                 285

Glu Ala Val Phe Ala Arg Cys Leu Ser Ala Leu Lys Gln Glu Arg Val
    290                 295                 300

Arg Ala Ser Lys Val Leu Asp Gly Pro Glu Pro Val Lys Phe Thr Gly
305                 310                 315                 320

Asp Lys Lys Glu Phe Val Asp Gln Leu Glu Gln Ala Leu Tyr Ala Ser
                325                 330                 335

Lys Ile Ile Ser Tyr Ala Gln Gly Phe Met Leu Ile Arg Glu Ala Ala
            340                 345                 350

Lys Thr Tyr Gly Trp Glu Leu Asn Asn Ala Gly Ile Ala Leu Met Trp
        355                 360                 365

Arg Gly Gly Cys Ile Ile Arg Ser Val Phe Leu Ala Asp Ile Thr Lys
    370                 375                 380

Ala Tyr Arg Gln Asp Pro Asn Leu Glu Asn Leu Leu Phe Asn Asp Phe
385                 390                 395                 400

Phe Lys Asn Ala Ile Ser Lys Ala Asn Pro Ser Trp Arg Ala Thr Val
                405                 410                 415

Ala Lys Ala Val Thr Trp Gly Val Pro Thr Pro Ala Phe Ala Ser Ala
            420                 425                 430

Leu Ala Phe Tyr Asp Gly Tyr Arg Ser Ala Lys Leu Pro Ala Asn Leu
        435                 440                 445

Leu Gln Ala Gln Arg Asp Tyr Phe Gly Ala His Thr Tyr Gln Leu Leu
    450                 455                 460

Asp Gly Asp Gly Lys Trp Ile His Thr Asn Trp Thr Gly Arg Gly Gly
465                 470                 475                 480

Glu Val Ser Ser Ser Thr Tyr Asp Ala
                485

<210> SEQ ID NO 43
<211> LENGTH: 747
<212> TYPE: DNA
<213> ORGANISM: Yarrowia lipolytica

<400> SEQUENCE: 43
atgcccaagg tcatctctaa gaacgaatcg caactggtcg ctgaggctgc tgccgctgag      60
atcattcgac tccagaacga gtcaattgct gccactggag ctttccatgt tgccgtatct     120
ggaggctctc tggtgtctgc tctccgaaag ggtctggtca acaactcgga gaccaagttc     180
cccaagtgga agattttctt ctccgacgaa cggctggtca agctggacga tgccgactcc     240

```
aactacggtc tcctcaagaa ggatctgctc gatcacatcc ccaaggatca gcaaccacag    300
gtcttcaccg tcaaggagtc tcttctgaac gactctgatg ccgtctccaa ggactaccag    360
gagcagattg tcaagaatgt gcctctcaac ggccagggag tgcctgtttt cgatctcatt    420
ctgctcggat gcggtcctga tggccacact tgctcgctgt ccctggaca cgctctgctc     480 aaggaggaga ccaagtttgt cgccaccatt gaggactctc ccaagcctcc tcctcgacga    540
atcaccatca ctttccccgt tctcaaggct gccaaggcca tcgctttcgt cgccgaggga    600
gccggaaagg cccctgtcct caagcagatc ttcgaggagc ccgagcccac tcttccctct    660
gccattgtca acaaggtcgc taccggaccc gttttctggt ttgtttccga ctctgccgtt    720
gagggcgtca acctctccaa gatctag                                       747
```

<210> SEQ ID NO 44
<211> LENGTH: 248
<212> TYPE: PRT
<213> ORGANISM: Yarrowia lipolytica

<400> SEQUENCE: 44

```
Met Pro Lys Val Ile Ser Lys Asn Glu Ser Gln Leu Val Ala Glu Ala
1               5                   10                  15

Ala Ala Ala Glu Ile Ile Arg Leu Gln Asn Glu Ser Ile Ala Ala Thr
            20                  25                  30

Gly Ala Phe His Val Ala Val Ser Gly Gly Ser Leu Val Ser Ala Leu
        35                  40                  45

Arg Lys Gly Leu Val Asn Asn Ser Glu Thr Lys Phe Pro Lys Trp Lys
    50                  55                  60

Ile Phe Phe Ser Asp Glu Arg Leu Val Lys Leu Asp Asp Ala Asp Ser
65                  70                  75                  80

Asn Tyr Gly Leu Leu Lys Lys Asp Leu Leu Asp His Ile Pro Lys Asp
                85                  90                  95

Gln Gln Pro Gln Val Phe Thr Val Lys Glu Ser Leu Leu Asn Asp Ser
            100                 105                 110

Asp Ala Val Ser Lys Asp Tyr Gln Glu Gln Ile Val Lys Asn Val Pro
        115                 120                 125

Leu Asn Gly Gln Gly Val Pro Val Phe Asp Leu Ile Leu Leu Gly Cys
    130                 135                 140

Gly Pro Asp Gly His Thr Cys Ser Leu Phe Pro Gly His Ala Leu Leu
145                 150                 155                 160

Lys Glu Glu Thr Lys Phe Val Ala Thr Ile Glu Asp Ser Pro Lys Pro
                165                 170                 175

Pro Pro Arg Arg Ile Thr Ile Thr Phe Pro Val Leu Lys Ala Ala Lys
            180                 185                 190

Ala Ile Ala Phe Val Ala Glu Gly Ala Gly Lys Ala Pro Val Leu Lys
        195                 200                 205

Gln Ile Phe Glu Glu Pro Glu Pro Thr Leu Pro Ser Ala Ile Val Asn
    210                 215                 220

Lys Val Ala Thr Gly Pro Val Phe Trp Phe Val Ser Asp Ser Ala Val
225                 230                 235                 240

Glu Gly Val Asn Leu Ser Lys Ile
                245
```

<210> SEQ ID NO 45
<211> LENGTH: 182
<212> TYPE: PRT
<213> ORGANISM: Talaromyces marneffei

<400> SEQUENCE: 45

Met Ser Ser Arg Val Gly Leu Arg Phe Leu Ala Asn Ser Arg Ala Ala
1               5                   10                  15

Phe Arg Asn Leu Arg Gln Asn Val Ser Asn Asn Lys Gly Phe Arg Phe
                20                  25                  30

Ser Ser Thr Glu Ala Ser Ala Ala Gly Ala Glu Gln Ser Gln Asn Ala
            35                  40                  45

Phe Gln Arg Met Trp Asn Ser Pro Val Gly Phe Lys Thr Val His Phe
50                  55                  60

Trp Ala Pro Val Met Lys Trp Ser Leu Val Ile Ala Gly Ile Ser Asp
65                  70                  75                  80

Leu Ala Arg Pro Ala Glu Lys Leu Ser Leu Thr Gln Asn Leu Ala Leu
                85                  90                  95

Val Ala Thr Gly Thr Ile Trp Thr Arg Trp Cys Phe Val Ile Thr Pro
            100                 105                 110

Lys Asn Met Leu Leu Ala Ala Val Asn Phe Phe Leu Ala Cys Thr Gly
                115                 120                 125

Ala Ala Gln Leu Thr Arg Ile Phe Leu Trp Arg Arg Ser Gln Asp Gly
130                 135                 140

Ser Ala Lys Glu Ala Val Lys Asp Met Ala Val Asp Thr Val Glu Ser
145                 150                 155                 160

Ala Lys Leu Val Thr Asp Gly Ala Lys Gly Ala Val Lys Ala Ala Glu
                165                 170                 175

Glu Lys Phe Lys Ser Ser
            180

<210> SEQ ID NO 46
<211> LENGTH: 165
<212> TYPE: PRT
<213> ORGANISM: Hanseniaspora osmophila
<220> FEATURE:
<221> NAME/KEY: SITE
<222> LOCATION: (58)..(58)
<223> OTHER INFORMATION: Xaa can be any naturally occurring amino acid

<400> SEQUENCE: 46

Met Ser Phe Thr Arg Ala Thr Ile Asn Ala Gly Lys Lys Thr Gln Trp
1               5                   10                  15

Ser Ser Lys Phe Asn Ser Phe Ile Asn Ser Glu Ala Gly Pro Lys Thr
                20                  25                  30

Ile His Phe Trp Ala Pro Thr Leu Lys Trp Gly Leu Val Phe Ala Gly
            35                  40                  45

Ile Ser Asp Leu Gln Arg Pro Val Asp Xaa Ile Ser Gly Ala Gln Asn
50                  55                  60

Leu Ser Leu Leu Ala Thr Ala Met Ile Trp Thr Arg Trp Ser Phe Val
65                  70                  75                  80

Ile Lys Pro Lys Asn Met Leu Leu Ala Ser Val Asn Phe Phe Leu Gly
                85                  90                  95

Cys Thr Ala Gly Tyr Gln Leu Gly Arg Ile Val Asp Tyr Arg Leu Lys
            100                 105                 110

Glu Gly Asp Ser Lys Ser Gln Val Leu Asp Tyr Ile Ile Asn Gly Gly
                115                 120                 125

Lys Glu Thr Gly Val Lys Ala Pro Glu Gln Glu Ala Asn Val Asn Lys
130                 135                 140

Pro Leu Ile His His Pro Leu Asn Asp Asn Asn Asp Val Val Ile Gly

Asp Ala Arg Thr Asn
            165

<210> SEQ ID NO 47
<211> LENGTH: 393
<212> TYPE: PRT
<213> ORGANISM: Streptococcus mutans UA159

<400> SEQUENCE: 47

Met Ala Glu Lys Val Ser Phe Glu Glu Gly Lys Leu Gln Val Pro Asp
1               5                   10                  15

Lys Pro Val Ile Pro Tyr Ile Glu Gly Asp Gly Val Gly Gln Asp Ile
            20                  25                  30

Trp Lys Asn Ala Gln Ile Val Phe Asp Lys Ala Ile Ala Lys Val Tyr
        35                  40                  45

Gly Gly His Lys Gln Val Ile Trp Arg Glu Val Leu Ala Gly Lys Lys
    50                  55                  60

Ala Tyr Asn Glu Thr Gly Asn Trp Leu Pro Asn Glu Thr Leu Glu Ile
65                  70                  75                  80

Ile Lys Thr His Leu Leu Ala Ile Lys Gly Pro Leu Glu Thr Pro Val
                85                  90                  95

Gly Gly Gly Ile Arg Ser Leu Asn Val Ala Leu Arg Gln Glu Leu Asp
            100                 105                 110

Leu Phe Ala Cys Val Arg Pro Val Arg Tyr Phe Lys Gly Val Pro Ser
        115                 120                 125

Pro Leu Lys His Pro Glu Lys Thr Ala Ile Thr Ile Phe Arg Glu Asn
    130                 135                 140

Thr Glu Asp Ile Tyr Ala Gly Ile Glu Trp Asn Ala Gly Thr Ala Glu
145                 150                 155                 160

Val Gln Lys Val Ile Asn Phe Leu Gln Asp Asp Met Gln Val Lys Lys
                165                 170                 175

Ile Arg Phe Pro Lys Ser Ser Ile Gly Ile Lys Pro Ile Ser Ile
            180                 185                 190

Glu Gly Ser Gln Arg Leu Ile Arg Ala Ala Ile Glu Tyr Ala Leu Ala
        195                 200                 205

Asn Asn Leu Thr Lys Val Thr Leu Val His Lys Gly Asn Ile Gln Lys
    210                 215                 220

Phe Thr Glu Gly Gly Phe Arg Lys Trp Gly Tyr Glu Leu Ala Lys Arg
225                 230                 235                 240

Glu Tyr Ala Ala Glu Leu Ala Ser Gly Gln Leu Val Val Asp Asp Ile
                245                 250                 255

Ile Ala Asp Asn Phe Leu Gln Gln Ile Leu Leu Lys Pro Glu Arg Phe
            260                 265                 270

Asp Val Val Ala Leu Thr Asn Leu Asn Gly Asp Tyr Ala Ser Asp Ala
        275                 280                 285

Leu Ala Ala Gln Val Gly Gly Ile Gly Ile Ser Pro Gly Ala Asn Ile
    290                 295                 300

Asn Tyr Gln Thr Gly His Ala Ile Phe Glu Ala Thr His Gly Thr Ala
305                 310                 315                 320

Pro Asp Ile Ala Gly Gln Asp Leu Ala Asn Pro Ser Ser Val Leu Leu
                325                 330                 335

Ser Gly Cys Met Leu Phe Asp Tyr Ile Gly Trp Ser Lys Val Ser Asp
            340                 345                 350

```
Leu Ile Met Lys Ala Val Glu Lys Ala Ile Ala Asn Gly Gln Val Thr
        355                 360                 365

Ile Asp Phe Ala Lys Glu Leu Gly Val Glu Ala Leu Thr Thr Arg Gln
370                 375                 380

Phe Ser Glu Val Leu Leu Thr Tyr Leu
385                 390

<210> SEQ ID NO 48
<211> LENGTH: 423
<212> TYPE: PRT
<213> ORGANISM: Unknown
<220> FEATURE:
<223> OTHER INFORMATION: Bacillales sp.

<400> SEQUENCE: 48

Met Ala Gln Gly Glu Lys Ile Thr Val Ser Asn Gly Val Leu Asn Val
1               5                   10                  15

Pro Asn Asn Pro Ile Ile Pro Phe Ile Glu Gly Asp Gly Thr Gly Pro
            20                  25                  30

Asp Ile Trp Asn Ala Ala Ser Lys Val Leu Glu Ala Val Glu Lys
        35                  40                  45

Ala Tyr Lys Gly Glu Lys Ile Thr Trp Lys Glu Val Tyr Ala Gly
50                  55                  60

Glu Lys Ala Tyr Asn Lys Thr Gly Glu Trp Leu Pro Ala Glu Thr Leu
65                  70                  75                  80

Asp Val Ile Arg Glu Tyr Phe Ile Ala Ile Lys Gly Pro Leu Thr Thr
                85                  90                  95

Pro Val Gly Gly Gly Ile Arg Ser Leu Asn Val Ala Leu Arg Gln Glu
            100                 105                 110

Leu Asp Leu Phe Val Cys Leu Arg Pro Val Arg Tyr Phe Thr Gly Val
            115                 120                 125

Pro Ser Pro Val Lys Arg Pro Glu Asp Thr Asp Met Val Ile Phe Arg
130                 135                 140

Glu Asn Thr Glu Asp Ile Tyr Ala Gly Ile Glu Tyr Ala Lys Gly Ser
145                 150                 155                 160

Glu Glu Val Gln Lys Leu Ile Ser Phe Leu Gln Asn Glu Leu Asn Val
                165                 170                 175

Asn Lys Ile Arg Phe Pro Glu Thr Ser Gly Ile Gly Ile Lys Pro Val
            180                 185                 190

Ser Glu Glu Gly Thr Ser Arg Leu Val Arg Ala Ala Ile Asp Tyr Ala
            195                 200                 205

Ile Glu His Gly Arg Lys Ser Val Thr Leu Val His Lys Gly Asn Ile
        210                 215                 220

Met Lys Phe Thr Glu Gly Ala Phe Lys Asn Trp Gly Tyr Glu Leu Ala
225                 230                 235                 240

Glu Lys Glu Tyr Gly Asp Lys Val Phe Thr Trp Ala Gln Tyr Asp Arg
                245                 250                 255

Ile Ala Glu Glu Gln Gly Lys Asp Ala Ala Asn Lys Ala Gln Ser Glu
            260                 265                 270

Ala Glu Ala Ala Gly Lys Ile Ile Ile Lys Asp Ser Ile Ala Asp Ile
            275                 280                 285

Phe Leu Gln Gln Ile Leu Thr Arg Pro Asn Glu Phe Asp Val Val Ala
        290                 295                 300

Thr Met Asn Leu Asn Gly Asp Tyr Ile Ser Asp Ala Leu Ala Ala Gln
305                 310                 315                 320
```

```
Val Gly Gly Ile Gly Ile Ala Pro Gly Ala Asn Ile Asn Tyr Glu Thr
                325                 330                 335

Gly His Ala Ile Phe Glu Ala Thr His Gly Thr Ala Pro Lys Tyr Ala
            340                 345                 350

Gly Leu Asp Lys Val Asn Pro Ser Ser Val Ile Leu Ser Gly Val Leu
            355                 360                 365

Leu Leu Glu His Leu Gly Trp Asn Glu Ala Ala Asp Leu Val Ile Lys
        370                 375                 380

Ser Met Glu Lys Thr Ile Ala Ser Lys Val Val Thr Tyr Asp Phe Ala
385                 390                 395                 400

Arg Leu Met Asp Gly Ala Thr Glu Val Lys Cys Ser Glu Phe Gly Glu
                405                 410                 415

Glu Leu Ile Lys Asn Met Asp
                420

<210> SEQ ID NO 49
<211> LENGTH: 423
<212> TYPE: PRT
<213> ORGANISM: Bacillus subtilis

<400> SEQUENCE: 49

Met Ala Gln Gly Glu Lys Ile Thr Val Ser Asn Gly Val Leu Asn Val
1               5                   10                  15

Pro Asn Asn Pro Ile Ile Pro Phe Ile Glu Gly Asp Gly Thr Gly Pro
                20                  25                  30

Asp Ile Trp Asn Ala Ala Ser Lys Val Leu Glu Ala Ala Val Glu Lys
            35                  40                  45

Ala Tyr Lys Gly Glu Lys Lys Ile Thr Trp Lys Glu Val Tyr Ala Gly
    50                  55                  60

Glu Lys Ala Tyr Asn Lys Thr Gly Glu Trp Leu Pro Ala Glu Thr Leu
65                  70                  75                  80

Asp Val Ile Arg Glu Tyr Phe Ile Ala Ile Lys Gly Pro Leu Thr Thr
                85                  90                  95

Pro Val Gly Gly Gly Ile Arg Ala Leu Asn Val Ala Leu Arg Gln Glu
                100                 105                 110

Leu Asp Leu Phe Val Cys Leu Arg Pro Val Arg Tyr Phe Thr Gly Val
            115                 120                 125

Pro Ser Pro Val Lys Arg Pro Glu Asp Thr Asp Met Val Ile Phe Arg
    130                 135                 140

Glu Asn Thr Glu Asp Ile Tyr Ala Gly Ile Glu Tyr Ala Lys Gly Ser
145                 150                 155                 160

Glu Glu Val Gln Lys Leu Ile Ser Phe Leu Gln Asn Glu Leu Asn Val
                165                 170                 175

Asn Lys Ile Arg Phe Pro Glu Thr Ser Gly Ile Gly Ile Lys Pro Val
            180                 185                 190

Ser Glu Glu Gly Thr Ser Arg Leu Val Arg Ala Ala Ile Asp Tyr Ala
    195                 200                 205

Ile Glu His Gly Arg Lys Ser Val Thr Leu Val His Lys Gly Asn Ile
210                 215                 220

Met Lys Phe Thr Glu Gly Ala Phe Lys Asn Trp Gly Tyr Glu Leu Ala
225                 230                 235                 240

Glu Lys Glu Tyr Gly Asp Lys Val Phe Thr Trp Ala Gln Tyr Asp Arg
                245                 250                 255

Ile Ala Glu Glu Gln Gly Lys Asp Ala Ala Asn Lys Ala Gln Ser Glu
            260                 265                 270
```

```
Ala Glu Ala Ala Gly Lys Ile Ile Lys Asp Ser Ile Ala Asp Ile
            275                 280                 285

Phe Leu Gln Gln Ile Leu Thr Arg Pro Asn Glu Phe Asp Val Val Ala
        290                 295                 300

Thr Met Asn Leu Asn Gly Asp Tyr Ile Ser Asp Ala Leu Ala Ala Gln
305                 310                 315                 320

Val Gly Gly Ile Gly Ile Ala Pro Gly Ala Asn Ile Asn Tyr Glu Thr
                325                 330                 335

Gly His Ala Ile Phe Glu Ala Thr His Gly Thr Ala Pro Lys Tyr Ala
            340                 345                 350

Gly Leu Asp Lys Val Asn Pro Ser Ser Val Ile Leu Ser Gly Val Leu
        355                 360                 365

Leu Leu Glu His Leu Gly Trp Asn Glu Ala Ala Asp Leu Val Ile Lys
    370                 375                 380

Ser Met Glu Lys Thr Ile Ala Ser Lys Val Val Thr Tyr Asp Phe Ala
385                 390                 395                 400

Arg Leu Met Asp Gly Ala Thr Glu Val Lys Cys Ser Glu Phe Gly Glu
                405                 410                 415

Glu Leu Ile Lys Asn Met Asp
            420

<210> SEQ ID NO 50
<211> LENGTH: 2345
<212> TYPE: PRT
<213> ORGANISM: Rattus norvegicus

<400> SEQUENCE: 50

Met Asp Glu Pro Ser Pro Leu Ala Lys Thr Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Glu Glu Lys Glu Gly Ser Leu
        35                  40                  45

Ser Pro Ala Ser Val Ser Ser Asp Thr Leu Ser Asp Leu Gly Ile Ser
    50                  55                  60

Ala Leu Gln Asp Gly Leu Ala Phe His Met Arg Ser Ser Met Ser Gly
65              70                  75                  80

Leu His Leu Val Lys Gln Gly Arg Asp Arg Lys Lys Ile Asp Ser Gln
            85                  90                  95

Arg Asp Phe Thr Val Ala Ser Pro Ala Glu Phe Val Thr Arg Phe Gly
            100                 105                 110

Gly Asn Lys Val Ile Glu Lys Val Leu Ile Ala Asn Asn Gly Ile Ala
            115                 120                 125

Ala Val Lys Cys Met Arg Ser Ile Arg Arg Trp Ser Tyr Glu Met Phe
    130                 135                 140

Arg Asn Glu Arg Ala Ile Arg Phe Val Val Met Val Thr Pro Glu Asp
145                 150                 155                 160

Leu Lys Ala Asn Ala Glu Tyr Ile Lys Met Ala Asp His Tyr Val Pro
                165                 170                 175

Val Pro Gly Gly Ala Asn Asn Asn Tyr Ala Asn Val Glu Leu Ile
                180                 185                 190

Leu Asp Ile Ala Lys Arg Ile Pro Val Gln Ala Val Trp Ala Gly Trp
        195                 200                 205

Gly His Ala Ser Glu Asn Pro Lys Leu Pro Glu Leu Leu Leu Lys Asn
```

```
            210                 215                 220
Gly Ile Ala Phe Met Gly Pro Pro Ser Gln Ala Met Trp Ala Leu Gly
225                 230                 235                 240

Asp Lys Ile Ala Ser Ser Ile Val Ala Gln Thr Ala Gly Ile Pro Thr
                245                 250                 255

Leu Pro Trp Ser Gly Ser Gly Leu Arg Val Asp Trp Gln Glu Asn Asp
                260                 265                 270

Phe Ser Lys Arg Ile Leu Asn Val Pro Gln Asp Leu Tyr Glu Lys Gly
            275                 280                 285

Tyr Val Lys Asp Val Asp Gly Leu Lys Ala Ala Glu Glu Val Gly
        290                 295                 300

Tyr Pro Val Met Ile Lys Ala Ser Glu Gly Gly Gly Lys Gly Ile
305                 310                 315                 320

Arg Lys Val Asn Asn Ala Asp Asp Phe Pro Asn Leu Phe Arg Gln Val
                325                 330                 335

Gln Ala Glu Val Pro Gly Ser Pro Ile Phe Val Met Arg Leu Ala Lys
                340                 345                 350

Gln Ser Arg His Leu Glu Val Gln Ile Leu Ala Asp Gln Tyr Gly Asn
            355                 360                 365

Ala Ile Ser Leu Phe Gly Arg Asp Cys Ser Val Gln Arg Arg His Gln
370                 375                 380

Lys Ile Ile Glu Glu Ala Pro Ala Ala Ile Ala Thr Pro Ala Val Phe
385                 390                 395                 400

Glu His Met Glu Gln Cys Ala Val Lys Leu Ala Lys Met Val Gly Tyr
                405                 410                 415

Val Ser Ala Gly Thr Val Glu Tyr Leu Tyr Ser Gln Asp Gly Ser Phe
                420                 425                 430

Tyr Phe Leu Glu Leu Asn Pro Arg Leu Gln Val Glu His Pro Cys Thr
            435                 440                 445

Glu Met Val Ala Asp Val Asn Leu Pro Ala Ala Gln Leu Gln Ile Ala
450                 455                 460

Met Gly Ile Pro Leu Phe Arg Ile Lys Asp Ile Arg Met Met Tyr Gly
465                 470                 475                 480

Val Ser Pro Trp Gly Asp Ala Pro Ile Asp Phe Glu Asn Ser Ala His
                485                 490                 495

Val Pro Cys Pro Arg Gly His Val Ile Ala Ala Arg Ile Thr Ser Glu
                500                 505                 510

Asn Pro Asp Glu Gly Phe Lys Pro Ser Ser Gly Thr Val Gln Glu Leu
            515                 520                 525

Asn Phe Arg Ser Asn Lys Asn Val Trp Gly Tyr Phe Ser Val Ala Ala
530                 535                 540

Ala Gly Gly Leu His Glu Phe Ala Asp Ser Gln Phe Gly His Cys Phe
545                 550                 555                 560

Ser Trp Gly Glu Asn Arg Glu Glu Ala Ile Ser Asn Met Val Val Ala
                565                 570                 575

Leu Lys Glu Leu Ser Ile Arg Gly Asp Phe Arg Thr Thr Val Glu Tyr
                580                 585                 590

Leu Ile Lys Leu Leu Glu Thr Glu Ser Phe Gln Leu Asn Arg Ile Asp
            595                 600                 605

Thr Gly Trp Leu Asp Arg Leu Ile Ala Glu Lys Val Gln Ala Glu Arg
610                 615                 620

Pro Asp Thr Met Leu Gly Val Val Cys Gly Ala Leu His Val Ala Asp
625                 630                 635                 640
```

```
Val Asn Leu Arg Asn Ser Ile Ser Asn Phe Leu His Ser Leu Glu Arg
            645                 650                 655

Gly Gln Val Leu Pro Ala His Thr Leu Leu Asn Thr Val Asp Val Glu
            660                 665                 670

Leu Ile Tyr Glu Gly Ile Lys Tyr Val Leu Lys Val Thr Arg Gln Ser
            675                 680                 685

Pro Asn Ser Tyr Val Val Ile Met Asn Gly Ser Cys Val Glu Val Asp
            690                 695                 700

Val His Arg Leu Ser Asp Gly Gly Leu Leu Leu Ser Tyr Asp Gly Ser
705                 710                 715                 720

Ser Tyr Thr Thr Tyr Met Lys Glu Glu Val Asp Arg Tyr Arg Ile Thr
                725                 730                 735

Ile Gly Asn Lys Thr Cys Val Phe Glu Lys Glu Asn Asp Pro Ser Val
                740                 745                 750

Met Arg Ser Pro Ser Ala Gly Lys Leu Ile Gln Tyr Ile Val Glu Asp
                755                 760                 765

Gly Gly His Val Phe Ala Gly Gln Cys Tyr Ala Glu Ile Glu Val Met
            770                 775                 780

Lys Met Val Met Thr Leu Thr Ala Val Glu Ser Gly Cys Ile His Tyr
785                 790                 795                 800

Val Lys Arg Pro Gly Ala Ala Leu Asp Pro Gly Cys Val Ile Ala Lys
                805                 810                 815

Met Gln Leu Asp Asn Pro Ser Lys Val Gln Gln Ala Glu Leu His Thr
                820                 825                 830

Gly Ser Leu Pro Gln Ile Gln Ser Thr Ala Leu Arg Gly Glu Lys Leu
            835                 840                 845

His Arg Val Phe His Tyr Val Leu Asp Asn Leu Val Asn Val Met Asn
850                 855                 860

Gly Tyr Cys Leu Pro Asp Pro Phe Phe Ser Ser Lys Val Lys Asp Trp
865                 870                 875                 880

Val Glu Arg Leu Met Lys Thr Leu Arg Asp Pro Ser Leu Pro Leu Leu
                885                 890                 895

Glu Leu Gln Asp Ile Met Thr Ser Val Ser Gly Arg Ile Pro Leu Asn
                900                 905                 910

Val Glu Lys Ser Ile Lys Lys Glu Met Ala Gln Tyr Ala Ser Asn Ile
            915                 920                 925

Thr Ser Val Leu Cys Gln Phe Pro Ser Gln Ile Ala Asn Ile Leu
930                 935                 940

Asp Ser His Ala Ala Thr Leu Asn Arg Lys Ser Glu Arg Glu Val Phe
945                 950                 955                 960

Phe Met Asn Thr Gln Ser Ile Val Gln Leu Val Gln Arg Tyr Arg Ser
                965                 970                 975

Gly Ile Arg Gly His Met Lys Ala Val Val Met Asp Leu Leu Arg Gln
            980                 985                 990

Tyr Leu Arg Val Glu Thr Gln Phe Gln Asn Gly His Tyr Asp Lys Cys
            995                 1000                1005

Val Phe Ala Leu Arg Glu Glu Asn Lys Ser Asp Met Asn Thr Val
    1010                1015                1020

Leu Asn Tyr Ile Phe Ser His Ala Gln Val Thr Lys Lys Asn Leu
    1025                1030                1035

Leu Val Thr Met Leu Ile Asp Gln Leu Cys Gly Arg Asp Pro Thr
    1040                1045                1050
```

```
Leu Thr Asp Glu Leu Leu Asn Ile Leu Thr Glu Leu Thr Gln Leu
    1055                1060                1065

Ser Lys Thr Thr Asn Ala Lys Val Ala Leu Arg Ala Arg Gln Val
    1070                1075                1080

Leu Ile Ala Ser His Leu Pro Ser Tyr Asp Val Arg His Asn Gln
    1085                1090                1095

Val Glu Ser Ile Phe Leu Ser Ala Ile Asp Met Tyr Gly His Gln
    1100                1105                1110

Phe Cys Ile Glu Asn Leu Gln Lys Leu Ile Leu Ser Glu Thr Ser
    1115                1120                1125

Ile Phe Asp Val Leu Pro Asn Phe Phe Tyr His Ser Asn Gln Val
    1130                1135                1140

Val Arg Met Ala Ala Leu Glu Val Tyr Val Arg Arg Ala Tyr Ile
    1145                1150                1155

Ala Tyr Glu Leu Asn Ser Val Gln His Arg Gln Leu Lys Asp Asn
    1160                1165                1170

Thr Cys Val Val Glu Phe Gln Phe Met Leu Pro Thr Ser His Pro
    1175                1180                1185

Asn Arg Gly Asn Ile Pro Thr Leu Asn Arg Met Ser Phe Ala Ser
    1190                1195                1200

Asn Leu Asn His Tyr Gly Met Thr His Val Ala Ser Val Ser Asp
    1205                1210                1215

Val Leu Leu Asp Asn Ala Phe Thr Pro Pro Cys Gln Arg Met Gly
    1220                1225                1230

Gly Met Val Ser Phe Arg Thr Phe Glu Asp Phe Val Arg Ile Phe
    1235                1240                1245

Asp Glu Val Met Gly Cys Phe Cys Asp Ser Pro Pro Gln Ser Pro
    1250                1255                1260

Thr Phe Pro Glu Ser Gly His Thr Ser Leu Tyr Asp Glu Asp Lys
    1265                1270                1275

Val Pro Arg Asp Glu Pro Ile His Ile Leu Asn Val Ala Ile Lys
    1280                1285                1290

Thr Asp Gly Asp Ile Glu Asp Asp Arg Leu Ala Ala Met Phe Arg
    1295                1300                1305

Glu Phe Thr Gln Gln Asn Lys Ala Thr Leu Val Glu His Gly Ile
    1310                1315                1320

Arg Arg Leu Thr Phe Leu Val Ala Gln Lys Asp Phe Arg Lys Gln
    1325                1330                1335

Val Asn Cys Glu Val Asp Gln Arg Phe His Arg Glu Phe Pro Lys
    1340                1345                1350

Phe Phe Thr Phe Arg Ala Arg Asp Lys Phe Glu Glu Asp Arg Ile
    1355                1360                1365

Tyr Arg His Leu Glu Pro Ala Leu Ala Phe Gln Leu Glu Leu Asn
    1370                1375                1380

Arg Met Arg Asn Phe Asp Leu Thr Ala Ile Pro Cys Ala Asn His
    1385                1390                1395

Lys Met His Leu Tyr Leu Gly Ala Ala Lys Val Glu Val Gly Thr
    1400                1405                1410

Glu Val Thr Asp Tyr Arg Phe Phe Val Arg Ala Ile Ile Arg His
    1415                1420                1425

Ser Asp Leu Val Thr Lys Glu Ala Ser Phe Glu Tyr Leu Gln Asn
    1430                1435                1440

Glu Gly Glu Arg Leu Leu Leu Glu Ala Met Asp Glu Leu Glu Val
```

```
                1445                1450                1455
Ala Phe Asn Asn Thr Asn Val Arg Thr Asp Cys Asn His Ile Phe
        1460                1465                1470
Leu Asn Phe Val Pro Thr Val Ile Met Asp Pro Ser Lys Ile Glu
        1475                1480                1485
Glu Ser Val Arg Ser Met Val Met Arg Tyr Gly Ser Arg Leu Trp
        1490                1495                1500
Lys Leu Arg Val Leu Gln Ala Glu Leu Lys Ile Asn Ile Arg Leu
        1505                1510                1515
Thr Thr Thr Gly Lys Ala Ile Pro Ile Arg Leu Phe Leu Thr Asn
        1520                1525                1530
Glu Ser Gly Tyr Tyr Leu Asp Ile Ser Leu Tyr Lys Glu Val Thr
        1535                1540                1545
Asp Ser Arg Thr Ala Gln Ile Met Phe Gln Ala Tyr Gly Asp Lys
        1550                1555                1560
Gln Gly Pro Leu His Gly Met Leu Ile Asn Thr Pro Tyr Val Thr
        1565                1570                1575
Lys Asp Leu Leu Gln Ser Lys Arg Phe Gln Ala Gln Ser Leu Gly
        1580                1585                1590
Thr Thr Tyr Ile Tyr Asp Ile Pro Glu Met Phe Arg Gln Ser Leu
        1595                1600                1605
Ile Lys Leu Trp Glu Ser Met Ser Thr Gln Ala Phe Leu Pro Ser
        1610                1615                1620
Pro Pro Leu Pro Ser Asp Ile Leu Thr Tyr Thr Glu Leu Val Leu
        1625                1630                1635
Asp Asp Gln Gly Gln Leu Val His Met Asn Arg Leu Pro Gly Gly
        1640                1645                1650
Asn Glu Ile Gly Met Val Ala Trp Lys Met Ser Leu Lys Ser Pro
        1655                1660                1665
Glu Tyr Pro Asp Gly Arg Asp Val Ile Val Ile Gly Asn Asp Ile
        1670                1675                1680
Thr Tyr Arg Ile Gly Ser Phe Gly Pro Gln Glu Asp Leu Leu Phe
        1685                1690                1695
Leu Arg Ala Ser Glu Leu Ala Arg Ala Glu Gly Ile Pro Arg Ile
        1700                1705                1710
Tyr Val Ala Ala Asn Ser Gly Ala Arg Ile Gly Leu Ala Glu Glu
        1715                1720                1725
Ile Arg His Met Phe His Val Ala Trp Val Asp Ser Glu Asp Pro
        1730                1735                1740
Tyr Lys Gly Tyr Lys Tyr Leu Tyr Leu Thr Pro Gln Asp Tyr Lys
        1745                1750                1755
Arg Val Ser Ala Leu Asn Ser Val His Cys Glu His Val Glu Asp
        1760                1765                1770
Glu Gly Glu Ser Arg Tyr Lys Ile Thr Asp Ile Ile Gly Lys Glu
        1775                1780                1785
Glu Gly Leu Gly Ala Glu Asn Leu Arg Gly Ser Gly Met Ile Ala
        1790                1795                1800
Gly Glu Ser Ser Leu Ala Tyr Asp Glu Ile Ile Thr Ile Ser Leu
        1805                1810                1815
Val Thr Cys Arg Ala Ile Gly Ile Gly Ala Tyr Leu Val Arg Leu
        1820                1825                1830
Gly Gln Arg Thr Ile Gln Val Glu Asn Ser His Leu Ile Leu Thr
        1835                1840                1845
```

```
Gly Ala Gly Ala Leu Asn Lys Val Leu Gly Arg Glu Val Tyr Thr
1850            1855                1860

Ser Asn Asn Gln Leu Gly Gly Ile Gln Ile Met His Asn Asn Gly
1865            1870                1875

Val Thr His Cys Thr Val Cys Asp Asp Phe Glu Gly Val Phe Thr
1880            1885                1890

Val Leu His Trp Leu Ser Tyr Met Pro Lys Asn Val His Ser Ser
1895            1900                1905

Val Pro Leu Leu Asn Ser Lys Asp Pro Ile Asp Arg Ile Ile Glu
1910            1915                1920

Phe Val Pro Thr Lys Ala Pro Tyr Asp Pro Arg Trp Met Leu Ala
1925            1930                1935

Gly Arg Pro His Pro Thr Gln Lys Gly Gln Trp Leu Ser Gly Phe
1940            1945                1950

Phe Asp Tyr Gly Ser Phe Ser Glu Ile Met Gln Pro Trp Ala Gln
1955            1960                1965

Thr Val Val Val Gly Arg Ala Arg Leu Gly Gly Ile Pro Val Gly
1970            1975                1980

Val Val Ala Val Glu Thr Arg Thr Val Glu Leu Ser Val Pro Ala
1985            1990                1995

Asp Pro Ala Asn Leu Asp Ser Glu Ala Lys Ile Ile Gln Gln Ala
2000            2005                2010

Gly Gln Val Trp Phe Pro Asp Ser Ala Phe Lys Thr Tyr Gln Ala
2015            2020                2025

Ile Lys Asp Phe Asn Arg Glu Gly Leu Pro Leu Met Val Phe Ala
2030            2035                2040

Asn Trp Arg Gly Phe Ser Gly Gly Met Lys Asp Met Tyr Asp Gln
2045            2050                2055

Val Leu Lys Phe Gly Ala Tyr Ile Val Asp Gly Leu Arg Glu Cys
2060            2065                2070

Ser Gln Pro Val Met Val Tyr Ile Pro Pro Gln Ala Glu Leu Arg
2075            2080                2085

Gly Gly Ser Trp Val Val Ile Asp Pro Thr Ile Asn Pro Arg His
2090            2095                2100

Met Glu Met Tyr Ala Asp Arg Glu Ser Arg Gly Ser Val Leu Glu
2105            2110                2115

Pro Glu Gly Thr Val Glu Ile Lys Phe Arg Lys Lys Asp Leu Val
2120            2125                2130

Lys Thr Met Arg Arg Val Asp Pro Val Tyr Ile Arg Leu Ala Glu
2135            2140                2145

Arg Leu Gly Thr Pro Glu Leu Ser Pro Thr Glu Arg Lys Glu Leu
2150            2155                2160

Glu Ser Lys Leu Lys Glu Arg Glu Glu Phe Leu Ile Pro Ile Tyr
2165            2170                2175

His Gln Val Ala Val Gln Phe Ala Asp Leu His Asp Thr Pro Gly
2180            2185                2190

Arg Met Gln Glu Lys Gly Val Ile Asn Asp Ile Leu Asp Trp Lys
2195            2200                2205

Thr Ser Arg Thr Phe Phe Tyr Trp Arg Leu Arg Arg Leu Leu Leu
2210            2215                2220

Glu Asp Leu Val Lys Lys Lys Ile His Ser Ala Asn Pro Glu Leu
2225            2230                2235
```

-continued

```
Thr Asp Gly Gln Ile Gln Ala Met Leu Arg Arg Trp Phe Val Glu
    2240                2245                2250

Val Glu Gly Thr Val Lys Ala Tyr Val Trp Asp Asn Asn Lys Asp
    2255                2260                2265

Leu Val Glu Trp Leu Glu Lys Gln Leu Thr Glu Asp Gly Val
    2270                2275                2280

Arg Ser Val Ile Glu Glu Asn Ile Lys Tyr Ile Ser Arg Asp Tyr
    2285                2290                2295

Val Leu Lys Gln Ile Arg Ser Leu Val Gln Ala Asn Pro Glu Val
    2300                2305                2310

Ala Met Asp Ser Ile Val His Met Thr Gln His Ile Ser Pro Thr
    2315                2320                2325

Gln Arg Ala Glu Val Val Arg Ile Leu Ser Thr Met Asp Ser Pro
    2330                2335                2340

Ser Thr
    2345

<210> SEQ ID NO 51
<211> LENGTH: 2345
<212> TYPE: PRT
<213> ORGANISM: Mus musculus

<400> SEQUENCE: 51

Met Asp Glu Pro Ser Pro Leu Ala Lys Thr Leu Glu Leu Asn Gln His
  1               5                  10                  15

Ser Arg Phe Ile Ile Gly Ser Val Ser Glu Asp Asn Ser Glu Asp Glu
                 20                  25                  30

Ile Ser Asn Leu Val Lys Leu Asp Leu Glu Glu Lys Glu Gly Ser Leu
             35                  40                  45

Ser Pro Ala Ser Val Ser Ser Asp Thr Leu Ser Asp Leu Gly Ile Ser
         50                  55                  60

Gly Leu Gln Asp Gly Leu Ala Phe His Met Arg Ser Ser Met Ser Gly
     65                  70                  75                  80

Leu His Leu Val Lys Gln Gly Arg Asp Arg Lys Lys Ile Asp Ser Gln
                 85                  90                  95

Arg Asp Phe Thr Val Ala Ser Pro Ala Glu Phe Val Thr Arg Phe Gly
                100                 105                 110

Gly Asn Lys Val Ile Glu Lys Val Leu Ile Ala Asn Asn Gly Ile Ala
            115                 120                 125

Ala Val Lys Cys Met Arg Ser Ile Arg Arg Trp Ser Tyr Glu Met Phe
        130                 135                 140

Arg Asn Glu Arg Ala Ile Arg Phe Val Val Met Val Thr Pro Glu Asp
145                 150                 155                 160

Leu Lys Ala Asn Ala Glu Tyr Ile Lys Met Ala Asp His Tyr Val Pro
                165                 170                 175

Val Pro Gly Gly Pro Asn Asn Asn Asn Tyr Ala Asn Val Glu Leu Ile
            180                 185                 190

Leu Asp Ile Ala Lys Arg Ile Pro Val Gln Ala Val Trp Ala Gly Trp
        195                 200                 205

Gly His Ala Ser Glu Asn Pro Lys Leu Pro Glu Leu Leu Leu Lys Asn
    210                 215                 220

Gly Ile Ala Phe Met Gly Pro Pro Ser Gln Ala Met Trp Ala Leu Gly
225                 230                 235                 240

Asp Lys Ile Ala Ser Ser Ile Val Ala Gln Thr Ala Gly Ile Pro Thr
                245                 250                 255
```

```
Leu Pro Trp Ser Gly Ser Gly Leu Arg Val Asp Trp Gln Glu Asn Asp
            260                 265                 270

Phe Ser Lys Arg Ile Leu Asn Val Pro Gln Asp Leu Tyr Glu Lys Gly
            275                 280                 285

Tyr Val Lys Asp Val Asp Gly Leu Lys Ala Glu Glu Val Gly
    290                 295                 300

Tyr Pro Val Met Ile Lys Ala Ser Glu Gly Gly Gly Lys Gly Ile
305                 310                 315                 320

Arg Lys Val Asn Asn Ala Asp Asp Phe Pro Asn Leu Phe Arg Gln Val
                325                 330                 335

Gln Ala Glu Val Pro Gly Ser Pro Ile Phe Val Met Arg Leu Ala Lys
            340                 345                 350

Gln Ser Arg His Leu Glu Val Gln Ile Leu Ala Asp Gln Tyr Gly Asn
            355                 360                 365

Ala Ile Ser Leu Phe Gly Arg Asp Cys Ser Val Gln Arg Arg His Gln
    370                 375                 380

Lys Ile Ile Glu Glu Ala Pro Ala Ala Ile Ala Thr Pro Ala Val Phe
385                 390                 395                 400

Glu His Met Glu Gln Cys Ala Val Lys Leu Ala Lys Met Val Gly Tyr
                405                 410                 415

Val Ser Ala Gly Thr Val Glu Tyr Leu Tyr Ser Gln Asp Gly Ser Phe
            420                 425                 430

Tyr Phe Leu Glu Leu Asn Pro Arg Leu Gln Val Glu His Pro Cys Thr
    435                 440                 445

Glu Met Val Ala Asp Val Asn Leu Pro Ala Ala Gln Leu Gln Ile Ala
450                 455                 460

Met Gly Ile Pro Leu Phe Arg Ile Lys Asp Ile Arg Met Met Tyr Gly
465                 470                 475                 480

Val Ser Pro Trp Gly Asp Ala Pro Ile Asp Phe Glu Asn Ser Ala His
                485                 490                 495

Val Pro Cys Pro Arg Gly His Val Ile Ala Ala Arg Ile Thr Ser Glu
            500                 505                 510

Asn Pro Asp Glu Gly Phe Lys Pro Ser Ser Gly Thr Val Gln Glu Leu
            515                 520                 525

Asn Phe Arg Ser Asn Lys Asn Val Trp Gly Tyr Phe Ser Val Ala Ala
    530                 535                 540

Ala Gly Gly Leu His Glu Phe Ala Asp Ser Gln Phe Gly His Cys Phe
545                 550                 555                 560

Ser Trp Gly Glu Asn Arg Glu Glu Ala Ile Ser Asn Met Val Val Ala
                565                 570                 575

Leu Lys Glu Leu Ser Ile Arg Gly Asp Phe Arg Thr Thr Val Glu Tyr
            580                 585                 590

Leu Ile Lys Leu Leu Glu Thr Glu Ser Phe Gln Leu Asn Arg Ile Asp
    595                 600                 605

Thr Gly Trp Leu Asp Arg Leu Ile Ala Glu Lys Val Gln Ala Glu Arg
610                 615                 620

Pro Asp Thr Met Leu Gly Val Val Cys Gly Ala Leu His Val Ala Asp
625                 630                 635                 640

Val Ser Leu Arg Asn Ser Ile Ser Asn Phe Leu His Ser Leu Glu Arg
                645                 650                 655

Gly Gln Val Leu Pro Ala His Thr Leu Leu Asn Thr Val Asp Val Glu
            660                 665                 670
```

-continued

Leu Ile Tyr Glu Gly Ile Lys Tyr Val Leu Lys Val Thr Arg Gln Ser
675                 680                 685

Pro Asn Ser Tyr Val Val Ile Met Asn Gly Ser Cys Val Glu Val Asp
690                 695                 700

Val His Arg Leu Ser Asp Gly Gly Leu Leu Ser Tyr Asp Gly Ser
705                 710                 715                 720

Ser Tyr Thr Thr Tyr Met Lys Glu Val Asp Arg Tyr Arg Ile Thr
                725                 730                 735

Ile Gly Asn Lys Thr Cys Val Phe Glu Lys Asn Asp Pro Ser Val
            740                 745                 750

Met Arg Ser Pro Ser Ala Gly Lys Leu Ile Gln Tyr Ile Val Glu Asp
755                 760                 765

Gly Gly His Val Phe Ala Gly Gln Cys Tyr Ala Glu Ile Glu Val Met
        770                 775                 780

Lys Met Val Met Thr Leu Thr Ala Val Glu Ser Gly Cys Ile His Tyr
785                 790                 795                 800

Val Lys Arg Pro Gly Ala Ala Leu Asp Pro Gly Cys Val Ile Ala Lys
                805                 810                 815

Met Gln Leu Asp Asn Pro Ser Lys Val Gln Gln Ala Glu Leu His Thr
            820                 825                 830

Gly Ser Leu Pro Gln Ile Gln Ser Thr Ala Leu Arg Gly Glu Lys Leu
        835                 840                 845

His Arg Val Phe His Tyr Val Leu Asp Asn Leu Val Asn Val Met Asn
    850                 855                 860

Gly Tyr Cys Leu Pro Asp Pro Phe Phe Ser Ser Arg Val Lys Asp Trp
865                 870                 875                 880

Val Glu Arg Leu Met Lys Thr Leu Arg Asp Pro Ser Leu Pro Leu Leu
                885                 890                 895

Glu Leu Gln Asp Ile Met Thr Ser Val Ser Gly Arg Ile Pro Leu Asn
            900                 905                 910

Val Glu Lys Ser Ile Lys Lys Glu Met Ala Gln Tyr Ala Ser Asn Ile
        915                 920                 925

Thr Ser Val Leu Cys Gln Phe Pro Ser Gln Gln Ile Ala Asn Ile Leu
    930                 935                 940

Asp Ser His Ala Ala Thr Leu Asn Arg Lys Ser Glu Arg Glu Val Phe
945                 950                 955                 960

Phe Met Asn Thr Gln Ser Ile Val Gln Leu Val Gln Arg Tyr Arg Ser
                965                 970                 975

Gly Ile Arg Gly His Met Lys Ala Val Val Met Asp Leu Leu Arg Gln
            980                 985                 990

Tyr Leu Arg Val Glu Thr Gln Phe Gln Asn Gly His Tyr Asp Lys Cys
        995                 1000                1005

Val Phe Ala Leu Arg Glu Glu Asn Lys Ser Asp Met Asn Thr Val
    1010                1015                1020

Leu Asn Tyr Ile Phe Ser His Ala Gln Val Thr Lys Lys Asn Leu
    1025                1030                1035

Leu Val Thr Met Leu Ile Asp Gln Leu Cys Gly Arg Asp Pro Thr
    1040                1045                1050

Leu Thr Asp Glu Leu Leu Asn Ile Leu Thr Glu Leu Thr Gln Leu
    1055                1060                1065

Ser Lys Thr Thr Asn Ala Lys Val Ala Leu Arg Ala Arg Gln Val
    1070                1075                1080

Leu Ile Ala Ser His Leu Pro Ser Tyr Glu Leu Arg His Asn Gln

```
                1085                1090                1095
Val Glu Ser Ile Phe Leu Ser Ala Ile Asp Met Tyr Gly His Gln
                1100                1105                1110
Phe Cys Ile Glu Asn Leu Gln Lys Leu Ile Leu Ser Glu Thr Ser
                1115                1120                1125
Ile Phe Asp Val Leu Pro Asn Phe Phe Tyr His Ser Asn Gln Val
                1130                1135                1140
Val Arg Met Ala Ala Leu Glu Val Tyr Val Arg Arg Ala Tyr Ile
                1145                1150                1155
Ala Tyr Glu Leu Asn Ser Val Gln His Arg Gln Leu Lys Asp Asn
                1160                1165                1170
Thr Cys Val Val Glu Phe Gln Phe Met Leu Pro Thr Ser His Pro
                1175                1180                1185
Asn Arg Gly Asn Ile Pro Thr Leu Asn Arg Met Ser Phe Ala Ser
                1190                1195                1200
Asn Leu Asn His Tyr Gly Met Thr His Val Ala Ser Val Ser Asp
                1205                1210                1215
Val Leu Leu Asp Asn Ala Phe Thr Pro Pro Cys Gln Arg Met Gly
                1220                1225                1230
Gly Met Val Ser Phe Arg Thr Phe Glu Asp Phe Val Arg Ile Phe
                1235                1240                1245
Asp Glu Ile Met Gly Cys Phe Cys Asp Ser Pro Pro Gln Ser Pro
                1250                1255                1260
Thr Phe Pro Glu Ser Gly His Thr Ser Leu Tyr Asp Glu Asp Lys
                1265                1270                1275
Val Pro Arg Asp Glu Pro Ile His Ile Leu Asn Val Ala Ile Lys
                1280                1285                1290
Thr Asp Gly Asp Ile Glu Asp Asp Arg Leu Ala Ala Met Phe Arg
                1295                1300                1305
Glu Phe Thr Gln Gln Asn Lys Ala Thr Leu Val Glu His Gly Ile
                1310                1315                1320
Arg Arg Leu Thr Phe Leu Val Ala Gln Lys Asp Phe Arg Lys Gln
                1325                1330                1335
Val Asn Cys Glu Val Asp Gln Arg Phe His Arg Glu Phe Pro Lys
                1340                1345                1350
Phe Phe Thr Phe Arg Ala Arg Asp Lys Phe Glu Glu Asp Arg Ile
                1355                1360                1365
Tyr Arg His Leu Glu Pro Ala Leu Ala Phe Gln Leu Glu Leu Asn
                1370                1375                1380
Arg Met Arg Asn Phe Asp Leu Thr Ala Ile Pro Cys Ala Asn His
                1385                1390                1395
Lys Met His Leu Tyr Leu Gly Ala Ala Lys Val Glu Val Gly Thr
                1400                1405                1410
Glu Val Thr Asp Tyr Arg Phe Phe Val Arg Ala Ile Ile Arg His
                1415                1420                1425
Ser Asp Leu Val Thr Lys Glu Ala Ser Phe Glu Tyr Leu Gln Asn
                1430                1435                1440
Glu Gly Glu Arg Leu Leu Leu Glu Ala Met Asp Glu Leu Glu Val
                1445                1450                1455
Ala Phe Asn Asn Thr Asn Val Arg Thr Asp Cys Asn His Ile Phe
                1460                1465                1470
Leu Asn Phe Val Pro Thr Val Ile Met Asp Pro Ser Lys Ile Glu
                1475                1480                1485
```

-continued

```
Glu Ser Val Arg Ser Met Val Met Arg Tyr Gly Ser Arg Leu Trp
    1490                1495                1500

Lys Leu Arg Val Leu Gln Ala Glu Leu Lys Ile Asn Ile Arg Leu
    1505                1510                1515

Thr Thr Thr Gly Lys Ala Ile Pro Ile Arg Leu Phe Leu Thr Asn
    1520                1525                1530

Glu Ser Gly Tyr Tyr Leu Asp Ile Ser Leu Tyr Lys Glu Val Thr
    1535                1540                1545

Asp Ser Arg Thr Ala Gln Ile Met Phe Gln Ala Tyr Gly Asp Lys
    1550                1555                1560

Gln Gly Pro Leu His Gly Met Leu Ile Asn Thr Pro Tyr Val Thr
    1565                1570                1575

Lys Asp Leu Leu Gln Ser Lys Arg Phe Gln Ala Gln Ser Leu Gly
    1580                1585                1590

Thr Thr Tyr Ile Tyr Asp Ile Pro Glu Met Phe Arg Gln Ser Leu
    1595                1600                1605

Ile Lys Leu Trp Glu Ser Met Ser Thr Gln Ala Phe Leu Pro Ser
    1610                1615                1620

Pro Pro Leu Pro Ser Asp Ile Leu Thr Tyr Thr Glu Leu Val Leu
    1625                1630                1635

Asp Asp Gln Gly Gln Leu Val His Met Asn Arg Leu Pro Gly Gly
    1640                1645                1650

Asn Glu Ile Gly Met Val Ala Trp Lys Met Ser Leu Lys Ser Pro
    1655                1660                1665

Glu Tyr Pro Asp Gly Arg Asp Ile Ile Val Ile Gly Asn Asp Ile
    1670                1675                1680

Thr Tyr Arg Ile Gly Ser Phe Gly Pro Gln Glu Asp Leu Leu Phe
    1685                1690                1695

Leu Arg Ala Ser Glu Leu Ala Arg Ala Glu Gly Ile Pro Arg Ile
    1700                1705                1710

Tyr Val Ala Ala Asn Ser Gly Ala Arg Ile Gly Leu Ala Glu Glu
    1715                1720                1725

Ile Arg His Met Phe His Val Ala Trp Val Asp Pro Glu Asp Pro
    1730                1735                1740

Tyr Lys Gly Tyr Lys Tyr Leu Tyr Leu Thr Pro Gln Asp Tyr Lys
    1745                1750                1755

Arg Val Ser Ala Leu Asn Ser Val His Cys Glu His Val Glu Asp
    1760                1765                1770

Glu Gly Glu Ser Arg Tyr Lys Ile Thr Asp Ile Ile Gly Lys Glu
    1775                1780                1785

Glu Gly Leu Gly Ala Glu Asn Leu Arg Gly Ser Gly Met Ile Ala
    1790                1795                1800

Gly Glu Ser Ser Leu Ala Tyr Asp Glu Val Ile Thr Ile Ser Leu
    1805                1810                1815

Val Thr Cys Arg Ala Ile Gly Ile Gly Ala Tyr Leu Val Arg Leu
    1820                1825                1830

Gly Gln Arg Thr Ile Gln Val Glu Asn Ser His Leu Ile Leu Thr
    1835                1840                1845

Gly Ala Gly Ala Leu Asn Lys Val Leu Gly Arg Glu Val Tyr Thr
    1850                1855                1860

Ser Asn Asn Gln Leu Gly Gly Ile Gln Ile Met His Asn Asn Gly
    1865                1870                1875
```

```
Val Thr His Ser Thr Val Cys Asp Asp Phe Glu Gly Val Phe Thr
    1880            1885            1890

Val Leu His Trp Leu Ser Tyr Met Pro Lys Ser Val His Ser Ser
    1895            1900            1905

Val Pro Leu Leu Asn Ser Lys Asp Pro Ile Asp Arg Ile Ile Glu
    1910            1915            1920

Phe Val Pro Thr Lys Ala Pro Tyr Asp Pro Arg Trp Met Leu Ala
    1925            1930            1935

Gly Arg Pro His Pro Thr Gln Lys Gly Gln Trp Leu Ser Gly Phe
    1940            1945            1950

Phe Asp Tyr Gly Ser Phe Ser Glu Ile Met Gln Pro Trp Ala Gln
    1955            1960            1965

Thr Val Val Val Gly Arg Ala Arg Leu Gly Gly Ile Pro Val Gly
    1970            1975            1980

Val Val Ala Val Glu Thr Arg Thr Val Glu Leu Ser Ile Pro Ala
    1985            1990            1995

Asp Pro Ala Asn Leu Asp Ser Glu Ala Lys Ile Ile Gln Gln Ala
    2000            2005            2010

Gly Gln Val Trp Phe Pro Asp Ser Ala Phe Lys Thr Tyr Gln Ala
    2015            2020            2025

Ile Lys Asp Phe Asn Arg Glu Gly Leu Pro Leu Met Val Phe Ala
    2030            2035            2040

Asn Trp Arg Gly Phe Ser Gly Gly Met Lys Asp Met Tyr Asp Gln
    2045            2050            2055

Val Leu Lys Phe Gly Ala Tyr Ile Val Asp Gly Leu Arg Glu Cys
    2060            2065            2070

Ser Gln Pro Val Met Val Tyr Ile Pro Pro Gln Ala Glu Leu Arg
    2075            2080            2085

Gly Gly Ser Trp Val Val Ile Asp Pro Thr Ile Asn Pro Arg His
    2090            2095            2100

Met Glu Met Tyr Ala Asp Arg Glu Ser Arg Gly Ser Val Leu Glu
    2105            2110            2115

Pro Glu Gly Thr Val Glu Ile Lys Phe Arg Lys Lys Asp Leu Val
    2120            2125            2130

Lys Thr Met Arg Arg Val Asp Pro Val Tyr Ile Arg Leu Ala Glu
    2135            2140            2145

Arg Leu Gly Thr Pro Glu Leu Ser Pro Thr Glu Arg Lys Glu Leu
    2150            2155            2160

Glu Ser Lys Leu Lys Glu Arg Glu Glu Phe Leu Ile Pro Ile Tyr
    2165            2170            2175

His Gln Val Ala Val Gln Phe Ala Asp Leu His Asp Thr Pro Gly
    2180            2185            2190

Arg Met Gln Glu Lys Gly Val Ile Asn Asp Ile Leu Asp Trp Lys
    2195            2200            2205

Thr Ser Arg Thr Phe Phe Tyr Trp Arg Leu Arg Arg Leu Leu Leu
    2210            2215            2220

Glu Asp Leu Val Lys Lys Lys Ile His Asn Ala Asn Pro Glu Leu
    2225            2230            2235

Thr Asp Gly Gln Ile Gln Ala Met Leu Arg Arg Trp Phe Val Glu
    2240            2245            2250

Val Glu Gly Thr Val Lys Ala Tyr Val Trp Asp Asn Asn Lys Asp
    2255            2260            2265

Leu Val Glu Trp Leu Glu Lys Gln Leu Thr Glu Glu Asp Gly Val
```

```
                  2270              2275              2280

Arg Ser Val Ile Glu Glu Asn Ile Lys Tyr Ile Ser Arg Asp Tyr
    2285              2290              2295

Val Leu Lys Gln Ile Arg Ser Leu Val Gln Ala Asn Pro Glu Val
    2300              2305              2310

Ala Met Asp Ser Ile Val His Met Thr Gln His Ile Ser Pro Thr
    2315              2320              2325

Gln Arg Ala Glu Val Val Arg Ile Leu Ser Thr Met Asp Ser Pro
    2330              2335              2340

Ser Thr
    2345

<210> SEQ ID NO 52
<211> LENGTH: 2233
<212> TYPE: PRT
<213> ORGANISM: Saccharomyces cerevisiae

<400> SEQUENCE: 52

Met Ser Glu Glu Ser Leu Phe Glu Ser Ser Pro Gln Lys Met Glu Tyr
1               5                   10                  15

Glu Ile Thr Asn Tyr Ser Glu Arg His Thr Glu Leu Pro Gly His Phe
            20                  25                  30

Ile Gly Leu Asn Thr Val Asp Lys Leu Glu Glu Ser Pro Leu Arg Asp
        35                  40                  45

Phe Val Lys Ser His Gly Gly His Thr Val Ile Ser Lys Ile Leu Ile
    50                  55                  60

Ala Asn Asn Gly Ile Ala Ala Val Lys Glu Ile Arg Ser Val Arg Lys
65                  70                  75                  80

Trp Ala Tyr Glu Thr Phe Gly Asp Asp Arg Thr Val Gln Phe Val Ala
                85                  90                  95

Met Ala Thr Pro Glu Asp Leu Glu Ala Asn Ala Glu Tyr Ile Arg Met
            100                 105                 110

Ala Asp Gln Tyr Ile Glu Val Pro Gly Gly Thr Asn Asn Asn Asn Tyr
        115                 120                 125

Ala Asn Val Asp Leu Ile Val Asp Ile Ala Glu Arg Ala Asp Val Asp
    130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
            180                 185                 190

Ala Gln Ser Ala Lys Val Pro Cys Ile Pro Trp Ser Gly Thr Gly Val
        195                 200                 205

Asp Thr Val His Val Asp Glu Lys Thr Gly Leu Val Ser Val Asp Asp
    210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
            260                 265                 270

Ala Leu Tyr His Gln Ala Ala Asn Glu Ile Pro Gly Ser Pro Ile Phe
        275                 280                 285
```

```
Ile Met Lys Leu Ala Gly Arg Ala Arg His Leu Glu Val Gln Leu Leu
290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

Ala Lys Ala Glu Thr Phe His Glu Met Glu Lys Ala Ala Val Arg Leu
                340                 345                 350

Gly Lys Leu Val Gly Tyr Val Ser Ala Gly Thr Val Glu Tyr Leu Tyr
            355                 360                 365

Ser His Asp Asp Gly Lys Phe Tyr Phe Leu Glu Leu Asn Pro Arg Leu
370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
                405                 410                 415

Asp Ile Arg Thr Leu Tyr Gly Met Asn Pro His Ser Ala Ser Glu Ile
                420                 425                 430

Asp Phe Glu Phe Lys Thr Gln Asp Ala Thr Lys Lys Gln Arg Arg Pro
            435                 440                 445

Ile Pro Lys Gly His Cys Thr Ala Cys Arg Ile Thr Ser Glu Asp Pro
450                 455                 460

Asn Asp Gly Phe Lys Pro Ser Gly Gly Thr Leu His Glu Leu Asn Phe
465                 470                 475                 480

Arg Ser Ser Ser Asn Val Trp Gly Tyr Phe Ser Val Gly Asn Asn Gly
                485                 490                 495

Asn Ile His Ser Phe Ser Asp Ser Gln Phe Gly His Ile Phe Ala Phe
                500                 505                 510

Gly Glu Asn Arg Gln Ala Ser Arg Lys His Met Val Val Ala Leu Lys
            515                 520                 525

Glu Leu Ser Ile Arg Gly Asp Phe Arg Thr Thr Val Glu Tyr Leu Ile
530                 535                 540

Lys Leu Leu Glu Thr Glu Asp Phe Glu Asp Asn Thr Ile Thr Thr Gly
545                 550                 555                 560

Trp Leu Asp Asp Leu Ile Thr His Lys Met Thr Ala Glu Lys Pro Asp
                565                 570                 575

Pro Thr Leu Ala Val Ile Cys Gly Ala Ala Thr Lys Ala Phe Leu Ala
                580                 585                 590

Ser Glu Glu Ala Arg His Lys Tyr Ile Glu Ser Leu Gln Lys Gly Gln
            595                 600                 605

Val Leu Ser Lys Asp Leu Leu Gln Thr Met Phe Pro Val Asp Phe Ile
610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
                645                 650                 655

Gln Leu Ser Asp Gly Gly Leu Leu Ile Ala Ile Gly Gly Lys Ser His
                660                 665                 670

Thr Ile Tyr Trp Lys Glu Val Ala Ala Thr Arg Leu Ser Val Asp
            675                 680                 685

Ser Met Thr Thr Leu Leu Glu Val Glu Asn Asp Pro Thr Gln Leu Arg
690                 695                 700

Thr Pro Ser Pro Gly Lys Leu Val Lys Phe Leu Val Glu Asn Gly Glu
```

```
                705                 710                 715                 720
        His Ile Ile Lys Gly Gln Pro Tyr Ala Glu Ile Glu Val Met Lys Met
                        725                 730                 735
        Gln Met Pro Leu Val Ser Gln Glu Asn Gly Ile Val Gln Leu Leu Lys
                        740                 745                 750
        Gln Pro Gly Ser Thr Ile Val Ala Gly Asp Ile Met Ala Ile Met Thr
                        755                 760                 765
        Leu Asp Asp Pro Ser Lys Val Lys His Ala Leu Pro Phe Glu Gly Met
                        770                 775                 780
        Leu Pro Asp Phe Gly Ser Pro Val Ile Glu Gly Thr Lys Pro Ala Tyr
        785                 790                 795                 800
        Lys Phe Lys Ser Leu Val Ser Thr Leu Glu Asn Ile Leu Lys Gly Tyr
                        805                 810                 815
        Asp Asn Gln Val Ile Met Asn Ala Ser Leu Gln Gln Leu Ile Glu Val
                        820                 825                 830
        Leu Arg Asn Pro Lys Leu Pro Tyr Ser Glu Trp Lys Leu His Ile Ser
                        835                 840                 845
        Ala Leu His Ser Arg Leu Pro Ala Lys Leu Asp Glu Gln Met Glu Glu
        850                 855                 860
        Leu Val Ala Arg Ser Leu Arg Arg Gly Ala Val Phe Pro Ala Arg Gln
        865                 870                 875                 880
        Leu Ser Lys Leu Ile Asp Met Ala Val Lys Asn Pro Glu Tyr Asn Pro
                        885                 890                 895
        Asp Lys Leu Leu Gly Ala Val Glu Pro Leu Ala Asp Ile Ala His
                        900                 905                 910
        Lys Tyr Ser Asn Gly Leu Glu Ala His Glu His Ser Ile Phe Val His
                        915                 920                 925
        Phe Leu Glu Glu Tyr Tyr Glu Val Glu Lys Leu Phe Asn Gly Pro Asn
                        930                 935                 940
        Val Arg Glu Glu Asn Ile Ile Leu Lys Leu Arg Asp Glu Asn Pro Lys
        945                 950                 955                 960
        Asp Leu Asp Lys Val Ala Leu Thr Val Leu Ser His Ser Lys Val Ser
                        965                 970                 975
        Ala Lys Asn Asn Leu Ile Leu Ala Ile Leu Lys His Tyr Gln Pro Leu
                        980                 985                 990
        Cys Lys Leu Ser Ser Lys Val Ser  Ala Ile Phe Ser Thr  Pro Leu Gln
                        995                 1000                1005
        His Ile  Val Glu Leu Glu Ser  Lys Ala Thr Ala Lys  Val Ala Leu
                        1010                1015                1020
        Gln Ala  Arg Glu Ile Leu Ile  Gln Gly Ala Leu Pro  Ser Val Lys
                        1025                1030                1035
        Glu Arg  Thr Glu Gln Ile Glu  His Ile Leu Lys Ser  Ser Val Val
                        1040                1045                1050
        Lys Val  Ala Tyr Gly Ser Ser  Asn Pro Lys Arg Ser  Glu Pro Asp
                        1055                1060                1065
        Leu Asn  Ile Leu Lys Asp Leu  Ile Asp Ser Asn Tyr  Val Val Phe
                        1070                1075                1080
        Asp Val  Leu Leu Gln Phe Leu  Thr His Gln Asp Pro  Val Val Thr
                        1085                1090                1095
        Ala Ala  Ala Ala Gln Val Tyr  Ile Arg Arg Ala Tyr  Arg Ala Tyr
                        1100                1105                1110
        Thr Ile  Gly Asp Ile Arg Val  His Glu Gly Val Thr  Val Pro Ile
                        1115                1120                1125
```

```
Val Glu Trp Lys Phe Gln Leu Pro Ser Ala Ala Phe Ser Thr Phe
1130                1135                1140

Pro Thr Val Lys Ser Lys Met Gly Met Asn Arg Ala Val Ser Val
1145                1150                1155

Ser Asp Leu Ser Tyr Val Ala Asn Ser Gln Ser Ser Pro Leu Arg
1160                1165                1170

Glu Gly Ile Leu Met Ala Val Asp His Leu Asp Val Asp Glu
1175                1180                1185

Ile Leu Ser Gln Ser Leu Glu Val Ile Pro Arg His Gln Ser Ser
1190                1195                1200

Ser Asn Gly Pro Ala Pro Asp Arg Ser Gly Ser Ser Ala Ser Leu
1205                1210                1215

Ser Asn Val Ala Asn Val Cys Val Ala Ser Thr Glu Gly Phe Glu
1220                1225                1230

Ser Glu Glu Glu Ile Leu Val Arg Leu Arg Glu Ile Leu Asp Leu
1235                1240                1245

Asn Lys Gln Glu Leu Ile Asn Ala Ser Ile Arg Arg Ile Thr Phe
1250                1255                1260

Met Phe Gly Phe Lys Asp Gly Ser Tyr Pro Lys Tyr Tyr Thr Phe
1265                1270                1275

Asn Gly Pro Asn Tyr Asn Glu Asn Glu Thr Ile Arg His Ile Glu
1280                1285                1290

Pro Ala Leu Ala Phe Gln Leu Glu Leu Gly Arg Leu Ser Asn Phe
1295                1300                1305

Asn Ile Lys Pro Ile Phe Thr Asp Asn Arg Asn Ile His Val Tyr
1310                1315                1320

Glu Ala Val Ser Lys Thr Ser Pro Leu Asp Lys Arg Phe Phe Thr
1325                1330                1335

Arg Gly Ile Ile Arg Thr Gly His Ile Arg Asp Asp Ile Ser Ile
1340                1345                1350

Gln Glu Tyr Leu Thr Ser Glu Ala Asn Arg Leu Met Ser Asp Ile
1355                1360                1365

Leu Asp Asn Leu Glu Val Thr Asp Thr Ser Asn Ser Asp Leu Asn
1370                1375                1380

His Ile Phe Ile Asn Phe Ile Ala Val Phe Asp Ile Ser Pro Glu
1385                1390                1395

Asp Val Glu Ala Ala Phe Gly Gly Phe Leu Glu Arg Phe Gly Lys
1400                1405                1410

Arg Leu Leu Arg Leu Arg Val Ser Ser Ala Glu Ile Arg Ile Ile
1415                1420                1425

Ile Lys Asp Pro Gln Thr Gly Ala Pro Val Pro Leu Arg Ala Leu
1430                1435                1440

Ile Asn Asn Val Ser Gly Tyr Val Ile Lys Thr Glu Met Tyr Thr
1445                1450                1455

Glu Val Lys Asn Ala Lys Gly Glu Trp Val Phe Lys Ser Leu Gly
1460                1465                1470

Lys Pro Gly Ser Met His Leu Arg Pro Ile Ala Thr Pro Tyr Pro
1475                1480                1485

Val Lys Glu Trp Leu Gln Pro Lys Arg Tyr Lys Ala His Leu Met
1490                1495                1500

Gly Thr Thr Tyr Val Tyr Asp Phe Pro Glu Leu Phe Arg Gln Ala
1505                1510                1515
```

-continued

Ser Ser Ser Gln Trp Lys Asn Phe Ser Ala Asp Val Lys Leu Thr
1520              1525              1530

Asp Asp Phe Phe Ile Ser Asn Glu Leu Ile Glu Asp Glu Asn Gly
1535              1540              1545

Glu Leu Thr Glu Val Glu Arg Glu Pro Gly Ala Asn Ala Ile Gly
1550              1555              1560

Met Val Ala Phe Lys Ile Thr Val Lys Thr Pro Glu Tyr Pro Arg
1565              1570              1575

Gly Arg Gln Phe Val Val Val Ala Asn Asp Ile Thr Phe Lys Ile
1580              1585              1590

Gly Ser Phe Gly Pro Gln Glu Asp Glu Phe Phe Asn Lys Val Thr
1595              1600              1605

Glu Tyr Ala Arg Lys Arg Gly Ile Pro Arg Ile Tyr Leu Ala Ala
1610              1615              1620

Asn Ser Gly Ala Arg Ile Gly Met Ala Glu Glu Ile Val Pro Leu
1625              1630              1635

Phe Gln Val Ala Trp Asn Asp Ala Ala Asn Pro Asp Lys Gly Phe
1640              1645              1650

Gln Tyr Leu Tyr Leu Thr Ser Glu Gly Met Glu Thr Leu Lys Lys
1655              1660              1665

Phe Asp Lys Glu Asn Ser Val Leu Thr Glu Arg Thr Val Ile Asn
1670              1675              1680

Gly Glu Glu Arg Phe Val Ile Lys Thr Ile Ile Gly Ser Glu Asp
1685              1690              1695

Gly Leu Gly Val Glu Cys Leu Arg Gly Ser Gly Leu Ile Ala Gly
1700              1705              1710

Ala Thr Ser Arg Ala Tyr His Asp Ile Phe Thr Ile Thr Leu Val
1715              1720              1725

Thr Cys Arg Ser Val Gly Ile Gly Ala Tyr Leu Val Arg Leu Gly
1730              1735              1740

Gln Arg Ala Ile Gln Val Glu Gly Gln Pro Ile Ile Leu Thr Gly
1745              1750              1755

Ala Pro Ala Ile Asn Lys Met Leu Gly Arg Glu Val Tyr Thr Ser
1760              1765              1770

Asn Leu Gln Leu Gly Gly Thr Gln Ile Met Tyr Asn Asn Gly Val
1775              1780              1785

Ser His Leu Thr Ala Val Asp Asp Leu Ala Gly Val Glu Lys Ile
1790              1795              1800

Val Glu Trp Met Ser Tyr Val Pro Ala Lys Arg Asn Met Pro Val
1805              1810              1815

Pro Ile Leu Glu Thr Lys Asp Thr Trp Asp Arg Pro Val Asp Phe
1820              1825              1830

Thr Pro Thr Asn Asp Glu Thr Tyr Asp Val Arg Trp Met Ile Glu
1835              1840              1845

Gly Arg Glu Thr Glu Ser Gly Phe Glu Tyr Gly Leu Phe Asp Lys
1850              1855              1860

Gly Ser Phe Phe Glu Thr Leu Ser Gly Trp Ala Lys Gly Val Val
1865              1870              1875

Val Gly Arg Ala Arg Leu Gly Gly Ile Pro Leu Gly Val Ile Gly
1880              1885              1890

Val Glu Thr Arg Thr Val Glu Asn Leu Ile Pro Ala Asp Pro Ala
1895              1900              1905

Asn Pro Asn Ser Ala Glu Thr Leu Ile Gln Glu Pro Gly Gln Val

```
                1910                1915                1920

Trp His Pro Asn Ser Ala Phe Lys Thr Ala Gln Ala Ile Asn Asp
        1925                1930                1935

Phe Asn Asn Gly Glu Gln Leu Pro Met Met Ile Leu Ala Asn Trp
    1940                1945                1950

Arg Gly Phe Ser Gly Gly Gln Arg Asp Met Phe Asn Glu Val Leu
        1955                1960                1965

Lys Tyr Gly Ser Phe Ile Val Asp Ala Leu Val Asp Tyr Lys Gln
    1970                1975                1980

Pro Ile Ile Ile Tyr Ile Pro Pro Thr Gly Glu Leu Arg Gly Gly
        1985                1990                1995

Ser Trp Val Val Val Asp Pro Thr Ile Asn Ala Asp Gln Met Glu
    2000                2005                2010

Met Tyr Ala Asp Val Asn Ala Arg Ala Gly Val Leu Glu Pro Gln
        2015                2020                2025

Gly Met Val Gly Ile Lys Phe Arg Arg Glu Lys Leu Leu Asp Thr
    2030                2035                2040

Met Asn Arg Leu Asp Asp Lys Tyr Arg Glu Leu Arg Ser Gln Leu
        2045                2050                2055

Ser Asn Lys Ser Leu Ala Pro Glu Val His Gln Gln Ile Ser Lys
    2060                2065                2070

Gln Leu Ala Asp Arg Glu Arg Glu Leu Leu Pro Ile Tyr Gly Gln
        2075                2080                2085

Ile Ser Leu Gln Phe Ala Asp Leu His Asp Arg Ser Ser Arg Met
    2090                2095                2100

Val Ala Lys Gly Val Ile Ser Lys Glu Leu Glu Trp Thr Glu Ala
        2105                2110                2115

Arg Arg Phe Phe Phe Trp Arg Leu Arg Arg Arg Leu Asn Glu Glu
    2120                2125                2130

Tyr Leu Ile Lys Arg Leu Ser His Gln Val Gly Glu Ala Ser Arg
        2135                2140                2145

Leu Glu Lys Ile Ala Arg Ile Arg Ser Trp Tyr Pro Ala Ser Val
    2150                2155                2160

Asp His Glu Asp Asp Arg Gln Val Ala Thr Trp Ile Glu Glu Asn
        2165                2170                2175

Tyr Lys Thr Leu Asp Asp Lys Leu Lys Gly Leu Lys Leu Glu Ser
    2180                2185                2190

Phe Ala Gln Asp Leu Ala Lys Lys Ile Arg Ser Asp His Asp Asn
        2195                2200                2205

Ala Ile Asp Gly Leu Ser Glu Val Ile Lys Met Leu Ser Thr Asp
    2210                2215                2220

Asp Lys Glu Lys Leu Leu Lys Thr Leu Lys
        2225                2230

<210> SEQ ID NO 53
<211> LENGTH: 2268
<212> TYPE: PRT
<213> ORGANISM: Homo sapiens

<400> SEQUENCE: 53

Met Ser Gly Leu His Leu Val Lys Gln Gly Arg Asp Arg Lys Lys Ile
1               5                   10                  15

Asp Ser Gln Arg Asp Phe Thr Val Ala Ser Pro Ala Glu Phe Val Thr
            20                  25                  30
```

```
Arg Phe Gly Gly Asn Lys Val Ile Glu Lys Val Leu Ile Ala Asn Asn
                 35                  40                  45
Gly Ile Ala Ala Val Lys Cys Met Arg Ser Ile Arg Arg Trp Ser Tyr
 50                  55                  60
Glu Met Phe Arg Asn Glu Arg Ala Ile Arg Phe Val Val Met Val Thr
 65                  70                  75                  80
Pro Glu Asp Leu Lys Ala Asn Ala Glu Tyr Ile Lys Met Ala Asp His
                 85                  90                  95
Tyr Val Pro Val Pro Gly Pro Asn Asn Asn Tyr Ala Asn Val
                100                 105                 110
Glu Leu Ile Leu Asp Ile Ala Lys Arg Ile Pro Val Gln Ala Val Trp
                115                 120                 125
Ala Gly Trp Gly His Ala Ser Glu Asn Pro Lys Leu Pro Glu Leu Leu
130                 135                 140
Leu Lys Asn Gly Ile Ala Phe Met Gly Pro Ser Gln Ala Met Trp
145                 150                 155                 160
Ala Leu Gly Asp Lys Ile Ala Ser Ser Ile Val Ala Gln Thr Ala Gly
                165                 170                 175
Ile Pro Thr Leu Pro Trp Ser Gly Ser Gly Leu Arg Val Asp Trp Gln
                180                 185                 190
Glu Asn Asp Phe Ser Lys Arg Ile Leu Asn Val Pro Gln Glu Leu Tyr
                195                 200                 205
Glu Lys Gly Tyr Val Lys Asp Val Asp Asp Gly Leu Gln Ala Ala Glu
                210                 215                 220
Glu Val Gly Tyr Pro Val Met Ile Lys Ala Ser Glu Gly Gly Gly Gly
225                 230                 235                 240
Lys Gly Ile Arg Lys Val Asn Asn Ala Asp Asp Phe Pro Asn Leu Phe
                245                 250                 255
Arg Gln Val Gln Ala Glu Val Pro Gly Ser Pro Ile Phe Val Met Arg
                260                 265                 270
Leu Ala Lys Gln Ser Arg His Leu Glu Val Gln Ile Leu Ala Asp Gln
                275                 280                 285
Tyr Gly Asn Ala Ile Ser Leu Phe Gly Arg Asp Cys Ser Val Gln Arg
                290                 295                 300
Arg His Gln Lys Ile Ile Glu Glu Ala Pro Ala Thr Ile Ala Thr Pro
305                 310                 315                 320
Ala Val Phe Glu His Met Glu Gln Cys Ala Val Lys Leu Ala Lys Met
                325                 330                 335
Val Gly Tyr Val Ser Ala Gly Thr Val Glu Tyr Leu Tyr Ser Gln Asp
                340                 345                 350
Gly Ser Phe Tyr Phe Leu Glu Leu Asn Pro Arg Leu Gln Val Glu His
                355                 360                 365
Pro Cys Thr Glu Met Val Ala Asp Val Asn Leu Pro Ala Ala Gln Leu
370                 375                 380
Gln Ile Ala Met Gly Ile Pro Leu Tyr Arg Ile Lys Asp Ile Arg Met
385                 390                 395                 400
Met Tyr Gly Val Ser Pro Trp Gly Asp Ser Pro Ile Asp Phe Glu Asp
                405                 410                 415
Ser Ala His Val Pro Cys Pro Arg Gly His Val Ile Ala Ala Arg Ile
                420                 425                 430
Thr Ser Glu Asn Pro Asp Glu Gly Phe Lys Pro Ser Ser Gly Thr Val
                435                 440                 445
Gln Glu Leu Asn Phe Arg Ser Asn Lys Asn Val Trp Gly Tyr Phe Ser
```

```
            450                 455                 460
Val Ala Ala Gly Gly Leu His Glu Phe Ala Asp Ser Gln Phe Gly
465                 470                 475                 480

His Cys Phe Ser Trp Gly Glu Asn Arg Glu Glu Ala Ile Ser Asn Met
                485                 490                 495

Val Val Ala Leu Lys Glu Leu Ser Ile Arg Gly Asp Phe Arg Thr Thr
            500                 505                 510

Val Glu Tyr Leu Ile Lys Leu Leu Glu Thr Glu Ser Phe Gln Met Asn
            515                 520                 525

Arg Ile Asp Thr Gly Trp Leu Asp Arg Leu Ile Ala Glu Lys Val Gln
        530                 535                 540

Ala Glu Arg Pro Asp Thr Met Leu Gly Val Val Cys Gly Ala Leu His
545                 550                 555                 560

Val Ala Asp Val Ser Leu Arg Asn Ser Val Ser Asn Phe Leu His Ser
                565                 570                 575

Leu Glu Arg Gly Gln Val Leu Pro Ala His Thr Leu Leu Asn Thr Val
            580                 585                 590

Asp Val Glu Leu Ile Tyr Glu Gly Val Lys Tyr Val Leu Lys Val Thr
        595                 600                 605

Arg Gln Ser Pro Asn Ser Tyr Val Val Ile Met Asn Gly Ser Cys Val
    610                 615                 620

Glu Val Asp Val His Arg Leu Ser Asp Gly Gly Leu Leu Leu Ser Tyr
625                 630                 635                 640

Asp Gly Ser Ser Tyr Thr Thr Tyr Met Lys Glu Glu Val Asp Arg Tyr
                645                 650                 655

Arg Ile Thr Ile Gly Asn Lys Thr Cys Val Phe Glu Lys Glu Asn Asp
            660                 665                 670

Pro Ser Val Met Arg Ser Pro Ser Ala Gly Lys Leu Ile Gln Tyr Ile
        675                 680                 685

Val Glu Asp Gly Gly His Val Phe Ala Gly Gln Cys Tyr Ala Glu Ile
    690                 695                 700

Glu Val Met Lys Met Val Met Thr Leu Thr Ala Val Glu Ser Gly Cys
705                 710                 715                 720

Ile His Tyr Val Lys Arg Pro Gly Ala Ala Leu Asp Pro Gly Cys Val
                725                 730                 735

Leu Ala Lys Met Gln Leu Asp Asn Pro Ser Lys Val Gln Gln Ala Glu
            740                 745                 750

Leu His Thr Gly Ser Leu Pro Arg Ile Gln Ser Thr Ala Leu Arg Gly
        755                 760                 765

Glu Lys Leu His Arg Val Phe His Tyr Val Leu Asp Asn Leu Val Asn
    770                 775                 780

Val Met Asn Gly Tyr Cys Leu Pro Asp Pro Phe Phe Ser Ser Lys Val
785                 790                 795                 800

Lys Asp Trp Val Glu Arg Leu Met Lys Thr Leu Arg Asp Pro Ser Leu
                805                 810                 815

Pro Leu Leu Glu Leu Gln Asp Ile Met Thr Ser Val Ser Gly Arg Ile
            820                 825                 830

Pro Pro Asn Val Glu Lys Ser Ile Lys Lys Glu Met Ala Gln Tyr Ala
        835                 840                 845

Ser Asn Ile Thr Ser Val Leu Cys Gln Phe Pro Ser Gln Gln Ile Ala
    850                 855                 860

Asn Ile Leu Asp Ser His Ala Ala Thr Leu Asn Arg Lys Ser Glu Arg
865                 870                 875                 880
```

```
Glu Val Phe Phe Met Asn Thr Gln Ser Ile Val Gln Leu Val Gln Arg
            885                 890                 895

Tyr Arg Ser Gly Ile Arg Gly His Met Lys Ala Val Val Met Asp Leu
            900                 905                 910

Leu Arg Gln Tyr Leu Arg Val Glu Thr Gln Phe Gln Asn Gly His Tyr
            915                 920                 925

Asp Lys Cys Val Phe Ala Leu Arg Glu Glu Asn Lys Ser Asp Met Asn
930                 935                 940

Thr Val Leu Asn Tyr Ile Phe Ser His Ala Gln Val Thr Lys Lys Asn
945                 950                 955                 960

Leu Leu Val Thr Met Leu Ile Asp Gln Leu Cys Gly Arg Asp Pro Thr
                965                 970                 975

Leu Thr Asp Glu Leu Leu Asn Ile Leu Thr Glu Leu Thr Gln Leu Ser
                980                 985                 990

Lys Thr Thr Asn Ala Lys Val Ala Leu Arg Ala Arg Gln Val Leu Ile
            995                 1000                1005

Ala Ser His Leu Pro Ser Tyr Glu Leu Arg His Asn Gln Val Glu
    1010                1015                1020

Ser Ile Phe Leu Ser Ala Ile Asp Met Tyr Gly His Gln Phe Cys
    1025                1030                1035

Ile Glu Asn Leu Gln Lys Leu Ile Leu Ser Glu Thr Ser Ile Phe
    1040                1045                1050

Asp Val Leu Pro Asn Phe Phe Tyr His Ser Asn Gln Val Val Arg
    1055                1060                1065

Met Ala Ala Leu Glu Val Tyr Val Arg Arg Ala Tyr Ile Ala Tyr
    1070                1075                1080

Glu Leu Asn Ser Val Gln His Arg Gln Leu Lys Asp Asn Thr Cys
    1085                1090                1095

Val Val Glu Phe Gln Phe Met Leu Pro Thr Ser His Pro Asn Arg
    1100                1105                1110

Gly Asn Ile Pro Thr Leu Asn Arg Met Ser Phe Ser Ser Asn Leu
    1115                1120                1125

Asn His Tyr Gly Met Thr His Val Ala Ser Val Ser Asp Val Leu
    1130                1135                1140

Leu Asp Asn Ser Phe Thr Pro Pro Cys Gln Arg Met Gly Gly Met
    1145                1150                1155

Val Ser Phe Arg Thr Phe Glu Asp Phe Val Arg Ile Phe Asp Glu
    1160                1165                1170

Val Met Gly Cys Phe Ser Asp Ser Pro Pro Gln Ser Pro Thr Phe
    1175                1180                1185

Pro Glu Ala Gly His Thr Ser Leu Tyr Asp Glu Asp Lys Val Pro
    1190                1195                1200

Arg Asp Glu Pro Ile His Ile Leu Asn Val Ala Ile Lys Thr Asp
    1205                1210                1215

Cys Asp Ile Glu Asp Asp Arg Leu Ala Ala Met Phe Arg Glu Phe
    1220                1225                1230

Thr Gln Gln Asn Lys Ala Thr Leu Val Asp His Gly Ile Arg Arg
    1235                1240                1245

Leu Thr Phe Leu Val Ala Gln Lys Asp Phe Arg Lys Gln Val Asn
    1250                1255                1260

Tyr Glu Val Asp Arg Arg Phe His Arg Glu Phe Pro Lys Phe Phe
    1265                1270                1275
```

```
Thr Phe Arg Ala Arg Asp Lys Phe Glu Glu Asp Arg Ile Tyr Arg
    1280                1285                1290

His Leu Glu Pro Ala Leu Ala Phe Gln Leu Glu Leu Asn Arg Met
    1295                1300                1305

Arg Asn Phe Asp Leu Thr Ala Ile Pro Cys Ala Asn His Lys Met
    1310                1315                1320

His Leu Tyr Leu Gly Ala Ala Lys Val Glu Val Gly Thr Glu Val
    1325                1330                1335

Thr Asp Tyr Arg Phe Phe Val Arg Ala Ile Ile Arg His Ser Asp
    1340                1345                1350

Leu Val Thr Lys Glu Ala Ser Phe Glu Tyr Leu Gln Asn Glu Gly
    1355                1360                1365

Glu Arg Leu Leu Leu Glu Ala Met Asp Glu Leu Glu Val Ala Phe
    1370                1375                1380

Asn Asn Thr Asn Val Arg Thr Asp Cys Asn His Ile Phe Leu Asn
    1385                1390                1395

Phe Val Pro Thr Val Ile Met Asp Pro Ser Lys Ile Glu Glu Ser
    1400                1405                1410

Val Arg Ser Met Val Met Arg Tyr Gly Ser Arg Leu Trp Lys Leu
    1415                1420                1425

Arg Val Leu Gln Ala Glu Leu Lys Ile Asn Ile Arg Leu Thr Pro
    1430                1435                1440

Thr Gly Lys Ala Ile Pro Ile Arg Leu Phe Leu Thr Asn Glu Ser
    1445                1450                1455

Gly Tyr Tyr Leu Asp Ile Ser Leu Tyr Lys Glu Val Thr Asp Ser
    1460                1465                1470

Arg Thr Ala Gln Ile Met Phe Gln Ala Tyr Gly Asp Lys Gln Gly
    1475                1480                1485

Pro Leu His Gly Met Leu Ile Asn Thr Pro Tyr Val Thr Lys Asp
    1490                1495                1500

Leu Leu Gln Ser Lys Arg Phe Gln Ala Gln Ser Leu Gly Thr Thr
    1505                1510                1515

Tyr Ile Tyr Asp Ile Pro Glu Met Phe Arg Gln Ser Leu Ile Lys
    1520                1525                1530

Leu Trp Glu Ser Met Ser Thr Gln Ala Phe Leu Pro Ser Pro Pro
    1535                1540                1545

Leu Pro Ser Asp Met Leu Thr Tyr Thr Glu Leu Val Leu Asp Asp
    1550                1555                1560

Gln Gly Gln Leu Val His Met Asn Arg Leu Pro Gly Gly Asn Glu
    1565                1570                1575

Ile Gly Met Val Ala Trp Lys Met Thr Phe Lys Ser Pro Glu Tyr
    1580                1585                1590

Pro Glu Gly Arg Asp Ile Ile Val Ile Gly Asn Asp Ile Thr Tyr
    1595                1600                1605

Arg Ile Gly Ser Phe Gly Pro Gln Glu Asp Leu Leu Phe Leu Arg
    1610                1615                1620

Ala Ser Glu Leu Ala Arg Ala Glu Gly Ile Pro Arg Ile Tyr Val
    1625                1630                1635

Ser Ala Asn Ser Gly Ala Arg Ile Gly Leu Ala Glu Glu Ile Arg
    1640                1645                1650

His Met Phe His Val Ala Trp Val Asp Pro Glu Asp Pro Tyr Lys
    1655                1660                1665

Gly Tyr Arg Tyr Leu Tyr Leu Thr Pro Gln Asp Tyr Lys Arg Val
```

-continued

```
                        1670                1675                1680

Ser Ala Leu Asn Ser Val His Cys Glu His Val Glu Asp Glu Gly
        1685                1690                1695

Glu Ser Arg Tyr Lys Ile Thr Asp Ile Ile Gly Lys Glu Glu Gly
        1700                1705                1710

Ile Gly Pro Glu Asn Leu Arg Gly Ser Gly Met Ile Ala Gly Glu
        1715                1720                1725

Ser Ser Leu Ala Tyr Asn Glu Ile Ile Thr Ile Ser Leu Val Thr
        1730                1735                1740

Cys Arg Ala Ile Gly Ile Gly Ala Tyr Leu Val Arg Leu Gly Gln
        1745                1750                1755

Arg Thr Ile Gln Val Glu Asn Ser His Leu Ile Leu Thr Gly Ala
        1760                1765                1770

Gly Ala Leu Asn Lys Val Leu Gly Arg Glu Val Tyr Thr Ser Asn
        1775                1780                1785

Asn Gln Leu Gly Gly Ile Gln Ile Met His Asn Asn Gly Val Thr
        1790                1795                1800

His Cys Thr Val Cys Asp Asp Phe Glu Gly Val Phe Thr Val Leu
        1805                1810                1815

His Trp Leu Ser Tyr Met Pro Lys Ser Val His Ser Ser Val Pro
        1820                1825                1830

Leu Leu Asn Ser Lys Asp Pro Ile Asp Arg Ile Ile Glu Phe Val
        1835                1840                1845

Pro Thr Lys Thr Pro Tyr Asp Pro Arg Trp Met Leu Ala Gly Arg
        1850                1855                1860

Pro His Pro Thr Gln Lys Gly Gln Trp Leu Ser Gly Phe Phe Asp
        1865                1870                1875

Tyr Gly Ser Phe Ser Glu Ile Met Gln Pro Trp Ala Gln Thr Val
        1880                1885                1890

Val Val Gly Arg Ala Arg Leu Gly Gly Ile Pro Val Gly Val Val
        1895                1900                1905

Ala Val Glu Thr Arg Thr Val Glu Leu Ser Ile Pro Ala Asp Pro
        1910                1915                1920

Ala Asn Leu Asp Ser Glu Ala Lys Ile Ile Gln Gln Ala Gly Gln
        1925                1930                1935

Val Trp Phe Pro Asp Ser Ala Phe Lys Thr Tyr Gln Ala Ile Lys
        1940                1945                1950

Asp Phe Asn Arg Glu Gly Leu Pro Leu Met Val Phe Ala Asn Trp
        1955                1960                1965

Arg Gly Phe Ser Gly Gly Met Lys Asp Met Tyr Asp Gln Val Leu
        1970                1975                1980

Lys Phe Gly Ala Tyr Ile Val Asp Gly Leu Arg Glu Cys Cys Gln
        1985                1990                1995

Pro Val Leu Val Tyr Ile Pro Pro Gln Ala Glu Leu Arg Gly Gly
        2000                2005                2010

Ser Trp Val Val Ile Asp Ser Ser Ile Asn Pro Arg His Met Glu
        2015                2020                2025

Met Tyr Ala Asp Arg Glu Ser Arg Gly Ser Val Leu Glu Pro Glu
        2030                2035                2040

Gly Thr Val Glu Ile Lys Phe Arg Arg Lys Asp Leu Val Lys Thr
        2045                2050                2055

Met Arg Arg Val Asp Pro Val Tyr Ile His Leu Ala Glu Arg Leu
        2060                2065                2070
```

```
Gly Thr Pro Glu Leu Ser Thr Ala Glu Arg Lys Glu Leu Glu Asn
    2075                2080                2085

Lys Leu Lys Glu Arg Glu Glu Phe Leu Ile Pro Ile Tyr His Gln
    2090                2095                2100

Val Ala Val Gln Phe Ala Asp Leu His Asp Thr Pro Gly Arg Met
    2105                2110                2115

Gln Glu Lys Gly Val Ile Ser Asp Ile Leu Asp Trp Lys Thr Ser
    2120                2125                2130

Arg Thr Phe Phe Tyr Trp Arg Leu Arg Arg Leu Leu Leu Glu Asp
    2135                2140                2145

Leu Val Lys Lys Lys Ile His Asn Ala Asn Pro Glu Leu Thr Asp
    2150                2155                2160

Gly Gln Ile Gln Ala Met Leu Arg Arg Trp Phe Val Glu Val Glu
    2165                2170                2175

Gly Thr Val Lys Ala Tyr Val Trp Asp Asn Asn Lys Asp Leu Ala
    2180                2185                2190

Glu Trp Leu Glu Lys Gln Leu Thr Glu Glu Asp Gly Val His Ser
    2195                2200                2205

Val Ile Glu Glu Asn Ile Lys Cys Ile Ser Arg Asp Tyr Val Leu
    2210                2215                2220

Lys Gln Ile Arg Ser Leu Val Gln Ala Asn Pro Glu Val Ala Met
    2225                2230                2235

Asp Ser Ile Ile His Met Thr Gln His Ile Ser Pro Thr Gln Arg
    2240                2245                2250

Ala Glu Val Ile Arg Ile Leu Ser Thr Met Asp Ser Pro Ser Thr
    2255                2260                2265

<210> SEQ ID NO 54
<211> LENGTH: 2346
<212> TYPE: PRT
<213> ORGANISM: Homo sapiens

<400> SEQUENCE: 54

Met Asp Glu Pro Ser Pro Leu Ala Gln Pro Leu Glu Leu Asn Gln His
1               5                   10                  15

Ser Arg Phe Ile Ile Gly Ser Val Ser Glu Asp Asn Ser Glu Asp Glu
                20                  25                  30

Ile Ser Asn Leu Val Lys Leu Asp Leu Leu Glu Glu Lys Glu Gly Ser
            35                  40                  45

Leu Ser Pro Ala Ser Val Gly Ser Asp Thr Leu Ser Asp Leu Gly Ile
        50                  55                  60

Ser Ser Leu Gln Asp Gly Leu Ala Leu His Ile Arg Ser Ser Met Ser
65                  70                  75                  80

Gly Leu His Leu Val Lys Gln Gly Arg Asp Arg Lys Lys Ile Asp Ser
                85                  90                  95

Gln Arg Asp Phe Thr Val Ala Ser Pro Ala Glu Phe Val Thr Arg Phe
                100                 105                 110

Gly Gly Asn Lys Val Ile Glu Lys Val Leu Ile Ala Asn Asn Gly Ile
            115                 120                 125

Ala Ala Val Lys Cys Met Arg Ser Ile Arg Arg Trp Ser Tyr Glu Met
        130                 135                 140

Phe Arg Asn Glu Arg Ala Ile Arg Phe Val Val Met Val Thr Pro Glu
145                 150                 155                 160

Asp Leu Lys Ala Asn Ala Glu Tyr Ile Lys Met Ala Asp His Tyr Val
```

```
                165                 170                 175
Pro Val Pro Gly Gly Pro Asn Asn Asn Tyr Ala Asn Val Glu Leu
            180                 185                 190
Ile Leu Asp Ile Ala Lys Arg Ile Pro Val Gln Ala Val Trp Ala Gly
            195                 200                 205
Trp Gly His Ala Ser Glu Asn Pro Lys Leu Pro Glu Leu Leu Lys
            210                 215                 220
Asn Gly Ile Ala Phe Met Gly Pro Pro Ser Gln Ala Met Trp Ala Leu
225                 230                 235                 240
Gly Asp Lys Ile Ala Ser Ser Ile Val Ala Gln Thr Ala Gly Ile Pro
                245                 250                 255
Thr Leu Pro Trp Ser Gly Ser Gly Leu Arg Val Asp Trp Gln Glu Asn
            260                 265                 270
Asp Phe Ser Lys Arg Ile Leu Asn Val Pro Gln Glu Leu Tyr Glu Lys
            275                 280                 285
Gly Tyr Val Lys Asp Val Asp Asp Gly Leu Gln Ala Ala Glu Glu Val
            290                 295                 300
Gly Tyr Pro Val Met Ile Lys Ala Ser Glu Gly Gly Gly Lys Gly
305                 310                 315                 320
Ile Arg Lys Val Asn Asn Ala Asp Asp Phe Pro Asn Leu Phe Arg Gln
                325                 330                 335
Val Gln Ala Glu Val Pro Gly Ser Pro Ile Phe Val Met Arg Leu Ala
            340                 345                 350
Lys Gln Ser Arg His Leu Glu Val Gln Ile Leu Ala Asp Gln Tyr Gly
            355                 360                 365
Asn Ala Ile Ser Leu Phe Gly Arg Asp Cys Ser Val Gln Arg Arg His
            370                 375                 380
Gln Lys Ile Ile Glu Glu Ala Pro Ala Thr Ile Ala Thr Pro Ala Val
385                 390                 395                 400
Phe Glu His Met Glu Gln Cys Ala Val Lys Leu Ala Lys Met Val Gly
                405                 410                 415
Tyr Val Ser Ala Gly Thr Val Glu Tyr Leu Tyr Ser Gln Asp Gly Ser
            420                 425                 430
Phe Tyr Phe Leu Glu Leu Asn Pro Arg Leu Gln Val Glu His Pro Cys
            435                 440                 445
Thr Glu Met Val Ala Asp Val Asn Leu Pro Ala Ala Gln Leu Gln Ile
            450                 455                 460
Ala Met Gly Ile Pro Leu Tyr Arg Ile Lys Asp Ile Arg Met Met Tyr
465                 470                 475                 480
Gly Val Ser Pro Trp Gly Asp Ser Pro Ile Asp Phe Glu Asp Ser Ala
                485                 490                 495
His Val Pro Cys Pro Arg Gly His Val Ile Ala Ala Arg Ile Thr Ser
            500                 505                 510
Glu Asn Pro Asp Glu Gly Phe Lys Pro Ser Ser Gly Thr Val Gln Glu
            515                 520                 525
Leu Asn Phe Arg Ser Asn Lys Asn Val Trp Gly Tyr Phe Ser Val Ala
            530                 535                 540
Ala Ala Gly Gly Leu His Glu Phe Ala Asp Ser Gln Phe Gly His Cys
545                 550                 555                 560
Phe Ser Trp Gly Glu Asn Arg Glu Glu Ala Ile Ser Asn Met Val Val
                565                 570                 575
Ala Leu Lys Glu Leu Ser Ile Arg Gly Asp Phe Arg Thr Thr Val Glu
            580                 585                 590
```

```
Tyr Leu Ile Lys Leu Leu Glu Thr Glu Ser Phe Gln Met Asn Arg Ile
        595                 600                 605

Asp Thr Gly Trp Leu Asp Arg Leu Ile Ala Glu Lys Val Gln Ala Glu
        610                 615                 620

Arg Pro Asp Thr Met Leu Gly Val Val Cys Gly Ala Leu His Val Ala
625                 630                 635                 640

Asp Val Ser Leu Arg Asn Ser Val Ser Asn Phe Leu His Ser Leu Glu
                645                 650                 655

Arg Gly Gln Val Leu Pro Ala His Thr Leu Asn Thr Val Asp Val
                660                 665                 670

Glu Leu Ile Tyr Glu Gly Val Lys Tyr Val Leu Lys Val Thr Arg Gln
        675                 680                 685

Ser Pro Asn Ser Tyr Val Val Ile Met Asn Gly Ser Cys Val Glu Val
        690                 695                 700

Asp Val His Arg Leu Ser Asp Gly Gly Leu Leu Leu Ser Tyr Asp Gly
705                 710                 715                 720

Ser Ser Tyr Thr Thr Tyr Met Lys Glu Glu Val Asp Arg Tyr Arg Ile
                725                 730                 735

Thr Ile Gly Asn Lys Thr Cys Val Phe Glu Lys Glu Asn Asp Pro Ser
                740                 745                 750

Val Met Arg Ser Pro Ser Ala Gly Lys Leu Ile Gln Tyr Ile Val Glu
        755                 760                 765

Asp Gly Gly His Val Phe Ala Gly Gln Cys Tyr Ala Glu Ile Glu Val
        770                 775                 780

Met Lys Met Val Met Thr Leu Thr Ala Val Glu Ser Gly Cys Ile His
785                 790                 795                 800

Tyr Val Lys Arg Pro Gly Ala Ala Leu Asp Pro Gly Cys Val Leu Ala
                805                 810                 815

Lys Met Gln Leu Asp Asn Pro Ser Lys Val Gln Gln Ala Glu Leu His
                820                 825                 830

Thr Gly Ser Leu Pro Arg Ile Gln Ser Thr Ala Leu Arg Gly Glu Lys
        835                 840                 845

Leu His Arg Val Phe His Tyr Val Leu Asp Asn Leu Val Asn Val Met
        850                 855                 860

Asn Gly Tyr Cys Leu Pro Asp Pro Phe Phe Ser Ser Lys Val Lys Asp
865                 870                 875                 880

Trp Val Glu Arg Leu Met Lys Thr Leu Arg Asp Pro Ser Leu Pro Leu
                885                 890                 895

Leu Glu Leu Gln Asp Ile Met Thr Ser Val Ser Gly Arg Ile Pro Pro
                900                 905                 910

Asn Val Glu Lys Ser Ile Lys Lys Glu Met Ala Gln Tyr Ala Ser Asn
        915                 920                 925

Ile Thr Ser Val Leu Cys Gln Phe Pro Ser Gln Gln Ile Ala Asn Ile
        930                 935                 940

Leu Asp Ser His Ala Ala Thr Leu Asn Arg Lys Ser Glu Arg Glu Val
945                 950                 955                 960

Phe Phe Met Asn Thr Gln Ser Ile Val Gln Leu Val Gln Arg Tyr Arg
                965                 970                 975

Ser Gly Ile Arg Gly His Met Lys Ala Val Val Met Asp Leu Leu Arg
                980                 985                 990

Gln Tyr Leu Arg Val Glu Thr Gln  Phe Gln Asn Gly His Tyr Asp Lys
        995                 1000                1005
```

```
Cys Val Phe Ala Leu Arg Glu Glu Asn Lys Ser Asp Met Asn Thr
    1010            1015            1020

Val Leu Asn Tyr Ile Phe Ser His Ala Gln Val Thr Lys Lys Asn
    1025            1030            1035

Leu Leu Val Thr Met Leu Ile Asp Gln Leu Cys Gly Arg Asp Pro
    1040            1045            1050

Thr Leu Thr Asp Glu Leu Leu Asn Ile Leu Thr Glu Leu Thr Gln
    1055            1060            1065

Leu Ser Lys Thr Thr Asn Ala Lys Val Ala Leu Arg Ala Arg Gln
    1070            1075            1080

Val Leu Ile Ala Ser His Leu Pro Ser Tyr Glu Leu Arg His Asn
    1085            1090            1095

Gln Val Glu Ser Ile Phe Leu Ser Ala Ile Asp Met Tyr Gly His
    1100            1105            1110

Gln Phe Cys Ile Glu Asn Leu Gln Lys Leu Ile Leu Ser Glu Thr
    1115            1120            1125

Ser Ile Phe Asp Val Leu Pro Asn Phe Phe Tyr His Ser Asn Gln
    1130            1135            1140

Val Val Arg Met Ala Ala Leu Glu Val Tyr Val Arg Arg Ala Tyr
    1145            1150            1155

Ile Ala Tyr Glu Leu Asn Ser Val Gln His Arg Gln Leu Lys Asp
    1160            1165            1170

Asn Thr Cys Val Val Glu Phe Gln Phe Met Leu Pro Thr Ser His
    1175            1180            1185

Pro Asn Arg Gly Asn Ile Pro Thr Leu Asn Arg Met Ser Phe Ser
    1190            1195            1200

Ser Asn Leu Asn His Tyr Gly Met Thr His Val Ala Ser Val Ser
    1205            1210            1215

Asp Val Leu Leu Asp Asn Ser Phe Thr Pro Pro Cys Gln Arg Met
    1220            1225            1230

Gly Gly Met Val Ser Phe Arg Thr Phe Glu Asp Phe Val Arg Ile
    1235            1240            1245

Phe Asp Glu Val Met Gly Cys Phe Ser Asp Ser Pro Pro Gln Ser
    1250            1255            1260

Pro Thr Phe Pro Glu Ala Gly His Thr Ser Leu Tyr Asp Glu Asp
    1265            1270            1275

Lys Val Pro Arg Asp Glu Pro Ile His Ile Leu Asn Val Ala Ile
    1280            1285            1290

Lys Thr Asp Cys Asp Ile Glu Asp Asp Arg Leu Ala Ala Met Phe
    1295            1300            1305

Arg Glu Phe Thr Gln Gln Asn Lys Ala Thr Leu Val Asp His Gly
    1310            1315            1320

Ile Arg Arg Leu Thr Phe Leu Val Ala Gln Lys Asp Phe Arg Lys
    1325            1330            1335

Gln Val Asn Tyr Glu Val Asp Arg Arg Phe His Arg Glu Phe Pro
    1340            1345            1350

Lys Phe Phe Thr Phe Arg Ala Arg Asp Lys Phe Glu Glu Asp Arg
    1355            1360            1365

Ile Tyr Arg His Leu Glu Pro Ala Leu Ala Phe Gln Leu Glu Leu
    1370            1375            1380

Asn Arg Met Arg Asn Phe Asp Leu Thr Ala Ile Pro Cys Ala Asn
    1385            1390            1395

His Lys Met His Leu Tyr Leu Gly Ala Ala Lys Val Glu Val Gly
```

```
        1400            1405            1410
Thr Glu Val Thr Asp Tyr Arg Phe Phe Val Arg Ala Ile Ile Arg
    1415            1420            1425
His Ser Asp Leu Val Thr Lys Glu Ala Ser Phe Glu Tyr Leu Gln
    1430            1435            1440
Asn Glu Gly Glu Arg Leu Leu Leu Glu Ala Met Asp Glu Leu Glu
    1445            1450            1455
Val Ala Phe Asn Asn Thr Asn Val Arg Thr Asp Cys Asn His Ile
    1460            1465            1470
Phe Leu Asn Phe Val Pro Thr Val Ile Met Asp Pro Ser Lys Ile
    1475            1480            1485
Glu Glu Ser Val Arg Ser Met Val Met Arg Tyr Gly Ser Arg Leu
    1490            1495            1500
Trp Lys Leu Arg Val Leu Gln Ala Glu Leu Lys Ile Asn Ile Arg
    1505            1510            1515
Leu Thr Pro Thr Gly Lys Ala Ile Pro Ile Arg Leu Phe Leu Thr
    1520            1525            1530
Asn Glu Ser Gly Tyr Tyr Leu Asp Ile Ser Leu Tyr Lys Glu Val
    1535            1540            1545
Thr Asp Ser Arg Thr Ala Gln Ile Met Phe Gln Ala Tyr Gly Asp
    1550            1555            1560
Lys Gln Gly Pro Leu His Gly Met Leu Ile Asn Thr Pro Tyr Val
    1565            1570            1575
Thr Lys Asp Leu Leu Gln Ser Lys Arg Phe Gln Ala Gln Ser Leu
    1580            1585            1590
Gly Thr Thr Tyr Ile Tyr Asp Ile Pro Glu Met Phe Arg Gln Ser
    1595            1600            1605
Leu Ile Lys Leu Trp Glu Ser Met Ser Thr Gln Ala Phe Leu Pro
    1610            1615            1620
Ser Pro Pro Leu Pro Ser Asp Met Leu Thr Tyr Thr Glu Leu Val
    1625            1630            1635
Leu Asp Asp Gln Gly Gln Leu Val His Met Asn Arg Leu Pro Gly
    1640            1645            1650
Gly Asn Glu Ile Gly Met Val Ala Trp Lys Met Thr Phe Lys Ser
    1655            1660            1665
Pro Glu Tyr Pro Glu Gly Arg Asp Ile Ile Val Ile Gly Asn Asp
    1670            1675            1680
Ile Thr Tyr Arg Ile Gly Ser Phe Gly Pro Gln Glu Asp Leu Leu
    1685            1690            1695
Phe Leu Arg Ala Ser Glu Leu Ala Arg Ala Glu Gly Ile Pro Arg
    1700            1705            1710
Ile Tyr Val Ser Ala Asn Ser Gly Ala Arg Ile Gly Leu Ala Glu
    1715            1720            1725
Glu Ile Arg His Met Phe His Val Ala Trp Val Asp Pro Glu Asp
    1730            1735            1740
Pro Tyr Lys Gly Tyr Arg Tyr Leu Tyr Leu Thr Pro Gln Asp Tyr
    1745            1750            1755
Lys Arg Val Ser Ala Leu Asn Ser Val His Cys Glu His Val Glu
    1760            1765            1770
Asp Glu Gly Glu Ser Arg Tyr Lys Ile Thr Asp Ile Ile Gly Lys
    1775            1780            1785
Glu Glu Gly Ile Gly Pro Glu Asn Leu Arg Gly Ser Gly Met Ile
    1790            1795            1800
```

-continued

Ala Gly Glu Ser Ser Leu Ala Tyr Asn Glu Ile Ile Thr Ile Ser
1805               1810                    1815

Leu Val Thr Cys Arg Ala Ile Gly Ile Gly Ala Tyr Leu Val Arg
1820               1825                    1830

Leu Gly Gln Arg Thr Ile Gln Val Glu Asn Ser His Leu Ile Leu
1835               1840                    1845

Thr Gly Ala Gly Ala Leu Asn Lys Val Leu Gly Arg Glu Val Tyr
1850               1855                    1860

Thr Ser Asn Asn Gln Leu Gly Gly Ile Gln Ile Met His Asn Asn
1865               1870                    1875

Gly Val Thr His Cys Thr Val Cys Asp Asp Phe Glu Gly Val Phe
1880               1885                    1890

Thr Val Leu His Trp Leu Ser Tyr Met Pro Lys Ser Val His Ser
1895               1900                    1905

Ser Val Pro Leu Leu Asn Ser Lys Asp Pro Ile Asp Arg Ile Ile
1910               1915                    1920

Glu Phe Val Pro Thr Lys Thr Pro Tyr Asp Pro Arg Trp Met Leu
1925               1930                    1935

Ala Gly Arg Pro His Pro Thr Gln Lys Gly Gln Trp Leu Ser Gly
1940               1945                    1950

Phe Phe Asp Tyr Gly Ser Phe Ser Glu Ile Met Gln Pro Trp Ala
1955               1960                    1965

Gln Thr Val Val Val Gly Arg Ala Arg Leu Gly Gly Ile Pro Val
1970               1975                    1980

Gly Val Val Ala Val Glu Thr Arg Thr Val Glu Leu Ser Ile Pro
1985               1990                    1995

Ala Asp Pro Ala Asn Leu Asp Ser Glu Ala Lys Ile Ile Gln Gln
2000               2005                    2010

Ala Gly Gln Val Trp Phe Pro Asp Ser Ala Phe Lys Thr Tyr Gln
2015               2020                    2025

Ala Ile Lys Asp Phe Asn Arg Glu Gly Leu Pro Leu Met Val Phe
2030               2035                    2040

Ala Asn Trp Arg Gly Phe Ser Gly Gly Met Lys Asp Met Tyr Asp
2045               2050                    2055

Gln Val Leu Lys Phe Gly Ala Tyr Ile Val Asp Gly Leu Arg Glu
2060               2065                    2070

Cys Cys Gln Pro Val Leu Val Tyr Ile Pro Pro Gln Ala Glu Leu
2075               2080                    2085

Arg Gly Gly Ser Trp Val Val Ile Asp Ser Ser Ile Asn Pro Arg
2090               2095                    2100

His Met Glu Met Tyr Ala Asp Arg Glu Ser Arg Gly Ser Val Leu
2105               2110                    2115

Glu Pro Glu Gly Thr Val Glu Ile Lys Phe Arg Arg Lys Asp Leu
2120               2125                    2130

Val Lys Thr Met Arg Arg Val Asp Pro Val Tyr Ile His Leu Ala
2135               2140                    2145

Glu Arg Leu Gly Thr Pro Glu Leu Ser Thr Ala Glu Arg Lys Glu
2150               2155                    2160

Leu Glu Asn Lys Leu Lys Glu Arg Glu Glu Phe Leu Ile Pro Ile
2165               2170                    2175

Tyr His Gln Val Ala Val Gln Phe Ala Asp Leu His Asp Thr Pro
2180               2185                    2190

```
Gly Arg Met Gln Glu Lys Gly Val Ile Ser Asp Ile Leu Asp Trp
    2195                2200                2205

Lys Thr Ser Arg Thr Phe Phe Tyr Trp Arg Leu Arg Arg Leu Leu
    2210                2215                2220

Leu Glu Asp Leu Val Lys Lys Ile His Asn Ala Asn Pro Glu
    2225                2230                2235

Leu Thr Asp Gly Gln Ile Gln Ala Met Leu Arg Arg Trp Phe Val
    2240                2245                2250

Glu Val Glu Gly Thr Val Lys Ala Tyr Val Trp Asp Asn Asn Lys
    2255                2260                2265

Asp Leu Ala Glu Trp Leu Glu Lys Gln Leu Thr Glu Glu Asp Gly
    2270                2275                2280

Val His Ser Val Ile Glu Glu Asn Ile Lys Cys Ile Ser Arg Asp
    2285                2290                2295

Tyr Val Leu Lys Gln Ile Arg Ser Leu Val Gln Ala Asn Pro Glu
    2300                2305                2310

Val Ala Met Asp Ser Ile Ile His Met Thr Gln His Ile Ser Pro
    2315                2320                2325

Thr Gln Arg Ala Glu Val Ile Arg Ile Leu Ser Thr Met Asp Ser
    2330                2335                2340

Pro Ser Thr
    2345

<210> SEQ ID NO 55
<211> LENGTH: 2234
<212> TYPE: PRT
<213> ORGANISM: Lipomyces starkeyi

<400> SEQUENCE: 55

Met Ser Ala Ala Ala Ser Ser Leu Pro Ser His Phe Ile Gly Leu Asn
1               5                   10                  15

Thr Val Asp Val Ala Ala Asn Ser Pro Val Lys Asp Phe Val Gln Asn
            20                  25                  30

His Gly Gly His Thr Val Ile Thr Ser Val Leu Ile Ala Asn Asn Gly
        35                  40                  45

Ile Ala Ala Val Lys Glu Ile Arg Ser Val Arg Lys Trp Ala Tyr Glu
    50                  55                  60

Thr Phe Gly Asp Glu Arg Ala Ile Ser Phe Thr Val Met Ala Thr Pro
65                  70                  75                  80

Glu Asp Leu Lys Ala Asn Ala Asp Tyr Ile Arg Met Ala Asp Gln Tyr
                85                  90                  95

Val Glu Val Pro Gly Gly Thr Asn Asn Asn Asn Phe Ala Asn Val Glu
            100                 105                 110

Leu Ile Val Asp Ile Ala Glu Arg Met Asn Val His Ala Val Trp Ala
        115                 120                 125

Gly Trp Gly His Ala Ser Glu Asn Pro Lys Leu Pro Glu Ser Leu Ala
    130                 135                 140

Gln Ser Pro Lys Lys Ile Val Phe Ile Gly Pro Pro Gly Ser Ala Met
145                 150                 155                 160

Arg Ser Leu Gly Asp Lys Ile Ser Thr Ile Val Ala Gln His Ala
                165                 170                 175

Lys Val Pro Cys Ile Pro Trp Ser Gly Thr Gly Val Asp Glu Val Gln
            180                 185                 190

Ile Asp Ser Val Ser Gly Leu Val Thr Val Ser Asp Glu Ile Tyr Ala
        195                 200                 205
```

```
Lys Gly Cys Thr Ser Thr Ala Glu Glu Ala Leu Glu Lys Ala Arg Ile
    210                 215                 220
Ile Gly Phe Pro Val Met Ile Lys Ala Ser Glu Gly Gly Gly Gly Lys
225                 230                 235                 240
Gly Ile Arg Lys Val Glu Ser Glu Asp Asn Phe His Ser Leu Tyr Ser
            245                 250                 255
Gln Val Ala Asn Glu Val Pro Gly Ser Pro Ile Phe Val Met Lys Leu
        260                 265                 270
Ala Gly Asn Ala Arg His Leu Glu Val Gln Leu Leu Ala Asp Gln Tyr
    275                 280                 285
Gly Asn Asn Ile Ser Leu Phe Gly Arg Asp Cys Ser Val Gln Arg Arg
290                 295                 300
His Gln Lys Ile Ile Glu Glu Ala Pro Val Thr Val Ala Asn Pro Ala
305                 310                 315                 320
Thr Phe Ser Ala Met Glu His Ala Ala Val Arg Leu Gly Gln Leu Val
            325                 330                 335
Gly Tyr Val Ser Ala Gly Thr Val Glu Tyr Leu Tyr Ser His Asp Asp
        340                 345                 350
Asp Lys Phe Tyr Phe Leu Glu Leu Asn Pro Arg Leu Gln Val Glu His
    355                 360                 365
Pro Thr Thr Glu Met Val Thr Gly Val Asn Leu Pro Ala Ala Gln Leu
370                 375                 380
Gln Ile Ala Met Gly Val Ser Leu His Arg Ile Arg Asp Ile Arg Leu
385                 390                 395                 400
Phe Tyr Gly Val Asp Pro His Thr Ser Thr Glu Ile Asp Phe Asp Phe
            405                 410                 415
Ser Lys Glu Gly Ser Leu Gln Thr Gln Arg Arg Pro Val Pro Lys Gly
        420                 425                 430
His Thr Thr Ala Cys Arg Ile Thr Ser Glu Asp Pro Gly Glu Gly Phe
    435                 440                 445
Lys Pro Ser Ser Gly Val Met His Glu Leu Asn Phe Arg Ser Ser Ser
450                 455                 460
Asn Val Trp Gly Tyr Phe Ser Val Gly Asn Gln Gly Gly Ile His Ser
465                 470                 475                 480
Phe Ser Asp Ser Gln Phe Gly His Ile Phe Ala Phe Gly Glu Asn Arg
            485                 490                 495
Ser Ala Ser Arg Lys His Met Val Val Ala Leu Lys Glu Leu Ser Ile
        500                 505                 510
Arg Gly Asp Phe Arg Thr Thr Val Glu Tyr Leu Ile Lys Leu Leu Glu
    515                 520                 525
Thr Pro Asp Phe Glu Ser Asn Lys Ile Thr Thr Gly Trp Leu Asp Glu
530                 535                 540
Leu Ile Ser Lys Lys Leu Thr Ala Glu Arg Pro Asp Pro Val Val Ala
545                 550                 555                 560
Val Val Cys Gly Ala Val Thr Lys Ala His Leu Ala Ser Glu Ala Cys
            565                 570                 575
Phe Gln Glu Tyr Lys Asn Ser Leu Glu Lys Gly Gln Val Pro Ser Lys
        580                 585                 590
Asp Ile Leu Lys Thr Leu Phe Pro Val Asp Phe Ile Tyr Glu Gly Ser
    595                 600                 605
Arg Tyr Lys Phe Thr Val Thr Arg Ser Ser Met Asp Leu Tyr Gln Ile
610                 615                 620
```

```
Phe Ile Asn Gly Ser Lys Cys Leu Val Gly Val Lys Ser Leu Ser Asp
625                 630                 635                 640

Gly Gly Leu Leu Val Leu Leu Gly Gly Lys Ser His Asn Val Tyr Trp
            645                 650                 655

Lys Asp Glu Val Gly Thr Thr Arg Leu Ser Val Asp Ser Lys Thr Cys
            660                 665                 670

Leu Leu Glu Gln Glu Asn Asp Pro Thr Gln Leu Arg Thr Pro Ser Pro
            675                 680                 685

Gly Lys Leu Val Lys Phe Leu Val Glu Asn Gly Glu His Val Lys Thr
690                 695                 700

Gly Gln Pro Phe Ala Glu Val Glu Val Met Lys Met Tyr Met Pro Leu
705                 710                 715                 720

Ile Ala Gln Glu Asp Gly Ile Val Gln Leu Ile Lys Gln Pro Gly Ala
                725                 730                 735

Thr Leu Glu Ala Gly Asp Ile Leu Gly Ile Leu Ala Leu Asp Asp Pro
                740                 745                 750

Ser Arg Val Lys His Ala Lys Pro Phe Glu Gly Gln Leu Pro Asp Phe
            755                 760                 765

Gly Ser Pro Leu Val Leu Gly Ser Lys Pro Ser Gln Arg Phe Asn Leu
770                 775                 780

Leu Leu Ser Thr Leu Arg Asn Ile Leu Ala Gly Phe Asp Asn Gln Val
785                 790                 795                 800

Leu Leu Ala Ser Thr Leu Lys Asp Leu Ser Gln Val Leu Lys Asp Asp
                805                 810                 815

Ala Leu Pro Tyr Ser Glu Trp Asn Ala Gln Phe Ser Ala Leu His Ser
                820                 825                 830

Arg Ile Pro Gln Lys Leu Asp Ala Thr Leu Ser Ser Leu Ile Glu Arg
            835                 840                 845

Ser Lys Ser Lys Asp Ala Glu Phe Pro Ala Lys Leu Leu Leu Arg Ala
850                 855                 860

Ile Glu Arg Phe Ala Glu Glu Phe Ile Gln Pro Gln Asp Leu Phe Val
865                 870                 875                 880

Phe Lys Gln Gln Val Glu Pro Leu Val Thr Ile Ala Thr Arg Tyr Gln
                885                 890                 895

Ala Gly Leu Lys Ala His Glu Tyr Gly Val Ile Ala Glu Leu Leu Glu
                900                 905                 910

Gln Tyr Leu Ala Val Glu Lys Leu Phe Ser Gly Ala Asn Ile Arg Asp
            915                 920                 925

Glu Asp Val Phe Leu Arg Leu Arg Asp Glu Asn Lys Asp Ile Phe
930                 935                 940

Lys Val Val Met Thr Val Phe Ser His Gly Arg Val Gly Ala Lys Asn
945                 950                 955                 960

Asn Leu Ile Leu Ala Ile Leu Ala Ala Leu Arg Ser Asp Arg Ser Glu
                965                 970                 975

Val Ser Glu Val Ala Lys Tyr Leu Arg Pro Ala Leu Lys Thr Leu Thr
                980                 985                 990

Glu Leu Asp Ser Gly Val Thr Ala Pro Val Ala Leu Lys Ala Arg Glu
            995                 1000                1005

Leu Leu Ile Gln Cys Ala Leu Pro Ser Leu Glu Glu Arg Thr Ala
            1010                1015                1020

Gln Leu Glu His Ile Leu Arg Ser Ser Val Val Glu Ser Arg Tyr
            1025                1030                1035

Gly Glu Val Gly Phe Glu His Ser Ala Pro Arg Ile Asp Val Leu
```

-continued

```
                1040                1045                1050
Lys Glu Val Ile Asp Ser Gln Tyr Ile Val Phe Asp Val Leu Pro
                1055                1060                1065
Lys Phe Phe Ala His Ser Asp Arg Tyr Val Thr Leu Ala Ala Leu
                1070                1075                1080
Glu Leu Tyr Val Arg Arg Ala Tyr Arg Ala Tyr Asn Val Met Ser
                1085                1090                1095
Met Glu Tyr His Asn Glu Gly Asp Leu Val Pro Val Val Thr Phe
                1100                1105                1110
Lys Phe Leu Leu Ala Ala Ile Gly Asn Pro Ala Tyr Asn Ile Val
                1115                1120                1125
Gly Gln Gly Ala Pro Ser Gly Asp Ser Arg Ile Asp Phe Gln Arg
                1130                1135                1140
Ala Ala Ser Val Ser Asp Leu Thr Phe Met Met Ser Lys Ser Asp
                1145                1150                1155
Ser Glu Ser Leu Arg Ser Gly Val Ile Val Pro Val Ala Asp Ile
                1160                1165                1170
Ala Asp Ile Asp Glu Val Leu Pro Arg Ala Leu Asp Tyr Leu Pro
                1175                1180                1185
Gln Arg Ala Gly Ala Gly Ser Gly Gly Phe Ser Phe Ser Ala Lys
                1190                1195                1200
Ser Asp Leu Asp Ser Lys Arg Arg Pro Ala Pro Lys Pro Glu
                1205                1210                1215
Ser Leu Ser Asn Ile Cys Asn Val Leu Ile Arg Lys Thr Ala Lys
                1220                1225                1230
Thr Asp Asp Ala Ala Leu Val Ser Asp Ile Lys Phe Ile Val Asp
                1235                1240                1245
Glu Tyr Lys Glu Glu Phe Leu Leu Arg Ser Ile Arg Arg Val Thr
                1250                1255                1260
Phe Val Cys Gly Arg Glu Asp Gly Ser Tyr Pro Gly Tyr Phe Thr
                1265                1270                1275
Phe Arg Gly Pro Asp Tyr Val Glu Asp Glu Ser Ile Arg His Ile
                1280                1285                1290
Glu Pro Ala Leu Ala Tyr Gln Leu Glu Leu Gly Arg Leu Ser Asn
                1295                1300                1305
Phe Asn Tyr Lys Pro Ile Phe Thr Asp Asn Arg Asn Ile His Val
                1310                1315                1320
Tyr Gln Ala Ile Gly Lys Asp Val Pro Ser Asp Lys Arg Phe Phe
                1325                1330                1335
Val Arg Gly Ile Val Arg Pro Gly Arg Leu Arg Asp Glu Ile Pro
                1340                1345                1350
Thr Ser Glu Tyr Leu Ile Ser Glu Thr Asp Arg Leu Met Ser Asp
                1355                1360                1365
Ile Leu Asp Ala Leu Glu Val Ile Gly Pro Asn Asn Thr Asp Met
                1370                1375                1380
Asn His Ile Phe Ile Asn Phe Ser Pro Ile Phe His Leu Val Pro
                1385                1390                1395
Glu Glu Val Glu Ala Ala Phe Gly Gln Phe Leu Glu Arg Phe Gly
                1400                1405                1410
Arg Arg Leu Trp Arg Leu Arg Val Thr Gly Ala Glu Ile Arg Ile
                1415                1420                1425
Met Cys Thr Asp Pro Glu Thr Asn Val Pro Tyr Pro Leu Arg Ala
                1430                1435                1440
```

```
Ile Ile Thr Asn Val Ser Gly Tyr Val Val Gln Ser Glu Leu Tyr
    1445                1450                1455

Thr Glu Val Lys Asn Asp Lys Gly Gln Trp Val Phe Lys Ser Leu
    1460                1465                1470

Gly Lys Pro Gly Asn Met His Leu Arg Ser Ile Thr Thr Pro Tyr
    1475                1480                1485

Ala Thr Lys Glu Trp Leu Gln Pro Lys Arg Tyr Lys Ala His Leu
    1490                1495                1500

Met Gly Thr Thr Phe Val Tyr Asp Phe Pro Glu Leu Phe Asn Gln
    1505                1510                1515

Ala Ile Arg Ala Ser Trp Arg Ala Ala Gln Gln Gln Ser Pro Glu
    1520                1525                1530

Asn Val Leu Thr Tyr Lys Glu Leu Ile Met Asp Asp Ser Gly Glu
    1535                1540                1545

Leu Ser Glu Val Ser Arg Glu Pro Gly Ala Asn Thr Cys Gly Met
    1550                1555                1560

Val Ala Trp Leu Phe Thr Ala Leu Thr Pro Glu Tyr Pro Thr Gly
    1565                1570                1575

Arg Gln Phe Ile Val Val Ala Asn Asp Ile Thr Tyr Lys Ile Gly
    1580                1585                1590

Ser Phe Gly Pro Gln Glu Asp Lys Tyr Phe His Thr Val Thr Gln
    1595                1600                1605

Leu Ala Val Lys Leu Gly Ile Pro Arg Ile Tyr Leu Ser Ala Asn
    1610                1615                1620

Ser Gly Ala Arg Ile Gly Val Ala Asp Glu Phe Val Ser Leu Phe
    1625                1630                1635

Ser Val Ala Trp Asn Asp Ser Ser Asn Pro Glu Lys Gly Phe Lys
    1640                1645                1650

Tyr Leu Tyr Leu Thr Pro Ala Ile Tyr Asn Gly Leu Ser Asp Ala
    1655                1660                1665

Ala Lys Lys Thr Val Leu Thr Glu Arg Ile Val Glu Glu Gly Glu
    1670                1675                1680

Glu Arg Tyr Val Ile Thr Thr Ile Ile Gly Ala Glu Asp Gly Leu
    1685                1690                1695

Gly Val Glu Cys Leu Arg Gly Ser Gly Leu Ile Ala Gly Ala Thr
    1700                1705                1710

Ser Lys Ala Tyr Lys Asp Ile Phe Thr Ile Thr Leu Val Thr Cys
    1715                1720                1725

Arg Ser Val Gly Ile Gly Ala Tyr Leu Val Arg Leu Gly Gln Arg
    1730                1735                1740

Ala Ile Gln Ile Glu Gly Gln Pro Ile Ile Leu Thr Gly Ala Pro
    1745                1750                1755

Ala Ile Asn Lys Leu Leu Gly Arg Glu Val Tyr Ser Ser Asn Leu
    1760                1765                1770

Gln Leu Gly Gly Thr Gln Ile Met Tyr Lys Asn Gly Val Ser His
    1775                1780                1785

Leu Thr Ala Asn Asp Asp Leu Ala Gly Val Met Lys Ile Ile Glu
    1790                1795                1800

Trp Met Ser Tyr Val Pro Tyr Lys Lys Gly Gly Gln Leu Pro Ile
    1805                1810                1815

Tyr Pro Ser Ser Asp Thr Trp Asp Arg Asp Val Thr Tyr Thr Pro
    1820                1825                1830
```

```
Pro Lys Gln Val Pro Tyr Asp Val Arg Trp Leu Ile Ala Gly Arg
1835                1840                1845

Glu Asp Glu Glu Gly Gly Phe Glu Tyr Gly Leu Phe Asp Lys Asp
1850                1855                1860

Ser Phe Gln Glu Thr Leu Ser Gly Trp Ala Arg Thr Val Val Val
1865                1870                1875

Gly Arg Ala Arg Leu Gly Gly Ile Pro Val Gly Val Ile Gly Val
1880                1885                1890

Glu Val Arg Ser Val Glu Asn Ile Phe Pro Ala Asp Pro Ala Asn
1895                1900                1905

Pro Asp Ser Thr Glu Met Val Val Gln Glu Ala Gly Gln Val Trp
1910                1915                1920

Tyr Pro Asn Ser Ala Phe Lys Thr Ala Gln Ala Ile Asn Asp Phe
1925                1930                1935

Asn His Gly Glu Glu Leu Pro Leu Val Ile Leu Ala Asn Trp Arg
1940                1945                1950

Gly Phe Ser Gly Gly Gln Arg Asp Met Tyr Asn Glu Val Leu Lys
1955                1960                1965

Tyr Gly Ser Phe Ile Val Asp Ala Leu Val Gly Tyr Lys Gln Pro
1970                1975                1980

Ile Phe Val Tyr Ile Pro Pro His Ala Glu Leu Arg Gly Gly Ser
1985                1990                1995

Trp Val Val Ile Asp Pro Thr Ile Asn Ser Asp Gln Met Glu Met
2000                2005                2010

Tyr Ala Asp Asp Glu Ala Arg Ala Gly Val Leu Glu Pro Glu Gly
2015                2020                2025

Met Val Gly Ile Lys Tyr Arg Arg Asp Arg Leu Leu Glu Thr Met
2030                2035                2040

Thr Arg Leu Asp Pro Val Tyr Ala Ser Leu Lys Arg Gln Ala Asp
2045                2050                2055

Lys Lys Asp Leu Ala Pro Ala Ile Ala Gln Asp Leu Lys Val Lys
2060                2065                2070

Leu Ser Glu Arg Glu Ser Thr Leu Met Pro Ile Tyr Arg Gln Ile
2075                2080                2085

Ser Leu Gln Phe Ala Asp Leu His Asp Arg Ala Gly Arg Met Lys
2090                2095                2100

Ala Lys Gly Thr Ile Arg Glu Val Leu His Trp Arg Glu Ala Arg
2105                2110                2115

Arg Phe Phe Tyr Trp Arg Val Arg Arg Arg Val Gly Glu Ser Tyr
2120                2125                2130

Ile Leu Arg Asp Leu Glu Ala Ala Asn Pro Lys Ser Thr Arg Leu
2135                2140                2145

Glu Arg Val Ala Arg Leu Lys Ser Trp Tyr Ala Glu Ala Gly Ile
2150                2155                2160

Asn Glu Ser Ser Asp Ala Asp Val Ala Ser Trp Ile Glu Lys Ser
2165                2170                2175

Gly Ala Ala Ile Thr Ser Lys Val Lys Gln Val Arg Lys Asp Ala
2180                2185                2190

Lys Ile Gln Asp Leu Leu Ala Leu Val Arg Ala Asp Lys Asp Val
2195                2200                2205

Ala Leu Gln Gly Leu Val Glu Ser Leu Lys Ala Leu Ser Thr Glu
2210                2215                2220

Glu Arg Asp Ala Ile Phe Lys Gln Ala Ser Asn
```

2225          2230

<210> SEQ ID NO 56
<211> LENGTH: 2234
<212> TYPE: PRT
<213> ORGANISM: Komagataella phaffii

<400> SEQUENCE: 56

Met Ser Ser Val Asn His Ser Leu Arg His Ser Lys Leu Pro Pro His
1               5                   10                  15

Phe Leu Gly Leu Asn Ser Val Glu Val Ala Ala Pro Ser Lys Val Arg
            20                  25                  30

Asp Phe Val Arg Asp His Gly Gly His Ser Val Ile Thr Arg Val Leu
        35                  40                  45

Ile Ala Asn Asn Gly Ile Ala Ala Val Lys Glu Ile Arg Ser Val Arg
    50                  55                  60

Lys Trp Ala Tyr Glu Thr Phe Gly Asn Asp Arg Ala Ile Gln Phe Ile
65                  70                  75                  80

Val Met Ala Thr Pro Glu Asp Leu Glu Ala Asn Ala Glu Tyr Ile Arg
                85                  90                  95

Met Ala Asp Gln Tyr Val Met Val Pro Gly Gly Thr Ala Asn Asn Asn
            100                 105                 110

Tyr Ala Asn Val Asp Leu Ile Val Glu Ile Ala Glu Ser Thr Asp Ala
        115                 120                 125

His Ala Val Trp Ala Gly Trp Gly Phe Ala Ser Glu Asn Pro His Leu
    130                 135                 140

Pro Glu Gln Leu Ala Ala Ser Pro Lys Lys Ile Ile Phe Ile Gly Pro
145                 150                 155                 160

Pro Gly Ser Ala Met Arg Ser Leu Gly Asp Lys Ile Ser Ser Thr Ile
                165                 170                 175

Val Ala Gln His Ala Lys Val Pro Cys Ile Pro Trp Ser Gly Thr Gly
            180                 185                 190

Val Asp Gln Val Ile Ile Asp Pro Val Ser Asn Leu Val Ser Val Asp
        195                 200                 205

Glu Glu Thr Tyr Ala Lys Gly Cys Cys Ser Asp Pro Gln Asp Gly Leu
    210                 215                 220

Ala Lys Ala Lys Ala Ile Gly Phe Pro Val Met Ile Lys Ala Ser Glu
225                 230                 235                 240

Gly Gly Gly Gly Lys Gly Ile Arg Lys Val Asp Arg Glu Glu Asp Phe
                245                 250                 255

Leu Ser Leu Tyr Asp Gln Ala Ala Asn Glu Ile Pro Gly Ser Pro Ile
            260                 265                 270

Phe Ile Met Lys Leu Ala Gly Asp Ala Arg His Leu Glu Val Gln Leu
        275                 280                 285

Leu Ala Asp Gln Tyr Gly Thr Asn Ile Ser Leu Phe Gly Arg Asp Cys
    290                 295                 300

Ser Val Gln Arg Arg His Gln Lys Ile Ile Glu Glu Ala Pro Val Thr
305                 310                 315                 320

Ile Ala Lys Gln Asp Thr Phe Arg Gln Met Glu Gln Ala Ala Val Arg
                325                 330                 335

Leu Gly Gln Leu Val Gly Tyr Val Ser Ala Gly Thr Val Glu Tyr Leu
            340                 345                 350

Tyr Ser His Ala Glu Asp Lys Phe Tyr Phe Leu Glu Leu Asn Pro Arg
        355                 360                 365

```
Leu Gln Val Glu His Pro Thr Thr Glu Met Ala Thr Gly Val Asn Leu
370                 375                 380

Pro Val Ala Gln Leu Leu Ile Ala Met Gly Ile Pro Leu Asn Arg Ile
385                 390                 395                 400

Arg Asp Ile Arg Val Leu Tyr Gly Leu Glu Pro Asn Gly Ala Thr Glu
            405                 410                 415

Ile Asp Phe Glu Phe Lys Thr Glu Glu Ser Leu Lys Ser Gln Arg Lys
            420                 425                 430

Pro Ile Pro Lys Gly His Thr Ile Ala Cys Arg Ile Thr Ser Glu Asp
            435                 440                 445

Pro Gly Glu Gly Phe Lys Pro Ser Gly Gly Ala Leu Tyr Glu Leu Asn
450                 455                 460

Phe Arg Ser Ser Ser Val Trp Gly Tyr Phe Ser Val Gly Asn Lys
465                 470                 475                 480

Ser Ser Ile His Ser Phe Ser Asp Ser Gln Phe Gly His Ile Phe Ser
                485                 490                 495

Phe Gly Glu Asn Arg Gln Ile Ala Arg Lys Asn Met Val Val Ala Leu
            500                 505                 510

Lys Glu Leu Ser Ile Arg Gly Asp Phe Arg Thr Thr Ile Glu Tyr Leu
            515                 520                 525

Ile Lys Leu Leu Glu Thr Ala Asp Phe Glu Asn Asn Thr Ile Thr Thr
530                 535                 540

Gly Trp Leu Asp Glu Leu Ile Ser Lys Lys Leu Thr Ala Glu Arg Pro
545                 550                 555                 560

Asp Glu Thr Thr Ala Ile Leu Cys Gly Ala Val Thr Lys Ala Tyr Ile
                565                 570                 575

Gln Trp Asp Leu Cys Arg Lys Glu Tyr Val Ala Ser Leu Glu Lys Gly
            580                 585                 590

Gln Ile Pro Gly Lys Glu Leu Leu Arg Thr Ile Phe Pro Ile Glu Phe
            595                 600                 605

Ile Tyr Glu Gly Lys Lys Tyr Lys Phe Thr Val Val Gln Ala Ala Phe
610                 615                 620

Asp Lys Tyr Asn Val Phe Val Asn Gly Cys Met Ile Thr Val Ser Val
625                 630                 635                 640

Thr His Leu Lys Asp Gly Ser Leu Leu Val Ala Leu Asp Gly Lys Ser
            645                 650                 655

His Ser Val Tyr Tyr Leu Gln Glu Glu Val Gly Asn Thr Arg Leu Ser
            660                 665                 670

Val Asp Gly Lys Ser Cys Ile Leu Glu Val Glu His Glu Pro Thr Glu
            675                 680                 685

Leu Arg Thr Pro Ser Pro Gly Lys Leu Ile Lys Tyr Leu Val Glu His
690                 695                 700

Gly Asp His Val Lys Ile Gly Gln Pro Tyr Ala Glu Val Glu Val Met
705                 710                 715                 720

Lys Met Cys Met Pro Leu Val Ser Gln Glu Asn Gly Thr Ile Arg Leu
            725                 730                 735

Leu Lys Gln Pro Gly Ser Ser Val Ala Ala Gly Asp Ile Leu Ala Ile
            740                 745                 750

Leu Ala Leu Asp Asp Pro Ser Lys Val Lys His Ala Leu Pro Phe Asp
            755                 760                 765

Gly Thr Ile Pro Asp Met Lys Gln Pro Phe Ile His Ser Asn Lys Pro
770                 775                 780

Val Tyr Lys Phe Ile Ser Leu Leu Ser Val Leu Lys Asn Ile Leu Ala
```

-continued

```
          785                 790                 795                 800
Gly Tyr Asp Asn Gln Val Val Met Asn Asp Thr Leu Gln Ser Leu Leu
                    805                 810                 815
Asp Val Leu Lys Asn Pro Glu Leu Pro Tyr Ser Glu Trp Asn His Ser
                    820                 825                 830
Ile Ser Ala Leu His Ser Arg Leu Pro Ile His Leu Asp Glu Gln Leu
                    835                 840                 845
Thr Ser Leu Ile Glu Arg Ser His Gln Arg Gly Ala Asp Phe Pro Ala
                    850                 855                 860
Lys His Leu Leu Lys Leu Leu Asp Lys Glu Gln Ala Val Asn Pro Asp
865                 870                 875                 880
Pro Leu Phe Ser Gln Val Ile Ala Pro Leu Thr Ala Val Ala Lys Ser
                    885                 890                 895
Tyr Glu His Gly Leu Glu Val His Glu His Asn Val Phe Ala Asp Leu
                    900                 905                 910
Ile Thr Gln Tyr Tyr Asp Ile Glu Ser Leu Phe Ala Asp Lys Arg Glu
                    915                 920                 925
Glu Asp Val Ile Leu Gln Leu Arg Asp Glu Asn Lys Ser Ser Leu Asp
                    930                 935                 940
Lys Val Ile Asp Val Val Leu Ser His Ser Arg Val Gly Ala Lys Asn
945                 950                 955                 960
His Leu Ile Arg Ala Ile Leu Glu Ile Tyr Gln Thr Ile Cys Gln Asn
                    965                 970                 975
Asp Leu Gln Ala Ala Thr Ile Leu Lys Lys Pro Leu Lys Lys Ile Val
                    980                 985                 990
Glu Leu Asp Ser Arg Phe Thr Ala Lys Val Ser Leu Lys Ala Arg Glu
                    995                 1000                1005
Ile Leu Ile Gln Cys Ser Leu Pro Ser Ile Lys Glu Arg Ser Asp
                    1010                1015                1020
Gln Leu Glu His Ile Leu Arg Ser Ser Val Val Gln Thr Gln Tyr
                    1025                1030                1035
Gly Glu Ser Phe Asn Gly Asn Tyr Lys Leu Pro Asn Leu Asp Val
                    1040                1045                1050
Ile Gln Asp Val Ile Asp Ser Lys Tyr Ile Val Phe Asp Val Leu
                    1055                1060                1065
Thr Gln Phe Val Val Ser Pro Asn Lys Tyr Ile Phe Ala Ala Ala
                    1070                1075                1080
Ala Glu Val Tyr Leu Arg Arg Ala Tyr Arg Ala Tyr Ser Val Arg
                    1085                1090                1095
Glu Val Lys His His Phe Val Gly Asp Ser Ala Leu Pro Ile Val
                    1100                1105                1110
Glu Trp Lys Phe Gln Leu Pro Leu Leu Ser Thr Ala Ala Tyr Asn
                    1115                1120                1125
Ser Val Pro Glu Ala Met Arg Asn Ser Ser Ser Asn Arg Ser Ser
                    1130                1135                1140
Ile Ser Met Asp Arg Ala Val Ser Val Ser Asp Leu Thr Phe Met
                    1145                1150                1155
Ile Asn Lys Asn Asp Ser Gln Pro Leu Arg Thr Gly Ile Ile Ile
                    1160                1165                1170
Pro Thr Asn His Leu Asp Asp Ile Glu Glu Ser Leu Ser Ser Ala
                    1175                1180                1185
Ile Asp Val Phe Pro Lys Arg Pro Arg Asn Asn Gly Pro Ala Pro
                    1190                1195                1200
```

Asp Arg Thr Asn Val Ala Pro Glu Gln Pro Thr Asn Val Cys Asn
    1205                1210                1215

Val Phe Ile Ala Asn Val Ser Gly Tyr Asn Ser Glu Ala Glu Ile
    1220                1225                1230

Val Asp Lys Ile Ser Ser Val Leu Ser Glu Leu Lys Asp Asp Leu
    1235                1240                1245

Arg Ala Ser Gly Val Arg Arg Val Thr Phe Val Leu Gly Asp Lys
    1250                1255                1260

Val Gly Thr Tyr Pro Lys Tyr Tyr Thr Phe Lys Phe Pro Asp Tyr
    1265                1270                1275

Phe Glu Asp Glu Thr Ile Arg His Ile Glu Pro Ala Leu Ala Phe
    1280                1285                1290

Gln Leu Glu Leu Arg Arg Leu Ser Asn Phe Asn Ile Lys Pro Val
    1295                1300                1305

Pro Thr Glu Asn Arg Asn Ile His Val Tyr Glu Ala Val Ala Lys
    1310                1315                1320

Asn Thr Ser Cys Ile Asp Arg Arg Phe Phe Thr Arg Gly Ile Ile
    1325                1330                1335

Arg Thr Ser Arg Ile Arg Glu Asp Val Thr Ile Ser Glu Tyr Leu
    1340                1345                1350

Ile Ser Glu Ala Asn Arg Leu Met Ser Asp Ile Leu Asp Ala Leu
    1355                1360                1365

Glu Ile Ile Asp Thr Ser Asn Thr Asp Leu Asn His Ile Phe Ile
    1370                1375                1380

Asn Phe Ser Ala Val Phe Asn Val Thr Pro Asp Asp Val Glu Ala
    1385                1390                1395

Ala Phe Gly Gly Phe Leu Glu Arg Phe Gly Arg Arg Leu Trp Arg
    1400                1405                1410

Leu Arg Val Ser Ala Ala Glu Ile Arg Ile Met Cys Thr Asp Pro
    1415                1420                1425

Glu Thr Gly Ile Pro Phe Pro Leu Arg Ala Leu Ile Asn Asn Val
    1430                1435                1440

Ser Gly Tyr Val Val Lys Ser Glu Met Tyr Gln Glu Val Lys Asn
    1445                1450                1455

Asp His Gly Glu Trp Val Phe Lys Ser Leu Gly Pro Thr Pro Gly
    1460                1465                1470

Ser Met His Leu Arg Pro Ile Ser Thr Pro Tyr Pro Thr Lys Glu
    1475                1480                1485

Trp Leu Gln Pro Lys Arg Tyr Lys Ala His Leu Met Gly Thr Thr
    1490                1495                1500

Tyr Val Tyr Asp Phe Pro Glu Leu Phe Arg Gln Ala Thr Leu Ser
    1505                1510                1515

Gln Trp Lys Lys Tyr Ser Pro Thr Ala Arg Val Pro Ser Asp Val
    1520                1525                1530

Phe Val Ala Asn Glu Leu Ile Val Asp Asp Ser Gly Glu Leu Thr
    1535                1540                1545

Glu Val Ser Arg Glu Pro Gly Ala Asn Val Val Gly Met Val Ala
    1550                1555                1560

Phe Lys Val Thr Ala Lys Thr Pro Glu Tyr Pro Arg Gly Arg His
    1565                1570                1575

Phe Ile Ile Ile Ala Asn Asp Ile Thr Phe Lys Ile Gly Ser Phe
    1580                1585                1590

```
Gly Pro Gln Glu Asp Glu Tyr Phe Asn Lys Ala Thr Gln Leu Ala
    1595                1600                1605

Arg Lys Leu Gly Ile Pro Arg Ile Tyr Leu Ser Ala Asn Ser Gly
    1610                1615                1620

Ala Arg Ile Gly Val Ala Glu Glu Leu Leu Pro Leu Phe Lys Val
    1625                1630                1635

Ala Trp Lys Glu Glu Gly Lys Pro Ser Lys Gly Phe Glu Tyr Leu
    1640                1645                1650

Tyr Leu Thr Ser Glu Asp Leu Thr Leu Leu Glu Lys Ser Gly Lys
    1655                1660                1665

Ser Asn Ser Val Thr Thr Gln Arg Ile Val Glu Glu Gly Glu Glu
    1670                1675                1680

Arg His Val Ile Thr Ala Ile Ile Gly Ala Ser Asp Gly Leu Gly
    1685                1690                1695

Val Glu Cys Leu Arg Gly Ser Gly Leu Ile Ala Gly Ala Thr Ser
    1700                1705                1710

Arg Ala Tyr Lys Asp Ile Phe Thr Ile Thr Leu Val Thr Cys Arg
    1715                1720                1725

Ser Val Gly Ile Gly Ala Tyr Leu Val Arg Leu Gly Gln Arg Ala
    1730                1735                1740

Ile Gln Ile Glu Gly Gln Pro Ile Ile Leu Thr Gly Ala Pro Ala
    1745                1750                1755

Ile Asn Lys Leu Leu Gly Arg Glu Val Tyr Ser Ser Asn Leu Gln
    1760                1765                1770

Leu Gly Gly Thr Gln Ile Met Tyr Lys Asn Gly Val Ser His Leu
    1775                1780                1785

Thr Ala Asn Asp Asp Leu Ala Gly Val Glu Lys Ile Met Asp Trp
    1790                1795                1800

Leu Ala Tyr Val Pro Ala Lys Arg Asn Met Pro Val Pro Ile Leu
    1805                1810                1815

Glu Ser Leu His Asp Lys Trp Asp Arg Asp Val Asp Tyr Lys Pro
    1820                1825                1830

Thr Arg Asn Glu Pro Tyr Asp Val Arg Trp Met Ile Ser Gly Arg
    1835                1840                1845

Glu Thr Pro Asp Gly Glu Phe Glu Ser Gly Leu Phe Asp Ser Gly
    1850                1855                1860

Ser Phe Thr Glu Thr Leu Ser Gly Trp Ala Lys Gly Val Val Val
    1865                1870                1875

Gly Arg Ala Arg Leu Gly Gly Ile Pro Met Gly Val Ile Gly Val
    1880                1885                1890

Glu Thr Arg Val Thr Glu Asn Leu Ile Pro Ala Asp Pro Ala Asn
    1895                1900                1905

Pro Asp Ser Thr Glu Met Met Ile Gln Glu Ala Gly Gln Val Trp
    1910                1915                1920

Tyr Pro Asn Ser Ala Phe Lys Thr Ala Gln Ala Ile Asn Asp Phe
    1925                1930                1935

Asn Asn Gly Glu Gln Leu Pro Leu Met Ile Leu Ala Asn Trp Arg
    1940                1945                1950

Gly Phe Ser Gly Gly Gln Arg Asp Met Tyr Asn Glu Val Leu Lys
    1955                1960                1965

Tyr Gly Ser Phe Ile Val Asp Ala Leu Val Asp Phe Lys Gln Pro
    1970                1975                1980

Ile Phe Thr Tyr Ile Pro Pro Thr Ala Glu Leu Arg Gly Gly Ser
```

```
                1985                1990                1995
Trp Val Val Val Asp Pro Thr Ile Asn Glu Asp Met Met Glu Met
           2000                2005                2010

Tyr Ala Asp Val Glu Ser Arg Ala Gly Val Leu Glu Pro Glu Gly
           2015                2020                2025

Met Val Gly Ile Lys Tyr Arg Lys Asp Lys Leu Leu Ala Thr Met
           2030                2035                2040

Glu Arg Leu Asp Ala Lys Tyr Ala Glu Leu Lys Ser Lys Val Ser
           2045                2050                2055

Asp Thr Ser Leu Ser Glu Lys Asp Val Ser Glu Ile Lys Lys Gln
           2060                2065                2070

Ile Glu Gln Arg Glu Lys Gln Leu Leu Pro Ile Tyr Ala Gln Ile
           2075                2080                2085

Ser Ile Gln Phe Ala Asp Leu His Asp Arg Ser Gly Arg Met Leu
           2090                2095                2100

Ala Lys Gly Val Ile Lys Lys Glu Leu Glu Trp Val Asn Ser Arg
           2105                2110                2115

Arg Phe Phe Phe Trp Arg Val Arg Arg Arg Leu Asn Glu Glu Tyr
           2120                2125                2130

Leu Ile Lys Arg Ile Thr Glu Phe Leu Ser Ala Ser Ala Thr Arg
           2135                2140                2145

Leu Asp Lys Ile Ser Arg Ile Asn Ser Trp Leu Pro Thr Ser Ile
           2150                2155                2160

Asp Leu Glu Asp Asp Gln Lys Val Ala Ile Trp Leu Glu Glu Asn
           2165                2170                2175

Arg Lys Ala Leu Asp Ala Asn Ile Lys Glu Leu Arg Ala Glu His
           2180                2185                2190

Val Arg Arg Thr Leu Ala Thr Leu Val Arg Thr Asp Met Asp Thr
           2195                2200                2205

Thr Ser Lys Ser Leu Ala Glu Leu Ile Asn Leu Leu Pro Glu Thr
           2210                2215                2220

Glu Lys Glu Ser Ile Leu Ser Lys Ile Lys Ser
           2225                2230
```

<210> SEQ ID NO 57
<211> LENGTH: 2266
<212> TYPE: PRT
<213> ORGANISM: Yarrowia lipolytica

<400> SEQUENCE: 57

```
Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Phe Gly Leu Asn Ser Val His Thr
        35                  40                  45

Ala Lys Pro Ser Lys Val Lys Glu Phe Val Ala Ser His Gly Gly His
    50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110
```

```
Ala Asn Ala Asp Tyr Ile Arg Met Ala Asp Gln Tyr Glu Val Pro
            115                 120                 125
Gly Gly Thr Asn Asn Asn Tyr Ala Asn Val Glu Leu Ile Val Asp
        130                 135                 140
Val Ala Glu Arg Phe Gly Val Asp Ala Val Trp Ala Gly Trp Gly His
145                 150                 155                 160
Ala Ser Glu Asn Pro Leu Leu Pro Glu Ser Leu Ala Ala Ser Pro Arg
                165                 170                 175
Lys Ile Val Phe Ile Gly Pro Pro Ala Ala Met Arg Ser Leu Gly
            180                 185                 190
Asp Lys Ile Ser Ser Thr Ile Val Ala Gln His Ala Lys Val Pro Cys
            195                 200                 205
Ile Pro Trp Ser Gly Thr Gly Val Asp Glu Val Val Val Asp Lys Ser
    210                 215                 220
Thr Asn Leu Val Ser Val Ser Glu Glu Val Tyr Thr Lys Gly Cys Thr
225                 230                 235                 240
Thr Gly Pro Lys Gln Gly Leu Glu Lys Ala Lys Gln Ile Gly Phe Pro
                245                 250                 255
Val Met Ile Lys Ala Ser Glu Gly Gly Gly Gly Lys Gly Ile Arg Lys
            260                 265                 270
Val Glu Arg Glu Glu Asp Phe Glu Ala Ala Tyr His Gln Val Glu Gly
        275                 280                 285
Glu Ile Pro Gly Ser Pro Ile Phe Ile Met Gln Leu Ala Gly Asn Ala
        290                 295                 300
Arg His Leu Glu Val Gln Leu Leu Ala Asp Gln Tyr Gly Asn Asn Ile
305                 310                 315                 320
Ser Leu Phe Gly Arg Asp Cys Ser Val Gln Arg Arg His Gln Lys Ile
                325                 330                 335
Ile Glu Glu Ala Pro Val Thr Val Ala Gly Gln Gln Thr Phe Thr Ala
            340                 345                 350
Met Glu Lys Ala Ala Val Arg Leu Gly Lys Leu Val Gly Tyr Val Ser
            355                 360                 365
Ala Gly Thr Val Glu Tyr Leu Tyr Ser His Glu Asp Asp Lys Phe Tyr
    370                 375                 380
Phe Leu Glu Leu Asn Pro Arg Leu Gln Val Glu His Pro Thr Thr Glu
385                 390                 395                 400
Met Val Thr Gly Val Asn Leu Pro Ala Ala Gln Leu Gln Ile Ala Met
                405                 410                 415
Gly Ile Pro Leu Asp Arg Ile Lys Asp Ile Arg Leu Phe Tyr Gly Val
            420                 425                 430
Asn Pro His Thr Thr Thr Pro Ile Asp Phe Asp Phe Ser Gly Glu Asp
            435                 440                 445
Ala Asp Lys Thr Gln Arg Arg Pro Val Pro Arg Gly His Thr Thr Ala
    450                 455                 460
Cys Arg Ile Thr Ser Glu Asp Pro Gly Glu Gly Phe Lys Pro Ser Gly
465                 470                 475                 480
Gly Thr Met His Glu Leu Asn Phe Arg Ser Ser Asn Val Trp Gly
                485                 490                 495
Tyr Phe Ser Val Gly Asn Gln Gly Gly Ile His Ser Phe Ser Asp Ser
            500                 505                 510
Gln Phe Gly His Ile Phe Ala Phe Gly Glu Asn Arg Ser Ala Ser Arg
            515                 520                 525
Lys His Met Val Val Ala Leu Lys Glu Leu Ser Ile Arg Gly Asp Phe
```

```
            530                 535                 540
Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                565                 570                 575

Lys Leu Thr Ala Glu Arg Pro Asp Ser Phe Leu Ala Val Val Cys Gly
                580                 585                 590

Ala Ala Thr Lys Ala His Arg Ala Ser Glu Asp Ser Ile Ala Thr Tyr
                595                 600                 605

Met Ala Ser Leu Glu Lys Gly Gln Val Pro Ala Arg Asp Ile Leu Lys
                610                 615                 620

Thr Leu Phe Pro Val Asp Phe Ile Tyr Glu Gly Gln Arg Tyr Lys Phe
625                 630                 635                 640

Thr Ala Thr Arg Ser Ser Glu Asp Ser Tyr Thr Leu Phe Ile Asn Gly
                645                 650                 655

Ser Arg Cys Asp Ile Gly Val Arg Pro Leu Ser Asp Gly Gly Ile Leu
                660                 665                 670

Cys Leu Val Gly Gly Arg Ser His Asn Val Tyr Trp Lys Glu Glu Val
                675                 680                 685

Gly Ala Thr Arg Leu Ser Val Asp Ser Lys Thr Cys Leu Leu Glu Val
                690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
                725                 730                 735

Ala Glu Ile Glu Val Met Lys Met Tyr Met Thr Leu Thr Ala Gln Glu
                740                 745                 750

Asp Gly Ile Val Gln Leu Met Lys Gln Pro Gly Ser Thr Ile Glu Ala
                755                 760                 765

Gly Asp Ile Leu Gly Ile Leu Ala Leu Asp Asp Pro Ser Lys Val Lys
                770                 775                 780

His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
                805                 810                 815

Leu His Asn Ile Leu Leu Gly Phe Asp Asn Gln Val Val Met Lys Ser
                820                 825                 830

Thr Leu Gln Glu Met Val Gly Leu Leu Arg Asn Pro Glu Leu Pro Tyr
                835                 840                 845

Leu Gln Trp Ala His Gln Val Ser Ser Leu His Thr Arg Met Ser Ala
850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Gln Thr Leu Ala Pro
                900                 905                 910

Leu Phe Asp Leu Ala Arg Glu Tyr Gln Asp Gly Leu Ala Ile His Glu
                915                 920                 925

Leu Gln Val Ala Ala Gly Leu Leu Gln Ala Tyr Tyr Asp Ser Glu Ala
                930                 935                 940

Arg Phe Cys Gly Pro Asn Val Arg Asp Glu Asp Val Ile Leu Lys Leu
945                 950                 955                 960
```

```
Arg Glu Glu Asn Arg Asp Ser Leu Arg Lys Val Val Met Ala Gln Leu
            965                 970                 975

Ser His Ser Arg Val Gly Ala Lys Asn Asn Leu Val Leu Ala Leu Leu
            980                 985                 990

Asp Glu Tyr Lys Val Ala Asp Gln Ala Gly Thr Asp Ser Pro Ala Ser
            995                 1000                1005

Asn Val His Val Ala Lys Tyr Leu Arg Pro Val Leu Arg Lys Ile
        1010                1015                1020

Val Glu Leu Glu Ser Arg Ala Ser Ala Lys Val Ser Leu Lys Ala
        1025                1030                1035

Arg Glu Ile Leu Ile Gln Cys Ala Leu Pro Ser Leu Lys Glu Arg
        1040                1045                1050

Thr Asp Gln Leu Glu His Ile Leu Arg Ser Ser Val Val Glu Ser
        1055                1060                1065

Arg Tyr Gly Glu Val Gly Leu Glu His Arg Thr Pro Arg Ala Asp
        1070                1075                1080

Ile Leu Lys Glu Val Val Asp Ser Lys Tyr Ile Val Phe Asp Val
        1085                1090                1095

Leu Ala Gln Phe Phe Ala His Asp Asp Pro Trp Ile Val Leu Ala
        1100                1105                1110

Ala Leu Glu Leu Tyr Ile Arg Arg Ala Cys Lys Ala Tyr Ser Ile
        1115                1120                1125

Leu Asp Ile Asn Tyr His Gln Asp Ser Asp Leu Pro Pro Val Ile
        1130                1135                1140

Ser Trp Arg Phe Arg Leu Pro Thr Met Ser Ser Ala Leu Tyr Asn
        1145                1150                1155

Ser Val Val Ser Ser Gly Ser Lys Thr Pro Thr Ser Pro Ser Val
        1160                1165                1170

Ser Arg Ala Asp Ser Val Ser Asp Phe Ser Tyr Thr Val Glu Arg
        1175                1180                1185

Asp Ser Ala Pro Ala Arg Thr Gly Ala Ile Val Ala Val Pro His
        1190                1195                1200

Leu Asp Asp Leu Glu Asp Ala Leu Thr Arg Val Leu Glu Asn Leu
        1205                1210                1215

Pro Lys Arg Gly Ala Gly Leu Ala Ile Ser Val Gly Ala Ser Asn
        1220                1225                1230

Lys Ser Ala Ala Ser Ala Arg Asp Ala Ala Ala Ala Ala
        1235                1240                1245

Ser Ser Val Asp Thr Gly Leu Ser Asn Ile Cys Asn Val Met Ile
        1250                1255                1260

Gly Arg Val Asp Glu Ser Asp Asp Asp Thr Leu Ile Ala Arg
        1265                1270                1275

Ile Ser Gln Val Ile Glu Asp Phe Lys Glu Asp Phe Glu Ala Cys
        1280                1285                1290

Ser Leu Arg Arg Ile Thr Phe Ser Phe Gly Asn Ser Arg Gly Thr
        1295                1300                1305

Tyr Pro Lys Tyr Phe Thr Phe Arg Gly Pro Ala Tyr Glu Glu Asp
        1310                1315                1320

Pro Thr Ile Arg His Ile Glu Pro Ala Leu Ala Phe Gln Leu Glu
        1325                1330                1335

Leu Ala Arg Leu Ser Asn Phe Asp Ile Lys Pro Val His Thr Asp
        1340                1345                1350
```

-continued

```
Asn Arg Asn Ile His Val Tyr Glu Ala Thr Gly Lys Asn Ala Ala
1355                1360                1365

Ser Asp Lys Arg Phe Phe Thr Arg Gly Ile Val Arg Pro Gly Arg
1370                1375                1380

Leu Arg Glu Asn Ile Pro Thr Ser Glu Tyr Leu Ile Ser Glu Ala
1385                1390                1395

Asp Arg Leu Met Ser Asp Ile Leu Asp Ala Leu Glu Val Ile Gly
1400                1405                1410

Thr Thr Asn Ser Asp Leu Asn His Ile Phe Ile Asn Phe Ser Ala
1415                1420                1425

Val Phe Ala Leu Lys Pro Glu Glu Val Glu Ala Ala Phe Gly Gly
1430                1435                1440

Phe Leu Glu Arg Phe Gly Arg Arg Leu Trp Arg Leu Arg Val Thr
1445                1450                1455

Gly Ala Glu Ile Arg Met Met Val Ser Asp Pro Glu Thr Gly Ser
1460                1465                1470

Ala Phe Pro Leu Arg Ala Met Ile Asn Asn Val Ser Gly Tyr Val
1475                1480                1485

Val Gln Ser Glu Leu Tyr Ala Glu Ala Lys Asn Asp Lys Gly Gln
1490                1495                1500

Trp Ile Phe Lys Ser Leu Gly Lys Pro Gly Ser Met His Met Arg
1505                1510                1515

Ser Ile Asn Thr Pro Tyr Pro Thr Lys Glu Trp Leu Gln Pro Lys
1520                1525                1530

Arg Tyr Lys Ala His Leu Met Gly Thr Thr Tyr Cys Tyr Asp Phe
1535                1540                1545

Pro Glu Leu Phe Arg Gln Ser Ile Glu Ser Asp Trp Lys Lys Tyr
1550                1555                1560

Asp Gly Lys Ala Pro Asp Asp Leu Met Thr Cys Asn Glu Leu Ile
1565                1570                1575

Leu Asp Glu Asp Ser Gly Leu Gln Glu Val Asn Arg Glu Pro
1580                1585                1590

Gly Ala Asn Asn Val Gly Met Val Ala Trp Lys Phe Glu Ala Lys
1595                1600                1605

Thr Pro Glu Tyr Pro Arg Gly Arg Ser Phe Ile Val Val Ala Asn
1610                1615                1620

Asp Ile Thr Phe Gln Ile Gly Ser Phe Gly Pro Ala Glu Asp Gln
1625                1630                1635

Phe Phe Phe Lys Val Thr Glu Leu Ala Arg Lys Leu Gly Ile Pro
1640                1645                1650

Arg Ile Tyr Leu Ser Ala Asn Ser Gly Ala Arg Ile Gly Ile Ala
1655                1660                1665

Asp Glu Leu Val Gly Lys Tyr Lys Val Ala Trp Asn Asp Glu Thr
1670                1675                1680

Asp Pro Ser Lys Gly Phe Lys Tyr Leu Tyr Phe Thr Pro Glu Ser
1685                1690                1695

Leu Ala Thr Leu Lys Pro Asp Thr Val Val Thr Thr Glu Ile Glu
1700                1705                1710

Glu Glu Gly Pro Asn Gly Val Glu Lys Arg His Val Ile Asp Tyr
1715                1720                1725

Ile Val Gly Glu Lys Asp Gly Leu Gly Val Glu Cys Leu Arg Gly
1730                1735                1740

Ser Gly Leu Ile Ala Gly Ala Thr Ser Arg Ala Tyr Lys Asp Ile
```

```
            1745                1750                1755
Phe Thr Leu Thr Leu Val Thr Cys Arg Ser Val Gly Ile Gly Ala
            1760                1765                1770

Tyr Leu Val Arg Leu Gly Gln Arg Ala Ile Gln Ile Glu Gly Gln
            1775                1780                1785

Pro Ile Ile Leu Thr Gly Ala Pro Ala Ile Asn Lys Leu Leu Gly
            1790                1795                1800

Arg Glu Val Tyr Ser Ser Asn Leu Gln Leu Gly Gly Thr Gln Ile
            1805                1810                1815

Met Tyr Asn Asn Gly Val Ser His Leu Thr Ala Arg Asp Asp Leu
            1820                1825                1830

Asn Gly Val His Lys Ile Met Gln Trp Leu Ser Tyr Ile Pro Ala
            1835                1840                1845

Ser Arg Gly Leu Pro Val Pro Val Leu Pro His Lys Thr Asp Val
            1850                1855                1860

Trp Asp Arg Asp Val Thr Phe Gln Pro Val Arg Gly Glu Gln Tyr
            1865                1870                1875

Asp Val Arg Trp Leu Ile Ser Gly Arg Thr Leu Glu Asp Gly Ala
            1880                1885                1890

Phe Glu Ser Gly Leu Phe Asp Lys Asp Ser Phe Gln Glu Thr Leu
            1895                1900                1905

Ser Gly Trp Ala Lys Gly Val Val Val Gly Arg Ala Arg Leu Gly
            1910                1915                1920

Gly Ile Pro Phe Gly Val Ile Gly Val Glu Thr Ala Thr Val Asp
            1925                1930                1935

Asn Thr Thr Pro Ala Asp Pro Ala Asn Pro Asp Ser Ile Glu Met
            1940                1945                1950

Ser Thr Ser Glu Ala Gly Gln Val Trp Tyr Pro Asn Ser Ala Phe
            1955                1960                1965

Lys Thr Ser Gln Ala Ile Asn Asp Phe Asn His Gly Glu Ala Leu
            1970                1975                1980

Pro Leu Met Ile Leu Ala Asn Trp Arg Gly Phe Ser Gly Gly Gln
            1985                1990                1995

Arg Asp Met Tyr Asn Glu Val Leu Lys Tyr Gly Ser Phe Ile Val
            2000                2005                2010

Asp Ala Leu Val Asp Tyr Lys Gln Pro Ile Met Val Tyr Ile Pro
            2015                2020                2025

Pro Thr Gly Glu Leu Arg Gly Gly Ser Trp Val Val Asp Pro
            2030                2035                2040

Thr Ile Asn Ser Asp Met Met Glu Met Tyr Ala Asp Val Glu Ser
            2045                2050                2055

Arg Gly Gly Val Leu Glu Pro Glu Gly Met Val Gly Ile Lys Tyr
            2060                2065                2070

Arg Arg Asp Lys Leu Leu Asp Thr Met Ala Arg Leu Asp Pro Glu
            2075                2080                2085

Tyr Ser Ser Leu Lys Lys Gln Leu Glu Glu Ser Pro Asp Ser Glu
            2090                2095                2100

Glu Leu Lys Val Lys Leu Ser Val Arg Glu Lys Ser Leu Met Pro
            2105                2110                2115

Ile Tyr Gln Gln Ile Ser Val Gln Phe Ala Asp Leu His Asp Arg
            2120                2125                2130

Ala Gly Arg Met Glu Ala Lys Gly Val Ile Arg Glu Ala Leu Val
            2135                2140                2145
```

```
Trp Lys Asp Ala Arg Arg Phe Phe Phe Trp Arg Ile Arg Arg Arg
    2150            2155            2160

Leu Val Glu Glu Tyr Leu Ile Thr Lys Ile Asn Ser Ile Leu Pro
    2165            2170            2175

Ser Cys Thr Arg Leu Glu Cys Leu Ala Arg Ile Lys Ser Trp Lys
    2180            2185            2190

Pro Ala Thr Leu Asp Gln Gly Ser Asp Arg Gly Val Ala Glu Trp
    2195            2200            2205

Phe Asp Glu Asn Ser Asp Ala Val Ser Ala Arg Leu Ser Glu Leu
    2210            2215            2220

Lys Lys Asp Ala Ser Ala Gln Ser Phe Ala Ser Gln Leu Arg Lys
    2225            2230            2235

Asp Arg Gln Gly Thr Leu Gln Gly Met Lys Gln Ala Leu Ala Ser
    2240            2245            2250

Leu Ser Glu Ala Glu Arg Ala Glu Leu Leu Lys Gly Leu
    2255            2260            2265
```